United States Patent
Bartkovitz et al.

(10) Patent No.: US 7,157,455 B2
(45) Date of Patent: Jan. 2, 2007

(54) 4-AMINOPYRIMIDINE-5-ONE DERIVATIVES

(75) Inventors: David Joseph Bartkovitz, Nutley, NJ (US); Xin-Jie Chu, Livingston, NJ (US); Qingjie Ding, Bridgewater, NJ (US); Nan Jiang, Fairfield, NJ (US); Allen John Lovey, North Caldwell, NJ (US); John Anthony Moliterni, Staten Island, NY (US); John Guilfoyle Mullin, Jr., Hawthorne, NJ (US); Binh Thanh Vu, North Caldwell, NJ (US); Peter Michael Wovkulich, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 345 days.

(21) Appl. No.: 10/770,379

(22) Filed: Feb. 2, 2004

(65) Prior Publication Data

US 2004/0162303 A1    Aug. 19, 2004

Related U.S. Application Data

(60) Provisional application No. 60/514,926, filed on Oct. 28, 2003, provisional application No. 60/446,273, filed on Feb. 10, 2003.

(51) Int. Cl.
*C07D 401/12* (2006.01)
*C07D 403/12* (2006.01)
*C07D 413/12* (2006.01)
*A61K 31/4468* (2006.01)
*C07D 239/42* (2006.01)

(52) U.S. Cl. .............. 514/235.8; 514/252.18; 514/275; 544/122; 544/295; 544/323; 544/324; 544/325

(58) Field of Classification Search ........ 544/122, 544/295, 323, 324, 325; 514/235.8, 252.18, 514/275
See application file for complete search history.

(56) References Cited

U.S. PATENT DOCUMENTS 6,262,096 B1    7/2001  Kim et al.

2004/0063737 A1    4/2004  Lucking et al.
2004/0102630 A1    5/2004  Brumby et al.

FOREIGN PATENT DOCUMENTS

| WO | WO 91/18887 | 12/1991 |
|---|---|---|
| WO | WO 99/21845 | 5/1999 |
| WO | WO 00/12485 | 3/2000 |
| WO | WO 00/39101 | 7/2000 |
| WO | WO 01/19825 | 3/2001 |
| WO | WO 01/38315 | 5/2001 |
| WO | WO 01/64653 | 9/2001 |
| WO | WO 01/64654 | 9/2001 |
| WO | WO 01/64656 | 9/2001 |
| WO | WO 01/79198 | 10/2001 |
| WO | WO 04/048343 | 6/2004 |
| WO | WO 05/037800 | 4/2005 |

OTHER PUBLICATIONS

Harris, W. and Wilkinson, S., Emerging Drugs, 2000, vol. 5, pp. 287-297.
Dumas, J., Exp. Opin. Ther. Patents, 2001, vol. 11, pp. 405-429.
Sielecki T., et al., J. Med. Chem., 2000, vol. 43, pp. 1-18.
Abstract corresponding to WO 05/037800 (B2), 2005.

*Primary Examiner*—Deepak Rao
(74) *Attorney, Agent, or Firm*—George W. Johnston; Patricia S. Rocha-Tramaloni

(57) ABSTRACT

Novel 4-aminopyrimidine-5-one derivatives are disclosed. These compounds inhibit cyclin-dependent kinases, in particular cyclin-dependent kinase 4 (Cdk4). These compounds and their pharmaceutically acceptable salts and esters have antiproliferative activity and are useful in the treatment or control of cancer, in particular solid tumors. This invention is also directed to pharmaceutical compositions containing such compounds and to methods of treating or controlling cancer, most particularly the treatment or control of breast, lung, colon and prostate tumors. Also disclosed are intermediates useful in the preparation of these novel 4-aminopyrimidine-5-one derivatives.

44 Claims, No Drawings

4-AMINOPYRIMIDINE-5-ONE DERIVATIVES

PRIORITY TO RELATED APPLICATIONS

This application claims the benefit of Provisional Applications Ser. No. 60/514,926, filed Oct. 28, 2003, and Ser. No. 60/446,273, filed Feb. 10, 2003.

FIELD OF THE INVENTION

The present invention relates to novel 4-aminopyrimidine-5-one derivatives that inhibit cyclin-dependent kinases, most particularly cyclin-dependent kinase 4 (Cdk4). These compounds and their pharmaceutically acceptable salts and esters have antiproliferative activity and are useful, inter alia, in the treatment or control of cancer, in particular solid tumors. This invention also relates to pharmaceutical compositions containing such compounds and to methods of treating or controlling cancer, most particularly the treatment or control of breast, lung, colon and prostate tumors. Finally, this invention is also directed to novel intermediate compounds useful in the preparation of the novel diaminopyrimidines herein disclosed.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The four primary phases of cell cycle control are generally describes as $G_1$, S, $G_2$, and M. Some essential enzymes for cell cycle control appear to be cyclin D/Cdk4, cyclin D/Cdk6, cyclin E/Cdk2, cyclin A/Cdk2, and cyclin B/Cdk1 (also known as Cdc2/cyclin B). Cyclin D/Cdk4, cyclin D/Cdk6, and cyclin E/Cdk2 control passage through the $G_1$-phase and the $G_1$- to S-phase transition by phosphorylation of the retinoblastoma phosphoprotein, pRb. Cyclin A/Cdk2 regulates passage through the S-phase, and cyclin B/Cdk1 controls the $G_2$ checkpoint and regulates entry into M (mitosis) phase.

The cell cycle progression is regulated by Cdk1 (cdc2) and Cdk2 beyond early $G_1$ when cells are committed to cytokinesis. Therefore, drug inhibition of these Cdks is likely not only to arrest cell proliferation, but also to trigger apoptotic cell death. Once the cells pass the $G_1$ restriction point and are committed to S phase, they become independent of growth factor stimulation for continued cell cycle progression.

Following completion of DNA replication, cells enter the $G_2$ phase of the cell cycle in preparation for M phase and cytokinesis. Cdk1 has been shown to regulate passage of cells through these later phases of the cell cycle in association with both cyclins A and B. Complete activation of Cdk1 requires both cyclin binding and specific phosphorylation (Morgan, D. O., De Bondt, H. L., Curr. Opin. Cell. Biol. 1994, 6, 239–246). Once activated, Cdk1/cyclin complexes prepare the cell for division during M phase.

The transition from $G_1$ phase into S phase as stated above is regulated by the complex of Cdk4 with cyclin D and Cdk2.with cyclin E. These complexes phosphorylate the tumor suppressor protein Retinoblastoma (pRb), releasing the transcription factor E2F and allowing the expression of genes required in S phase (Nevins, J. R. Science 1992, 258, 424-429; Lavia, P. BioEssays 1999, 21, 221–230). Blocking the activity of the Cdk4/cyclin D and Cdk2/cyclin E complexes arrests the cell cycle in $G_1$ phase. For example, the proteins of the INK4 family, including $p16^{INK4a}$, which block the kinase activity of the Cdk4/cyclin D complex, cause arrest in $G_1$ (Sherr, C. J. Science 1996, 274, 1672–1677). The specific block has been reviewed (Vidal, A. Gene 2000, 247, 1–15).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. J. Biol. Chem. 1999, 274, 13961–13969).

Numerous defects in the pRb pathway have been shown to be involved in various cancers. For example, overexpression of Cdk4 has been observed in cases of hereditary melanoma (Webster, K. R. Exp. Opin. Invest. Drugs 1998, 7, 865–887); cyclin D is overexpressed in many human cancers (Sherr, C. J. Science 1996, 274, 1672–1677); p16 is mutated or deleted in many tumors (Webster, K. R. Exp. Opin. Invest Drugs 1998, 7, 865–887); and pRb function is lost through mutation or deletion in many human cancers (Weinberg, R. A. Cell 1995, 81, 323–330). Defects in this pathway have also been shown to have an effect on prognosis. For example, loss of p16 is correlated with poor prognosis in non-small-cell lung carcinoma (NSCLC) and malignant melanoma (Tsihlias, J. et al. Annu. Rev. Med. 1999, 50, 401423). Abnormalities of cyclin D1 and/or pRb at the gene and/or expression level were present in more than 90% of a series of non-small cell lung cancer specimens, indicating that cyclin D1 and/or pRb represent an important step in lung tumorigenesis (Marchetti, A. et al. Int. J. Cancer 1998, 75, 573–582). In 49 out of 50 pancreatic carcinomas (98%), the pRb/p16 pathway was abrogated exclusively through inactivation of the p16 gene and cyclin D connected (Schutte, M. et al. Cancer Res. 1998, 57, 3126–3134). For a review on the relation between expression of pRb and the cyclin/cyclin dependent kinases in a number of tissues see Teicher, B. A. Cancer Chemother. Pharmacol. 2000, 46, 293–304.

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and overexpression or addition of proteins involved in the pathway. See, e.g., Lukas, J. et al. *Nature* 1995, 79, 573–582; Nevins, J. R. *Science* 1992, 258, 424–429; Lim, I. K. et al. *Molecular Carcinogenesis* 1998, 23, 25–35; Tam, S. W. et al. *Oncogene* 1994, 9, 2663–2674; Driscoll, B. et al. *Am. J. Physiol.* 1997, 273 (*Lung Cell. Mol. Physiol.*), L941–L949; and Sang, J. et al. *Chin. Sci. Bull.* 1999, 44, 541–544).

The role of cdks in the regulation of cellular proliferation is thus well established. For example, as shown above, there is an extensive body of literature validating the use of compounds inhibiting targets in the Cdk4, Cdk2 and Cdk1 pathways as anti-proliferative therapeutic agents. Inhibitors of cellular proliferation thus act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neurofibromatosis, atherosclerosis, pulmonary fibrosis, arthritis, psoriasis, inflammatory bowel disease, transplantation rejections infections), viral infections (including, but not limited to herpervirus, poxvirus, Epstein-Barr virus), autoimmune disease (e.g. lupus, rheumatoid arthritis, psoriasis, inflammatory bowel disease), neurodegenerative disorders (including but not limited to Alzheimer's disease), and neurodegenerative diseases (e.g. Parkinson's disease, amyotrophic lateral sclerosis, retinitis pigmentosa, spinal muscular atrophy, and cerebral degeneration).

Several distinct classes of small molecules have been identified as inhibitors of Cdks: olomoucine and other purine analogs, flavopiridol, staurosporine, UCN-01 and other indolocarbazoles, 9-hydroxyellipticine, indirubin, paullones, diaryl ureas, quinazolines, indopyrazoles, [2,3-d] pyridopyrimidines, fascaplysin, aminothiazoles, diaminothiazoles, pteridinones, and pyrazoles or example (Carlson et. al., *Cancer Res.* 1996, 56, 2973–2978: De Azevedo et al., *Eur. J. Biochem.*, 1997, 243, 518–526; Bridges, A. J., *Exp. Opin. Ther. Patents.* 1995, 5, 12451257; Reinhold et al., *J. Biol. Chem.* 1998, 278, 3803–3807; Kakeya, H. et. al., *Cancer Res.* 1998, 58, 704–710; Harper, J. W., *Cancer Surveys* 1997, 29, 91–107; Harrington, E. A., et al., *Proc. Natl. Acad. Sci. USA* 1998, 95, 11945–11950; Meijer, L., et al., *Eur. J. Biochem.* 2000, 267, 1–13; Garrett, M. D. et. al., *Current Opin. Genetics Develop.* 1999, 9,104–111; Mgbonyebi, O. P. et al., *Cancer Res.* 1999, 59, 1903–1910; Hoessel et al., *Nature Cell Biology.* 1999, 1, 60–67; Zaherevitz et al., *Cancer Res.*, 1999, 59, 2566–2569; Honma, T., et al., *221st National ACS Meeting.* 2001: Medi 136; Sielecki, T. M., et al., *Bioorg. Med. Chem. Left.* 2001, 11, 1157–1160; Nugiel, D. A., et al., *J. Med. Chem.*, 2001, 44, 1334–1336; Fry, D. W. et al., *J. Biol. Chem.* 2001, 276, 16617–15523; Soni, R., et al., *Biochem. Biophys. Res. Commun.* 2000, 275, 877; Ryu, C-K. et al., *Bioorg. Med. Chem. Left.*, 2000, 10, 461; Jeong, H-W., et al., *Bioorg. Med. Chem. Lett.* 2000, 10, 1819; Toogood et al., *J. Med. Chem.*, 2000, 43, 4606–4616; Chong, W., Fischer, *Curr. Opin. in Drug Discov. and Develop.*, 2001, 4, 623–634, WO0009921845, Toogood. P., WO0119825, Toogood P., WO0138315, Reich S. H., WO0179198, Webster, K. U.S. Pat. No. 6,262,096.

The class of diaminopyridimines is represented by compounds of formula

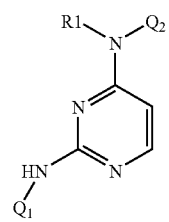

stated to inhibit Cdk4 and FAK3. See WO0012485 (Astra Zeneca).

WO9118887 (Smith Kline Beecham) relates to diaminopyrimidines of formula

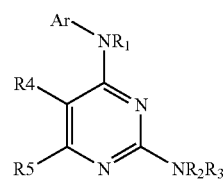

that are stated to inhibit gastric secretion.

WO0039101 (Astra Zeneca) relates to pyrimidine compounds of formula

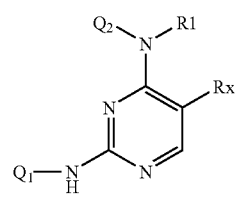

stated to act as anti-cancer agents.

WO0164653 (Astra Zeneca) relates to pyrimidine compounds of the formula

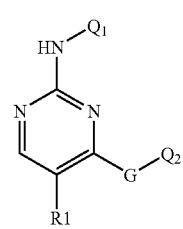

described to act as Cdk inhibitors and FAK inhibitors.

WO0164654 (Astra Zeneca) relates to pyrimidine compounds of formula

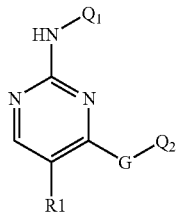

described to act as Cdk inhibitors and FAK inhibitors.

Additionally, WO0164656 (Astra Zeneca) relates to pyrimidine compounds of formula

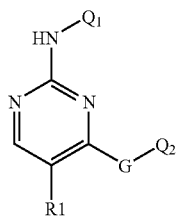

also described as Cdk inhibitors and FAK inhibitors.

For reviews of compounds inhibiting the Cdk4/cyclin D pathway see: Harris, W. and Wilkinson, S., *Emerging Drugs.* 2000, 5, 287–297; Dumas, J., *Exp. Opin. Ther. Patents.* 2001, 11, 405–429; Sielecki T., et. al., *J. Med. Chem.* 2000, 43, 1–18.

SUMMARY OF THE INVENTION

The present invention relates to novel diaminopyrimidines of the formula

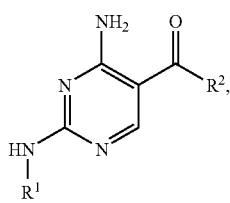

I wherein
$R^1$ is selected from the group
heterocycle and lower alkyl-heterocycle, wherein the heterocycle moiety in both instances optionally may be substituted by up to four substituents independently selected from
H,
lower alkyl,
lower alkyl substituted by oxo, $OR^{12}$, $CO_2R^{12}$, $NR^5R^6$, $S(O)_nR^{15}$ or $C(O)NR^5R^6$,
$CO_2R^7$,
$COR^{11}$,
$COR^{12}$,
$C(O)NR^{13}R^{14}$,
$S(O)_nR^{15}$,
oxo,
$OR^{12}$; or
$NR^5R^6$,
aryl,
aryl substituted by
H,
$S(O)_n$—$R^{15}$,
$NR^5R^6$,
carbonyl,
carbonyl substituted by lower alkyl, $OR^{12}$ or $NR^5R^6$,
lower alkyl,
lower alkyl substituted by $OR^{10}$ or $NR^5R^6$,
$OR^8$;
halogen,
cycloalkyl,
cycloalkyl substituted by $OR^7$, $NR^5R^6$ or $S(O)_nR^{15}$,
lower alkyl, and
lower alkyl substituted by
$NR^5R^6$,
$NR^{11}SO_2R^{15}$,
$CO_2R^{10}$,
$S(O)_nR^{15}$,
heterocycle,
heterocycle substituted by
lower alkyl,
$CO_2R^{12}$ or
$SO_2R^{15}$,
heteroaryl,
heteroaryl substituted by
lower alkyl,
$CO_2R^{12}$ or
$SO_2R^{15}$,
aryl, and
aryl substituted by
lower alkyl,
halogen,
$NR^5R^6$,
$COR^{12}$ or
$CO_2R^{12}$;
$R^2$ is selected from the group
aryl, heteroaryl, cycloalkyl and heterocycle, wherein each may be substituted by up to four substituents independently selected from the group
lower alkyl,
lower alkyl substituted by halogen or $OR^{10}$,
halogen,
$OR^{12}$,
$NO_2$,
CN,
$NR^5R^6$,
$S(O)_n$—$R^9$, and
$SO_2$—$NR^{16}R^{17}$;
$R^5$ and $R^6$ are each independently selected from the group
H,
lower alkyl,
lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^{13}R^{14}$, $C(O)NR^{13}R^{14}$ or $SO_2R^{15}$,
aryl,
aryl substituted by $NR^{13}R^{14}$, $OR^{12}$, $CO_2R^{12}$, $C(O)NR^{13}R^{14}$, $SO_2R^{15}$, halogen, lower alkyl, or lower alkyl substituted by halogen, $OR^{12}$, oxo, $CO_2R^{12}$, $C(O)NR^{13}R^{14}$ or $NR^{13}R^{14}$, SO$_2$R$^{15}$,
CO$_2$R$^{12}$,
COR$^{12}$, and

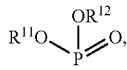

or alternatively, the group —NR$^5$R$^6$ can form a ring having a total of from 3 to 7 ring atoms, said ring atoms comprising in addition to the nitrogen to which R$^5$ and R$^6$ are bonded, carbon ring atoms, said carbon ring atoms optionally being replaced by one or more additional N or O ring atoms or the group SO$_2$, and said ring atoms optionally being substituted by OH, oxo, NR$^{13}$R$^{14}$, lower alkyl and lower alkyl substituted by OR$^{12}$;

R$^7$ is selected from the group
  H,
  lower alkyl,
  lower alkyl substituted by OR$^{12}$, CO$_2$R$^{12}$, NR$^5$R$^6$, or C(O)NR$^5$R$^6$,
  halogen,
  oxo,
  aryl,
  aryl substituted by up to three substituents independently selected from lower alkyl, halogen and NR$^5$R$^6$,
  cycloalkyl,
  cycloalkyl substituted by OH, oxo, or NH$_2$,
  SO$_2$R$^{15}$, and
  COR$^{12}$;

R$^8$ is selected from the group
  H,
  lower alkyl,
  lower alkyl substituted by NR$^5$R$^6$,
  heterocycle, and
  heterocycle substituted by lower alkyl, CO$_2$R$^{12}$ or SO$_2$R$^{15}$;

R$^9$ is selected from the group
  H, and
  lower alkyl;

R$^{10}$ is selected from the group
  lower alkyl,
  aryl, and
  aryl substituted by halogen or NR$^5$R$^6$;

R$^{11}$ is selected from the group
  H,
  lower alkyl, and
  lower alkyl substituted by oxo and halogen;

R$^{12}$ is selected from the group
  H,
  lower alkyl, and
  lower alkyl substituted by NR$^5$R$^6$ or OR$^{11}$;

R$^{13}$ and R$^{14}$ are each independently selected from the group
  H,
  lower alkyl,
  lower alkyl substituted by CO$_2$R$^{12}$, OR$^{12}$, NR$^5$R$^6$, C(O)NR$^5$R$^6$, SO$_2$R$^{15}$, NSO$_2$R$^{12}$, heteroaryl, heterocycle, or heterocycle substituted by oxo,
  cycloalkyl,
  cycloalkyl substituted by CO$_2$R$^{12}$, OR$^{12}$, NR$^5$R$^6$, CONR$^5$R$^6$ or SO$_2$R$^{15}$,
  aryl,
  aryl substituted by NR$^5$R$^6$, OR$^{12}$, CO$_2$R$^{12}$, CONR$^5$R$^6$, SO$_2$R$^{15}$, halogen, lower alkyl, and lower alkyl substituted by halogen, OR$^{12}$, oxo, CO$_2$R$^{12}$, C(O)NR$^5$R$^6$ or NR$^5$R$^6$;
  SO$_2$R$^{15}$,
  CO$_2$R$^{12}$,
  COR$^{12}$, and

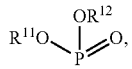

or alternatively, the group —NR$^{13}$R$^{14}$ can form a ring having a total of from 3 to 7 ring atoms, said ring atoms comprising in addition to the nitrogen to which R$^{13}$ and R$^{14}$ are bonded, carbon ring atoms, said carbon ring atoms optionally being replaced by one or more additional N or O ring atoms, and said ring atoms optionally being substituted by OH, oxo, NR$^5$R$^6$, lower alkyl and lower alkyl substituted by OR$^{12}$;

R$^{15}$ is selected from the group
  aryl,
  aryl substituted by the group halogen, CO$_2$R$^{12}$, SO$_2$R$^{10}$, COR$^{12}$, lower alkyl and lower alkyl substituted by halogen, OR$^{12}$, oxo, CO$_2$R$^{12}$, C(O)NR$^5$R$^6$ or NR$^5$R$^6$,
  heteroaryl,
  heteroaryl substituted by the group halogen, CO$_2$R$^{12}$, SO$_2$R$^{10}$, COR$^{12}$, lower alkyl and lower alkyl alkyl substituted by halogen, OR$^{12}$, oxo, CO$_2$R$^{12}$, NR$^5$R$^6$ or NR$^5$R$^6$,
  NR$^5$R$^6$,
  lower alkyl,
  lower alkyl substituted by halogen, OR$^{12}$, oxo, CO$_2$R$^{12}$, C(O)NR$^5$R$^6$ or NR$^5$R$^6$,
  heterocycle, and
  heterocycle substituted by the group CO$_2$R$^{12}$, COR$^{12}$, SO$_2$R$^{12}$, lower alkyl, C(O)NR$^5$R$^6$ or NR$^5$R$^6$;

R$^{16}$ and R$^{17}$ are each independently selected from the group
  H, and
  lower alkyl,
  or, alternatively, the group —NR$^{16}$R$^{17}$ can form a ring having a total of from 3 to 7 ring atoms, said ring atoms comprising in addition to the nitrogen to which R$^{16}$ and R$^{17}$ are bonded, carbon ring atoms, said carbon ring atoms optionally being replaced by one or more additional N or O ring atoms, and said ring atoms optionally being substituted by lower alkyl, OH, oxo and NH$_2$; and n is 0, 1 or 2;

or the pharmaceutically acceptable salts or esters thereof.

These compounds inhibit cyclin-dependent kinases, most particularly Cdk4. These compounds and their pharmaceutically acceptable salts and esters have antiproliferative activity and are useful in the treatment or control of cancer, in particular solid tumors.

The present invention also relates to pharmaceutical compositions comprising one or more compounds of the invention, or a pharmaceutically acceptable salt or ester thereof, and a pharmaceutically acceptable carrier or excipient.

The present invention further relates to a method for treating or controlling cancer, more particularly the treatment or control of a solid tumor, most particularly to the treatment or control of breast, lung and colon and prostate tumors by administering to a patient in need of such therapy a therapeutically effective amount of a compound of formula I, or a pharmaceutically salt or ester thereof.

Finally, this invention also relates to novel intermediate compounds useful in the preparation of a compound of formula I.

DETAILED DESCRIPTION OF THE INVENTION

Definitions

As used herein, the following terms shall have the following definitions.

"Aryl" means a monovalent, monocyclic or bicyclic, aromatic carbocyclic hydrocarbon radical, preferably a 6–10 membered aromatic aromatic ring system. Preferred aryl groups include, but are not limited to, phenyl, naphthyl, tolyl and xylyl.

"Carbonyl" means the radical C=O.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably fluorine or chlorine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole, benzofuran and tetrazolyl.

"Heterocycle" or "heterocyclyl" means a saturated or partially unsaturated, non-aromatic cyclic radical of 3 to 8 ring atoms in which from one to 3 ring atoms are hetero atoms selected from nitrogen, oxygen, $S(O)_n$ (where n is an integer from 0 to 2), or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$IC_{50}$" refers to the concentration of a particular compound according to the invention required to inhibit 50% of a specific measured activity. $IC_{50}$ can be measured, inter alia, as is described in Example 390A, infra.

"$K_i$" refers to a measure of the thermodynamic binding of the ligand/inhibitor (that is, a compound according to the invention) to the target protein. $K_i$ can be measured, inter alia, as is described in Example 390B, infra.

"Lower alkyl" alone or in conjunction with another term, e.g. lower alkyl-heterocycle, denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Oxo" means =O.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids ($R^{40}C(=O)OH$) are lower alkyl esters which may be substituted with $NR^{41}R^{42}$ where $R^{41}$ and $R^{42}$ are lower alkyl, or where $NR^{41}R^{42}$ taken together form a monocyclic aliphatic heterocycle, such as pyrrolidine, piperidine, morpholine, N-methylpiperazine, etc.; acyloxyalkyl esters of the formula $R^{40}C(=O)OCHR^{43}OC(=O)R^{44}$ where $R^{43}$ is hydrogen or methyl, and $R^{44}$ is lower alkyl or cycloalkyl; carbonate esters of the formula $R^{40}C(=O)OCHR^{43}OC(=O)OR^{45}$ where $R^{43}$ is hydrogen or methyl, and $R^{45}$ is lower alkyl or cycloalkyl; or aminocarbonylmethyl esters of the formula $R^{40}C(=O)OCH_2C(=O)NR^{41}R^{42}$ where $R^{41}$ and $R^{42}$ are hydrogen or lower alkyl, or where $NR^{41}R^{42}$ taken together form a monocyclic aliphatic heterocycle, such as pyrrolidine, piperidine, morpholine, N-methylpiperazine, etc.

Examples of lower alkyl esters are the methyl, ethyl, and n-propyl esters, and the like. Examples of lower alkyl esters substituted with $NR^{41}R^{42}$ are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy)ethyl and 1-(cyclohexyloxycarbonyloxy)ethyl esters. Examples of aminocarbonylmethyl esters are the N,N-dimethylcarbamoylmethyl and carbamoylmethyl esters.

Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., *Textbook of Drug Design and Development* (2d Ed. 1996) at pp. 152–191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In one embodiment, the present invention relates to compounds of formula I

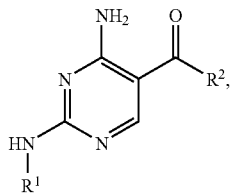

I or the pharmaceutically acceptable salts or esters thereof, wherein $R^1$ and $R^2$ are as defined above.

In a preferred embodiment of the compounds of formula I, $R^2$ is phenyl, preferably phenyl substituted by halogen, most preferably F, or $OR^{12}$ wherein $R^{12}$ is lower alkyl. In a most preferred embodiment, $R^2$ is phenyl substituted by one or two F molecules and one $OR^{12}$ group wherein $R^{12}$ is lower alkyl, preferably methyl.

In another preferred embodiment of the compounds of formula I, $R^2$ is as defined above and $R^1$ is selected from the group

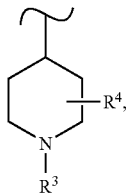

(a)

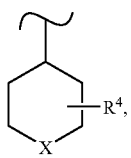

(b)

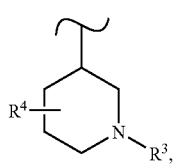

(c)

-continued

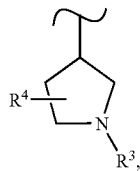

(d)

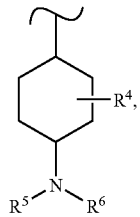

(e)

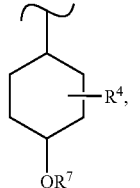

(f)

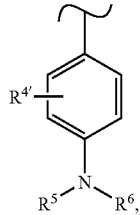

(g)

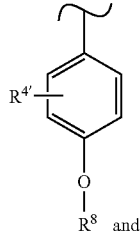

(h)

and

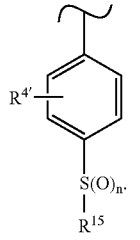

(i)

wherein
$R^3$ is selected from the group
H,
lower alkyl,
lower alkyl substituted by oxo, $OR^{12}$, $CO_2R^{12}$, $NR^5R^6$, $SO_2R^{15}$ or $C(O)NR^5R^6$,
$CO_2R^7$,
$COR^{12}$,
$C(O)NR^5R^6$, and
$SO_2R^{15}$;

R⁴ is selected from the group
  H,
  OR¹¹,
  lower alkyl,
  NR⁵R⁶,
  NO₂,
  oxo
  CN, and
  halogen;
R⁴' is selected from the group
  H,
  OR¹¹,
  lower alkyl,
  NR⁵R⁶,
  NO₂,
  CN, and
  halogen;
R⁵ and R⁶ are each independently selected from the group
  H,
  lower alkyl,
  lower alkyl substituted by oxo, CO₂R¹², OR¹², NR¹³R¹⁴, C(O)NR¹³R¹⁴, SO₂R¹⁵, NSO₂R¹², heteroaryl, heterocycle, or heterocycle substituted by oxo,
  cycloalkyl,
  cycloalkyl substituted by CO₂R¹², OR¹², NR¹³R¹⁴, C(O)NR¹³R¹⁴ or SO₂R¹⁵,
  aryl,
  aryl substituted by NR¹³R¹⁴, OR¹², CO₂R¹², CONR¹³R¹⁴, SO₂R¹⁵, halogen, lower alkyl, and lower alkyl substituted by halogen, OR¹², oxo, CO₂R¹², CONR¹³R¹⁴ or NR¹³R¹⁴;
  SO₂R¹⁵,
  CO₂R¹²,
  COR¹², and

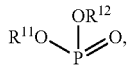

or alternatively, the group —NR⁵R⁶ can form a ring having a total of from 3 to 7 ring atoms, said ring atoms comprising in addition to the nitrogen to which R⁵ and R⁶ are bonded, carbon ring atoms, said carbon ring atoms optionally being replaced by one or more additional N or O ring atoms or the group SO₂, and said ring atoms optionally being substituted by OH, oxo, N¹³R¹⁴, lower alkyl and lower alkyl substituted by OR¹²;
R⁷ is selected from the group
  H,
  lower alkyl,
  lower alkyl substituted by OR¹², CO₂R¹², NR⁵R⁶, or CONR⁵R⁶,
  halogen,
  oxo,
  aryl,
  aryl substituted by up to three substituents independently selected from lower alkyl, halogen, or NR⁵R⁶,
  cycloalkyl,
  cycloalkyl substituted by OH, oxo, or NH₂,
  SO₂R¹⁵ and
  COR¹²;

R⁸ is selected from the group
  H,
  lower alkyl,
  lower alkyl substituted by NR⁵R⁶,
  heterocycle, and
  heterocycle substituted by lower alkyl, CO₂R¹² or SO₂R¹⁵;
R¹⁰ is selected from the group
  lower alkyl,
  aryl, and
  aryl substituted by halogen or NR⁵R⁶;
R¹¹ is selected from the group
  H,
  lower alkyl, and
  lower alkyl substituted by oxo and halogen;
R¹² is selected from the group
  H
  lower alkyl, and
  lower alkyl substituted by halogen, oxo, NR⁵R⁶ or OR¹¹;
R¹³ and R¹⁴ are independently selected from
  H,
  lower alkyl,
  lower alkyl substituted by CO₂R¹², OR¹², NR⁵R⁶, C(O)NR⁵R⁶, SO₂R¹⁵, NSO₂R¹², heteroaryl, heterocycle, or heterocycle substituted by oxo,
  cycloalkyl,
  cycloalkyl substituted by CO₂R¹², OR¹², NR⁵R⁶, C(O)NR⁵R⁶ or SO₂R¹⁵,
  aryl,
  aryl substituted by NR⁵R⁶, OR¹², CO₂R¹², C(O)NR⁵R⁶, SO₂R¹⁵, halogen, lower alkyl, and lower alkyl substituted by halogen, OR¹², oxo, CO₂R¹², C(O)NR⁵R⁶ and NR⁵R⁶;
  SO₂R¹⁵,
  CO₂R¹²,
  COR¹², and

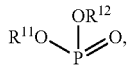

or alternatively, the group —NR¹³R¹⁴ can form a ring having a total of from 3 to 7 ring atoms, said ring atoms comprising in addition to the nitrogen to which R¹³ and R¹⁴ are bonded, carbon ring atoms, said carbon ring atoms optionally being replaced by one or more additional N or O ring atoms, and said ring atoms optionally being substituted by OH, oxo, NR⁵R⁶, lower alkyl and lower alkyl substituted by OR¹²;
R¹⁵ is selected from the group
  aryl,
  aryl substituted by the group halogen, CO₂R¹², SO₂R¹⁰, COR¹², lower alkyl and lower alkyl substituted by halogen, OR¹², oxo, CO₂R¹², C(O)NR⁵R⁶ or NR⁵R⁶,
  heteroaryl,
  heteroaryl substituted by the group halogen, CO₂R¹², SO₂R¹⁰, COR¹², lower alkyl and lower alkyl alkyl substituted by halogen, OR¹², oxo, CO₂R¹², C(O)NR⁵R⁶ or NR⁵R⁶,
  NR⁵R⁶,
  lower alkyl,
  lower alkyl substituted by the group halogen, OR¹², oxo, CO₂R¹², C(O)NR⁵R⁶ or NR⁵R⁶, heterocycle, and heterocycle substituted by the group $CO_2R^{12}$, $COR^{12}$, $SO_2R^{12}$, lower alkyl, $C(O)NR^5R^6$ or $NR^5R^6$;

X is selected from the group

S,
SO,
$SO_2$,
O; and n is 0, 1 or 2, or the pharmaceutically acceptable salts or esters thereof.

In another preferred embodiment, the invention relates to compounds of formula

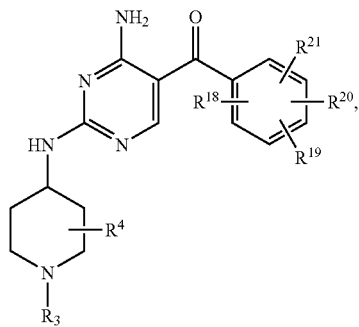

I(a)

wherein $R^3$ and $R^4$ are as defined above and $R^{18}$, $R^{19}$, $R^{20}$ and $R^{21}$ are each independently selected from lower alkyl, halogen and $OR^{12}$. Preferably, $R^3$ is selected from the group $CO_2R^7$, $COR^{12}$ and $SO_2R^{15}$ Most preferably $R^3$ is $SO_2R^{15}$ and $R^{15}$ is lower alkyl or $NR^5R^6$. Preferred $R^4$ groups include H, $OR^{11}$ and lower alkyl. Preferred $R^5$ and $R^6$ groups are those wherein the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms and said ring atoms optionally being substituted by OH, oxo and $NH_2$, lower alkyl or lower alkyl substituted by $OR^{12}$.

Examples of compounds of formula I(a) include:

4-[4-Amino-5-(2-methoxy-benzoyl)-pyrimidin-2-ylamino]-piperidine-1-carboxylic acid ethyl ester (Example 9), 4-[4-Amino-5-(2,6-difluoro-benzoyl)-pyrimidin-2-ylamino]-piperidine-1-carboxylic acid ethyl ester (Example 16), 4-[4-Amino-5-(5-fluoro-2-methoxy-benzoyl)-pyrimidin-2-ylamino]-piperidine-1-carboxylic acid ethyl ester (Example 51), 1-[4-[4-Amino-5-(2-methoxy-benzoyl)-pyrimidin-2-ylamino]-piperidin-1-yl]-ethanone (Example 20), 1-[4-[4-Amino-5-(2-methoxy-benzoyl)-pyrimidin-2-ylamino]-piperidin-1-yl]-propan-1-one (Example 21), 1-[4-[4-Amino-5-(2-methoxy-benzoyl)-pyrimidin-2-ylamino]-piperidin-1-yl]-butan-1-one (Example 22), 1-[4-[4-Amino-5-(2-methoxy-benzoyl)-pyrimidin-2-ylamino]-piperidin-1-yl]-3-methyl-butan-1-one (Example 23), 1-[4-[4-Amino-5-(2-methoxy-benzoyl)-pyrimidin-2-ylamino]-piperidin-1-yl]-3-diethylamino-propan-1-one (Example 24), 4-[4-Amino-5-(2-methyl-benzoyl)-pyrimidin-2-ylamino]-piperidine-1-carboxylic acid ethyl ester (Example 35), 4-[4-Amino-5-(2-methoxy-benzoyl)-pyrimidin-2-ylamino]-piperidine-1-carboxylic acid methyl ester (Example 17), 4-[4-Amino-5-(2-methoxy-benzoyl)-pyrimidin-2-ylamino]-piperidine-1-carboxylic acid propyl ester (Example 18), 4-[4-Amino-5-(2-methoxy-benzoyl)-pyrimidin-2-ylamino]-piperidine-1-carboxylic acid iso-butyl ester (Example 19), 4-[4-Amino-5-(2-methoxy-benzoyl)-pyrimidin-2-ylamino]-piperidine-1-carboxylic acid methylamide (Example 25), 4-[4-Amino-5-(2-methoxy-benzoyl)-pyrimidin-2-ylamino]-piperidine-1-carboxylic acid ethylamide (Example 26), 4-[4-Amino-5-(2-methoxy-benzoyl)-pyrimidin-2-ylamino]-piperidine-1-carboxylic acid propylamide (Example 27),

[4-Amino-2-(1-methanesulfonyl-piperidin-4-ylamino)-pyrimidin-5-yl]-(2-methoxy-phenyl)-methanone (Example 28),

[4-Amino-2-(1-ethanesulfonyl-piperidin-4-ylamino)-pyrimidin-5-yl]-(2-methoxy-phenyl)-methanone (Example 29),

[4-Amino-2-[1-(propane-1-sulfonyl)-piperidin-4-ylamino]-pyrimidin-5-yl]-(2-methoxy-phenyl)-methanone (Example 30), 1-[4-[4-Amino-5-(5-fluoro-2-methoxy-benzoyl)-pyrimidin-2-ylamino]-piperidin-1-yl]-ethanone (Example 62), 4-[4-Amino-5-(5-fluoro-2-methoxy-benzoyl)-pyrimidin-2-ylamino]-piperidine-1-carboxylic acid methyl ester (Example 60) 4-[4-Amino-5-(5-fluoro-2-methoxy-benzoyl)-pyrimidin-2-ylamino]-piperidine-1-carboxylic acid propyl ester (Example 61), 1-[4-[4-Amino-5-(5-fluoro-2-methoxy-benzoyl)-pyrimidin-2-ylamino]-piperidin-1-yl]-propan-1-one (Example 63), 1-[4-[4-Amino-5-(5-fluoro-2-methoxy-benzoyl)-pyrimidin-2-ylamino]-piperidin-1-yl]-butan-1-one (Example 64), 4-[4-Amino-5-(2-methoxy-benzoyl)-pyrimidin-2-ylamino]-piperidine-1-carboxylic acid dimethylamide (Example 57),

[4-Amino-2-(1-methanesulfonyl-piperidin-4-ylamino)-pyrimidin-5-yl]-(5-fluoro-2-methoxy-phenyl)-methanone (Example 65),

[4-Amino-2-(1-ethanesulfonyl-piperidin-4-ylamino)-pyrimidin-5-yl]-(5-fluoro-2-methoxy-phenyl)-methanone (Example 66),

[4-Amino-2-[1-(propane-1-sulfonyl)-piperidin-4-ylamino]-pyrimidin-5-yl]-(5-fluoro-2-methoxy-phenyl)-methanone (Example 67),

[4-Amino-2-(1-methanesulfonyl-piperidin-4-ylamino)-pyrimidin-5-yl]-(2-fluoro-phenyl)-methanone (Example 41),

[4-Amino-2-(1-ethanesulfonyl-piperidin-4-ylamino)-pyrimidin-5-yl]-(2-fluoro-phenyl)-methanone (Example 42), 4-[4-Amino-5-(2-fluoro-benzoyl)-pyrimidin-2-ylamino]-piperidine-1-carboxylic acid ethyl ester (Example 40),

[4-Amino-2-(1-trifluoromethanesulfonyl-piperidin-4-ylamino)-pyrimidin-5-yl]-(5-fluoro-2-methoxy-phenyl)-methanone (Example 68), 4-[4-Amino-5-(5-fluoro-2-methoxy-benzoyl)-pyrimidin-2-ylamino]-piperidine-1-sulfonic acid dimethylamide (Example 160),
1-[4-[4-Amino-5-(5-fluoro-2-methoxy-benzoyl)-pyrimidin-2-ylamino]-piperidin-1-yl]-2-dimethylamino-ethanone (Example 81), 1-[4-[4-Amino-5-(5-fluoro-2-methoxy-benzoyl)-pyrimidin-2-ylamino]-piperidin-1-yl]-2-diethylamino-ethanone (Example 82),
1-[4-[4-Amino-5-(5-fluoro-2-methoxy-benzoyl)-pyrimidin-2-ylamino]-piperidin-1-yl]-2-morpholin-4-yl-ethanone (Example 83),
1-[4-[4-Amino-5-(5-fluoro-2-methoxy-benzoyl)-pyrimidin-2-ylamino]-piperidin-1-yl]-3-dimethylamino-propan-1-one (Example 84),
1-[4-[4-Amino-5-(5-fluoro-2-methoxy-benzoyl)-pyrimidin-2-ylamino]-piperidin-1-yl]-3-diethylamino-propan-1-one (Example 85),
1-[4-[4-Amino-5-(5-fluoro-2-methoxy-benzoyl)-pyrimidin-2-ylamino]-piperidin-yl]-3-piperidin-1-yl-propan-1-one (Example 86),
1-[4-[4-Amino-5-(5-fluoro-2-methoxy-benzoyl)-pyrimidin-2-ylamino]-piperidin-1-yl]-3-morpholin-4-yl-propan-1-one (Example 87),
[4-Amino-2-[1-(3,5-dimethyl-isoxazole-4-sulfonyl)-piperidin-4-ylamino]-pyrimidin-5-yl]-(5-fluoro-2-methoxy-phenyl)-methanone (Example 161),
[4-[4-Amino-5-(5-fluoro-2-methoxy-benzoyl)-pyrimidin-2-ylamino]-piperidin-1-yl]-acetic acid methyl ester (Example 159),
1-[4-[4-Amino-5-(2,6-difluoro-3-methoxy-benzoyl)-pyrimidin-2-ylamino]-piperidin-1-yl]-ethanone (Example 90),
[4-Amino-2-(1-methanesulfonyl-piperidin-4-ylamino)-pyrimidin-5-yl]-(2,6-difluoro-3-methoxy-phenyl)-methanone (Example 91),
4-[4-Amino-5-(2,6-difluoro-3-methoxy-benzoyl)-pyrimidin-2-ylamino]-piperidine-1-carboxylic acid methyl ester (Example 94),
1-[4-[4-Amino-5-(2-ethoxy-benzoyl)-pyrimidin-2-ylamino]-piperidin-1-yl]-ethanone (Example 97),
[4-Amino-2-[1-(thiophene-3-sulfonyl)-piperidin-4-ylamino]-pyrimidin-5-yl]-(5-fluoro-2-methoxy-phenyl)-methanone (Example 153),
[4-Amino-2-[1-(benzo[b]thiophene-3-sulfonyl)-piperidin-4-ylamino]-pyrimidin-5-yl]-(5-fluoro-2-methoxy-phenyl)-methanone (Example 154),
[4-Amino-2-[1-(1,3,5-trimethyl-1H-pyrazole-4-sulfonyl)-piperidin-4-ylamino]-pyrimidin-5-yl]-(5-fluoro-2-methoxy-phenyl)-methanone (Example 155), 3-[4-[4-Amino-5-(5-fluoro-2-methoxy-benzoyl)-pyrimidin-2-ylamino]-piperidine-1-sulfonyl]-thiophene-2-carboxylic acid methyl ester (Example 156),
[4-Amino-2-[1-(2,5-dimethyl-thiophene-3-sulfonyl)-piperidin-4-ylamino]-pyrimidin-5-yl]-(5-fluoro-2-methoxy-phenyl)-methanone (Example 152),
4-[4-Amino-5-(5-fluoro-2-methoxy-benzoyl)-pyrimidin-2-ylamino]-piperidine-1-carboxylic acid cyclohexylamide (Example 145),
1-[4-[4-Amino-5-(2,3-difluoro-6-methoxy-benzoyl)-pyrimidin-2-ylamino]-piperidin-1-yl]-ethanone (Example 104),
[4-Amino-2-(1-methanesulfonyl-piperidin-4-ylamino)-pyrimidin-5-yl]-(2,3-difluoro-6-methoxy-phenyl)-methanone (Example 105),
[4-Amino-2-(piperidin-4-ylamino)-pyrimidin-5-yl]-(2-methoxy-phenyl)-methanone (Example 11),
[4-Amino-2-(piperidin-4-ylamino)-pyrimidin-5-yl]-(5-fluoro-2-methoxy-phenyl)-methanone (Example 59),
[4-Amino-2-(piperidin-4-ylamino)-pyrimidin-5-yl]-(2,3-difluoro-6-methoxy-phenyl)-methanone (Example 107),
1-[4-[4-Amino-5-(2,3,4-trifluoro-6-methoxy-benzoyl)-pyrimidin-2-ylamino]-piperidin-1-yl]-ethanone (Example 204),
[4-Amino-2-(1-methanesulfonyl-piperidin-4-ylamino)-pyrimidin-5-yl]-(3,4,5-trifluoro-2-methoxy-phenyl)-methanone (Example 206),
[4-Amino-2-(1-methanesulfonyl-piperidin-4-ylamino)-pyrimidin-5-yl]-(2,3,4-trifluoro-6-methoxy-phenyl)-methanone (Example 207),
[4-Amino-2-[1-(2-methanesulfonyl-ethyl)-piperidin-4-ylamino]-pyrimidin-5-yl]-(5-fluoro-2-methoxy-phenyl)-methanone (Example 209),
1-[4-[4-Amino-5-(5-fluoro-2-methyl-benzoyl)-pyrimidin-2-ylamino]-piperidin-1-yl]-ethanone (Example 211),
[4-Amino-2-(1-methanesulfonyl-piperidin-4-ylamino)-pyrimidin-5-yl]-(5-fluoro-2-methyl-phenyl)-methanone (Example 213),
[4-Amino-2-(1-methanesulfonyl-piperidin-4-ylamino)-pyrimidin-5-yl]-(5-fluoro-2-trifluoromethyl-phenyl)-methanone (Example 214), [4-Amino-2-(1-methanesulfonyl-piperidin-4-ylamino)-pyrimidin-5-yl]-(5-fluoro-2-isopropoxy-phenyl)-methanone (Example 215),
[4-Amino-2-(1-methanesulfonyl-piperidin-4-ylamino)-pyrimidin-5-yl]-(2-ethoxy-5-fluoro-phenyl)-methanone (Example 216),
[4-Amino-2-(1-methanesulfonyl-piperidin-4-ylamino)-pyrimidin-5-yl]-(2-ethyl-5-fluoro-phenyl)-methanone (Example 217),
[4-Amino-2-(1-methanesulfonyl-piperidin-4-ylamino)-pyrimidin-5-yl]-(2-methoxy-4-trifluoromethyl-phenyl)-methanone (Example 218),
4-[4-Amino-5-(2-fluoro-6-methoxy-benzoyl)-pyrimidin-2-ylamino]-piperidine-1-carboxylic acid tert-butyl ester (Example 222),
[4-Amino-2-(piperidin-4-ylamino)-pyrimidin-5-yl]-(2-fluoro-6-methoxy-phenyl)-methanone (Example 223),
[4-Amino-2-(1-methanesulfonyl-piperidin-4-ylamino)-pyrimidin-5-yl]-(2-fluoro-6-methoxy-phenyl)-methanone (Example 224),
1-[4-[4-Amino-5-(2-fluoro-6-methoxy-benzoyl)-pyrimidin-2-ylamino]-piperidin-1-yl]-2,2,2-trifluoro-ethanone (Example 225),
[4-Amino-2-[1-(3-chloro-propane-1-sulfonyl)-piperidin-4-ylamino]-pyrimidin-5-yl]-(2,3-difluoro-6-methoxy-phenyl)-methanone (Example 226),
(4-Amino-2-[1-[3-(2-hydroxy-1-methyl-ethylamino)-propane-1-sulfonyl]-piperidin-4-ylamino]-pyrimidin-5-yl)-(2,3-difluoro-6-methoxy-phenyl)-methanone (Example 227),
(4-Amino-2-[1-[3-(4-methyl-piperazin-1-yl)-propane-1-sulfonyl]-piperidin-4-ylamino]-pyrimidin-5-yl)-(2,3-difluoro-6-methoxy-phenyl)-methanone (Example 228),
(4-Amino-2-[1-[3-((R)-1-hydroxymethyl-propylamino)-propane-1-sulfonyl]-piperidin-4-ylamino]-pyrimidin-5-yl)-(2,3-difluoro-6-methoxy-phenyl)-methanone (Example 229),
[4-Amino-2-[1-(3-hydroxy-propane-1-sulfonyl)-piperidin-4-ylamino]-pyrimidin-5-yl]-(2,3-difluoro-6-methoxy-phenyl)-methanone (Example 230),

[4-Amino-2-[1-(3-pyrrolidin-1-yl-propane-1-sulfonyl)-piperidin-4-ylamino]-pyrimidin-5-yl]-(2,3-difluoro-6-methoxy-phenyl)-methanone (Example 231),

[4-Amino-2-[1-(3-morpholin-4-yl-propane-1-sulfonyl)-piperidin-4-ylamino]-pyrimidin-5-yl]-(2,3-difluoro-6-methoxy-phenyl)-methanone (Example 232),

[4-Amino-2-(1-[3-[4-(2-hydroxy-ethyl)-piperazin-1-yl]-propane-1-sulfonyl]-piperidin-4-ylamino)-pyrimidin-5-yl]-(2,3-difluoro-6-methoxy-phenyl)-methanone (Example 233),

[4-Amino-2-(1-[3-[(2-methoxy-ethyl)-methyl-amino]-propane-1-sulfonyl]-piperidin-4-ylamino)-pyrimidin-5-yl]-(2,3-difluoro-6-methoxy-phenyl)-methanone (Example 234), (4-Amino-2-[1-[3-(2-hydroxy-1,1-dimethyl-ethylamino)-propane-1-sulfonyl]-piperidin-4-ylamino]-pyrimidin-5-yl)-(2,3-difluoro-6-methoxy-phenyl)-methanone (Example 235), (4-Amino-2-[1-[3-(2-hydroxy-propylamino)-propane-1-sulfonyl]-piperidin-4-ylamino]-pyrimidin-5-yl)-(2,3-difluoro-6-methoxy-phenyl)-methanone (Example 236), (4-Amino-2-[1-[3-((S)-2-hydroxy-1-methyl-ethylamino)-propane-1-sulfonyl]-piperidin-4-ylamino]-pyrimidin-5-yl)-(2,3-difluoro-6-methoxy-phenyl)-methanone (Example 237), (4-Amino-2-[1-[3-((R)-1-hydroxymethyl-2-methyl-propylamino)-propane-1-sulfonyl]-piperidin-4-ylamino]-pyrimidin-5-yl)-(2,3-difluoro-6-methoxy-phenyl)-methanone (Example 238), (4-Amino-2-[1-[3-((R)-2-hydroxy-1-methyl-ethylamino)-propane-1-sulfonyl]-piperidin-4-ylamino]-pyrimidin-5-yl)-(2,3-difluoro-6-methoxy-phenyl)-methanone (Example 239), (4-Amino-2-[1-[3-((S)-1-hydroxymethyl-propylamino)-propane-1-sulfonyl]-piperidin-4-ylamino]-pyrimidin-5-yl)-(2,3-difluoro-6-methoxy-phenyl)-methanone (Example 240), (4-Amino-2-(1-[3-[3-hydroxy-1-(2-hydroxy-ethyl)-propylamino]-propane-1-sulfonyl]-piperidin-4-ylamino)-pyrimidin-5-yl)-(2,3-difluoro-6-methoxy-phenyl)-methanone (Example 241),

[4-Amino-2-[1-(3-chloro-propane-1-sulfonyl)-piperidin-4-ylamino]-pyrimidin-5-yl]-(5-fluoro-2-methoxy-phenyl)-methanone (Example 242),

[4-Amino-2-(1-[3-[(2-methoxy-ethyl)-methyl-amino]-propane-1-sulfonyl]-piperidin-4-ylamino)-pyrimidin-5-yl]-(5-fluoro-2-methoxy-phenyl)-methanone (Example 243),

[4-Amino-2-(1-[3-[4-(2-hydroxy-ethyl)-piperazin-1-yl]-propane-1-sulfonyl]-piperidin-4-ylamino)-pyrimidin-5-yl]-(5-fluoro-2-methoxy-phenyl)-methanone (Example 244), (4-Amino-2-[1-[3-((S)-2-hydroxy-1-methyl-ethylamino)-propane-1-sulfonyl]-piperidin-4-ylamino]-pyrimidin-5-yl)-(5-fluoro-2-methoxy-phenyl)-methanone (Example 245), (4-Amino-2-[1-[3-((R)-1-hydroxymethyl-propylamino)-propane-1-sulfonyl]-piperidin-4-ylamino]-pyrimidin-5-yl)-(5-fluoro-2-methoxy-phenyl)-methanone (Example 246), (4-Amino-2-[1-[3-(2-hydroxy-propylamino)-propane-1-sulfonyl]-piperidin-4-ylamino]-pyrimidin-5-yl)-(5-fluoro-2-methoxy-phenyl)-methanone (Example 247), (4-Amino-2-[1-[3-((R)-1-hydroxymethyl-2-methyl-propylamino)-propane-1-sulfonyl]-piperidin-4-ylamino]-pyrimidin-5-yl)-(5-fluoro-2-methoxy-phenyl)-methanone (Example 248), (4-Amino-2-[1-[3-(2-methoxy-1-methyl-ethylamino)-propane-1-sulfonyl]-piperidin-4-ylamino]-pyrimidin-5-yl)-(5-fluoro-2-methoxy-phenyl)-methanone (Example 249), (4-Amino-2-[1-[3-(2-hydroxy-1,1-dimethyl-ethylamino)-propane-1-sulfonyl]-piperidin-4-ylamino]-pyrimidin-5-yl)-(5-fluoro-2-methoxy-phenyl)-methanone (Example 250), (4-Amino-2-[1-[3-((R)-2-hydroxy-1-methyl-ethylamino)-propane-1-sulfonyl]-piperidin-4-ylamino]-pyrimidin-5-yl)-(5-fluoro-2-methoxy-phenyl)-methanone (Example 251), (4-Amino-2-[1-[3-((S)-1-hydroxymethyl-propylamino)-propane-1-sulfonyl]-piperidin-4-ylamino]-pyrimidin-5-yl)-(5-fluoro-2-methoxy-phenyl)-methanone (Example 252),

[4-Amino-2-[1-(4-hydroxy-butane-1-sulfonyl)-piperidin-4-ylamino]-pyrimidin-5-yl]-(5-fluoro-2-methoxy-phenyl)-methanone (Example 253),

[4-Amino-2-[1-(4-chloro-butane-1-sulfonyl)-piperidin-4-ylamino]-pyrimidin-5-yl]-(5-fluoro-2-methoxy-phenyl)-methanone (Example 255), (4-Amino-2-[1-[4-(4-methyl-piperazin-1-yl)-butane-1-sulfonyl]-piperidin-4-ylamino]-pyrimidin-5-yl)-(5-fluoro-2-methoxy-phenyl)-methanone (Example 256),

[4-Amino-2-[1-(4-pyrrolidin-1-yl-butane-1-sulfonyl)-piperidin-4-ylamino]-pyrimidin-5-yl]-(5-fluoro-2-methoxy-phenyl)-methanone (Example 257), (4-Amino-2-[1-[4-(2-hydroxy-propylamino)-butane-1-sulfonyl]-piperidin-4-ylamino]-pyrimidin-5-yl)-(5-fluoro-2-methoxy-phenyl)-methanone (Example 258),

[4-Amino-2-(1-methanesulfonyl-piperidin-4-ylamino)-pyrimidin-5-yl]-(2,3-difluoro-5,6-dimethoxy-phenyl)-methanone (Example 261),

[4-Amino-2-(1-methanesulfonyl-piperidin-4-ylamino)-pyrimidin-5-yl]-(2,3-difluoro-6-hydroxy-5-methoxy-phenyl)-methanone (Example 262),

[4-Amino-2-(1-methanesulfonyl-piperidin-4-ylamino)-pyrimidin-5-yl]-(2,3-difluoro-5,6-dihydroxy-phenyl)-methanone (Example 263),

[4-Amino-2-(1-methanesulfonyl-piperidin-4-ylamino)-pyrimidin-5-yl]-(2,3-difluoro-5-hydroxy-6-methoxy-phenyl)-methanone (Example 271),

[4-Amino-2-[1-(3-chloro-propane-1-sulfonyl)-piperidin-4-ylamino]-pyrimidin-5-yl]-(5-fluoro-2-methoxy-phenyl)-methanone (Example 272),

[4-Amino-2-[1-(3-pyrrolidin-1-yl-propane-1-sulfonyl)-piperidin-4-ylamino]-pyrimidin-5-yl]-(5-fluoro-2-methoxy-phenyl)-methanone (Example 273), Acetic acid 3-[4-[4-amino-5-(5-fluoro-2-methoxy-benzoyl)-pyrimidin-2-ylamino]-piperidine-1-sulfonyl]-propyl ester (Example 274),

[4-Amino-2-[1-(3-hydroxy-propane-1-sulfonyl)-piperidin-4-ylamino]-pyrimidin-5-yl]-(5-fluoro-2-methoxy-phenyl)-methanone (Example 275),

[4-Amino-2-[1-(3-morpholin-4-yl-propane-1-sulfonyl)-piperidin-4-ylamino]-pyrimidin-5-yl]-(5-fluoro-2-methoxy-phenyl)-methanone (Example 276), N-(3-[4-[4-Amino-5-(5-fluoro-2-methoxy-benzoyl)-pyrimidin-2-ylamino]-piperidine-1-sulfonyl]-propyl)-methanesulfonamide (Example 277), (4-Amino-2-[1-[3-(4-methyl-piperazin-1-yl)-propane-1-sulfonyl]-piperidin-4-ylamino]-pyrimidin-5-yl)-(5-fluoro-2-methoxy-phenyl)-methanone (Example 278),
[4-Amino-2-(1-methanesulfonyl-piperidin-4-ylamino)-pyrimidin-5-yl]-(2,3-difluoro-6-hydroxy-phenyl)-methanone (Example 279),
[4-Amino-2-(1-methanesulfonyl-piperidin-4-ylamino)-pyrimidin-5-yl]-phenyl-methanone (Example 283),
4-[4-Amino-5-(2,3-difluoro-6-methoxy-benzoyl)-pyrimidin-2-ylamino]-piperidine-1-carbaldehyde (Example 284),
4-[4-Amino-5-(2,3-difluoro-6-methoxy-benzoyl)-pyrimidin-2-ylamino]-piperidine-1-sulfonic acid amide (Example 285),
4-[4-Amino-5-(2,3-difluoro-6-methoxy-benzoyl)-pyrimidin-2-ylamino]-piperidine-1-sulfonic acid acetyl-amide (Example 286),
rac-[4-Amino-2-(3-hydroxy-1-methanesulfonyl-piperidin-4-ylamino)-pyrimidin-5-yl]-(2,3-difluoro-6-methoxy-phenyl)-methanone (Example 306),
rac-[4-Amino-2-(3-hydroxy-1-methanesulfonyl-piperidin-4-ylamino)-pyrimidin-5-yl]-(2,3-difluoro-6-methoxy-phenyl)-methanone (Example 310),
rac-[4-Amino-2-(1-methanesulfonyl-3-methoxy-piperidin-4-ylamino)-pyrimidin-5-yl]-(2,3-difluoro-6-methoxy-phenyl)-methanone (Example 313),
rac-4-[4-Amino-5-(2,3-difluoro-6-methoxy-benzoyl)-pyrimidin-2-ylamino]-1-methanesulfonyl-piperidin-3-one (Example 314),
1-[4-[4-Amino-5-(2-methoxy-5-methyl-benzoyl)-pyrimidin-2-ylamino]-piperidin-1-yl]-ethanone (Example 326),
[4-Amino-2-(1-methanesulfonyl-piperidin-4-ylamino)-pyrimidin-5-yl]-(2-methoxy-5-methyl-phenyl)-methanone (Example 327),
(4-Amino-2-ethylsulfanyl-pyrimidin-5-yl)-(2,5-dimethoxy-phenyl)-methanone (Example 328),
1-[4-[4-Amino-5-(2,5-dimethoxy-benzoyl)-pyrimidin-2-ylamino]-piperidin-1-yl]-ethanone (Example 330),
[4-Amino-2-(1-methanesulfonyl-piperidin-4-ylamino)-pyrimidin-5-yl]-(2,5-dimethoxy-phenyl)-methanone (Example 331),
1-[4-[4-Amino-5-(2,6-dimethoxy-benzoyl)-pyrimidin-2-ylamino]-piperidin-1-yl]-ethanone (Example 334),
[4-Amino-2-(1-methanesulfonyl-piperidin-4-ylamino)-pyrimidin-5-yl]-(2,6-dimethoxy-phenyl)-methanone (Example 335),
1-[4-[4-Amino-5-(5-fluoro-2-methoxy-4-methyl-benzoyl)-pyrimidin-2-ylamino]-piperidin-1-yl]-ethanone (Example 342),
[4-Amino-2-(1-methanesulfonyl-piperidin-4-ylamino)-pyrimidin-5-yl]-(5-fluoro-2-methoxy-4-methyl-phenyl)-methanone (Example 343),
[4-Amino-2-(1-methanesulfonyl-piperidin-4-ylamino)-pyrimidin-5-yl]-(3-fluoro-2,6-dimethoxy-phenyl)-methanone (Example 348),
[4-Amino-2-(1-methanesulfonyl-piperidin-4-ylamino)-pyrimidin-5-yl]-(2-ethoxy-3-fluoro-6-methoxy-phenyl)-methanone (Example 349),
1-[4-[4-Amino-5-(3-fluoro-6-methoxy-2-methyl-benzoyl)-pyrimidin-2-ylamino]-piperidin-1-yl]-ethanone (Example 351),
[4-Amino-2-(1-methanesulfonyl-piperidin-4-ylamino)-pyrimidin-5-yl]-(3-fluoro-6-methoxy-2-methyl-phenyl)-methanone (Example 352),
1-[4-[4-Amino-5-(4-methyl-benzoyl)-pyrimidin-2-ylamino]-piperidin-1-yl]-ethanone (Example 355),
[4-Amino-2-(1-methanesulfonyl-piperidin-4-ylamino)-pyrimidin-5-yl]-p-tolyl-methanone (Example 356),
1-[4-[4-Amino-5-(4-methoxy]-benzoyl)-pyrimidin-2-ylamino]-piperidin-1-yl]-ethanone (Example 359),
[4-Amino-2-(1-methanesulfonyl-piperidin-4-ylamino)-pyrimidin-5-yl]-(4-methoxy-phenyl)-methanone (Example 360),
1-[4-[4-Amino-5-(4-chloro-benzoyl)-pyrimidin-2-ylamino]-piperidin-1-yl]-ethanone (Example 363),
[4-amino-2-(1-methanesulfonyl-piperidin-4-ylamino)-pyrimidin-5-yl]-(4-chloro-phenyl)-methanone (Example 364),
1-[4-[4-Amino-5-(4-fluoro-benzoyl)-pyrimidin-2-ylamino]-piperidin-1-yl]-ethanone (Example 367),
[4-Amino-2-(1-methanesulfonyl-piperidin-4-ylamino)-pyrimidin-5-yl]-(4-fluoro-phenyl)-methanone (Example 368),
[4-Amino-2-(1-methanesulfonyl-piperidin-4-ylamino)-pyrimidin-5-yl]-(5-fluoro-2,4-dimethoxy-phenyl)-methanone (Example 369),
[4-Amino-2-(1-methanesulfonyl-piperidin-4-ylamino)-pyrimidin-5-yl]-(4-ethoxy-5-fluoro-2-methoxy-phenyl)-methanone (Example 370),
[4-Amino-2-(1-methanesulfonyl-piperidin-4-ylamino)-pyrimidin-5-yl]-(3-fluoro-4-methoxy-phenyl)-methanone (Example 373),
4-[4-Amino-5-(5-fluoro-2-methoxy-4-methyl-benzoyl)-pyrimidin-2-ylamino]-piperidine-1-carboxylic acid tert-butyl ester (Example 374),
[4-Amino-2-(1-methanesulfonyl-piperidin-4-ylamino)-pyrimidin-5-yl]-(4-chloro-5-fluoro-2-methoxy-phenyl)-methanone (Example 378),
[4-Amino-2-(1-methanesulfonyl-piperidin-4-ylamino)-pyrimidin-5-yl]-(3,5-difluoro-2-methoxy-phenyl)-methanone (Example 381),
[4-Amino-2-(1-methanesulfonyl-piperidin-4-ylamino)-pyrimidin-5-yl]-(2-fluoro-5-methoxy-4-methyl-phenyl)-methanone (Example 385), and
[4-Amino-2-(1-methanesulfonyl-piperidin-4-ylamino)-pyrimidin-5-yl]-(5-fluoro-2-methoxy-3-methyl-phenyl)-methanone (Example 388).

Another preferred embodiment of the invention relates to compounds of formula

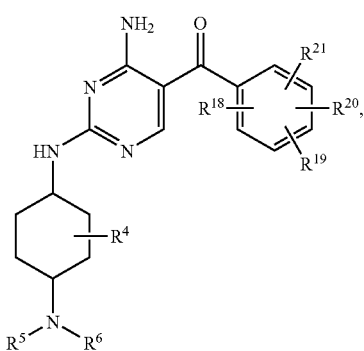

I(e)

wherein $R^4$, $R^5$, $R^6$, $R^{18}$, $R^{19}$, $R^{20}$ and $R^{21}$ are as defined above.

Examples of such compounds include:

Trans-[4-[4-amino-5-(5-fluoro-2-methoxy-benzoyl)-pyrimidin-2-ylamino]-cyclohexyl]-carbamic acid tert-butyl ester (Example 113), Trans-[4-amino-2-(4-amino-cyclohexylamino)-pyrimidin-5-yl]-(5-fluoro-2-methoxy-phenyl)-methanone (Example 114), Trans-N-[4-[4-amino-5-(5-fluoro-2-methoxy-benzoyl)-pyrimidin-2-ylamino]-cyclohexyl]-acetamide (Example 119), N-[4-[4-Amino-5-(5-fluoro-2-methoxy-benzoyl-pyrimidin-2-ylamino]-cyclohexyl]-methanesulfonamide (Example 115), Ethanesulfonic acid [4-[4-amino-5-(5-fluoro-2-methoxy-benzoyl)-pyrimidin-2-ylamino]-cyclohexyl]-amide (Example 116),

[4-[4-Amino-5-(5-fluoro-2-methoxy-benzoyl)-pyrimidin-2-ylamino]-cyclohexyl]-carbamic acid ethyl ester (Example 117),

[4-[4-Amino-5-(5-fluoro-2-methoxy-benzoyl)-pyrimidin-2-ylamino]-cyclohexyl]-carbamic acid isopropyl ester (Example 149),

[4-[4-amino-5-(5-fluoro-2-methoxy-benzoyl)-pyrimidin-2-ylamino]-cyclohexyl]-carbamic acid 2-methoxyethyl ester (Example 118), Trans-N-[4-[4-Amino-5-(2,3-difluoro-6-methoxy-benzoyl)-pyrimidin-2-ylamino]-cyclohexyl]-acetamide (Example 121), Trans-N-[4-[4-amino-5-(2,3-difluoro-6-methoxy-benzoyl)-pyrimidin-2-ylamino]-cyclohexyl]-methanesulfonamide (Example 124), Trans-[4-Amino-2-[4-(2-hydroxy-ethylamino)-cyclohexylamino]-pyrimidin-5-yl]-(2,3-difluoro-6-methoxy-phenyl)-methanone (Example 290), Trans-(4-Amino-2-[4-[bis-(2-hydroxy-ethyl)-amino]-cyclohexylamino]-pyrimidin-5-yl)-(2,3-difluoro-6-methoxy-phenyl)-methanone (Example 291), Trans-N-[4-[4-Amino-5-(2,3-difluoro-6-methoxy-benzoyl)-pyrimidin-2-ylamino]-cyclohexyl]-succinamic acid (Example 292), Trans-3-Chloro-propane-1-sulfonic acid [4-[4-amino-5-(2,3-difluoro-6-methoxy-benzoyl)-pyrimidin-2-ylamino]-cyclohexyl]-amide (Example 293), Trans-3-Morpholin-4-yl-propane-1-sulfonic acid [4-[4-amino-5-(2,3-difluoro-6-methoxy-benzoyl)-pyrimidin-2-ylamino]-cyclohexyl]-amide (Example 294), Trans-3-(4-Methyl-piperazin-1-yl)-propane-1-sulfonic acid [4-[4-amino-5-(2,3-difluoro-6-methoxy-benzoyl)-pyrimidin-2-ylamino]-cyclohexyl]-amide (Example 295), Trans-3-Pyrrolidin-1-yl-propane-1-sulfonic acid [4-[4-amino-5-(2,3-difluoro-6-methoxy-benzoyl)-pyrimidin-2-ylamino]-cyclohexyl]-amide (Example 296), Trans-3-Hydroxy-propane-1-sulfonic acid [4-[4-amino-5-(2,3-difluoro-6-methoxy-benzoyl)-pyrimidin-2-ylamino]-cyclohexyl]-amide (Example 297), Trans-[4-Amino-2-[4-(1,1-dioxo-1$\lambda^6$-isothiazolidin-2-yl)-cyclohexylamino]-pyrimidin-5-yl]-(2,3-difluoro-6-methoxy-phenyl)-methanone (Example 298), Trans-[4-Amino-2-[4-(4-methyl-piperazin-1-yl)-cyclohexylamino]-pyrimidin-5-yl]-(2,3-difluoro-6-methoxy-phenyl)-methanone (Example 299), Trans-[4-Amino-2-(4-pyrrolidin-1-yl-cyclohexylamino)-pyrimidin-5-yl]-(2,3-difluoro-6-methoxy-phenyl)-methanone (Example 300), Trans-[4-Amino-2-(4-dimethylamino-cyclohexylamino)-pyrimidin-5-yl]-(2,3-difluoro-6-methoxy-phenyl)-methanone (Example 301),

[4-[4-Amino-5-(2-methoxy-5-methyl-benzoyl)-pyrimidin-2-ylamino]-cyclohexyl]-carbamic acid tert-butyl ester (Example 336),

[4-Amino-2-(4-amino-cyclohexylamino)-pyrimidin-5-yl]-(2-methoxy-5-methyl-phenyl)-methanone (Example 337), N-[4-[4-Amino-5-(2-methoxy-5-methyl-benzoyl)-pyrimidin-2-ylamino]-cyclohexyl]-acetamide (Example 338), N-[4-[4-Amino-5-(2-methoxy-5-methyl-benzoyl)-pyrimidin-2-ylamino]-cyclohexyl]-methanesulfonamide (Example 339),

[4-[4-Amino-5-(5-fluoro-2-methoxy-4-methyl-benzoyl)-pyrimidin-2-ylamino]-cyclohexyl]-carbamic acid tert-butyl ester (Example 344),

[4-Amino-2-(4-amino-cyclohexylamino)-pyrimidin-5-yl]-(5-fluoro-2-methoxy-4-methyl-phenyl)-methanone (Example 345), N-[4-[4-Amino-5-(5-fluoro-2-methoxy-4-methyl-benzoyl)-pyrimidin-2-ylamino]-cyclohexyl]-acetamide (Example 346), and N-[4-[4-Amino-5-(5-fluoro-2-methoxy-4-methyl-benzoyl)-pyrimidin-2-ylamino]-cyclohexyl]-methanesulfonamide (Example 347).

Preferred $R^5$ and $R^6$ groups are independently selected from H, $COR^{12}$ and $SO_2R^{15}$.

Another preferred embodiment of the invention relates to compounds of formula

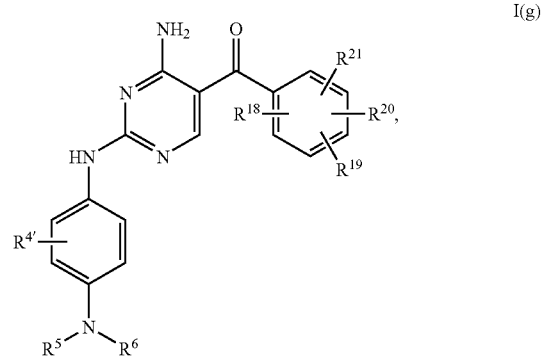

I(g)

wherein $R^{4'}$, $R^5$, $R^6$, $R^{18}$, $R^{19}$, $R^{20}$ and $R^{21}$ are as defined above. Examples of such compounds include:

[4-Amino-2-[4-(4-methyl-piperazin-1-yl)-phenylamino]-pyrimidin-5-yl]-(3-fluoro-phenyl)-methanone (Example 4),

[4-Amino-2-[4-(4-methyl-piperazin-1-yl)-phenylamino]-pyrimidin-5-yl]-(2-methoxyphenyl)-methanone (Example 7),

[4-Amino-2-[4-(4-methyl-piperazin-1-yl)-phenylamino]-pyrimidin-5-yl]-(2,6-difluoro-phenyl)-methanone (Example 14),

[4-Amino-2-[4-(4-isopropyl-piperazin-1-yl)-phenylamino]-pyrimidin-5-yl]-(2-methoxy-phenyl)-methanone (Example 8),

[4-Amino-2-[4-(4-isopropyl-piperazin-1-yl)-phenylamino]-pyrimidin-5-yl]-(2,6-difluoro-phenyl)-methanone (Example 15),

[4-Amino-2-[4-(4-methyl-piperazin-1-yl)-phenylamino]-pyrimidin-5-yl]-(5-fluoro-2-methoxy-phenyl)-methanone (Example 49),
[4-Amino-2-[4-(4-isopropyl-piperazin-1-yl)-phenylamino]-pyrimidin-5-yl]-(5-fluoro-2-methoxy-phenyl)-methanone (Example 50),
[4-Amino-2-[4-(4-methyl-piperazin-1-yl)-phenylamino]-pyrimidin-5-yl]-o-tolyl-methanone (Example 33),
[4-Amino-2-[4-(4-isopropyl-piperazin-1-yl)-phenylamino]-pyrimidin-5-yl]-o-tolyl-methanone (Example 34), and
4-[4-Amino-5-(5-fluoro-2-methoxy-benzoyl)-pyrimidin-2-ylamino]-piperidine-1-carboxylic acid (4-dimethylamino-phenyl)-amide (Example 144).

Preferred $R^{4'}$ groups include H, $OR^{11}$ and lower alkyl. Preferred $R^5$ and $R^6$ groups are those wherein the group $—NR^5R^6$ forms a ring having 3 to 7 ring atoms, said ring optionally including one or more additional N or O ring atoms and optionally being substituted by, OH, oxo, $NH_2$, lower alkyl or lower alkyl substituted by $OR^{12}$.

The following compounds are also preferred embodiments according to the instant invention:

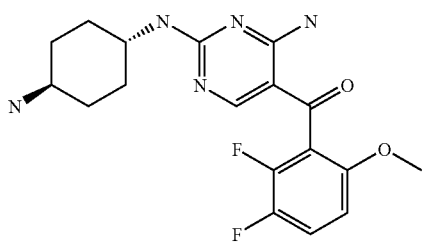

[4-Amino-2-(4-amino-cyclohexylamino)-pyrimidin-5-yl]-(2,3-difluoro-6-methoxy-phenyl)-methanone

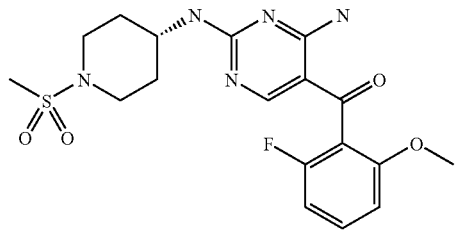

[4-Amino-2-(1-methanesulfonyl-piperidin-4-ylamino)-pyrimidin-5-yl]-(2-fluoro-6-methoxy-phenyl)-methanone The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

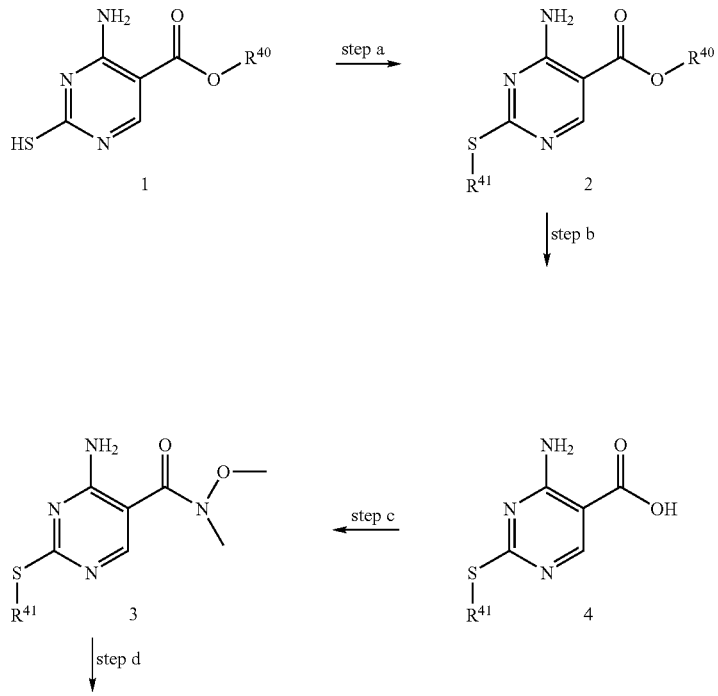

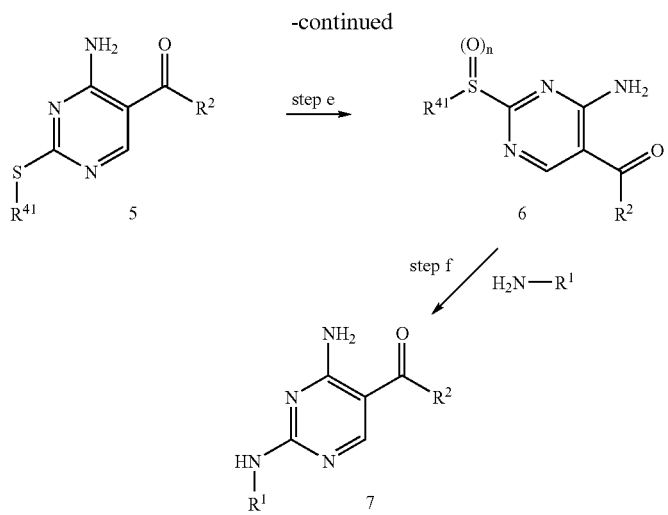

R40 = methyl, ethyl rather small alkyl or hydrolyzable group
R41 = methyl, ethyl rather small alkyl or aryl that can alkylate the sulfur
R2 = As previously defined.
R1 = As previously defined
n = 1 or 2

Separating a Mixture of Stereoisomers Into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87–124).

Converting a Compound of Formula I That Bears a Basic Nitrogen Into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Converting a Compound of Formula I That Bears a Carboxylic Acid Group Into a Pharmaceutically Acceptable Alkali Metal Salt The optional conversion of a compound of formula I that bears a carboxylic acid group into a pharmaceutically acceptable alkali metal salt can be effected by conventional means. For example, the compound can be treated with an inorganic base such as lithium hydroxide, sodium hydroxide, potassium hydroxide, or the like.

Converting a Compound of Formula I That Bears a Carboxylic Acid Group Into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0–10 mole %) of N,N-dimethylaminopyridine, in an inert solvent such as a halogenated hydrocarbon (e.g., dichloromethane) at a temperature between about 0 degrees and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0 degrees and about room temperature, preferably at about 0 degrees.

Compositions/Formulations

In an alternative embodiment, the present invention includes pharmaceutical compositions comprising at least one compound of formula I, or a pharmaceutically acceptable salt or ester thereof and an a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Combinations

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase 11 inhibitors such as etoposide: topoisomerase I inhibitors such as CPT-11 or topotecan; tublin interacting agents, such as paclitaxel, docetaxel or epothilones; hormonal agents such as tamoxifen: thymidilaate synthaes inhibitors, such as 5-fluorouracil; and antimetabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. For example, an early cdk1 inhibitor olomucine has been found to act synergistically with well known cytotoxic agents in inducing apoptosis. (*J. Cell Sci.,* 1995, 108, 2897–2904). Compounds of formula I may also be administered sequentially with known anticancer or cytoxic agents when concomitant administration or a combination is inappropriate. This invention is not limited in the sequence of administration: compounds of formula I may be administered either prior to or after administration of the known anticancer or cytotoxic agent. For example, the cytotoxic activity of the cdk inhibitor flavopiridol is affected by the sequence of administration with anticancer agents. (*Cancer Research,* 1997, 57, 3375).

Starting Materials

In another embodiment, the present invention also relates to novel intermediates useful in the preparation of compounds of formula I. These novel intermediates include the following compounds:

4-amino-2-methylsulfanyl-pyrimidine-5-carboxylic acid methoxy-methyl-amide,

4-Amino-2-ethylsulfanyl-pyrimidine-5-carboxylic acid methoxy-methyl-amide, (4-amino-2-ethylsulfanylpyrimidin-5-yl)-(2-methoxyphenyl)-methanone, (4-Amino-2-ethylsulfanyl-pyrimidin-5-yl)-(5-fluoro-2-methoxy-phenyl)-methanone,
(4-Amino-2-ethanesulfinyl-pyrimidin-5-yl)-(5-fluoro-2-methoxy-phenyl)-methanone,
(4-Amino-2-ethanesulfonyl-pyrimidin-5-yl)-(5-fluoro-2-methoxy-phenyl)-methanone,
(4-Amino-2-ethylsulfanyl-pyrimidin-5-yl)-(2,3-difluoro-6-methoxy-phenyl)-methanone,
Trans-ethanesulfonic acid (4-aminocyclohexyl)-amide, HCl Salt,
4-[4-Amino-5-(2-methoxy-benzoyl)-pyrimidin-2-ylamino]-piperidine-1-carboxylic acid tert-butyl ester,
4-[4-Amino-5-(5-fluoro-2-methoxy-benzoyl)-pyrimidin-2-ylamino]-piperidine-1-carboxylic acid tert-butyl ester,
4-[4-Amino-5-(2,3-difluoro-6-methoxy-benzoyl)-pyrimidin-2-ylamino]-piperidine-1-carboxylic acid tert-butyl ester,
(4-Amino-2-ethylsulfanyl-pyrimidin-5-yl)-(2,3,4-trifluoro-6-methoxy-phenyl)-methanone (Example 184),
(4-Amino-2-ethylsulfanyl-pyrimidin-5-yl)-(3-methoxy-pyridin-2-yl)-methanone (Example 185),
(4-Amino-2-ethylsulfanyl-pyrimidin-5-yl)-(3,4,5-trifluoro-2-methoxy-phenyl)-methanone (Example 186),
(4-Amino-2-ethylsulfanyl-pyrimidin-5-yl)-(3-methyl-thiophen-2-yl)-methanone (Example 187),
(4-Amino-2-ethylsulfanyl-pyrimidin-5-yl)-(5-fluoro-2-methyl-phenyl)-methanone (Example 188),
(4-Amino-2-ethylsulfanyl-pyrimidin-5-yl)-(5-fluoro-2-trifluoromethyl-phenyl)-methanone (Example 189),
(4-Amino-2-ethylsulfanyl-pyrimidin-5-yl)-(5-fluoro-2-isopropoxy-phenyl)-methanone (Example 190),
(4-Amino-2-methylsulfanyl-pyrimidin-5-yl)-(2-ethoxy-5-fluoro-phenyl)-methanone (Example 191),
(4-Amino-2-methylsulfanyl-pyrimidin-5-yl)-(2-ethyl-5-fluoro-phenyl)-methanone (Example 192),
(4-Amino-2-methylsulfanyl-pyrimidin-5-yl)-(2-methoxy-4-trifluoromethyl-phenyl)-methanone (Example 193),
(4-Amino-2-ethanesulfinyl-pyrimidin-5-yl)-(2,3,4-trifluoro-6-methoxy-phenyl)-methanone (Example 194),
(4-Amino-2-ethylsulfinyl-pyrimidin-5-yl)-(3-methoxy-pyridin-2-yl)-methanone (Example 195),
(4-Amino-2-ethylsulfinyl-pyrimidin-5-yl)-(3,4,5-trifluoro-2-methoxy-phenyl)-methanone (Example 196),
(4-Amino-2-ethylsulfinyl-pyrimidin-5-yl)-(3-methyl-thiophen-2-yl)-methanone (Example 197),
(4-Amino-2-ethylsulfinyl-pyrimidin-5-yl)-(5-fluoro-2-methyl-phenyl)-methanone (Example 198),
(4-Amino-2-ethylsulfinyl-pyrimidin-5-yl)-(5-fluoro-2-trifluoromethyl-phenyl)-methanone (Example 199),
(4-Amino-2-ethylsulfinyl-pyrimidin-5-yl)-(5-fluoro-2-isopropoxy-phenyl)-methanone (Example 200),
(4-Amino-2-methylsulfinyl-pyrimidin-5-yl)-(2-ethoxy-5-fluoro-phenyl)-methanone (Example 201),
(4-Amino-2-methylsulfinyl-pyrimidin-5-yl)-(2-ethyl-5-fluoro-phenyl)-methanone (Example 202),
(4-Amino-2-methylsulfinyl-pyrimidin-5-yl)-(2-methoxy-4-trifluoromethyl-phenyl)-methanone (Example 203),
(4-Amino-2-ethylsulfanyl-pyrimidin-5-yl)-thiophen-2-yl-methanone (Example 219),
(4-Amino-2-ethylsulfinyl-pyrimidin-5-yl)-thiophen-2-yl-methanone (Example 220),
(4-Amino-2-methylsulfanyl-pyrimidin-5-yl)-(2,3-difluoro-5,6-dimethoxy-phenyl)-methanone (Example 259),
(4-Amino-2-methylsulfinyl-pyrimidin-5-yl)-(2,3-difluoro-5,6-dimethoxy-phenyl)-methanone (Example 260),
tert-Butyl-(4,5-difluoro-2-methoxy-phenoxy)-dimethyl-silane(Example 265),
3-(tert-Butyl-dimethyl-silanyloxy)-5,6-difluoro-2-methoxy-benzaldehyde (Example 266),
[3-(tert-Butyl-dimethyl-silanyloxy)-5,6-difluoro-2-methoxy-phenyl]-(2,4-dichloro-pyrimidin-5-yl)-methanol (Example 267),
[3-(tert-Butyl-dimethyl-silanyloxy)-5,6-difluoro-2-methoxy-phenyl]-(2,4-dichloro-pyrimidin-5-yl)-methanone (Example 268),
(4-Amino-2-chloro-pyrimidin-5-yl)-[3-(tert-butyl-dimethyl-silanyloxy)-5,6-difluoro-2-methoxy-phenyl]-methanone (Example 269),
[4-Amino-2-(1-methanesulfonyl-piperidin-4-ylamino)-pyrimidin-5-yl]-[3-(tert-butyl-dimethyl-silanyloxy)-5,6-difluoro-2-methoxy-phenyl]-methanone (Example 270),
4-amino-2-methylsulfanyl-pyrimidin-5-yl)-phenyl-methanone (Example 281),
(4-Amino-2-methanesulfinyl-pyrimidin-5-yl)-phenyl-methanone (Example 282),
rac-(2,4-Dichloro-pyrimidin-5-yl)-(2,3-difluoro-6-methoxy-phenyl)-methanol (Example 287),
(2,4-Dichloro-pyrimidin-5-yl)-(2,3-difluoro-6-methoxy-phenyl)-methanone (Example 288),
(4-Amino-2-chloro-pyrimidin-5-yl)-(2,3-difluoro-6-methoxy-phenyl)-methanone (Example 289),
rac-4-Azido-1-methanesulfonyl-piperidin-3-ol (Example 304),
rac-4-Amino-1-methanesulfonyl-piperidin-3-ol (Example 305),
rac-4-Azido-1-methanesulfonyl-piperidin-3-ol (Example 308),
rac-4-Amino-1-methanesulfonyl-piperidin-3-ol (Example 309),
rac-4-Azido-1-methanesulfonyl-3-methoxy-piperidine (Example 311),
rac-1-Methanesulfonyl-3-methoxy-piperidin-4-ylamine (Example 312),
3-Azido-azetidine-1-carboxylic acid tert-butyl ester (Example 317),
3-Amino-azetidine-1-carboxylic acid tert-butyl ester (Example 318),
(4-Amino-2-ethylsulfanyl-pyrimidin-5-yl)-(2-methoxy-5-methyl-phenyl)-methanone (Example 324),
(4-Amino-2-ethanesulfinyl-pyrimidin-5-yl)-(2-methoxy-5-methyl-phenyl)-methanone (Example 325),
(4-Amino-2-ethylsulfanyl-pyrimidin-5-yl)-(2,5-dimethoxy-phenyl)-methanone (Example 328),
(4-Amino-2-ethanesulfinyl-pyrimidin-5-yl)-(2,5-Dimethoxyphenyl)-methanone (Example 329),
(4-Amino-2-ethylsulfanyl-pyrimidin-5-yl)-(2,6-dimethoxy-phenyl)-methanone (Example 332),
(4-Amino-2-ethanesulfinyl-pyrimidin-5-yl)-(2,5-Dimethoxyphenyl)-methanone (Example 333),
(4-Amino-2-ethylsulfanyl-pyrimidin-5-yl)-(5-fluoro-2-methoxy-4-methyl-phenyl)-methanone and
(4-Amino-2-ethylsulfanyl-pyrimidin-5-yl)-(3-fluoro-6-methoxy-2-methyl-phenyl)-methanone (Example 340), (4-Amino-2-ethanesulfinyl-pyrimidin-5-yl)-(5-fluoro-2-methoxy-4-methyl-phenyl)-methanone (Example 341), (4-Amino-2-ethanesulfinyl-pyrimidin-5-yl)-(3-fluoro-6-methoxy-2-methyl-phenyl)-methanone (Example 350), (4-Amino-2-ethylsulfanyl-pyrimidin-5-yl)-p-tolyl-methanone (Example 353), (4-Amino-2-ethanesulfinyl-pyrimidin-5-yl)-p-tolyl-methanone (Example 354), (4-Amino-2-ethylsulfanyl-pyrimidin-5-yl)-4-methoxy-phenyl-methanone (Example 357), (4-Amino-2-ethanesulfinyl-pyrimidin-5-yl)-(4-methoxy-phenyl)-methanone (Example 358), (4-Amino-2-ethylsulfanyl-pyrimidin-5-yl)-(4-chloro-phenyl)-methanone (Example 361), (4-Amino-2-ethanesulfinyl-pyrimidin-5-yl)-(4-chloro-phenyl)-methanone (Example 362), (4-Amino-2-ethylsulfanyl-pyrimidin-5-yl)-(4-fluoro-phenyl)-methanone (Example 365), (4-Amino-2-ethanesulfinyl-pyrimidin-5-yl)-(4-fluoro-phenyl)-methanone (Example 366), (4-Amino-2-ethylsulfanyl-pyrimidin-5-yl)-(3-fluoro-4-methoxy-phenyl)-methanone (Example 371), (4-Amino-2-ethanesulfonyl-pyrimidin-5-yl)-(5-fluoro-4-methoxy-phenyl)-methanone (Example 372), 5-Chloro-4-fluoro-2-iodoanisole (Example 375), (4-Amino-2-ethylsulfanyl-pyrimidin-5-yl)-(4-chloro-5-fluoro-2-methoxy-phenyl)-methanone (Example 376), (4-Amino-2-ethanesulfinyl-pyrimidin-5-yl)-(4-chloro-5-fluoro-2-methoxy-phenyl)-methanone (Example 377), (4-Amino-2-ethylsulfanyl-pyrimidin-5-yl)-(3,5-difluoro-2-methoxy-phenyl)-methanone (Example 379), (4-Amino-2-ethanesulfinyl-pyrimidin-5-yl)-(3,5-difluoro-2-methoxy-phenyl)-methanone (Example 380), Fluoro-2-iodo-4-methoxy-5-methylbenzene (Example 382), Fluoro-3-iodo-4-methoxy-5-methylbenzene (Example 382), (4-Amino-2-ethylsulfanyl-pyrimidin-5-yl)-(2-fluoro-5-methoxy-4-methyl-phenyl)-methanone (Example 383), (4-Amino-2-ethanesulfinyl-pyrimidin-5-yl)-(2-fluoro-5-methoxy-4-methyl-phenyl)-methanone (Example 384), (4-Amino-2-ethylsulfanyl-pyrimidin-5-yl)-(5-fluoro-2-methoxy-3-methyl-phenyl)-methanone (Example 386), and (4-Amino-2-ethanesulfinyl-pyrimidin-5-yl)-(5-fluoro-2-methoxy-3-methyl-phenyl)-methanone (Example 387).

EXAMPLES

The following examples illustrate preferred methods for synthesizing and using the compounds and formulations of the present invention. These examples and preparations are illustrative and are not intended to be limiting. It should be understood that there may be other embodiments which fall within the spirit and scope of the invention as defined by the claims appended hereto.

Example 1

4-Amino-2-ethylsulfanyl-pyrimidine-5-carboxylic acid methoxy-methyl-amide

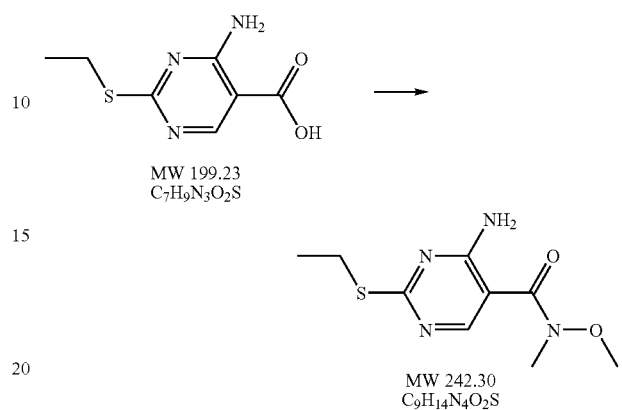

To a solution of 4-amino-2-ethylsulfanyl-pyrimidine-5-carboxylic acid (1.00 g, 5.40 mmol, Sigma) in dimethylformamide were added O-benzotriazol-1-yl-N,N,N',N'-tetramethyluronium hexafluorophosphate (3.06 g, 8.1 mmol, Aldrich), 1-hydroxy-benzotriazole hydrate (1.09 g, 8.1 mmol, Aldrich) followed by diisopropylethylamine (3.94 g, 29.7 mmol) at 0° C. After stirring for 10–15 minutes, N,O-dimethyl-hydroxylamine. HCl (790 mg, 8.1 mmol, Aldrich) was added. The reaction was stirred at 0° C. to room temperature for 2 hours and then diluted with ethyl acetate and water. The aqueous layer was separated and extracted with ethyl acetate. The combined organic extracts were washed with brine, dried and concentrated. The crude product was purified on silica gel with 1:1 hexane/ethyl acetate to give 4-amino-2-ethylsulfanyl-pyrimidine-5-carboxylic acid methoxy-methyl-amide as a white solid (1.189 g, 98% yield). HRMS, observed: 242.0836; Calcd for M+: 242.0837

Example 2

(4-Amino-2-ethylsulfanyl-pyrimidin-5-yl)-(3-fluorophenyl)-methanone

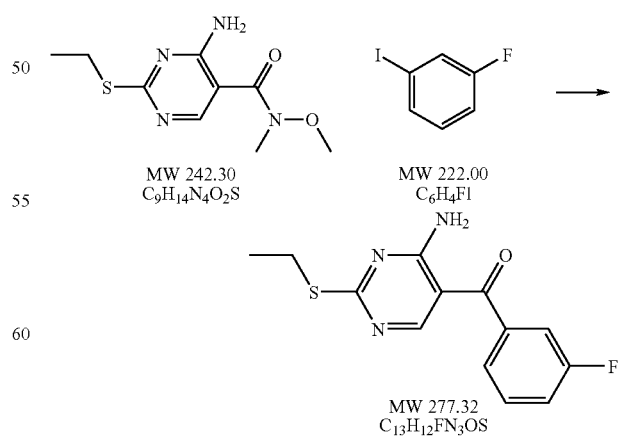

A) Preparation of Aryllithium

To a solution of 1-fluoro-3-iodobenzene (11.0 g, 4.975 mmol, Aldrich) in anhydrous tetrahydrofuran (8 mL) at −78°

C., was added slowly a solution of n-butyllithium in hexane (1.6 M, 3.42 mL, 5.47 mmol, Aldrich) over 20 minutes. The reaction was stirred at −78° C. for another 30 minutes to give a clear solution which was used in the next step.

B) 4-Amino-2-ethylsulfanylpyrimidine-5-carboxylic acid methoxymethylamide (200 mg, 0.8292 mmol, Example 1) was dissolved in anhydrous tetrahydrofuran (4 mL) and cooled to −78° C. A solution of freshly prepared 3-fluorophenyl lithium (~3 equiv, from Step A) was added and the orange colored reaction mixture was stirred at −78° C. for 1 to 2 hours until the complete consumption of the starting material. The resulting mixture was quenched with aqueous ammonium chloride solution, extracted with ethyl acetate (3×20 mL), washed with brine (2×10 mL), dried over sodium sulfate and evaporated in vacuo. The residue was purified on silica gel with 80/20→60/40 of hexane/ethyl acetate to give (4-amino-2-ethyl-sulfanylpyrimidin-5-yl)-(3-fluorophenyl)methanone as a light yellow solid (159 mg, 71% yield). MS (APCI): 278 (M+H).

Example 3

(4-Amino-2-ethanesulfonyl-pyrimidin-5-yl)-(3-fluoro-phenyl)-methanone

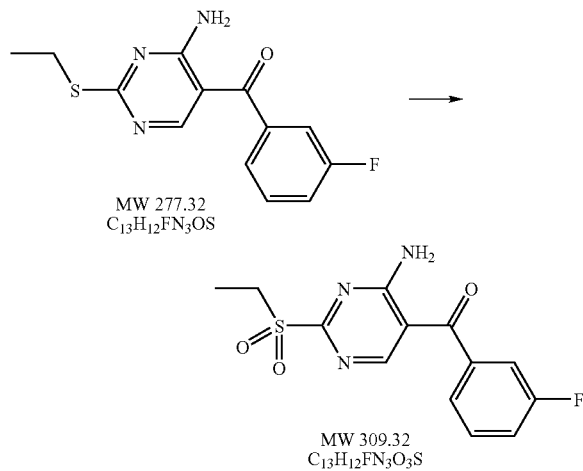

A solution of (4-amino-2-ethyl-sulfanyl-pyrimidin-5-yl)-(3-fluorophenyl)methanone (141.5 mg, 0.5102 mmol, Example 2) in chloroform (15 mL) was cooled to 0° C. and treated with 3-chloroperoxybenzoic acid (381.6 mg, ~1.55 mmol, ~70% purity from Aldrich) and the reaction was stirred at the same temperature for 1.5 hours. The reaction mixture was diluted with methylene chloride (50 mL) and washed with 10% aqueous sodium thiosulfate (2×10 mL), brine, dried and concentrated. The crude product was purified on silica gel with 60:40 of hexane/ethyl acetate to give (4-amino-2-ethanesulfonyl-pyrimidin-5-yl)-(3-fluoro-phenyl)-methanone as a white solid (118.2 mg, 75% yield). HRMS, observed: 309.0582; Calcd for M+: 309.0583

Example 4

[4-Amino-2-[4-(4-methyl-piperazin-1-yl)-phenylamino]-pyrimidin-5-yl]-(3-fluoro-phenyl)-methanone

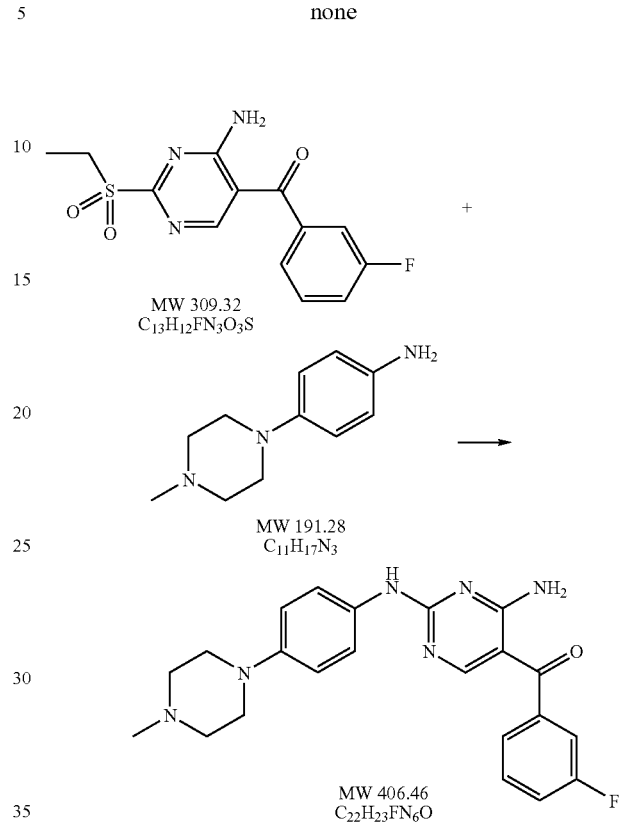

A suspension of (4-amino-2-ethanesulfonyl-pyrimidin-5-yl)-(3-fluoro-phenyl)-methanone (20.1 mg, 0.0650 mmol, Example 3), 4-(4-methylpiperazino)aniline (15.8 mg, 0.0826 mmol, Appolo Chemical) and p-toluenesulfonic acid hydrate (15 mg, 0.0777 mmol, Aldrich) in isopropanol (2.5 mL) was placed in a sealed tube and heated at 100 to 110° C. under microwave conditions for 1 hour. The resulting mixture was evaporated in vacuo and the crude product was purified on silica gel with 95:5 of dichloromethane/methanol to give [4-amino-2-[4-(4-methyl-piperazin-1-yl)-phenylamino]-pyrimidin-5-yl]-(3-fluoro-phenyl)-methanone as a light yellow solid (16.4 mg, 68% yield). HRMS, observed: 407.1994; Calcd for (M+H)+: 407.1990.

Example 5

(4-amino-2-ethylsulfanylpyrimidin-5-yl)-(2-methoxy-phenyl)-methanone

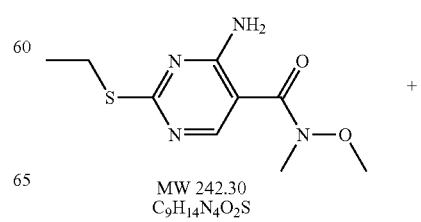

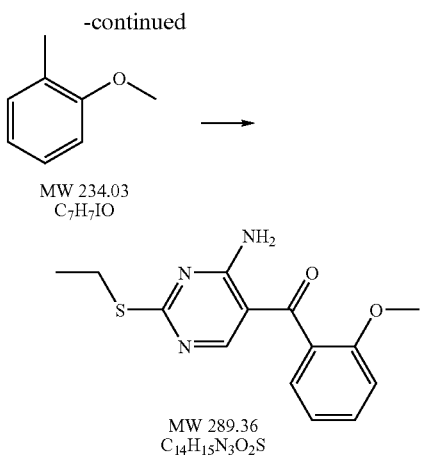

4-Amino-2-ethylsulfanylpyrimidine-5-carboxylic acid methoxymethylamide (200 mg, 0.830 mmol, Example 1) was dissolved in anhydrous tetrahydrofuran (3 mL) and cooled to −78° C. A solution of 2-methoxyphenyl lithium (~3 equiv, freshly prepared following the same procedure as Step A of Example 2) was added. The reaction was stirred at −78° C. for 1.5 hours and quenched with aqueous ammonium chloride solution. The resulting mixture was extracted with ethyl acetate (3×20 mL), washed with brine (2×10 mL), dried over sodium sulfate and evaporated in vacuo. The residue was purified on silica gel with 60:40 of hexane/ethyl acetate to give (4-amino-2-ethylsulfanylpyrimidin-5-yl)-(2-methoxy-phenyl)-methanone as a white solid (224.1 mg, 94% yield). HRMS, observed: 290.0961; Calcd for (M+H)$^+$: 290.0958.

Example 6

(4-Amino-2-ethanesulfonylpyrimidin-5-yl)-(2-methoxyphenyl)-methanone

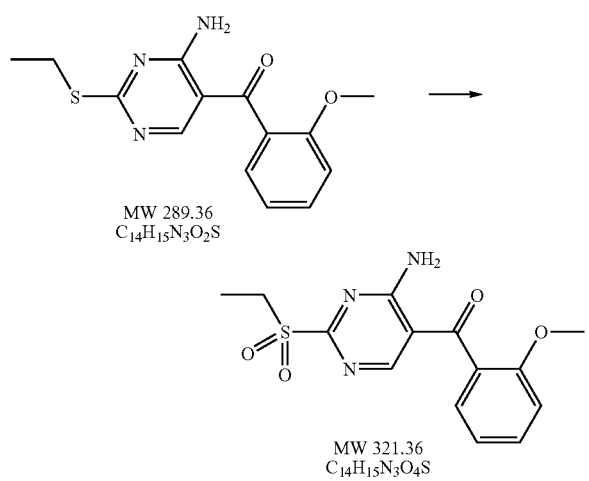

A solution of (4-amino-2-ethylsulfanylpyrimidin-5-yl)-(2-methoxy-phenyl)-methanone (1.25 g, 4.32 mmol, Example 5) in chloroform (80 mL) was cooled to 0° C. and treated with 3-chloroperoxybenzoic acid (2.8 g, ~12.5 mmol, ~77% purity from Aldrich) and the reaction was stirred at the same temperature for 1.5 hours. The reaction mixture was diluted with methylene chloride (150 mL) and washed with 10% aqueous sodium thiosulfate (2×20 mL), brine, dried and concentrated. The crude product was purified on silica gel with 60:40 of hexane/ethyl acetate to give (4-amino-2-ethanesulfonylpyrimidin-5-yl)-(2-methoxyphenyl)-methanone as a white solid (1.06 g, 76% yield). HRMS, observed: 344.0679; Calcd for (M+Na)$^+$: 344.0675.

Example 7

[4-Amino-2-[4-(4-methyl-piperazin-1-yl)-phnylamino]-pyrimidin-5-yl]-(2-methoxyphenyl)-methanone

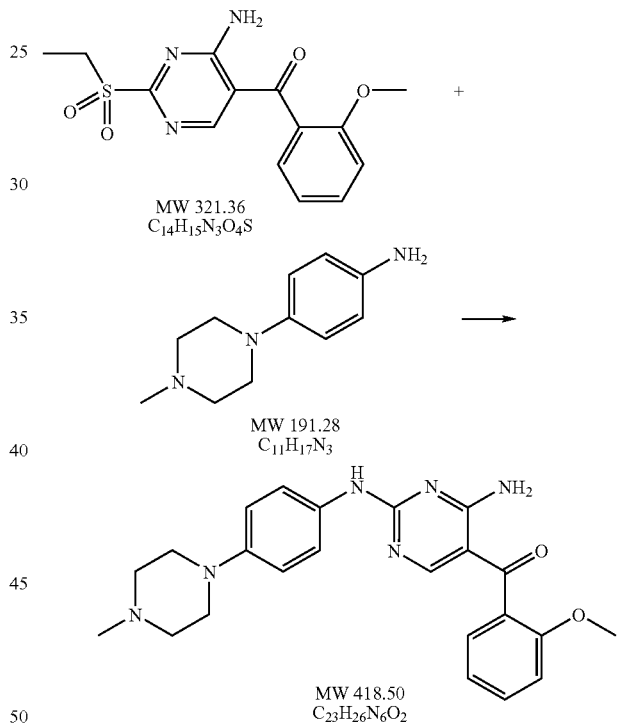

A suspension of (4-amino-2-ethanesulfonylpyrimidin-5-yl)-(2-methoxyphenyl)-methanone (20.0 mg, 0.062 mmol, Example 6), 4-(4-methylpiperazino)aniline (16.6 mg, 0.087 mmol, Appollo Chemical) and p-toluenesulfonic acid hydrate (15 mg, 0.0777 mmol, Aldrich) in isopropanol (2.5 mL) was placed in a sealed tube and heated at 100° C. under microwave conditions for 1 hour. The resulting mixture was concentrated in vacuo and the crude product was purified on silica gel with 95:5 of dichloromethane/methanol to give [4-amino-2-[4-(4-methyl-piperazin-1-yl)-phenylamino]-pyrimidin-5-yl]-(2-methoxyphenyl)-methanone as a light yellow solid (10.6 mg). HRMS, observed: 419.2190; Calcd for (M+H)$^+$: 419.2195.

Example 8

[4-Amino-2-[4-(4-isopropyl-piperazin-1-yl)-phenylamino]-pyrimidin-5-yl]-(2-methoxy-phenyl)-methanone

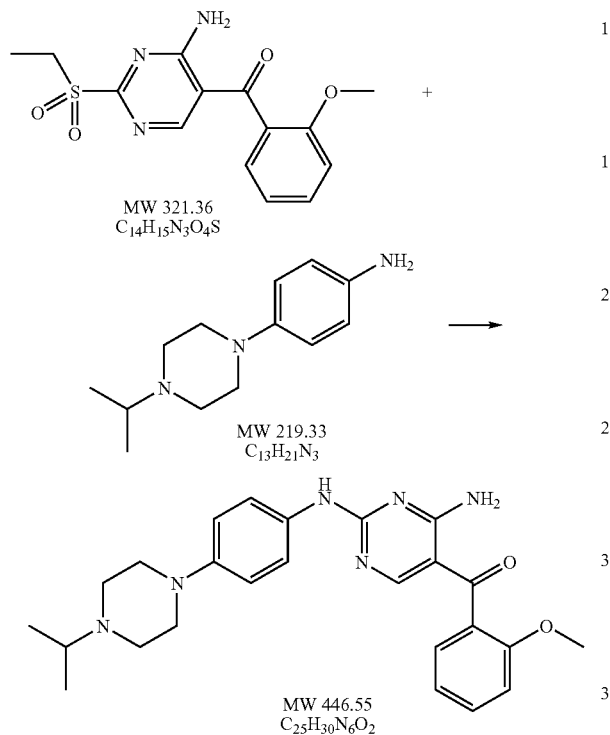

A suspension of (4-amino-2-ethanesulfonylpyrimidin-5-yl)-(2-methoxyphenyl)-methanone (26.6 mg, 0.0828 mmol, Example 6) and 4-(4-isopropylpiperazin-1-yl)phenylamine (19.5 mg, 0.0889 mmol) in isopropanol (2.5 mL) was placed in a sealed tube and heated at 110° C. under microwave conditions for 1 hour. The resulting mixture was concentrated and the crude product was purified on silica gel with 95:5 of dichloromethane/methanol to give [4-amino-2-[4-(4-isopropyl-piperazin-1-yl)-phenylamino]-pyrimidin-5-yl]-(2-methoxy-phenyl)-methanone as a light yellow solid (15.6 mg, 42% yield). HRMS, observed: 447.2507; Calcd for $(M+H)^+$: 447.2503.

The 4-(4-isopropylpiperazin-1-yl)phenylamine was prepared as follows:

A mixture of 1-(4-nitrophenyl)piperazine (2.00 g, 9.7 mmol) (Acros Organics), powdered potassium carbonate (2.7 g, 19.3 mmol), 2-bromopropane (0.96 mL, 10.1 mmol), potassium iodide (50 mg) and a catalytic amount of 18-crown-6 in acetonitrile (15 mL) was heated at reflux overnight. The mixture was filtered, and the filter cake was washed with acetonitrile. The solvent was evaporated from the combined filtrates and the residue was partitioned between water and ethyl acetate. The layers were separated and the aqueous layer was extracted twice with ethyl acetate. The combined organic layers were washed with brine, dried (MgSO4), filtered, evaporated and chromatographed (0–66% acetone/dichloromethane) to give 1-(1-methyl-ethyl)-4-(4-nitrophenylpiperazine).

A mixture of 1-(1-methylethyl)-4-(4-nitrophenylpiperazine) (1.7 g, 6.8 mmol) (prepared as above) and 10% palladium-on-charcoal in ethanol (30 mL) was hydrogenated at room temperature and atmospheric pressure overnight. The catalyst was filtered off and the filter cake washed thoroughly with ethanol. The mixture was evaporated under reduced pressure to give 4-(4-isopropylpiperazin-1-yl)phenylamine as a dark brown oil. CDK4 $IC_{50}$=0.171 µM; CDK1 $IC_{50}$=3.564 µM; CDK2 $IC_{50}$=10.000 µM; HCT 116 $IC_{90}$=20.890 µM.

Example 9

4-[4-Amino-5-(2-methoxy-benzoyl)-pyrimidin-2-ylamino]-piperidine-1-carboxylic acid ethyl ester

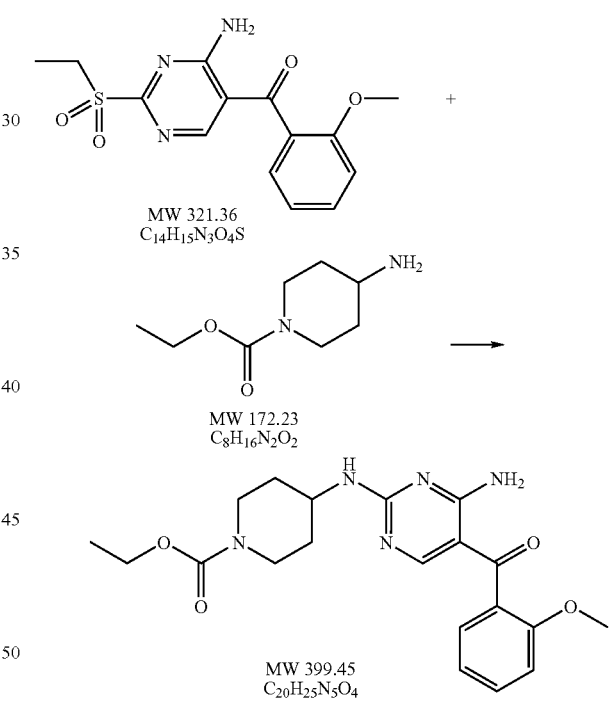

A suspension of (4-amino-2-ethanesulfonylpyrimidin-5-yl)-(2-methoxyphenyl)-methanone (20.0 mg, 0.0650 mmol, Example 6) and ethyl 4-amino-1-piperidinecarboxylate (15.1 mg, 0.0876 mmol, Aldrich) in isopropanol (2.5 mL) was placed in a sealed tube and heated at ~100–110° C. under microwave conditions for ~1 hour and the resulting mixture was evaporated in vacuo. The crude product was purified on silica gel with 95:5 of dichloromethane/methanol to give 4-[4-amino-5-(2-methoxy-benzoyl)-pyrimidin-2-ylamino]-piperidine-1-carboxylic acid ethyl ester as a light yellow solid (22.1 mg, 89% yield). HRMS, observed: 400.1984; Calcd for $(M+H)^+$: 400.1980.

Example 10

4-[4-Amino-5-(2-methoxy-benzoyl)-pyrimidin-2-ylamino]-piperidine-1-carboxylic acid tert-butyl ester

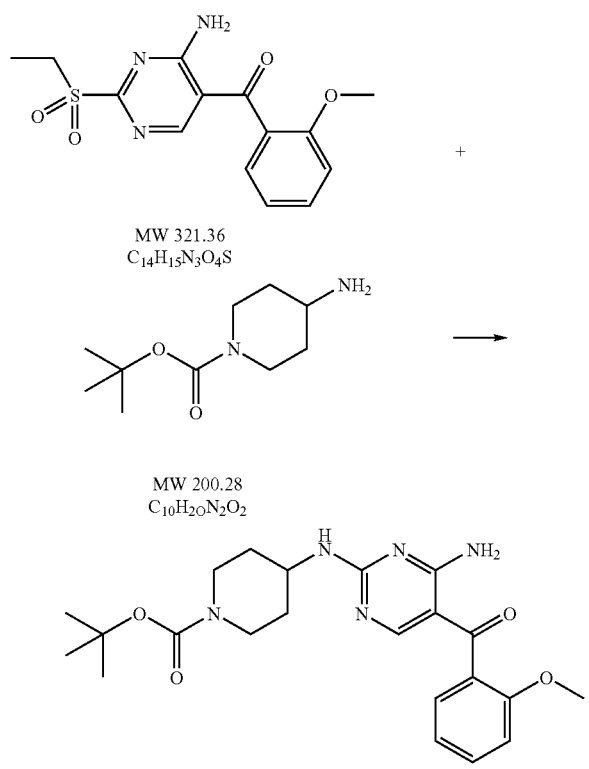

The same procedure was used as described in Example 9 starting from (4-amino-2-ethanesulfonylpyrimidin-5-yl)-(2-methoxyphenyl)-methanone (125.4 mg, 0.3902 mmol, Example 6) and 4-amino-1-Boc-piperidine (101.0 mg, 0.484 mmol, Astatech) to give 4-[4-amino-5-(2-methoxy-benzoyl)-pyrimidin-2-ylamino]-piperidine-1-carboxylic acid tert-butyl ester (158.2 mg, 95% yield). HRMS, observed: 428.2296; Calcd for (M+H)+: 428.2293.

Example 11

[4-Amino-2-(piperidin-4-ylamino)-pyrimidin-5-yl]-(2-methoxy-phenyl)-methanone

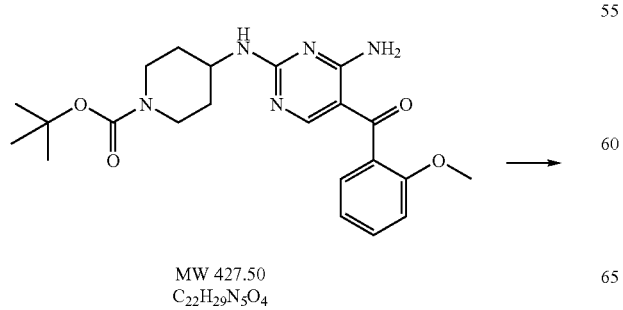

4-[4-Amino-5-(2-methoxy-benzoyl)-pyrimidin-2-ylamino]-piperidine-1-carboxylic acid tert-butyl ester (1.96 g, Example 10) was dissolved in dichloromethane (25 mL), cooled to 0° C. and treated with trifluoroacetic acid (12.5 mL). After stirring 1 hour at 0° C., the reaction mixture was concentrated in vacuo to give 4.29 g of [4-amino-2-(piperidin-4-ylamino)-pyrimidin-5-yl]-(2-methoxy-phenyl)-methanone as the trifluoroacetic acid salt. A portion of the crude product was purified on HPLC and then neutralized with sodium carbonate, washed with brine and dried to give [4-amino-2-(piperidin-4-ylamino)-pyrimidin-5-yl]-(2-methoxy-phenyl)-methanone free base. HRMS, observed: 328.1771; Calcd for (M+H)+: 328.1768.

Example 12

(4-Amino-2-ethylsulfanyl-pyrimidin-5-yl)-(2,6-difluoro-phenyl)-methanone

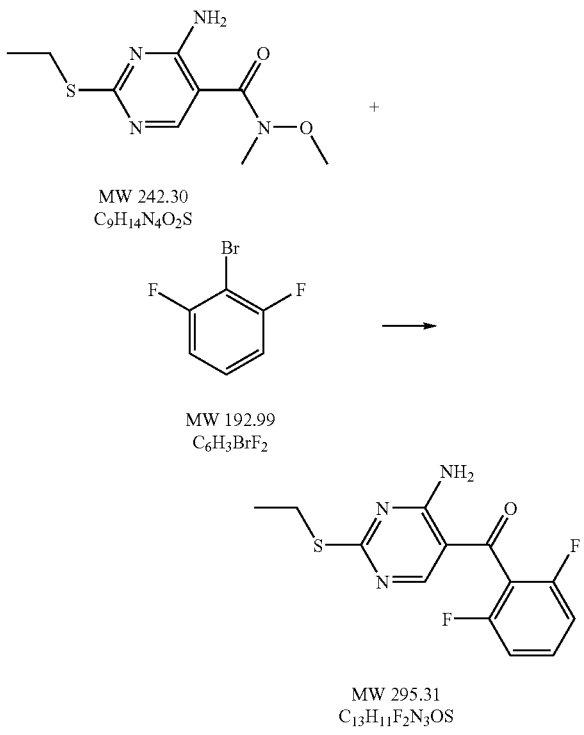

The same procedure was used as described in Example 2, starting from 4-amino-2-ethylsulfanyl-pyrimidine-5-carboxylic acid methoxy-methylamide (200 mg, 0.830 mmol, Example 1) and a solution of 2,6-difluorophenyl lithium (~3 equiv, freshly prepared from 1-bromo-2,6-difluorobenzene (Aldrich), as in Example 2A), to give (4-amino-2-ethylsulfanyl-pyrimidin-5-yl)-(2,6-difluoro-phenyl)-methanone as a white solid (170 mg, 70% yield). HRMS, observed: 296.0667; Calcd for (M+H)$^+$: 296.0664.

Example 13

(4-Amino-2-ethanesulfonyl-pyrimidin-5-yl)-(2,6-difluoro-phenyl)-methanone

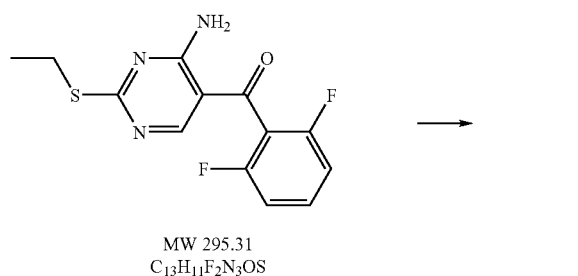

MW 295.31
$C_{13}H_{11}F_2N_3OS$

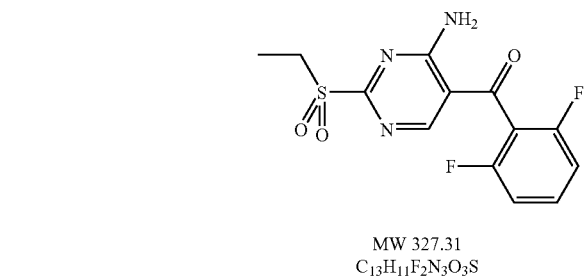

MW 327.31
$C_{13}H_{11}F_2N_3O_3S$

The same procedure as described in Example 3, starting from (4-amino-2-ethyl-sulfanyl-pyrimidin-5-yl)-(2,6-difluoro-phenyl)-methanone, Example 12, was used to give (4-amino-2-ethanesulfonyl-pyrimidin-5-yl)-(2,6-difluoro-phenyl)-methanone as a white solid (78% yield). HRMS, observed: 350.0385; Calcd for (M+Na)$^+$: 350.0381.

Example 14

[4-Amino-2-[4-(4-methyl-piperazin-1-yl)-phenylamino]-pyrimidin-5-yl]-(2,6-difluoro-phenyl)-methanone

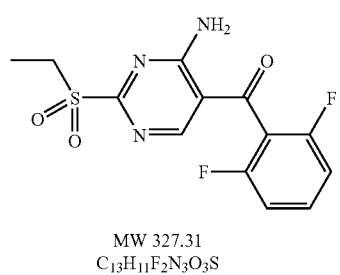

MW 327.31
$C_{13}H_{11}F_2N_3O_3S$

+

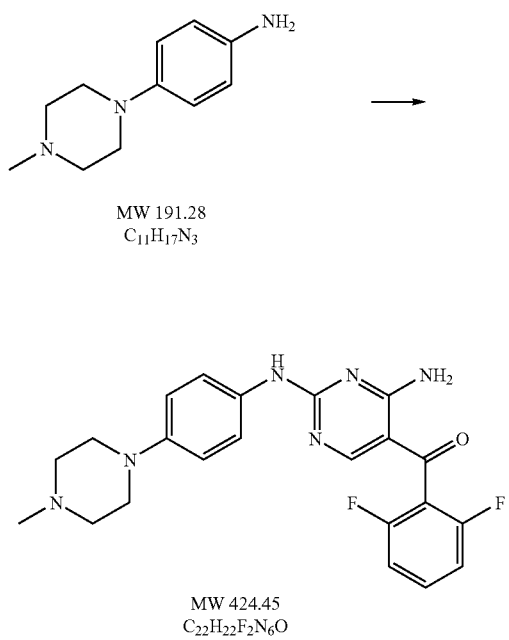

MW 191.28
$C_{11}H_{17}N_3$

→

MW 424.45
$C_{22}H_{22}F_2N_6O$

The same procedure as described in Example 7 was used, starting from (4-amino-2-ethanesulfonyl-pyrimidin-5-yl)-(2,6-difluoro-phenyl)-methanone (18.4 mg, 0.0565 mmol, Example 13) to give [4-amino-2-[4-(4-methyl-piperazin-1-yl)-phenylamino]-pyrimidin-5-yl]-(2,6-difluoro-phenyl)-methanone. HRMS, observed: 425.1901; Calcd for (M+H)$^+$: 425.1896.

Example 15

[4-Amino-2-[4-(4-isopropyl-piperazin-1-yl)-phenylamino]-pyrimidin-5-yl]-(2,6-difluoro-phenyl)-methanone

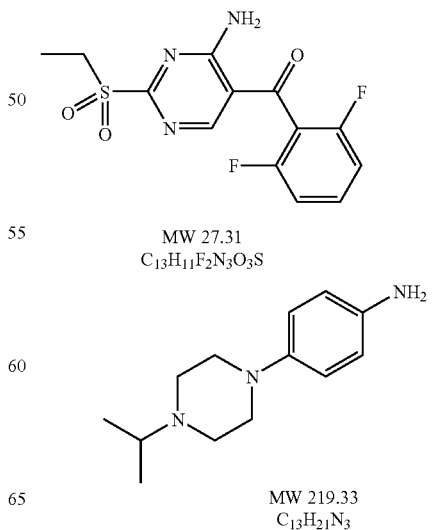

MW 27.31
$C_{13}H_{11}F_2N_3O_3S$

+

MW 219.33
$C_{13}H_{21}N_3$

→

-continued

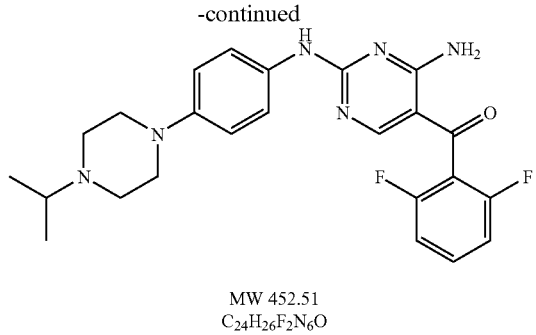

MW 452.51
$C_{24}H_{26}F_2N_6O$

The same procedure as described in Example 8, starting from (4-amino-2-ethanesulfonyl-pyrimidin-5-yl)-(2,6-difluoro-phenyl)-methanone, Example 13, was used to give [4-amino-2-[4-(4-isopropyl-piperazin-1-yl)-phenylamino]-pyrimidin-5-yl]-(2-methoxy-phenyl)-methanone. HRMS, observed: 453.2213; Calcd for (M+H)$^+$: 453.2209.

Example 16

4-[4-Amino-5-(2,6-difluoro-benzoyl)-pyrimidin-2-ylamino]-piperidine-1-carboxylic acid ethyl ester

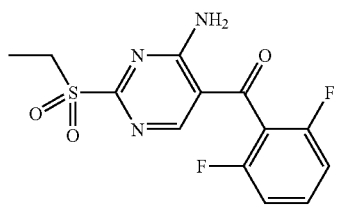

MW 327.31
$C_{13}H_{11}F_2N_3O_3S$

+

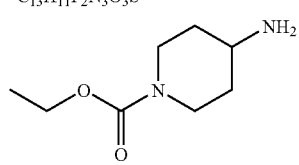

MW 172.23
$C_8H_{16}N_2O_2$

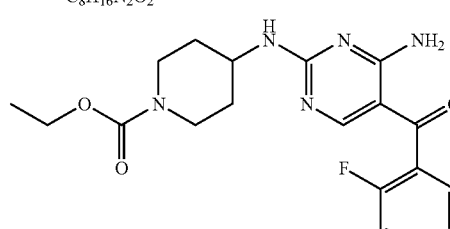

MW 405.40
$C_8H_{16}N_2O_2$

The same procedure as described in Example 9 was used, starting from (4-amino-2-ethanesulfonyl-pyrimidin-5-yl)-(2,6-difluoro-phenyl)-methanone, Example 13, to give 4-[4-amino-5-(2,6-difluoro-benzoyl)-pyrimidin-2-ylamino]-piperidine-1-carboxylic acid ethyl ester (158.2 mg, 95% yield). HRMS, observed: 406.1690; Calcd for (M+H)$^+$: 406.1685.

Example 17

4-[4-Amino-5-(2-methoxy-benzoyl)-pyrimidin-2-ylamino]-piperidine-1-carboxylic acid methyl ester

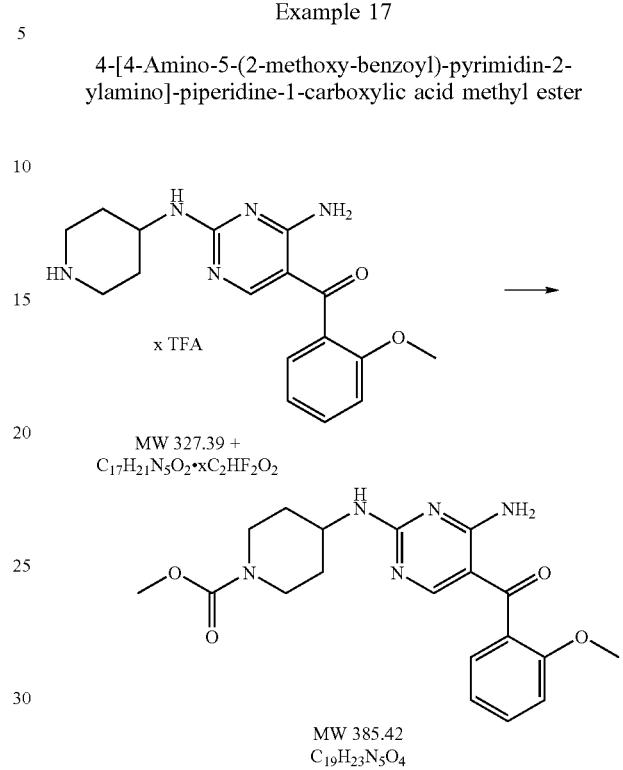

MW 327.39 +
$C_{17}H_{21}N_5O_2 \cdot xC_2HF_2O_2$

MW 385.42
$C_{19}H_{23}N_5O_4$

To a solution of [4-amino-2-(piperidin-4-ylamino)-pyrimidin-5-yl]-(2-methoxy-phenyl)-methanone trifluoroacetic acid salt (80.9 mg, Example 11) in methylene chloride (4 mL) were added triethylamine (0.095 mL, 0.681 mmol, Aldrich) and methyl chloroformate (9.0 mg, 0.0868 mmol, Aldrich) at 0° C. The mixture was stirred for 1 hour at 0° C., the reaction mixture was concentrated in vacuo and crude product was purified on silica gel with 95:5 of dichloromethane/methanol to give 4-[4-amino-5-(2-methoxy-benzoyl)-pyrimidin-2-ylamino]-piperidine-1-carboxylic acid methyl ester (27.0 mg). HRMS, observed: 386.1827; Calcd for (M+H)$^+$: 386.1823.

Example 18

4-[4-Amino-5-(2-methoxy-benzoyl)-pyrimidin-2-ylamino]-piperidine-1-carboxylic acid propyl ester

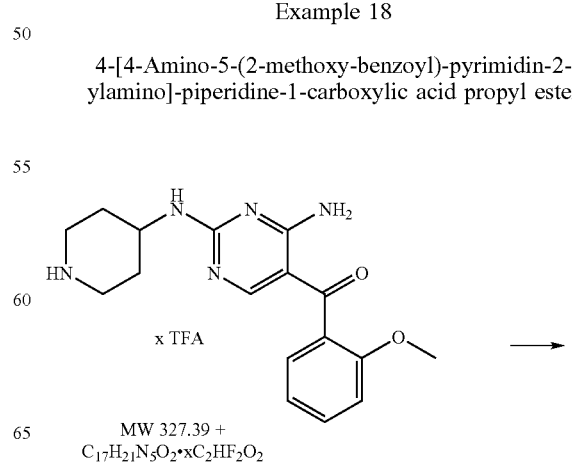

MW 327.39 +
$C_{17}H_{21}N_5O_2 \cdot xC_2HF_2O_2$

-continued

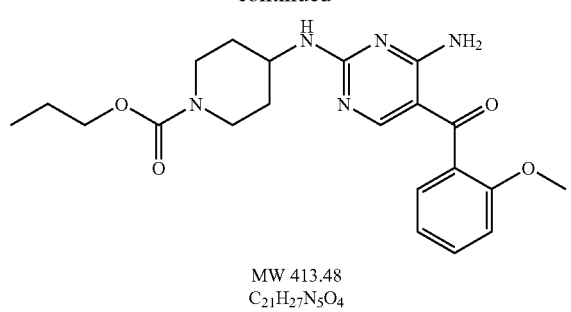

MW 413.48
$C_{21}H_{27}N_5O_4$

The same procedure as described in Example 17 was used, starting from [4-amino-2-(piperidin-4-ylamino)-pyrimidin-5-yl]-(2-methoxy-phenyl)-methanone trifluoroacetic acid salt, Example 11, and propylchloroformate (Aldrich), to afford 4-[4-amino-5-(2-methoxy-benzoyl)-pyrimidin-2-ylamino]-piperidine-1-carboxylic acid propyl ester. HRMS, observed: 414.2140; Calcd for (M+H)$^+$: 414.2136.

Example 19

4-[4-Amino-5-(2-methoxy-benzoyl)-pyrimidin-2-ylamino]-piperidine-1-carboxylic acid iso-butyl ester

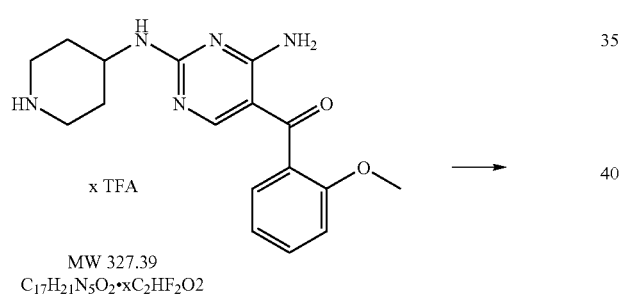

x TFA

MW 327.39
$C_{17}H_{21}N_5O_2 \cdot xC_2HF_2O2$

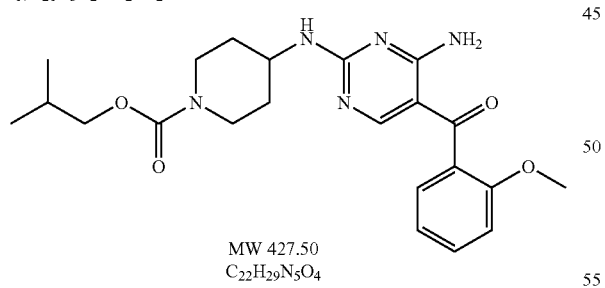

MW 427.50
$C_{22}H_{29}N_5O_4$

The same procedure as described in Example 17 was used, starting from [4-amino-2-(piperidin-4-ylamino)-pyrimidin-5-yl]-(2-methoxy-phenyl)-methanone trifluoroacetic acid salt, Example 11, and isobutyl chloroformate (Aldrich), to afford 4-[4-amino-5-(2-methoxy-benzoyl)-pyrimidin-2-ylamino]-piperidine-1-carboxylic acid iso-butyl ester. HRMS, observed: 428.2295; Calcd for (M+H)$^+$: 428.2293

Example 20

1-[4-[4-Amino-5-(2-methoxy-benzoyl)-pyrimidin-2-ylamino]-piperidin-1-yl]-ethanone

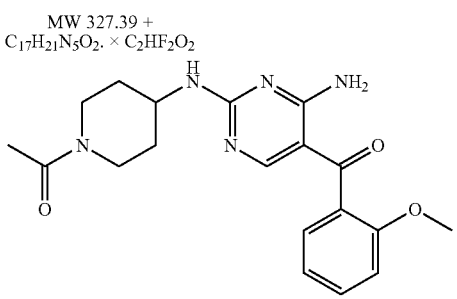

× TFA

MW 327.39 +
$C_{17}H_{21}N_5O_2 \cdot \times C_2HF_2O_2$

MW 369.42
$C_{19}H_{23}N_5O_3$

To a solution of [4-amino-2-(piperidin-4-ylamino)-pyrimidin-5-yl]-(2-methoxy-phenyl)-methanone trifluoroacetic acid salt, (31 mg, Example 11) in dimethylformamide (2 mL) were added triethylamine (19 mg, 0.193 mmol, Aldrich), 1-(3-dimethylaminopropyl)-3-ethylcarbodiimide hydrochloride (6.6 mg, 0.0344 mmol, Aldrich), 1-hydroxybenzotriazole hydrate (5.0 mg, 0.037 mmol, Aldrich), followed by acetic acid (2.3 mg, 0.034 mmol). The reaction mixture was stirred overnight at room temperature, taken up in ethyl acetate (15 mL), washed with brine and evaporated. The crude product was purified on silica gel with 95:5 of dichloromethane/methanol to give 1-[4-[4-amino-5-(2-methoxy-benzoyl)-pyrimidin-2-ylamino]-piperidin-1-yl]-ethanone (11.2 mg). HRMS, observed: 370.1875; Calcd for (M+H)$^+$: 370.1874.

Example 21

1-[4-[4-Amino-5-(2-methoxy-benzoyl)-pyrimidin-2-ylamino]-piperidin-1-yl]-propan-1-one

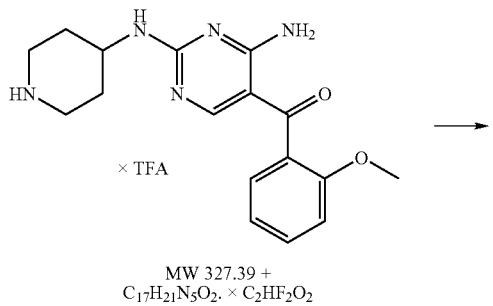

× TFA

MW 327.39 +
$C_{17}H_{21}N_5O_2 \cdot \times C_2HF_2O_2$

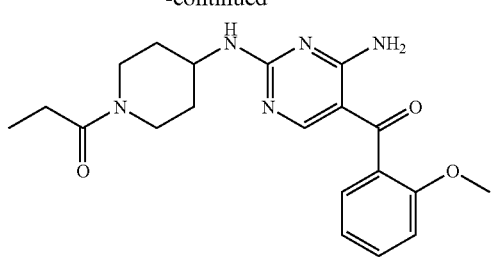

MW 383.45
$C_{20}H_{25}N_5O_3$

The same procedure as described in Example 20 was used, starting from [4-amino-2-(piperidin-4-ylamino)-pyrimidin-5-yl]-(2-methoxy-phenyl)-methanone trifluoroacetic acid salt, Example 11, and propionic acid (Aldrich), to give 1-[4-[4-amino-5-(2-methoxy-benzoyl)-pyrimidin-2-ylamino]-piperidin-1-yl]-propan-1-one. HRMS, observed: 384.2034; Calcd for (M+H)$^+$: 384.2030.

Example 22

1-[4-[4-Amino-5-(2-methoxy-benzoyl)-pyrimidin-2-ylamino]-piperidin-1-yl]-butan-1-one

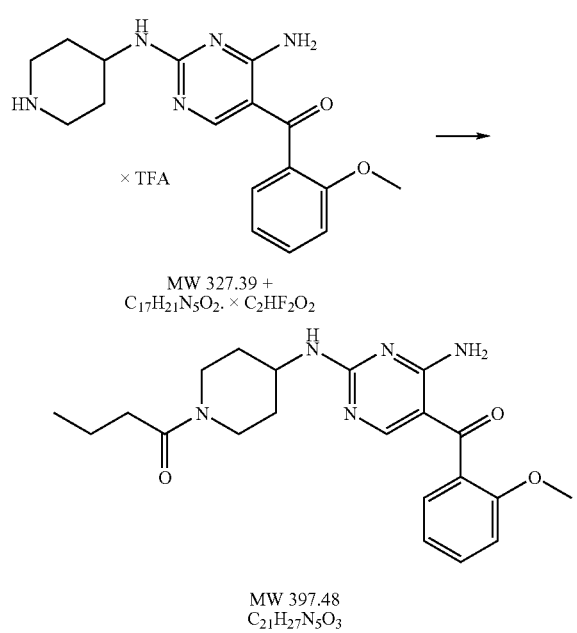

MW 327.39 +
$C_{17}H_{21}N_5O_2 \cdot \times C_2HF_3O_2$

MW 397.48
$C_{21}H_{27}N_5O_3$

The same procedure as described in Example 20 was used, starting from [4-amino-2-(piperidin-4-ylamino)-pyrimidin-5-yl]-(2-methoxy-phenyl)-methanone trifluoroacetic acid salt Example 11, and butyric acid (Aldrich), to give 1-[4-[4-mino-5-(2-methoxy-benzoyl)-pyrimidin-2-ylamino]-piperidin-1-yl]-butan-1-one. HRMS, observed: 398.2189; Calcd for (M+H)$^+$: 398.2187.

Example 23

1-[4-[4-Amino-5-(2-methoxy-benzoyl)-pyrimidin-2-ylamino]-piperidin-1-yl]-3-methyl-butan-1-one

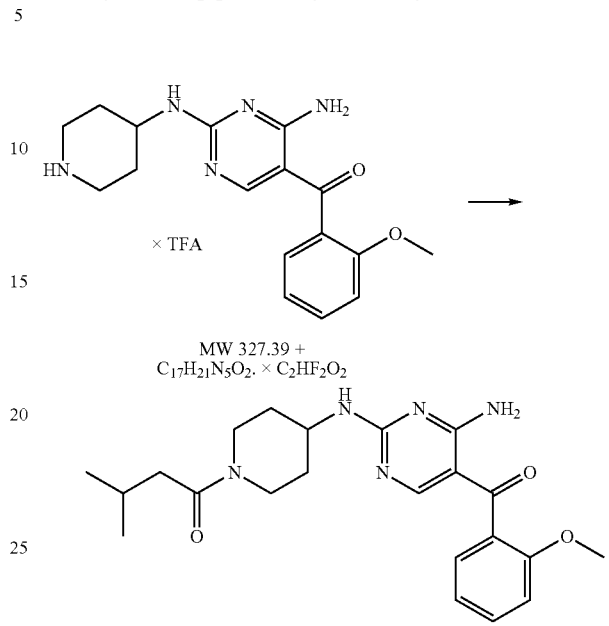

MW 327.39 +
$C_{17}H_{21}N_5O_2 \cdot \times C_2HF_3O_2$

MW 411.50
$C_{22}H_{29}N_5O_3$

The same procedure as described in Example 20 was used, starting from [4-amino-2-(piperidin-4-ylamino)-pyrimidin-5-yl]-(2-methoxy-phenyl)-methanone trifluoroacetic acid salt Example 11 and isobutyric acid (Aldrich), to give 1-[4-[4-amino-5-(2-methoxy-benzoyl)-pyrimidin-2-ylamino]-piperidin-1-yl]-3-methyl-butan-1-one. HRMS, observed: 412.2350; Calcd for (M+H)$^+$: 412.2343.

Example 24

1-[4-[4-Amino-5-(2-methoxy-benzoyl)-pyrimidin-2-ylamino]-piperidin-1-yl]-3-diethylamino-propan-1-one

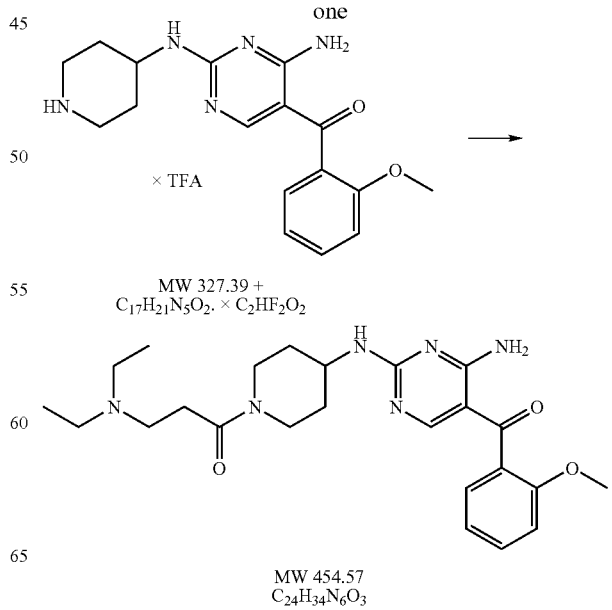

MW 327.39 +
$C_{17}H_{21}N_5O_2 \cdot \times C_2HF_3O_2$

MW 454.57
$C_{24}H_{34}N_6O_3$

The same procedure as described in Example 20 was used, starting from [4-amino-2-(piperidin-4-ylamino)-pyrimidin-5-yl]-(2-methoxy-phenyl)-methanone trifluoroacetic acid salt, Example 11, and diethylaminopropionic acid hydrochloride (Aldrich), to give 1-[4-[4-amino-5-(2-methoxy-benzoyl)-pyrimidin-2-ylamino]-piperidin-1-yl]-3-diethylamino-propan-1-one. HRMS, observed: 455.2769; Calcd for (M+H)$^+$: 455.2765.

Example 25

4-[4-Amino-5-(2-methoxy-benzoyl)-pyrimidin-2-ylamino]-piperidine-1-carboxylic acid methylamide

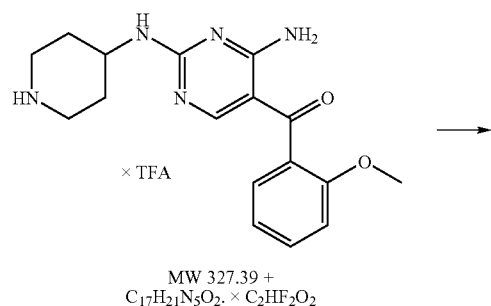

MW 327.39 +
$C_{17}H_{21}N_5O_2 \cdot C_2HF_2O_2$

MW 384.44
$C_{19}H_{24}N_6O_3$

To a solution of [4-amino-2-(piperidin-4-ylamino)-pyrimidin-5-yl]-(2-methoxy-phenyl)-methanone trifluoroacetic acid salt (92.4 mg, Example 11) in methylene chloride (3 mL) were added triethylamine (0.12 mL, 0.861 mmol, Aldrich) and methyl isocyanate (6.2 mg, 0.107 mmol, Fluka) at 0° C. After stirring for 1 hour at 0° C., the reaction mixture was concentrated in vacuo and crude product was purified on silica gel with 95:5 of dichloromethane/methanol to give 4-[4-amino-5-(2-methoxy-benzoyl)-pyrimidin-2-ylamino]-piperidine-1-carboxylic acid methylamide (32.8 mg). HRMS, observed: 385.1985; Calcd for (M+H)$^+$: 385.1983.

Example 26

4-[4-Amino-5-(2-methoxy-benzoyl)-pyrimidin-2-ylamino]-piperidine-1-carboxylic acid ethylamide

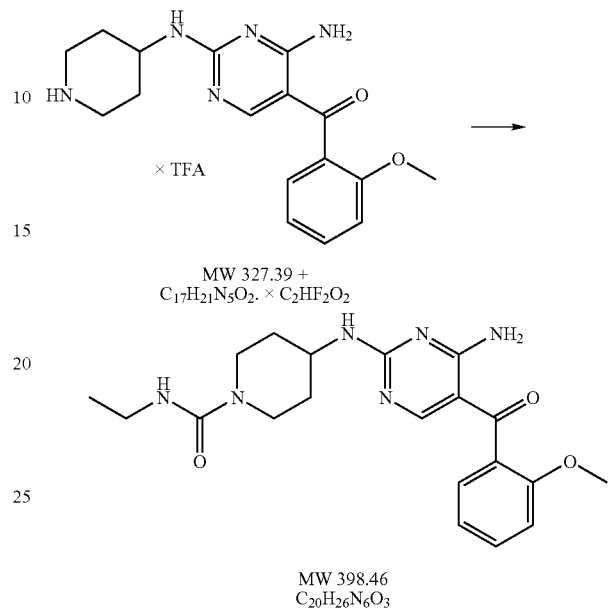

MW 327.39 +
$C_{17}H_{21}N_5O_2 \cdot C_2HF_2O_2$

MW 398.46
$C_{20}H_{26}N_6O_3$

The same procedure as described in Example 25 was used, starting from [4-amino-2-(piperidin-4-ylamino)-pyrimidin-5-yl]-(2-methoxy-phenyl)-methanone trifluoroacetic acid salt, Example 11, and ethyl isocyanate (Aldrich), to give 4-[4-amino-5-(2-methoxy-benzoyl)-pyrimidin-2-ylamino]-piperidine-1-carboxylic acid ethylamide. HRMS, observed: 399.2143; Calcd for (M+H)$^+$: 399.2139.

Example 27

4-[4-Amino-5-(2-methoxy-benzoyl)-pyrimidin-2-ylamino]-piperidine-1-carboxylic acid propylamide

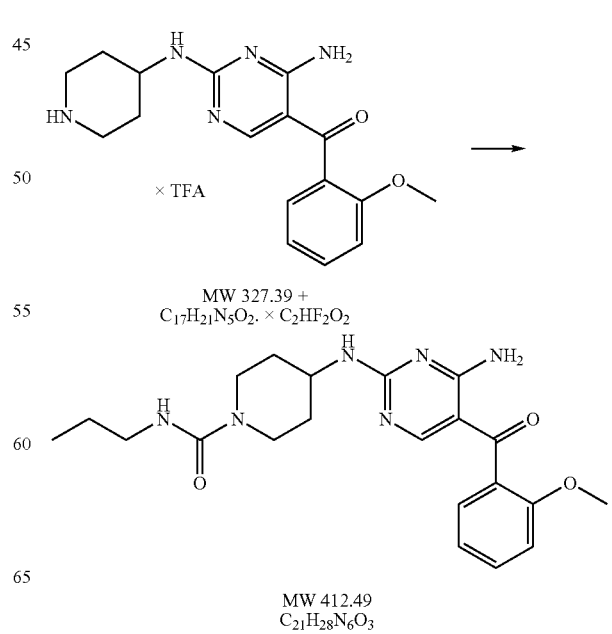

MW 327.39 +
$C_{17}H_{21}N_5O_2 \cdot C_2HF_2O_2$

MW 412.49
$C_{21}H_{28}N_6O_3$

The same procedure as described in Example 25 was used, starting from [4-amino-2-(piperidin-4-ylamino)-pyrimidin-5-yl]-(2-methoxy-phenyl)-methanone trifluoroacetic acid salt, Example 11, and propyl isocyanate (Aldrich), to give 4-[4-Amino-5-(2-methoxy-benzoyl)-pyrimidin-2-ylamino]-piperidine-1-carboxylic acid propylamide. HRMS, observed: 413.2299; Calcd for (M+H)$^+$: 413,2296.

Example 28

[4-Amino-2-(1-methanesulfonyl-piperidin-4-ylamino)-pyrimidin-5-yl]-(2-methoxy-phenyl)-methanone

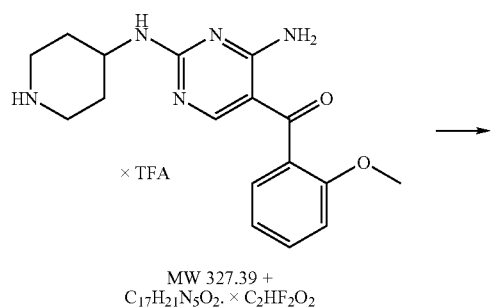

MW 327.39 +
$C_{17}H_{21}N_5O_2 \cdot \times C_2HF_2O_2$

MW 405.48
$C_{18}H_{23}N_5O_4S$

To a solution of [4-amino-2-(piperidin-4-ylamino)-pyrimidin-5-yl]-(2-methoxy-phenyl)-methanone trifluoroacetic acid salt (66.3 mg, Example 11) in methylene chloride (3 mL) were added triethylamine (0.09 mL, 0.617 mmol, Aldrich) and methanesulfonyl chloride (8.9 mg, 0.0774 mmol, Aldrich) at 0° C. After stirring for 0.5 to 1 hour at 0° C., the reaction mixture was concentrated in vacuo and crude product was purified on silica gel with 95:5 of dichloromethane/methanol to give [4-Amino-2-(1-methanesulfonyl-piperidin-4-ylamino)-pyrimidin-5-yl]-(2-methoxy-phenyl)-methanone (19.2 mg). HRMS, observed: 406.1546; Calcd for (M+H)$^+$: 406.1544.

Example 29

[4-Amino-2-(1-ethanesulfonyl-piperidin-4-ylamino)-pyrimidin-5-yl]-(2-methoxy-phenyl)-methanone

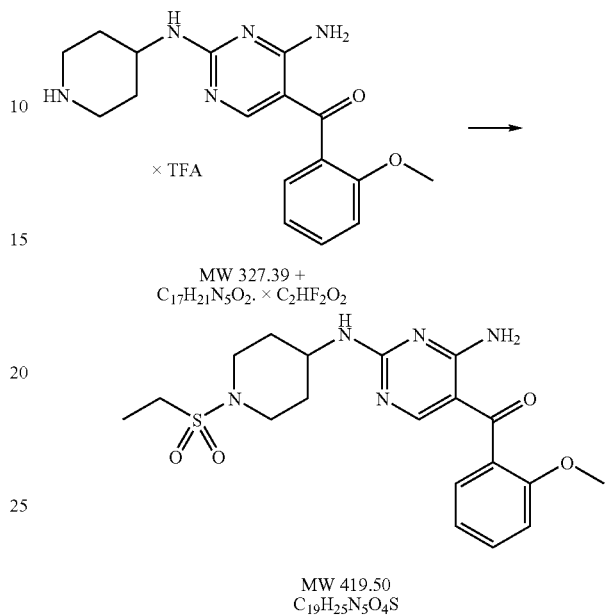

MW 327.39 +
$C_{17}H_{21}N_5O_2 \cdot \times C_2HF_2O_2$

MW 419.50
$C_{19}H_{25}N_5O_4S$

The same procedure as described in Example 28 was used, starting from [4-amino-2-(piperidin-4-ylamino)-pyrimidin-5-yl]-(2-methoxy-phenyl)-methanone trifluoroacetic acid salt, Example 11, and ethanesulfonyl chloride (Aldrich), to give [4-amino-2-(1-ethanesulfonyl-piperidin-4-ylamino)-pyrimidin-5-yl]-(2-methoxy-phenyl)-methanone. HRMS, observed: 420.1704; Calcd for (M+H)$^+$: 420.1700.

Example 30

[4-Amino-2-[1-(propane-1-sulfonyl)-piperidin-4-ylamino]-pyrimidin-5-yl]-(2-methoxy-phenyl)-methanone

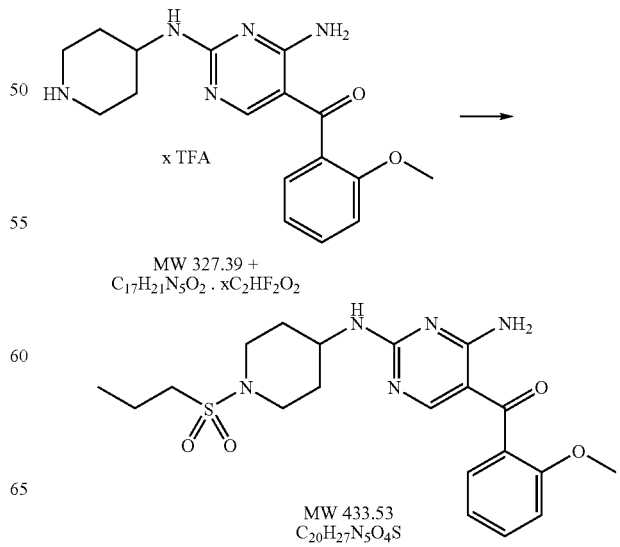

MW 327.39 +
$C_{17}H_{21}N_5O_2 \cdot xC_2HF_2O_2$

MW 433.53
$C_{20}H_{27}N_5O_4S$

The same procedure as described in Example 28 was used, starting from [4-amino-2-(piperidin-4-ylamino)-pyrimidin-5-yl]-(2-methoxy-phenyl)-methanone trifluoroacetic acid salt, Example 11, and propanesulfonyl chloride (Aldrich), to give [4-amino-2-[1-(propane-1-sulfonyl)-piperidin-4-ylamino]-pyrimidin-5-yl]-(2-methoxy-phenyl)-methanone. HRMS, observed: 434.1860; Calcd for (M+H)+: 434.1857.

Example 31

(4-Amino-2-ethylsulfanyl-pyrimidin-5-yl)-o-tolyl-methanone

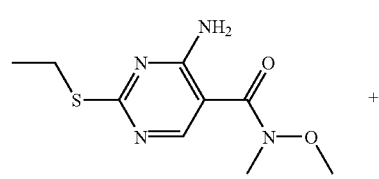

MW 242.30
C9H14N4O2S

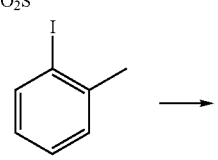

MW 218.03
C7H7I

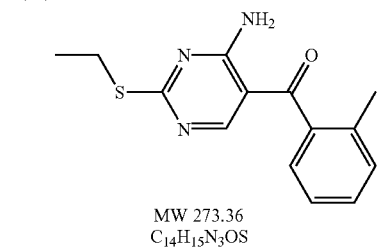

MW 273.36
C14H15N3OS

The same procedure was used as described in Example 2, starting from 4-amino-2-ethylsulfanyl-pyrimidine-5-carboxylic acid methoxy-methyl-amide (from Example 1) and a solution of 2-tolyllithium (~3 equiv, freshly prepared from 2-iodotoluene, as in Example 2A), to give (4-amino-2-ethylsulfanyl-pyrimidin-5-yl)-o-tolyl-methanone as a white solid. MS (M+H)+: 274.

Example 32

(4-Amino-2-ethanesulfonyl-pyrimidin-5-yl)-o-tolyl-methanone

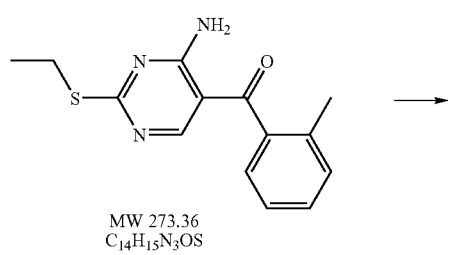

MW 273.36
C14H15N3OS

-continued

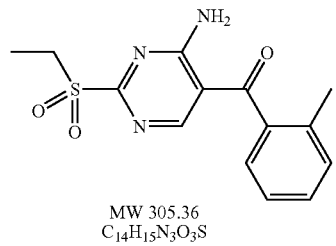

MW 305.36
C14H15N3O3S

The same procedure as described in Example 3 was used, starting from (4-amino-2-ethylsulfanyl-pyrimidin-5-yl)-o-tolyl-methanone, Example 31, to give (4-amino-2-ethanesulfonyl-pyrimidin-5-yl)-o-tolyl-methanone as a white solid. HRMS, observed: 306.0910; Calcd for (M+H)+: 306.0907.

Example 33

[4-Amino-2-[4-(4-methyl-piperazin-1-yl)-phenylamino]-pyrimidin-5-yl]-o-tolyl-methanone

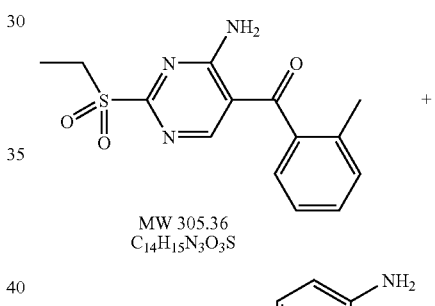

MW 305.36
C14H15N3O3S

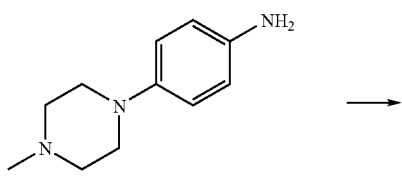

MW 191.28
C11H17N3

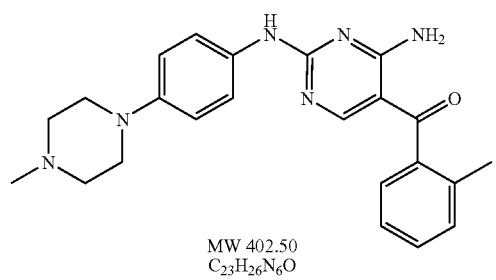

MW 402.50
C23H26N6O

The same procedure as described in Example 7 was used, starting from (4-amino-2-ethanesulfonyl-pyrimidin-5-yl)-o-tolyl-methanone, Example 32, to give [4-amino-2-[4-(4-methyl-piperazin-1-yl)-phenylamino]-pyrimidin-5-yl]-o-tolyl-methanone. MS (M+H)+, 403.

Example 34

[4-Amino-2-[4-(4-isopropyl-piperazin-1-yl)-phenylamino]-pyrimidin-5-yl]-o-tolyl-methanone

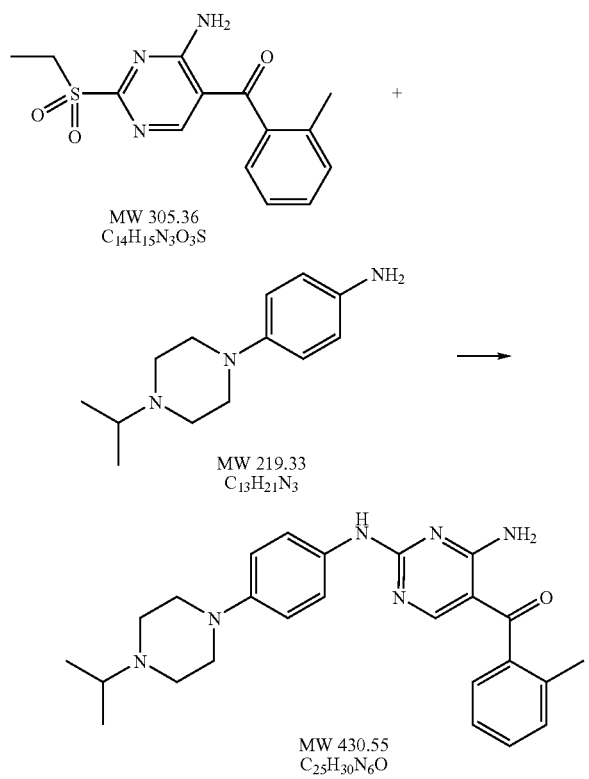

The same procedure as described in Example 8 was used, starting from (4-amino-2-ethanesulfonyl-pyrimidin-5-yl)-o-tolyl-methanone, Example 32, to give [4-amino-2-[4-(4-isopropyl-piperazin-1-yl)-phenylamino]-pyrimidin-5-yl]-o-tolyl-methanone. HRMS, observed: 431.2557; Calcd for $(M+H)^+$: 431.2554.

Example 35

4-[4-Amino-5-(2-methyl-benzoyl)-pyrimidin-2-ylamino]-piperidine-1-carboxylic acid ethyl ester

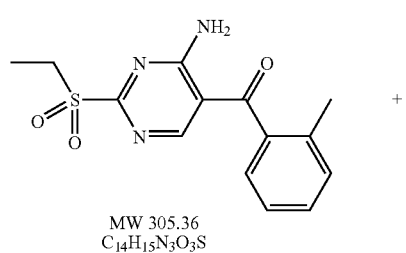

The same procedure as described in Example 9 was used, starting from (4-amino-2-ethanesulfonyl-pyrimidin-5-yl)-o-tolyl-methanone, Example 32, to give 4-[4-amino-5-(2-methyl-benzoyl)-pyrimidin-2-ylamino]-piperidine-1-carboxylic acid ethyl ester as a white solid. HRMS, observed: 384.2035; Calcd for $(M+H)^+$: 384.2030.

Example 36

(4-Amino-2-ethylsulfanyl-pyrimidin-5-yl)-(2-fluorophenyl)-methanone

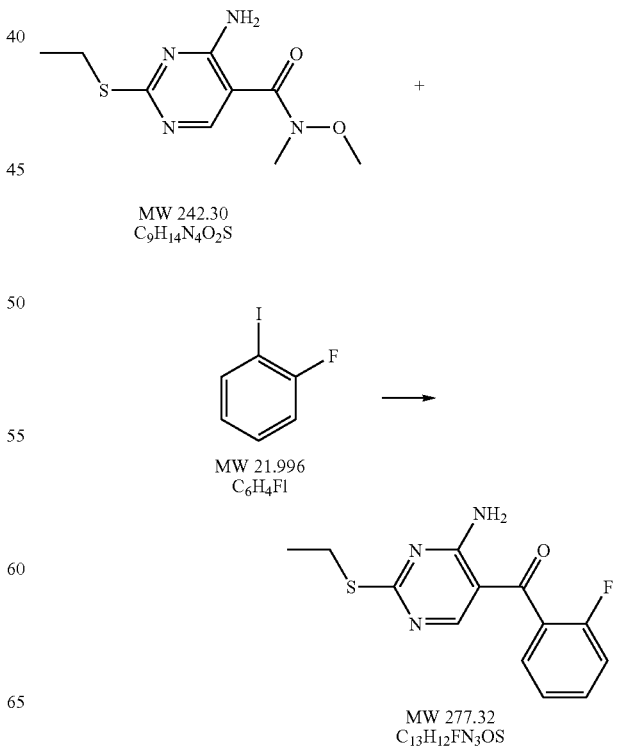

The same procedure was used as described in Example 2, starting from 4-amino-2-ethylsulfanyl-pyrimidine-5-carboxylic acid methoxy-methylamide (from Example 1) and a solution of 2-fluorophenyllithium (~3 equiv, freshly prepared from 1-fluoro-2-iodobenzene as in Example 2A), to give (4-amino-2-ethylsulfanyl-pyrimidin-5-yl)-(2-fluorophenyl)-methanone. MS (M+H)+: 278.

Example 37

(4-Amino-2-ethanesulfonyl-pyrimidin-5-yl)-(2-fluoro-phenyl)-methanone

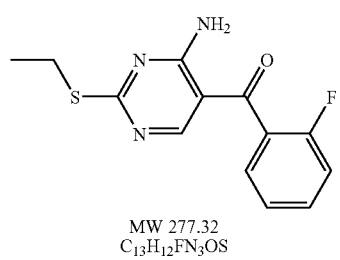

MW 277.32
C13H12FN3OS

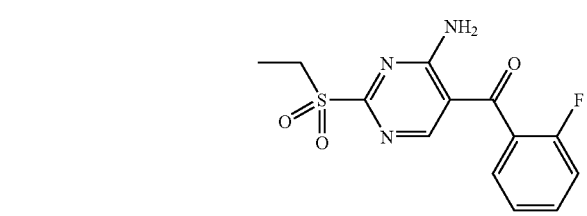

The same procedure as described in Example 3 was used, starting from (4-amino-2-ethylsulfanyl-pyrimidin-5-yl)-(2-fluoro-phenyl)-methanone, Example 36, to give (4-amino-2-ethanesulfonyl-pyrimidin-5-yl)-(2-fluoro-phenyl)-methanone as a white solid. MS (M+H)+: 310.

Example 38

[4-Amino-2-[4-(4-methyl-piperazin-1-yl)-phenylamino]-pyrimidin-5-y]-(2-fluoro-phenyl)-methanone

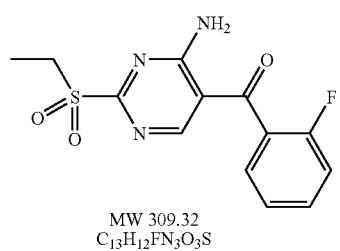

MW 309.32
C13H12FN3O3S

+

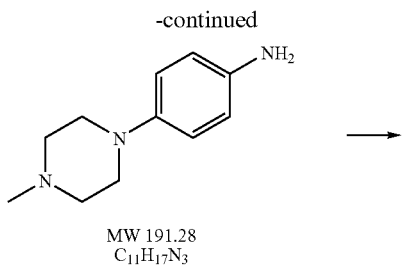

MW 191.28
C11H17N3

→

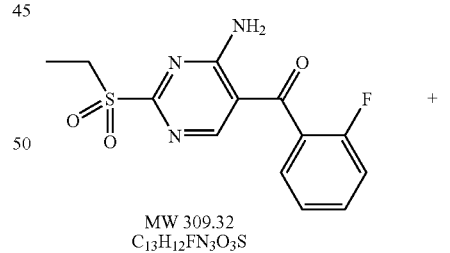

MW 406.46
C22H23FN6O

The same procedure as described in Example 7 was used, starting from (4-amino-2-ethanesulfonyl-pyrimidin-5-yl)-(2-fluoro-phenyl)-methanone, Example 37, to give [4-amino-2-[4-(4-methyl-piperazin-1-yl)-phenylamino]-pyrimidin-5-yl]-(2-fluoro-phenyl)-methanone. MS (M+H)+ 407.

Example 39

[4-Amino-2-[4-(4-isopropyl-piperazin-1-yl)-phenylamino]-pyrimidin-5-yl]-(2-fluoro-phenyl)-methanone

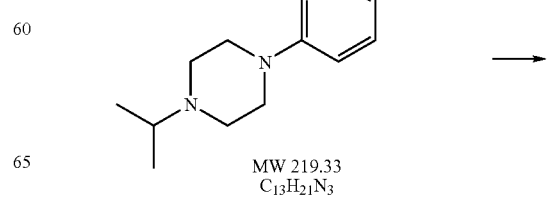

MW 309.32
C13H12FN3O3S

+

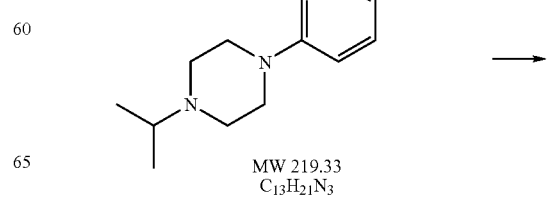

MW 219.33
C13H21N3

→

-continued

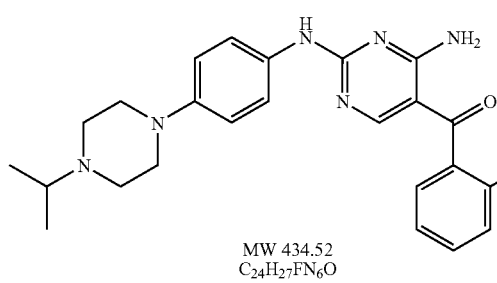

MW 434.52
C$_{24}$H$_{27}$FN$_6$O

The same procedure as described in Example 8 was used, starting from (4-amino-2-ethanesulfonyl-pyrimidin-5-yl)-(2-fluoro-phenyl)-methanone, Example 37, to give [4-amino-2-[4-(4-isopropyl-piperazin-1-yl)-phenylamino]-pyrimidin-5-yl]-(2-fluoro-phenyl)-methanone. MS (M+H)$^+$, 435.

Example 40

4-[4-Amino-5-(2-fluoro-benzoyl)-pyrimidin-2-ylamino]-piperidine-1-carboxylic acid ethyl ester

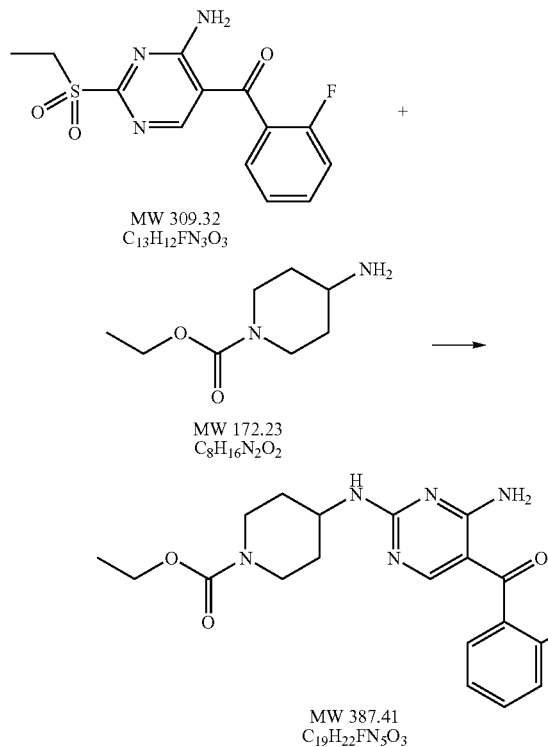

The same procedure as described in Example 9 was used, starting from (4-amino-2-ethanesulfonyl-pyrimidin-5-yl)-(2-fluoro-phenyl)-methanone, Example 37, to give 4-[4-amino-5-(2-fluoro-benzoyl)-pyrimidin-2-ylamino]-piperidine-1-carboxylic acid ethyl ester as a white solid. MS (M+H)$^+$, 388.

Example 41

[4-Amino-2-(1-methanesulfonyl-piperidin-4-ylamino)-pyrimidin-5-yl]-(2-fluoro-phenyl)-methanone

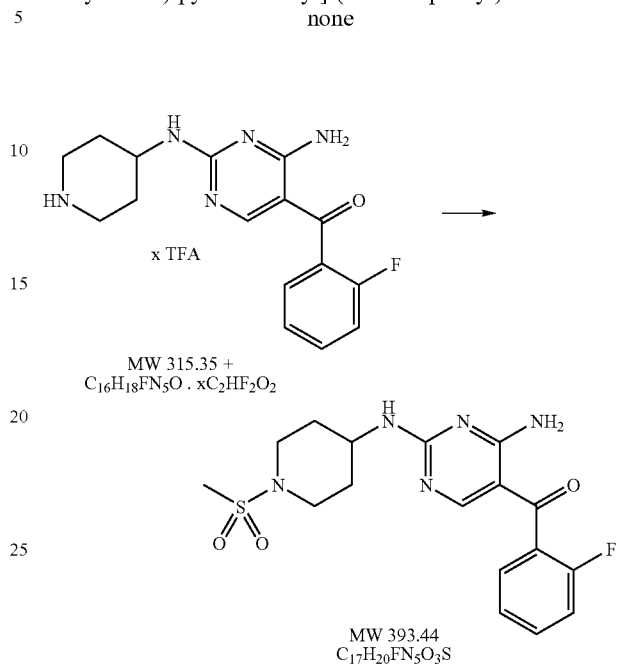

[4-amino-2-(piperidin-4-ylamino)-pyrimidin-5-yl]-(2-fluoro-phenyl)-methanone, Example 151, was treated as described in Example 28 to give [4-amino-2-(1-methanesulfonyl-piperidin-4-ylamino)-pyrimidin-5-yl]-(2-fluoro-phenyl)-methanone. MS (M+H)$^+$, 394.

Example 42

[4-Amino-2-(1-ethanesulfonyl-piperidin-4-ylamino)-pyrimidin-5-yl]-(2-fluoro-phenyl)-methanone

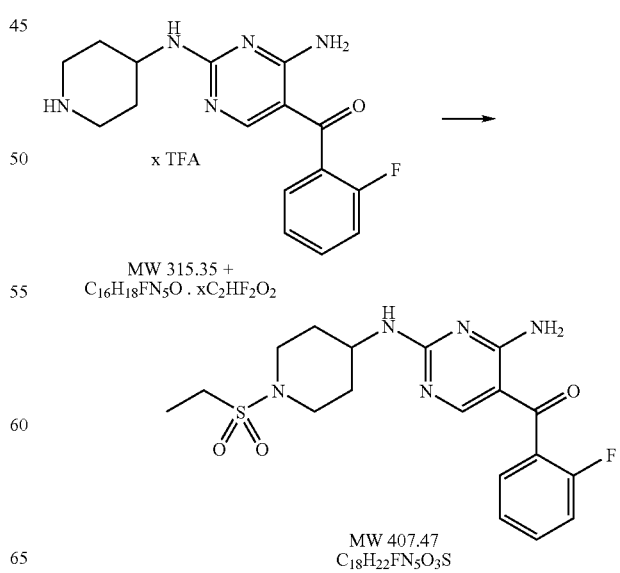

The same procedure as described in Example 29 was used, starting from [4-amino-2-(piperidin-4-ylamino)-pyrimidin-5-yl]-(2-fluoro-phenyl)-methanone, Example 151, to give [4-amino-2-(1-ethanesulfonyl-piperidin-4-ylamino)-pyrimidin-5-yl]-(2-fluoro-phenyl)-methanone. MS (M+H)$^+$, 408.

Example 43

(4-Amino-2-ethylsulfanyl-pyrimidin-5-yl)-(2-trifluoromethyl-phenyl)-methanon

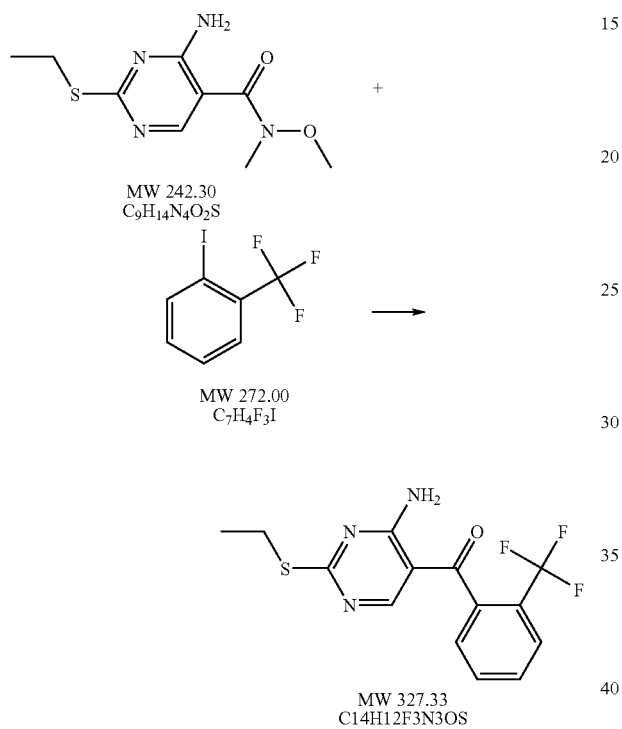

The same procedure was used as described in Example 2, starting from 4-amino-2-ethylsulfanyl-pyrimidine-5-carboxylic acid methoxy-methylamide (from Example 1) and a solution of 2-trifluoromethylphenyllithium (~3 equiv, freshly prepared from 1-iodo-2-trifluoromethylbenzene as in Example 2A), to give (4-Amino-2-ethylsulfanyl-pyrimidin-5-yl)-(2-trifluoromethyl-phenyl)-methanone. MS (M+H)$^+$: 328.

Example 44

(4-Amino-2-ethanesulfonyl-pyrimidin-5-yl)-(2-trifluoromethyl-phenyl)-methanone

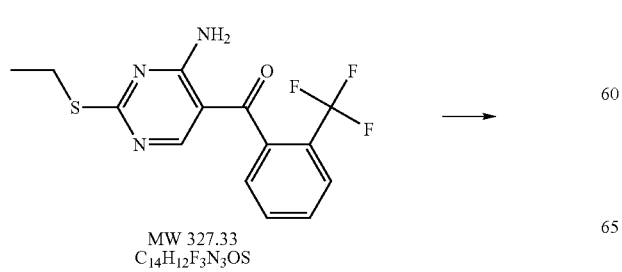

-continued

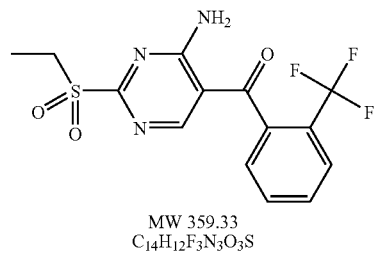

The same procedure as described in Example 3 was used, starting from (4-amino-2-ethylsulfanyl-pyrimidin-5-yl)-(2-trifluoromethyl-phenyl)-methanone, Example 43, to give (4-amino-2-ethanesulfonyl-pyrimidin-5-yl)-(2-trifluoromethyl-phenyl)-methanone as a white solid. MS (M+H)$^+$: 360.

Example 45

[4-Amino-2-[4-(4-methyl-piperazin-1-yl)-phenylamino]-pyrimidin-5-yl]-(2-trifluoromethyl-phenyl)-methanone

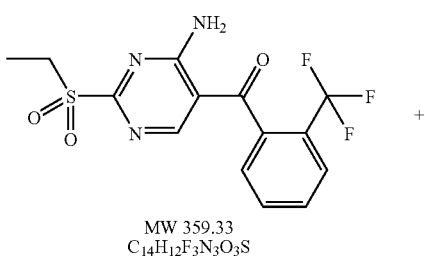

The same procedure as described in Example 7 was used, starting from (4-amino-2-ethylsulfanyl-pyrimidin-5-yl)-(2-trifluoromethyl-phenyl)-methanone, Example 43, to give [4-amino-2-[4-(4-methyl-piperazin-1-yl)-phenylamino]-pyrimidin-5-yl]-(2-trifluoromethyl-phenyl)-methanone. MS (M+H)$^+$, 457.

Example 46

[4-Amino-2-[4-(4-isopropyl-piperazin-1-yl)-phenylamino]-pyrimidin-5-yl]-(2-trifluoromethyl-phenyl)-methanone

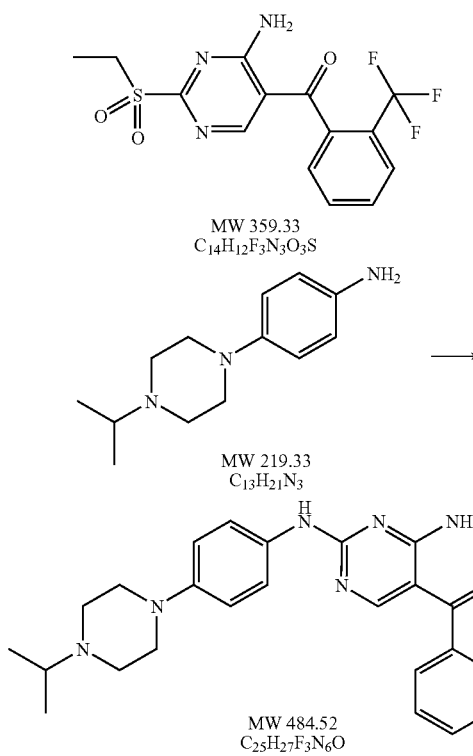

The same procedure as described in Example 8 was used, starting from (4-amino-2-ethylsulfanyl-pyrimidin-5-yl)-(2-trifluoromethyl-phenyl)-methanone, Example 43, to give [4-amino-2-[4-(4-isopropyl-piperazin-1-yl)-phenylamino]-pyrimidin-5-yl]-(2-trifluoromethyl-phenyl)-methanone. MS (M+H)$^+$, 485

Example 47

(4-Amino-2-ethylsulfanyl-pyrimidin-5-yl)-(5-fluoro-2-methoxy-phenyl)-methanone

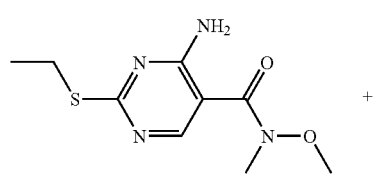

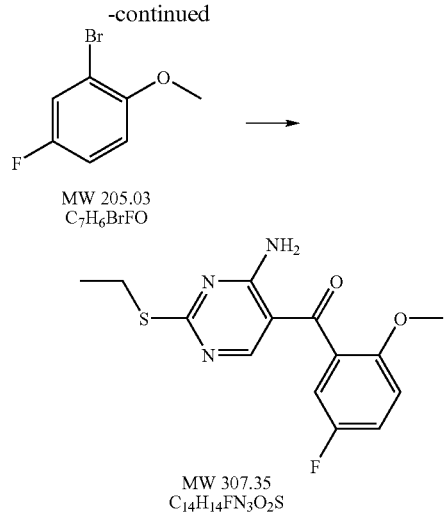

A solution of 4-amino-2-ethylsulfanyl-pyrimidine-5-carboxylic acid methoxy-methylamide (400 mg, 1.65 mmol, Example 1) was dissolved in anhydrous tetrahydrofuran (6 mL) and cooled to −78° C. A solution of the freshly prepared 2-methoxyl-5-fluorophenyl lithium (~5 equiv, prepared following the same procedure as described in Step A of Example 2) was added over 10–30 minutes and the orange colored reaction mixture was stirred at −78 to 0° C. for 1–3 hours until the complete consumption of the starting material. The resulting mixture was quenched with aqueous ammonium chloride solution, extracted with ethyl acetate (3×20 mL), washed with brine (2×10 mL), dried over sodium sulfate and evaporated in vacuo. The residue was purified on silica gel with 80/20→60/40 of hexane/ethyl acetate to give (4-amino-2-ethylsulfanyl-pyrimidin-5-yl)-(5-fluoro-2-methoxy-phenyl)-methanone as a white solid (277 mg). MS (M+H)$^+$, 308.

Example 48

(4-Amino-2-ethanesulfonyl-pyrimidin-5-yl)-(5-fluoro-2-methoxy-phenyl)-methanone

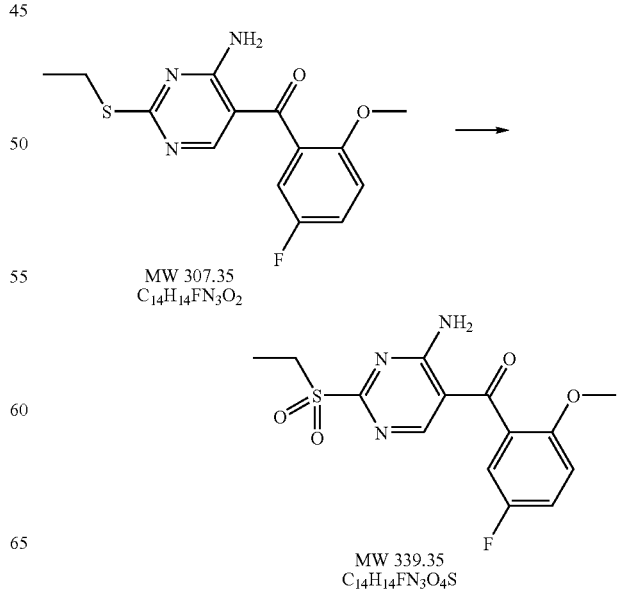

The same procedure as described in Example 3 was used, starting with (4-amino-2-ethylsulfanyl-pyrimidin-5-yl)-(5-fluoro-2-methoxy-phenyl)-methanone, Example 47, to give (4-amino-2-ethanesulfonyl-pyrimidin-5-yl)-(5-fluoro-2-methoxy-phenyl)-methanone as a white solid. MS (M+H)+: 340.

Example 49

[4-Amino-2-[4-(4-methyl-piperazin-1-yl)-phenylamino]-pyrimidin-5-yl]-(5-fluoro-2-methoxy-phenyl)-methanone

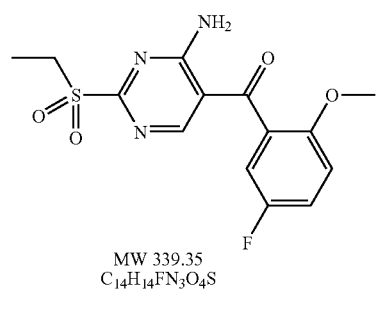

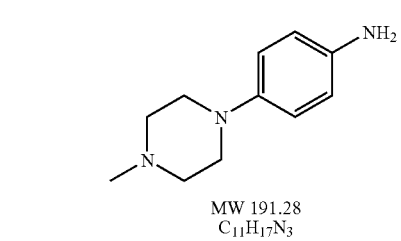

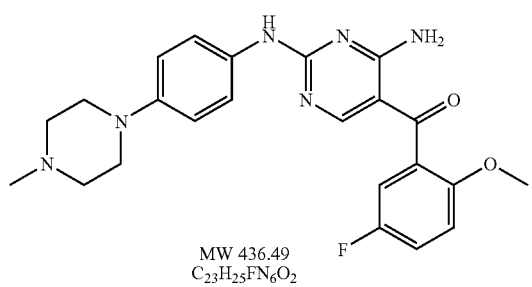

The same procedure as described in Example 7 was used, starting with (4-amino-2-ethylsulfanyl-pyrimidin-5-yl)-(5-fluoro-2-methoxy-phenyl)-methanone, Example 47, to give [4-amino-2-[4-(4-methyl-piperazin-1-yl)-phenylamino]-pyrimidin-5-yl]-(5-fluoro-2-methoxy-phenyl)-methanone. MS (M+H)+, 437.

Example 50

[4-Amino-2-[4-(4-isopropyl-piperazin-1-yl)-phenylamino]-pyrimidin-5-yl]-(5-fluoro-2-methoxy-phenyl)-methanone The same procedure as described in Example 8 was used, starting with (4-amino-2-ethylsulfanyl-pyrimidin-5-yl)-(5-fluoro-2-methoxy-phenyl)-methanone, Example 47, to give [4-amino-2-[4-(4-isopropyl-piperazin-1-yl)-phenylamino]-pyrimidin-5-yl]-(5-fluoro-2-methoxy-phenyl)-methanone. MS (M+H)+: 465.

Example 51

4-[4-Amino-5-(5-fluoro-2-methoxy-benzoyl)-pyrimidin-2-ylamino]-piperidine-1-carboxylic acid ethyl ester

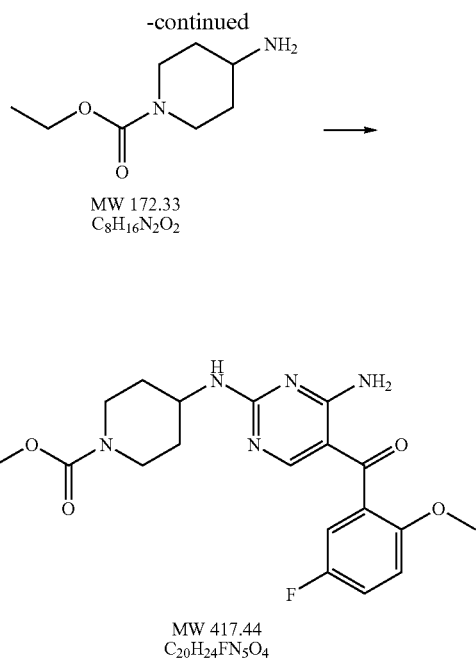

The same procedure as described in Example 9 was used, starting with (4-amino-2-ethylsulfanyl-pyrimidin-5-y)-(5-fluoro-2-methoxy-phenyl)-methanone, Example 47, to give 4-[4-amino-5-(5-fluoro-2-methoxy-benzoyl)-pyrimidin-2-ylamino]-piperidine-1-carboxylic acid ethyl ester as a white solid. MS (M+H)+, 418.

Example 52

3-[4-Amino-5-(2-methoxy-benzoyl)-pyrimidin-2-ylamino]-piperidine-1-carboxylic acid tert-butyl ester

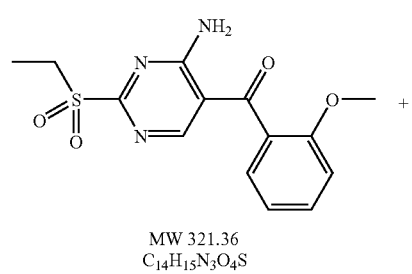

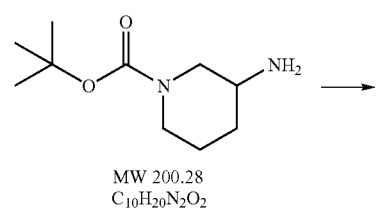

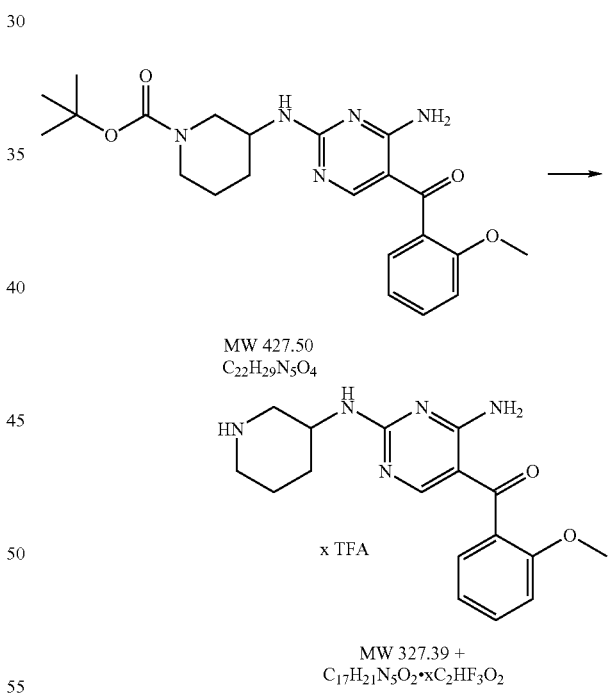

The same procedure was used as described in Example 9 starting from (4-amino-2-ethanesulfonylpyrimidin-5-yl)-(2-methoxyphenyl)-methanone, Example 6, and 3-amino-piperidine-1-carboxylic acid tert-butyl ester (Astatech) to give 3-[4-amino-5-(2-methoxy-benzoyl)-pyrimidin-2-ylamino]-piperidine-1-carboxylic acid tert-butyl ester. MS (M+H)+, 428.

Example 53

[4-Amino-2-(piperidin-3-ylamino)-pyrimidin-5-yl]-(2-methoxy-phenyl)-methanone

3-[4-Amino-5-(2-methoxy-benzoyl)-pyrimidin-2-ylamino]-piperidine-1-carboxylic acid tert-butyl ester (76 mg, Example 52) was dissolved in dichloromethane (4 mL), cooled to 0° C. and treated with trifluoroacetic acid (1 mL). After stirred 30 minutes at 0° C., the reaction mixture was concentrated in vacuo to give [4-amino-2-(piperidin-3-ylamino)-pyrimidin-5-yl]-(2-methoxy-phenyl)-methanone as a trifluoroacetic acid salt. A portion of this material was partitioned between ethyl acetate and aqueous sodium carbonate to give the free base. (129.5 mg). MS (M+H)+, 328.

Example 54

3-[4-Amino-5-(2-methoxy-benzoyl)-pyrimidin-2-ylamino]-piperidine-1-carboxylic acid methyl ester

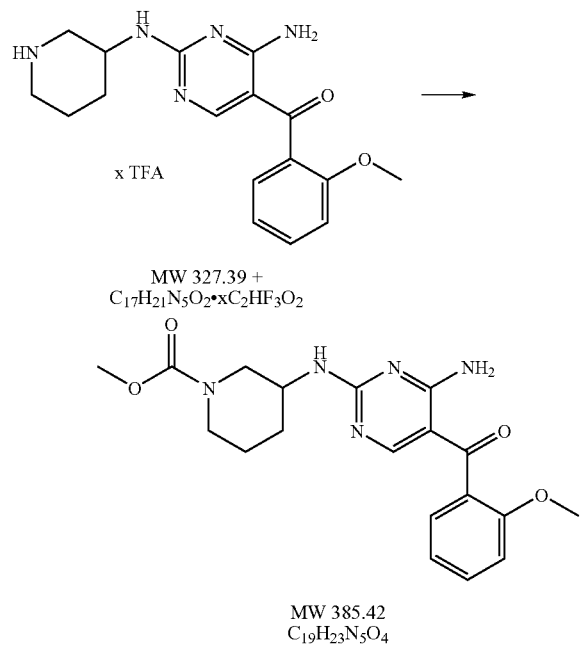

To a solution of [4-amino-2-(piperidin-3-ylamino)-pyrimidin-5-yl]-(2-methoxy-phenyl)-methanone trifluoroacetic acid salt (42 mg, Example 53) in dichloromethane (3 mL) were added triethylamine (48 mg, Aldrich) and methyl chloroformate (6.1 mg, Aldrich) at 0° C. After stirring for 1 hour at 0° C., the reaction mixture was concentrated in vacuo and crude product was purified on silica gel with 95:5 of dichloromethane/methanol to give 3-[4-amino-5-(2-methoxy-benzoyl)-pyrimidin-2-ylamino]-piperidine-1-carboxylic acid methyl ester (20.5 mg). MS (M+H)$^+$, 386. CDK4 IC$_{50}$=0.459 µM; CDK1 IC$_{50}$=0.469 µM; CDK2 IC$_{50}$=0.713 µM; HCT 116 IC$_{90}$=6.437 µM.

Example 55

3-[4-Amino-5-(2-methoxy-benzoyl)-pyrimidine-2-ylamino]-piperidine-1-carboxylic acid ethyl ester

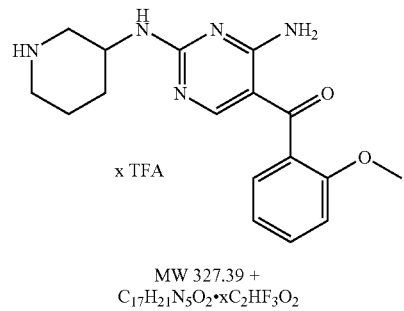

-continued

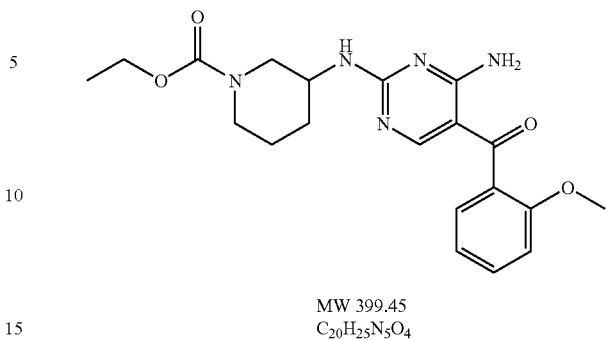

The same procedure as described in Example 54 was used, starting with [4-amino-2-(piperidin-3-ylamino)-pyrimidin-5-yl]-(2-methoxy-phenyl)-methanone trifluoroacetic acid salt, Example 53, and ethyl chloroformate (Aldrich) to give 3-[4-amino-5-(2-methoxy-benzoyl)-pyrimidin-2-ylamino]-piperidine-1-carboxylic acid ethyl ester. MS (M+H)$^+$, 400.

Example 56

1-[3-[4-Amino-5-(2-methoxy-benzoyl)-pyrimidin-2-ylamino]-piperidin-1-yl]-ethanone

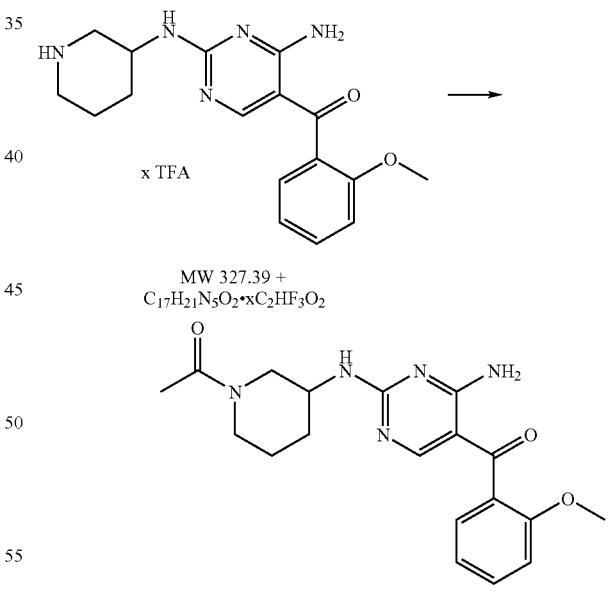

The same procedure as described in Example 20 was used, starting with [4-amino-2-(piperidin-3-ylamino)-pyrimidin-5-yl]-(2-methoxy-phenyl)-methanone trifluoroacetic acid salt, Example 53, to give 1-[3-[4-amino-5-(2-methoxy-benzoyl)-pyrimidin-2-ylamino]-piperidin-1-yl]-ethanone. MS (M+H)$^+$, 370.

Example 57

4-[4-Amino-5-(2-methoxy-benzoyl)-pyrimidin-2-ylamino]-piperidine-1-carboxylic acid dimethylamide

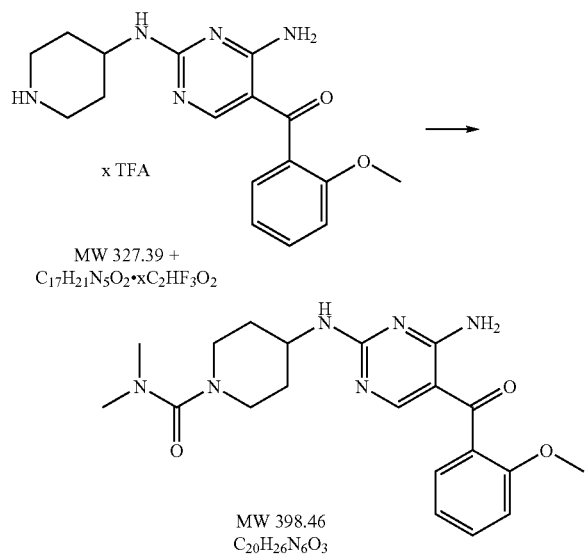

The same procedure as described in Example 25 was used, starting with [4-amino-2-(piperidin-3-ylamino)-pyrimidin-5-yl]-(2-methoxy-phenyl)-methanone trifluoroacetic acid salt, Example 53, and dimethylcarbamyl chloride (Aldrich) to give 4-[4-amino-5-(2-methoxy-benzoyl)-pyrimidin-2-ylamino]-piperidine-1-carboxylic acid dimethylamide. MS (M+H)+, 399.

Example 58

4-[4-Amino-5-(5-fluoro-2-methoxy-benzoyl)-pyrimidin-2-ylamino]-piperidine-1-carboxylic acid tert-butyl ester

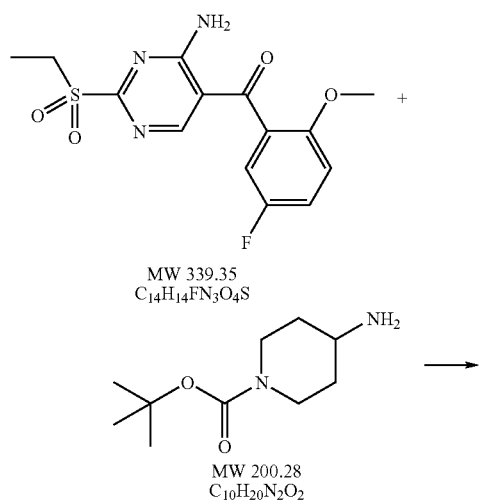

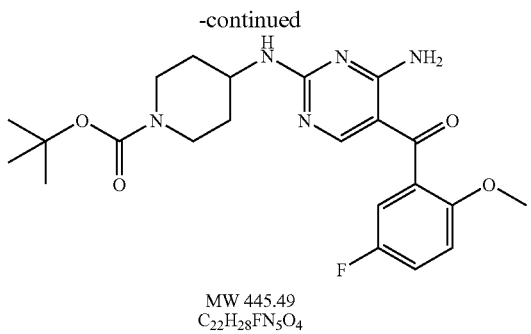

The same procedure was used as described in Example 10 starting from (4-amino-2-ethanesulfonyl-pyrimidin-5-yl)-(5-fluoro-2-methoxy-phenyl)-methanone (1.01 g, 2.979 mmol, Example 48), to give 4-[4-amino-5-(5-fluoro-2-methoxy-benzoyl)-pyrimidin-2-ylamino]-piperidine-1-carboxylic acid tert-butyl ester (921.7 mg) (which is the same compound that is prepared according to the process of Example 164). MS (M+H)+, 446.

Example 59

[4-Amino-2-(piperidin-4-ylamino)-pyrimidin-5-yl]-(5-fluoro-2-methoxy-phenyl)-methanone

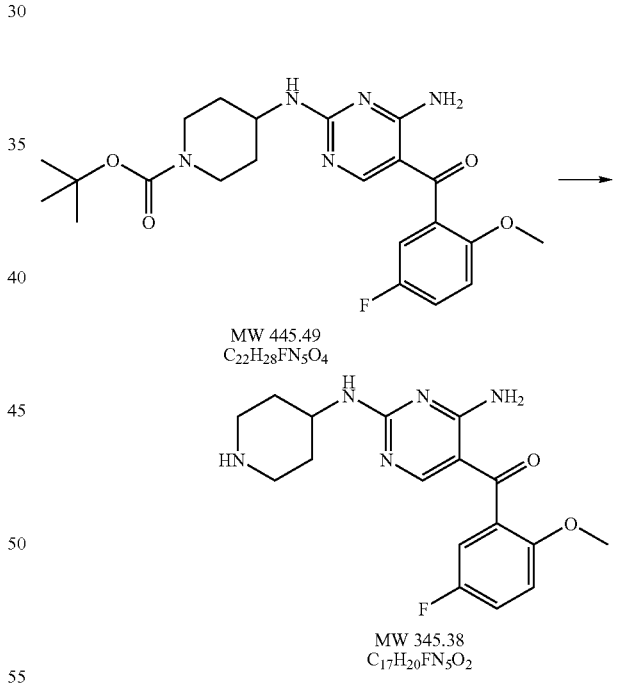

4-[4-Amino-(5-fluoro-2-methoxy-benzoyl)-pyrimidin-2-ylamino]-piperidine-1-carboxylic acid tert-butyl ester (839.6 mg, Example 58) was dissolved in dichloromethane (11 mL), cooled to 0° C. and treated with trifluoroacetic acid (5.5 mL). After stirring ~1 minute at 0° C., the reaction mixture was concentrated in vacuo to give the product as a trifluoroacetic acid salt (1.76 g). A portion of this salt (1.00 g) was dissolved in ethyl acetate, neutralized with excess aqueous sodium carbonate solution, washed with brine, dried and concentrated in vacuo to give [4-amino-2-(piperidin-4-ylamino)-pyrimidin-5-yl]-(5-fluoro-2-methoxy-phenyl)-methanone (423.7 mg). MS (M+H)+, 346.

Example 60

4-[4-Amino-5-(5-fluoro-2-methoxy-benzoyl)-pyrimidin-2-ylamino]-piperidine-1-carboxylic acid methyl ester

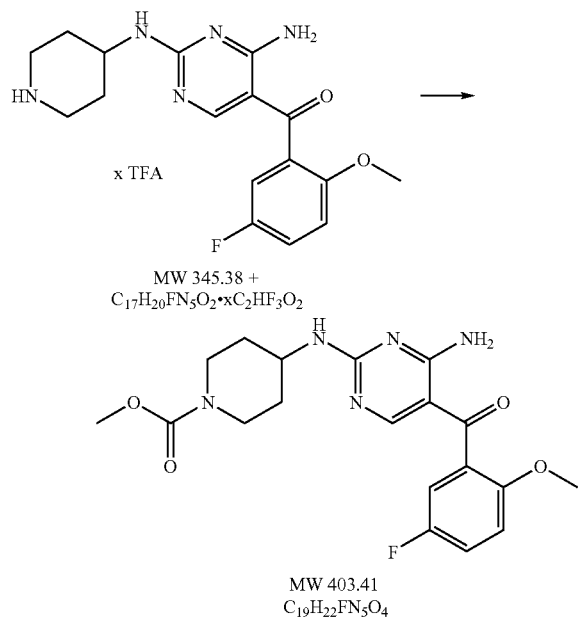

MW 345.38 +
$C_{17}H_{20}FN_5O_2 \cdot xC_2HF_3O_2$

MW 403.41
$C_{19}H_{22}FN_5O_4$

To a solution of [4-amino-2-(piperidin-4-ylamino)-pyrimidin-5-yl]-(5-fluoro-2-methoxy-phenyl)-methanone as a trifluoroacetic acid salt (57.1 mg, Example 59) in dichloromethane (2 mL) were added triethylamine (58 mg, 8 equiv, Aldrich) and methyl chloroformate (6.7 mg, 1 equiv, Aldrich) at 0° C. After stirring for ~2 hours at 0° C., the reaction mixture was concentrated in vacuo and crude product was purified on silica gel with 95:5 of dichloromethane/methanol to give 4-[4-amino-5-(5-fluoro-2-methoxy-benzoyl)-pyrimidin-2-ylamino]-piperidine-1-carboxylic acid methyl ester (23.7 mg). MS (M+H)+, 404.

Example 61

4-[4-Amino-5-(5-fluoro-2-methoxy-benzoyl)-pyrimidin-2-ylamino]-piperidine-1-carboxylic acid propyl ester

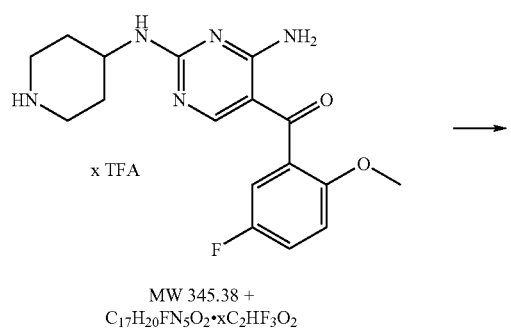

MW 345.38 +
$C_{17}H_{20}FN_5O_2 \cdot xC_2HF_3O_2$

-continued

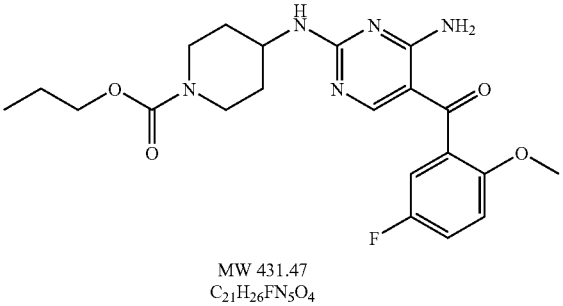

MW 431.47
$C_{21}H_{26}FN_5O_4$

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and propyl chloroformate (Aldrich) to give 4-[4-amino-5-(5-fluoro-2-methoxy-benzoyl)-pyrimidin-2-ylamino]-piperidine-1-carboxylic acid propyl ester. MS (M+H)+, 432.

Example 62

1-[4-[4-Amino-5-(5-fluoro-2-methoxy-benzoyl)-pyrimidin-2-ylamino]-1-yl]-ethanone

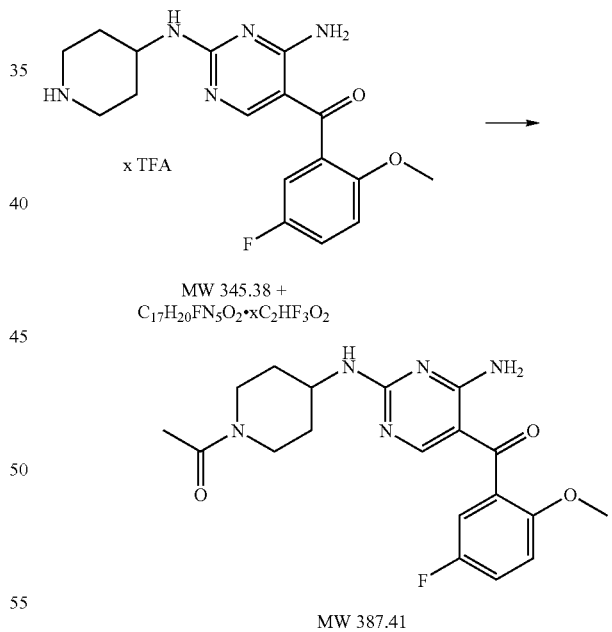

MW 345.38 +
$C_{17}H_{20}FN_5O_2 \cdot xC_2HF_3O_2$

MW 387.41
$C_{19}H_{22}FN_5O_3$

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and acetyl chloride (Aldrich) to give 1-[4-[4-amino-5-(5-fluoro-2-methoxy-benzoyl)-pyrimidin-2-ylamino]-piperidin-1-yl]-ethanone. MS (M+H)+, 388.

Example 63

1-[4-[4-Amino-5-(5-fluoro-2-methoxy-benzoyl)-pyrimidin-2-ylamino]-piperidin-1-yl]-propan-1-one

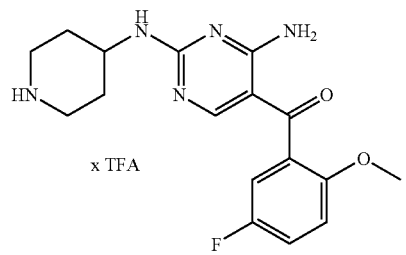

MW 345.38 +
$C_{17}H_{20}FN_5O_2 \cdot xC_2HF_3O_2$

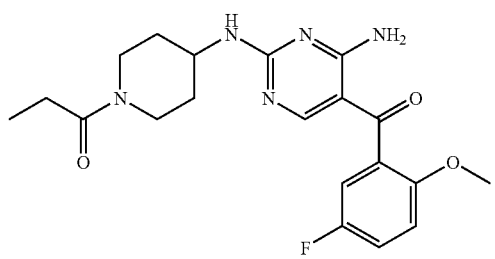

MW 401.44
$C_{20}H_{24}FN_5O_3$

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and propionyl chloride (Aldrich) to give 1-[4-[4-amino-5-(5-fluoro-2-methoxy-benzoyl)-pyrimidin-2-ylamino]-piperidin-1-yl]-propan-1-one. MS (M+H)$^+$, 402.

Example 64

1-[4-[4-Amino-5-(5-fluoro-2-methoxy-benzoyl)-pyrimidin-2-ylamino]-piperidin-1-yl]-butan-1-one

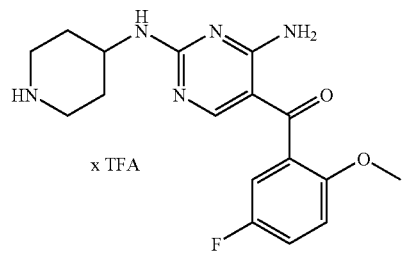

MW 345.38 +
$C_{17}H_{20}FN_5O_2 \cdot xC_2HF_3O_2$

-continued

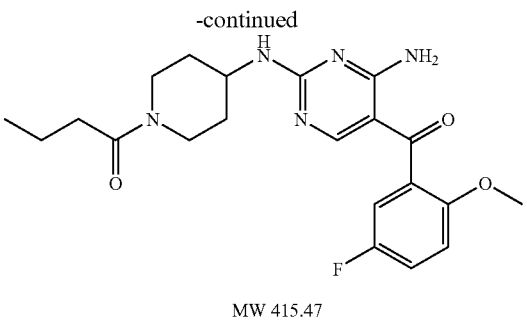

MW 415.47
$C_{21}H_{26}FN_5O_3$

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and butyryl chloride (Aldrich) to give 1-[4-[4-amino-5-(5-fluoro-2-methoxy-benzoyl)-pyrimidin-2-ylamino]-piperidin-1-yl]-butan-1-one. MS (M+H)$^+$, 416.

Example 65

[4-Amino-2-(1-methanesulfonyl-piperidin-4-ylamino)-pyrimidin-5-yl]-(5-fluoro-2-methoxy-phenyl)-methanone

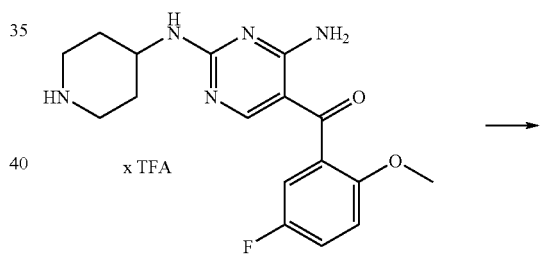

MW 345.38 +
$C_{17}H_{20}FN_5O_2 \cdot xC_2HF_3O_2$

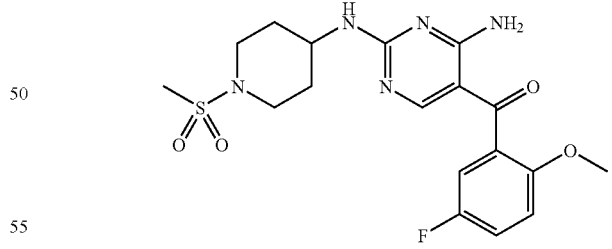

MW 423.47
$C_{18}H_{22}FN_5O_4S$

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and methanesulfonyl chloride (Aldrich), to give [4-amino-2-(1-methanesulfonylpiperidin-4-ylamino)-pyrimidin-5-yl]-(5-fluoro-2-methoxy-phenyl)-methanone. MS (M+H)⁺, 424.

Example 66

[4-Amino-2-(1-ethanesulfonyl-piperidin-4-ylamino)-pyrimidin-5-yl]-(5-fluoro-2-methoxy-phenyl)-methanone

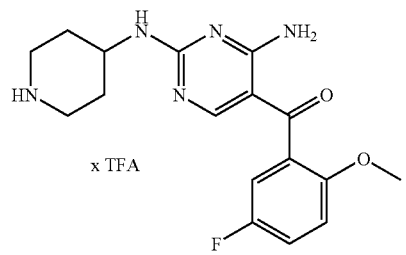

MW 345.38 +
C₁₇H₂₀FN₅O₂·xC₂HF₃O₂

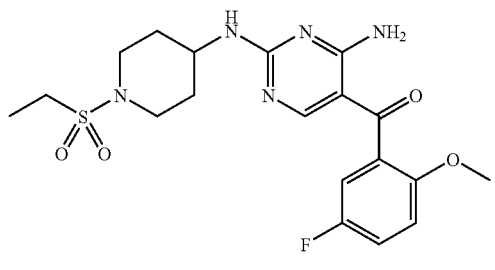

MW 437.49
C₁₉H₂₄FN₅O₄S

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and ethanesulfonyl chloride (Aldrich), to give [4-amino-2-(1-ethanesulfonyl-piperidin-4-ylamino)-pyrimidin-5-yl]-(5-fluoro-2-methoxy-phenyl)-methanone. MS (M+H)⁺, 438.

Example 67

[4-Amino-2-[1-(propane-1-sulfonyl)-piperidin-4-ylamino]-pyrimidin-5-yl]-(5-fluoro-2-methoxy-phenyl)-methanone

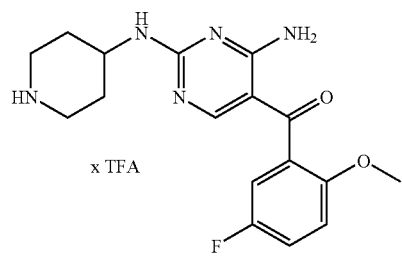

MW 345.38 +
C₁₇H₂₀FN₅O₂·xC₂HF₃O₂

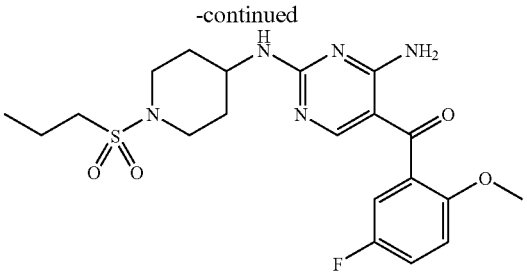

MW 451.52
C₂₀H₂₆FN₅O₄S

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and 1-propanesulfonyl chloride (Aldrich), to give [4-amino-2-[1-(propane-1-sulfonyl)-piperidin-4-ylamino]-pyrimidin-5-yl]-(5-fluoro-2-methoxy-phenyl)-methanone. MS (M+H)⁺, 452.

Example 68

[4-Amino-2-(1-trifluoromethanesulfonyl-piperidin-4-ylamino)-pyrimidin-5-yl]-(5-fluoro-2-methoxy-phenyl)-methanone

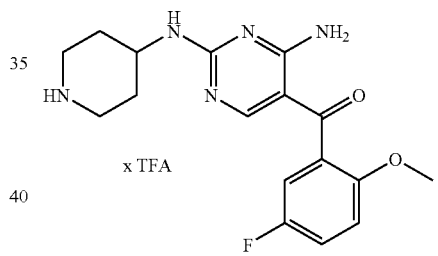

MW 345.38 +
C₁₇H₂₀FN₅O₂·xC₂HF₃O₂

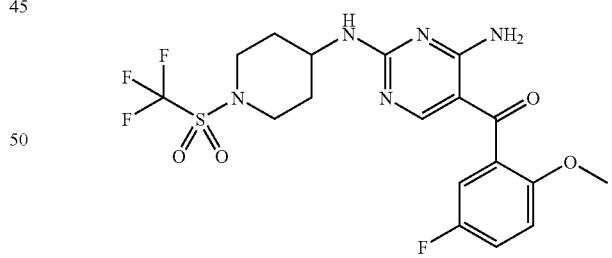

MW 477.44
C₁₈H₁₉F₄N₅O₄S

The same procedure as described in Example 60 was used, starting from [4-amino-2-(piperidin-4-ylamino)-pyrimidin-5-yl]-(5-fluoro-2-methoxy-phenyl)-methanone trifluoroacetic acid salt, Example 59, and trifluoromethanesulfonyl chloride (Aldrich), to give [4-amino-2-(1-trifluoromethanesulfonyl-piperidin-4-ylamino)-pyrimidin-5-yl]-(5-fluoro-2-methoxy-phenyl)-methanone. MS (M+H)⁺, 478.

Example 69

(R)-3-[4-Amino-5-(5-fluoro-2-methoxy-benzoyl)-pyrimidin-2-ylamino]-pyrrolidine-1-carboxylic acid tert-butyl ester

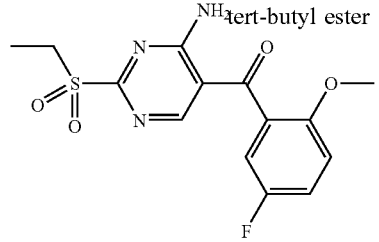

MW 339.35
$C_{14}H_{14}FN_3O_4S \cdot xC_2HF_3O_2$

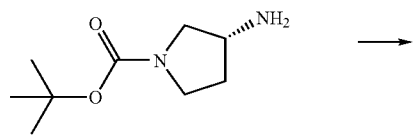

MW 186.25
$C_9H_{18}N_2O_2$

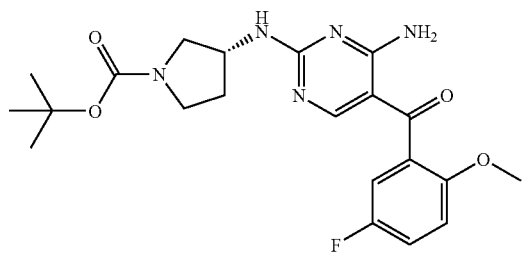

MW 431.47
$C_{21}H_{26}FN_5O_4$

The same procedure was used as described in Example 9 starting from (4-amino-2-ethanesulfonyl-pyrimidin-5-yl)-(5-fluoro-2-methoxy-phenyl)-methanone (400 mg, 1.18 mmol, Example 48) and (R)-3-amino-pyrrolidine-1-carboxylic acid tert-butyl ester (233 mg, 1.25 mmol, Astatech), to give (R)-3-[4-amino-5-(5-fluoro-2-methoxy-benzoyl)-pyrimidin-2-ylamino]-pyrrolidine-1-carboxylic acid tert-butyl ester (447 mg). MS $(M+H)^+$, 432.

Example 70

(R)-[4-Amino-2-(pyrrolidin-3-ylamino)-pyrimidin-5-yl]-(5-fluoro-2-methoxy-phenyl)-methanone

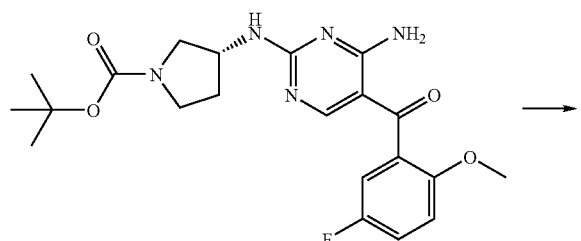

MW 431.47
$C_{21}H_{26}FN_5O_4$

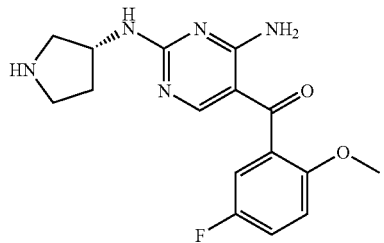

MW 331.35
$C_{16}H_{18}FN_5O_2$

The same procedure as described in Example 59 was used, starting from (R)-3-[4-amino-5-(5-fluoro-2-methoxy-benzoyl)-pyrimidin-2-ylamino]-pyrrolidine-1-carboxylic acid tert-butyl ester, Example 69, to give (R)-[4-amino-2-(pyrrolidin-3-ylamino)-pyrimidin-5-yl]-(5-fluoro-2-methoxy-phenyl)-methanone as a trifluoroacetic acid salt, and also as the free base. MS $(M+H)^+$, 332.

Example 71

(R)-3-[4-Amino-5-(5-fluoro-2-methoxy-benzoyl)-pyrimidin-2-ylamino]-pyrrolidine-1-carboxylic acid methyl ester

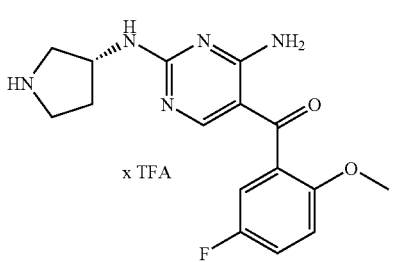

MW 331.35 +
$C_{16}H_{18}FN_5O_2 \cdot xC_2HF_3O_2$

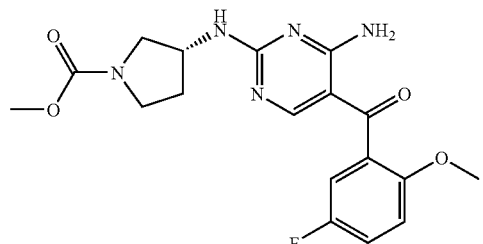

MW 389.39
$C_{18}H_{20}FN_5O_4$

The same procedure as described in Example 60 was used starting from (R)-[4-amino-2-(pyrrolidin-3-ylamino)-pyrimidin-5-yl]-(5-fluoro-2-methoxy-phenyl)-methanone trifluoroacetic acid salt, Example 70, to give (R)-3-[4-amino- 5-(5-fluoro-2-methoxy-benzoyl)-pyrimidin-2-ylamino]-pyrrolidine-1-carboxylic acid methyl ester. MS (M+H)+, 390.

Example 72

(R)-3-[4-Amino-5-(5-fluoro-2-methoxy-benzoyl)-pyrimidin-2-ylamino]-pyrrolidine-1-carboxylic acid ethyl ester

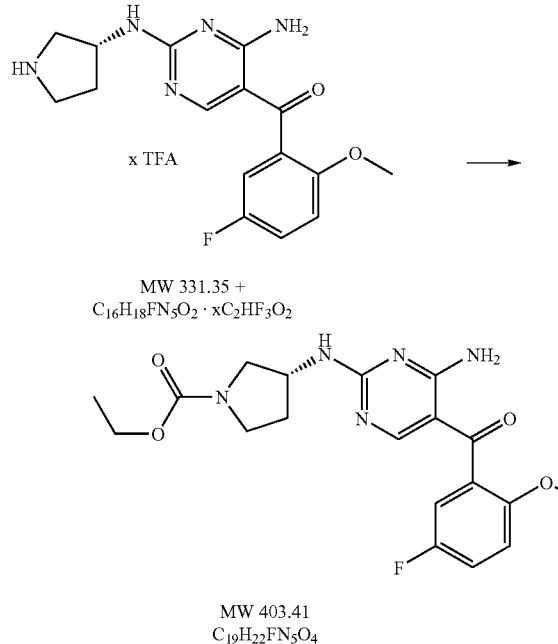

MW 331.35 +
C$_{16}$H$_{18}$FN$_5$O$_2$ · xC$_2$HF$_3$O$_2$

MW 403.41
C$_{19}$H$_{22}$FN$_5$O$_4$

The same procedure as described in Example 60 was used, starting from (R)-[4-amino-2-(pyrrolidin-3-ylamino)-pyrimidin-5-yl]-(5-fluoro-2-methoxy-phenyl)-methanone trifluoroacetic acid salt, Example 70, and ethyl chloroformate (Aldrich) to give (R)-3-[4-amino-5-(5-fluoro-2-methoxy-benzoyl)-pyrimidin-2-ylamino]-pyrrolidine-1-carboxylic acid ethyl ester. MS (M+H)+, 404.

Example 73

(R)-1-[3-[4-Amino-5-(5-fluoro-2-methoxy-benzoyl)-pyrimidin-2-ylamino]-pyrrolidin-1-yl]-ethanone

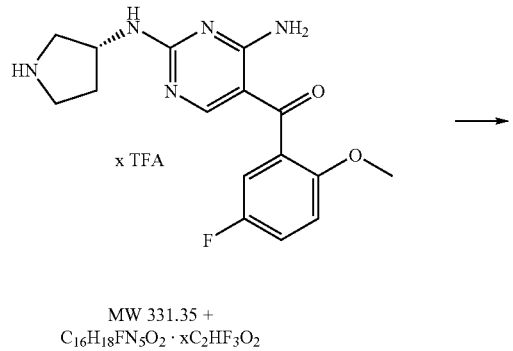

MW 331.35 +
C$_{16}$H$_{18}$FN$_5$O$_2$ · xC$_2$HF$_3$O$_2$

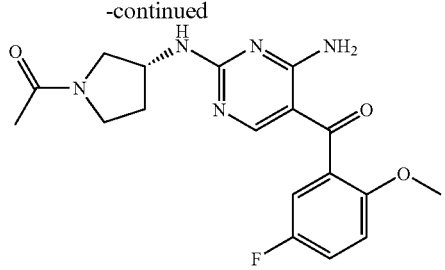

MW 373.39
C$_{18}$H$_{20}$FN$_5$O$_3$

The same procedure as described in Example 62 was used starting from (R)-[4-amino-2-(pyrrolidin-3-ylamino)-pyrimidin-5-yl]-(5-fluoro-2-methoxy-phenyl)-methanone trifluoroacetic acid salt, Example 70, to give (R)-1-[3-[4-amino-5-(5-fluoro-2-methoxy-benzoyl)-pyrimidin-2-ylamino]-pyrrolidin-1-yl]-ethanone. MS (M+H)+, 374

Example 74

(R)-1-[3-[4-Amino-5-(5-fluoro-2-methoxy-benzoyl)-pyrimidin-2-ylamino]-pyrrolidin-1-yl]-propan-1-one

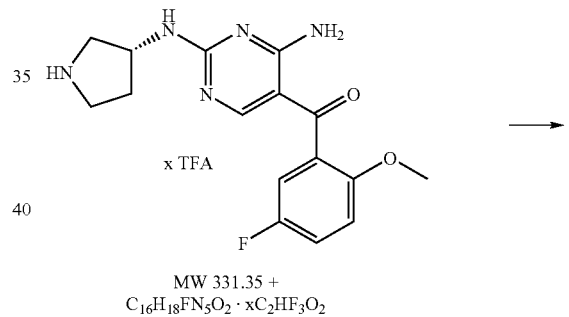

MW 331.35 +
C$_{16}$H$_{18}$FN$_5$O$_2$ · xC$_2$HF$_3$O$_2$

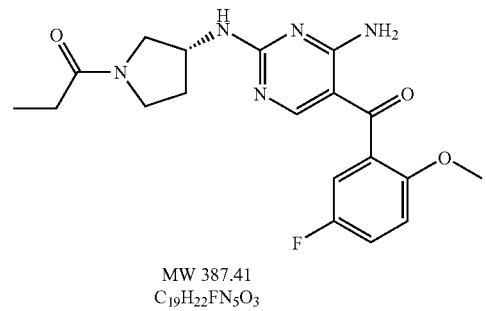

MW 387.41
C$_{19}$H$_{22}$FN$_5$O$_3$

The same procedure as described in Example 63 was used starting from (R)-[4-amino-2-(pyrrolidin-3-ylamino)-pyrimidin-5-yl]-(5-fluoro-2-methoxy-phenyl)-methanone trifluoroacetic acid salt, Example 70, to give (R)-1-[3-[4-amino-5-(5-fluoro-2-methoxy-benzoyl)-pyrimidin-2-ylamino]-pyrrolidin-1-yl]-propan-1-one. MS (M+H)+, 388.

Example 75

(R)-[4-Amino-2-(1-methanesulfonyl-pyrrolidin-3-ylamino)-pyrimidin-5-yl]-(5-fluoro-2-methoxy-phenyl)-methanone

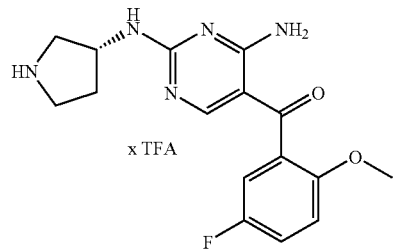

x TFA

MW 331.35 +
$C_{16}H_{18}FN_5O_2 \cdot xC_2HF_3O_2$

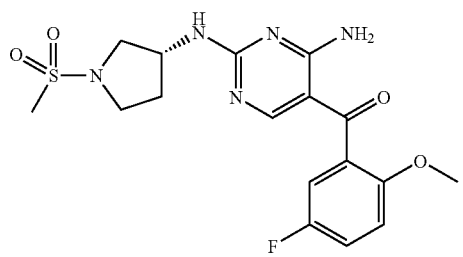

MW 409.44
$C_{17}H_{20}FN_5O_4S$

The same procedure as described in Example 65 was used, starting from (R)-[4-amino-2-(pyrrolidin-3-ylamino)-pyrimidin-5-yl]-(5-fluoro-2-methoxy-phenyl)-methanone trifluoroacetic acid salt, Example 70, to give (R)-[4-amino-2-(1-methanesulfonyl-pyrrolidin-3-ylamino)-pyrimidin-5-yl]-(5-fluoro-2-methoxy-phenyl)-methanone. MS (M+H)$^+$, 410.

Example 76

(R)-[4-Amino-2-(1-ethanesulfonyl-pyrrolidin-3-ylamino)-pyrimidin-5-yl]-(5-fluoro-2-methoxy-phenyl)-methanone

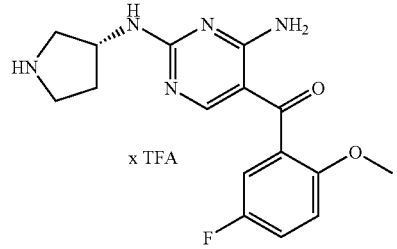

x TFA

MW 331.35 +
$C_{16}H_{18}FN_5O_2 \cdot xC_2HF_3O_2$

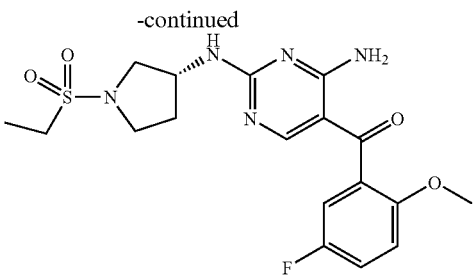

MW 423.47
$C_{18}H_{22}FN_5O_4S$

The same procedure as described in Example 66 was used, starting from (R)-[4-amino-2-(pyrrolidin-3-ylamino)-pyrimidin-5-yl]-(5-fluoro-2-methoxy-phenyl)-methanone trifluoroacetic acid salt, Example 70, to give (R)-[4-amino-2-(1-ethanesulfonyl-pyrrolidin-3-ylamino)-pyrimidin-5-yl]-(5-fluoro-2-methoxy-phenyl)-methanone. MS (M+H)$^+$, 424.

Example 77

(S)-3-[4-Amino-5-(5-fluoro-2-methoxy-benzoyl)-pyrimidin-2-ylamino]-pyrrolidine-1-carboxylic acid tert-butyl ester

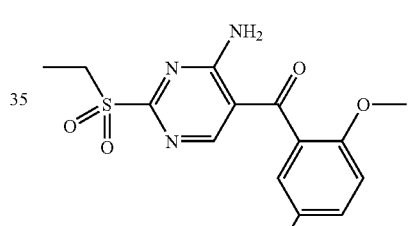

MW 339.35
$C_{14}H_{14}FN_3O_4S$

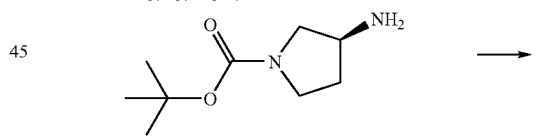

MW 186.25
$C_9H_{18}N_2O_2$

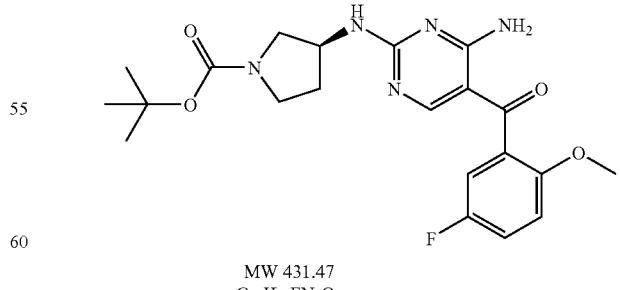

MW 431.47
$C_{21}H_{26}FN_5O_4$

The same procedure was used as described in Example 9 starting from (4-amino-2-ethanesulfonyl-pyrimidin-5-yl)-(5-fluoro-2-methoxy-phenyl)-methanone, Example 48, and (S)-3-amino-pyrrolidine-1-carboxylic acid tert-butyl ester (Astatech), to give (S)-3-[4-amino-5-(5-fluoro-2-methoxy-benzoyl)-pyrimidin-2-ylamino]-pyrrolidine-1-carboxylic acid tert-butyl ester. MS (M+H)+, 432.

Example 78

(S)-[4-Amino-2-(pyrrolidin-3-ylamino)-pyrimidin-5-yl]-(5-fluoro-2-methoxy-phenyl)-methanone

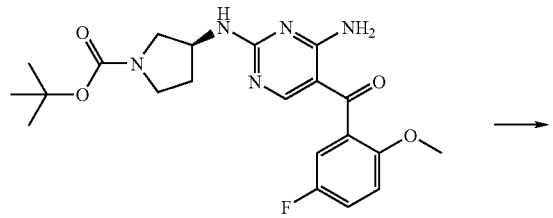

MW 431.47
C21H28FN5O4

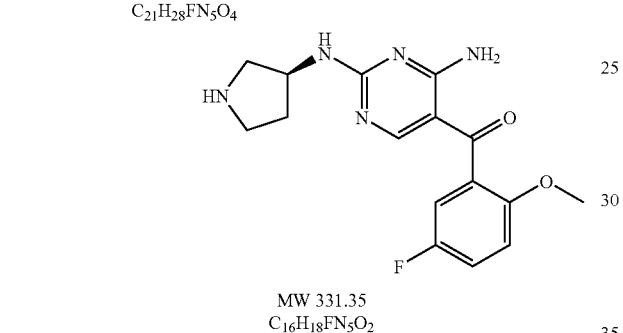

MW 331.35
C16H18FN5O2

The same procedure as described in Example 59 was used, starting from (S)-3-[4-amino-5-(5-fluoro-2-methoxy-benzoyl)-pyrimidin-2-ylamino]-pyrrolidine-1-carboxylic acid tert-butyl ester, Example 77, to give (S)-[4-amino-2-(pyrrolidin-3-ylamino)-pyrimidin-5-yl]-(5-fluoro-2-methoxy-phenyl)-methanone as a trifluoroacetic acid salt and also as the free base. MS (M+H)+, 332.

Example 79

(S)-[4-Amino-2-(1-methanesulfonyl-pyrrolidin-3-ylamino)-pyrimidin-5-yl]-(5-fluoro-2-methoxy-phenyl)-methanone

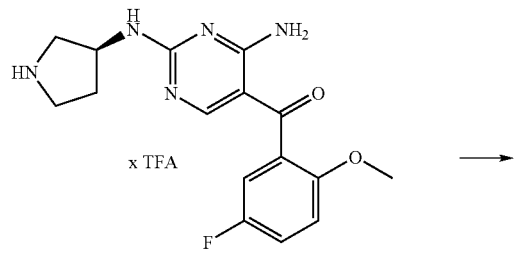

MW 331.35 +
C16H18FN5O2 · xC2HF3O2

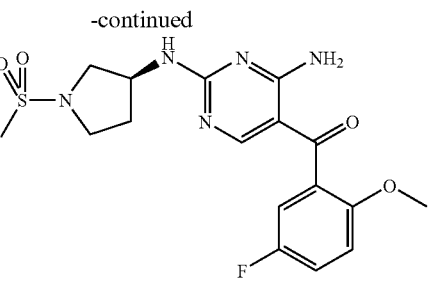

MW 409.44
C17H20FN5O4S

The same procedure as described in Example 75 was used, starting from (S)-[4-amino-2-(pyrrolidin-3-ylamino)-pyrimidin-5-yl]-(5-fluoro-2-methoxy-phenyl)-methanone trifluoroacetic acid salt, Example 78, to give (S)-[4-amino-2-(1-methanesulfonyl-pyrrolidin-3-ylamino)-pyrimidin-5-yl]-(5-fluoro-2-methoxy-phenyl)-methanone. MS (M+H)+, 410.

Example 80

(S)-[4-Amino-2-(1-ethanesulfonyl-pyrrolidin-3-ylamino)-pyrimidin-5-yl]-(5-fluoro-2-methoxy-phenyl)-methanone

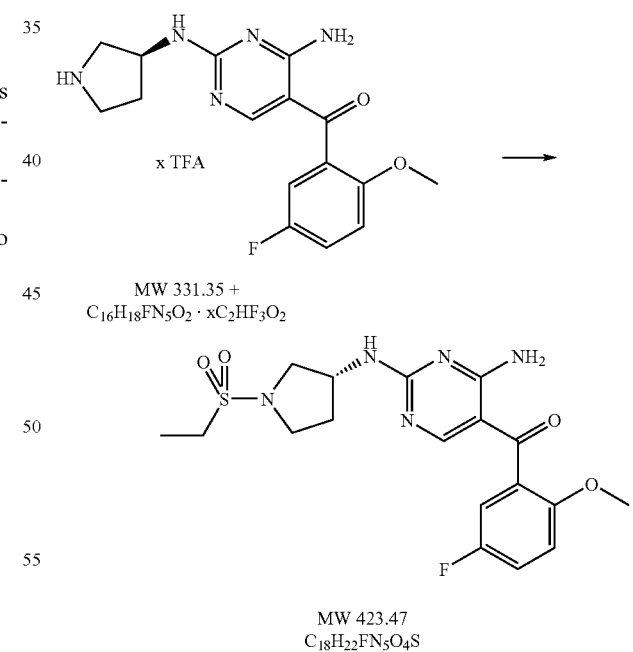

MW 331.35 +
C16H18FN5O2 · xC2HF3O2

MW 423.47
C18H22FN5O4S

The same procedure as described in Example 76 was used, starting from (S)-[4-amino-2-(pyrrolidin-3-ylamino)-pyrimidin-5-yl]-(5-fluoro-2-methoxy-phenyl)-methanone trifluoroacetic acid salt, Example 78, to give (S)-[4-amino-2-(1-ethanesulfonyl-pyrrolidin-3-ylamino)-pyrimidin-5-yl]-(5-fluoro-2-methoxy-phenyl)-methanone. MS (M+H)+, 424.

Example 81

1-[4-[4-Amino-5-(5-fluoro-2-methoxy-benzoyl)-pyrimidin-2-ylamino]-piperidine-1-yl]-2-dimethylamino-ethanone

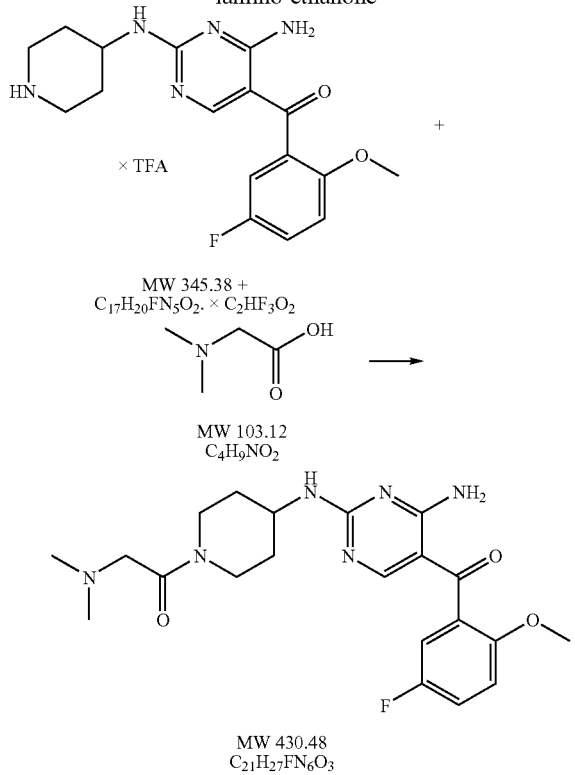

To a solution of N,N-dimethylaminoacetic acid (9.8 mg, 0.095 mmol, Aldrich) in dimethylformamide (2 mL) were added 1-hydroxybenzotriazole hydrate (16.5 mg, 0.108 mmol, Aldrich), O-benzotriazol-1-yl-N,N,N',N'-tetramethyluronium hexafluorophosphate (40.8 mg, 0.108 mmol, Aldrich). After it was stirred for 20 minutes, a solution of [4-amino-2-(piperidin-4-ylamino)-pyrimidin-5-yl]-(5-fluoro-2-methoxy-phenyl)-methanone trifluoroacetic acid salt (47 mg, Example 59) and triethylamine (47 mg, 0.469 mmol, Aldrich) in dimethylformamide (2 mL) were added. The mixture was stirred overnight at room temperature before it was concentrated, taken up in ethyl acetate, washed with brine and evaporated. The crude product was purified on HPLC to give 1-[4-[4-amino-5-(5-fluoro-2-methoxy-benzoyl)-pyrimidin-2-ylamino]-piperidin-1-yl]-2-dimethylamino-ethanone (12.5 mg). MS (M+H)$^+$: 431.

Example 82

1-[4-[4-Amino-5-(5-fluoro-2-methoxy-benzoyl)-pyrimidin-2-ylamino]-piperidin-1-yl]-2-diethylamino-ethanone

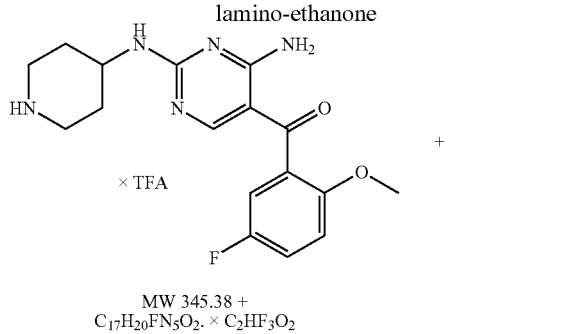

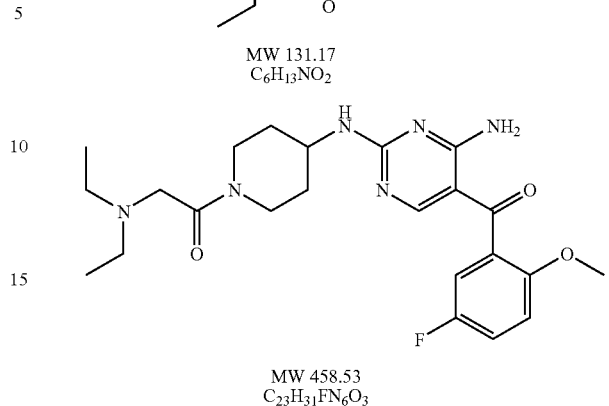

The same procedure as described in Example 81 was used, starting from [4-amino-2-(piperidin-4-ylamino)-pyrimidin-5-yl]-(5-fluoro-2-methoxy-phenyl)-methanone trifluoroacetic acid salt, Example 59, and N,N-diethylaminoacetic acid (Aldrich) to give 1-[4-[4-amino-5-(5-fluoro-2-methoxy-benzoyl)-pyrimidin-2-ylamino]-piperidin-1-yl]-2-diethylamino-ethanone. MS (M+H)$^+$: 459.

Example 83

1-[4-[4-Amino-5-(5-fluoro-2-methoxy-benzoyl)-pyrimidin-2-ylamino]-piperidin-1-yl-2-morpholin-4-yl-ethanone

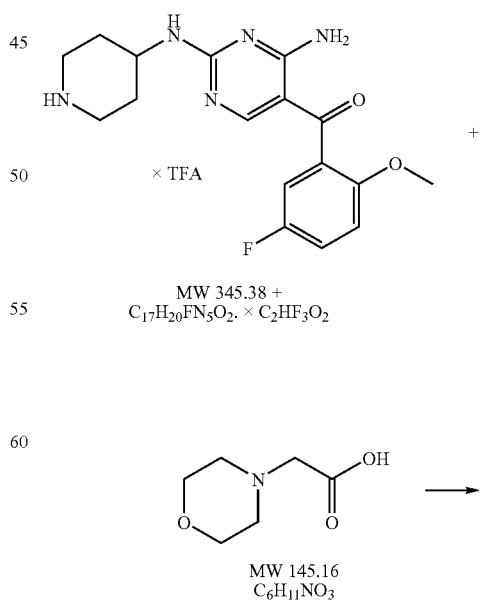

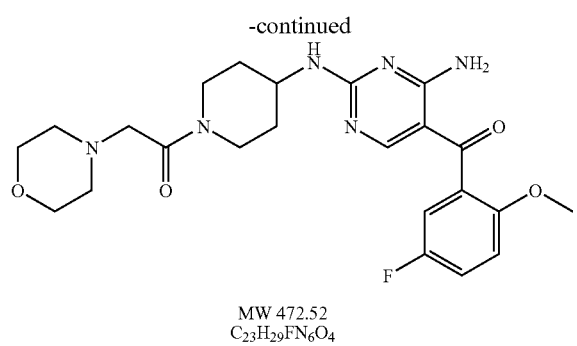

MW 472.52
$C_{23}H_{29}FN_6O_4$

The same procedure as described in Example 81 was used, starting from [4-amino-2-(piperidin-4-ylamino)-pyrimidin-5-yl]-(5-fluoro-2-methoxy-phenyl)-methanone trifluoroacetic acid salt, Example 59, and morpholin-4-yl-acetic acid (Aldrich) to give 1-[4-[4-amino-5-(5-fluoro-2-methoxy-benzoyl)-pyrimidin-2-ylamino]-piperidin-1-yl]-2-morpholin-4-yl-ethanone. MS (M+H)+: 473.

Example 84

1-[4-[4-Amino-5-(5-fluoro-2-methoxy-benzoyl)-pyrimidin-2-ylamino]-piperidin-1-yl]-3-dimethylamino-propan-1-one

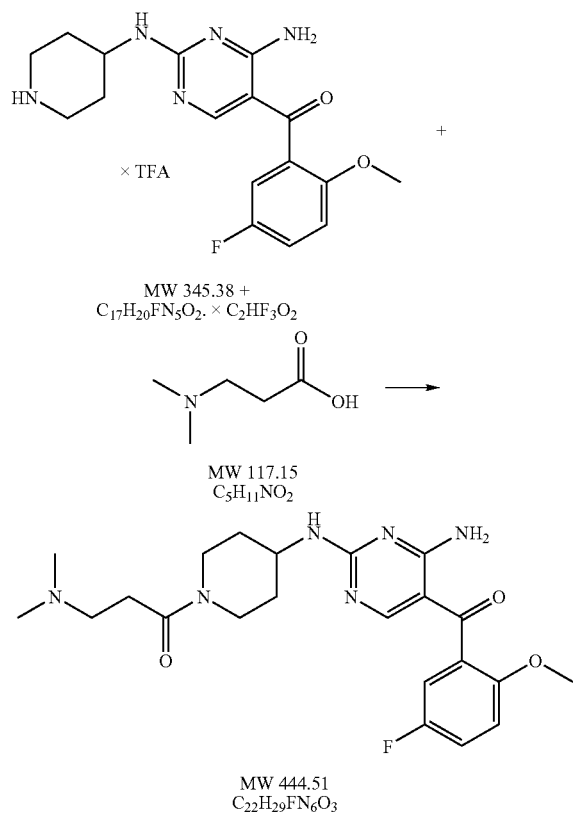

The same procedure as described in Example 81 was used, starting from [4-amino-2-(piperidin-4-ylamino)-pyrimidin-5-yl]-(5-fluoro-2-methoxy-phenyl)-methanone trifluoroacetic acid salt, Example 59, and dimethylaminopropionic acid (TCI-US) to give 1-[4-[4-amino-5-(5-fluoro-2-methoxy-benzoyl)-pyrimidin-2-ylamino]-piperidin-1-yl]-3-dimethylamino-propan-1-one. MS (M+H)+: 445.

Example 85

1-[4-[4-Amino-5-(5-fluoro-2-methoxy-benzoyl)-pyrimidin-2-ylamino]-piperidin-1-yl]-3-diethylamino-propan-1-one

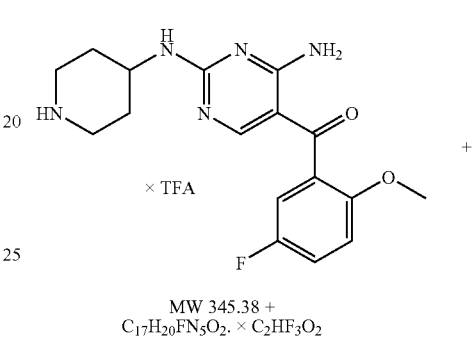

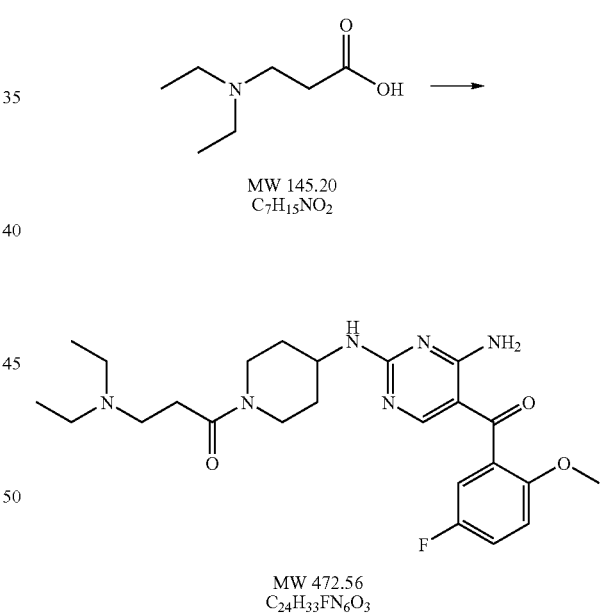

The same procedure as described in Example 81 was used, starting from [4-amino-2-(piperidin-4-ylamino)-pyrimidin-5-yl]-(5-fluoro-2-methoxy-phenyl)-methanone trifluoroacetic acid salt, Example 59, and diethylaminopropionic acid hydrochloride (Aldrich) to give 1-[4-[4-amino-5-(5-fluoro-2-methoxy-benzoyl)-pyrimidin-2-ylamino]-piperidin-1-yl]-3-diethylamino-propan-1-one. MS (M+H)+: 473.

Example 86

1-[4-[4-Amino-5-(5-fluoro-2-methoxy-benzoyl)-pyrimidin-2-ylamino]-piperidin-1-yl]-3-piperidin-1-yl-propan-1-one

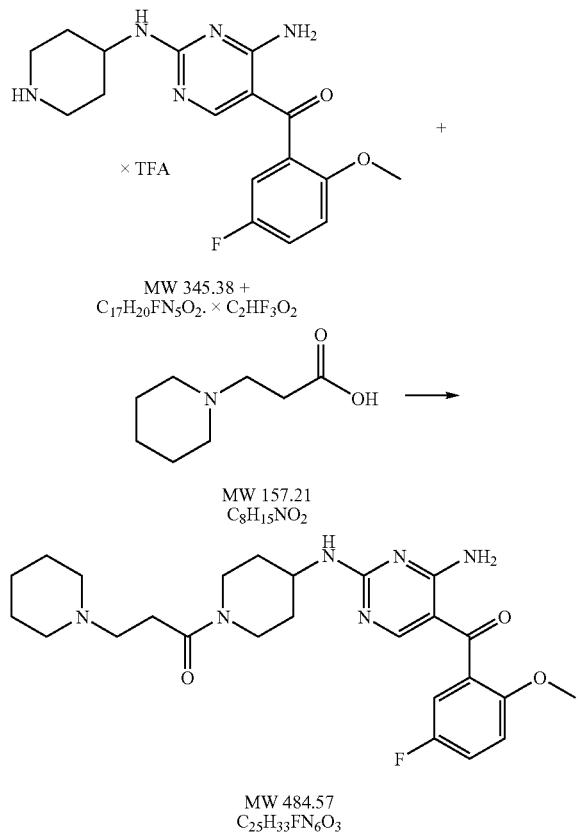

The same procedure as described in Example 81 was used, starting from [4-amino-2-(piperidin-4-ylamino)-pyrimidin-5-yl]-(5-fluoro-2-methoxy-phenyl)-methanone trifluoroacetic acid salt, Example 59, and 1-piperidine propionic acid (Aldrich) to give 1-[4-[4-amino-5-(5-fluoro-2-methoxy-benzoyl)-pyrimidin-2-ylamino]-piperidin-1-yl]-3-piperidin-1-yl-propan-1-one. MS (M+H)$^+$: 485.

Example 87

1-[4-[4-Amino-5-(5-fluoro-2-methoxy-benzoyl)-pyrimidin-2-ylamino]-piperidin-1-yl]-3-morpholin-4-yl-propan-1-one

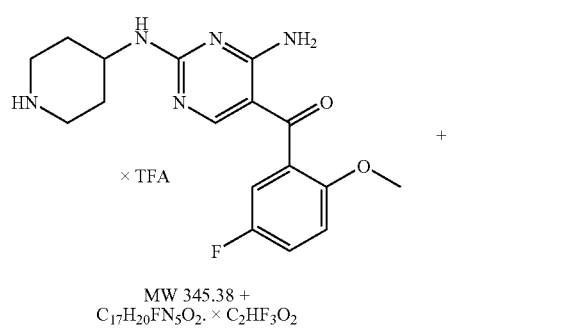

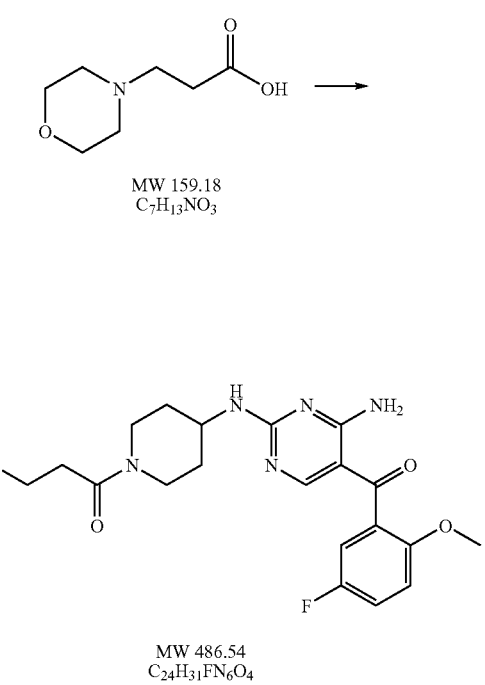

The same procedure as described in Example 81 was used, starting with 3-morpholin-4-yl-propionic acid (prepared by the method of Kempf, Dale J., et al., J. Med. Chem.; 36:3, 1993, pp 320–330), to give 1-[4-[4-amino-5-(5-fluoro-2-methoxy-benzoyl)-pyrimidin-2-ylamino]-piperidin-1-yl]-3-morpholin-4-yl-propan-1-one. MS (M+H)$^+$: 487.

Example 88

(4-Amino-2-ethylsulfanyl-pyrimidin-5-yl)-(2,6-difluoro-3-methoxy-phenyl)-methanone

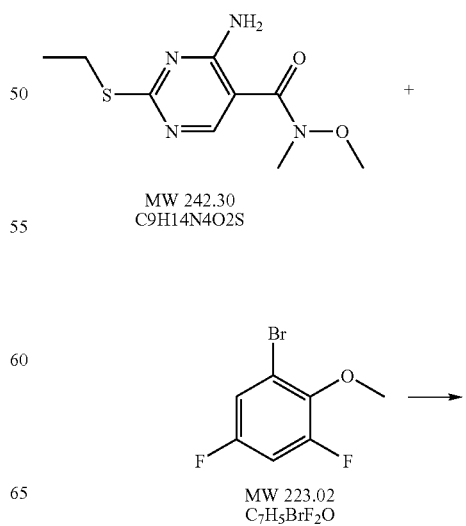

-continued

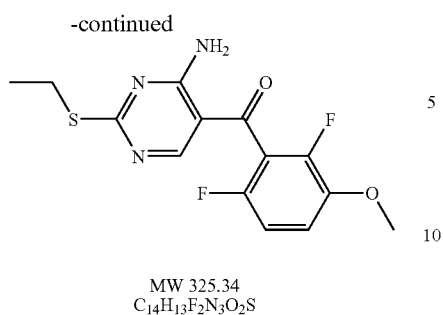

MW 325.34
C_{14}H_{13}F_2N_3O_2S

The same procedure as described in Example 47 was used, starting from 4-amino-2-ethylsulfanylpyrimidine-5-carboxylic acid, Example 1, and 2-bromo-4,6-difluoroanisole (Astatech), to give (4-amino-2-ethylsulfanyl-pyrimidin-5-yl)-(2,6-difluoro-3-methoxy-phenyl)-methanone as a white solid. MS (M+H)$^+$, 326.

Example 89

(4-Amino-2-ethanesulfonyl-pyrimidin-5-yl)-(2,6-difluoro-3-methoxy-phenyl)-methanone

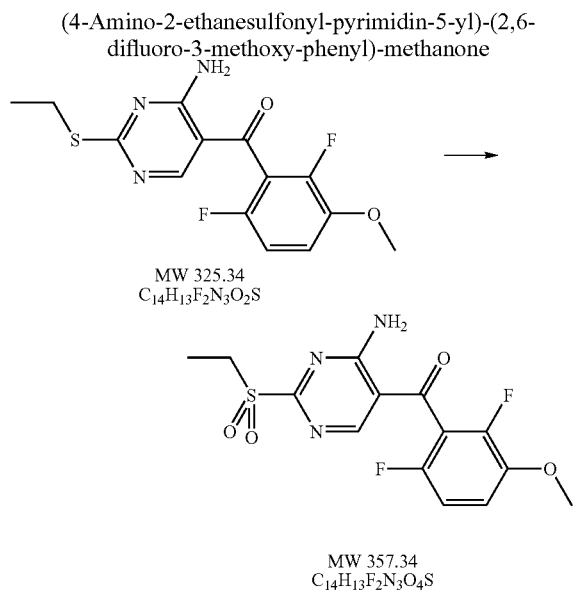

The same procedure as described in Example 3 was used, starting with (4-amino-2-ethylsulfanyl-pyrimidin-5-yl)-(2,6-difluoro-3-methoxy-phenyl)-methanone, Example 88, to give (4-amino-2-ethanesulfonyl-pyrimidin-5-yl)-(2,6-difluoro-3-methoxy-phenyl)-methanone as a white solid. MS (M+H)$^+$: 358.

Example 90
1-[4-[4-Amino-5-(2,6-difluoro-3-methoxy-benzoyl)-pyrimidin-2-ylamin]-piperidin-1-yl]-ethanone

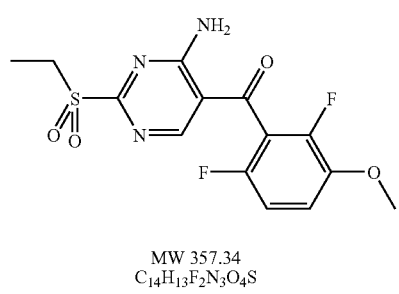

-continued

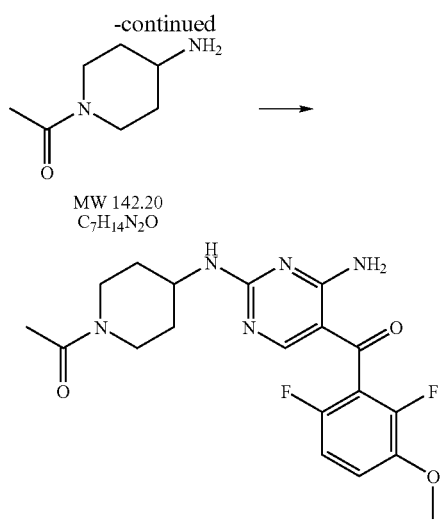

MW 405.40
C_{19}H_{21}F_2N_5O_3

A suspension of (4-amino-2-ethanesulfonyl-pyrimidin-5-yl)-(2,6-difluoro-3-methoxy-phenyl)-methanone (20.0 mg, 0.056 mmol, Example 89) and 1-(4-amino-piperidin-1-yl)-ethanone (21.1 mg, 0.148 mmol, prepared as described in U.S. Pat. No. 5,817,828) in isopropyl alcohol (2.5 mL) was heated at 120° C. in a sealed tube under microwave conditions for 0.3 to 1 hour. The resulting reaction mixture was evaporated in vacuo and crude product was purified on silica gel with 95:5 of dichloromethane/methanol to give 1-[4-[4-amino-5-(2,6-difluoro-3-methoxy-benzoyl)-pyrimidin-2-ylamino]-piperidin-1-yl]-ethanone as a white solid (18.3 mg). MS (M+H)$^+$, 406.

Example 91

[4-Amino-2-(1-methanesulfonyl-piperidin-4-ylamino)-pyrimidin-5-yl]-(2,6-difluoro-3-methoxy-phenyl)-methanone

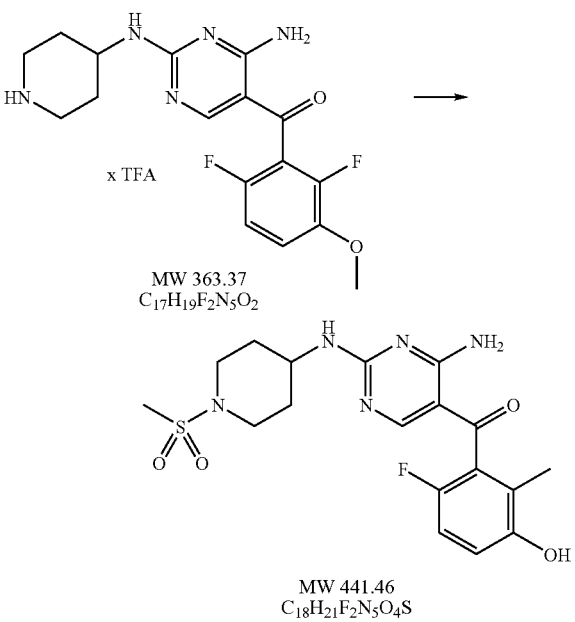

The same procedure as described in Example 28 was used, starting from [4-amino-2-(piperidin-4-ylamino)-pyrimidin-5-yl]-(2,6-difluoro-3-methoxy-phenyl)-methanone trifluoroacetic acid salt, Example 93, to give [4-amino-2-(1-methanesulfonyl-piperidin-4-ylamino)-pyrimidin-5-yl]-(2,6-difluoro-3-methoxy-phenyl)-methanone. MS (M+H)+, 442.

Example 92
4-[4-Amino-5-(2,6-difluoro-3-methoxy-benzoyl)-pyrimidin-2-ylamino]-piperidine-1-carboxylic acid tert-butyl ester

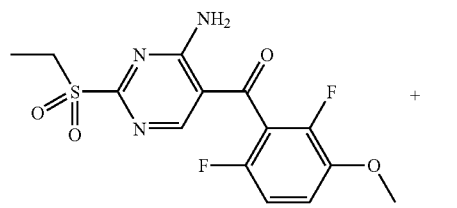

MW 357.34
$C_{14}H_{13}F_2N_3O_4S$

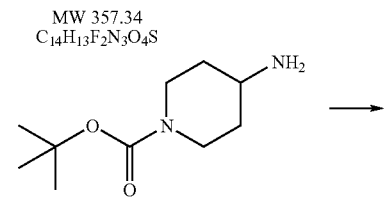

MW 200.28
$C_{10}H_{20}N_2O_2$

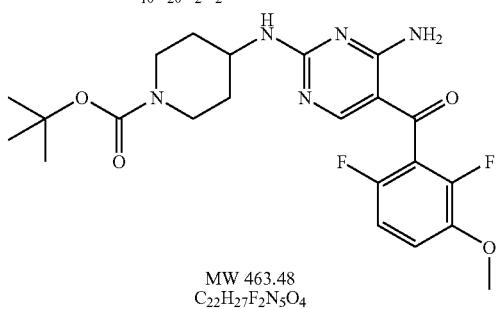

MW 463.48
$C_{22}H_{27}F_2N_5O_4$

The same procedure was used as described in Example 90 starting from (4-amino-2-ethanesulfonyl-pyrimidin-5-yl)-(2,6-difluoro-3-methoxy-phenyl)-methanone, Example 89, and 4-amino-1-Boc-piperidine (Astatech) to give 4-[4-amino-5-(2,6-difluoro-3-methoxy-benzoyl)-pyrimidin-2-ylamino]-piperidine-1-carboxylic acid tert-butyl ester. MS (M+H)+, 464.

Example 93
[4-Amino-2-(piperidin-4-ylamino)-pyrimidin-5-yl]-(2,6-difluoro-3-methoxy-phenyl)-methanone

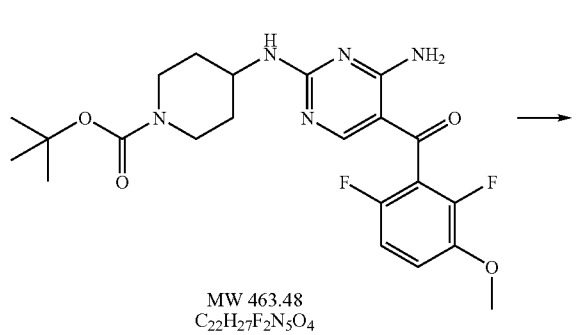

MW 463.48
$C_{22}H_{27}F_2N_5O_4$

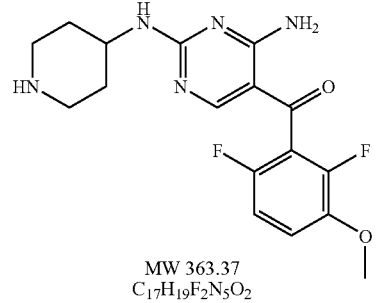

MW 363.37
$C_{17}H_{19}F_2N_5O_2$

The same procedure was used as described in Example 59 starting from 4-[4-amino-5-(2,6-difluoro-3-methoxy-benzoyl)-pyrimidin-2-ylamino]-piperidine-1-carboxylic acid tert-butyl ester, Example 92, to give [4-amino-2-(piperidin-4-ylamino)-pyrimidin-5-yl]-(2,6-difluoro-3-methoxy-phenyl)-methanone as a trifluoroacetic acid salt, and also as the free base. MS (M+H)+, 364.

Example 94
4-[4-Amino-5-(2,6-difluoro-3-methoxy-benzoyl)-pyrimidin-2-ylamino]-piperidine-1-carboxylic acid methyl ester

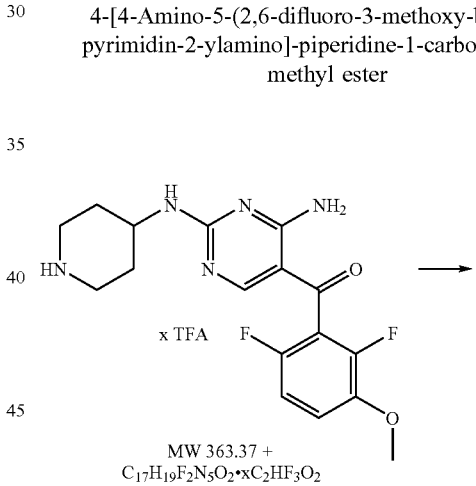

x TFA

MW 363.37 +
$C_{17}H_{19}F_2N_5O_2 \cdot xC_2HF_3O_2$

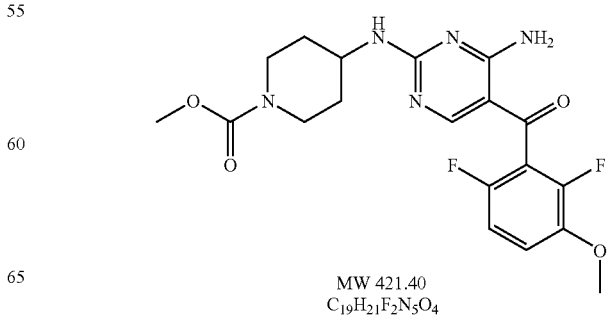

MW 421.40
$C_{19}H_{21}F_2N_5O_4$

The same procedure was used as described in Example 60, starting with [4-amino-2-(piperidin-4-ylamino)-pyrimidin-5-yl]-(2,6-difluoro-3-methoxy-phenyl)-methanone trifluoroacetic acid salt, Example 93, to give 4-[4-amino-5-(2,6-difluoro-3-methoxy-benzoyl)-pyrimidin-2-ylamino]-piperidine-1-carboxylic acid methyl ester. MS (M+H)$^+$, 422

Example 95

(4-Amino-2-ethylsulfanyl-pyrimidin-5-yl)-(2-ethoxy-phenyl)-methanone

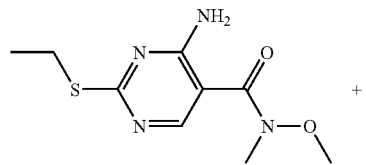

MW 242.30
C$_9$H$_{14}$N$_4$O$_2$S

+

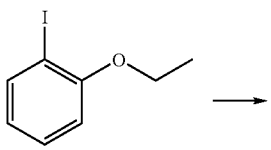

MW 248.06
C$_8$H$_9$IO

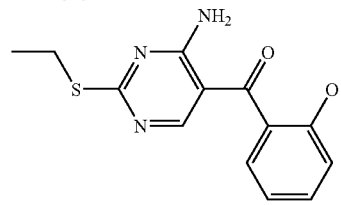

MW 303.38
C$_{15}$H$_{17}$N$_3$O$_2$S

The product of the reaction of 2-iodophenol (Aldrich) and ethyl iodide in hot acetone containing potassium carbonate was treated with n-butyl lithium as described in Example 2A and subsequently reacted with 4-amino-2-ethylsulfanyl-pyrimidine-5-carboxylic acid methoxy-methyl-amide, Example 1, using the procedure of Example 47 to give (4-amino-2-ethylsulfanyl-pyrimidin-5-yl)-(2-ethoxy-phenyl)-methanone as a white solid. MS (M+H)$^+$, 304

Example 96

(4-Amino-2-ethanesulfonyl-pyrimidin-5-yl)-(2-ethoxy-phenyl)-methanone

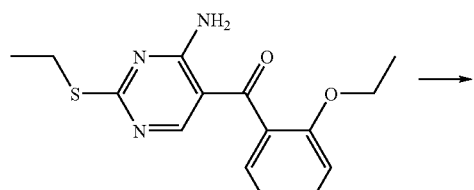

MW 303.38
C$_{15}$H$_{17}$N$_3$O$_2$S

-continued

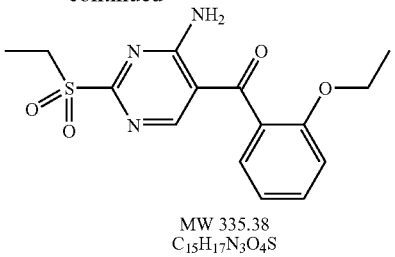

MW 335.38
C$_{15}$H$_{17}$N$_3$O$_4$S

The same procedure as described in Example 3 was used, starting from (4-amino-2-ethylsulfanyl-pyrimidin-5-yl)-(2-ethoxy-phenyl)-methanone, Example 95, to give (4-amino-2-ethanesulfonyl-pyrimidin-5-yl)-(2-ethoxy-phenyl)-methanone as a white solid. MS (M+H)$^+$: 336.

Example 97

1-[4-[4-Amino-5-(2-ethoxy-benzoyl)-pyrimidin-2-ylamino]-piperidin-1-yl]-ethanone

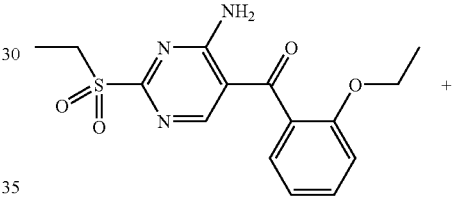

MW 335.38
C$_{15}$H$_{17}$N$_3$O$_4$S

+

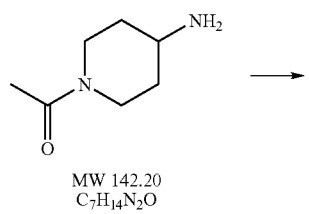

MW 142.20
C$_7$H$_{14}$N$_2$O

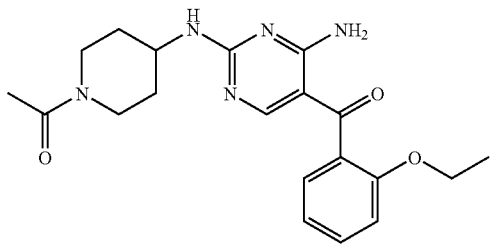

MW 383.45
C$_{20}$H$_{25}$N$_5$O$_3$

The same procedure as described in Example 90 was used, starting with (4-amino-2-ethanesulfonyl-pyrimidin-5-yl)-(2-ethoxy-phenyl)-methanone, Example 96, to give 1-[4-[4-amino-5-(2-ethoxy-benzoyl)-pyrimidin-2-ylamino]-piperidin-1-yl]-ethanone as a white solid. MS (M+H)$^+$: 384.

Example 98

(4-Amino-2-ethylsulfanyl-pyrimidin-5-yl)-(4,5-difluoro-2-methoxy-phenyl)-methanone

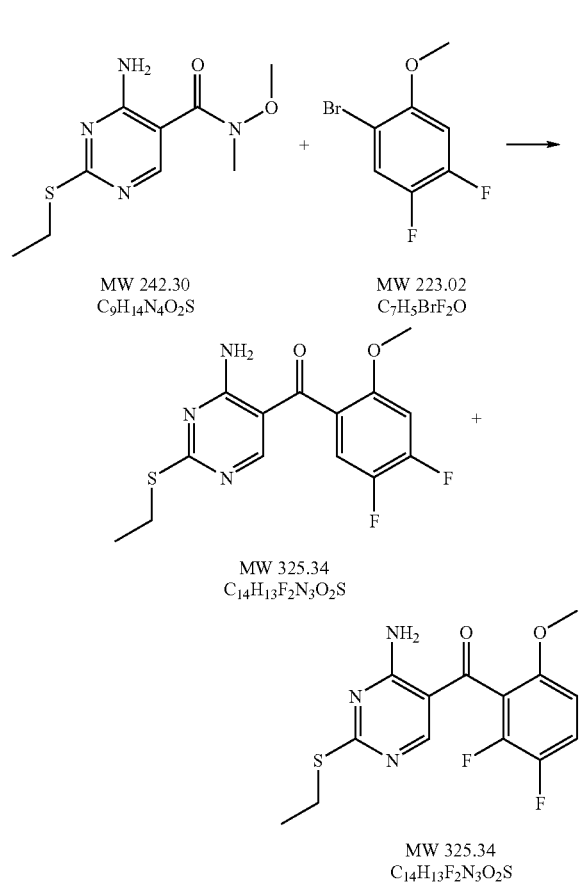

A solution of 2-bromo-4,5-difluoro-anisole (1.95 g, 8.75 mmol, Astatech) in a mixture of pentane/tetrahydrofuran (5 mL/17 mL) was cooled to −72° C. and treated with n-butyl lithium (2.5 M in hexane, 3.6 mL, 9.0 mmol). After stirring for 10 minutes, a solution of 4-amino-2-ethylsulfanyl-pyrimidine-5-carboxylic acid methoxy-methyl-amide (0.78 g, 3.21 mmol, Example 1) in tetrahydrofuran (3 mL) was added. The temperature was slowly raised to −35° C. for ~2 hours. The reaction was quenched at −35° C. with 5% aqueous ammonium chloride solution and the mixture was diluted with ethyl acetate/hexane (100 mL). The organic phase was separated, washed with 1:1 water/saturated aqueous sodium chloride solution and dried (Na$_2$SO$_4$). The residue after solvent removal was purified by HPLC chromatography (Waters Prep 500 eluting with 35% ethyl acetate/hexane) to give, in approximately 1:1 ratio, the two positional isomers (4-amino-2-ethylsulfanyl-pyrimidin-5-yl)-(2,3-difluoro-6-methoxy-phenyl)-methanone identical to material prepared in Example 102, and (4-Amino-2-ethylsulfanyl-pyrimidin-5-yl)-(4,5-difluoro-2-methoxy-phenyl)-methanone as a white solid after evaporation. HRMS, observed: 326.0772; Calcd for M$^+$: 326.0770.

Example 99

(4-Amino-2-ethanesulfonyl-pyrimidin-5-yl)-(4,5-difluoro-2-methoxy-phenyl)-methanone

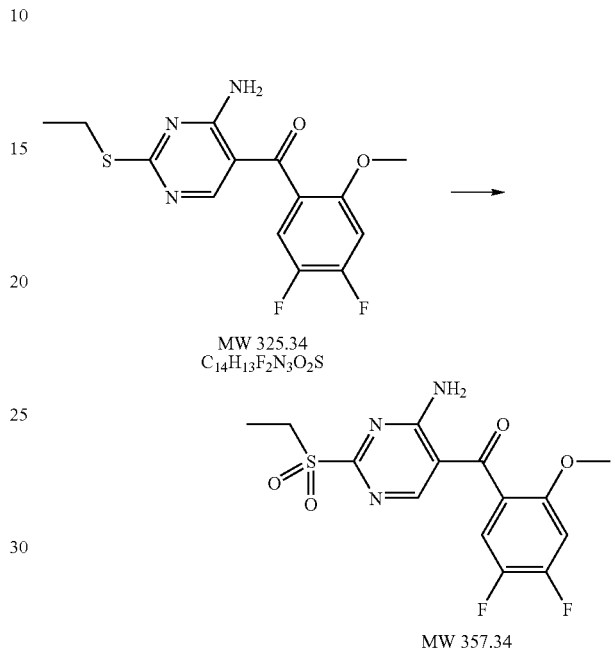

The same procedure as described in Example 3 was used, starting with (4-amino-2-ethylsulfanyl-pyrimidin-5-yl)-(4,5-difluoro-2-methoxy-phenyl)-methanone, Example 98, to give (4-amino-2-ethanesulfonyl-pyrimidin-5-yl)-(4,5-difluoro-2-methoxy-phenyl)-methanone as a white solid. MS (M+H)$^+$: 358.

Example 100

1-[4-[4-Amino-5-(4,5-difluoro-2-methoxy-benzoyl)-pyrimidin-2-ylamino]-piperidin-1-yl]-ethanone

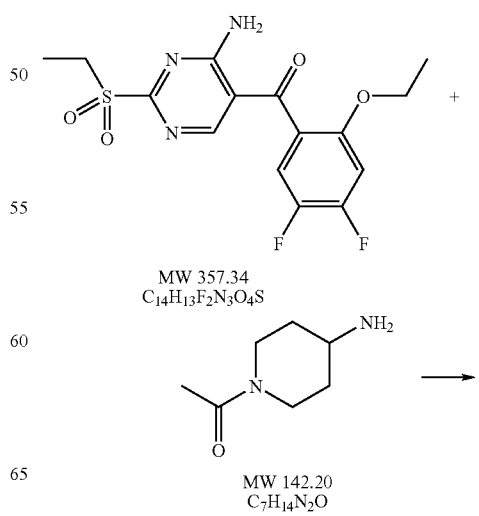

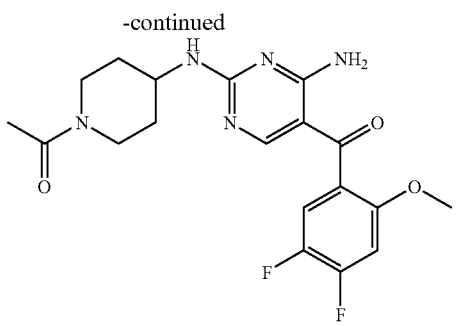

MW 405.40
C₁₉H₂₁F₂N₅O₃

The same procedure as described in Example 90 was used, starting with (4-amino-2-ethanesulfonyl-pyrimidin-5-yl)-(4,5-difluoro-2-methoxy-phenyl)-methanone, Example 99, to give 1-[4-[4-amino-5-(4,5-difluoro-2-methoxy-benzoyl)-pyrimidin-2-ylamino]-piperidin-1-yl]-ethanone as a white solid. MS (M+H)⁺: 406.

Example 101

[4-Amino-2-(1-methanesulfonyl-piperidin-4-ylamino)-pyrimidin-5-yl]-(4,5-difluoro-2-methoxy-phenyl)-methanone

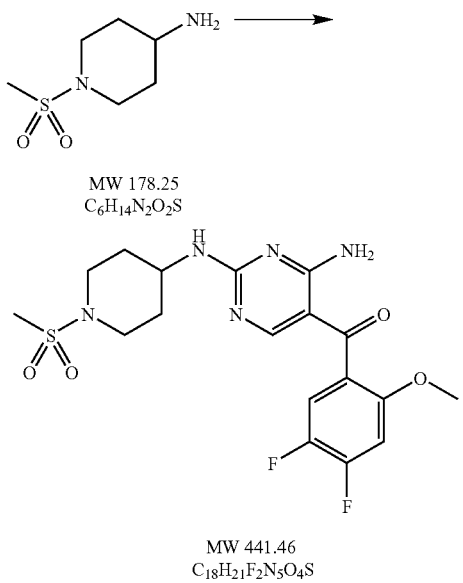

The same procedure as described in Example 90 was used, starting with (4-amino-2-ethanesulfonyl-pyrimidin-5-yl)-(4,5-difluoro-2-methoxy-phenyl)-methanone, Example 99, and 1-methanesulfonyl-piperidin-4-ylamine (compound with trifluoro-acetic acid), Example 162, to give [4-amino-2-(1-methanesulfonyl-piperidin-4-ylamino)-pyrimidin-5-yl]-(4,5-difluoro-2-methoxy-phenyl)-methanone as a white solid. MS (M+H)⁺: 442.

Example 102

(4-Amino-2-ethylsulfanyl-pyrimidin-5-yl)-(2,3-difluoro-6-methoxy-phenyl)-methanone

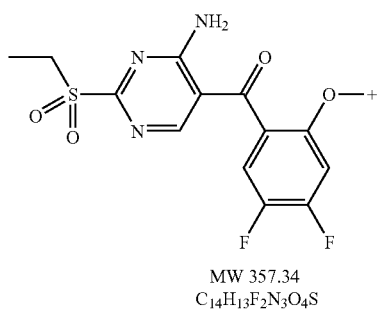

MW 242.30
C₉H₁₄N₄O₂S

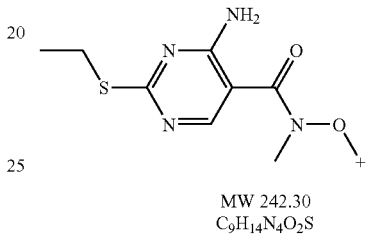

MW 223.02
C₇H₅BrF₂O

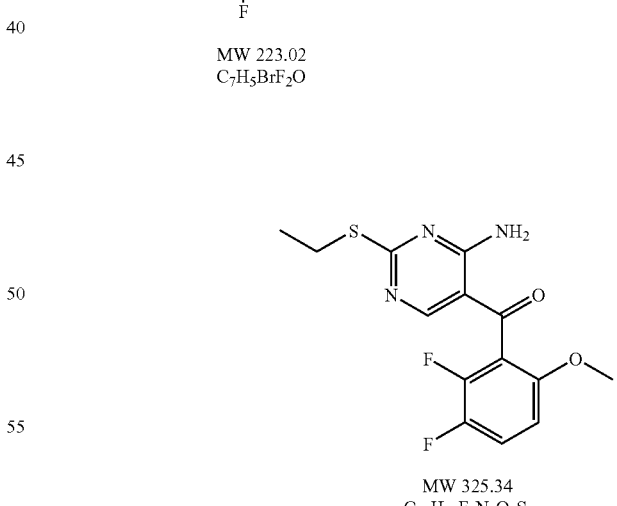

MW 325.34
C₁₄H₁₃F₂N₃O₂S

The same procedure as described in Example 47 was used, starting from 4-amino-2-ethylsulfanylpyrimidine-5-carboxylic acid methoxymethylamide, Example 1, and 2-bromo-4,5-difluoro-anisole (Astatech), to give (4-amino-2-ethylsulfanyl-pyrimidin-5-yl)-(2,3-difluoro-6-methoxy-phenyl)-methanone as a white solid. MS (M+H)⁺, 326.

Example 103

(4-Amino-2-ethanesulfonyl-pyrimidin-5-yl)-(2,3-difluoro-6-methoxy-phenyl)-methanone

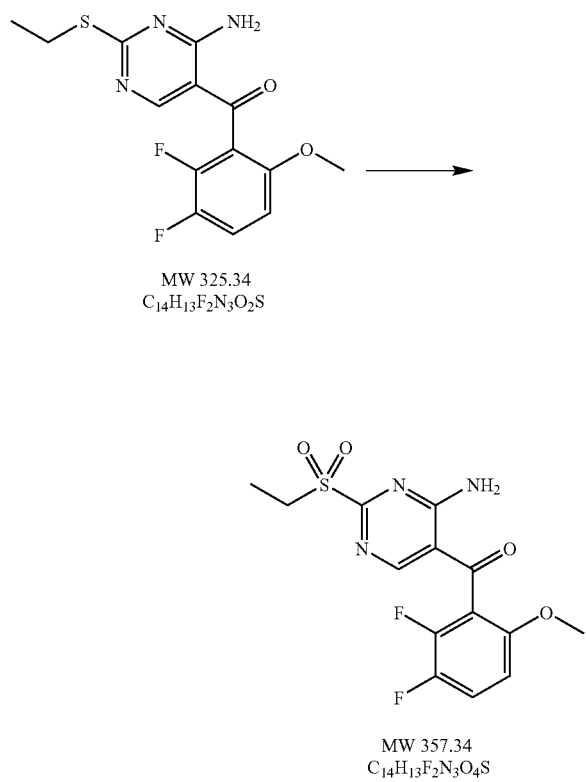

MW 325.34
C₁₄H₁₃F₂N₃O₂S

MW 357.34
C₁₄H₁₃F₂N₃O₄S

The same procedure as described in Example 3 was used, starting with (4-amino-2-ethylsulfanyl-pyrimidin-5-yl)-(2,3-difluoro-6-methoxy-phenyl)-methanone, Example 102, to give (4-amino-2-ethanesulfonyl-pyrimidin-5-yl)-(2,3-difluoro-6-methoxy-phenyl)-methanone as a white solid. MS (M+H)⁺: 358.

Example 104

1-[4-[4-Amino-5-(2,3-difluoro-6-methoxy-benzoyl)-pyrimidin-2-ylamino]-piperidin-1-yl]-ethanone

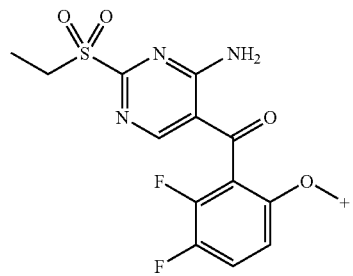

MW 357.34
C₁₄H₁₃F₂N₃O₄S

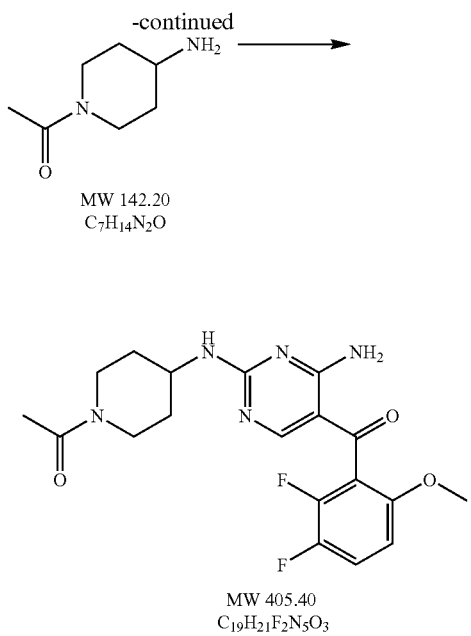

MW 142.20
C₇H₁₄N₂O

MW 405.40
C₁₉H₂₁F₂N₅O₃

The same procedure as described in Example 90 was used, starting from (4-amino-2-ethanesulfonyl-pyrimidin-5-yl)-(2,3-difluoro-6-methoxy-phenyl)-methanone, Example 103, to give 1-[4-[4-amino-5-(2,3-difluoro-6-methoxy-benzoyl)-pyrimidin-2-ylamino]-piperidin-1-yl]-ethanone as a white solid. MS (M+H)⁺: 406.

Example 105

[4-Amino-2-(1-methanesulfonyl-piperidin-4-ylamino)-pyrimidin-5-yl]-(2,3-difluoro-6-methoxy-phenyl)-methanone

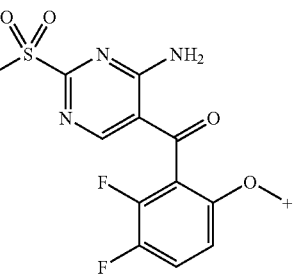

MW 357.34
C₁₄H₁₃F₂N₃O₄S

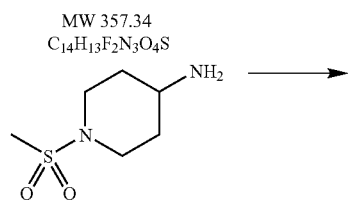

MW 178.25
C₆H₁₄N₂O₂S

-continued

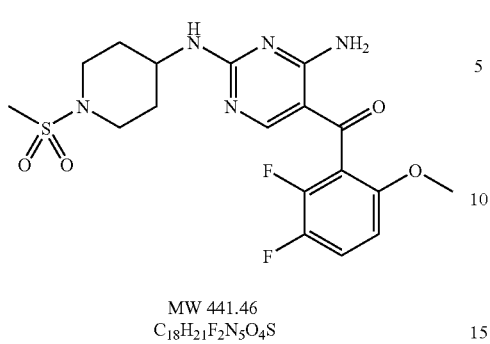

MW 441.46
$C_{18}H_{21}F_2N_5O_4S$

The same procedure as described in Example 90 was used, starting from (4-amino-2-ethanesulfonyl-pyrimidin-5-yl)-(2,3-difluoro-6-methoxy-phenyl)-methanone, Example 103, and 1-methanesulfonyl-piperidin-4-ylamine (with trifluoro-acetic acid), Example 162, to give [4-amino-2-(1-methanesulfonyl-piperidin-4-ylamino)-pyrimidin-5-yl]-(2,3-difluoro-6-methoxy-phenyl)-methanone. MS (M+H)$^+$, 442.

Example 106

4-[4-Amino-5-(2,3-difluoro-6-methoxy-benzoyl)-pyrimidin-2-ylamino]-piperidine-1-carboxylic acid tert-butyl ester

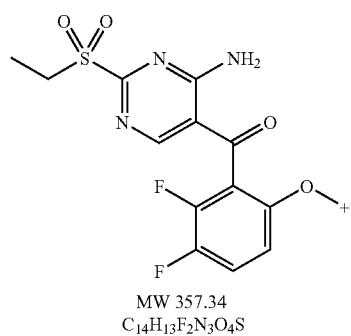

MW 357.34
$C_{14}H_{13}F_2N_3O_4S$

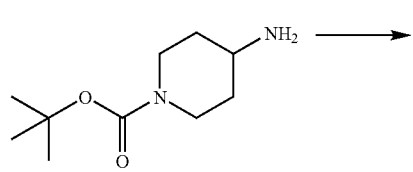

MW 200.28
$C_{10}H_{20}N_2O_2$

-continued

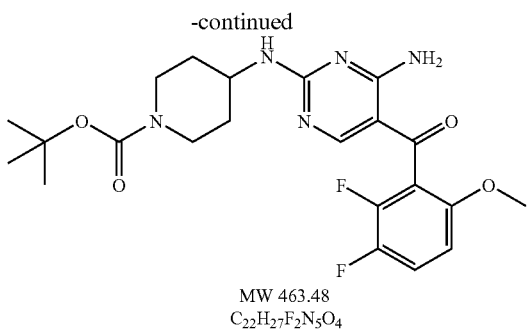

MW 463.48
$C_{22}H_{27}F_2N_5O_4$

The same procedure as described in Example 92 was used, starting from (4-amino-2-ethanesulfonyl-pyrimidin-5-yl)-(2,3-difluoro-6-methoxy-phenyl)-methanone, Example 103, to give 4-[4-amino-5-(2,3-difluoro-6-methoxy-benzoyl)-pyrimidin-2-ylamino]-piperidine-1-carboxylic acid tert-butyl ester identical to material prepared in Example 166. MS (M+H)$^+$, 464.

Example 107

[4-Amino-2-(piperidin-4-ylamino)-pyrimidin-5-yl]-(2,3-difluoro-6-methoxy-phenyl)-methanone

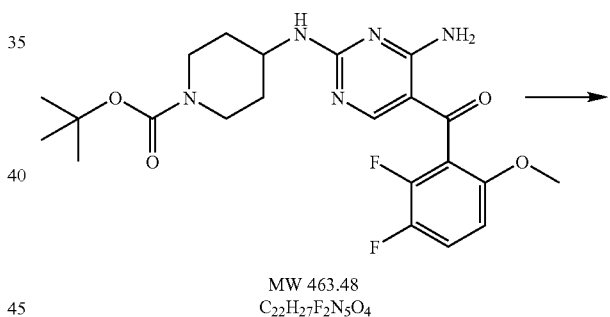

MW 463.48
$C_{22}H_{27}F_2N_5O_4$

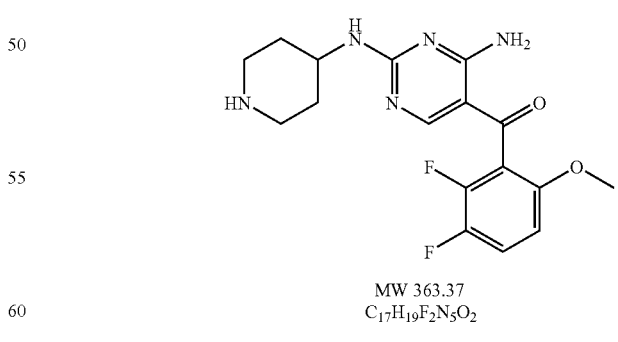

MW 363.37
$C_{17}H_{19}F_2N_5O_2$

The same procedure was used as described in Example 59, using material from Example 106, to give [4-amino-2-(piperidin-4-ylamino)-pyrimidin-5-yl]-(2,3-difluoro-6-

Example 108

4-[4-Amino-5-(2,3-difluoro-6-methoxy-benzoyl)-pyrimidin-2-ylamino]-piperidine-1-carboxylic acid methyl ester

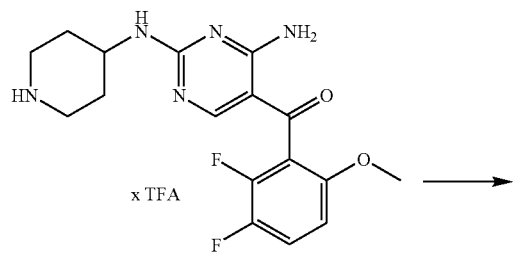

MW 363.37 +
$C_{17}H_{19}F_2N_5O_2 \cdot xC_2HF_3O_2$

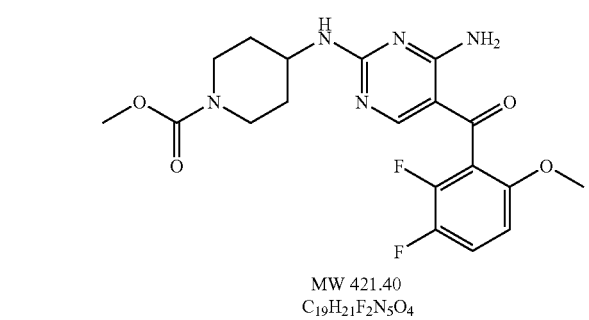

MW 421.40
$C_{19}H_{21}F_2N_5O_4$

The same procedure as described in Example 60 was used, starting from [4-amino-2-(piperidin-4-ylamino)-pyrimidin-5-yl]-(2,3-difluoro-6-methoxy-phenyl)-methanone trifluoroacetic acid salt, Example 107, to give 4-[4-amino-5-(2,3-difluoro-6-methoxy-benzoyl)-pyrimidin-2-ylamino]-piperidine-1-carboxylic acid methyl ester. MS (M+H)⁺, 422.

Example 109

(4-Amino-2-ethylsulfanyl-pyrimidin-5-yl)-(5-chloro-2-methoxy-phenyl)-methanone

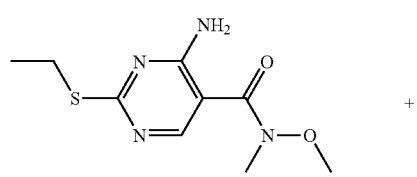

MW 242.30
$C_9H_{14}N_4O_2S$

+

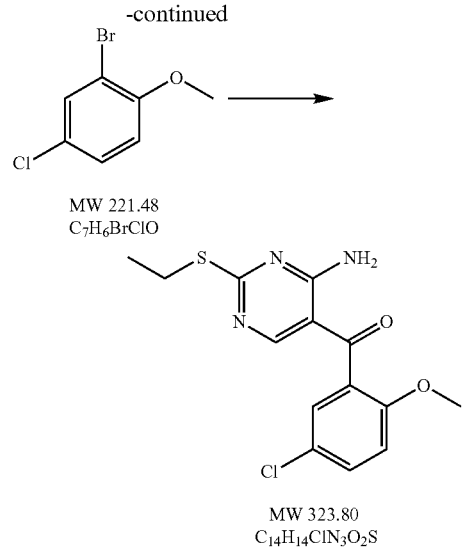

MW 221.48
$C_7H_6BrClO$

→

MW 323.80
$C_{14}H_{14}ClN_3O_2S$

The same procedure as described in Example 47 was used, starting from 4-amino-2-ethylsulfanyl-pyrimidine-5-carboxylic acid methoxy-methyl-amide, Example 1, and 2-bromo-4-chloroanisole (Aldrich), to give (4-amino-2-ethylsulfanyl-pyrimidin-5-yl)-(5-chloro-2-methoxy-phenyl)-methanone as a white solid. MS (M+H)⁺, 324.

Example 110

(4-Amino-2-ethanesulfonyl-pyrimidin-5-yl)-(5-chloro-2-methoxy-phenyl)-methanone

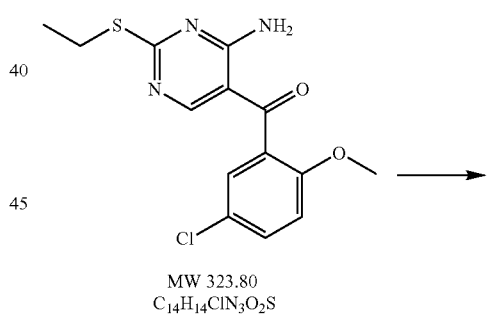

MW 323.80
$C_{14}H_{14}ClN_3O_2S$

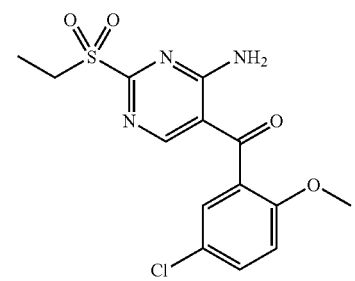

MW 355.80
$C_{14}H_{14}ClN_3O_4S$

111

The same procedure as described in Example 3 was used, starting from (4-amino-2-ethylsulfanyl-pyrimidin-5-yl)-(5-chloro-2-methoxy-phenyl)-methanone, Example 109, to give (4-amino-2-ethanesulfonyl-pyrimidin-5-yl)-(5-chloro-2-methoxy-phenyl)-methanone as a white solid. MS (M+H)⁺: 356.

Example 111

1-[4-[4-Amino-5-(5-chloro-2-methoxy-benzoyl)-pyrimidin-2-ylamino]-piperidin-1-yl]-ethanone

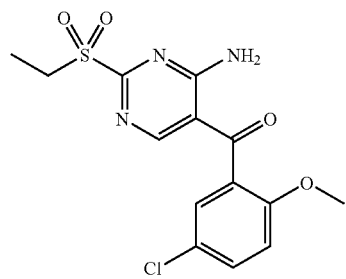

MW 355.80
$C_{14}H_{14}ClN_3O_4S$

+

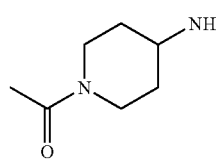

MW 142.20
$C_7H_{14}N_2O$

→

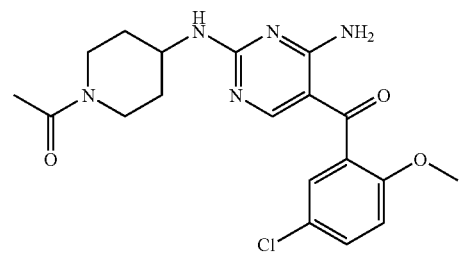

MW 403.87
$C_{19}H_{22}ClN_5O_3$

112

The same procedure as described in Example 90 was used, starting with (4-amino-2-ethanesulfonyl-pyrimidin-5-yl)-(5-chloro-2-methoxy-phenyl)-methanone, Example 110, to give 1-[4-[4-amino-5-(5-chloro-2-methoxy-benzoyl)-pyrimidin-2-ylamino]-piperidin-1-yl]-ethanone as a white solid. MS (M+H)⁺: 404.

Example 112

[4-Amino-2-(1-methanesulfonyl-piperidin-4-ylamino)-pyrimidin-5-yl]-(5-chloro-2-methoxy-phenyl)-methanone

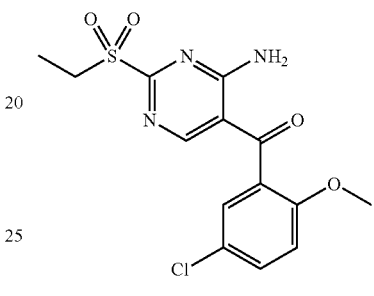

MW 355.80
$C_{14}H_{14}ClN_3O_4S$

+

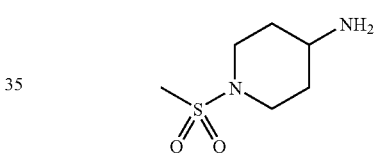

MW 178.25
$C_6H_{14}N_2O_2S$

→

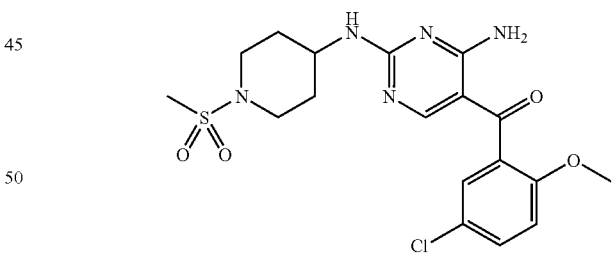

MW 439.92
$C_{18}H_{22}ClN_5O_4S$

The same procedure as described in Example 90 was used, starting with (4-amino-2-ethanesulfonyl-pyrimidin-5-yl)-(5-chloro-2-methoxy-phenyl)-methanone, Example 110, and 1-methanesulfonyl-piperidin-4-ylamine (with trifluoroacetic acid), Example 162, to give [4-amino-2-(1-methanesulfonyl-piperidin-4-ylamino)-pyrimidin-5-yl]-(5-chloro-2-methoxy-phenyl)-methanone. MS (M+H)⁺, 404.

Example 113

Trans-[4-[4-amino-5-(5-fluoro-2-methoxy-benzoyl)-pyrimidin-2-ylamino]-cyclohexyl]-carbamic acid tert-butyl ester

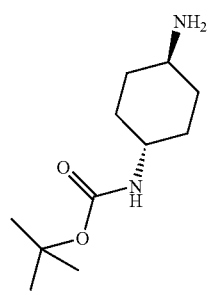

MW 214.31
C₁₁H₂₂N₂O₂

+

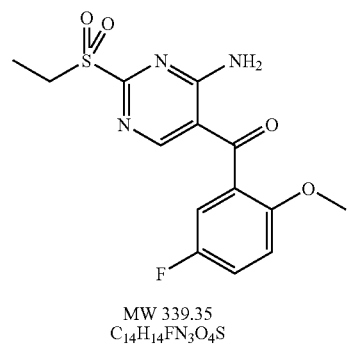

MW 339.35
C₁₄H₁₄FN₃O₄S

→

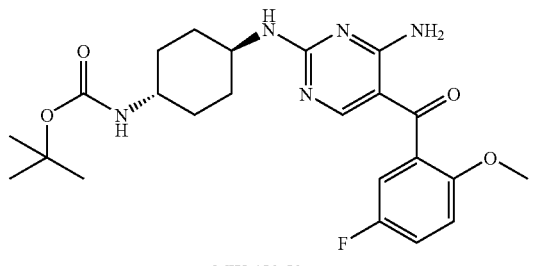

MW 459.52
C₂₃H₃₀FN₅O₄

(4-Amino-cyclohexyl)-carbamic acid tert-butyl ester (Astatech, 872 mg, 4.0 mmol) was added to a stirred solution of sulfone, (1.03 g, 3.30 mmol, Example 48) in dimethylformamide (10 mL). The mixture was stirred at 90° C. for 1 hour and then cooled to room temperature and poured into water. The solid was filtered and dried and passed through a short pad of silica gel column (eluted with 2% methanol/dichloromethane) to give a pale yellow solid. 1.42 g, 94%. MS (M+H)⁺=460.

Example 114

Trans-[4-amino-2-(4-amino-cyclohexylamino)-pyrimidin-5-yl]-(5-fluoro-2-methoxy-phenyl)-methanone

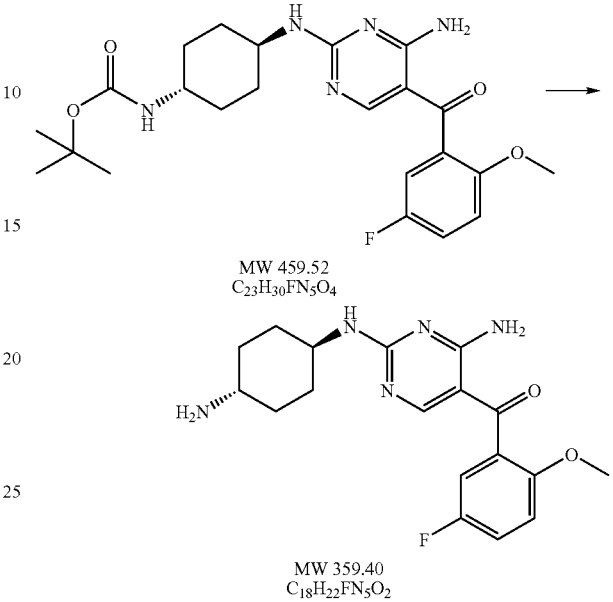

Trans-[4-[4-amino-5-(5-fluoro-2-methoxy-benzoyl)-pyrimidin-2-ylamino]-cyclohexyl]-carbamic acid tert-butylester (1.32 g) obtained from Example 113 was dissolved in 50% trifluoroacetic acid/dichloromethane (30 mL) and the solution was stirred at room temperature for 30 minutes. The solvent was removed and the residue was treated with saturated aqueous sodium bicarbonate solution. The mixture was extracted three times with ethyl acetate/tetrahydrofuran (3:1, 30 mL). The extracts were combined, dried (Na₂SO₄) and concentrated under reduced pressure to a solid (980 mg). Yield, 95%. MS(ES) (M+H)⁺=360.

Example 115
N-[4-[4-Amino-5-(5-fluoro-2-methoxy-benzoyl-pyrimidin-2-ylamino]-cyclohexyl]-methanesulfonamide

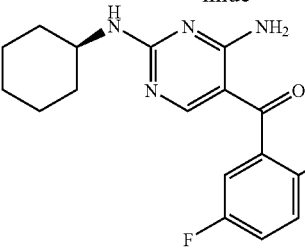

MW 359.40
C₁₈H₂₂FN₅O₂

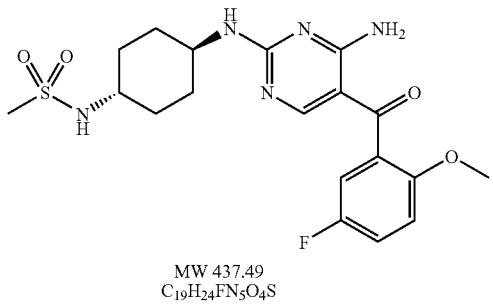

MW 437.49
C₁₉H₂₄FN₅O₄S

[4-Amino-2-(4-amino-cyclohexylamino)-pyrimidin-5-yl]-(5-fluoro-2-methoxy-phenyl)-methanone (250 mg, 0.70 mmol, Example 114) was dissolved in tetrahydrofuran (8 mL) and the solution was cooled to 0° C. To the stirred solution, triethylamine (81 mg, 0.80 mmol) and methanesulfonylchloride (Aldrich, 81 mg, 0.80 mmol) were added successively. The reaction was quenched 5 minutes later with saturated aqueous sodium bicarbonate solution (15 mL) and the mixture was extracted with methylene chloride (3×15 mL). The extracts were dried (Na$_2$SO$_4$) and concentrated to give a solid, which was chromatographed on silica gel (2.5% methanol in dichloromethane) to give a white solid. 195.08 mg. 64%. MS(ES) (M+H)$^+$=438.

Example 116

Ethanesulfonic acid [4-[4-amino-5-(5-fluoro-2-methoxy-benzoyl)-pyrimidin-2-ylamino]-cyclohexyl]-amide

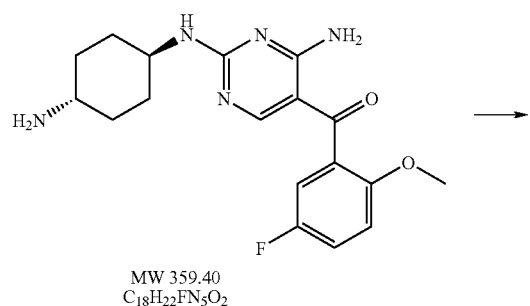

The title compound was made by a similar procedure as for Example 115 using [4-amino-2-(4-amino-cyclohexylamino)-pyrimidin-5-yl]-(5-fluoro-2-methoxy-phenyl)-methanone, Example 114, and ethanesulfonyl chloride (Aldrich). MS(ES) (M+H)$^+$=452.

Example 117

[4-[4-Amino-5-(5-fluoro-2-methoxy-benzoyl)-pyrimidin-2-ylamino]-cyclohexyl]-carbamic acid ethyl ester

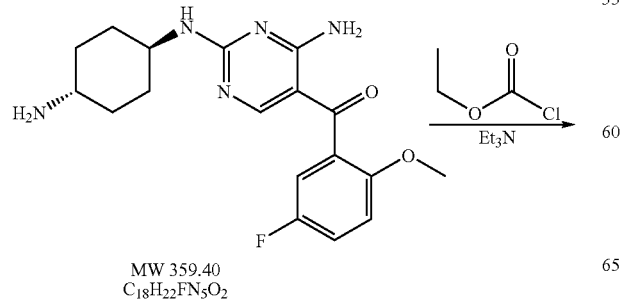

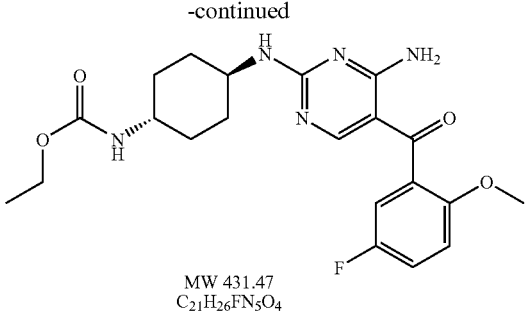

The title compound was made by a similar procedure as for Example 115 using [4-amino-2-(4-amino-cyclohexylamino)-pyrimidin-5-yl]-(5-fluoro-2-methoxy-phenyl)-methanone, Example 114, and ethylchloroformate (Aldrich). MS(ES) (M+H)$^+$=432.

Example 118

[4-[4-amino-5-(5-fluoro-2-methoxy-benzoyl)-pyrimidin-2-ylamino]-cyclohexyl]-carbamic acid 2-methoxy-ethyl ester

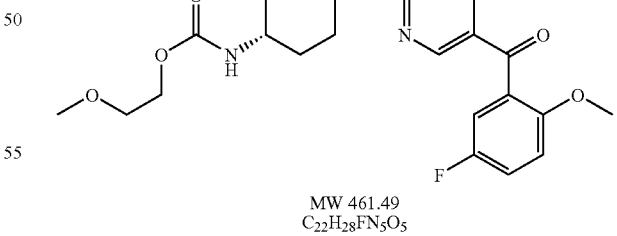

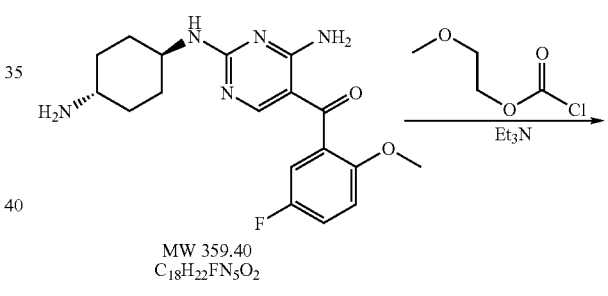

The title compound was made by a similar procedure as for Example 115 using [4-amino-2-(4-amino-cyclohexylamino)-pyrimidin-5-yl]-(5-fluoro-2-methoxy-phenyl)-methanone, Example 114, and 2-methoxyethylchloroformate (TCI-US). MS(ES) (M+H)$^+$=462.

Example 119

Trans-N-[4-[4-amino-5-(5-fluoro-2-methoxy-benzoyl)-pyrimidin-2-ylamino]-cyclohexyl]-acetamide

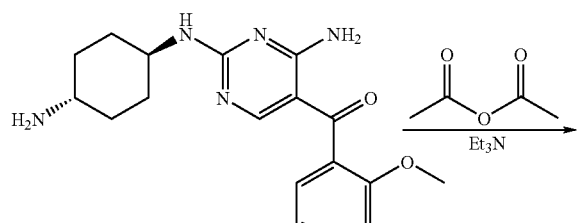

MW 359.40
C{18}H{22}FN{5}O{2}

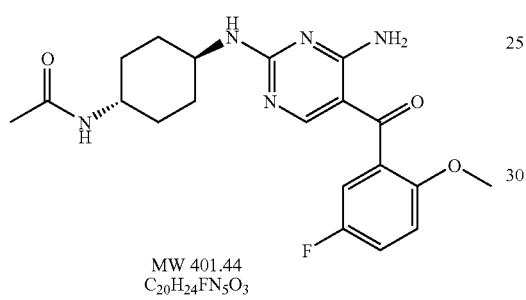

MW 401.44
C{20}H{24}FN{5}O{3}

The title compound was made by a similar procedure as for Example 115 using [4-amino-2-(4-amino-cyclohexylamino)-pyrimidin-5-yl]-(5-fluoro-2-methoxy-phenyl)-methanone, Example 114, and acetic anhydride (Aldrich). MS(ES) (M+H)$^+$=402.

Example 120

Trans-[4-Amino-2-(4-amino-cyclohexylamino)-pyrimidin-5-yl]-(2,3-difluoro-6-methoxy-phenyl)-methanone

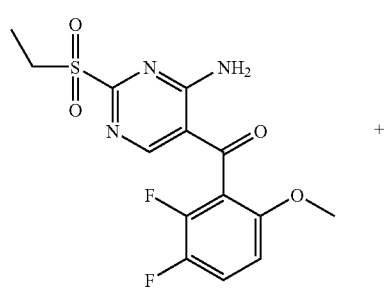

MW 357.34
C{14}H{13}F{2}N{3}O{4}S

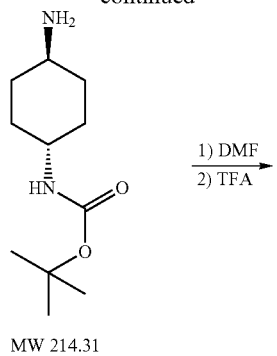

MW 214.31
C{11}H{22}N{2}O{2}

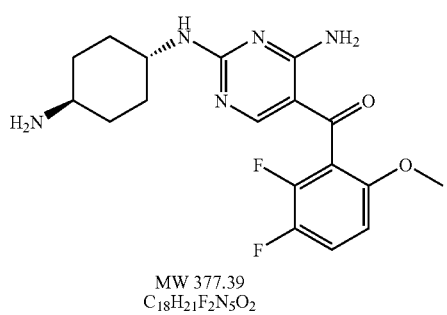

MW 377.39
C{18}H{21}F{2}N{5}O{2}

The title compound was prepared as in Example 113 and Example 114 using (4-amino-cyclohexyl)-carbamic acid tert-butyl ester (Altech) and (4-amino-2-ethanesulfonyl-pyrimidin-5-yl)-(2,3-difluoro-6-methoxy-phenyl)-methanone Example 103. MS (M+H)$^+$=378.

Example 121

Trans-N-[4-[4-Amino-5-(2,3-difluoro-6-methoxy-benzoyl)-pyrimidin-2-ylamino]-cyclohexyl]-acetamide

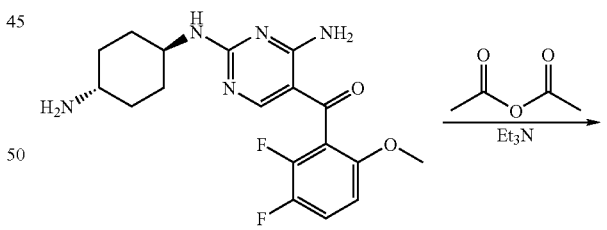

MW 377.39
C{18}H{21}F{2}N{5}O{2}

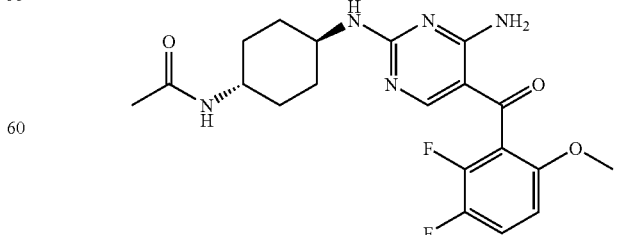

MW 419.43
C{20}H{23}F{2}N{5}O{3}

The title compound was made by a similar procedure as for Example 119 using trans-[4-amino-2-(4-amino-cyclohexylamino)-pyrimidin-5-yl]-(2,3-difluoro-6-methoxy-phenyl)-methanone Example 120, and acetic anhydride (Aldrich). MS(ES) (M+H)+=420.

Example 122

N-(4-Amino-cyclohexyl)-methanesulfonamide; compound with trifluoro-acetic acid

A. (4-Methanesulfonylamino-cyclohexyl)-carbamic acid tert-butyl ester

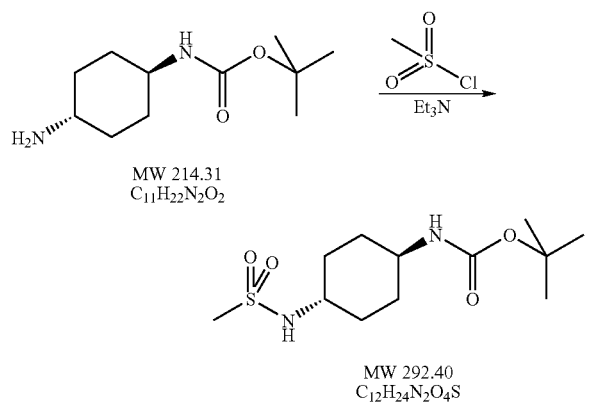

To a stirred solution of (4-amino-cyclohexyl)-carbamic acid tert-butyl ester (Altech, 1.24 g, 5.79 mmol) in methylene chloride (50 mL) at 0° C., triethylamine (202 mg, 6.95 mmol) and methansulfonylchloride (Aldrich, 796 mg, 6.95 mmol) were added successively and the mixture was stirred for 40 minutes. The solvent was removed and the residue was washed with water to give a white solid, which was directly used for the next step.

B. N-(4-Amino-cyclohexyl)-methanesulfonamide; Compound with trifluoro-acetic acid

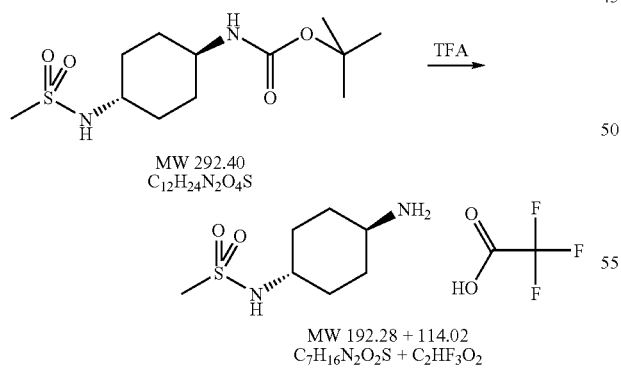

The compound obtained from step A was dissolved in 50% trifluoroacetic acid/dichloromethane and the mixture was stirred at room temperature for 30 minutes. The excess acid was removed under reduced pressure and the residue was triturated with ether to give a white powder, 1.51 g, 90% for two steps. MS(ES) (M+H)+=193.

Example 123
Trans-ethanesulfonic acid (4-aminocyclohexyl)-amide, HCl Salt

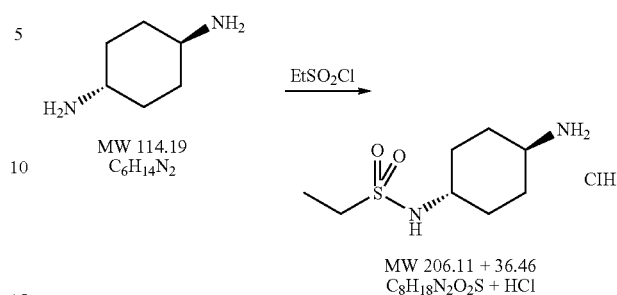

To a stirred solution of trans-1,4-diaminocyclohexane (5.12 g, 44.87 mmol, Aldrich) in tetrahydrofuran (200 mL) at 0° C., ethanesulfonylchloride (4.48 mL, 47.11 mmol) was added dropwise and the mixture was stirred for 3 hours. The solid was filtered and washed with tetrahydrofuran (3×50 mL) and dried to give a white solid which was dissolved in saturated aqueous sodium bicarbonate solution and the mixture was extracted with ethyl acetate (3×30 mL). The extracts were combined and dried with sodium sulfate and the solvent was removed to give a white solid. 2.8 g, MS(ES) (M+H)+=207.

Example 124
Trans-N-[4-[4-amino-5-(2,3-difluoro-6-methoxybenzoyl)-pyrimidin-2-ylamino]-cyclohexyl]-methanesulfonamide

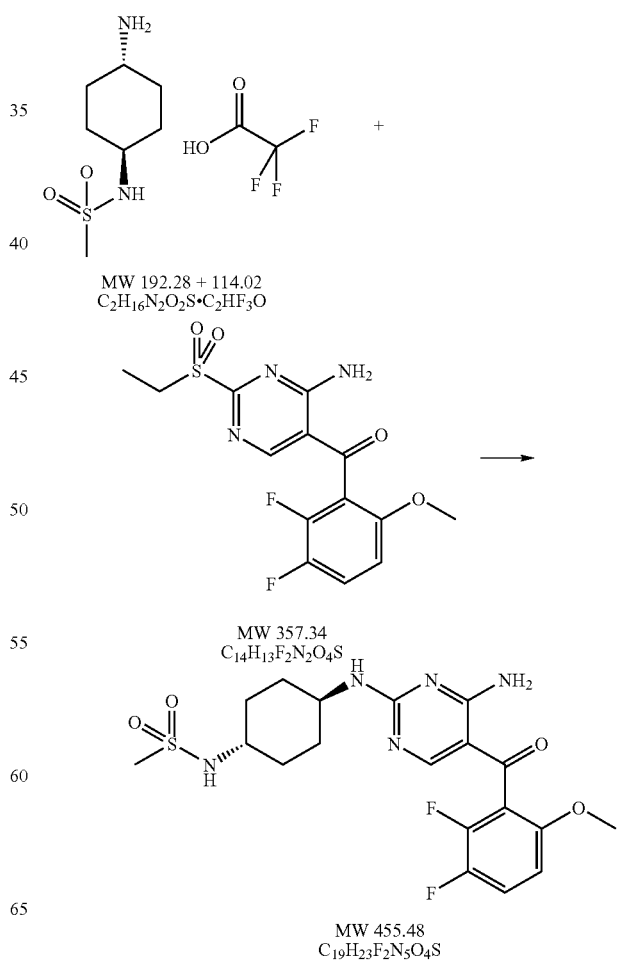

To a stirred solution of N-(4-amino-cyclohexyl)-methanesulfonamide, Example 122, (211 mg, 0.69 mmol) in dimethylformamide, triethylamine (40 μL, 2.87 mmol) and the compound of Example 103 (200 mg, 0.57 mmol) were added and the mixture was stirred at 90° C. for 1 hour. Then the mixture was poured into water and extracted with ethyl acetate, dried (sodium sulfate) and concentrated. The residue was chromatographed to give the product. 185 mg, 71%. MS(ES) (M+H)$^+$=456.

Example 125

[4-Amino-2-(4-hydroxy-cyclohexylamino)-pyrimidin-5-yl]-(5-fluoro-2-methoxy-phenyl)-methanone

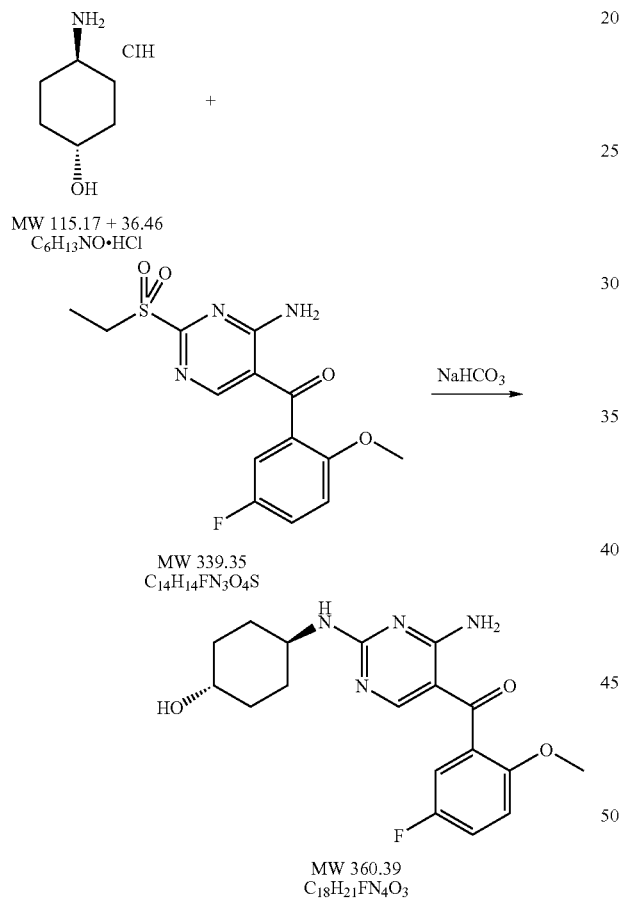

To a stirred solution of trans-4-amino-cyclohexanol hydrochloride (108 mg, 0.71 mmol, Aldrich) in dimethylformamide, were added sodium bicarbonate(98 mg, 0.92 mmol) and (4-amino-2-ethanesulfonyl-pyrimidin-5-yl)-(5-fluoro-2-methoxy-phenyl)-methanone (201 mg, 0.59 mmol, Example 48) and the mixture was stirred at 90° C. for 1 hour. The mixture was poured into water and extracted with ethyl acetate. The extracts were dried with sodium sulfate and concentrated. The residue was chromatographed (2.5% methanol in dichloromethane) to give a white solid. 172 mg, 81%. MS(ES) (M+H)$^+$=361.

Example 126

[4-Amino-2-(tetrahydro-thiopyran-4-ylamino)-pyrimidin-5-yl]-(5-fluoro-2-methoxy-phenyl)-methanone To a stirred solution of sulfoxide (300 mg, 0.93 mmol, Example 163), tetrahydro-thiopyran-4-ylamine (170 mg, 1.45 mmol, made by the procedure of K. Ramahingam et al. J. Org. Chem., 1981, 46(22), 4376), was added and the mixture was stirred at 80° C. for 2 hours. The solvent was removed under reduced pressure and the residue was chromatographed (ethyl acetate/hexane, 20% then 40%) to give a light yellow solid. 155 mg, 46%. MS (M+H)$^+$=363.

Example 127

[4-Amino-2-(1,1-dioxo-hexahydro-1I6-thiopyran-4-ylamino)-pyrimidin-5-yl]-(5-fluoro-2-methoxy-phenyl)-methanone -continued

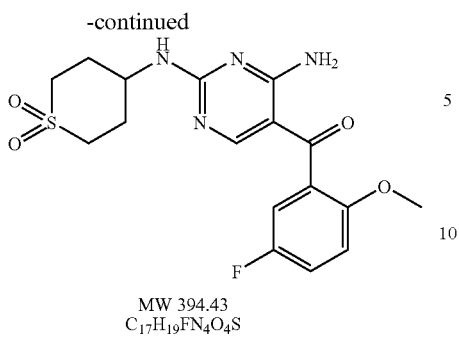

MW 394.43
C₁₇H₁₉FN₄O₄S

The thiopyran obtained from Example 126 (85 mg, 0.23 mmol) was dissolved in methylene chloride (10 mL) and cooled to 0° C. To the stirred solution, meta-chloroperoxybenzoic acid (Aldrich, 77%, 80 mg, 0.35 mmol) was added and the mixture was stirred for 90 minutes. The reaction was quenched with 10% aqueous sodium thiosulfate solution and the organic layer was separated and washed with aqueous sodium carbonate solution (10%). The solution was dried with sodium sulfate and the solvent was removed on a rotary evaporator. The residue was chromatographed (50% ethyl acetate/hexanes) to give the product. 31 mg, 34%. MS(ES) (M+H)⁺=395.

Example 128

[4-Amino-2-[4-(1-ethyl-piperidin-3-yloxy)-phenylamino]-pyrimidin-5-yl]-(5-fluoro-2-methoxy-phenyl)-methanone

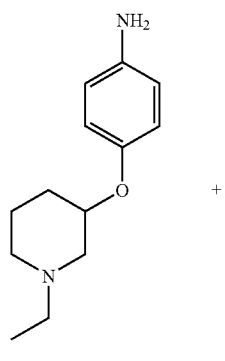

MW 220.31
C₁₃H₂₀N₂O

+

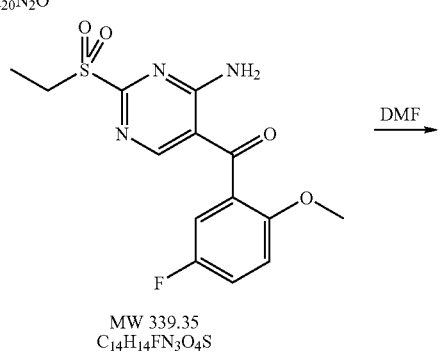

MW 339.35
C₁₄H₁₄FN₃O₄S

→ DMF

-continued

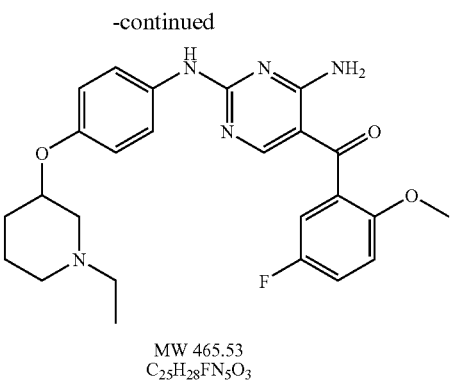

MW 465.53
C₂₅H₂₈FN₅O₃

The title compound was made by a similar procedure as for Example 113, using 4-(1-ethyl-piperidin-3-yloxy)-phenylamine and the compound of Example 48. MS(ES) (M+H)⁺=466.

The 4-(1-ethyl-piperidin-3-yloxy)-phenylamine was prepared as follows:

A. 1-Ethyl-3-(4-nitro-phenoxy)-pyrrolidine

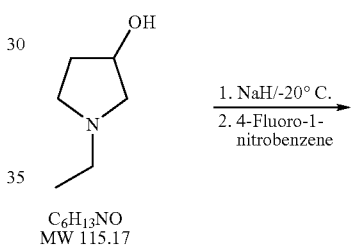

C₆H₁₃NO
MW 115.17

1. NaH/-20° C.
2. 4-Fluoro-1-nitrobenzene →

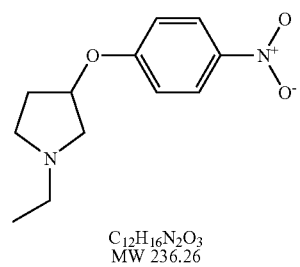

C₁₂H₁₆N₂O₃
MW 236.26

B. 4-(1-Ethyl-pyrrolidin-3-yloxy)-phenylamine

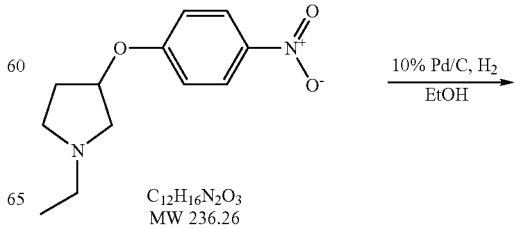

C₁₂H₁₆N₂O₃
MW 236.26

10% Pd/C, H₂
EtOH →

Example 129

[4-Amino-2-[4-(1-ethyl-pyrrolidin-3-yloxy)-phenylamino]-pyrimidin-5-yl]-(5-fluoro-2-methoxy-phenyl)-methanone

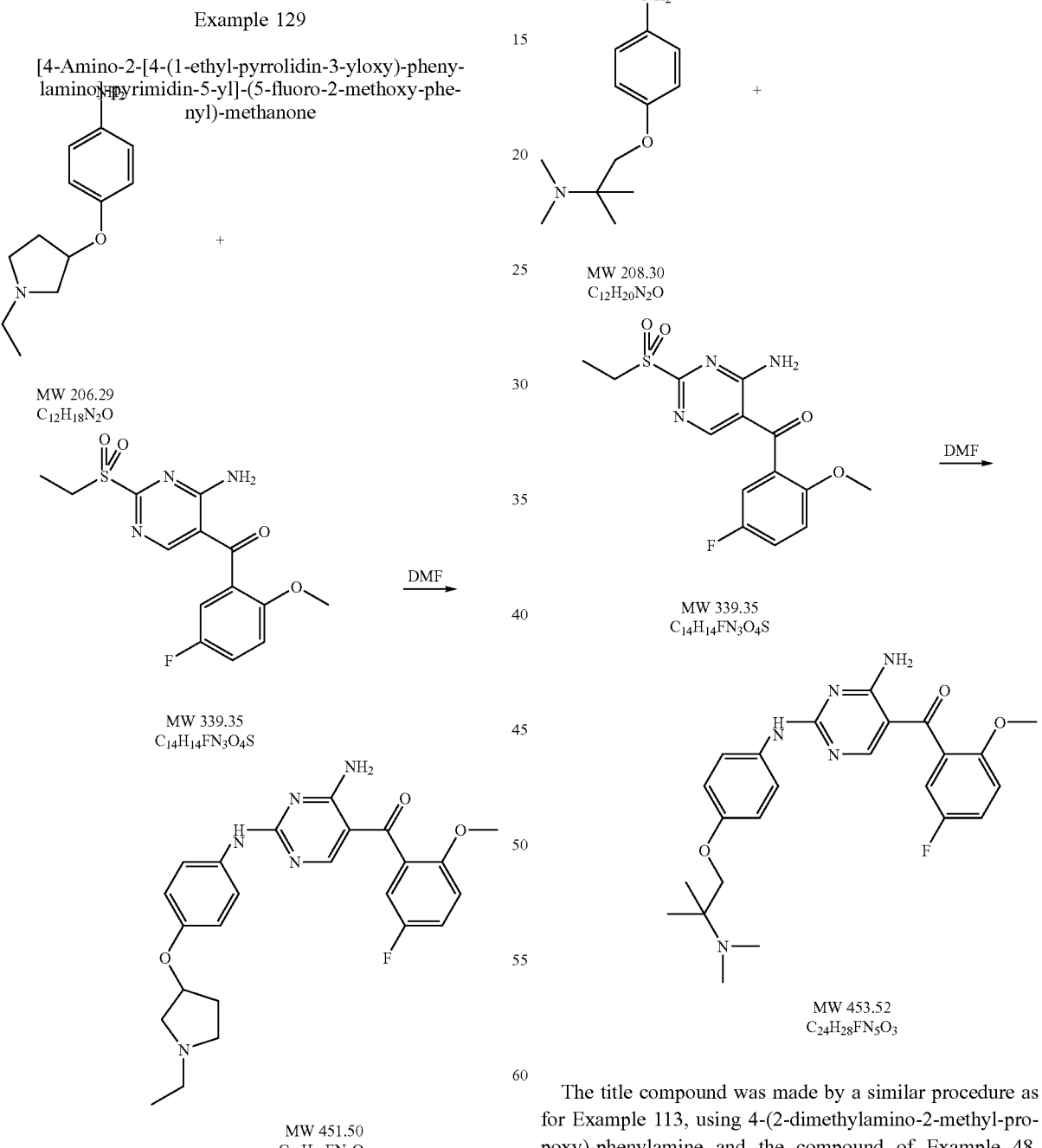

The title compound was made by a similar procedure as for Example 113, using 4-(1-ethyl-pyrrolidin-3-yloxy)-phenylamine (prepared as described above in Example 128) and the compound of Example 48. MS(ES) (M+H)$^+$=452.

Example 130

[4-Amino-2-[4-(2-dimethylamino-2-methyl-propoxy)-phenylamino]-pyrimidin-5-yl]-(5-fluoro-2-methoxy-phenyl)-methanone The title compound was made by a similar procedure as for Example 113, using 4-(2-dimethylamino-2-methyl-propoxy)-phenylamine and the compound of Example 48. MS(ES) (M+H)$^+$=454.

The 4-(2-dimethylamino-2-methyl-propoxy)-phenylamine was prepared as follows:

A. [1,1-Dimethyl-2-(4-nitro-phenoxy)-ethyl]-dimethyl-amine

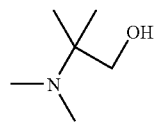

C₆H₁₅NO
MW 117.19

1. NaH/-20° C.
2. 4-Fluoro-1-nitrobenzene
→

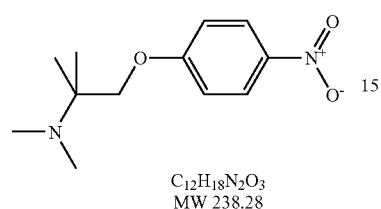

C₁₂H₁₈N₂O₃
MW 238.28

B. 4-(2-Dimethylamino-2-methyl-propoxy)-phenylamine

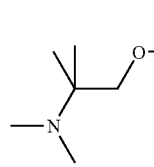

C₁₂H₁₈N₂O₃
MW 238.28

10% Pd/C, H₂
EtOH
→

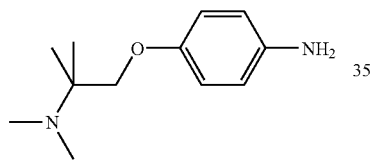

C₁₂H₂₀N₂O
MW 208.30

Example 131

[4-Amino-2-[4-(2-pyrrolidin-1-yl-propoxy)-phenylamino]-pyrimidin-5-yl]-(5-fluoro-2-methoxy-phenyl)-methanone

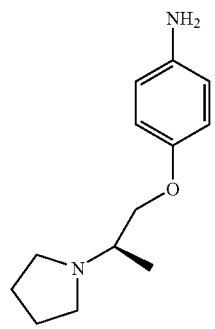

MW 220.31
C₁₃H₂₀N₂O

+

-continued

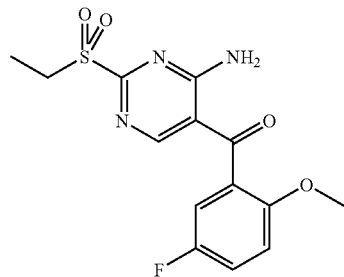

MW 339.35
C₁₄H₁₄FN₃O₄S

DMF →

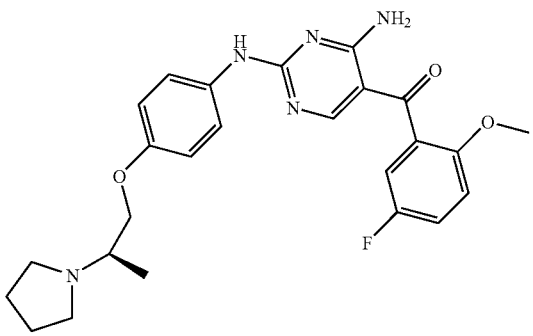

MW 465.53
C₂₅H₂₈FN₅O₃

The title compound was made by a similar procedure as for Example 113, using R-4-(2-pyrrolidin-1-yl-propoxy)-phenylamine and the compound of Example 48. MS(ES) (M+H)⁺=466.

The R-4-(2-pyrrolidin-1-yl-propoxy)-phenylamine was prepared as follows:

A. (R)-1-[1-Methyl-2-(4-nitro-phenoxy)-ethyl]-pyrrolidine

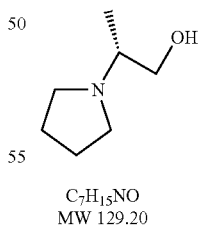

C₇H₁₅NO
MW 129.20

1. NaH/-20° C.
2. 4-Fluoro-1-nitrobenzene
→

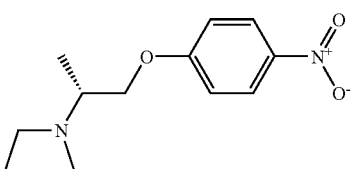

C₁₃H₁₈N₂O₃
MW 250.29

B. (R)-4-(2-Pyrrolidin-1-yl-propoxy)-phenylamine

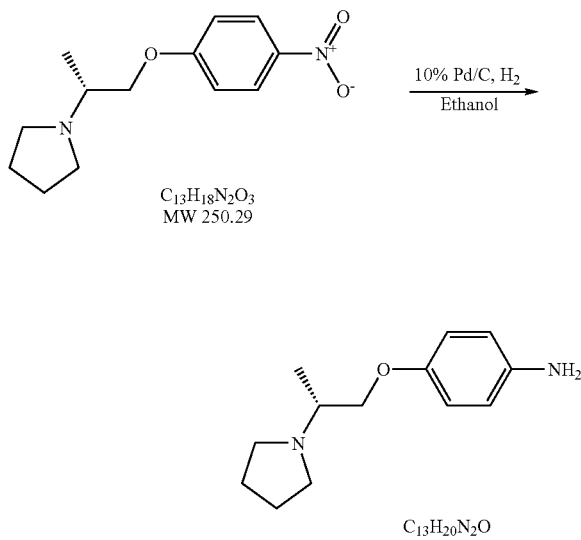

Example 132

(3-[4-[4-Amino-5-(5-fluoro-2-methoxy-benzoyl)-pyrimidin-2-ylamino]-phenyl]-2-hydroxy-propyl)-ethyl-carbamic acid tert-butyl ester

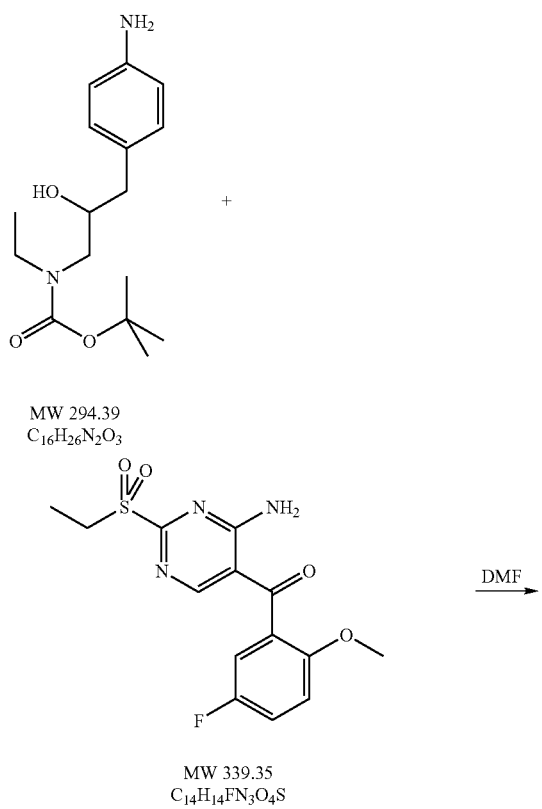

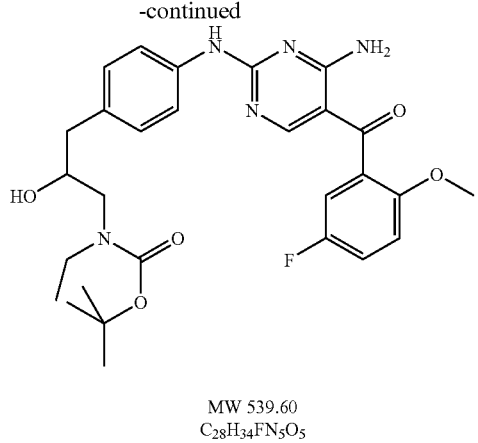

MW 539.60
C$_{28}$H$_{34}$FN$_5$O$_5$

The title compound was made by a similar procedure as for Example 113, using [3-(4-amino-phenyl)-2-hydroxy-propyl]-ethyl-carbamic acid tert-butyl ester and the compound of Example 48. MS(ES) (M+H)$^+$=540.

The [3-(4-amino-phenyl)-2-hydroxy-propyl]-ethyl-carbamic acid tert-butyl ester was prepared by the following procedure: To a stirred solution of 1-allyl-4-nitrobenzene (2.85 g, 17.47 mmol; prepared by the procedure of EP 1013636 A1, 1999) in dichloromethane (100 mL) at room temperature was added 3-chlorperoxybenzoic acid (6.03 g, 57–86%, Aldrich) and the mixture stirred overnight. The solution was washed with excess aqueous sodium thiosulfate, then with aqueous sodium bicarbonate solution and the organic solution was dried (magnesium sulfate), evaporated, and chromatographed on silica gel giving 1.94 g (62%) of 2-4-nitorbenzyloxirane as a yellow oil. This oil (0.92 g 5.13 mmol) in methanol was stirred overnight at room temperature with aqueous ethylamine (2 mL, 70% in water, Aldrich). The methanol was removed by evaporation and the residue was dissolved in 1N aqueous hydrochloric acid. The aqueous solution was washed with ether and the aqueous layer was made basic with 4N aqueous sodium hydroxide. Tetrahydrofuran was added to dissolve the solids and di-tert-butyl dicarbonate (1.35 g, 6.16 mmol, Aldrich) was added and the mixture stirred at room temperature for 2 hours. The reaction was extracted with dichloromethane, dried (magnesium sulfate), evaporated and chromatographed on silica gel to give ethyl-[2-hydroxy-3-(4-nitro-phenyl)-propyl]carbamic acid tert-butyl ester as a yellow oil, 1.23 g, 74%. MS(ES) (M+H)$^+$=325. This nitro compound (1.06 g, 3.26 mmol) in ethanol (40 mL) and 10% Palladium on Carbon was hydrogenated at 35 psi for 1.5 hours. The mixture was filtered and evaporated to give [3-(4-amino-phenyl)-2-hydroxy-propyl]-ethyl-carbamic acid tert-butyl ester as a yellow gum, 0.94 g (98%) MS(ES) (M+H)$^+$=295.

Example 133

3-[4-[4-Amino-5-(5-fluoro-2-methoxy-benzoyl)-pyrimidin-2-ylamino]-phenoxy]-pyrrolidine-1-carboxylic acid tert-butyl ester

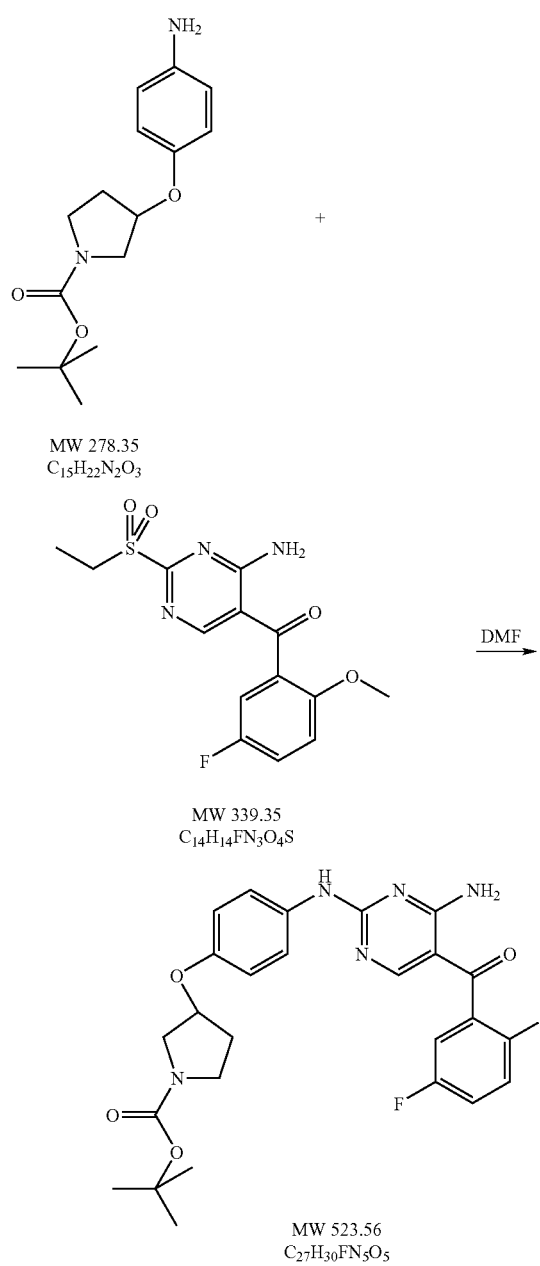

The title compound was made by a similar procedure as for Example 113 using 3-(4-amino-phenoxy)-pyrrolidine-1-carboxylic acid tert-butyl ester and the compound of Example 48. MS(ES) (M+H)$^+$=524.

The 3-(4-amino-phenoxy)-pyrrolidine-1-carboxylic acid tert-butyl ester was prepared as follows:

A. 3-(4-Nitro-phenoxy)-pyrrolidine-1-carboxylic acid tert-butyl ester

B. 3-(4-Amino-phenoxy)-pyrrolidine-1-carboxylic acid tert-butyl ester

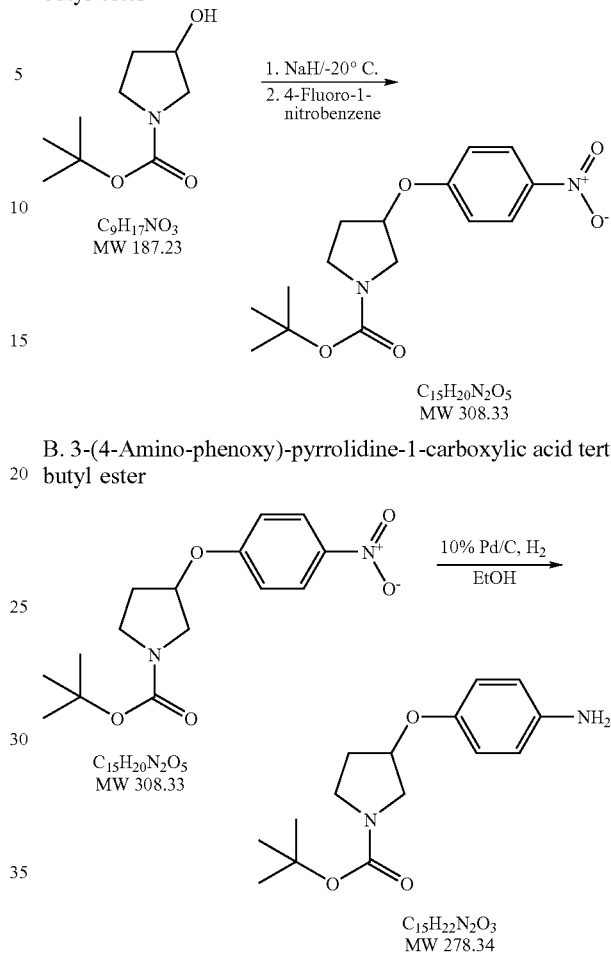

Example 134

[4-Amino-2-(4-dimethylamino-phenylamin)-pyrimidin-5-yl]-(5-fluoro-2-methoxy-phenyl)-methanone

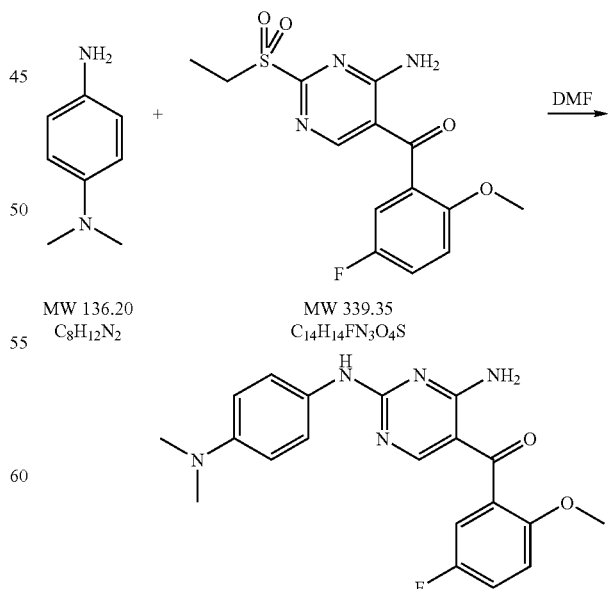

The title compound was made by a similar procedure as for Example 113, using 4-dimethylamino-aniline (Aldrich) and the compound of Example 48. MS(ES) (M+H)+=382.

Example 135

[4-Amino-2-[2-(1H-indol-3-yl)-ethylamino]-pyrimidin-5-yl]-(5-fluoro-2-methoxy-phenyl)-methanone

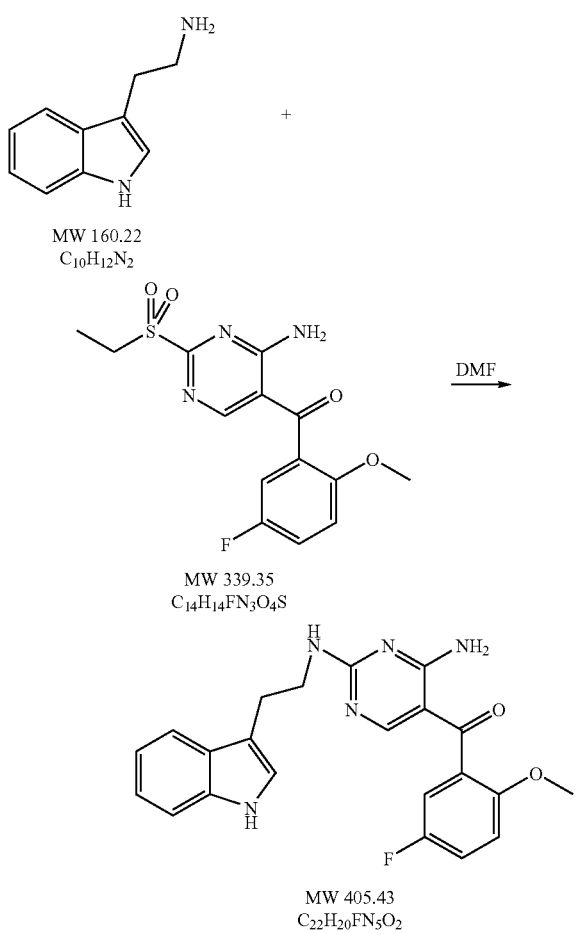

The title compound was made by a similar procedure as for Example 113, using 3-aminoethyl-indole (Aldrich) and the compound of Example 48. MS(ES) (M+H)+=406.

Example 136

1-[3-[4-Amino-5-(5-fluoro-2-methoxy-benzoyl)-pyrimidin-2-ylamino]-propyl]-pyrrolidin-2-one

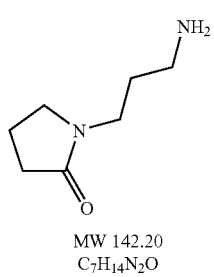

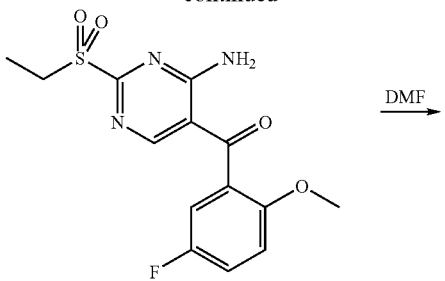

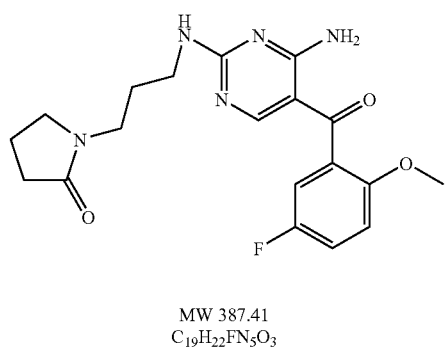

The title compound was made by a similar procedure as for Example 113, using N-(3-aminopropyl)-pyridone (Aldrich) and the compound of Example 48. MS(ES) (M+H)+ =388.

Example 137

[4-Amino-2-(4-amino-butylamino)-pyrimidin-5-yl]-(5-fluoro-2-methoxy-phenyl)-methanone

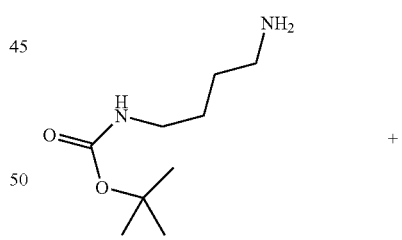

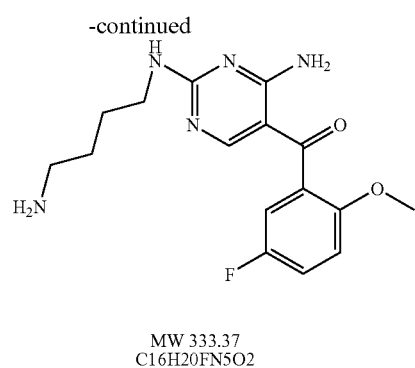

MW 333.37
C16H20FN5O2

The title compound was made by a similar procedure as for Example 113, using (4-amino-butyl)-carbamic acid tert-butyl ester (Aldrich) and the compound of Example 48. MS(ES) (M+H)⁺=334.

Example 138
[3-[4-Amino-5-(5-fluoro-2-methoxy-benzoyl)-pyrimidin-2-ylamino]-propyl]-carbamic acid tert-butyl ester

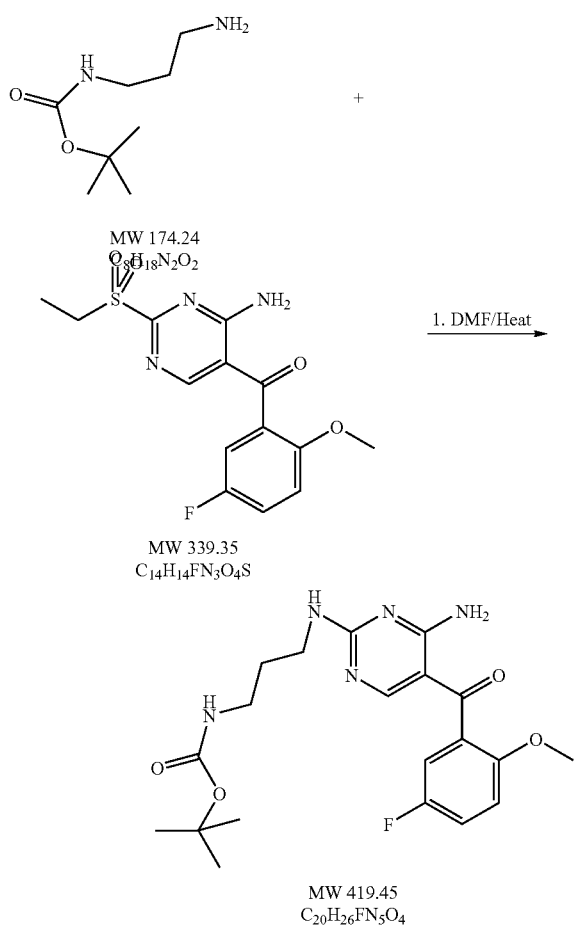

The title compound was made by a similar procedure as for Example 113, using (3-amino-propyl)-carbamic acid tert-butyl ester (Aldrich) and the compound of Example 48. MS(ES) (M+H)⁺=420.

Example 139

[4-Amino-2-[4-(1-methanesulfonyl-piperidin-3-yloxy)-phenylamino]-pyrimidin-5-yl]-(5-fluoro-2-methoxy-phenyl)-methanone

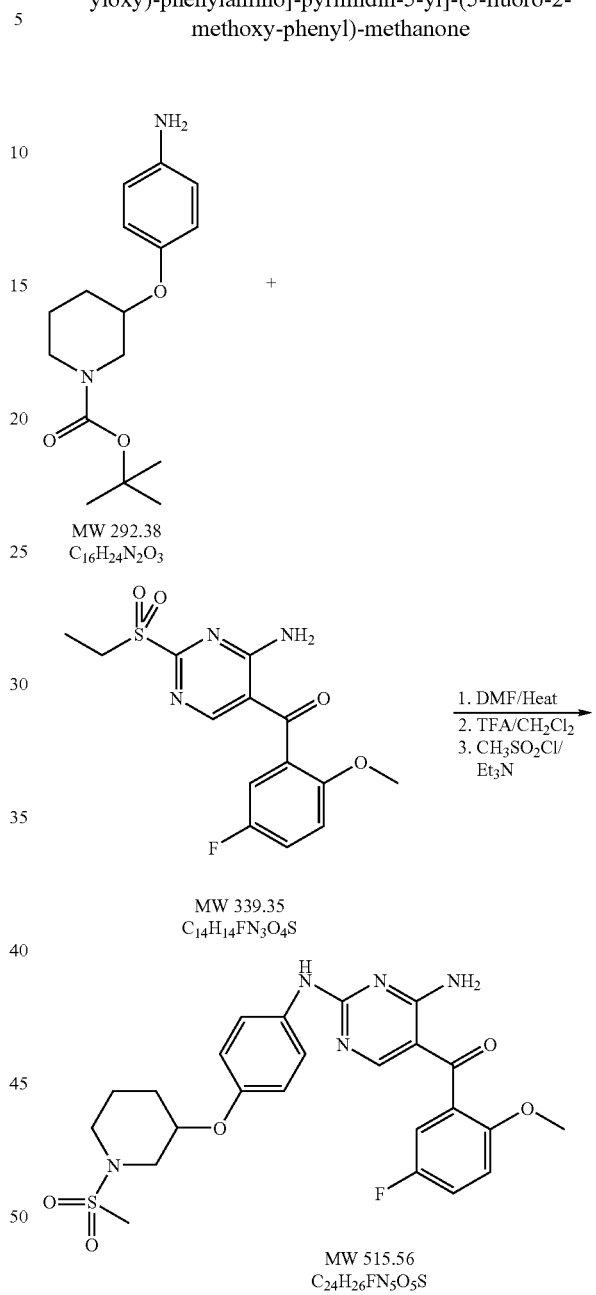

3-(4-Amino-phenoxy)-piperidine-1-carboxylic acid tert-butyl ester (see below) and the compound of Example 48 were treated as in Example 113, the resulting product was then treated as in Example 114, and then as in Example 115 to give [4-amino-2-[4-(1-methanesulfonyl-piperidin-3-yloxy)-phenylamino]-pyrimidin-5-yl]-(5-fluoro-2-methoxy-phenyl)-methanone. MS(ES) (M+H)⁺=516.

The 3-(4-amino-phenoxy)-piperidine-1-carboxylic acid tert-butyl ester was prepared as follows:

A. 3-(4-Nitro-phenoxy)-piperidine-1-carboxylic acid tert-butyl ester

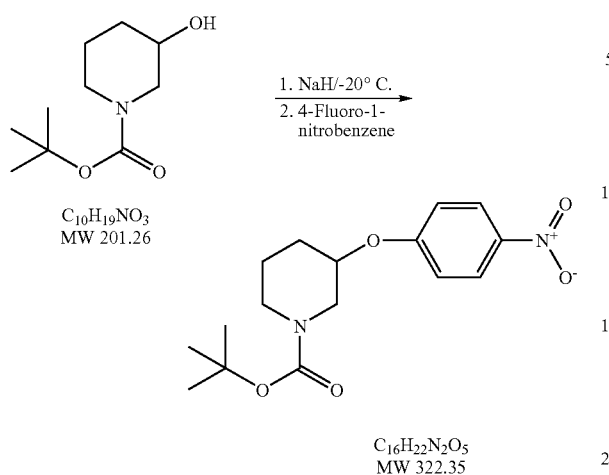

B. 3-(4-Amino-phenoxy)-piperidine-1-carboxylic acid tert-butyl ester

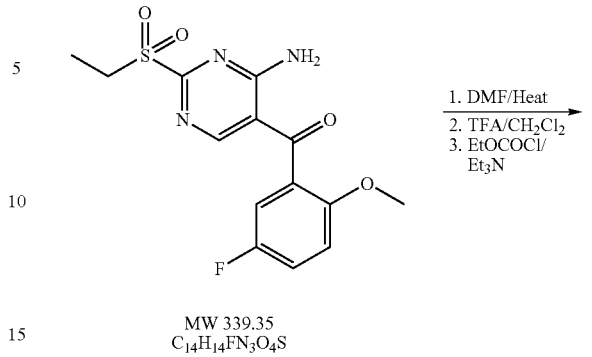

Example 140

3-[4-[4-Amino-5-(5-fluoro-2-methoxy-benzoyl)-pyrimidin-2-ylamino]-phenoxy]-piperidine-1-carboxylic acid ethyl ester

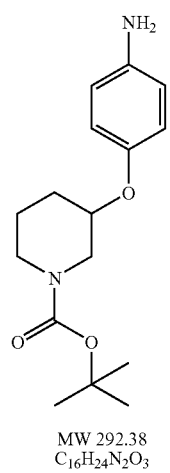

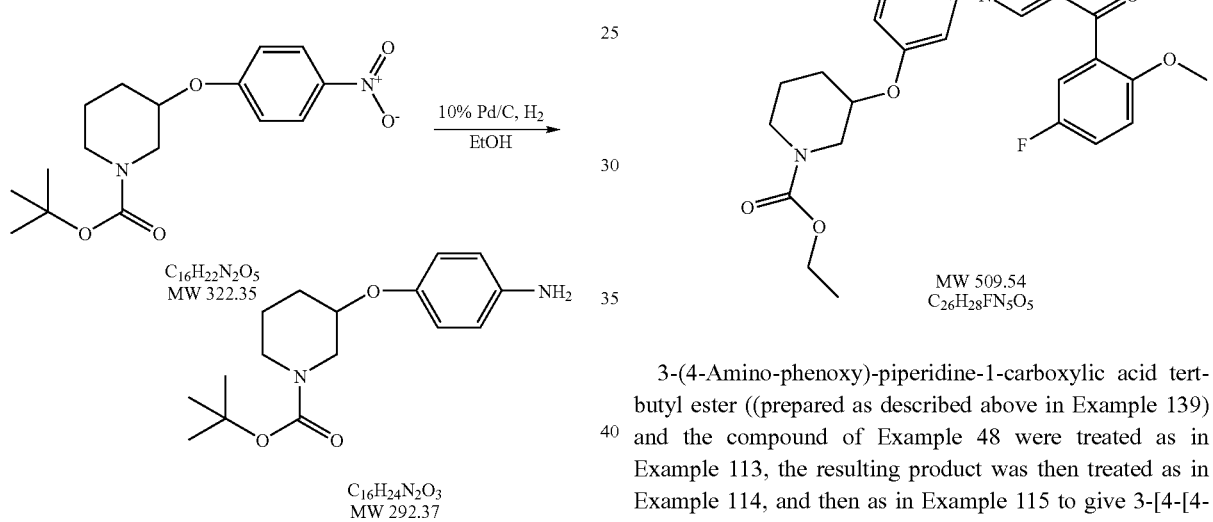

3-(4-Amino-phenoxy)-piperidine-1-carboxylic acid tert-butyl ester ((prepared as described above in Example 139) and the compound of Example 48 were treated as in Example 113, the resulting product was then treated as in Example 114, and then as in Example 115 to give 3-[4-[4-amino-5-(5-fluoro-2-methoxy-benzoyl)-pyrimidin-2-ylamino]-phenoxy]-piperidine-1-carboxylic acid ethyl ester. MS(ES) (M+H)$^+$=510.

Example 141

N-[4-[4-Amino-5-(5-fluoro-2-methoxy-benzoyl)-pyrimidin-2-ylamino]-butyl]-methanesulfonamide

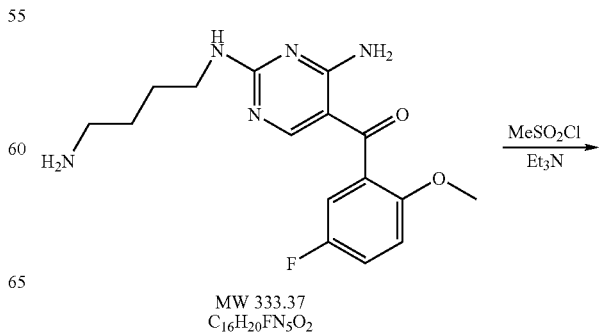

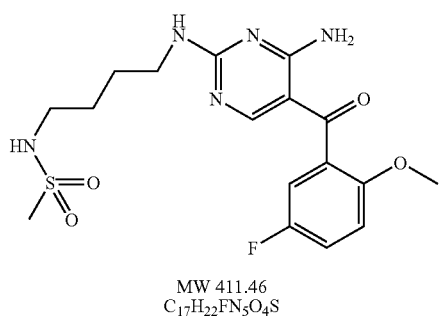

MW 411.46
C$_{17}$H$_{22}$FN$_5$O$_4$S

The title compound was made by a similar procedure as for Example 115 with methanesulfonylchloride (Aldrich) and the compound of Example 137. MS(ES) (M+H)$^+$=412.

Example 142

N-[4-[4-Amino-5-(5-fluoro-2-methoxy-benzoyl)-pyrimidin-2-ylamino]-butyl]-4-fluoro-benzene-sulfonamide

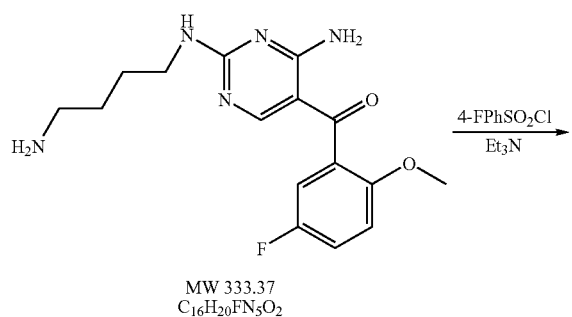

MW 333.37
C$_{16}$H$_{20}$FN$_5$O$_2$

MW 491.52
C$_{22}$H$_{23}$F$_2$N$_5$O$_4$S

The title compound was made by a similar procedure as for Example 115, using 4-fluorophenyl-sulfonyl chloride (Aldrich) and the compound of Example 137. MS(ES) (M+H)$^+$=492.

Example 143
N-[3-[4-Amino-5-(5-fluoro-2-methoxy-benzoyl)-pyrimidin-2-ylamino]-propyl]-benzenesulfonamide

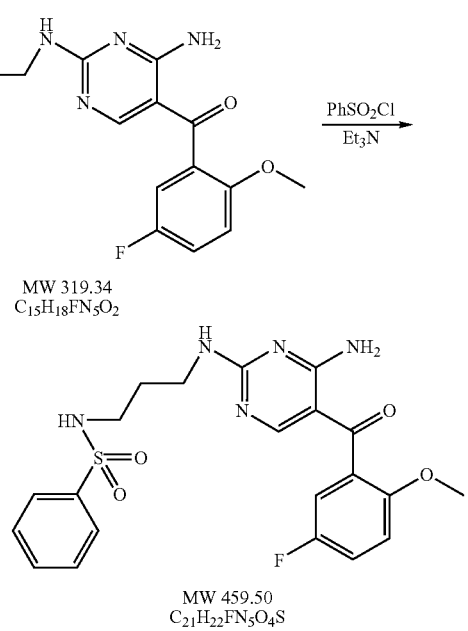

MW 319.34
C$_{15}$H$_{18}$FN$_5$O$_2$

MW 459.50
C$_{21}$H$_{22}$FN$_5$O$_4$S

The title compound was made by a similar procedure as for Example 115, using phenyl-sulfonylchloride (Aldrich) and [4-amino-2-(3-amino-propylamino)-pyrimidin-5-yl]-(5-fluoro-2-methoxy-phenyl)-methanone, which was made from the condensation of (3-amino-propyl)-carbamic acid tert-butyl ester (Aldrich) and the compound of Example 48 following the procedure of Example 113 and Example 114. MS(ES) (M+H)$^+$=460.

Example 144
4-[4Amino-5-(5-fluoro-2-methoxy-benzoyl)-pyrimidin-2-ylamino]-piperidine-1-carboxylic acid (4-dimethylamino-phenyl)-amide

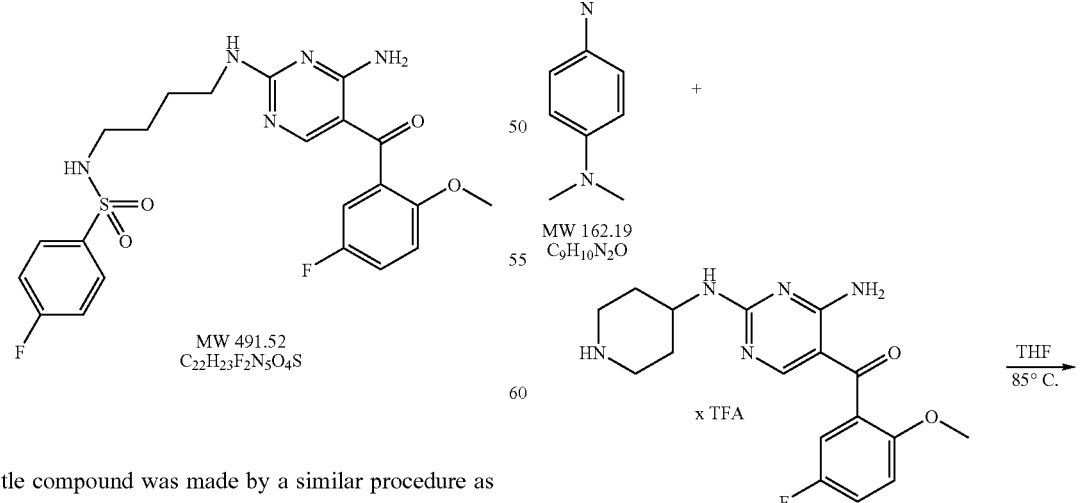

MW 162.19
C$_9$H$_{10}$N$_2$O

MW 345.38 +
C$_{17}$H$_{20}$FN$_5$O$_2$ . xC$_2$HF$_3$O$_2$

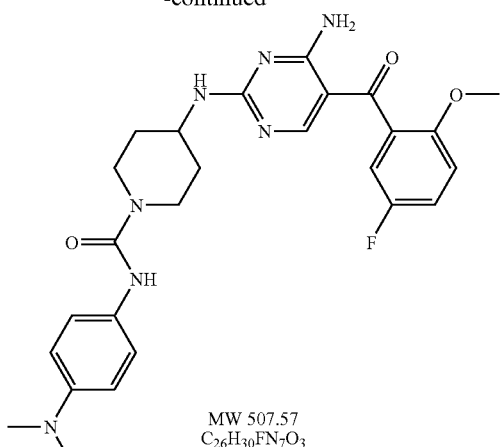

To a stirred suspension of the compound of Example 59 in the form of its trifluoroacetic acid salt (45 mg), triethylamine (150 µL, 1.08 mmol) was added followed by 4-dimethylamino-phenyl-isocyanate (Aldrich, 33 mg, 0.20 mmol), and the solution was stirred at room temperature for 1.5 hours. The solution was then concentrated and the residue was purified by reverse phase HPLC to give a solid, (34 mg). MS(ES) (M+H)$^+$=508.

Example 145
4-[4-Amino-5-(5-fluoro-2-methoxy-benzoyl)-pyrimidin-2-ylamino]-piperidine-1-carboxylic acid cyclohexylamide

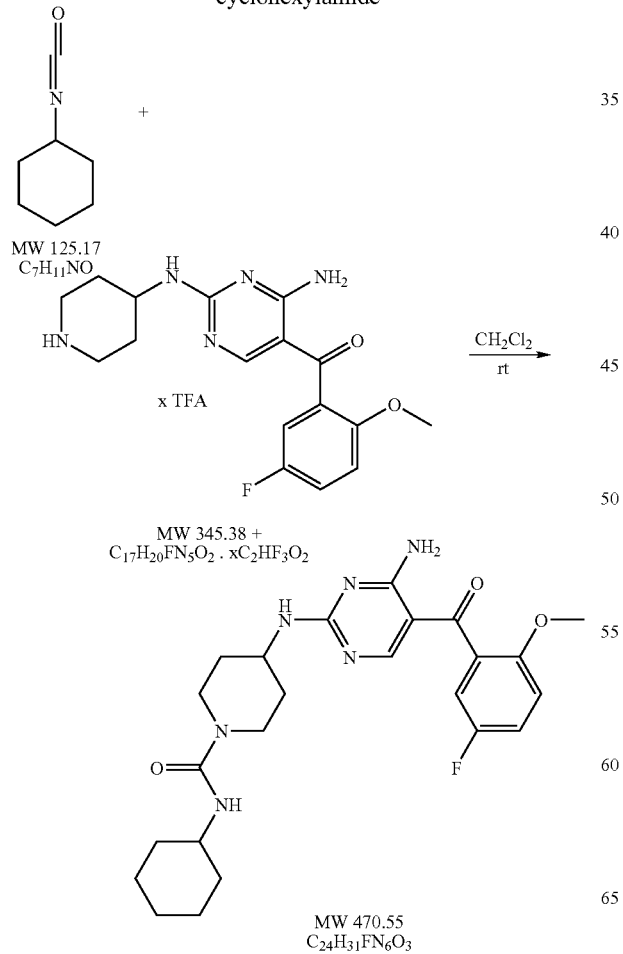

The title compound was made by a similar procedure as used in Example 144 using cyclohexyl isocyanate (Aldrich) and the compound of Example 59 to give 4-[4-amino-5-(5-fluoro-2-methoxy-benzoyl)-pyrimidin-2-ylamino]-piperidine-1-carboxylic acid cyclohexylamide. MS(ES) (M+H)$^+$=471.

Example 146

[4-[4-Amino-5-(5-fluoro-2-methoxy-benzoyl)-pyrimidin-2-ylamino]-piperidine-1-carbonyl]-phosphoramidic acid diethyl ester

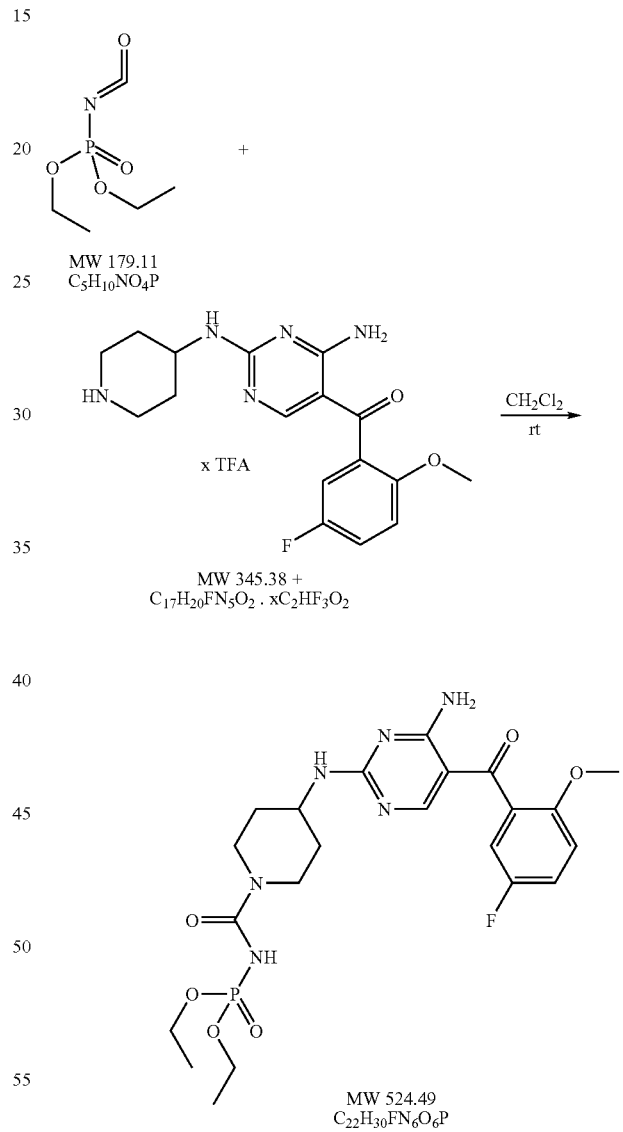

The title compound was made by a similar procedure as used in Example 144, using diethoxyphosphinyl isocyanate (Aldrich) and the compound of Example 59 to give [4-[4-amino-5-(5-fluoro-2-methoxy-benzoyl)-pyrimidin-2-ylamino]-piperidine-1-carbonyl]-phosphoramidic acid diethyl ester. MS(ES) (M+H)$^+$=525.

Example 147

[4-[4-Amino-5-(5-fluoro-2-methoxy-benzoyl)-pyrimidin-2-ylamino]-piperidine-1-carbonyl]-amino)-acetic acid ethyl ester

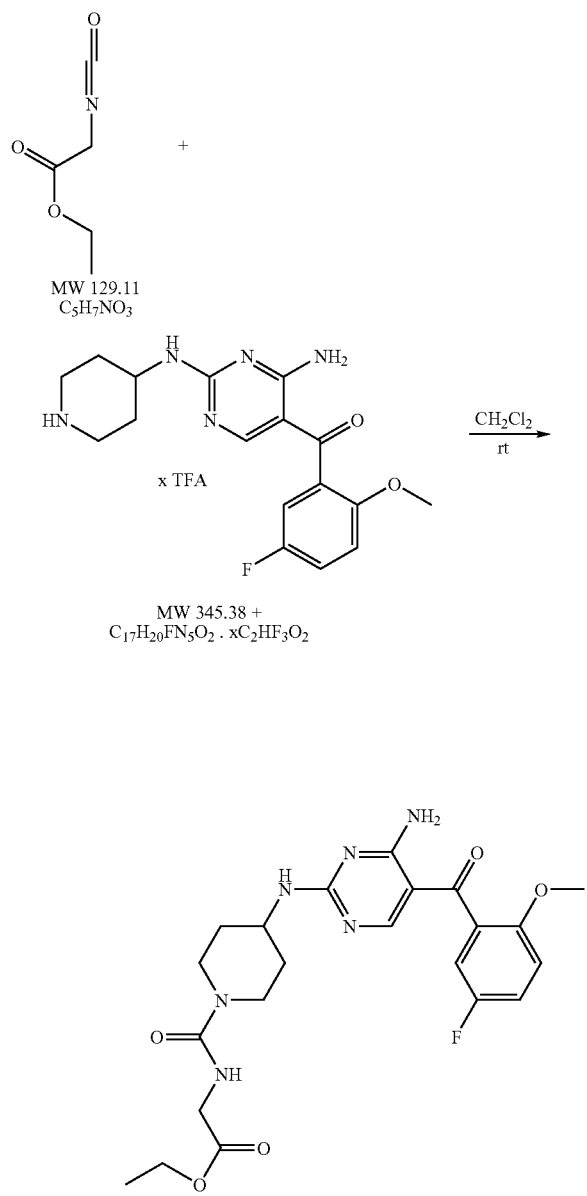

The title compound was made by a similar procedure as used in Example 144, using ethyl isocyanatoacetate (Aldrich) and the compound of Example 59, to give [4-[4-amino-5-(5-fluoro-2-methoxy-benzoyl)-pyrimidin-2-ylamino]-piperidine-1-carbonyl]-amino)-acetic acid ethyl ester. MS(ES) (M+H)$^+$=475.

Example 148

[4-Amino-2-[1-(propane-2-sulfonyl)-piperidin-4-ylamino]-pyrimidin-5-yl]-(5-fluoro-2-methoxy-phenyl)-methanone The title compound was made by a similar procedure as used in Example 115, starting with isopropylsulfonyl chloride (Aldrich) and the compound of Example 59, to give [4-amino-2-[1-(propane-2-sulfonyl)-piperidin-4-ylamino]-pyrimidin-5-yl]-(5-fluoro-2-methoxy-phenyl)-methanone MS(ES) (M+H)$^+$=452.

Example 149

[4-[4-Amino-5-(5-fluoro-2-methoxy-benzoyl)-pyrimidin-2-ylamino]-cyclohexyl]-carbamic acid isopropyl ester

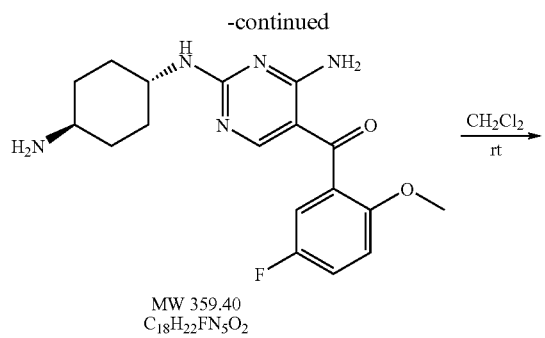

MW 359.40
C$_{18}$H$_{22}$FN$_5$O$_2$

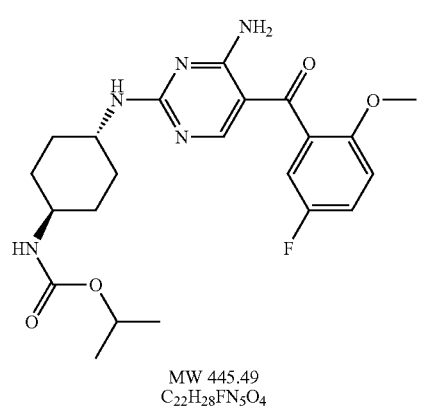

MW 445.49
C$_{22}$H$_{28}$FN$_5$O$_4$

The title compound was made by a similar procedure as used in Example 117, using Isopropyl chloroformate (Aldrich) and the compound of Example 113. MS(ES) (M+H)$^+$ =446.

Example 150

4-[4-Amino-5-(2-fluoro-benzoyl)-pyrimidin-2-ylamino]-piperidine-1-carboxylic acid tert-butyl ester

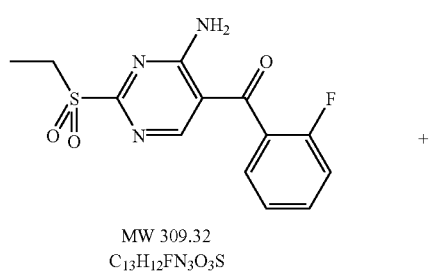

MW 309.32
C$_{13}$H$_{12}$FN$_3$O$_3$S

+

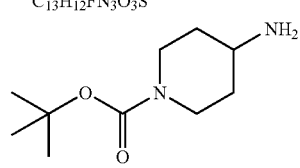

MW 200.28
C$_{10}$H$_{20}$N$_2$O$_2$

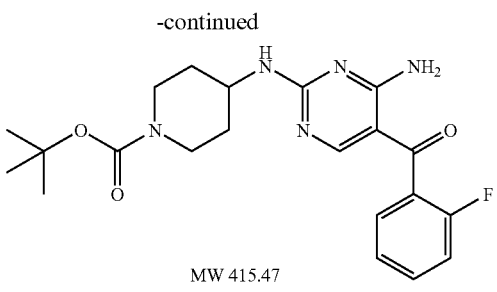

MW 415.47
C$_{21}$H$_{26}$FN$_5$O$_3$

The same procedure as described in Example 10 was used, starting from (4-amino-2-ethanesulfonyl-pyrimidin-5-yl)-(2-fluoro-phenyl)-methanone, Example 37, to give 4-[4-amino-5-(2-fluoro-benzoyl)-pyrimidin-2-ylamino]-piperidine-1-carboxylic acid tert-butyl ester. MS (M+H)$^+$, 416.

Example 151

[4-Amino-2-(piperidin-4-ylamino)-pyrimidin-5-yl]-(2-fluoro-phenyl)-methanone

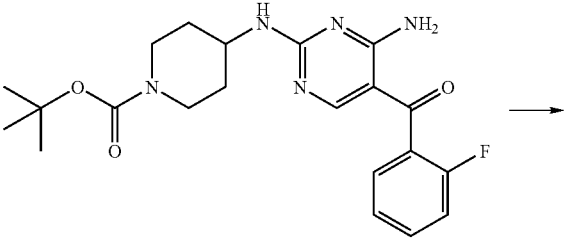

MW 415.47
C$_{21}$H$_{26}$FN$_5$O$_3$

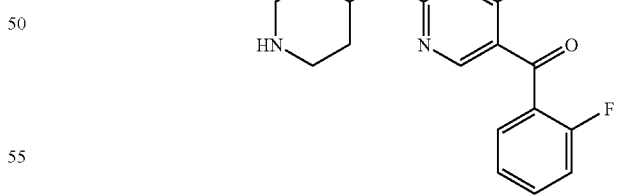

MW 315.35
C$_{16}$H$_{18}$FN$_5$O

The same procedure as described in Example 11 was used, starting from 4-[4-amino-5-(2-fluoro-benzoyl)-pyrimidin-2-ylamino]-piperidine-1-carboxylic acid tert-butyl ester, Example 150, to give [4-amino-2-(piperidin-4-ylamino)-pyrimidin-5-yl]-(2-fluoro-phenyl)-methanone. MS (M+H)$^+$, 315.

Example 152

[4-Amino-2-[1-(2,5-dimethyl-thiophene-3-sulfonyl)-piperidin-4-ylamino]-pyrimidin-5-yl]-(5-fluoro-2-methoxy-phenyl)-methanone

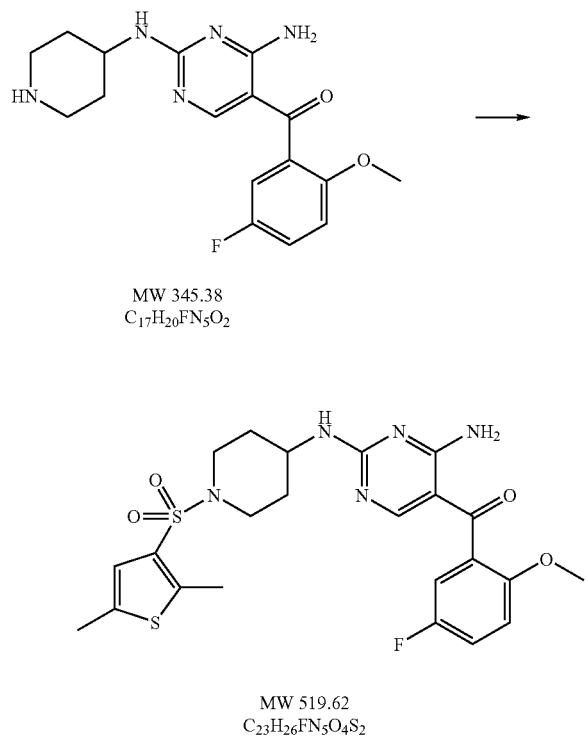

To a solution of [4-amino-2-(piperidin-4-ylamino)-pyrimidin-5-yl]-(5-fluoro-2-methoxy-phenyl)-methanone (50 mg, 0.145 mmol, Example 59) and diisopropylethylamine (Aldrich, 330 µL, 1.894 mmol) in anhydrous tetrahydrofuran (15 mL) cooled to 5° C., was added a solution of 2,5-dimethyl-3-thiophenesulfonyl chloride (Maybridge, 45.3 mg, 0.218 mmol) in methylene chloride (3 mL). The reaction mixture was stirred at room temperature overnight and then diluted with 50 mL of methylene chloride. The resulting solution was washed with saturated aqueous sodium bicarbonate (2×10 mL), dried over anhydrous magnesium sulfate and concentrated in vacuo. Purification of the crude residue by flash chromatography (Biotage system, KP-Sil™ 32–63 µm, 60 Å silica gel) eluting with 25% ethyl acetate in hexane yielded [4-amino-2-[1-(2,5-dimethyl-thiophene-3-sulfonyl)-piperidin-4-ylamino]-pyrimidin-5-yl]-(5-fluoro-2-methoxy-phenyl)-methanone (69 mg, 92%) as white solids. HR-MS (ES, m/z) calculated for $C_{23}H_{26}FN_5O_4S_2$ [(M+H)$^+$] 520.1483, observed 520.1494.

Example 153

[4-Amino-2-[1-(thiophene-3-sulfonyl)-piperidin-4-ylamino]-pyrimidin-5-yl]-(5-fluoro-2-methoxy-phenyl)-methanone

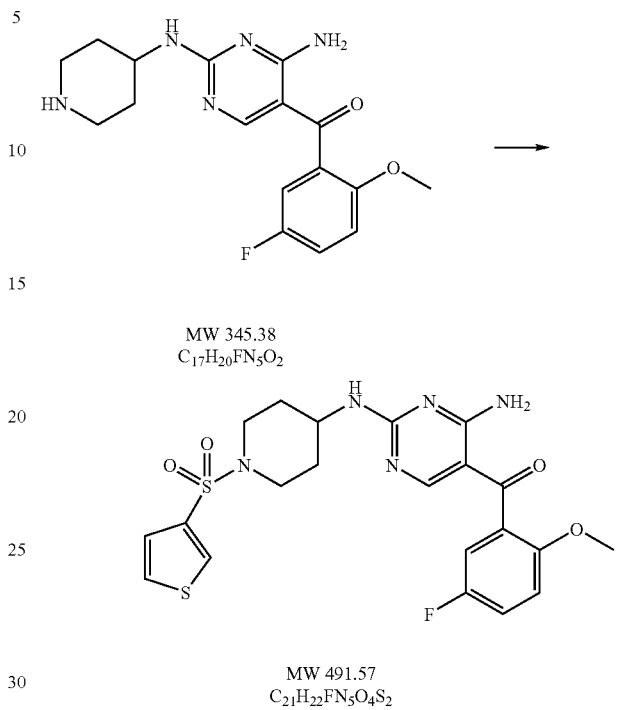

The title compound was prepared from [4-amino-2-(piperidin-4-ylamino)-pyrimidin-5-yl]-(5-fluoro-2-methoxy-phenyl)-methanone, Example 59, and 3-thiophenesulfonyl chloride (Maybridge) by the procedure described in Example 152. HR-MS (ES, m/z) calculated for $C_{21}H_{23}FN_5O_4S_2$ [(M+H)$^+$] 492.1170, observed 492.1175.

Example 154

[4-Amino-2-[1-(benzo[b]thiophene-3-sulfonyl)-piperidin-4-ylamino]-pyrimidin-5-yl]-(5-fluoro-2-methoxy-phenyl)-methanone

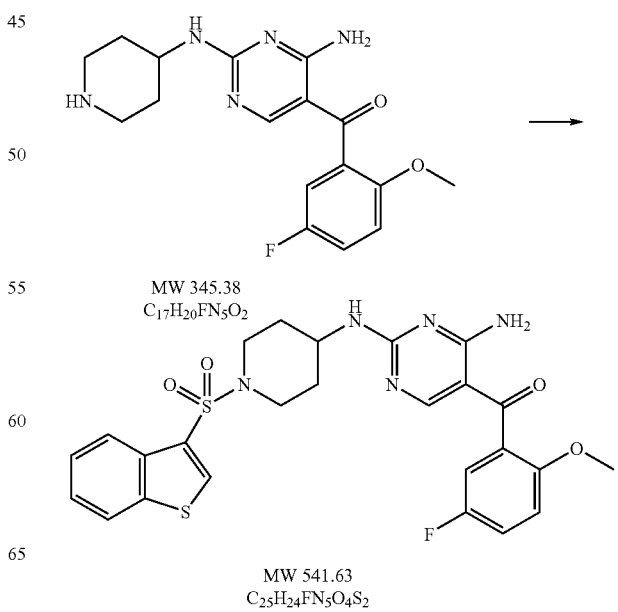

The title compound was prepared from [4-amino-2-(piperidin-4-ylamino)-pyrimidin-5-yl]-(5-fluoro-2-methoxyphenyl)-methanone, Example 59, and benzo[b]thiophene-3-sulfonyl chloride (Maybridge) by the procedure described in Example 152. HR-MS (ES, m/z) calculated for $C_{25}H_{25}FN_5O_4S_2$ [(M+H)$^+$] 542.1327, observed 542.1331.

Example 155

[4-Amino-2-[1-(1,3,5-trimethyl-1H-pyrazole-4-sulfonyl)-piperidin-4-ylamino]-pyrimidin-5-yl]-(5-fluoro-2-methoxy-phenyl)-methanone

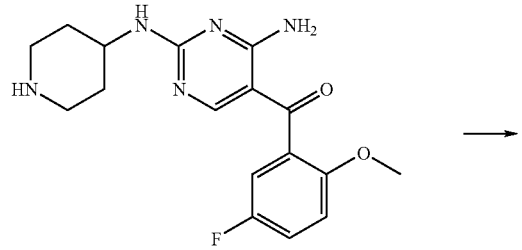

MW 345.38
$C_{17}H_{20}FN_5O_2$

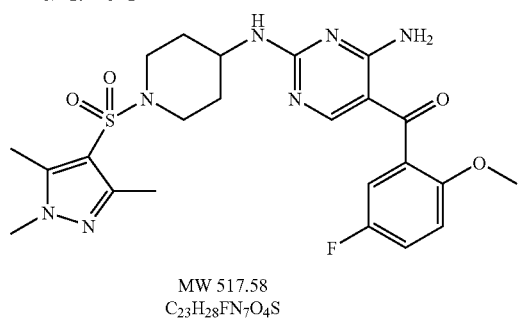

MW 517.58
$C_{23}H_{28}FN_7O_4S$

The title compound was prepared from [4-amino-2-(piperidin-4-ylamino)-pyrimidin-5-yl]-(5-fluoro-2-methoxyphenyl)-methanone, Example 59, and 1,3,5-trimethyl-1H-pyrazole-4-sulfonyl chloride (Maybridge) by the procedure described in Example 152. HR-MS (ES, m/z) calculated for $C_{23}H_{28}FN_7O_4S$ [(M+H)$^+$] 518.1981, observed 518.1986.

Example 156

3-[4-[4-Amino-5-(5-fluoro-2-methoxy-benzoyl)-pyrimidin-2-ylamino]-piperidine-1-sulfonyl]-thiophene-2-carboxylic acid methyl ester

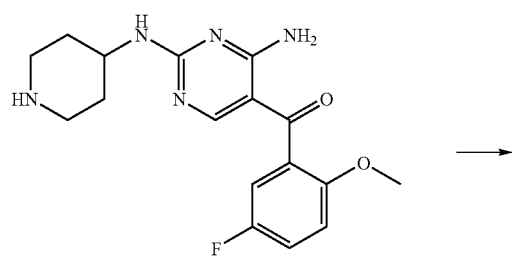

MW 345.38
$C_{17}H_{20}FN_5O_2$

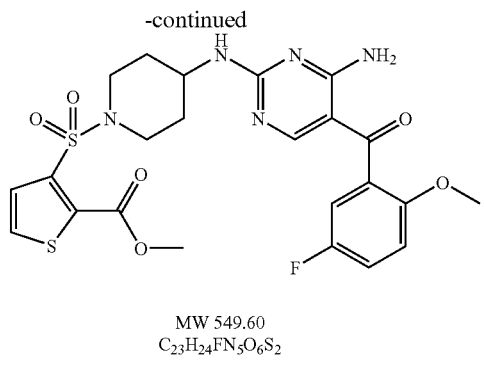

MW 549.60
$C_{23}H_{24}FN_5O_6S_2$

This compound was prepared from [4-amino-2-(piperidin-4-ylamino)-pyrimidin-5-yl]-(5-fluoro-2-methoxy-phenyl)-methanone, Example 59, and 2-carbomethoxy-3-thiophenesulfonyl chloride (Maybridge) by the procedure described in Example 152. HR-MS (ES, m/z) calculated for $C_{23}H_{25}FN_5O_6S_2$ [(M+H)$^+$] 550.1225, observed 550.1232.

Example 157

(4-Amino-2-methanesulfinyl-pyrimidin-5-yl)-(5-fluoro-2-methoxy-phenyl)-methanone

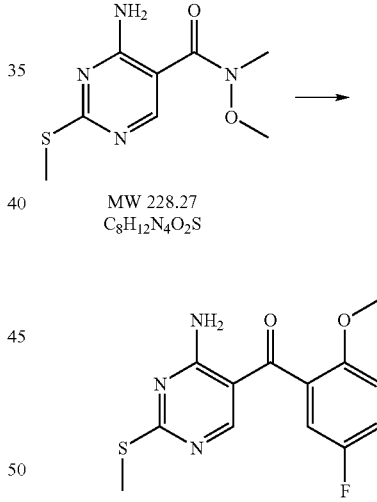

MW 228.27
$C_8H_{12}N_4O_2S$

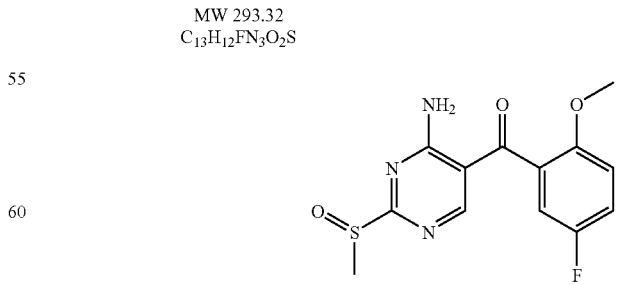

MW 293.32
$C_{13}H_{12}FN_3O_2S$

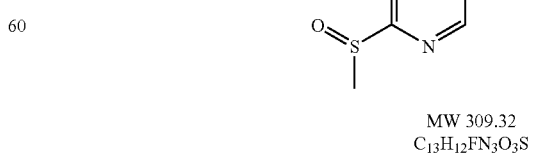

MW 309.32
$C_{13}H_{12}FN_3O_3S$ as in Example 165 to give (4-amino-2-methanesulfinyl-pyrimidin-5-yl)-(5-fluoro-2-methoxy-phenyl)-methanone (LR-ES) (M+H)⁺: 310.

Example 158
[4-Amino-2-(tetrahydro-pyran-4-ylamino)-pyrimidin-5-yl]-(5-fluoro-2-methoxy-phenyl)-methanone

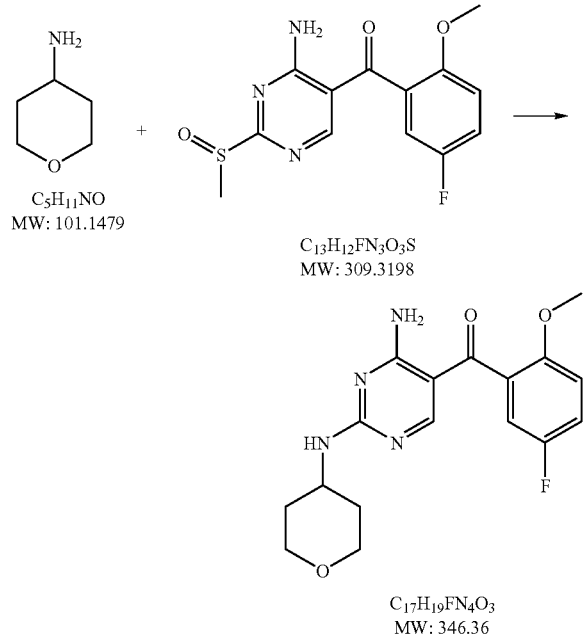

A solution of (4-amino-2-methanesulfinyl-pyrimidin-5-yl)-(5-fluoro-2-methoxy-phenyl)-methanone (235 mg, 0.73 mmol, Example 157) and tetrahydro-pyran-4-ylamine (Combi-Blocks) (260 mg, 2.3 mmol) in N-methylpyrrolidinone (15 ml) was heated for 30 minutes at 100° C. The solution was cooled, poured into water and extracted into ethyl acetate (2×). The combined organic extracts were washed with 5% sodium bicarbonate and saturated sodium chloride. The solution was dried (Na₂SO₄) and solvent was removed under vacuum to give a crude solid. Purification was by silica gel chromatography to give [4-amino-2-(tetrahydro-pyran-4-ylamino)-pyrimidin-5-yl]-(5-fluoro-2-methoxy-phenyl)-methanone as a white solid. HRMS, observed: 346.1445; Calcd for M⁺: 346.1441.

Example 159
[4-[4-Amino-5-(5-fluoro-2-methoxy-benzoyl)-pyrimidin-2-ylamino]-piperidin-1-yl]-acetic acid methyl ester

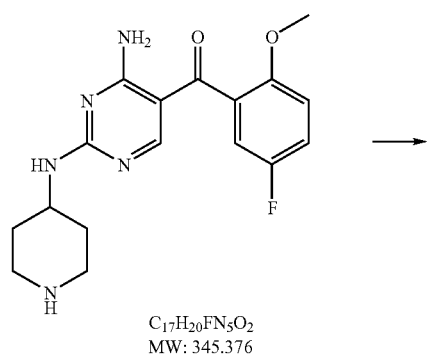

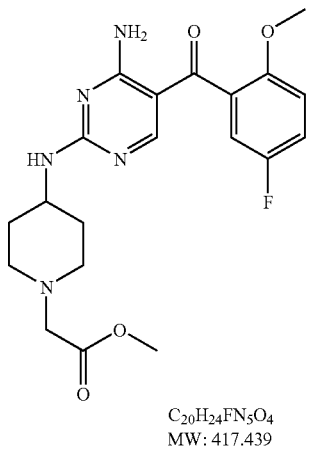

A solution of [4-amino-2-(piperidin-4-ylamino)-pyrimidin-5-yl]-(5-fluoro-2-methoxy-phenyl)-methanone (60 mg, 0.17 mmol, Example 59) and bromomethylacetate (60 mg, 0.39 mmol, Aldrich) in dimethylformamide (1.5 mL) was stirred at room temperature for 6 hours. The solution was poured into water and extracted into methylene chloride (2×). The combined organic extracts were washed with 5% aqueous sodium bicarbonate. The organic solution was dried (Na₂SO₄) and solvent was removed under vacuum to give a crude solid. Purification was by silica gel chromatography to give [4-[4-amino-5-(5-fluoro-2-methoxy-benzoyl)-pyrimidin-2-ylamino]-piperidin-1-yl]-acetic acid methyl ester as a white solid. HRMS, observed: 418.1888; Calcd for M⁺: 418.1885.

Example 160
4-[4-Amino-5-(5-fluoro-2-methoxy-benzoyl)-pyrimidin-2-ylamino]-piperidine-1-sulfonic acid dimethylamide

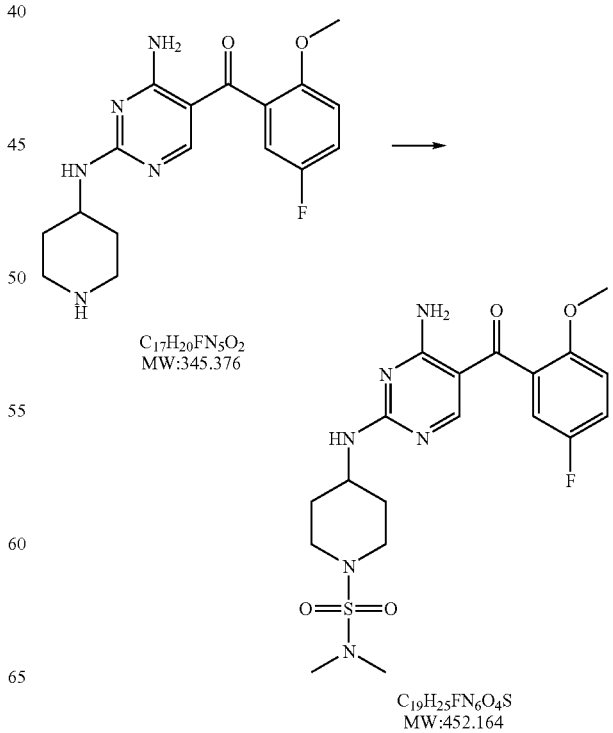

A solution of [4-amino-2-(piperidin-4-ylamino)-pyrimidin-5-yl]-(5-fluoro-2-methoxy-phenyl)-methanone (300 mg, 0.87 mmol, Example 59) and diisopropylethylamine (2 mL) in tetrahydrofuran (80 mL) was stirred at +5° C. To this was added dropwise dimethylsulfamoyl chloride (320 mg, 2.23 mmol, Aldrich) in methylene chloride (15 mL). The reaction was stirred at room temperature for 2 hours, poured into water and extracted into methylene chloride (2×50 mL). The combined organic extracts were washed with 5% aqueous sodium bicarbonate. The organic solution was dried ($Na_2SO_4$) and solvent was removed under vacuum to give a crude solid. Purification was by silica gel chromatography to give 4-[4-amino-5-(5-fluoro-2-methoxy-benzoyl)-pyrimidin-2-ylamino]-piperidine-1-sulfonic acid dimethylamide as a white solid. HRMS, observed: 453.1720; Calcd for M+: 453.1715.

Example 161

[4-Amino-2-[1-(3,5-dimethyl-isoxazole-4-sulfonyl)-piperidin-4-ylamino]-pyrimidin-5-yl]-(5-fluoro-2-methoxy-phenyl)-methanone

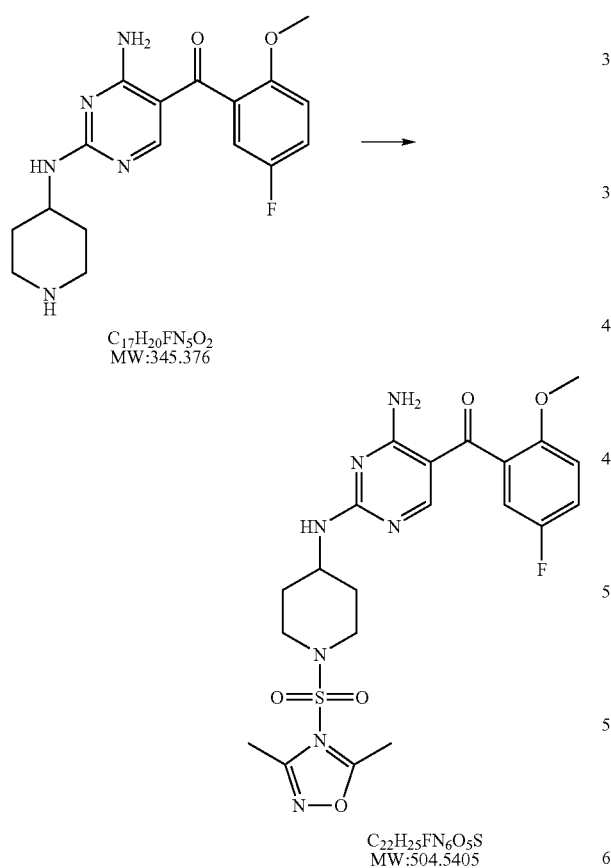

A solution of [4-amino-2-(piperidin-4-ylamino)-pyrimidin-5-yl]-(5-fluoro-2-methoxy-phenyl)-methanone (75 mg, 0.22 mmol, Example 59) and diisopropylethylamine (2 mL) in tetrahydrofuran (40 mL) was stirred at +5° C. To this was added dropwise 3,5-dimethyl-isoxazole-4-sulfonyl chloride (100 mg, 0.51 mmol, Maybridge). The reaction was stirred at room temperature for 2 hours, poured into water and extracted into methylene chloride (2×50 mL). The combined organic extracts were washed with 5% aqueous sodium bicarbonate. The organic solution was dried ($Na_2SO_4$) and solvent was removed under vacuum to give a crude solid. Purification was by silica gel chromatography to give [4-amino-2-[1-(3,5-dimethyl-isoxazole-4-sulfonyl)-piperidin-4-ylamino]-pyrimidin-5-yl]-(5-fluoro-2-methoxy-phenyl)-methanone as a white solid. HRMS, observed: 505.1669; Calcd for M+: 505.1664.

Example 162

Methanesulfonyl-piperidin-4-ylamino; compound with trifluoro-acetic acid

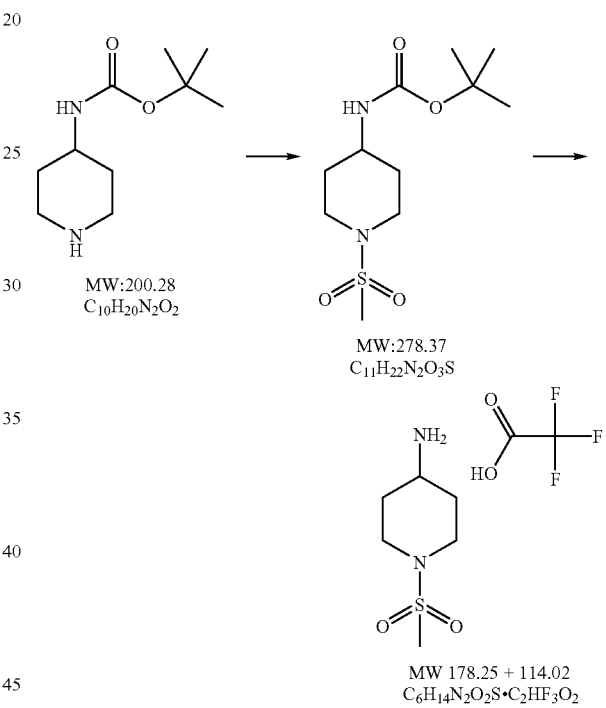

A) A solution of piperidin-4-yl-carbamic acid tert-butyl ester (1.0 g, 5.0 mmol, Astratech, Inc.) and diisopropylethylamine (4 mL) in tetrahydrofuran (40 mL) was stirred at +5° C. To this was added methanesulfonyl chloride (1.0 g, 8.8 mmol) in a bolus. The reaction was brought to room temperature for 1 hour, poured into water and extracted into methylene chloride (2×50 mL). The combined organic extracts were washed with 5% aqueous sodium bicarbonate. The organic solution was dried ($Na_2SO_4$) and solvent was removed under vacuum to give a crude solid. Purification was by trituration with ether/hexane to give (1-methanesulfonyl-piperidin-4-yl)-carbamic acid tert-butyl ester as a white solid. Mass spectrum (ES) H+: 278

B) A suspension of (1-methanesulfonyl-piperidin-4-yl)-carbamic acid tert-butyl ester (1.14 g, 4.1 mmol, from Example 162, Step A) in methylene chloride (15 mL) was treated at room temperature with trifluoroacetic acid (5.3 mL). After stirring for 2 hours, all solvent was removed and the residue was triturated with ether. This was filtered, washed with ether and dried in vacuum to give 1.20 g of 1-methanesulfonyl-piperidin-4-ylamine; compound with trifluoro-acetic acid (100% yield). HRMS, observed: 177.0692; Calcd for $M^+$: 177.0698

Example 163

(4-Amino-2-ethanesulfinyl-pyrimidin-5-yl)-(5-fluoro-2-methoxy-phenyl)-methanone and (4-Amino-2-ethanesulfonyl-pyrimidin-5-yl)-(5-fluoro-2-methoxy-phenyl)-methanone

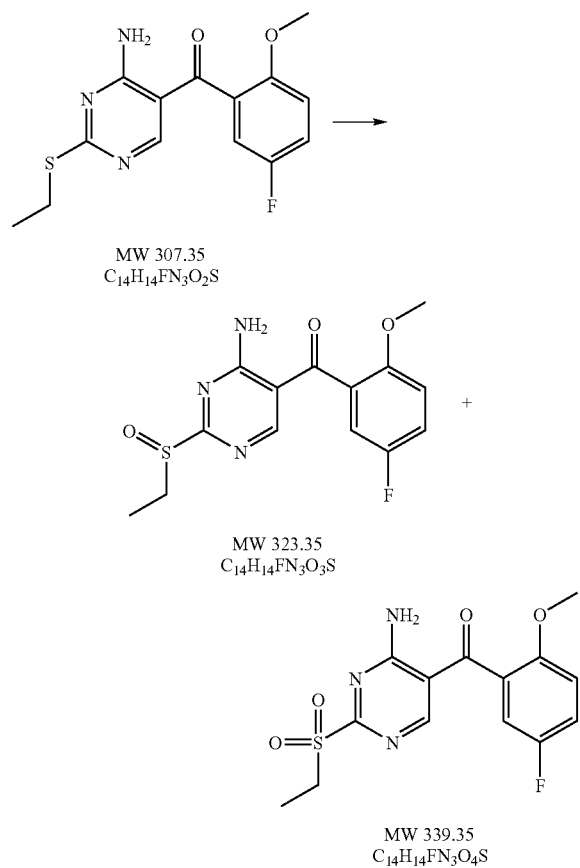

To a stirred solution of (4-amino-2-ethylsulfanyl-pyrimidin-5-yl)-(5-fluoro-2-methoxy-phenyl)-methanone (11.1 g, 36 mmol, Example 47) in dichloromethane (300 mL) chilled to 0° C. was added portionwise over about 30 minutes 74% meta-chloroperoxybenzoic acid (10.0 g, 43 mmol). The reaction was followed by thin layer chromatography and when the starting material was consumed (~45 minutes) the reaction mixture was quenched by the addition of 10% aqueous sodium thiosulfate (20 mL). The organic layer was removed and washed once with 10% aqueous sodium thiosulfate, twice with saturated aqueous sodium carbonate, and once with brine. The organic layer was dried ($Na_2SO_4$) and evaporated to give a quantitative yield of a mixture of 9:1 (by NMR) of oxidized products. A small portion of this material was chromatographed on silica gel. Eluting with 1:1 ethyl acetate/hexane provided the minor component, the same as in Example 59, pure (4-amino-2-ethanesulfonyl-pyrimidin-5-yl)-(5-fluoro-2-methoxy-phenyl)-methanone as a pale yellow solid, MP 174–175. Mass spectrum (LR-APCI) $M^+$: 339.

Eluting with 9:1 ethyl acetate/methanol provided the major component, (4-amino-2-ethanesulfinyl-pyrimidin-5-yl)-(5-fluoro-2-methoxy-phenyl)-methanone as a pale yellow solid, mp 150–152. Mass spectrum (LR-APCI) $M^+$: 323.

Example 164

4-[4-Amino-5-(5-fluoro-2-methoxy-benzoyl)-pyrimidin-2-ylamino]-piperidine-1-carboxylic acid tert-butyl ester A solution composed of a 9:1 mixture of (4-amino-2-ethanesulfinyl-pyrimidin-5-yl)-(5-fluoro-2-methoxy-phenyl)-methanone and (4-amino-2-ethanesulfonyl-pyrimidin-5-yl)-(5-fluoro-2-methoxy-phenyl)-methanone (11.6 g, 36 mmol, Example 163) and 4-amino-1-N-Boc-piperidine (Astatech Inc.) (10.8 g, 54 mmol) in 1-methyl-2-pyrrolidinone (50 mL, Aldrich) was heated at 70° C. for 30 minutes. The reaction was diluted with water and extracted with ethyl acetate. The dried ($Na_2SO_4$) organic solution was evaporated and the residue was triturated with ethyl ether/hexane to give 95% yield of 4-[4-amino-5-(5-fluoro-2-methoxy-benzoyl)-pyrimidin-2-ylamino]-piperidine-1-carboxylic acid tert-butyl ester as a colorless solid, mp 122–124 dec. Mass Spectrum (LR-ES) $M^+$: 445.

Example 165

(4-Amino-2-ethanesulfinyl-pyrimidin-5-yl)-(2,3-difluoro-6-methoxy-phenyl)-methanone

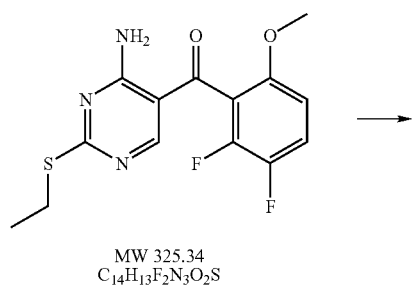

MW 325.34
C₁₄H₁₃F₂N₃O₂S

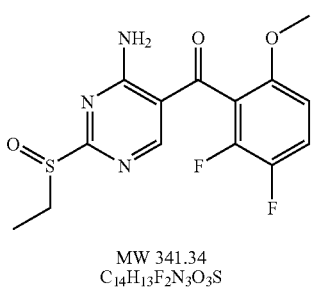

MW 341.34
C₁₄H₁₃F₂N₃O₃S

A stirred solution of (4-amino-2-ethylsulfanyl-pyrimidin-5-yl)-(2,3-difluoro-6-methoxy-phenyl)-methanone (7.4 g, 23 mmol, Example 102) in dichloromethane (150 mL) at 0° C. was treated portionwise with 74% meta-chloroperoxybenzoic acid (6 g, 26 mmol) over about 30 minutes. The cold reaction mixture was quenched with 25 ml of 10% aqueous sodium thiosulfate solution and the layers separated. The organic layer was washed once with 10% aqueous sodium thiosulfate solution, twice with saturated aqueous sodium carbonate solution, once with brine, dried (Na₂SO₄) and evaporated. Trituration of the residue with hexane provided a quantitative yield of (4-amino-2-ethanesulfinyl-pyrimidin-5-yl)-(2,3-difluoro-6-methoxy-phenyl)-methanone as a colorless solid, mp 165 dec. Mass Spectrum (LR-ES) (M+H)⁺: 342.

Example 166

4-[4-Amino-5-(2,3-difluoro-6-methoxy-benzoyl)-pyrimidin-2-ylamino]-piperidine-1-carboxylic acid tert-butyl ester

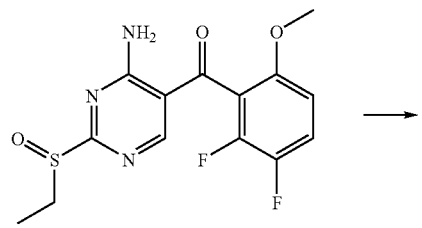

MW 341.34
C₁₄H₁₃F₂N₃O₃S

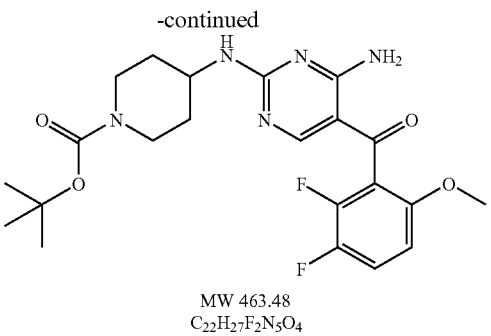

MW 463.48
C₂₂H₂₇F₂N₅O₄

A solution of (4-amino-2-ethanesulfinyl-pyrimidin-5-yl)-(2,3-difluoro-6-methoxy-phenyl)-methanone (7.7 g, 23 mmol, Example 165) and 4-amino-1N-Boc-piperidine (6.8 g, 34 mmol, Astatech) in 30 mL of 1-methyl-2-pyrrolidinone was heated at 70° C. for 30 minutes. The reaction mixture was diluted with water and extracted with ethyl acetate. The dried (Na₂SO₄) organic solution was evaporated and the residue was chromatographed on silica gel. Elution with 3:2 ethyl acetate/hexane provided 80% yield of 4-[4-amino-5-(2,3-difluoro-6-methoxy-benzoyl)-pyrimidin-2-ylamino]-piperidine-1-carboxylic acid tert-butyl ester as a colorless solid, mp 114 dec., identical to material prepared in Example 106. Mass Spectrum (LR-ES) M⁺: 463.

Example 167

4-amino-2-methylsulfanyl-pyrimidine-5-carboxylic acid

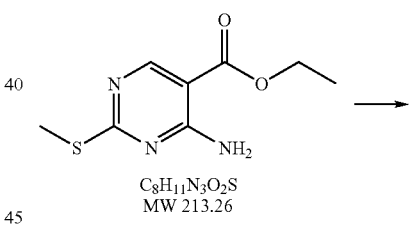

C₈H₁₁N₃O₂S
MW 213.26

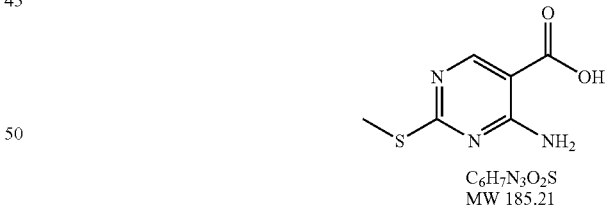

C₆H₇N₃O₂S
MW 185.21

To a stirred solution of 4-amino-2-methylsulfanyl-pyrimidine-5-carboxylic acid ethyl ester (24.0 g, 112.5 mmol, Salor) in ethanol (400 mL) and water (200 mL) was added lithium hydroxide (9.536 g, 225.0 mmol). The suspension was stirred at room temperature for 3 hours during which all the solids went into solution. The ethanol was removed in vacuo and additional water was added to make a total volume of 300 mL. The resulting solution was washed with 2×100 mL of ether which was discarded. To the aqueous solution was added concentrated hydrochloric acid (20 mL) to bring the pH of the aqueous solution to about pH 3 during which the desired product precipitated out. The product was

159 filtered, washed with 25 mL of water, suction dried and then dried in a vacuum oven at 50° C. to give 20.6 g (98.8%) of the product as a white solid.

Example 168

4-amino-2-methylsulfanyl-pyrimidine-5-carboxylic acid methoxy-methyl-amide

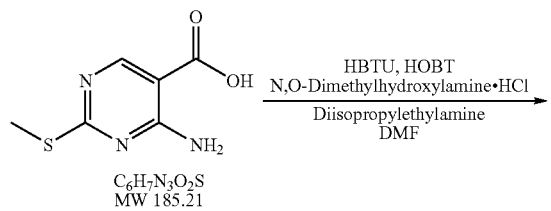

To a stirred solution of 4-amino-2-methylsulfanyl-pyrimidine-5-carboxylic acid (20.6 g, 111.2 mmol, Example 167) in dimethylformamide (200 mL) was added O-benzotriazol-1-yl-N,N,N',N'-tetramethyluronium hexafluorophosphate (63.91 g, 166.8 mmol, Aldrich) and 1-hydroxybenzotriazole hydrate (22.77 g, 166.8 mmol, Aldrich) and the resulting mixture was cooled to 0° C. (ice-water bath). Diisopropylethylamine (108 mL, Aldrich) was added followed by N,O-dimethylhydroxylamine hydrochloride (16.61 g, 166.8 mmol, Aldrich) and the resulting mixture was stirred at 0° C. for 2 hours. The reaction mixture was diluted with 1 L of ethyl acetate and washed with 800 mL of water. The aqueous phase was removed and extracted with 3×500 mL of ethyl acetate. The combined organic extracts were washed with 500 mL of water, dried over anhydrous magnesium sulfate, filtered and concentrated to give crude product. The crude product was loaded on the top of a 3 inch wide×4 inch long silica-gel column (230–400 mesh) and eluted with 20%, 50%, 75% ethyl acetate in hexane and 250 mL fractions were collected. Appropriate fractions containing the product were combined and concentrated to give 21.0 g of product. This was taken in 50 ml ethyl acetate to give a slurry and, while stirring, 200 mL of hexane was added. The product was filtered, washed with 50 mL of hexane, suction dried and then dried in the oven at 40° C. to give 16.3 g (64.2%) of 4-amino-2-methylsulfanyl-pyrimidine-5-carboxylic acid methoxy-methyl-amide.

Alternatively, a suspension of 4-amino-2-methylsulfanyl-pyrimidine-5-carboxylic acid (1.01 g, 5.45 mmol, Example 167), N,O-dimethylhydroxylamine hydrochloride (0.59 g, 6.0 mmol, Aldrich), triethylamine (0.84 mL, 6.0 mmol) in dichloromethane (25 mL) was treated with 1-ethyl-3-(dimethylaminopropyl)carbodiimide hydrochloride (1.25 g, 6.52 mmol, Aldrich). The mixture was stirred at room temperature overnight resulting in a clear solution. The reaction was diluted with ethyl acetate (100 mL), washed with water (2×25 mL), brine, and dried over magnesium sulfate. The dried organic solution was filtered through a plug of silica gel and eluted with ethyl acetate to give, after evaporation, 1.05 g, (85%) of 4-amino-2-methylsulfanyl-pyrimidine-5-carboxylic acid methoxy-methyl-amide. MS(ES) (M+H)$^+$ =229.

Example 169

(4-Amino-2-methylsulfanyl-pyrimidin-5-yl)-(2,3-difluoro-6-methoxy-phenyl)-methanone

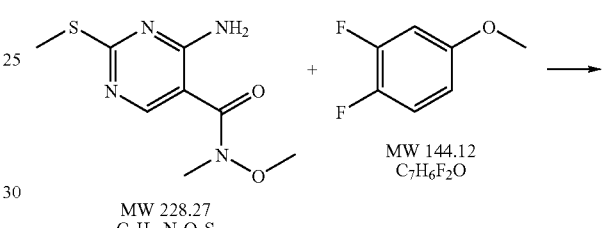

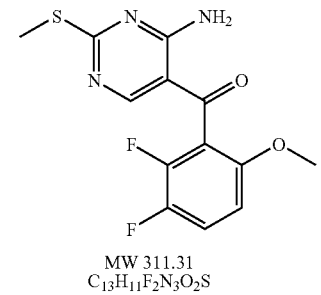

n-Butyl lithium (46 mL, 115 mmol, 2.5 M solution in hexanes, Aldrich) was added to a solution of 3,4-difluoroanisole (12.98 mL, 109.5 mmol, Aldrich) in anhydrous tetrahydrofuran (100 mL) cooled to −78° C. using an addition funnel. The resulting solution was warmed to −40° C. for 15 min then cooled back to −78° C. before a solution of Example 168 (5 g, 21.9 mmol) in anhydrous tetrahydrofuran (25 mL) was added slowly via syringe. The reaction mixture turned yellow. It was stirred at −78° C. for 30 minutes and then warmed up to −50° C. After stirring at −50° C. for 1 hour, the cooling bath was removed and the reaction mixture was allowed to warm up to −30° C. where it was quenched with a saturated aqueous solution of ammonium chloride. Water was added and the solution was extracted with ethyl acetate, the organic layers were washed with brine, dried (anhydrous sodium sulfate) and concentrated. The residue was triturated in hexanes, and the solids were filtered off.

Purification of the solids by flash chromatography (silica gel, eluting with 30%, 40%, 50% ethyl acetate in hexanes) gave the product. The product was recrystallized with ethyl acetate and hexanes to give ~3.6 g of off-white solids. The filtrate was concentrated, and the residue was purified by flash column chromatography (silica gel, eluting with 100% methylene chloride, then 10% ethyl acetate in methylene chloride) to give an additional amount of product. Total yield: 4.3561 g (64%), off-white solids. MS (M+H)$^+$: 312.

Example 170

4-Amino-2-ethanesulfanyl-pyrimidin-5-yl)-2-fluoro-6-methoxy-phenyl)-methanone

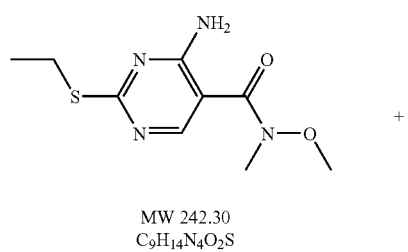

MW 242.30
C$_9$H$_{14}$N$_4$O$_2$S

+

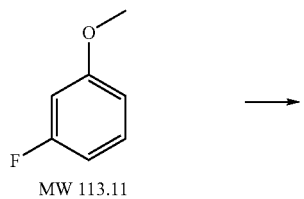

MW 113.11
C$_6$H$_6$FO

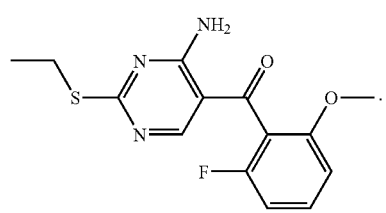

MW 307.35
C$_{14}$H$_{14}$FN$_3$O$_2$

4-Amino-2-ethylsulfanyl-pyrimidine-5-carboxylic acid methoxy-methyl-amide (300 mg, 1.238 mmol, Example 1) in tetrahydrofuran (1 mL) was added slowly via syringe to a stirred, −78° C. solution of 3 equiv. of alkyl lithium, prepared as in Example 2A from 3-fluoroanisole (Aldrich), and the reaction mixture was stirred for 1.5 hours at −78° C. and then 30 minutes at 0° C. The reaction was quenched with saturated aqueous sodium bicarbonate and extracted with ethyl ether. The organic layers were washed with brine, dried and concentrated. Purification was accomplished by chromatography on a Biotage flash column eluting with 20–40% ethyl acetate in hexane to give the product as a yellow oil.

Example 171

4-Amino-2-ethanesulfinyl-pyrimidin-5-yl)-2-fluoro-6-methoxy-phenyl)-methanone

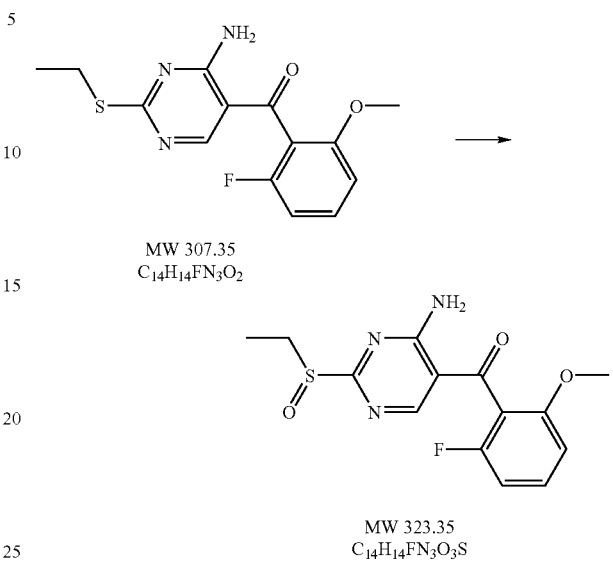

The title compound was prepared in a similar manner as described in Example 163 from the compound of Example 170 and the crude product was used without further purification.

Example 172

1-{4-Amino-5-(2-fluoro-6-methoxy-benzoyl)-pyrimidin-2-ylamino-piperidin-1-yl]-ethanone

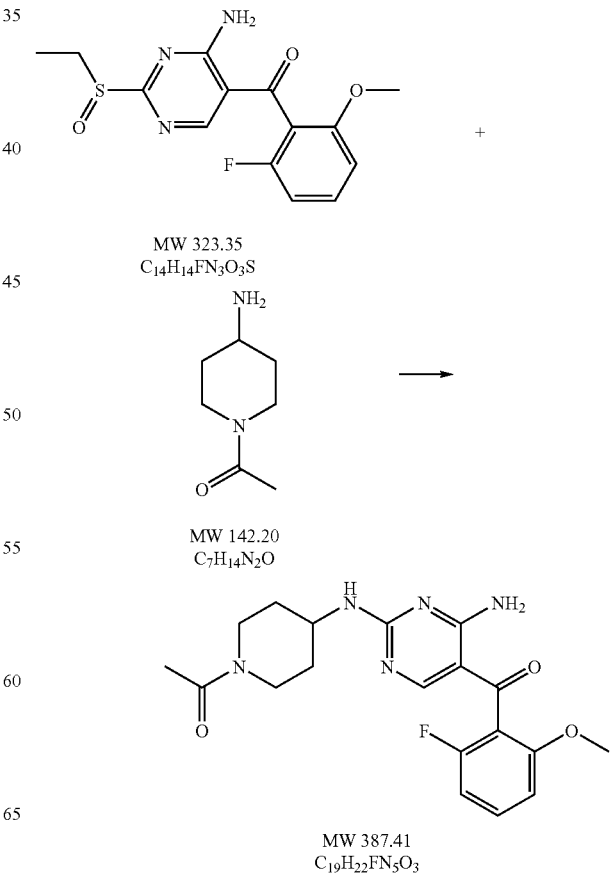

A mixture of 4-Amino-2-ethanesulfinyl-pyrimidin-5-yl)-2-fluoro-6-methoxy-phenyl)-methanone (53.38 mg, 0.165 mmol, Example 171), 1-actyl-4-aminopiperidine (35.19 mg, 0.248 mmol), diisopropylethylamine (0.1437 mL, 0.825 mmol, Aldrich) and ethanol (5 mL) was refluxed for 4 hours and evaporated. The resulting residue was chromatographed eluting with 5% methanol in ethyl acetate containing 0.1% of triethylamine to give the product as a yellow solid. HR-MS (ES) obs. 388.1784, calcd. (M+H)$^+$388.1780.

Example 173

4-Amino-2-ethanesulfanyl-pyrimidin-5-yl)-4-fluoro-2-methoxy-phenyl)-methanone

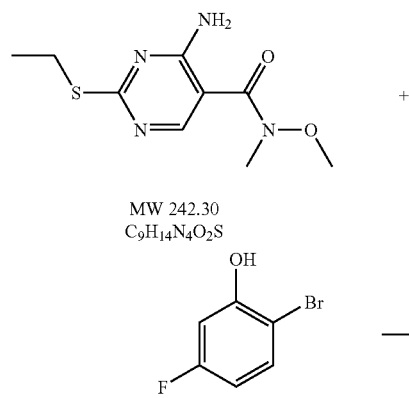

In a similar manner as that described in Example 170, the title compound was prepared from the compound of Example 1 and the alkyl lithium reagent prepared from the treatment of 2-bromo-5-fluorophenol (Crescent Chem.) with methyl iodide and potassium carbonate in hot acetone followed by treatment of this product with n-butyl lithium as in Example 2A, to give a white solid. LR-MS: (M+H)$^+$308.

Example 174

4-Amino-2-ethanesulfinyl-pyrimidin-5-yl)-4-fluoro-2-methoxy-phenyl)-methanone

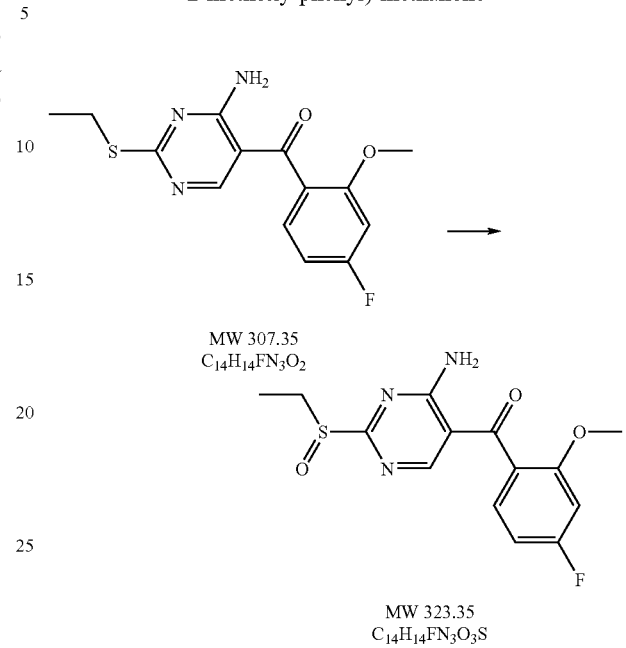

The title compound was prepared in a similar manner as described in Example 163 from the compound of Example 173 and the crude product was used without further purification.

Example 175

4-[4-Amino-5-(4-fluoro-2-methoxy-benzoyl)-pyrimidin-2-ylamino]-piperidin-1-carboxylic acid tert-butyl ester

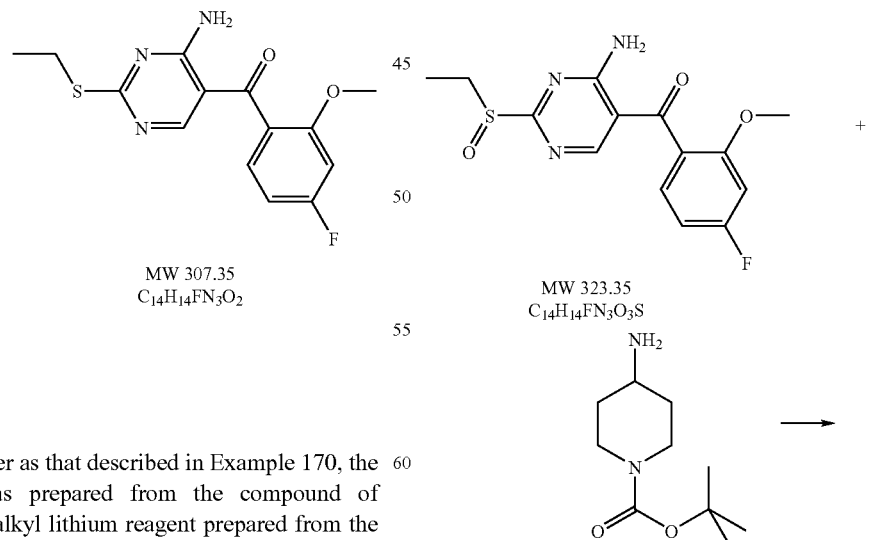

-continued

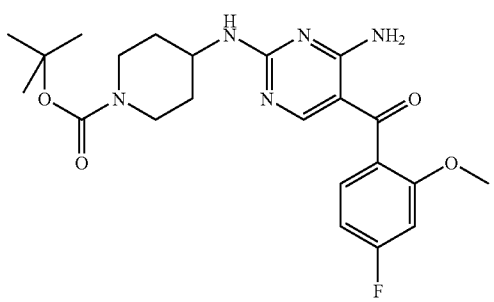

MW 445.49
$C_{22}H_{28}FN_5O_4$

The title compound was prepared in a similar manner as described in Example 172 from the material prepared in Example 174 (136 mg, 0.421 mmol) and 4-amino-1-Boc-piperidine (126.5 mg, 0.631 mmol, Astatech) to give, after chromatography, 70 mg (38%) of product as a white glass. LR-MS: (M+H)+446

Example 176

[4-Amino-2-(piperidin-4-ylamino)pyrimidin-5-yl-(4-fluoro-2-methoxy-phenyl)-methanone

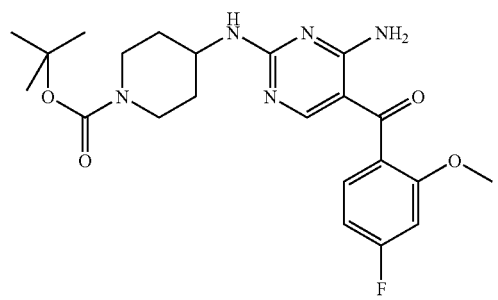

MW 445.49
$C_{22}H_{28}FN_5O_4$

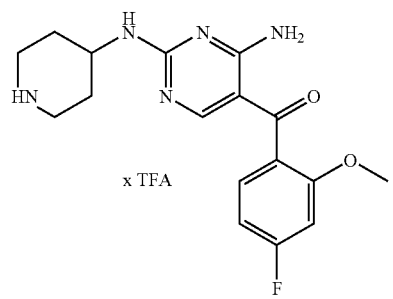

x TFA

MW 345.38
$C_{17}H_{20}FN_5O_2$

The compound of Example 175 (70 mg) in dichloromethane (2 mL) and trifluoroacetic acid (2 mL) was stirred for 2 hours at room temperature and evaporated to give the title compound (72 mg) as the trifluoroacetic acid salt.

Example 177

[4-Amino-2-(1-methanesulfonyl-piperidin-4-ylamino)-pyrimidin-5-yl]-(4-fluoro-2-methoxy-phenyl)-methanone

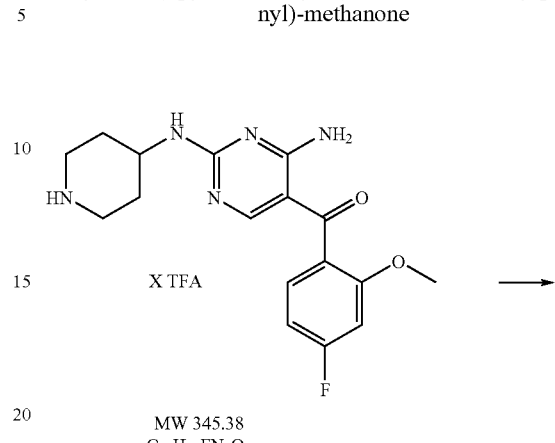

X TFA

MW 345.38
$C_{17}H_{20}FN_5O_2$

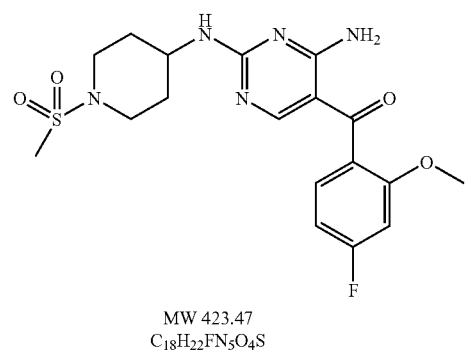

MW 423.47
$C_{18}H_{22}FN_5O_4S$

The trifluoroacetic acid salt of [4-amino-2-(piperidin-4-ylamino)pyrimidin-5-yl-(4-fluoro-2-methoxy-phenyl)-methanone (72.18 mg, 0.157 mmol, Example 176) in dichloromethane (5 mL) and triethylamine (0.2188 mL, 1.570 mmol) was chilled and methanesulfonyl chloride (0.017 mL, 0.22 mmol, Aldrich) was added and the mixture was stirred at room temperature for several hours. Chromatography provided 42 mg (63%) of the title compound as a white solid. HR-ES(+), observed: 424.1453; Calcd for (M+H)+: 424.1450.

Example 178

(4-Amino-2-ethanesulfanyl-pyrimidin-5-yl)-(2-fluoro-4,6-dmethoxy-phenyl)-methanone

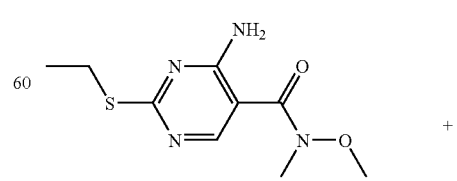

MW 242.30
$C_9H_{14}N_4O_2S$

+

-continued

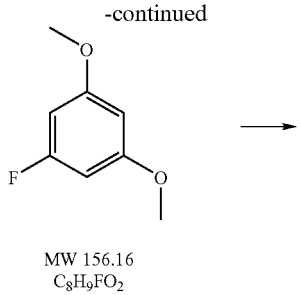

MW 156.16
$C_8H_9FO_2$

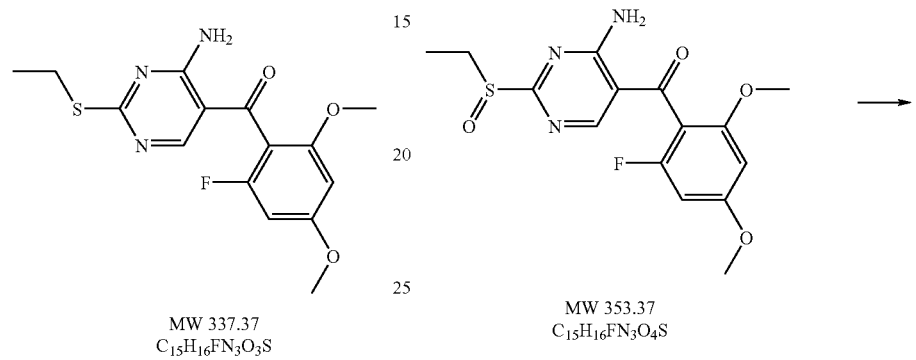

MW 337.37
$C_{15}H_{16}FN_3O_3S$

The title compound was prepared in a similar manner as described in Example 170 from 1-fluoro-3,5-dimethoxybenzene (Aldrich) to give the product as a yellow oil.

Example 179

(4-Amino-2-ethanesulfinyl-pyrimidin-5-yl)-(2-fluoro-4,6-dmethoxy-phenyl)-methanone

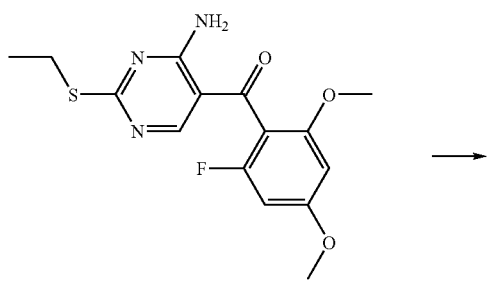

MW 337.37
$C_{15}H_{16}FN_3O_3S$

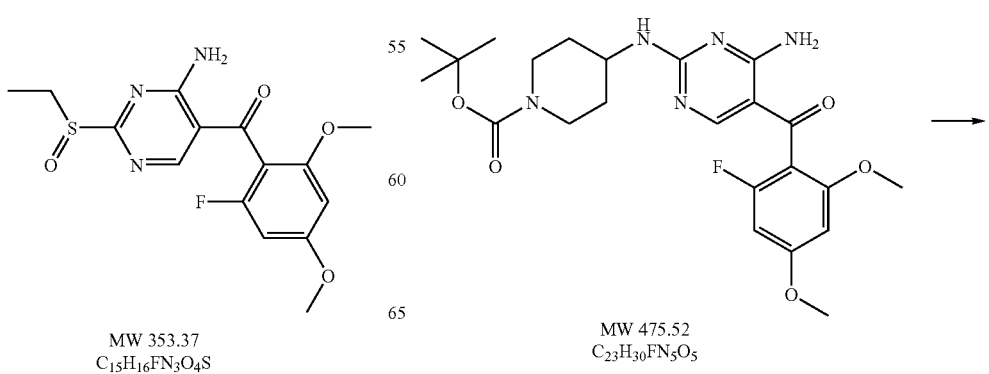

MW 353.37
$C_{15}H_{16}FN_3O_4S$

The title compound was prepared in a similar manner as described in Example 173 from Example 177 and the crude product was obtained in 100% yield and used without further purification.

Example 180

4-[4-Amino-5-(2-fluoro-4,6-dmethoxy-benzoyl)-pyrimidin-2-ylamino]-piperidine-1-carboxylic acid tert-butyl ester

MW 353.37
$C_{15}H_{16}FN_3O_4S$

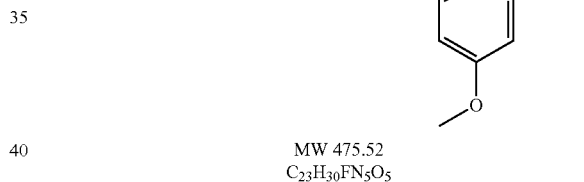

MW 475.52
$C_{23}H_{30}FN_5O_5$

The title compound was prepared in a similar manner as described in Example 175 from material prepared in Example 179 and the product was chromatographed on silica gel using 80% ethyl acetate/hexane as the eluting solvent to give product in 86% yield.

Example 181

[4-Amino-2-(piperidin-4-ylamino)pyrimidin-5-yl-(2-fluoro-4,6-dmethoxy-phenyl)-methanone

MW 475.52
$C_{23}H_{30}FN_5O_5$

-continued

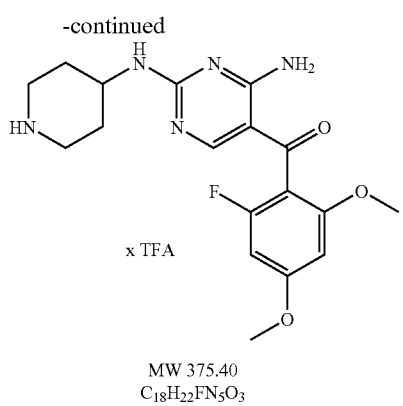

MW 375.40
C<sub>18</sub>H<sub>22</sub>FN<sub>5</sub>O<sub>3</sub>

The compound of Example 180 was treated with 1:1 dichloromethane and trifluoroacetic acid as in Example 176 and evaporated to give the title compound as the trifluoroacetic acid salt.

Example 182

[4-Amino-2-(1-methanesulfonyl-piperidin-4-ylamino)-pyrimidin-5-yl]-(2-fluoro 4,6-dmethoxy-phenyl)-methanone

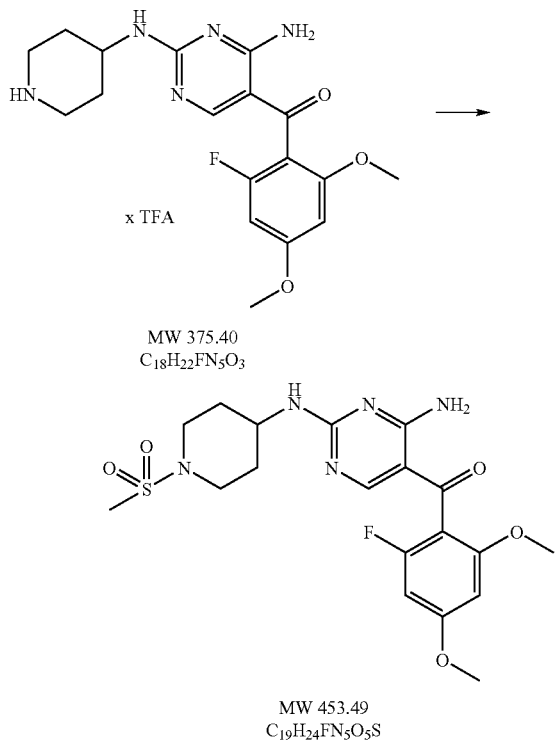

MW 375.40
C<sub>18</sub>H<sub>22</sub>FN<sub>5</sub>O<sub>3</sub>

MW 453.49
C<sub>19</sub>H<sub>24</sub>FN<sub>5</sub>O<sub>5</sub>S

In a manner similar to that used in Example 177, the trifluoroacetic acid salt of [4-Amino-2-(piperidin-4-ylamino)pyrimidin-5-yl-(2-fluoro-4,6-dimethoxy-phenyl)-methanone (84.5 mg, 0.173 mmol, Example 182) was treated with methanesulfonylchloride (0.026 mL, 0.346 mmol, Aldrich) and the product chromatographed to give 46% of yellow solids. HR-MS (ES): obs. 454.1558, calcd. 454.1555.

Example 183

1-{4-[4-Amino-5-(2-fluoro-4,6-dmethoxy-benzoyl)-pyrimidin-2-ylamino]-piperidin-1-yl}-ethanone

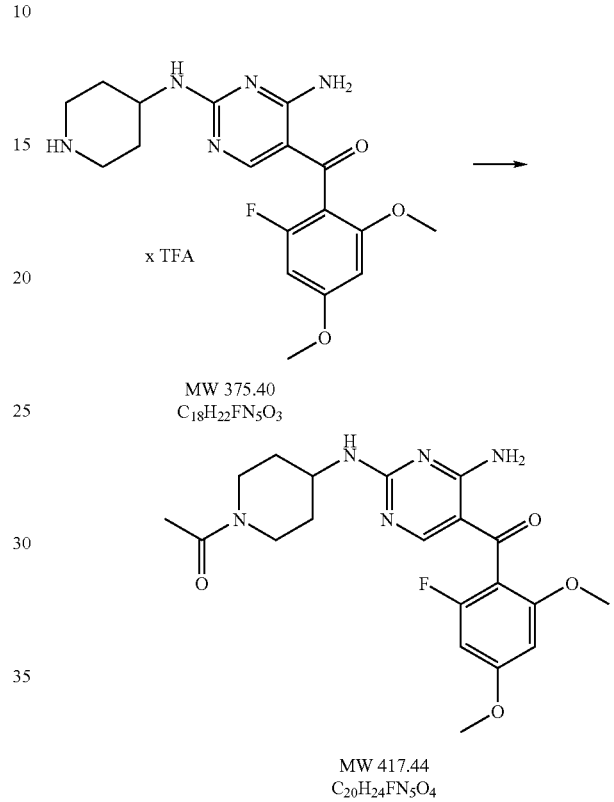

MW 375.40
C<sub>18</sub>H<sub>22</sub>FN<sub>5</sub>O<sub>3</sub>

MW 417.44
C<sub>20</sub>H<sub>24</sub>FN<sub>5</sub>O<sub>4</sub>

In a similar manner as used in Example 177, the trifluoroacetic acid salt of [4-amino-2-(piperidin-4-ylamino)pyrimidin-5-yl-(2-fluoro-4,6-dimethoxy-phenyl)-methanone (84.5 mg, 0.173 mmol, Example 182) was treated with acetic anhydride (0.0327 mL, 0.346 mmol, Fisher) to yield the title compound and the product chromatographed to give 66% of yellow solids. HR-MS (ES): obs. 418.1890, calcd. 418.1885.

Example 184

(4-Amino-2-ethylsulfanyl-pyrimidin-5-yl)-(2,3,4-trifluoro-6-methoxy-phenyl)-methanone

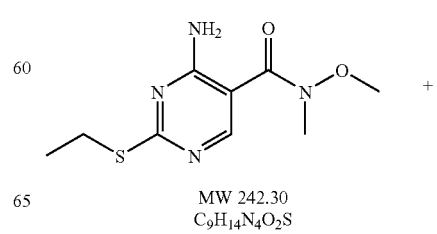

MW 242.30
C<sub>9</sub>H<sub>14</sub>N<sub>4</sub>O<sub>2</sub>S

-continued

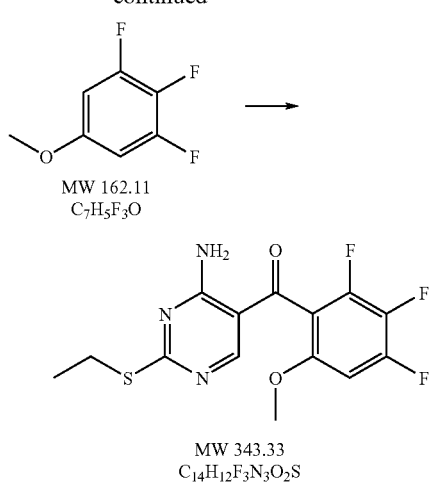

The compound was prepared from 4-amino-2-ethylsulfanyl-pyrimidine-5-carboxylic acid methoxy-methyl-amide, Example 1, and 3,4,5-trifluoroanisole (Aldrich) in an analogous manner as described in Example 169.

Example 185

(4-Amino-2-ethylsulfanyl-pyrimidin-5-yl)-(3-methoxy-pyridin-2-yl)-methanone

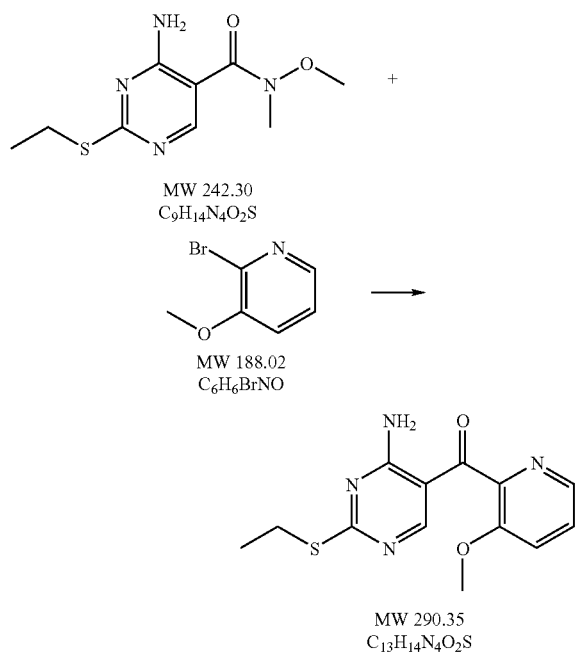

The compound was prepared from 4-amino-2-ethylsulfanyl-pyrimidine-5-carboxylic acid methoxy-methyl-amide, Example 1, and 2-bromo-6-methoxy-pyridine (Aldrich) in an analogous manner as described in Example 169.

Example 186

(4-Amino-2-ethylsulfanyl-pyrimidin-5-yl)-(3,4,5-trifluoro-2-methoxy-phenyl)-methanone

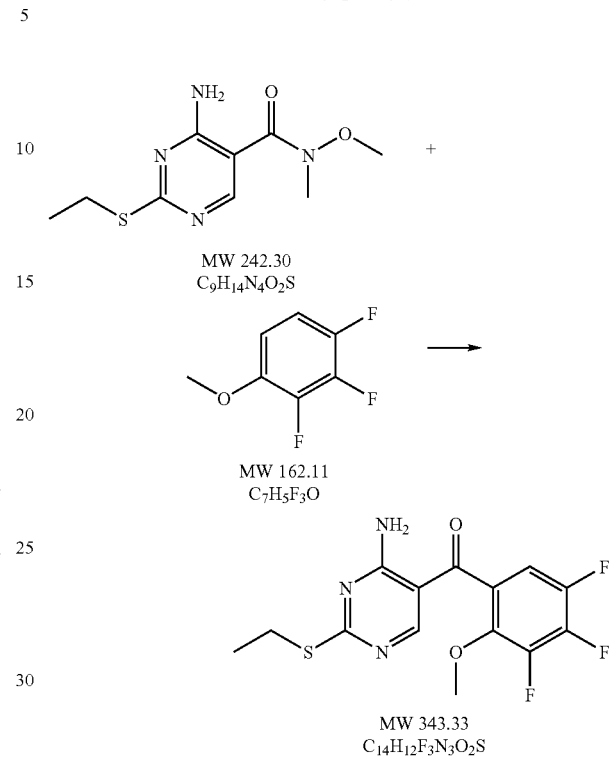

The compound was prepared from 4-amino-2-ethylsulfanyl-pyrimidine-5-carboxylic acid methoxy-methyl-amide, Example 1, and 2,3,4-trifluoroanisole (Matrix) in an analogous manner as described in Example 169.

Example 187

(4-Amino-2-ethylsulfanyl-pyrimidin-5-yl)-(3-methyl-thiophen-2-yl)-methanone

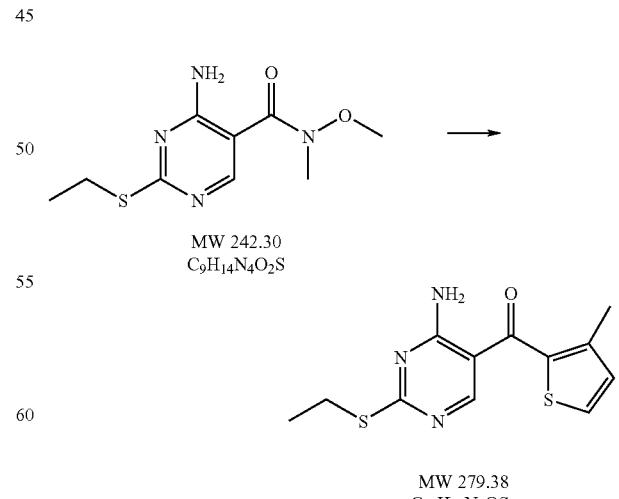

The compound was prepared from 4-amino-2-ethylsulfanyl-pyrimidine-5-carboxylic acid methoxy-methyl-amide, Example 1, and 2-bromo-3-methyl-thiophene (Aldrich) in an analogous manner as described in Example 169.

Example 188

(4-Amino-2-ethylsulfanyl-pyrimidin-5-yl)-(5-fluoro-2-methyl-phenyl)-methanon

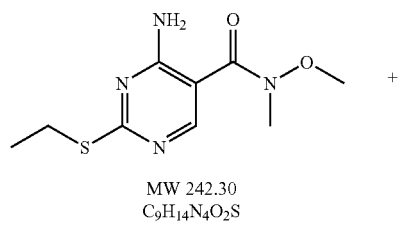

MW 242.30
C$_9$H$_{14}$N$_4$O$_2$S

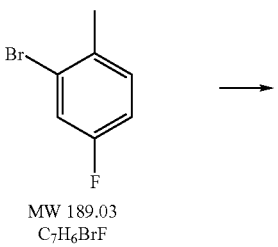

MW 189.03
C$_7$H$_6$BrF

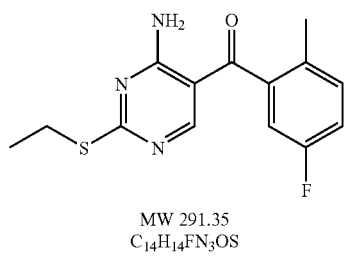

MW 291.35
C$_{14}$H$_{14}$FN$_3$OS

The compound was prepared from 4-amino-2-ethylsulfanyl-pyrimidine-5-carboxylic acid methoxy-methyl-amide, Example 1, and 2-bromo-4-fluorotoluene (Aldrich) in an analogous manner as described in Example 169.

Example 189

(4-Amino-2-ethylsulfanyl-pyrimidin-5-yl)-(5-fluoro-2-trifluoromethyl-phenyl)-methanone

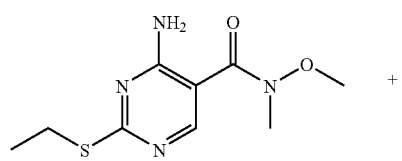

MW 242.30
C$_9$H$_{14}$N$_4$O$_2$S

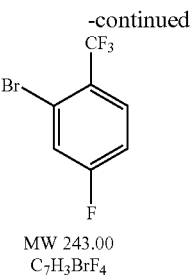

MW 243.00
C$_7$H$_3$BrF$_4$

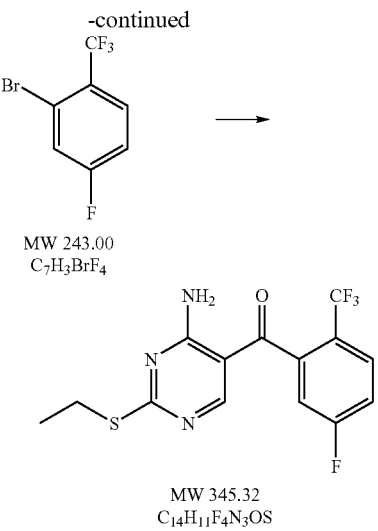

MW 345.32
C$_{14}$H$_{11}$F$_4$N$_3$OS

The compound was prepared from 4-amino-2-ethylsulfanyl-pyrimidine-5-carboxylic acid methoxy-methyl-amide, Example 1, and 2-bromo-4-fluoro-1-trifluoromethyl-benzene (Aldrich) in an analogous manner as described in Example 169.

Example 190

(4-Amino-2-ethylsulfanyl-pyrimidin-5-yl)-(5-fluoro-2-isopropoxy-phenyl)-methanone

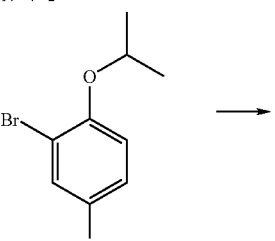

MW 242.30
C$_9$H$_{14}$N$_4$O$_2$S

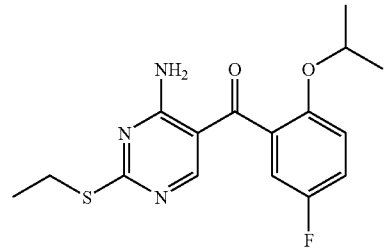

MW 233.08
C$_9$H$_{10}$BrFO

MW 335.40
C$_{16}$H$_{18}$FN$_3$O$_2$S

The compound was prepared from 4-amino-2-ethylsulfanyl-pyrimidine-5-carboxylic acid methoxy-methyl-amide, Example 1, and 2-bromo-4-fluoro-1-isopropoxy-benzene (prepared from 2-bromo-4-fluoro-phenol, Aldrich) in an analogous manner as described in Example 169.

Example 191

(4-Amino-2-methylsulfanyl-pyrimidin-5-yl)-(2-ethoxy-5-fluoro-phenyl)-methanone

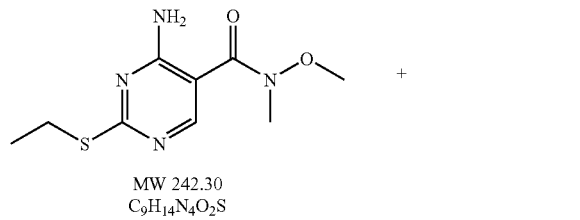

MW 242.30
C₉H₁₄N₄O₂S

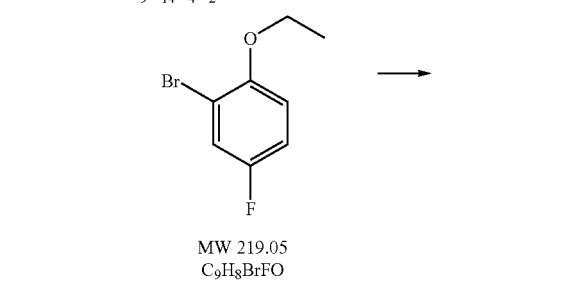

MW 219.05
C₉H₈BrFO

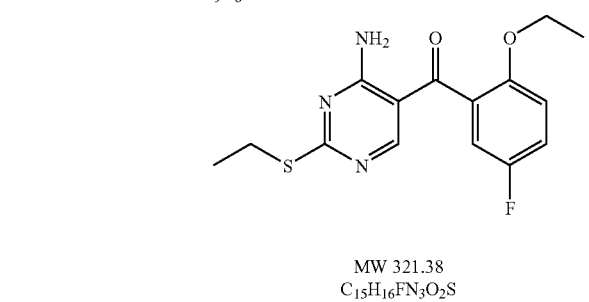

MW 321.38
C₁₅H₁₆FN₃O₂S

The compound was prepared from 4-amino-2-ethylsulfanyl-pyrimidine-5-carboxylic acid methoxy-methyl-amide, Example 1, and 2-bromo-1-ethoxy-4-fluoro-benzene (prepared from 2-bromo-4-fluoro-phenol, Aldrich) in an analogous manner as described in Example 169.

Example 192

(4-Amino-2-methylsulfanyl-pyrimidin-5-yl)-(2-ethyl-5-fluoro-phenyl)-methanone

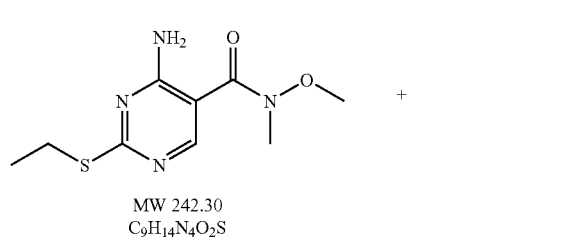

MW 242.30
C₉H₁₄N₄O₂S

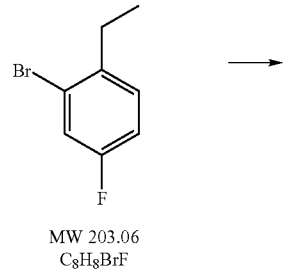

MW 203.06
C₈H₈BrF

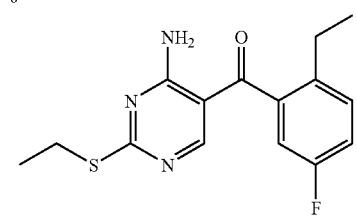

MW 305.38
C₁₅H₁₆FN₃OS

The compound was prepared from 4-amino-2-ethylsulfanyl-pyrimidine-5-carboxylic acid methoxy-methyl-amide, Example 1, and 2-bromo-1-ethyl-4-fluoro-benzene (prepared from 2-bromo-4-fluoroacetophenone, WO0015634) in an analogous manner as described in Example 169.

Example 193

(4-Amino-2-methylsulfanyl-pyrimidin-5-yl)-(2-methoxy-4-trifluoromethyl-phenyl)-methanone

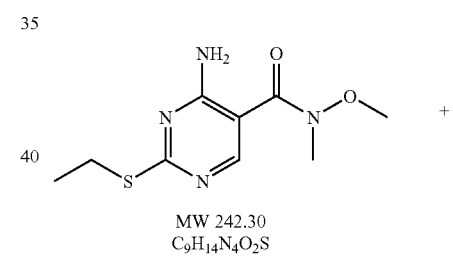

MW 242.30
C₉H₁₄N₄O₂S

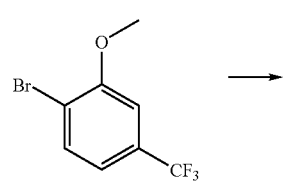

MW 255.04
C₈H₆BrF₃O

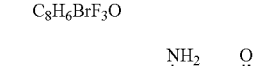

MW 357.36
C₁₅H₁₄F₃N₃O₂S

The compound was prepared from 4-amino-2-ethylsulfanyl-pyrimidine-5-carboxylic acid methoxy-methyl-amide, Example 1, and 1-bromo-2-methoxy-4-trifluoromethyl-benzene (prepared from 3-(trifluoromethyl)-anisole, Aldrich) in an analogous manner as described in Example 169.

Example 194

(4-Amino-2-ethanesulfinyl-pyrimidin-5-yl)-(2,3,4-trifluoro-6-methoxy-phenyl)-methanone

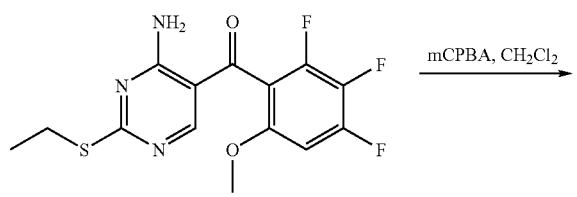

MW 343.33
C$_{14}$H$_{12}$F$_3$N$_3$O$_2$S

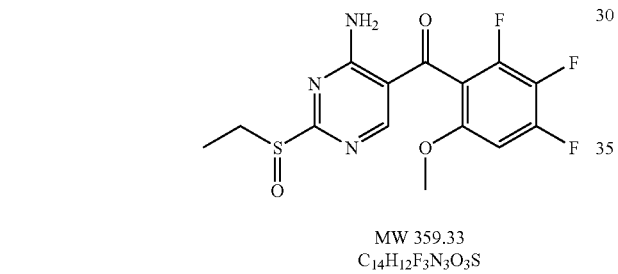

MW 359.33
C$_{14}$H$_{12}$F$_3$N$_3$O$_3$S

The compound was prepared from 4-amino-2-ethylsulfanyl-pyrimidin-5-yl)-(2,3,4-trifluoro-6-methoxy-phenyl)-methanone (Example 184) in an analogous manner as described in Example 163. The crude product was used without further purification.

Example 195

(4-Amino-2-ethylsulfinyl-pyrimidin-5-yl)-(3-methoxy-pyridin-2-yl)-methanone

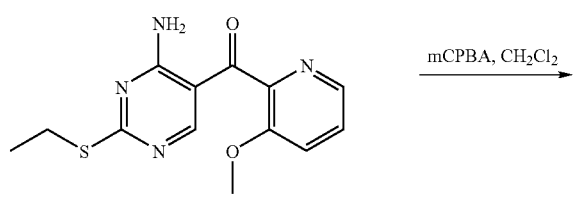

MW 290.35
C$_{13}$H$_{14}$N$_4$O$_2$S

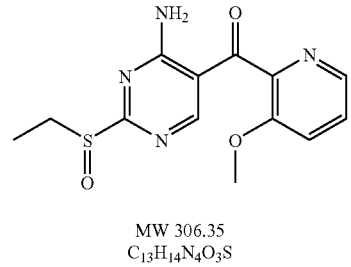

MW 306.35
C$_{13}$H$_{14}$N$_4$O$_3$S

The compound was prepared from (4-amino-2-ethylsulfanyl-pyrimidin-5-yl)-(3-methoxy-pyridin-2-yl)-methanone (Example 185) in an analogous manner as described in Example 163. The crude product was used without further purification.

Example 196

(4-Amino-2-ethylsulfinyl-pyrimidin-5-yl)-(3,4,5-trifluoro-2-methoxy-phenyl)-methanone

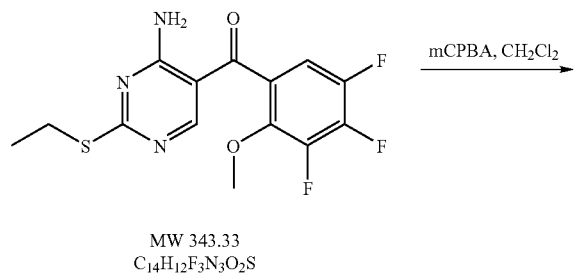

MW 343.33
C$_{14}$H$_{12}$F$_3$N$_3$O$_2$S

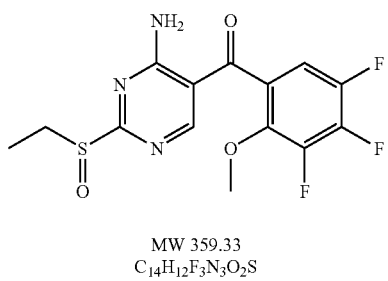

MW 359.33
C$_{14}$H$_{12}$F$_3$N$_3$O$_2$S

The compound was prepared from (4-amino-2-ethylsulfanyl-pyrimidin-5-yl)-(3,4,5-trifluoro-2-methoxy-phenyl)-methanone (Example 186) in an analogous manner as described in Example 163. The crude product was used without further purification.

Example 197

(4-Amino-2-ethylsulfinyl-pyrimidin-5-yl)-(3-methyl-thiophen-2-yl)-methanone

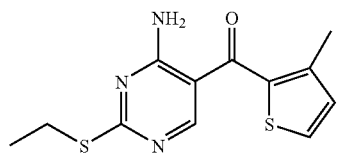

mCPBA, CH₂Cl₂

MW 279.38
C₁₂H₁₃N₃OS₂

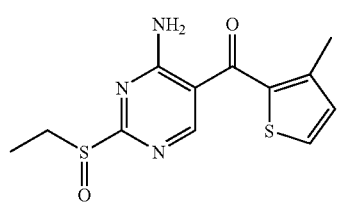

MW 295.38
C₁₂H₁₃N₃O₂S₂

The compound was prepared from (4-amino-2-ethylsulfanyl-pyrimidin-5-yl)-(3-methyl-thiophen-2-yl)-methanone (Example 187) in an analogous manner as described in Example 163. The crude product was used without further purification.

Example 198

(4-Amino-2-ethylsulfinyl-pyrimidin-5-yl)-(5-fluoro-2-methyl-phenyl)-methanone

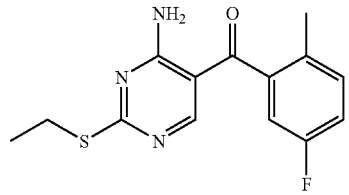

mCPBA, CH₂Cl₂

MW 291.35
C₁₄H₁₄FN₃OS

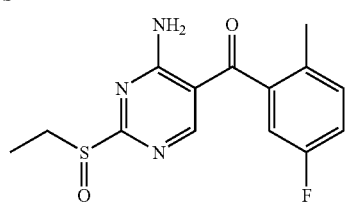

MW 307.35
C₁₄H₁₄FN₃O₂S

The compound was prepared from (4-amino-2-ethylsulfanyl-pyrimidin-5-yl)-(5-fluoro-2-methyl-phenyl)-methanone (Example 188) in an analogous manner as described in Example 163. The crude product was used without further purification.

Example 199

(4-Amino-2-ethylsulfinyl-pyrimidin-5-yl)-(5-fluoro-2-trifluoromethyl-phenyl)-methanone

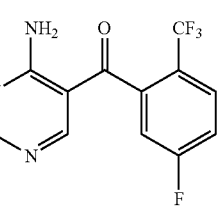

mCPBA, CH₂Cl₂

MW 345.32
C₁₄H₁₁F₄N₃OS

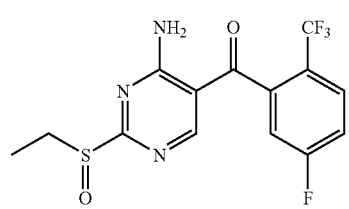

MW 361.32
C₁₄H₁₁F₄N₃O₂S

The compound was prepared from (4-amino-2-ethylsulfanyl-pyrimidin-5-yl)-(5-fluoro-2-trifluoromethyl-phenyl)-methanone (Example 189) in an analogous manner as described in Example 163. The crude product was used without further purification.

Example 200

(4-Amino-2-ethylsulfinyl-pyrimidin-5-yl)-(5-fluoro-2-isopropoxy-phenyl)-methanone

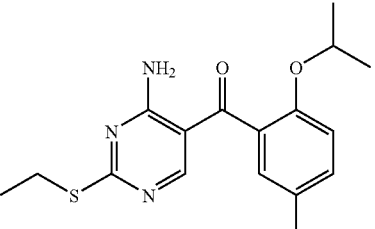

mCPBA, CH₂Cl₂

MW 335.40
C₁₆H₁₈FN₃O₂S

-continued

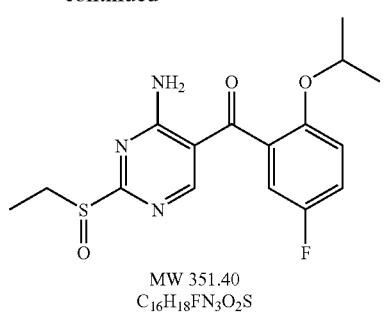

MW 351.40
C₁₆H₁₈FN₃O₂S

The compound was prepared from (4-amino-2-ethylsulfanyl-pyrimidin-5-yl)-(5-fluoro-2-isopropoxy-phenyl)-methanone (Example 190) in an analogous manner as described in Example 163. The crude product was used without further purification.

Example 201

(4-Amino-2-methylsulfinyl-pyrimidin-5-yl)-(2-ethoxy-5-fluoro-phenyl)-methanone

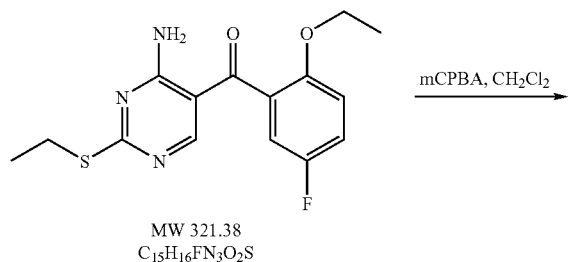

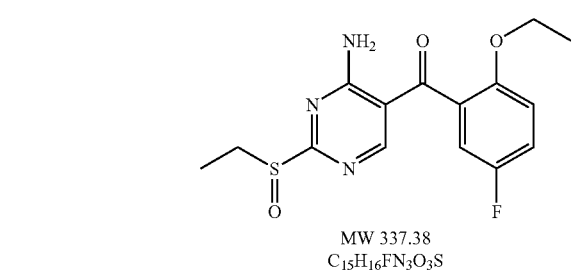

The compound was prepared from (4-amino-2-methylsulfanyl-pyrimidin-5-yl)-(2-ethoxy-5-fluoro-phenyl)-methanone (Example 191) in an analogous manner as described in Example 163. The crude product was used without further purification.

Example 202

(4-Amino-2-methylsulfinyl-pyrimidin-5-yl)-(2-ethyl-5-fluoro-phenyl)-methanone

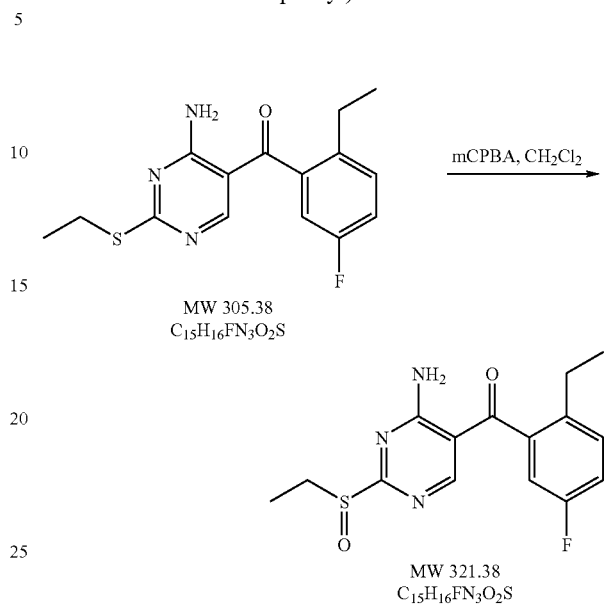

The compound was prepared from (4-amino-2-methylsulfanyl-pyrimidin-5-yl)-(2-ethyl-5-fluoro-phenyl)-methanone (Example 192) in an analogous manner as described in Example 163. The crude product was used without further purification.

Example 203

(4-Amino-2-methylsulfinyl-pyrimidin-5-yl)-(2-methoxy-4-trifluoromethyl-phenyl)-methanone

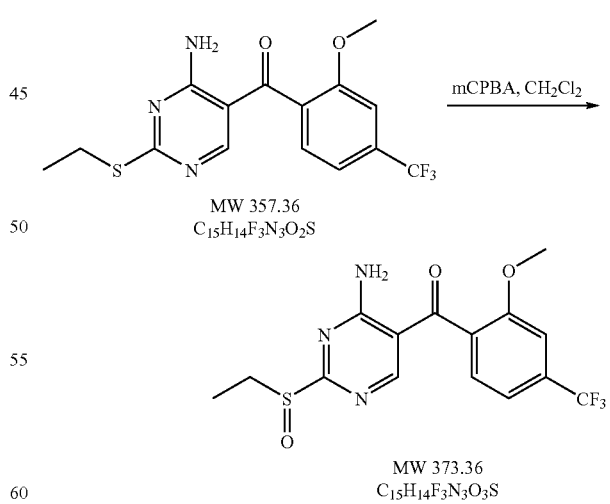

The compound was prepared from (4-amino-2-methylsulfanyl-pyrimidin-5-yl)-(2-methoxy-4-trifluoromethyl-phenyl)-methanone (Example 193) in an analogous manner as described in Example 163. The crude product was used without further purification.

Example 204

1-[4-[4Amino-5-(2,3,4-trifluoro-6-methoxy-benzoyl)-pyrimidin-2-ylamino]-piperidin-1-yl]-ethanone

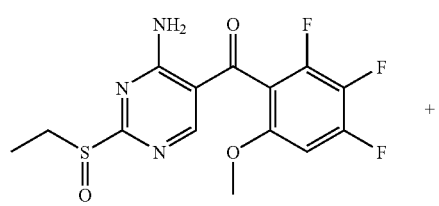

MW 359.33
$C_{14}H_{12}F_3N_3O_3S$

+

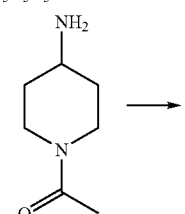

MW 142.20
$C_7H_{14}N_2O$

→

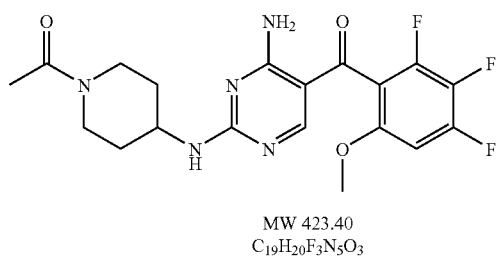

MW 423.40
$C_{19}H_{20}F_3N_5O_3$

The compound was prepared from (4-amino-2-ethylsulfinyl-pyrimidin-5-yl)-(2,3,4-trifluoro-6-methoxy-phenyl)-methanone (Example 194) in an analogous manner as described in Example 172. HR-MS (ES, m/z) calculated for $C_{19}H_{21}N_5O_3F_3$ [(M+H)$^+$] 424.1591, observed 424.1593. CDK4 IC$_{50}$=0.01 µM; CDK1 IC$_{50}$=0.128; CDK2 IC$_{50}$=0.051; HCT 116 IC$_{90}$=2.4 µM.

Example 205

1-[4-[4-Amino-5-(3-methoxy-pyridine-2-carbonyl)-pyrimidin-2-ylamino]-piperidin-1-yl]-ethanone

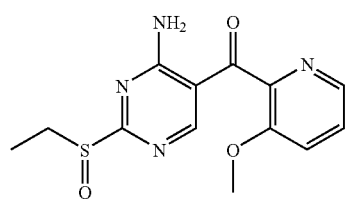

MW 306.35
$C_{13}H_{14}N_4O_3S$

+

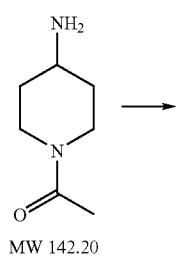

MW 142.20
$C_7H_{14}N_2O$

→

-continued

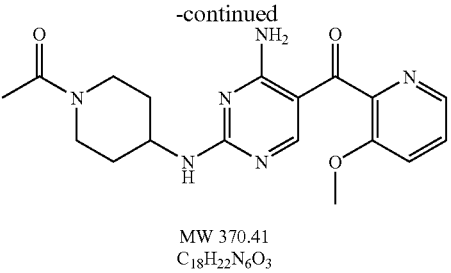

MW 370.41
$C_{18}H_{22}N_6O_3$

The compound was prepared from (4-amino-2-ethylsulfinyl-pyrimidin-5-yl)-(3-methoxy-pyridin-2-yl)-methanone (Example 195) in an analogous manner as described in Example 172. HR-MS (ES, m/z) calculated for $C_{18}H_{23}N_6O_3$ [(M+H)$^+$] 371.1826, observed 371.1829.

Example 206

[4-Amino-2-(1-methanesulfonyl-piperidin-4-ylamino)-pyrimidin-5-yl]-(3,4,5-trifluoro-2-methoxy-phenyl)-methanone

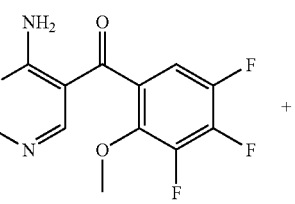

MW 359.33
$C_{14}H_{12}F_3N_3O_3S$

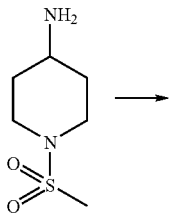

MW 178.25
$C_6H_{14}N_2O_2S$

→

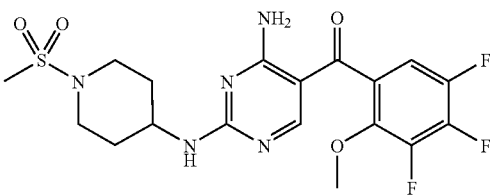

MW 459.45
$C_{18}H_{20}F_3N_5O_4S$

The compound was prepared from (4-amino-2-ethylsulfinyl-pyrimidin-5-yl)-(3,4,5-trifluoro-2-methoxy-phenyl)-methanone (Example 196) and 1-methanesulfonyl-piperidin-4-ylamine; compound with trifluoroacetic acid (Example 162) in an analogous manner as described in Example 172. HR-MS (ES, m/z) calculated for $C_{18}H_{21}N_5O_4SF_3$ [(M+H)$^+$] 460.1261, observed 460.1267.

Example 207

[4-Amino-2-(1-methanesulfonyl-piperidin-4-ylamino)-pyrimidin-5-yl]-(2,3,4-trifluoro-6-methoxyphenyl)-methanone

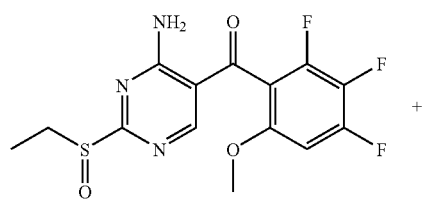

MW 359.33
C₁₄H₁₂F₃N₃O₃S

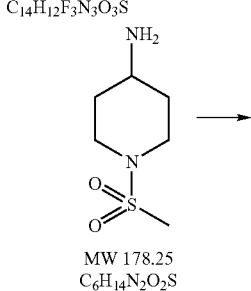

MW 178.25
C₆H₁₄N₂O₂S

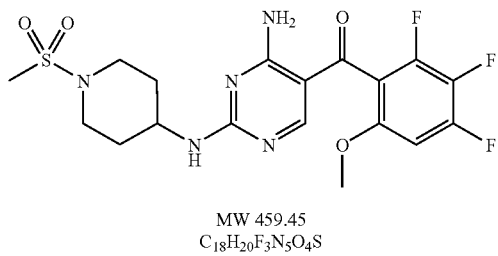

MW 459.45
C₁₈H₂₀F₃N₅O₄S

The compound was prepared from (4-amino-2-ethylsulfinyl-pyrimidin-5-yl)-(2,3,4-trifluoro-6-methoxy-phenyl)-methanone (Example 194) and 1-methanesulfonyl-piperidin-4-ylamine; compound with trifluoroacetic acid (Example 162) in an analogous manner as described in Example 172. HR-MS (ES, m/z) calculated for C₁₈H₂₁N₅O₄SF₃ [(M+H)⁺] 460.1261, observed 460.1267. CDK4 IC₅₀=0.001; CDK1 IC₅₀=0.005; CDK2 IC₅₀=0.002; HCT 116 IC₉₀=0.630 μM.

Example 208

[4-Amino-2-(1-methanesulfonyl-piperidin-4-ylamino)-pyrimidin-5-yl]-(3-methoxy-pyridin-2-yl)-methanone

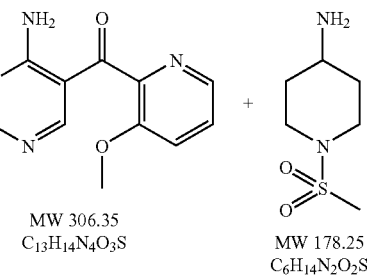

MW 306.35
C₁₃H₁₄N₄O₃S

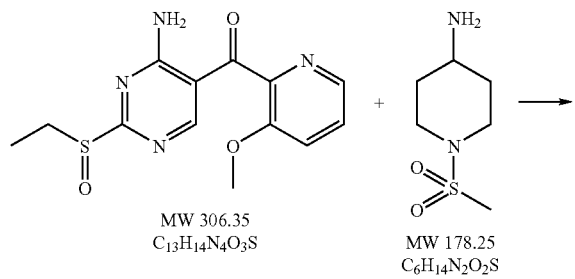

MW 178.25
C₆H₁₄N₂O₂S

-continued

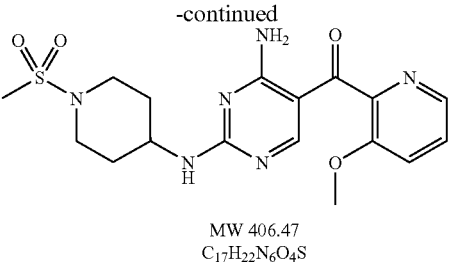

MW 406.47
C₁₇H₂₂N₆O₄S

The compound was prepared from (4-amino-2-ethylsulfinyl-pyrimidin-5-yl)-(3-methoxy-pyridin-2-yl)-methanone (Example 195) and 1-methanesulfonyl-piperidin-4-ylamine; compound with trifluoroacetic acid (Example 162) in an analogous manner as described in Example 172. HR-MS (ES, m/z) calculated for C₁₇H₂₃N₆O₄S [(M+H)⁺] 407.1496, observed 407.1501.

Example 209

[4-Amino-2-[1-(2-methanesulfonyl-ethyl)-piperidin-4-ylamino]-pyrimidin-5-yl]-(5-fluoro-2-methoxyphenyl)-methanone

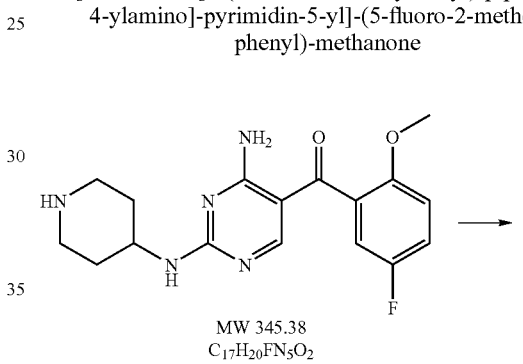

MW 345.38
C₁₇H₂₀FN₅O₂

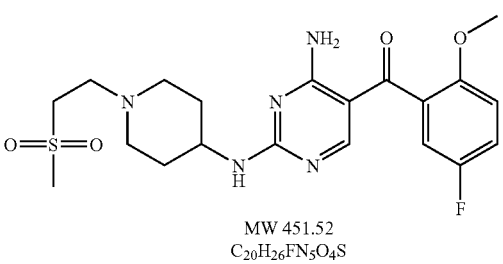

MW 451.52
C₂₀H₂₆FN₅O₄S

To a mixture of [4-amino-2-(piperidin-4-ylamino)-pyrimidin-5-yl]-(5-fluoro-2-methoxy-phenyl)-methanone (100 mg, 0.290 mmol, Example 59) and triethylamine (243 uL, 1.740 mmol) in tetrahydrofuran (3 mL) was added methyl vinyl sulfone (76 uL, 0.870 mmol, Aldrich). The reaction mixture was stirred at room temperature for 2 days and concentrated. The residue was partitioned between ethyl acetate (20 mL) and water (20 mL). The layers were separated and the aqueous layer was extracted with ethyl acetate (10 mL). The combined organic layers were washed with brine and dried over anhydrous magnesium sulfate. The solids were filtered off, and the filtrate was concentrated in vacuo to give a yellow solid (160 mg). Recrystallization from ethanol give [4-amino-2-[1-(2-methanesulfonyl-ethyl)-piperidin-4-ylamino]-pyrimidin-5-yl]-(5-fluoro-2-methoxy-phenyl)-methanone as white solids (63.1 mg, 48% yield). HR-MS (ES, m/z) calculated for C₂₀H₂₇N₅O₄SF [(M+H)⁺] 452.1763, observed 452.1766.

Example 210

1-[4-[4-Amino-5-(3-methyl-thiophene-2-carbonyl)-pyrimidin-2-ylamino]-piperidin-1-yl]-ethanone

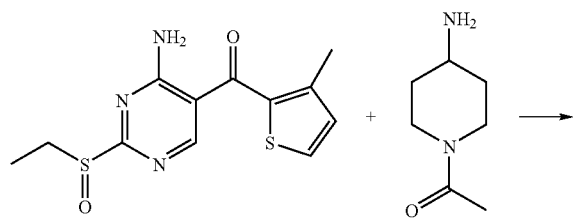

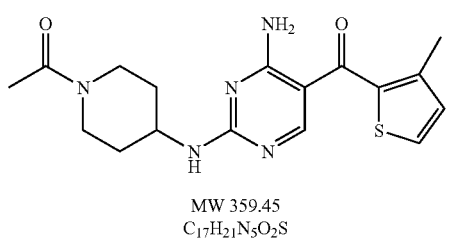

The compound was prepared from (4-amino-2-ethylsulfinyl-pyrimidin-5-yl)-(3-methyl-thiophen-2-yl)-methanone (Example 197) in an analogous manner as described in Example 172. HR-MS (ES, m/z) calculated for $C_{17}H_{22}N_5O_2S$ [(M+H)$^+$] 360.1489, observed 360.1492.

Example 211

1-[4-[4-Amino-5-(5-fluoro-2-methyl-benzoyl)-pyrimidin-2-ylamino]-piperidin-1-yl]-ethanone

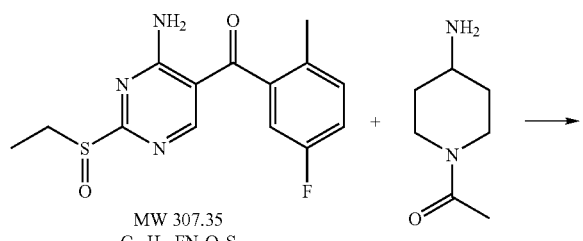

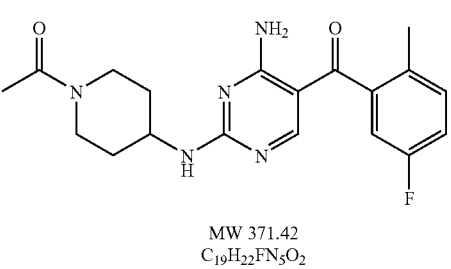

The compound was prepared from (4-amino-2-ethylsulfinyl-pyrimidin-5-yl)-(5-fluoro-2-methyl-phenyl)-methanone (Example 198) in an analogous manner as described in Example 172. HR-MS (ES, m/z) calculated for $C_{19}H_{23}N_5O_2F$ [(M+H)$^+$] 372.1831, observed 372.1834.

Example 212

[4-Amino-2-(1-methanesulfonyl-piperidin-4-ylamino)-pyrimidin-5-yl]-(3-methyl-thiophen-2-yl)-methanone

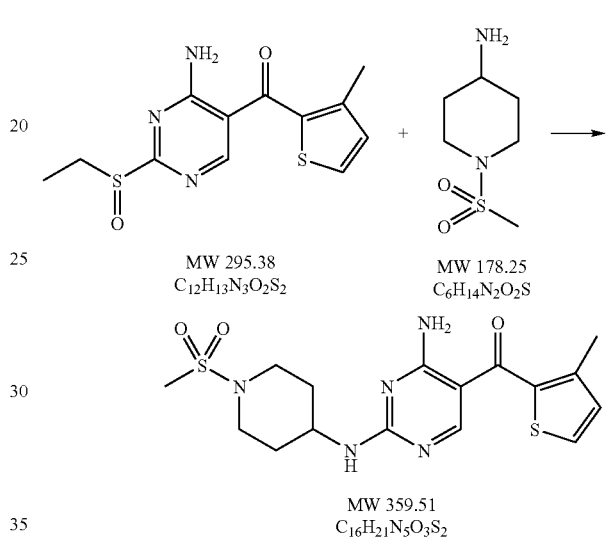

The compound was prepared from (4-amino-2-ethylsulfinyl-pyrimidin-5-yl)-(3-methyl-thiophen-2-yl)-methanone (Example 197) and 1-methanesulfonyl-piperidin-4-ylamine; compound with trifluoroacetic acid (Example 162) in an analogous manner as described in Example 172. HR-MS (ES, m/z) calculated for $C_{16}H_{22}N_5O_3S_2$ [(M+H)$^+$] 396.1159, observed 396.1162.

Example 213

[4-Amino-2-(1-methanesulfonyl-piperidin-4-ylamino)-pyrimidin-5-yl]-(5-fluoro-2-methyl-phenyl)-methanone

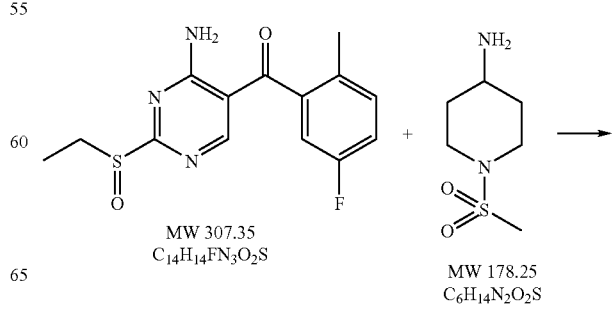

-continued

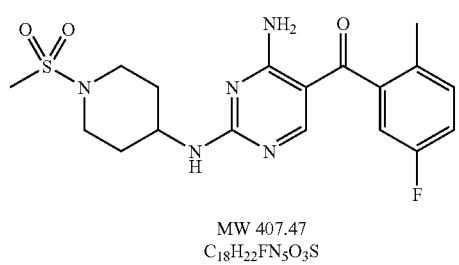

MW 407.47
$C_{18}H_{22}FN_5O_3S$

The compound was prepared from (4-amino-2-ethylsulfinyl-pyrimidin-5-yl)-(5-fluoro-2-methyl-phenyl)-methanone (Example 198) and 1-methanesulfonyl-piperidin-4-ylamine; compound with trifluoroacetic acid (Example 162) in an analogous manner as described in Example 172. HR-MS (ES, m/z) calculated for $C_{18}H_{23}N_5O_3SF$ [(M+H)$^+$] 408.1500, observed 408.1504.

Example 214

[4-Amino-2-(1-methanesulfonyl-piperidin-4-ylamino)-pyrimidin-5-yl]-(5-fluoro-2-trifluoromethyl-phenyl)-methanone

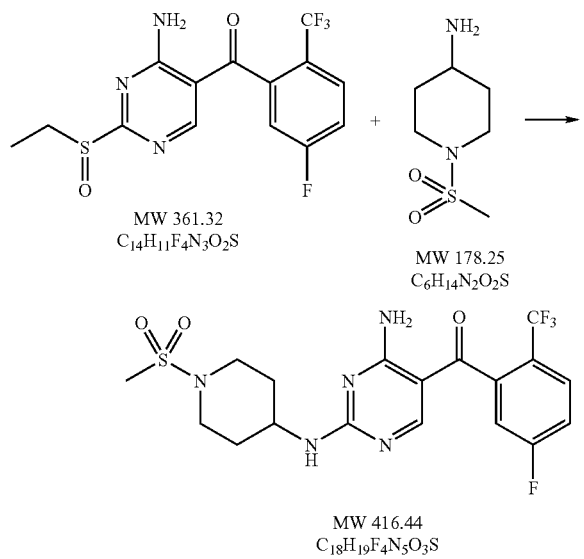

The compound was prepared from (4-amino-2-ethylsulfinyl-pyrimidin-5-yl)-(5-fluoro-2-trifluoromethyl-phenyl)-methanone (Example 199) and 1-methanesulfonyl-piperidin-4-ylamine; compound with trifluoroacetic acid (Example 162) in an analogous manner as described in Example 172. HR-MS (ES, m/z) calculated for $C_{18}H_{20}N_5O_3SF_4$ [(M+H)$^+$] 462.1218, observed 462.1222.

Example 215

[4-Amino-2-(1-methanesulfonyl-piperidin-4-ylamino)-pyrimidin-5-yl]-(5-fluoro-2-isopropoxy-phenyl)-methanone

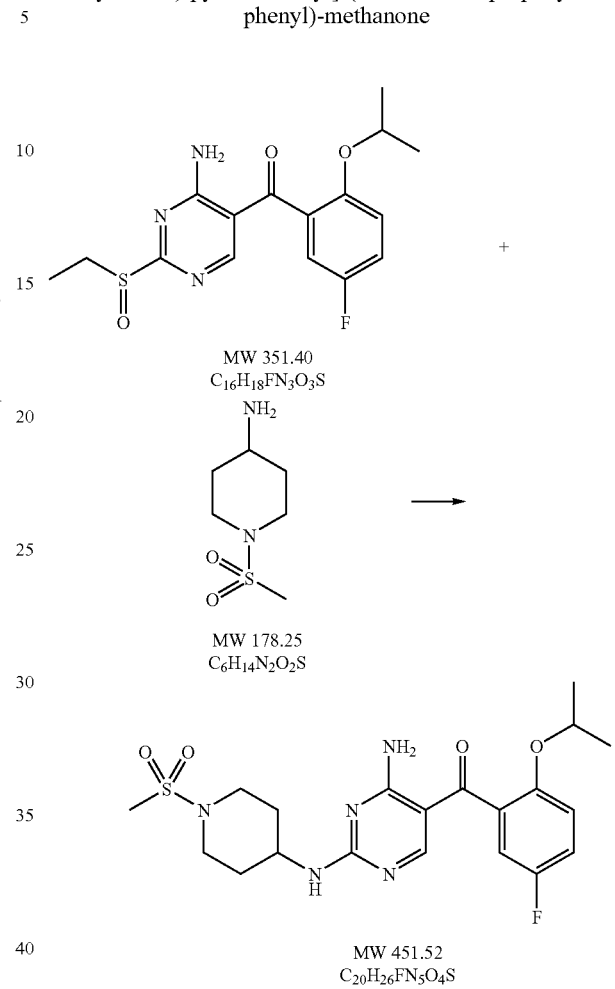

The compound was prepared from (4-amino-2-ethylsulfinyl-pyrimidin-5-yl)-(5-fluoro-2-isopropoxy-phenyl)-methanone (Example 200) and 1-methanesulfonyl-piperidin-4-ylamine; compound with trifluoroacetic acid (Example 162) in an analogous manner as described in Example 172. HR-MS (ES, m/z) calculated for $C_{20}H_{27}N_5O_4SF$ [(M+H)$^+$] 452.1766, observed 452.1766.

Example 216

[4-Amino-2-(1-methanesulfonyl-piperidin-4-ylamino)-pyrimidin-5-yl]-(2-ethoxy-5-fluoro-phenyl)-methanone

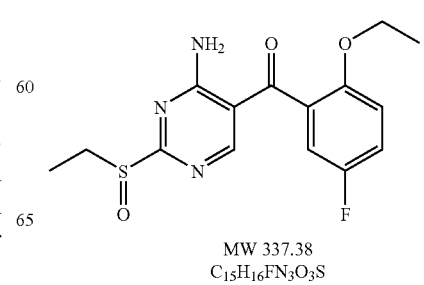

-continued

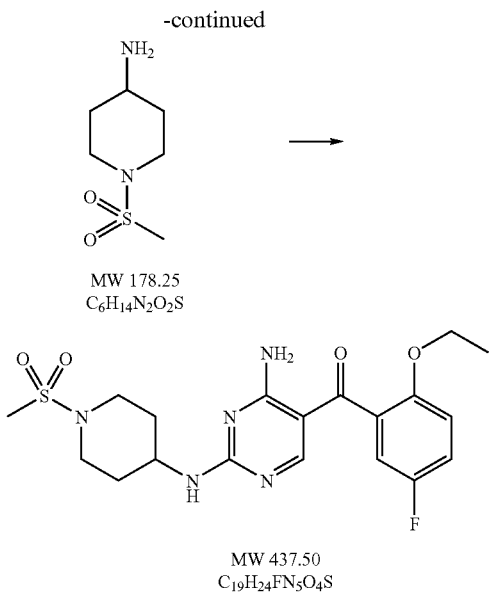

MW 178.25
C₆H₁₄N₂O₂S

MW 437.50
C₁₉H₂₄FN₅O₄S

The compound was prepared from (4-amino-2-ethylsulfinyl-pyrimidin-5-yl)-(2-ethoxy-5-fluoro-phenyl)-methanone (Example 201) and 1-methanesulfonyl-piperidin-4-ylamine; compound with trifluoroacetic acid (Example 162) in an analogous manner as described in Example 172. HR-MS (ES, m/z) calculated for $C_{19}H_{25}N_5O_4SF$ $[(M+H)^+]$ 438.1606, observed 438.1610.

Example 217

[4-Amino-2-(1-methanesulfonyl-piperidin-4-ylamino)-pyrimidin-5-yl]-(2-ethyl-5-fluoro-phenyl)-methanone

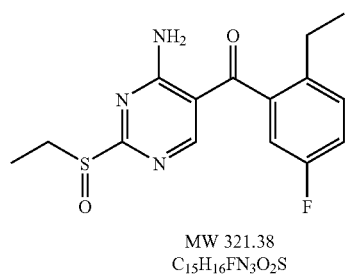

MW 321.38
C₁₅H₁₆FN₃O₂S

+

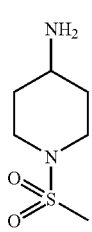

MW 178.25
C₆H₁₄N₂O₂S

-continued

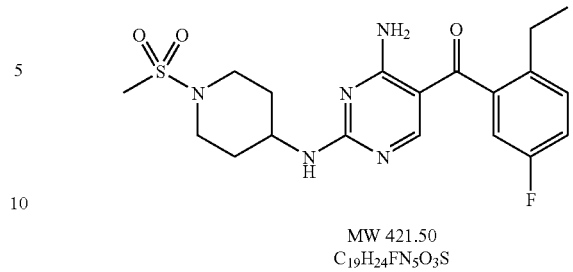

MW 421.50
C₁₉H₂₄FN₅O₃S

The compound was prepared from (4-amino-2-ethylsulfinyl-pyrimidin-5-yl)-(2-ethyl-5-fluoro-phenyl)-methanone (Example 202) and 1-methanesulfonyl-piperidin-4-ylamine; compound with trifluoroacetic acid (Example 162) in an analogous manner as described in Example 172. HR-MS (ES, m/z) calculated for $C_{19}H_5N_5O_3SF$ $[(M+H)^+]$ 422.1660, observed 422.1657.

Example 218

[4-Amino-2-(1-methanesulfonyl-piperidin-4-ylamino)-pyrimidin-5-yl]-(2-methoxy-4-trifluoromethyl-phenyl)-methanone

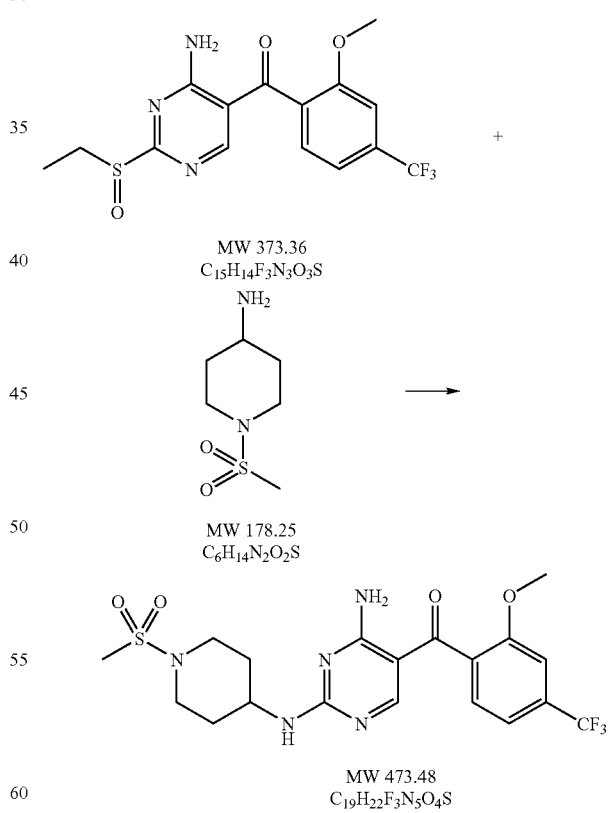

MW 373.36
C₁₅H₁₄F₃N₃O₃S

MW 178.25
C₆H₁₄N₂O₂S

MW 473.48
C₁₉H₂₂F₃N₅O₄S

The compound was prepared from (4-amino-2-ethylsulfinyl-pyrimidin-5-yl)-(2-methoxy-4-trifluoromethyl-phenyl)-methanone (Example 203) and 1-methanesulfonyl-piperidin-4-ylamine; compound with trifluoroacetic acid (Example 162) in an analogous manner as described in Example 172. HR-MS (ES, m/z) calculated for $C_{19}H_{23}N_5O_4SF3$ [(M+H)$^+$] 474.1418, observed 474.1418.

Example 219

(4-Amino-2-ethylsulfanyl-pyrimidin-5-yl)-thiophen-2-yl-methanone

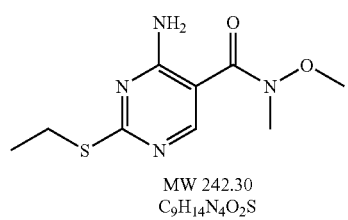

MW 242.30
$C_9H_{14}N_4O_2S$

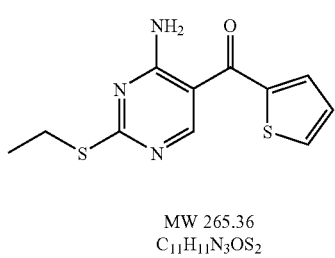

MW 265.36
$C_{11}H_{11}N_3OS_2$

To a solution of 4-amino-2-ethylsulfanyl-pyrimidine-5-carboxylic acid methoxy-methyl-amide (600 mg, 2.476 mmol, Example 167) in tetrahydrofuran (20 mL) cooled to −20° C. was added thiophen-2-yl-magnesium bromide (9.9 mL, 9.9 mmol, 1 M in tetrahydrofuran, Aldrich) over a period of 15 minutes. The reaction mixture was stirred at −20° C. for 1 hour and at 0° C. for another hour then the ice bath was removed to allow the temperature to go up to room temperature. After standing at room temperature for 12 hours, saturated solution of sodium bicarbonate (1 mL), water (100 mL) and diethyl ether (20 mL) were each added. The mixture was filtered and the layers were separated. The product was extracted with diethyl ether (2×20 mL). The combined organic layers were washed with brine and dried over anhydrous magnesium sulfate. The solids were filtered off, and the filtrate was concentrated in vacuo. Purification of the crude residue by flash chromatography (Biotage system, 60 Å silica gel, eluting with 1.4% ethyl acetate and 0.1% triethylamine in methylene chloride) yield 4-amino-2-ethylsulfanyl-pyrimidin-5-yl)-thiophen-2-yl-methanone as off-white solids (465 mg, 71%).

Example 220

(4-Amino-2-ethylsulfinyl-pyrimidin-5-yl)-thiophen-2-yl-methanon

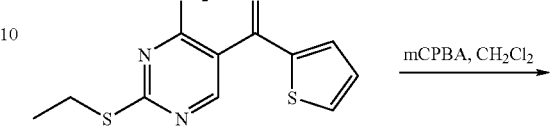

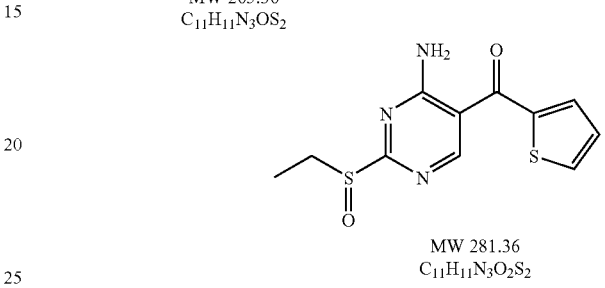

MW 281.36
$C_{11}H_{11}N_3O_2S_2$

The compound was prepared from (4-amino-2-ethylsulfanyl-pyrimidin-5-yl)-thiophen-2-yl-methanone (Example 219) in an analogous manner as described in Example 163. The crude product was used without further purification.

Example 221

[4-Amino-2-(1-methanesulfonyl-piperidin-4-ylamino)-pyrimidin-5-yl]-thiophen-2-yl-methanone

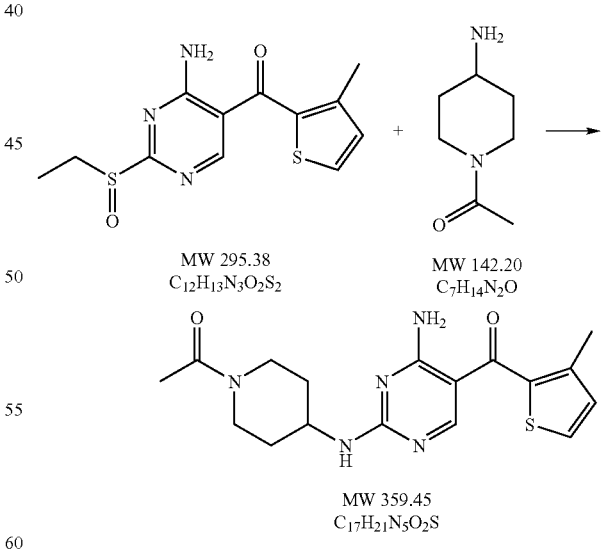

MW 359.45
$C_{17}H_{21}N_5O_2S$

The compound was prepared from (4-amino-2-ethylsulfinyl-pyrimidin-5-yl)-(3-methyl-thiophen-2-yl)-methanone (Example 220) in an analogous manner as described in Example 172. HR-MS (ES, m/z) calculated for $C_{17}H_{22}N_5O_2S$ [(M+H)$^+$] 360.1489, observed 360.1492.

Example 222

4-[4-Amino-5-(2-fluoro-6-methoxy-benzoyl)-pyrimidin-2-ylamino]-piperidine-1-carboxylic acid tert-butyl ester

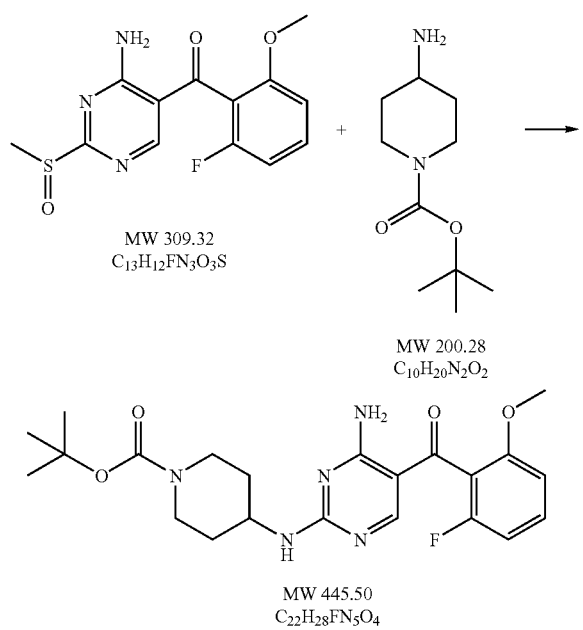

The compound was prepared from (4-amino-2-methylsulfinyl-pyrimidin-5-yl)-(2-fluoro-6-methoxy-phenyl)-methanone (Example 171) in an analogous manner as described in Example 175. HR-MS (ES, m/z) calculated for $C_{22}H_{29}N_5O_4F$ [(M+H)$^+$] 446.2198, observed 446.2203.

Example 223

[4-Amino-2-(piperidin-4-ylamino)-pyrimidin-5-yl]-(2-fluoro-6-methoxy-phenyl)-methanone

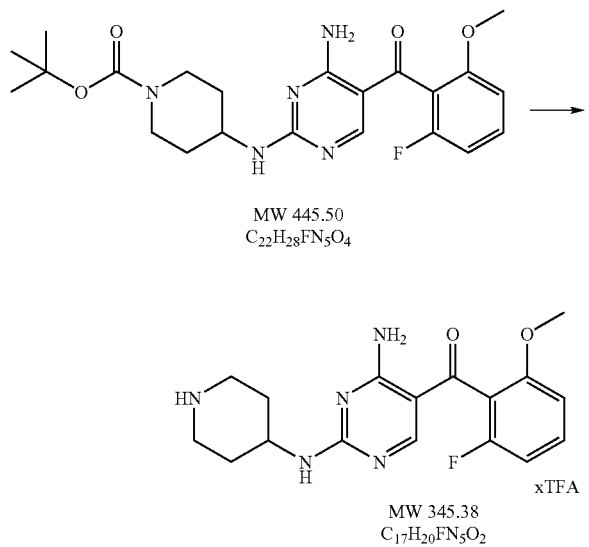

The compound was prepared from 4-[4-amino-5-(2-fluoro-6-methoxy-benzoyl)-pyrimidin-2-ylamino]-piperidine-1-carboxylic acid tert-butyl ester (Example 222) in an analogous manner as described in Example 176.

Example 224

[4-Amino-2-(1-methanesulfonyl-piperidin-4-ylamino)-pyrimidin-5-yl]-(2-fluoro-6-methoxy-phenyl)-methanone

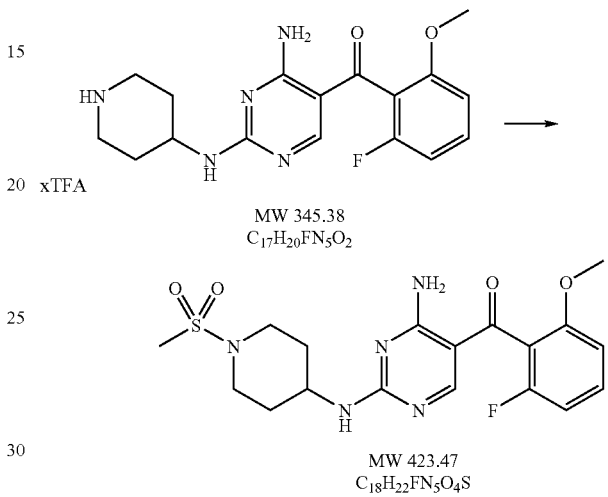

The compound was prepared from [4-amino-2-(piperidin-4-ylamino)-pyrimidin-5-yl]-(2-fluoro-6-methoxy-phenyl)-methanone (Example 223) in an analogous manner as described in Example 177.

Example 225

1-[4-[4-Amino-5-(2-fluoro-6-methoxy-benzoyl)-pyrimidin-2-ylamino]-piperidin-1-yl]-2,2,2-trifluoro-ethanone

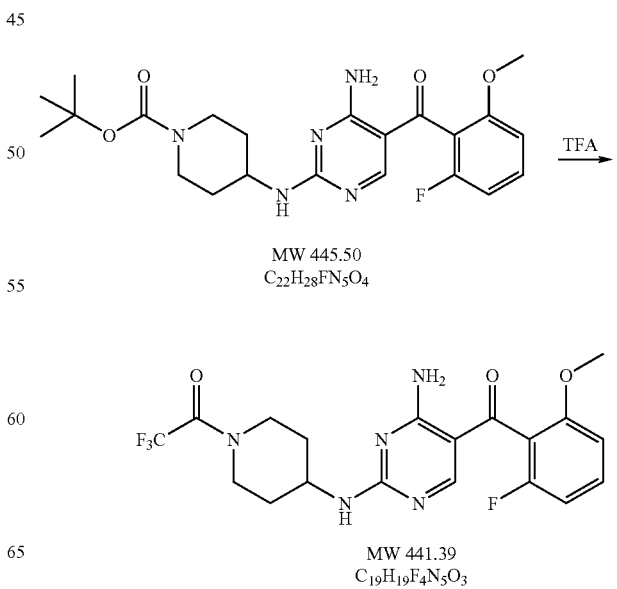

The compound was isolated as a side product from the preparation of [4-amino-2-(piperidin-4-ylamino)-pyrimidin-5-yl]-(2-fluoro-6-methoxy-phenyl)-methanone (Example 223). HR-MS (ES, m/z) calculated for $C_{19}H_{20}N_5O_3F_4$ [(M+H)$^+$] 442.1497, observed 442.1501.

Example 226

[4-Amino-2-[1-(3-chloro-propane-1-sulfonyl)-piperidin-4-ylamino]-pyrimidin-5-yl]-(2,3-difluoro-6-methoxy-phenyl)-methanone

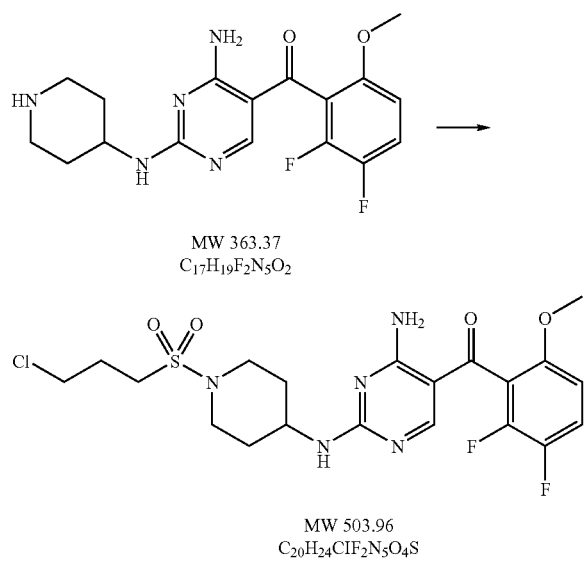

MW 363.37
$C_{17}H_{19}F_2N_5O_2$

MW 503.96
$C_{20}H_{24}ClF_2N_5O_4S$

The compound was prepared from [4-amino-2-(piperidin-4-ylamino)-pyrimidin-5-yl]-(2,3-difluoro-6-methoxy-phenyl)-methanone (Example 107) and chloropropanesulfonyl chloride (Aldrich) in an analogous manner as described in Example 177. HR-MS (ES, m/z) calculated for $C_{20}H_{25}N_5O_4SF_2Cl$ [(M+H)$^+$] 504.1279, observed 504.1284.

Example 227

(4-Amino-2-[1-[3-(2-hydroxy-1-methyl-ethylamino)-propane-1-sulfonyl]-piperidin-4-ylamino]-pyrimidin-5-yl)-(2,3-difluoro-6-methoxy-phenyl)-methanone

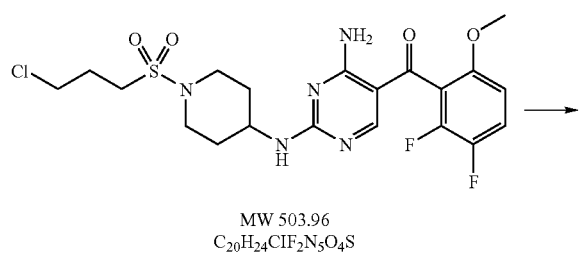

MW 503.96
$C_{20}H_{24}ClF_2N_5O_4S$

-continued

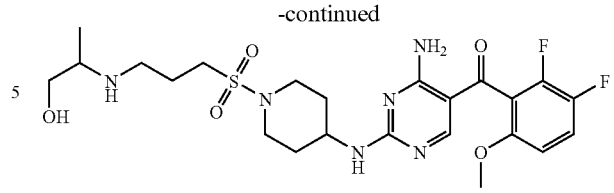

MW 542.61
$C_{23}H_{32}F_2N_6O_5S$

The reaction mixture of [4-amino-2-[1-(3-chloro-propane-1-sulfonyl)-piperidin-4-ylamino]-pyrimidin-5-yl]-(2,3-difluoro-6-methoxy-phenyl)-methanone (100 mg, 0.198 mmol, Example 226), dl-2-amino-1-propanol (158 uL, 1.980 mmol, TCI) and sodium iodide (30 mg, 0.198 mmol) in tetrahydrofuran (4 mL) was heated at 150° C. for 1 hour using a Smith Creator microwave synthesizer. Upon cooling to room temperature, the solvent was removed and acetonitrile (3 mL) was added. The mixture was filtered and trifluoroacetic acid (0.25 mL) was added. Purification by reverse phase HPLC (C18, eluting with acetonitrile and water) gave (4-amino-2-[1-[3-(2-hydroxy-1-methyl-ethylamino)-propane-1-sulfonyl]-piperidin-4-ylamino]-pyrimidin-5-yl)-(2,3-difluoro-6-methoxy-phenyl)-methanone (70 mg, 65% yield) as off-white solids. HR-MS (ES, m/z) calculated for $C_{23}H_{33}N_6O_5SF_2$ [(M+H)$^+$] 543.2196, observed 543.2202.

Example 228

(4-Amino-2-[1-[3-(4-methyl-piperazin-1-yl)-propan-1-sulfonyl]-piperidin-4-ylamino]-pyrimidin-5-yl)-(2,3-difluoro-6-methoxy-phenyl)-methanone

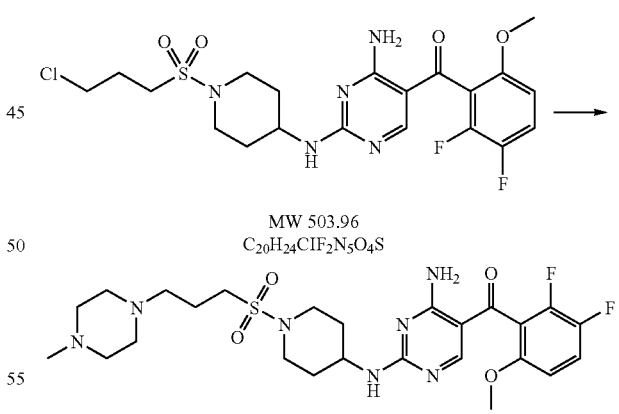

MW 503.96
$C_{20}H_{24}ClF_2N_5O_4S$

MW 567.66
$C_{25}H_{35}F_2N_7O_4S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and 1-methylpiperazine (Fluka) in an analogous manner as described in Example 227. HR-MS (ES, m/z) calculated for $C_{25}H_{36}N_7O_4SF_2$ [(M+H)$^+$] 568.2512, observed 568.2519. CDK4 $IC_{50}$=0.001; CDK1 $IC_{50}$=0.039; CDK2 $IC_{50}$=0.017; HCT $IC_{90}$=0.274 μM.

Example 229

(4-Amino-2-[1-[3-((R)-1-hydroxymethyl-propylamino)-propane-1-sulfonyl]-piperidin-4-ylamino]-pyrimidin-5-yl)-(2,3-difluoro-6-methoxy-phenyl)-methanone

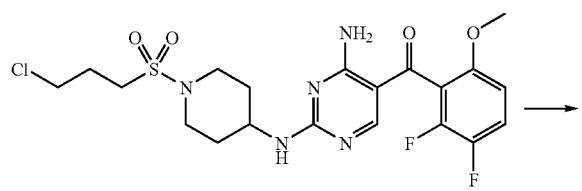

MW 503.96
$C_{20}H_{24}ClF_2N_5O_4S$

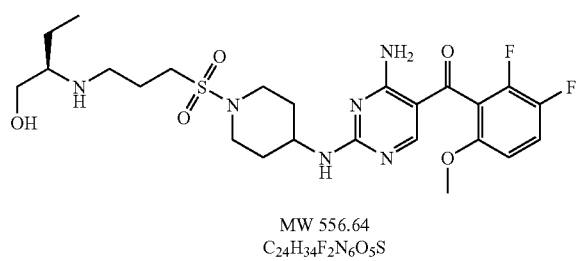

MW 556.64
$C_{24}H_{34}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and (R)-2-amino-1-butanol (Aldrich) in an analogous manner as described in Example 227. HR-MS (ES, m/z) calculated for $C_{24}H_{35}N_6O_5SF_2$ [(M+H)$^+$] 557.2352, observed 557.2360.

Example 230

[4-Amino-2-[1-(3-hydroxy-propane-1-sulfonyl)-piperidin-4-ylamino]-pyrimidin-5-yl]-(2,3-difluoro-6-methoxy-phenyl)-methanone

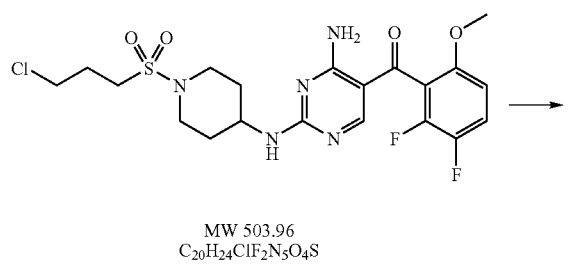

MW 503.96
$C_{20}H_{24}ClF_2N_5O_4S$

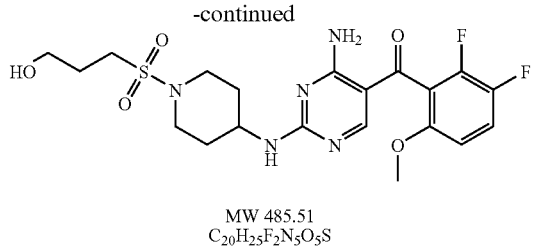

MW 485.51
$C_{20}H_{25}F_2N_5O_5S$

[4-Amino-2-[1-(3-chloro-propane-1-sulfonyl)-piperidin-4-ylamino]-pyrimidin-5-yl]-(2,3-difluoro-6-methoxy-phenyl)-methanone (Example 226) was reacted with sodium acetate in an analogous manner as described in Example 227 to give acetic acid 3-[4-[4-amino-5-(2,3-difluoro-6-methoxy-benzoyl)-pyrimidin-2-ylamino]-piperidine-1-sulfonyl]-propyl ester. The crude acetic acid 3-[4-[4-amino-5-(2,3-difluoro-6-methoxy-benzoyl)-pyrimidin-2-ylamino]-piperidine-1-sulfonyl]-propyl ester was hydrolyzed with 5% potassium hydroxide to give [4-amino-2-[1-(3-hydroxy-propane-1-sulfonyl)-piperidin-4-ylamino]-pyrimidin-5-yl]-(2,3-difluoro-6-methoxy-phenyl)-methanone. HR-MS (ES, m/z) calculated for $C_{20}H_{26}N_5O_5SF_2$ [(M+H)$^+$] 486.1617, observed 486.1623.

Example 231

[4-Amino-2-[1-(3-pyrrolidin-1-yl-propane-1-sulfonyl)-piperidin-4-ylamino]-pyrimidin-5-yl]-(2,3-difluoro-6-methoxy-phenyl)-methanone

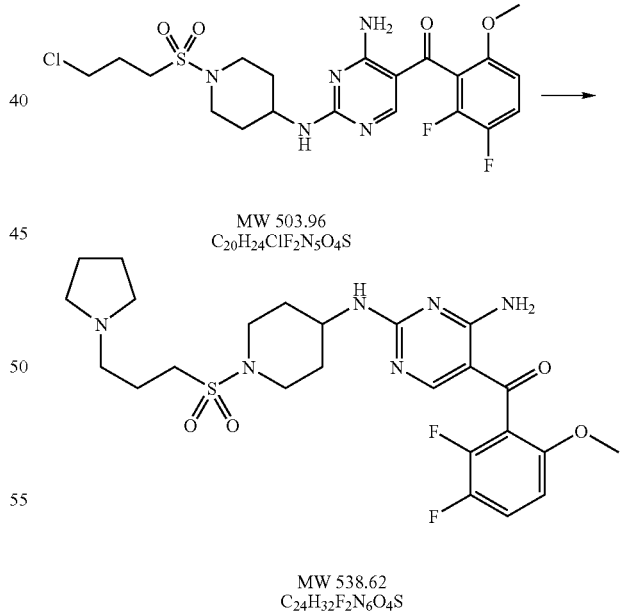

MW 503.96
$C_{20}H_{24}ClF_2N_5O_4S$

MW 538.62
$C_{24}H_{32}F_2N_6O_4S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and pyrrolidine (Aldrich) in an analogous manner as described in Example 227. HR-MS (ES, m/z) calculated for $C_{24}H_{33}N_6O_4SF_2$ [(M+H)$^+$] 539.2247, observed 539.2252.

Example 232

[4-Amino-2-[1-(3-morpholin-4-yl-propane-1-sulfonyl)-piperidin-4-ylamino]-pyrimidin-5-yl]-(2,3-difluoro-6-methoxy-phenyl)-methanone

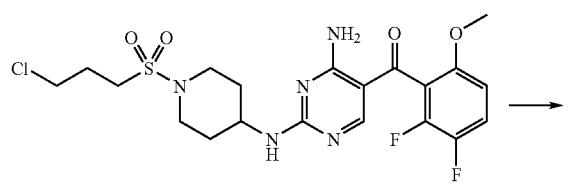

MW 503.96
$C_{20}H_{24}ClF_2N_5O_4S$

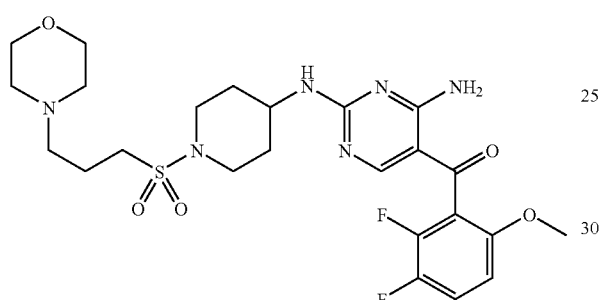

MW 554.62
$C_{24}H_{32}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and morpholine (Aldrich) in an analogous manner as described in Example 227. HR-MS (ES, m/z) calculated for $C_{24}H_{33}N_6O_5SF_2$ [(M+H)$^+$] 555.2196, observed 555.2199.

Example 233

[4-Amino-2-(1-[3-[4-(2-hydroxy-ethyl)-piperazin-1-yl]-propane-1-sulfonyl]-piperidin-4-ylamino)-pyrimidin-5-yl]-(2,3-difluoro-6-methoxy-phenyl)-methanone

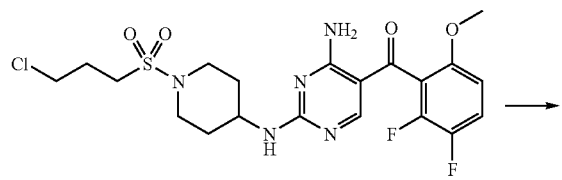

MW 503.96
$C_{20}H_{24}ClF_2N_5O_4S$

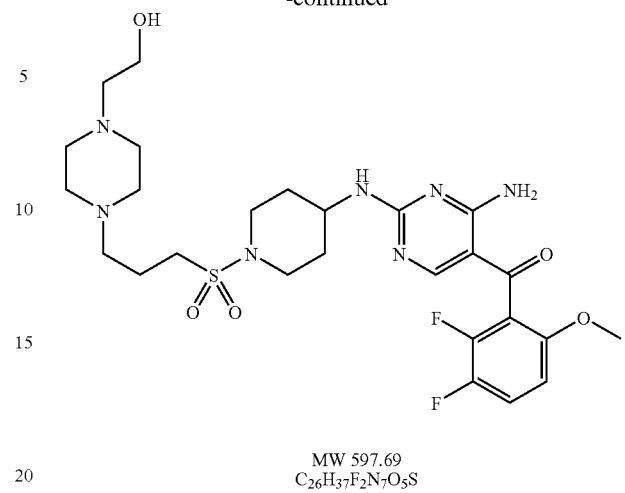

MW 597.69
$C_{26}H_{37}F_2N_7O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and 1-(2-hydroxyethyl)piperazine (Aldrich) in an analogous manner as described in Example 227. HR-MS (ES, m/z) calculated for $C_{26}H_{38}N_7O_5SF_2$ [(M+H)$^+$] 598.2618, observed 598.2624.

Example 234

[4-Amino-2-(1-[3-[(2-methoxy-ethyl)-methyl-amino]-propane-1-sulfonyl]-piperidin-4-ylamino)-pyrimidin-5-yl]-(2,3-difluoro-6-methoxy-phenyl)-methanone

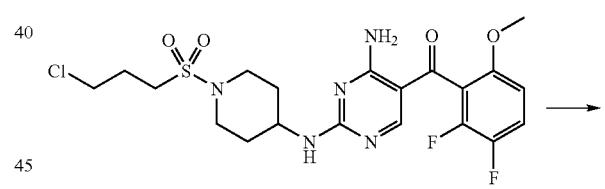

MW 503.96
$C_{20}H_{24}ClF_2N_5O_4S$

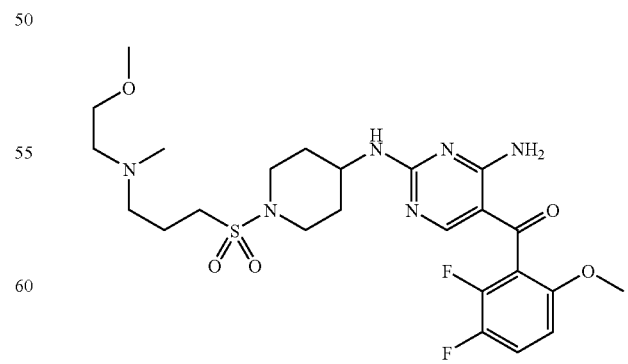

MW 556.64
$C_{24}H_{34}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and N-(2-methoxyethyl)methylamine (TCI America) in an analogous manner as described in Example 227. HR-MS (ES, m/z) calculated for $C_{24}H_{35}N_6O_5SF_2$ [(M+H)$^+$] 557.2352, observed 557.2357.

Example 235

(4-Amino-2-[1-[3-(2-hydroxy-1,1-dimethyl-ethylamino)-propane-1-sulfonyl]-piperidin-4-ylamino]-pyrimidin-5-yl)-(2,3-difluoro-6-methoxy-phenyl)-methanone

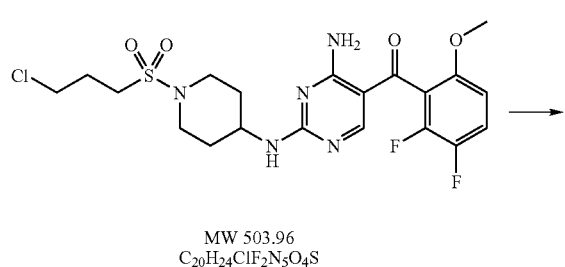

MW 503.96
$C_{20}H_{24}ClF_2N_5O_4S$

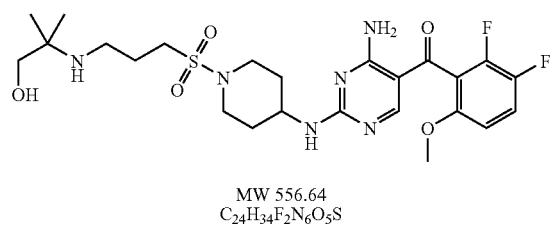

MW 556.64
$C_{24}H_{34}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and 2-amino-2-methyl-1-propanol (Aldrich) in an analogous manner as described in Example 227. HR-MS (ES, m/z) calculated for $C_{24}H_{35}N_6O_5SF_2$ [(M+H)$^+$] 557.2352, observed 557.2359.

Example 236

(4-Amino-2-[1-[3-(2-hydroxy-propylamino)-propane-1-sulfonyl]-piperidin-4-ylamino]-pyrimidin-5-yl)-(2,3-difluoro-6-methoxy-phenyl)-methanone

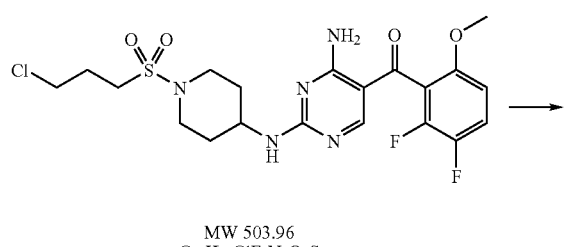

MW 503.96
$C_{20}H_{24}ClF_2N_5O_4S$

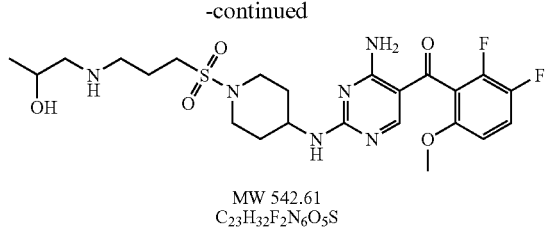

MW 542.61
$C_{23}H_{32}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and 1-amino-2-propanol (Eastman Kodak) in an analogous manner as described in Example 227. HR-MS (ES, m/z) calculated for $C_{23}H_{33}N_6O_5SF_2$ [(M+H)$^+$] 543.2196, observed 543.2200.

Example 237

(4-Amino-2-[1-[3-((S)-2-hydroxy-1-methyl-ethylamino)-propane-1-sulfonyl]-piperidin-4-ylamino]-pyrimidin-5-yl)-(2,3-difluoro-6-methoxy-phenyl)-methanone

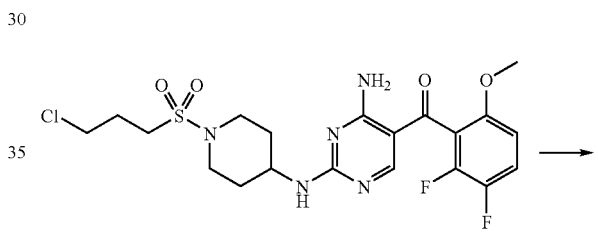

MW 503.96
$C_{20}H_{24}ClF_2N_5O_4S$

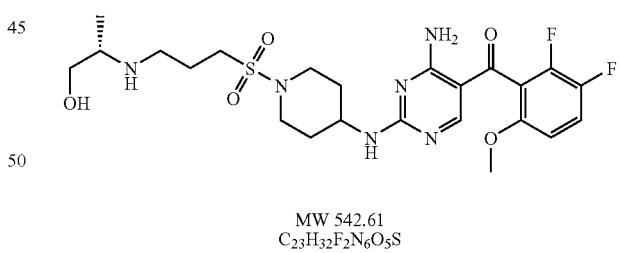

MW 542.61
$C_{23}H_{32}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and (S)-(+)-2-amino-1-propanol (Aldrich) in an analogous manner as described in Example 227. HR-MS (ES, m/z) calculated for $C_{23}H_{33}N_6O_5SF_2$ [(M+H)$^+$] 543.2196, observed 543.2200.

Example 238

(4-Amino-2-[1-[3-((R)-1-hydroxymethyl-2-methyl-propylamino)-propane-1-sulfonyl]-piperidin-4-ylamino]-pyrimidin-5-yl)-(2,3-difluoro-6-methoxy-phenyl)-methanone

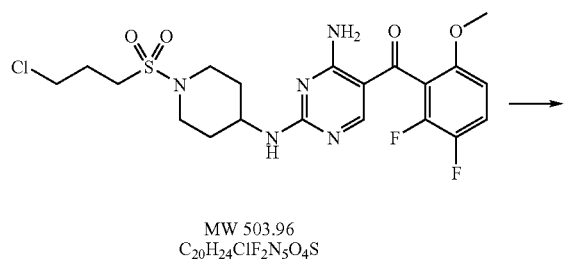

MW 503.96
$C_{20}H_{24}ClF_2N_5O_4S$

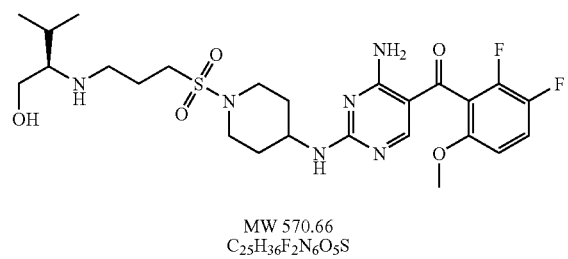

MW 570.66
$C_{25}H_{36}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and (R)-2-amino-3-methyl-1-butanol (Aldrich) in an analogous manner as described in Example 227. HR-MS (ES, m/z) calculated for $C_{25}H_{37}N_6O_5SF_2$ [(M+H)$^+$] 571.2509, observed 571.2514.

Example 239

(4-Amino-2-[1-[3-((R)-2-hydroxy-1-methyl-ethylamino)-propane-1-sulfonyl]-piperidin-4-ylamino]-pyrimidin-5-yl)-(2,3-difluoro-6-methoxy-phenyl)-methanone

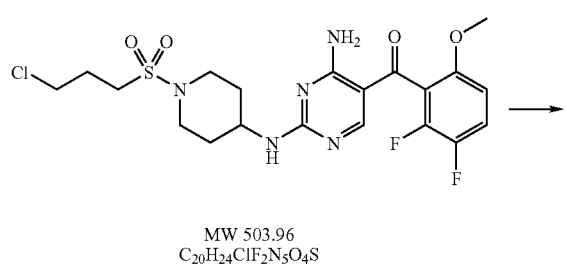

MW 503.96
$C_{20}H_{24}ClF_2N_5O_4S$

-continued

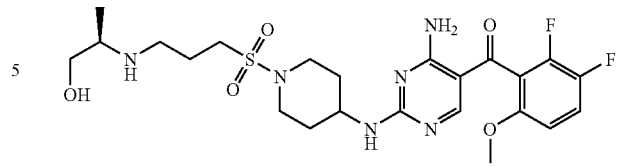

MW 542.61
$C_{23}H_{32}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and (R)-2-amino-1-propanol (Aldrich) in an analogous manner as described in Example 227. HR-MS (ES, m/z) calculated for $C_{23}H_{33}N_6O_5SF_2$ [(M+H)$^+$] 543.2196, observed 543.2201.

Example 240

(4-Amino-2-[1-[3-((S)-1-hydroxymethyl-propylamino)-propane-1-sulfonyl]-piperidin-4-ylamino]-pyrimidin-5-yl)-(2,3-difluoro-6-methoxy-phenyl)-methanone

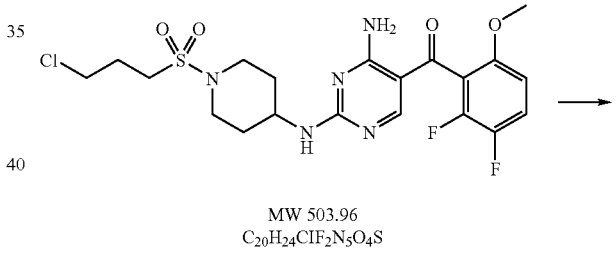

MW 503.96
$C_{20}H_{24}ClF_2N_5O_4S$

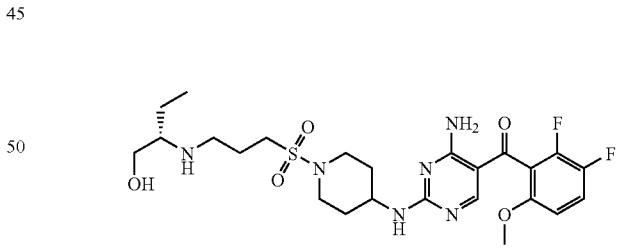

MW 556.64
$C_{24}H_{34}F_2N_6O_5S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and (S)-2-amino-1-butanol (Aldrich) in an analogous manner as described in Example 227. HR-MS (ES, m/z) calculated for $C_{24}H_{35}N_6O_5SF_2$ [(M+H)$^+$] 557.2352, observed 557.2356.

Example 241

[4-Amino-2-(1-[3-[3-hydroxy-1-(2-hydroxy-ethyl)-propylamino]-propane-1-sulfonyl]-piperidin-4-ylamino)-pyrimidin-5-yl]-(2,3-difluoro-6-methoxy-phenyl)-methanone

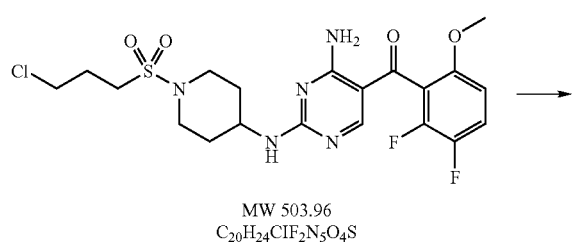

MW 503.96
$C_{20}H_{24}ClF_2N_5O_4S$

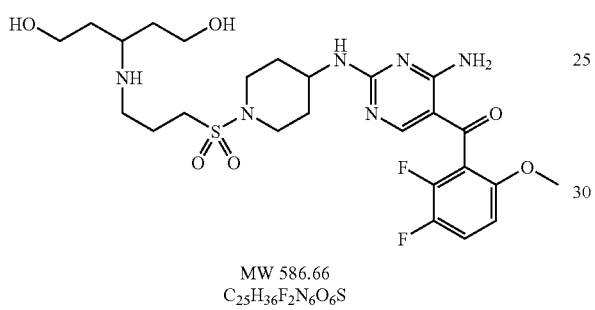

MW 586.66
$C_{25}H_{36}F_2N_6O_6S$

The compound was prepared from [4-amino-2-[1-(3-chloro-propane-1-sulfonyl)-piperidin-4-ylamino]-pyrimidin-5-yl]-(2,3-difluoro-6-methoxy-phenyl)-methanone (Example 226) and 3-amino-pentane-1,5-diol (prepared from the methyl oxime of diethyl 1,3-acetonedicarboxylate, Aldrich, by reduction with lithium aluminum hydride in diethyl ether) in an analogous manner as described in Example 227. HR-MS (ES, m/z) calculated for $C_{25}H_{37}N_6O_6SF_2$ $[(M+H)^+]$ 587.2458, observed 587.2464.

Example 242

[4-Amino-2-[1-(3-chloro-propane-1-sulfonyl)-piperidin-4-ylamino]-pyrimidin-5-yl]-(5-fluoro-2-methoxy-phenyl)-methanone

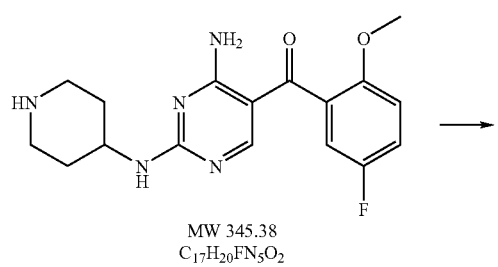

MW 345.38
$C_{17}H_{20}FN_5O_2$

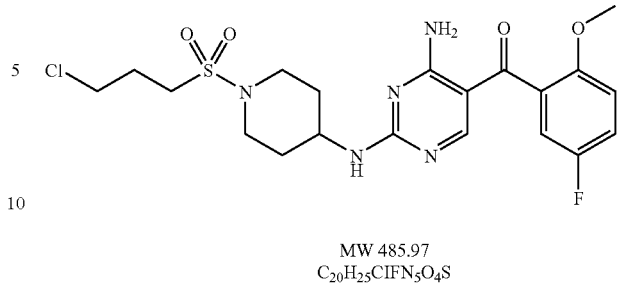

MW 485.97
$C_{20}H_{25}ClFN_5O_4S$

The compound was prepared from [4-amino-2-(piperidin-4-ylamino)-pyrimidin-5-yl]-(5-fluoro-2-methoxy-phenyl)-methanone (Example 59) and chloropropanesulfonyl chloride (Aldrich) in an analogous manner as described in Example 177. HR-MS (ES, m/z) calculated for $C_{20}H_{26}N_5O_4SFCl$ $[(M+H)^+]$ 486.1373, observed 486.1375.

Example 243

[4-Amino-2-(1-[3-[(2-methoxy-ethyl)-methyl-amino]-propane-1-sulfonyl]-piperidin-4-ylamino)-pyrimidin-5-yl]-(5-fluoro-2-methoxy-phenyl)-methanone

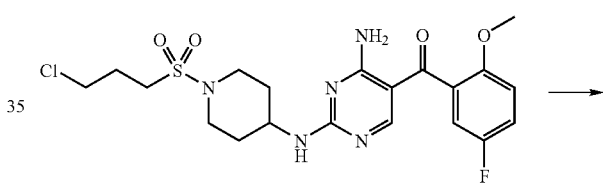

MW 485.97
$C_{20}H_{25}ClFN_5O_4S$

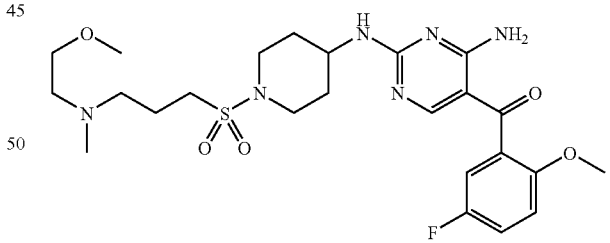

MW 538.65
$C_{24}H_{35}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and N-(2-methoxyethyl)methylamine (TCI America) in an analogous manner as described in Example 227. HR-MS (ES, m/z) calculated for $C_{24}H_{36}N_6O_5SF$ $[(M+H)^+]$ 539.2447, observed 539.2449.

Example 244

[4-Amino-2-(1-[3-[4-(2-hydroxy-ethyl)-piperazin-1-yl]-propane-1-sulfonyl]-piperidin-4-ylamino)-pyrimidin-5-yl]-(5-fluoro-2-methoxy-phenyl)-methanone

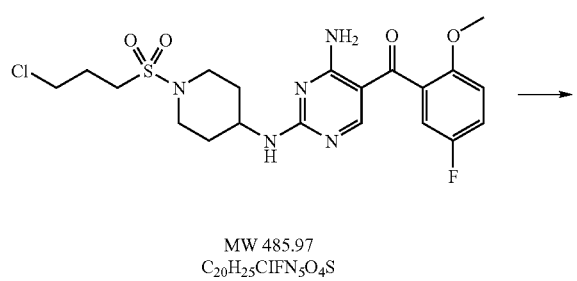

MW 485.97
$C_{20}H_{25}ClFN_5O_4S$

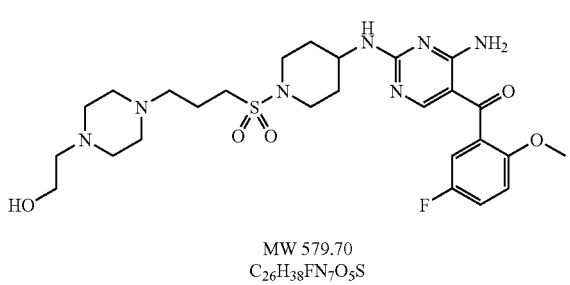

MW 579.70
$C_{26}H_{38}FN_7O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and 1-(2-hydroxyethyl)piperazine (Aldrich) in an analogous manner as described in Example 227. HR-MS (ES, m/z) calculated for $C_{26}H_{39}N_7O_5SF$ [(M+H)$^+$] 580.2712, observed 580.2716.

Example 245

(4-Amino-2-[1-[3-((S)-2-hydroxy-1-methyl-ethylamino)-propane-1-sulfonyl]-piperidin-4-ylamino]-pyrimidin-5-yl)-(5-fluoro-2-methoxy-phenyl)-methanone

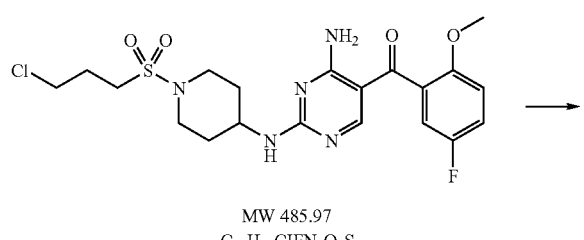

MW 485.97
$C_{20}H_{25}ClFN_5O_4S$

-continued

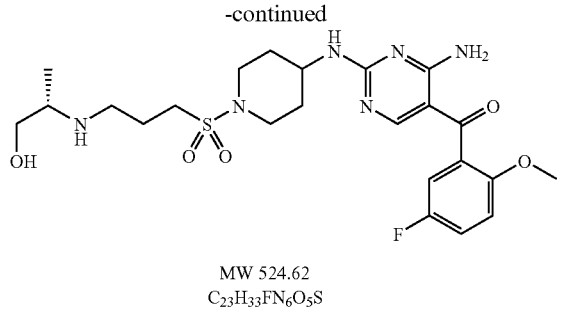

MW 524.62
$C_{23}H_{33}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and (S)-2-amino-1-propanol (Aldrich) in an analogous manner as described in Example 227. HR-MS (ES, m/z) calculated for $C_{23}H_{34}N_6O_5SF$ [(M+H)$^+$] 525.2290, observed 525.2294.

Example 246

(4-Amino-2-[1-[3-((R)-1-hydroxymethyl-propylamino)-propane-1-sulfonyl]-piperidin-4-ylamino]-pyrimidin-5-yl)-(5-fluoro-2-methoxy-phenyl)-methanone

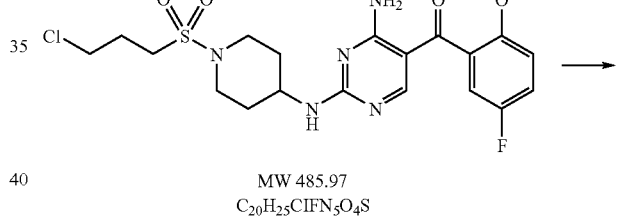

MW 485.97
$C_{20}H_{25}ClFN_5O_4S$

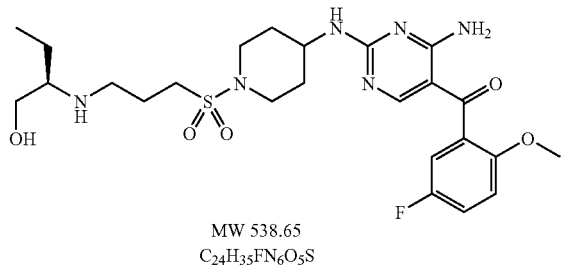

MW 538.65
$C_{24}H_{35}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and (R)-2-amino-1-butanol (Aldrich) in an analogous manner as described in Example 227. HR-MS (ES, m/z) calculated for $C_{24}H_{36}N_6O_5SF$ [(M+H)$^+$] 539.2450, observed 539.2447.

Example 247

(4-Amino-2-[1-[3-(2-hydroxy-propylamino)-propane-1-sulfonyl]-piperidin-4-ylamino]-pyrimidin-5-yl)-(5-fluoro-2-methoxy-phenyl)-methanone

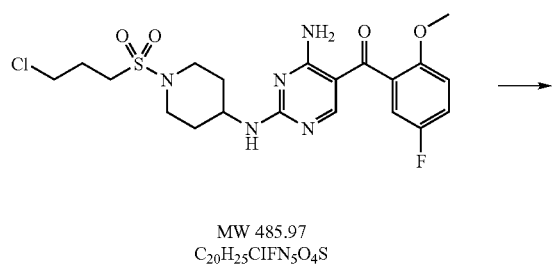

MW 485.97
$C_{20}H_{25}ClFN_5O_4S$

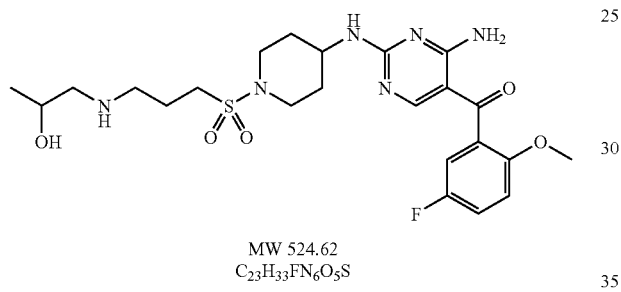

MW 524.62
$C_{23}H_{33}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and 1-amino-2-propanol (Eastman Kodak) in an analogous manner as described in Example 227. HR-MS (ES, m/z) calculated for $C_{23}H_{34}N_6O_5SF$ [(M+H)$^+$] 525.2290, observed 525.2295.

Example 248

(4-Amino-2-[1-[3-((R)-1-hydroxymethyl-2-methyl-propylamino)-propane-1-sulfonyl]-piperidin-4-ylamino]-pyrimidin-5-yl)-(5-fluoro-2-methoxy-phenyl)-methanone

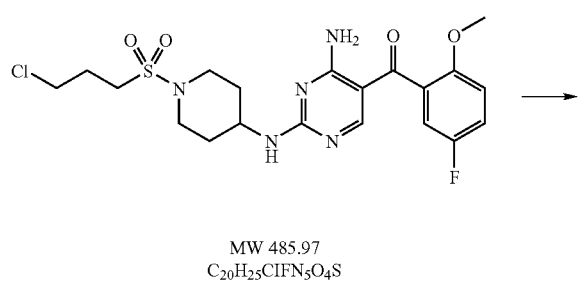

MW 485.97
$C_{20}H_{25}ClFN_5O_4S$

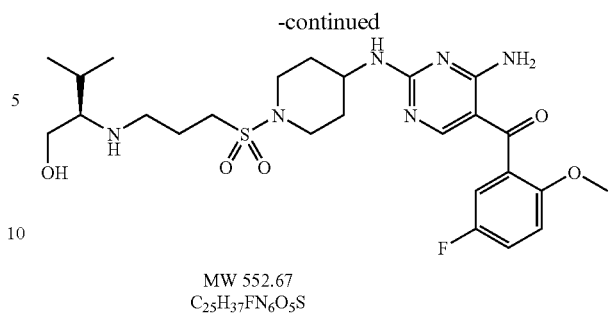

MW 552.67
$C_{25}H_{37}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and (R)-2-amino-3-methyl-1-butanol (Aldrich) in an analogous manner as described in Example 227. HR-MS (ES, m/z) calculated for $C_{25}H_{38}N_6O_5SF$ [(M+H)$^+$] 553.2603, observed 553.2600.

Example 249

(4-Amino-2-[1-[3-(2-methoxy-1-methyl-ethylamino)-propane-1-sulfonyl]-piperidin-4-ylamino]-pyrimidin-5-yl)-(5-fluoro-2-methoxy-phenyl)-methanone

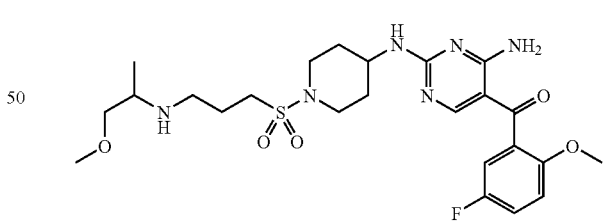

MW 485.97
$C_{20}H_{25}ClFN_5O_4S$

MW 538.65
$C_{24}H_{35}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and 2-amino-1-methoxy-propane (Aldrich) in an analogous manner as described in Example 227. HR-MS (ES, m/z) calculated for $C_{24}H_{36}N_6O_5SF$ [(M+H)$^+$] 539.2447, observed 539.2450.

Example 250

(4-Amino-2-[1-[3-(2-hydroxy-1,1-dimethyl-ethylamino)-propane-1-sulfonyl]-piperidin-4-ylamino]-pyrimidin-5-yl)-(5-fluoro-2-methoxy-phenyl)-methanone

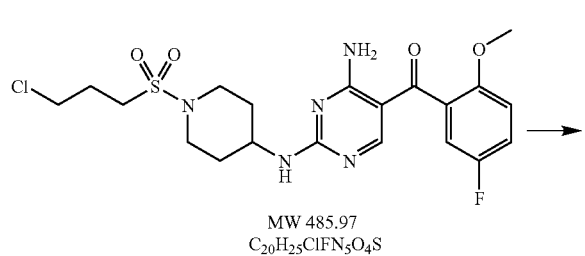

MW 485.97
$C_{20}H_{25}ClFN_5O_4S$

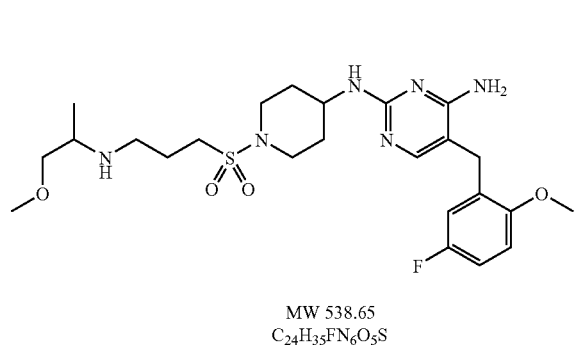

MW 538.65
$C_{24}H_{35}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and 2-amino-2-methyl-1-propanol (Aldrich) in an analogous manner as described in Example 227. HR-MS (ES, m/z) calculated for $C_{24}H_{36}N_6O_5SF$ [(M+H)$^+$] 539.2447, observed 539.2449.

Example 251

(4-Amino-2-[1-[3-((R)-2-hydroxy-1-methyl-ethylamino)-propane-1-sulfonyl]-piperidin-4-ylamino]-pyrimidin-5-yl)-(5-fluoro-2-methoxy-phenyl)-methanone

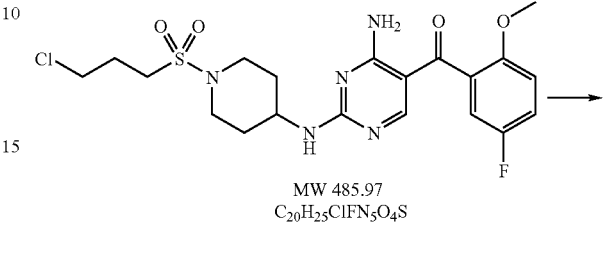

MW 485.97
$C_{20}H_{25}ClFN_5O_4S$

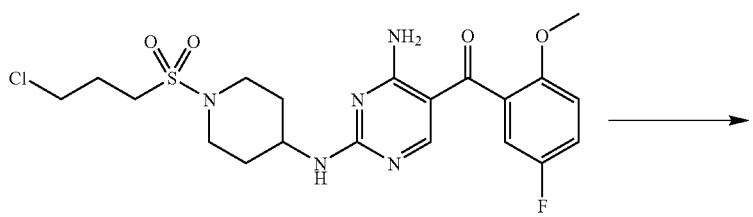

MW 524.62
$C_{23}H_{33}FN_6O_5S$

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 2) and (R)-2-amino-1-propanol (Aldrich) in an analogous manner as described in Example 227. HR-MS (ES, m/z) calculated for $C_{23}H_{34}N_6O_5SF$ [(M+H)$^+$] 525.2290, observed 525.2294.

Example 252

(4-Amino-2-[1-[3-((S)-1-hydroxymethyl-propylamino)-propan-1-sulfonyl]-piperidin-4-ylamino]-pyrimidin-5-yl)-(5-fluoro-2-methoxy-phenyl)-methanone MW 485.97
$C_{20}H_{25}ClFN_5O_4S$

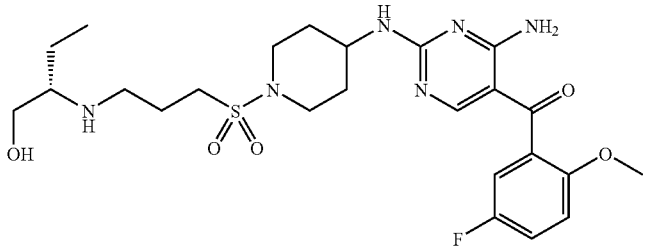

MW 538.65
C$_{24}$H$_{35}$FN$_6$O$_5$S

The compound was prepared from [4-amino-2-[1-(3-chloro-propane-1-sulfonyl)-piperidin-4-ylamino]-pyrimidin-5-yl]-(5-fluoro-2-methoxy-phenyl)-methanone (Example 242) and (S)-2-amino-1-butanol (Aldrich) in an analogous manner as described in Example 227. HR-MS (ES, m/z) calculated for C$_{24}$H$_{36}$N$_6$O$_5$SF [(M+H)$^+$] 539.2447, observed 539.2449.

Example 253

[4-Amino-2-[1-(4-hydroxy-butane-1-sulfonyl)-piperidin-4-ylamino]-pyrimidin-5-yl]-(5-fluoro-2-methoxy-phenyl)-methanone

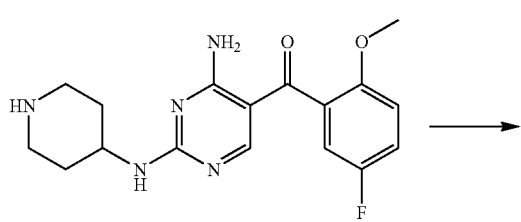

MW 345.38
C$_{17}$H$_{20}$FN$_5$O$_2$

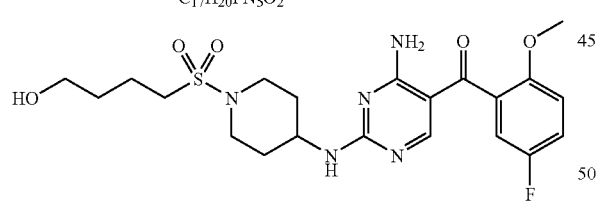

MW 481.55
C$_{21}$H$_{28}$FN$_5$O$_5$S

The mixture of [4-amino-2-(piperidin-4-ylamino)-pyrimidin-5-yl]-(5-fluoro-2-methoxy-phenyl)-methanone (100 mg, 0.290 mmol, Example 59), 1,4-butane sultone (81 uL, 0.870 mmol, Aldrich) and triethylamine (41 uL, 0.290 mmol) in tetrahydrofuran (3 mL) was heated at 150° C. for 1 hour using the Smith Creator microwave synthesizer. Upon cooling to room temperature, the reaction mixture was concentrated. Purification of the crude residue by reverse phase HPLC (C18, eluting with water and acetonitrile) gave [4-amino-2-[1-(4-hydroxy-butane-1-sulfonyl)-piperidin-4-ylamino]-pyrimidin-5-yl]-(5-fluoro-2-methoxy-phenyl)-methanone as white solids (120 mg, 86%). HR-MS (ES, m/z) calculated for C$_{21}$H$_{29}$N$_5$O$_5$SF [(M+H)$^+$] 482. Example 221, observed 482.1874.

Example 254

4-Chloro-butane-1-sulfonyl Chloride

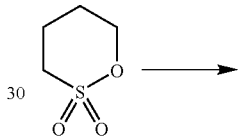

MW 136.17
C$_4$H$_8$O$_3$S

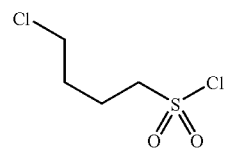

MW 191.08
C$_4$H$_8$Cl$_2$O$_2$S

To a mixture of 1,4-butane sultone (5 g, 36.72 mmol, Aldrich) and thionyl chloride (2.92 mL, 39.66 mmol, Aldrich) was added dimethylformamide (0.2 mL). The reaction mixture was heated at reflux for 4 hours and then concentrated to give 4-chloro-butane-1-sulfonyl chloride as yellow oil. The crude product was used without further purification.

Example 255

[4-Amino-2-[1-(4-chloro-butane-1-sulfonyl)-piperidin-4-ylamino]-pyrimidin-5-yl]-(5-fluoro-2-methoxy-phenyl)-methanone

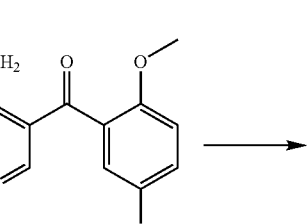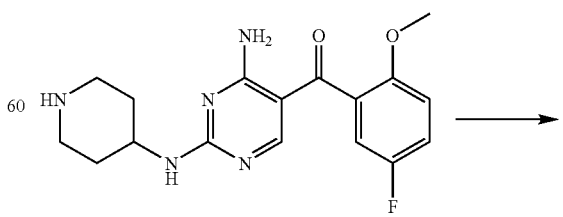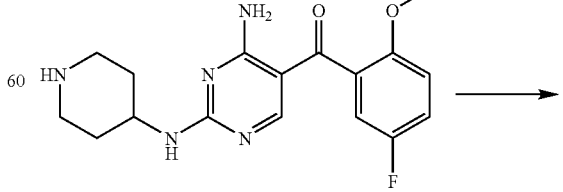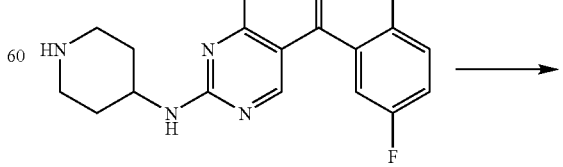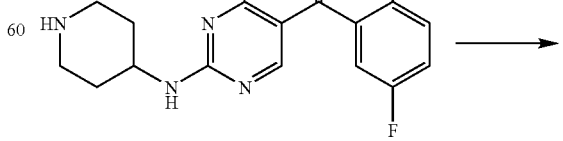

MW 345.38
C$_{17}$H$_{20}$FN$_5$O$_2$

217
-continued

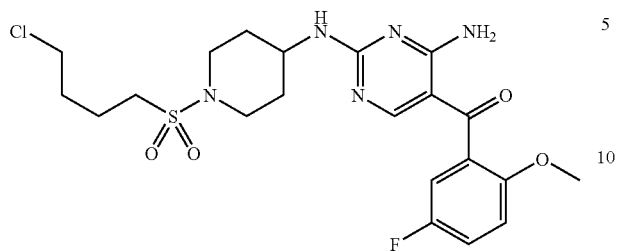

MW 500.00
$C_{21}H_{27}ClFN_5O_4S$

218

The compound was prepared from [4-amino-2-(piperidin-4-ylamino)-pyrimidin-5-yl]-(5-fluoro-2-methoxy-phenyl)-methanone (Example 59) and 4-chloro-butane-1-sulfonyl chloride (Example 254) in an analogous manner as described in Example 177. HR-MS (ES, m/z) calculated for $C_{21}H_{27}N_5O_4SFCl$ [(M+H)$^+$] 500.1532, observed 500.1529.

Example 256

(4-Amino-2-[1-[4-(4-methyl-piperazin-1-yl)-butane-1-sulfonyl]-piperidin-4-ylamino]-pyrimidin-5-yl)-(5-fluoro-2-methoxy-phenyl)-methanone

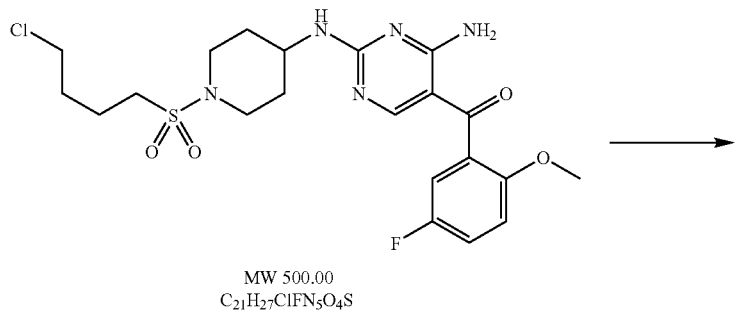

MW 500.00
$C_{21}H_{27}ClFN_5O_4S$

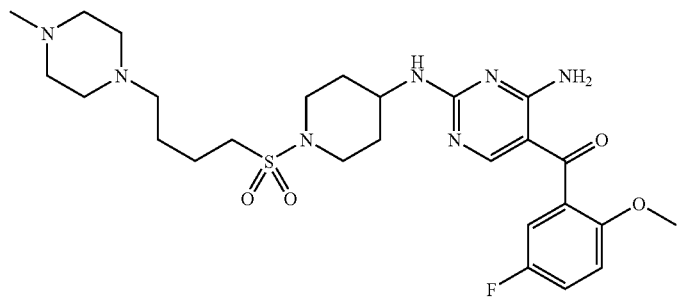

MW 563.70
$C_{26}H_{38}FN_7O_4S$

The compound was prepared from [4-amino-2-[1-(4-chloro-butane-1-sulfonyl)-piperidin-4-ylamino]-pyrimidin-5-yl]-(5-fluoro-2-methoxy-phenyl)-methanone (Example 255) and 1-methyl-piperazine (Aldrich) in an analogous manner as described in Example 227. HR-MS (ES, m/z) calculated for $C_{26}H_{39}N_7O_4SF$ [(M+H)$^+$] 564.2767, observed 564.2763.

Example 257

[4-Amino-2-[1-(4-pyrrolidin-1-yl-butane-1-sulfonyl)-piperidin-4-ylamino]-pyrimidin-5-yl]-(5-fluoro-2-methoxy-phenyl)-methanone

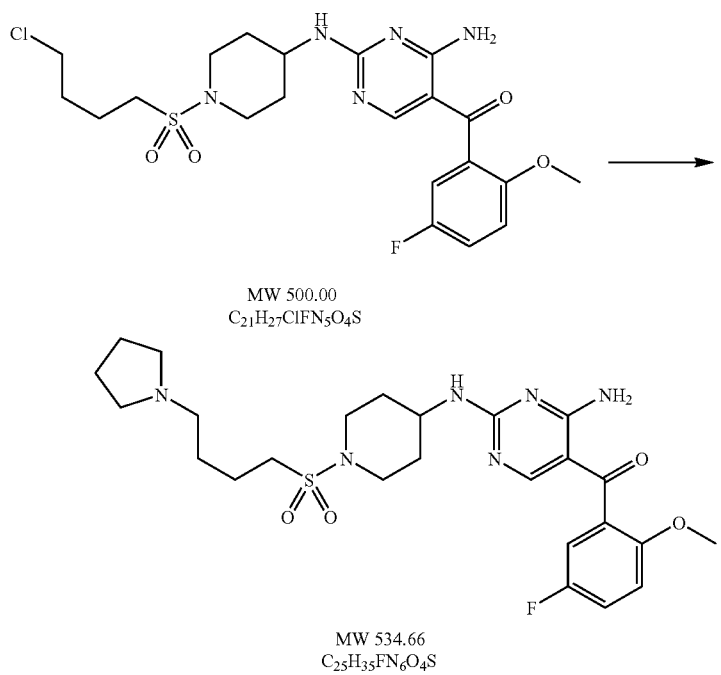

MW 500.00
$C_{21}H_{27}ClFN_5O_4S$

MW 534.66
$C_{25}H_{35}FN_6O_4S$

The compound was prepared from [4-amino-2-[1-(4-chloro-butane-1-sulfonyl)-piperidin-4-ylamino]-pyrimidin-5-yl]-(5-fluoro-2-methoxy-phenyl)-methanone (Example 255) and pyrrolidine (Aldrich) in an analogous manner as described in Example 227. HR-MS (ES, m/z) calculated for $C_{25}H_{36}N_6O_4SF$ [(M+H)$^+$] 535.2500, observed 535.2498.

Example 258

(4-Amino-2-[1-[4-(2-hydroxy-propylamino)-butane-1-sulfonyl]-piperidin-4-ylamino]-pyrimidin-5-yl)-(5-fluoro-2-methoxy-phenyl)-methanone

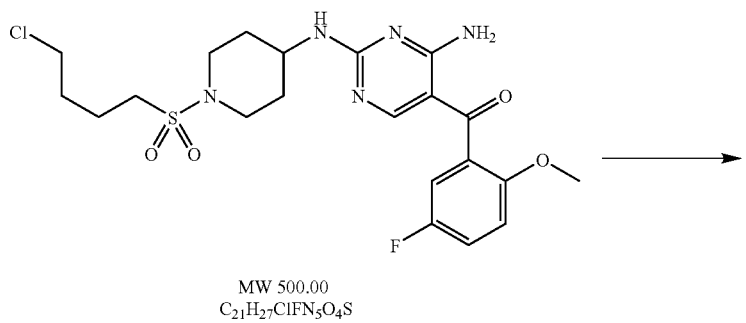

MW 500.00
$C_{21}H_{27}ClFN_5O_4S$

-continued

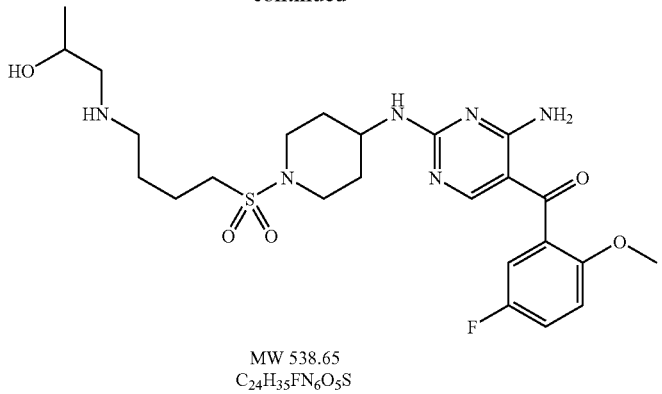

MW 538.65
$C_{24}H_{35}FN_6O_5S$

The compound was prepared from [4-amino-2-[1-(4-chloro-butane-1-sulfonyl)-255) and 1-amino-2-propanol (Eastman Kodak) in an analogous manner as described in Example 227. HR-MS (ES, m/z) calculated for $C_{24}H_{35}N_6O_5SF$ $[(M+H)^+]$ 539.2451, observed 539.2447.

Example 259

(4-Amino-2-methylsulfanyl-pyrimidin-5-yl)-(2,3-difluoro-5,6-dimethoxy-phenyl)-methanone

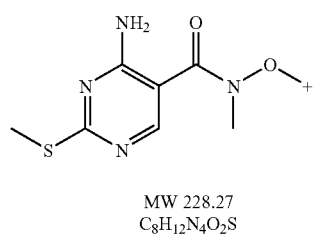

MW 228.27
$C_8H_{12}N_4O_2S$

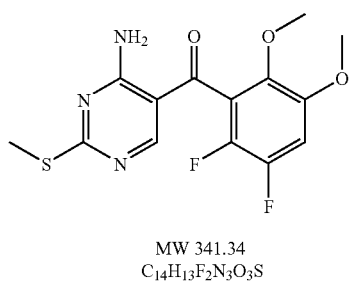

MW 174.15
$C_8H_8F_2O_2$

MW 341.34
$C_{14}H_{13}F_2N_3O_3S$

The compound was prepared from 4-amino-2-methylsulfanyl-pyrimidine-5-carboxylic acid methoxy-methyl-amide (Example 168) and 1,2-difluoro-4,5-dimethoxy-benzene (Aldrich) in an analogous manner as described in Example 169. HR-MS (ES, m/z) calculated for $C_{14}H_{14}N_3O_3SF_2$ $(M^+)$ 341.0646, observed 341.0644.

Example 260

(4-Amino-2-methylsulfinyl-pyrimidin-5-yl)-(2,3-difluoro-5,6-dimethoxy-phenyl)-methanone

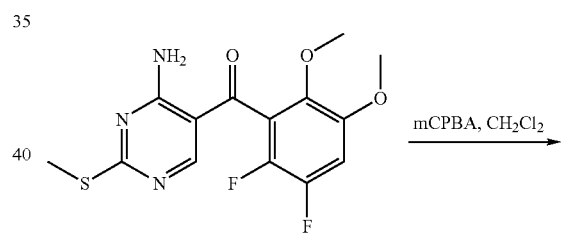

MW 341.34
$C_{14}H_{13}F_2N_3O_3S$

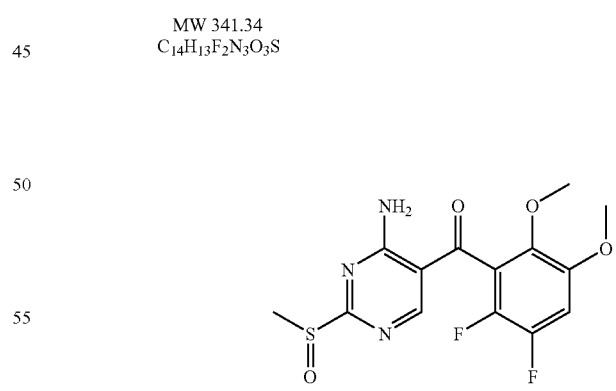

MW 357.34
$C_{14}H_{13}F_2N_3O_4S$

The compound was prepared from (4-amino-2-methylsulfanyl-pyrimidin-5-yl)-(2,3-difluoro-5,6-dimethoxy-phenyl)-methanone (Example 259) in an analogous manner as described in Example 163. The crude product was used without further purification.

Example 261

[4-Amino-2-(1-methanesulfonyl-piperidin-4-ylamino)-pyrimidin-5-yl]-(2,3-difluoro-5,6-dimethoxy-phenyl)-methanone

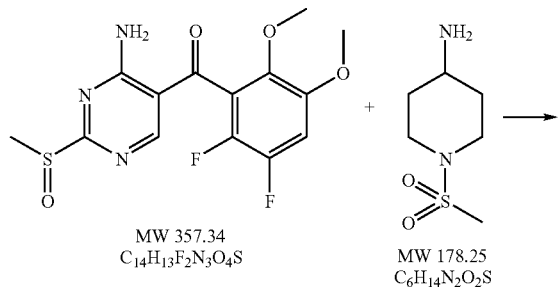

MW 357.34
C$_{14}$H$_{13}$F$_2$N$_3$O$_4$S

MW 178.25
C$_6$H$_{14}$N$_2$O$_2$S

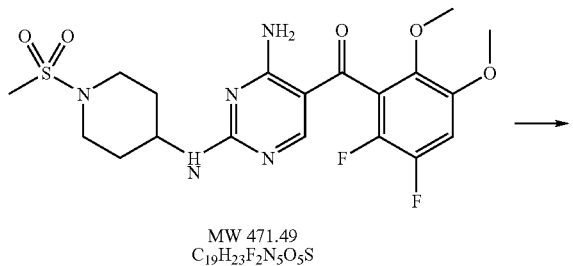

MW 471.49
C$_{19}$H$_{23}$F$_2$N$_5$O$_5$S

The compound was prepared from (4-amino-2-methylsulfinyl-pyrimidin-5-yl)-(2,3-difluoro-5,6-dimethoxy-phenyl)-methanone (Example 260) and 1-methanesulfonyl-piperidin-4-ylamine; compound with trifluoroacetic acid (Example 162) in an analogous manner as described in Example 172. HR-MS (ES, m/z) calculated for C$_{19}$H$_{24}$N$_5$O$_5$SF [(M+H)$^+$] 472.1465, observed 472.1461.

Example 262

[4-Amino-2-(1-methanesulfonyl-piperidin-4-ylamino)-pyrimidin-5-yl]-(2,3-difluoro-6-hydroxy-5-methoxy-phenyl)-methanone

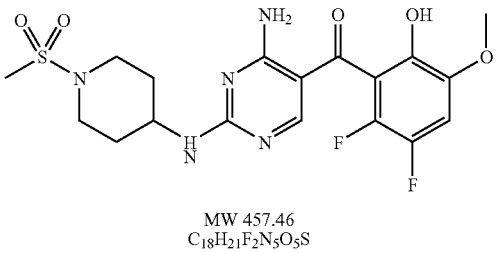

MW 471.49
C$_{19}$H$_{23}$F$_2$N$_5$O$_5$S

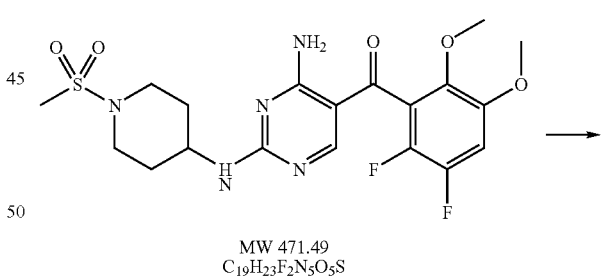

MW 457.46
C$_{18}$H$_{21}$F$_2$N$_5$O$_5$S

To a solution of [4-amino-2-(1-methanesulfonyl-piperidin-4-ylamino)-pyrimidin-5-yl]-(2,3-difluoro-5,6-dimethoxy-phenyl)-methanone (30 mg, 0.0636 mmol, Example 261) in methylene chloride (20 mL) cooled to 5° C. was added aluminum chloride (129 mg, 0.954 mmol, Fluka). The reaction mixture was stirred at room temperature for 24 hours and quenched with water. Tetrahydrofuran (40 mL) was added and the layers were separated. The organic layer was washed with water (1×5 mL), brine (1×5 mL) and dried over anhydrous sodium sulfate. The solids were filtered off and the filtrate was concentrated in vacuo. Purification of the crude residue by flash chromatography (Biotage system, 60 Å silica gel, eluting with ethyl acetate) yielded [4-amino-2-(1-methanesulfonyl-piperidin-4-ylamino)-pyrimidin-5-yl]-(2,3-difluoro-6-hydroxy-5-methoxy-phenyl)-methanone as yellow solids (15 mg, 52%). HR-MS (ES, m/z) calculated for C$_{18}$H$_{22}$N$_5$O$_5$SF2 [(M+H)$^+$] 458.1307, observed 458.1304.

Example 263

[4-Amino-2-(1-methanesulfonyl-piperidin-4-ylamino)-pyrimidin-5-yl]-(2,3-difluoro-5,6-dihydroxy-phenyl)-methanone

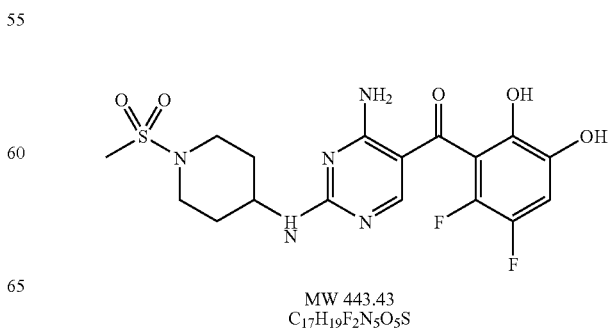

MW 471.49
C$_{19}$H$_{23}$F$_2$N$_5$O$_5$S

MW 443.43
C$_{17}$H$_{19}$F$_2$N$_5$O$_5$S

To a solution of [4-amino-2-(1-methanesulfonyl-piperidin-4-ylamino)-pyrimidin-5-yl]-(2,3-difluoro-5,6-dimethoxy-phenyl)-methanone (100 mg, 0.212 mmol, Example 261) in methylene chloride (50 mL) cooled to −78° C. was added boron tribromide (2.19 mL, 2.190 mmol, 1 M solution in methylene chloride, Aldrich). The reaction mixture was warmed slowly to 0° C. over a period of 1 hour. After being stirred at 0° C. for 1 hour, the reaction was quenched with a solution of aqueous sodium bicarbonate. The aqueous layer was extracted with methylene chloride. The combined layers were washed with water and dried over anhydrous sodium sulfate. The solids were filtered off and the filtrate was concentrated in vacuo. Purification of the crude residue by reversed phase HPLC (C18, eluting with water and acetonitrile) yielded [4-amino-2-(1-methanesulfonyl-piperidin-4-ylamino)-pyrimidin-5-yl]-(2,3-difluoro-5,6-dihydroxy-phenyl)-methanone as yellow solids (50 mg, 52%). HR-MS (ES, m/z) calculated for $C_{17}H_{20}N_5O_5SF_2$ [(M+H)$^+$] 444.1151, observed 444.1148.

Example 264

4,5-Difluoro-2-methoxy-phenol

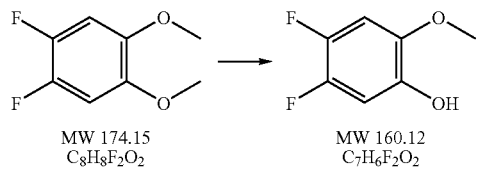

MW 174.15
$C_8H_8F_2O_2$

MW 160.12
$C_7H_6F_2O_2$

To a solution of 1,2-difluoro-4,5-dimethoxybenzene (5 g, 28.71 mmol, Aldrich) in methylene chloride (300 mL) cooled to 0° C. was added aluminum chloride (14.16 g, 106.2 mmol, Fluka) in several portions. At the end of the addition, the ice bath was removed and the reaction mixture was stirred at room temperature for 12 hours. Water was added to quench the reaction. Diethyl ether (200 mL) was added and the layers were separated. The aqueous layer was extracted with diethyl ether (50 mL). The combined organic layers were washed with water, brine and dried over anhydrous magnesium sulfate. The solids were filtered off and the filtrate was concentrated in vacuo. Purification of the crude residue by flash chromatography (Biotage system, 60 Å silica gel, eluting with 10% ethyl acetate in hexanes) yielded 4,5-difluoro-2-methoxy-phenol as dark oil (3.75 g, 82%).

Example 265 tert-Butyl-(4,5-difluoro-2-methoxy-phenoxy)-dimethyl-silane

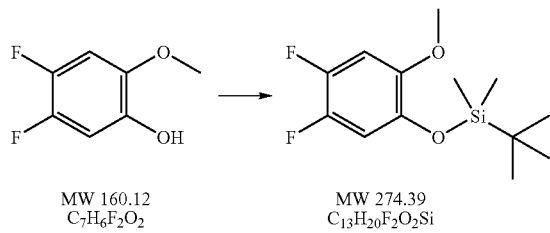

MW 160.12
$C_7H_6F_2O_2$

MW 274.39
$C_{13}H_{20}F_2O_2Si$

To a solution of 4,5-difluoro-2-methoxy-phenol (3.75 g, 23.42 mmol, Example 264) in methylene chloride (60 mL) cooled to 0° C. were added N,N-diisopropylethylamine (4.895 mL, 28.10 mmol), tert-butyldimethylsilyl chloride (4.367 g, 28.10 mmol, Aldrich), and dimethylaminopyridine (286 mg, 2.342 mmol, Aldrich). At the end of addition, the ice bath was removed and the reaction mixture was stirred at room temperature for 90 minutes. Water (30 mL) was added and the layers were separated. The aqueous layer was extracted with methylene chloride (20 mL). The combined organic layers were washed with brine and dried over anhydrous magnesium sulfate. The solids were filtered off and the filtrate was concentrated in vacuo. Purification of the crude residue by flash chromatography (Biotage system, 60 Å silica gel, eluting with 3% ethyl acetate in hexanes) yielded tert-butyl-(4,5-difluoro-2-methoxy-phenoxy)-dimethyl. silane as a clear oil (5.22 g, 81%).

Example 266

3-(tert-Butyl-dimethyl-silanyloxy)-5,6-difluoro-2-methoxy-benzaldehyde

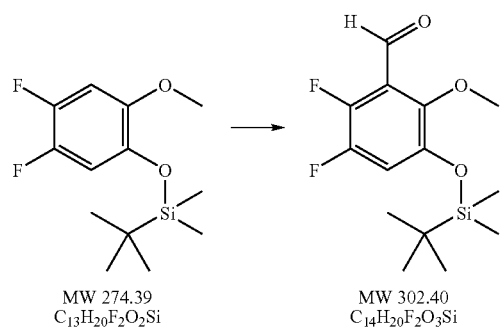

MW 274.39
$C_{13}H_{20}F_2O_2Si$

MW 302.40
$C_{14}H_{20}F_2O_3Si$

To a solution of tert-butyl-(4,5-difluoro-2-methoxy-phenoxy)-dimethyl-silane (5.2 g, 18.95 mmol) in tetrahydrofuran (60 mL) cooled to −78° C. was added n-butyllithium (9.096 mL, 22.74 mmol) dropwise over a period of 15 minutes. At the end of the addition, the reaction mixture was stirred at −78° C. for 1 hour. Dimethylformamide (1.737 mL, 22.74 mmol) was added and the reaction mixture was stirred at −78° C. for 2 hours. Saturated solution of ammonium chloride (~5 mL) was added, and then the mixture was diluted with 100 mL of water. The aqueous layer was extracted with ethyl acetate (2×75 mL). The combined organic layers were washed with brine and dried over anhydrous magnesium sulfate. The solids were filtered off and the filtrate was concentrated in vacuo. Purification of the crude residue by flash chromatography (Biotage system, 60 Å silica gel, eluting with 4% ethyl acetate in hexanes) yielded 3-(tert-butyl-dimethyl-silanyloxy)-5,6-difluoro-2-methoxy-benzaldehyde as clear oil (3.96 g, 69%). LR-MS (M$^+$) 302.2.

Example 267

[3-(tert-Butyl-dimethyl-silanyloxy)-5,6-difluoro-2-methoxy-phenyl]-(2,4-dichloro-pyrimidin-5-yl)-methanol

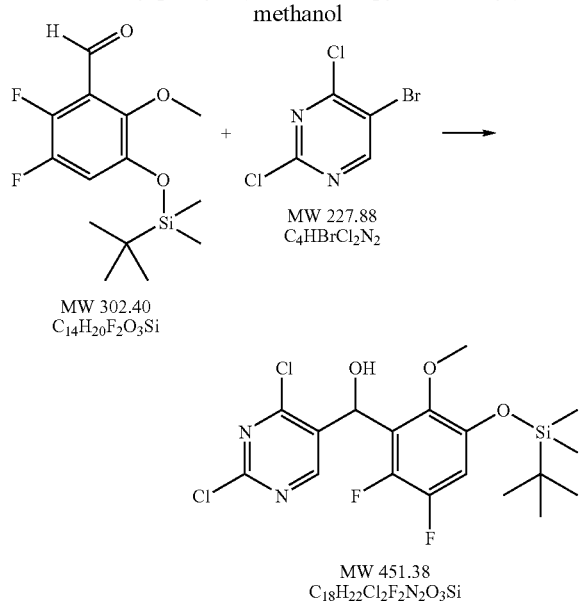

MW 302.40
C$_{14}$H$_{20}$F$_2$O$_3$Si

MW 227.88
C$_4$HBrCl$_2$N$_2$

MW 451.38
C$_{18}$H$_{22}$Cl$_2$F$_2$N$_2$O$_3$Si

To a solution of 5-bromo-2,4-dichloropyrimidine (753.6 mg, 3.307 mmol, Matrix Chemicals) in tetrahydrofuran (20 mL) cooled to −30° C. was added dropwise isopropylmagnesium chloride. The temperature was maintained below −25° C. throughout the addition. At the end of addition, the reaction mixture was stirred at −30° C. for 20 minutes and a solution of 3-(tert-butyl-dimethyl-silanyloxy)-5,6-difluoro-2-methoxy-benzaldehyde (1 g, 3.307 mmol, Example 266) in tetrahydrofuran was added dropwise. The temperature was maintained below −25° C. throughout the addition. The reaction mixture was allowed to warm up to 0° C. after the addition was completed. After being stirred at 0° C. for 45 minutes, saturated solution of ammonium chloride (−3 mL) was added. The mixture was taken up in water and ethyl acetate. The aqueous layer was extracted with ethyl acetate. The combined organic layers were washed with brine and dried over anhydrous magnesium sulfate. The solids were filtered off and the filtrate was concentrated in vacuo. Purification of the crude residue by flash chromatography (Biotage system, 60 Å silica gel, eluting with 5–10% ethyl acetate in hexanes) yielded [3-(tert-butyl-dimethyl-silanyloxy)-5,6-difluoro-2-methoxy-phenyl]-(2,4-dichloro-pyrimidin-5-yl)-methanol as white solids (965 mg, 65%). LR-MS (M+) 451.1.

Example 268

[3-(tert-Butyl-dimethyl-silanyloxy)-5,6-difluoro-2-methoxy-phenyl]-(2,4-dichloro-pyrimidin-5-yl)-methanone

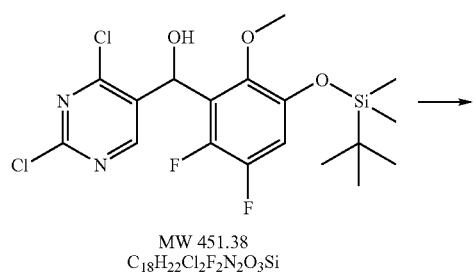

MW 451.38
C$_{18}$H$_{22}$Cl$_2$F$_2$N$_2$O$_3$Si

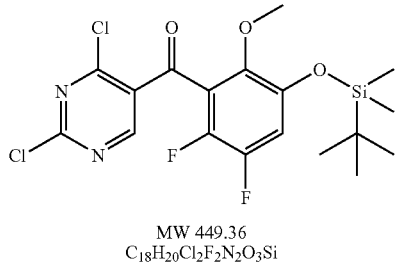

MW 449.36
C$_{18}$H$_{20}$Cl$_2$F$_2$N$_2$O$_3$Si

To a solution of [3-(tert-butyl-dimethyl-silanyloxy)-5,6-difluoro-2-methoxy-phenyl]-(2,4-dichloro-pyrimidin-5-yl)-methanol (955 mg, 2.116 mmol, Example 267) in methylene chloride (6 mL) and water (1 mL) were added sodium bicarbonate (80 mg, 0.952 mmol), tetrabutylammonium bromide (21 mg, 0.0635 mmol), TEMPO (3.3 mg, 0.0212 mmol, Aldrich). The mixture was cooled to 0° C. and sodium hypochlorite (2.548 mL, 2.539 mmol, Clorox™) was added. The reaction mixture was stirred at 0° C. for 30 minutes and more sodium hypochlorite (0.5 mL) was added. Thin layer chromatography (silica gel, 10% ethyl acetate in hexanes) still showed the alcohol starting material. More sodium hypochlorite (3×0.5 mL) was added until no alcohol was seen. The reaction mixture was diluted with methylene chloride (30 mL) and water (20 mL). The layers were separated, and the organic phase was washed with water (2×10 mL), brine (1×10 mL) and dried over anhydrous magnesium sulfate. The solids were filtered off and the filtrate was concentrated in vacuo to give [3-(tert-butyl-dimethyl-silanyloxy)-5,6-difluoro-2-methoxy-phenyl]-(2,4-dichloro-pyrimidin-5-yl)-methanone as pale yellow oil (910 mg, 96%). The crude product was used without further purification.

Example 269

(4-Amino-2-chloro-pyrimidin-5-yl)-[3-(tert-butyl-dimethyl-silanyloxy)-5,6-difluoro-2-methoxy-phenyl]-methanone

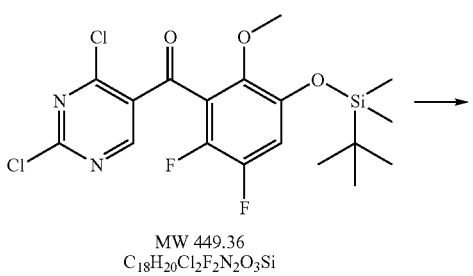

MW 449.36
C$_{18}$H$_{20}$Cl$_2$F$_2$N$_2$O$_3$Si

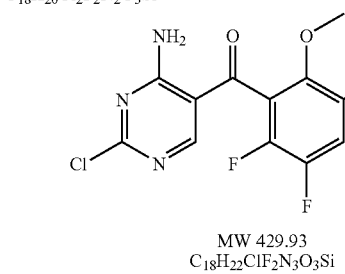

MW 429.93
C$_{18}$H$_{22}$ClF$_2$N$_3$O$_3$Si

Ammonia gas was bubbled through a solution of [3-(tert-butyl-dimethyl-silanyloxy)-5,6-difluoro-2-methoxy-phenyl]-(2,4-dichloro-pyrimidin-5-yl)-methanone (900 mg, 2.003 mmol, Example 268) in toluene (10 mL) for about 30 minutes. The reaction mixture was concentrated to dryness to give (4-amino-2-chloro-pyrimidin-5-yl)-[3-(tert-butyl-dimethyl-silanyloxy)-5,6-difluoro-2-methoxy-phenyl]-methanone (1.02 g, yellow gum). The crude product was used without further purification.

Example 270

[4-Amino-2-(1-methanesulfonyl-piperidin-4-ylamino)-pyrimidin-5-yl]-[3-(tert-butyl-dimethyl-silanyloxy)-5,6-difluoro-2-methoxy-phenyl]-methanone

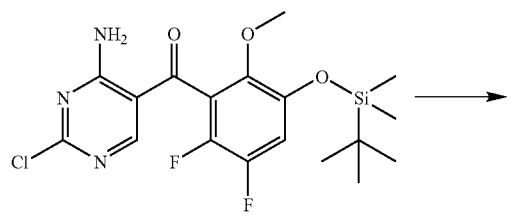

MW 429.93
$C_{18}H_{22}ClF_2N_3O_3Si$

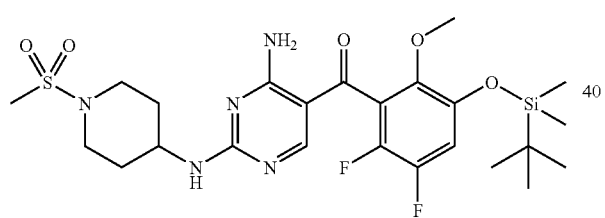

MW 571.72
$C_{24}H_{35}F_2N_5O_5SSi$

To a solution of (4-amino-2-chloro-pyrimidin-5-yl)-[3-(tert-butyl-dimethyl-silanyloxy)-5,6-difluoro-2-methoxy-phenyl]-methanone (860 mg, 2.0 mmol, Example 269) in ethanol (12 mL) was added 1-methanesulfonyl-piperidin-4-ylamine trifluoroacetate salt (613.8 mg, 2.1 mmol, Example 162) and diisopropylethylamine (1.2 mL, 6.889 mmol). The mixture was heated at reflux for 4 hours and then concentrated to dryness. The residue was dissolved in ethyl acetate (20 mL). The solution was washed with brine (1×10 mL) and dried over anhydrous magnesium sulfate. The solids were filtered off and the filtrate was concentrated in vacuo. Purification of the crude residue by flash chromatography (Biotage system, 60 Å silica gel, eluting with 45–60% ethyl acetate in hexanes) yielded [4-amino-2-(1-methanesulfonyl-piperidin-4-ylamino)-pyrimidin-5-yl]-[3-(tert-butyl-dimethyl-silanyloxy)-5,6-difluoro-2-methoxy-phenyl]-methanone as white glass (684 mg, 60%). LR-MS ($M^+$) 572.1.

Example 271

[4-Amino-2-(1-methanesulfonyl-piperidin-4-ylamino)-pyrimidin-5-yl]-(2,3-difluoro-5-hydroxy-6-methoxy-phenyl)-methanone

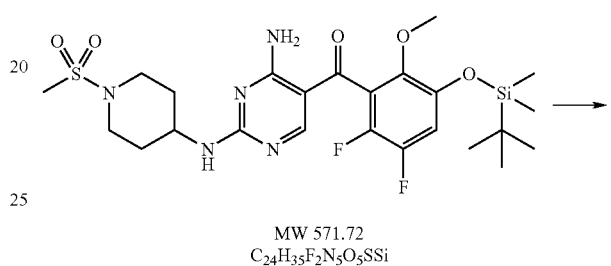

MW 571.72
$C_{24}H_{35}F_2N_5O_5SSi$

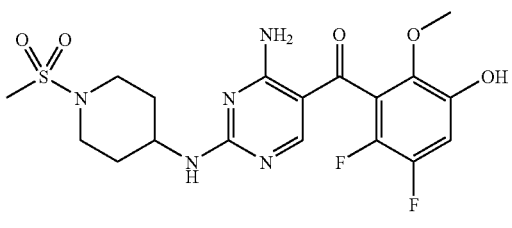

MW 457.46
$C_{18}H_{21}F_2N_5O_5S$

To a solution of [4-amino-2-(1-methanesulfonyl-piperidin-4-ylamino)-pyrimidin-5-yl]-[3-(tert-butyl-dimethyl-silanyloxy)-5,6-difluoro-2-methoxy-phenyl]-methanone (675 mg, 1.181 mmol, Example 270) in tetrahydrofuran (10 mL) was added tetrabutylammonium fluoride (1.240 mL, 1.24 mmol, 1 M solution in tetrahydrofuran, Aldrich). The mixture was stirred at room temperature for 15 minutes and then concentrated to dryness. The residue was taken up in methylene chloride and washed with saturated solution of sodium bicarbonate. The organic layer was dried over anhydrous magnesium sulfate. The solids were filtered off and the filtrate was concentrated in vacuo. Purification of the crude residue by flash chromatography (Biotage system, 60 Å silica gel, eluting with 65–80% ethyl acetate in hexanes then 5% methanol in ethyl acetate) yielded [4-amino-2-(1-methanesulfonyl-piperidin-4-ylamino)-pyrimidin-5-yl]-(2,3-difluoro-5-hydroxy-6-methoxy-phenyl)-methanone as white solids (315 mg, 58%). HR-MS (ES, m/z) calculated for $C_{18}H_{22}N_5O_5SF_2$ $[(M+H)^+]$ 458.1308, observed 458.1304.

Example 272

[4-Amino-2-[1-(3-chloro-propane-1-sulfonyl)-piperidin-4-ylamino]-pyrimidin-5-yl]-(5-fluoro-2-methoxy-phenyl)-methanone

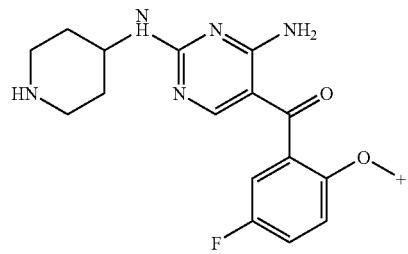

MW 345.38
C₁₇H₂₀FN₅O₂

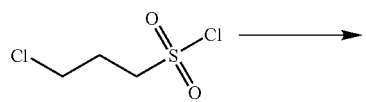

MW 177.05
C₃H₆Cl₂O₂S

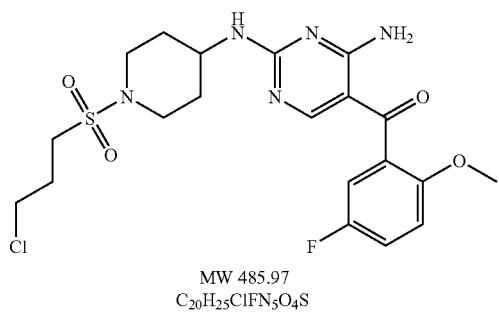

MW 485.97
C₂₀H₂₅ClFN₅O₄S

A solution of [4-amino-2-(piperidin-4-ylamino)-pyrimidin-5-yl]-(5-fluoro-2-methoxy-phenyl)-methanone (290 mg, 0.72 mmol, Example 59 and 3-chloropropanesulfonyl chloride (165 mg, 0.93 mmol, Aldrich) was treated with diisopropylethyl amine (102 mg, 102 mmol, Aldrich) in methylene chloride (200 mL). This was stirred for 1 hour at 5° C. The reaction was washed with 5% aqueous sodium bicarbonate, dried (MgSO₄), and the solvent concentrated in vacuum. This solid was dissolved in tetrahydrofuran, filtered through celite, reduced in volume and triturated with ether to give 300 mg (82%) of [4-amino-2-[1-(3-chloro-propane-1-sulfonyl)-piperidin-4-ylamino]-pyrimidin-5-yl]-(5-fluoro-2-methoxy-phenyl)-methanone as a white solid. HRMS, observed: 486.1375; Calcd for (M+H)⁺: 486.1373

Example 273

[4-Amino-2-[1-(3-pyrrolidin-1-yl-propane-1-sulfonyl)-piperidin-4-ylamino]-pyrimidin-5-yl]-(5-fluoro-2-methoxy-phenyl)-methanone

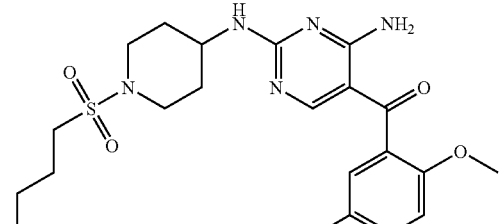

MW 485.97
C₂₀H₂₅ClFN₅O₄S

-continued

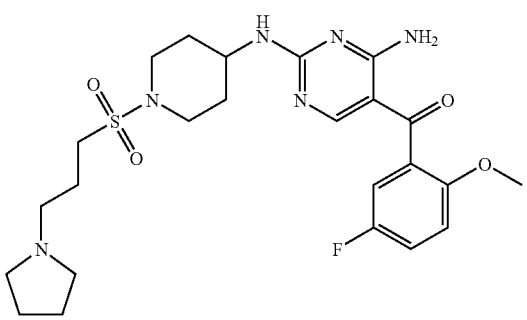

MW 520.63
C₂₄H₃₃FN₆O₄S

A suspension of [4-amino-2-[1-(3-chloro-propane-1-sulfonyl)-piperidin-4-ylamino]-pyrimidin-5-yl]-(5-fluoro-2-methoxy-phenyl)-methanone (25 mg, 0.051 mmol, Example 272), potassium iodide (30 mg, 0.18 mmol), and pyrollidine (400 mg, 5.6 mmol) in dioxane (8 mL) was heated at 90° C. under nitrogen for 14 hours. The resulting solution was concentrated to ~1 mL and triturated with water. Solids were filtered and dissolved in methylene chloride. After washing with water, the organic layer was separated and dried (Na₂SO₄). The product was purified by trituration with tetrahydrofuran/ethyl ether and filtered to give [4-amino-2-[1-(3-pyrrolidin-1-yl-propane-1-sulfonyl)-piperidin-4-ylamino]-pyrimidin-5-yl]-(5-fluoro-2-methoxy-phenyl)-methanone as a white solid (12 mg, 40% yield). HRMS, observed: 521.2343; Calcd for (M+H)⁺: 521.2341

Example 274

Acetic acid 3-[4-[4-amino-5-(5-fluoro-2-methoxy-benzoyl)-pyrimidin-2-ylamino]-piperidine-1-sulfonyl]-propyl ester

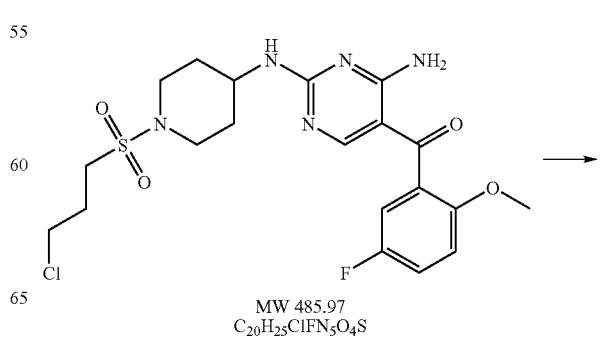

MW 485.97
C₂₀H₂₅ClFN₅O₄S

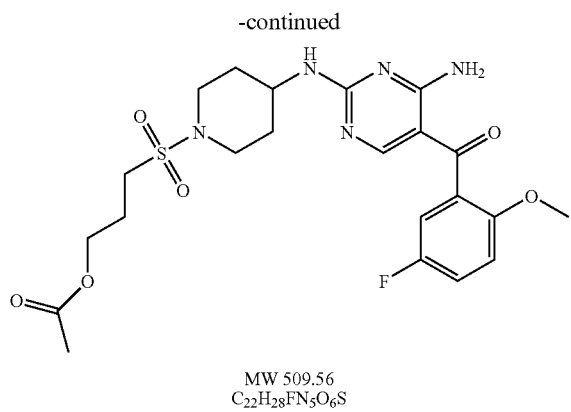

MW 509.56
$C_{22}H_{28}FN_5O_6S$

A suspension of [4-amino-2-[1-(3-chloro-propane-1-sulfonyl)-piperidin-4-ylamino]-pyrimidin-5-yl]-(5-fluoro-2-methoxy-phenyl)-methanone (80 mg, 0.16 mmol, Example 273), potassium iodide (100 mg, 0.61 mmol), and potassium acetate (120 mg, 1.22 mmol) in dimethylformamide (6 mL) was heated at 65–85° C. under nitrogen for 14 hours. The resulting solution was diluted with 50 mL of cold water plus 20 mL of saturated aqueous sodium chloride. Solids were filtered, collected and dissolved in methylene chloride. After washing with water, the organic layer was separated and dried ($Na_2SO_4$). The residue was purified by silica gel chromatography (ethyl acetate/hexane) and crystallized from methylene chloride/ethyl ether to give acetic acid 3-[4-[4-amino-5-(5-fluoro-2-methoxy-benzoyl)-pyrimidin-2-ylamino]-piperidine-1-sulfonyl]-propyl ester as a white solid (42 mg, 51% yield). HRMS, observed: 510.1822; Calcd for $(M+H)^+$: 510.1817

Example 275

[4-Amino-2-[1-(3-hydroxy-propane-1-sulfonyl)-piperidin-4-ylamino]-pyrimidin-5-yl]-(5-fluoro-2-methoxy-phenyl)-methanone

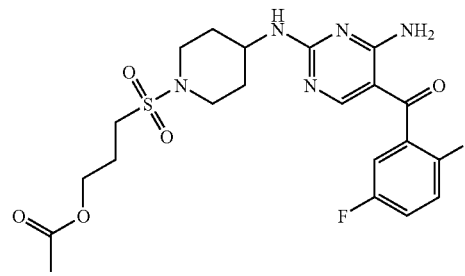

MW 509.56
$C_{22}H_{28}ClFN_5O_6S$

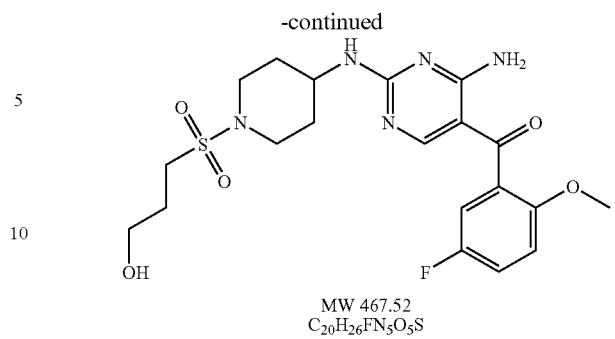

MW 467.52
$C_{20}H_{26}FN_5O_5S$

A suspension of acetic acid 3-[4-[4-amino-5-(5-fluoro-2-methoxy-benzoyl)-pyrimidin-2-ylamino]-piperidine-1-sulfonyl]-propyl ester (25 mg, 0.049 mmol, Example 274) in a solution of potassium hydroxide (50 mg, 0.9 mmol), water (1 mL) and ethanol (6 mL) was stirred at 25° C. for 1 hour. The solution was cooled, acidified with acetic acid and reduced in volume to 2 mL. This was diluted with water and the product extracted into methylene chloride. After washing with water, the organic layer was separated and dried ($Na_2SO_4$). The residue was purified by silica gel chromatography (ethyl acetate) and crystallized from methylene chloride/hexane to give [4-amino-2-[1-(3-hydroxy-propane-1-sulfonyl)-piperidin-4-ylamino]-pyrimidin-5-yl]-(5-fluoro-2-methoxy-phenyl)-methanone as a white solid (12 mg, 50% yield). HRMS, observed: 468.1716; Calcd for $(M+H)^+$: 468.1712

Example 276

[4-Amino-2-[1-(3-morpholin-4-yl-propane-1-sulfonyl)-piperidin-4-ylamino]-pyrimidin-5-yl]-(5-fluoro-2-methoxy-phenyl)-methanone

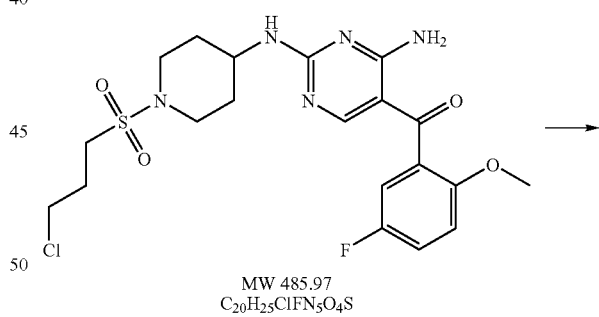

MW 485.97
$C_{20}H_{25}ClFN_5O_4S$

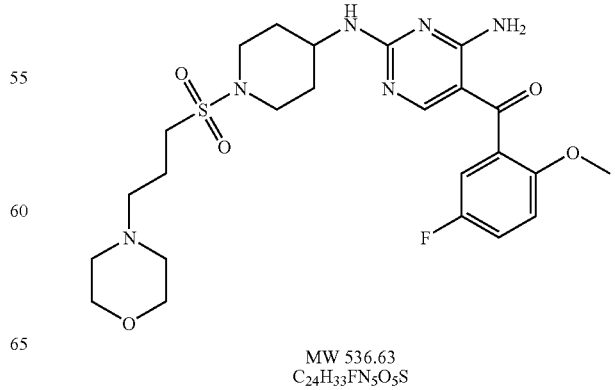

MW 536.63
$C_{24}H_{33}FN_5O_5S$

A suspension of [4-amino-2-[1-(3-chloro-propane-1-sulfonyl)-piperidin-4-ylamino]-pyrimidin-5-yl]-(5-fluoro-2-methoxy-phenyl)-methanone (80 mg, 0.16 mmol, Example 272), potassium iodide (200 mg, 1.2 mmol), morpholine (200 mg, 4.3 mmol) in dioxane (12 mL) was heated at reflux under nitrogen for 48 hours. The resulting solution was diluted with 20 mL of cold water plus 20 mL of saturated aqueous sodium chloride. Solids were filtered and dissolved in methylene chloride. The organic layer was separated and dried (Na$_2$SO$_4$). The residue was purified by silica gel chromatography (triethylamine/methanol/methylene chloride 1:10:90) and crystallized from methylene chloride/hexane to give [4-amino-2-[1-(3-morpholin-4-yl-propane-1-sulfonyl)-piperidin-4-ylamino]-pyrimidin-5-yl]-(5-fluoro-2-methoxy-phenyl)-methanone as a white solid (15 mg, 17% yield). HRMS, observed: 537.2296; Calcd for (M+H)$^+$: 537.2290

Example 277

N-(3-[4-[4-Amino-5-(5-fluoro-2-methoxy-benzoyl)-pyrimidin-2-ylamino]-piperidine-1-sulfonyl]-propyl)-methanesulfonamide

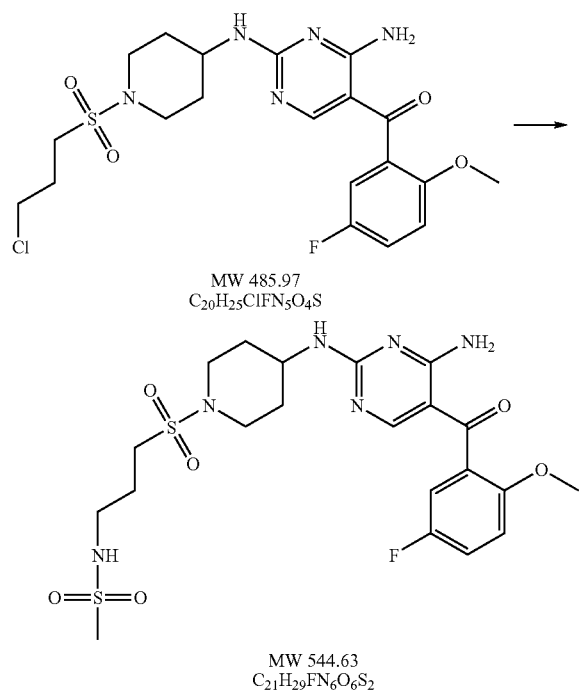

MW 485.97
C$_{20}$H$_{25}$ClFN$_5$O$_4$S

MW 544.63
C$_{21}$H$_{29}$FN$_6$O$_6$S$_2$

A suspension of [4-amino-2-[1-(3-chloro-propane-1-sulfonyl)-piperidin-4-ylamino]-pyrimidin-5-yl]-(5-fluoro-2-methoxy-phenyl)-methanone (210 mg, 0.43 mmol, Example 272), potassium iodide (200 mg, 1.2 mmol) and ammonia (1.5 mL, 7M in methanol, Aldrich) was heated at 100–110° C. in a sealed tube with stirring for 6 hours. Solvent was removed and the crude amine product was dissolved in tetrahydrofuran (12 mL). The resulting solution was cooled to 0–5° C., treated with diisopropylethylamine (200 mg, 2.0 mmol, Aldrich) and then with a bolus of methanesulfonyl chloride (100 mg, 0.88 mmol, Aldrich). After stirring at ambient temperature for 3 hours, the solution was washed with 10% NaHCO$_3$. The organic layer was separated and dried (Na$_2$SO$_4$). The residue was purified by silica gel chromatography (5% methanol/methylene chloride) and precipitated from tetrahydrofuran/ethyl ether to give N-(3-[4-[4-amino-5-(5-fluoro-2-methoxy-benzoyl)-pyrimidin-2-ylamino]-piperidine-1-sulfonyl]-propyl)-methanesulfonamide as a white solid (60 mg, 26% yield). HRMS, observed: 445.1652; Calcd for (M+H)$^+$: 445.1647

Example 278

(4-Amino-2-[1-[3-(4-methyl-piperazin-1-yl)-propane-1-sulfonyl]-piperidin-4-ylamino]-pyrimidin-5-yl)-(5-fluoro-2-methoxy-phenyl)-methanone

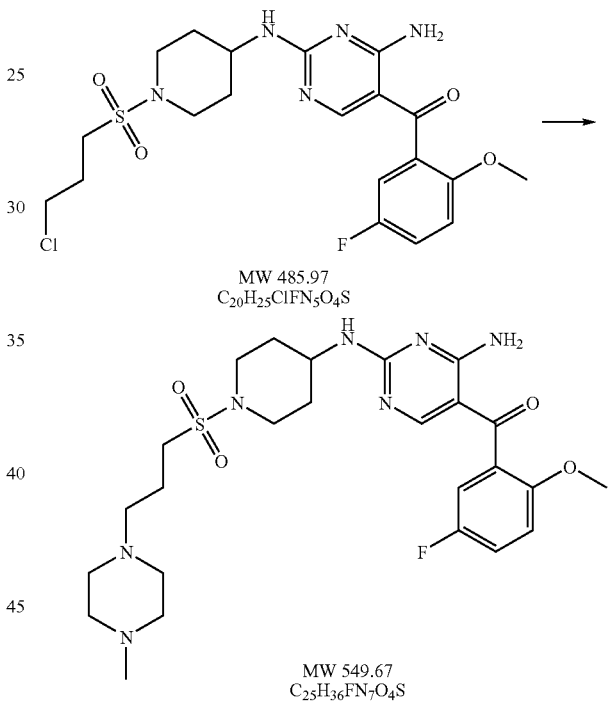

MW 485.97
C$_{20}$H$_{25}$ClFN$_5$O$_4$S

MW 549.67
C$_{25}$H$_{36}$FN$_7$O$_4$S

A suspension of [4-amino-2-[1-(3-chloro-propane-1-sulfonyl)-piperidin-4-ylamino]-pyrimidin-5-yl]-(5-fluoro-2-methoxy-phenyl)-methanone (32 mg, 0.066 mmol, Example 272), potassium iodide (50 mg, 0.3 mmol), N-methylpiperazine (500 mg, 5.0 mmol, Aldrich) in dioxane (15 mL) was heated at reflux under nitrogen for 16 hours. The reaction was diluted with methylene chloride (40 mL) and washed (2×) with water. The organic layer was separated and dried (Na$_2$SO$_4$). The residue was purified by silica gel chromatography (methanol/methylene chloride) and triturated from ethyl ether and filtered to give (4-amino-2-[1-[3-(4-methyl-piperazin-1-yl)-propane-1-sulfonyl]-piperidin-4-ylamino]-pyrimidin-5-yl)-(5-fluoro-2-methoxy-phenyl)-methanone as a white solid (12 mg, 33% yield). HRMS, observed: 550.2612; Calcd for (M+H)$^+$: 550.2607

Example 279

[4-Amino-2-(1-methanesulfonyl-piperidin-4-ylamino)-pyrimidin-5-yl]-(2,3-difluoro-6-hydroxyphenyl)-methanone

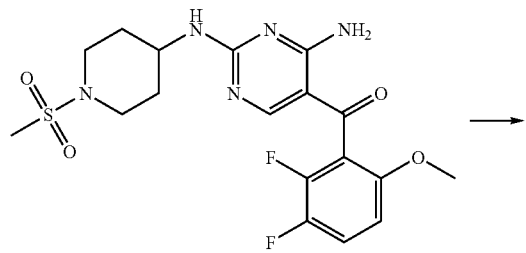

MW 441.46
C$_{18}$H$_{21}$F$_2$N$_5$O$_4$S

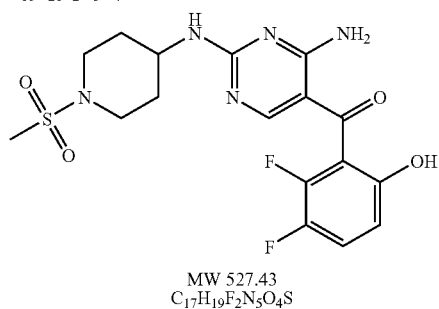

MW 527.43
C$_{17}$H$_{19}$F$_2$N$_5$O$_4$S

A suspension of [4-amino-2-(1-methanesulfonyl-piperidin-4-ylamino)-pyrimidin-5-yl]-(2,3-difluoro-6-methoxyphenyl)-methanone (200 mg, 0.45 mmol, Example 105) in methylene chloride (40 mL) was treated at 0–5° C. with aluminum chloride (620 mg, 4.7 mmol). The solution was stirred at ~7° C. for 2.5 hours and treated with ice water (20 mL). The mixture was treated with 10% NaHCO$_3$ (15 mL) and extracted with a mixture of tetrahydrofuran and methylene chloride (2×), dried (Na$_2$SO$_4$), and filtered. Removal of solvent gave an oil that crystallized upon trituration with methylene chloride. This crude solid was purified by silica gel chromatography (5–10% methanol/methylene chloride to give [4-amino-2-(1-methanesulfonyl-piperidin-4-ylamino)-pyrimidin-5-yl]-(2,3-difluoro-6-hydroxy-phenyl)-methanone as a white solid (75 mg, 39%) after solvent removal. HRMS, observed: 428.1203; Calcd for (M+H)$^+$: 428.1199

Example 280

[4-Amino-2-(1-methanesulfonyl-piperidin-4-ylamino)-pyrimidin-5-yl]-(2,3-difluoro-6-hydroxyphenyl)-methanone A) 2-Bromo-1-(2,2-diethoxy-ethoxy)-4-fluoro-benzene

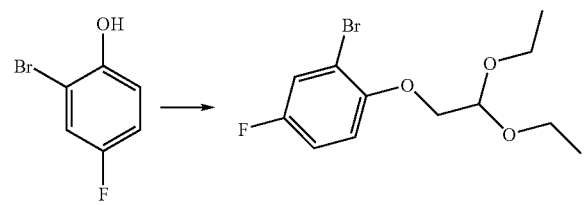

MW 191.00   MW 277.09
C$_6$H$_4$BrFO   C$_{10}$H$_{10}$BrFO3

Bromo-4-fluorophenol (50 g, 0.26 mol, Lancaster) was combined with 2-bromodiethylacetal (52 g, 0.26 mol, Aldrich) and potassium carbonate (37 g, 0.266 mol) in dimethylformamide (500 mL) and was heated at 125° C. internally for 14 hours. The reaction was cooled, filtered (cake washed with methylene chloride) and the organics diluted with 1.5 L of water. The mixture was extracted with 20% ether/hexane (2×), washed with water (2×) and dried (Na$_2$SO$_4$). Removal of solvent afforded ~60 g of 2-bromo-1-(2,2-diethoxy-ethoxy)-4-fluoro-benzene (~70%) as a decomposing oil and taken to the next step.

B) 7-Bromo-5-fluoro-benzofuran

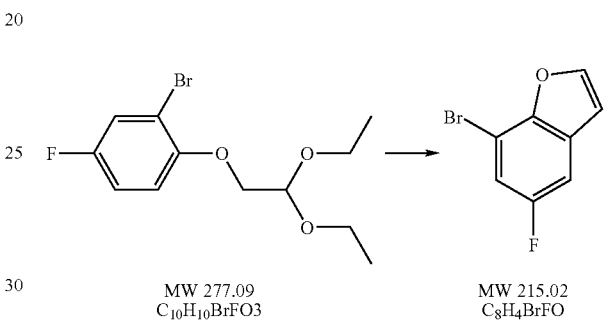

MW 277.09   MW 215.02
C$_{10}$H$_{10}$BrFO3   C$_8$H$_4$BrFO

2-Bromo-1-(2,2-diethoxy-ethoxy)-4-fluoro-benzene (60 g, 0.22 mol, Step A) was combined with Amberlyst-15 (20 g, Aldrich) in chlorobenzene (500 mL, Aldrich) and stirred with a paddle stirrer while the temperature was maintained at very gentle reflux. At the same time an azeotrope containing ethanol and chlorobenzene was removed via downward distillation. After 2 hours, more chlorobenzene was added (200 mL) and additional azeotrope was collected. The content of the flask was filtered and excess chlorobenzene was distilled (45° C., at ~1 mm). The residue was purified by silica gel chromatography (5–10% ethyl ether/hexane) to give 7-bromo-5-fluoro-benzofuran (14 g, ~33%) and taken to the next step. H$^1$NMR (300 MHz, DMSO$_{d6}$), ppm: 8.20 (d), 1H, 7.52 (m), 2H, 7.10 (d), 1H.

C) 5-Fluoro-benzofuran-7-carbaldehyde

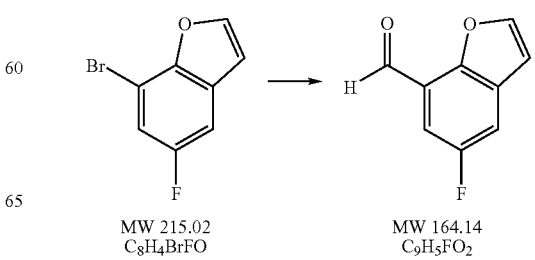

MW 215.02   MW 164.14
C$_8$H$_4$BrFO   C$_9$H$_5$FO$_2$

7-Bromo-5-fluoro-benzofuran (7 g, 32 mmol, Step B) was dissolved in a mixture of tetrahydrofuran (350 mL) and pentane (100 mL), cooled to −95 to −100° C., and treated with n-butyl lithium (14 mL, 35 mmol, 2.5M in hexane, Aldrich). After stirring for 5 minutes, a solution of dimethylformamide (5 mL) in tetrahydrofuran (15 mL) was added dropwise and the reaction temperature raised to −20° C. This was treated with aqueous ammonium chloride (50 mL) and stirred for 0.5 hour at ambient temperature. The reaction mixture was concentrated in vacuo and diluted with hexane. The organic fraction was washed with water and dried ($Na_2SO_4$). Removal of solvent afforded crude 5-fluoro-benzofuran-7-carbaldehyde (~30%) as an oil. Purification was by silica gel chromatography (5–10% ethyl ether/hexane). HRMS, observed: 163.0201; Calcd for $(M+H)^+$: 163.0195

D) (2,4-Dichloro-pyrimidin-5-yl)-(5-fluoro-benzofuran-7-yl)-methanol

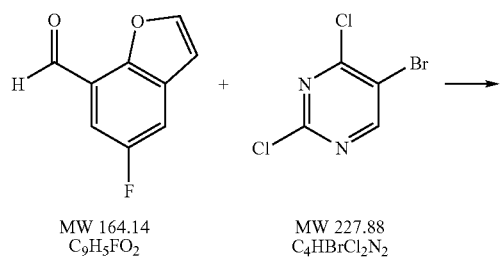

A solution of 5-bromo-2,4-dichloro-pyrimidine (1.0 g, 4.4 mmol, Aldrich) was dissolved in tetrahydrofuran (50 mL), cooled to −30° C., and treated slowly with isopropylmagnesium chloride (2.2 mL, 4.4 mmol, 2M in tetrahydrofuran, Aldrich). After stirring 0.5 hour between −30° C. and −25° C., the reaction was treated with a solution of 5-fluoro-benzofuran-7-carbaldehyde (0.65 g, 0.40 mmol, Step C) in tetrahydrofuran (10 mL). The temperature was slowly raised to −10° C. and then the reaction was quenched with aqueous 20% ammonium chloride. After 0.5 hours of stirring at ambient temperature, the mixture was diluted with hexane (100 mL), washed with water and dried ($Na_2SO_4$). Removal of solvent afforded crude (2,4-dichloro-pyrimidin-5-yl)-(5-fluoro-benzofuran-7-yl)-methanol as an oil. Purification was by silica gel chromatography (50% ethyl acetate/hexane) to give 930 mg of oil (~70%). HRMS, observed: 311.9863; Calcd for $(M+H)^+$: 311.9869

E) (2,4-Dichloro-pyrimidin-5-yl)-(5-fluoro-benzofuran-7-yl)-methanone

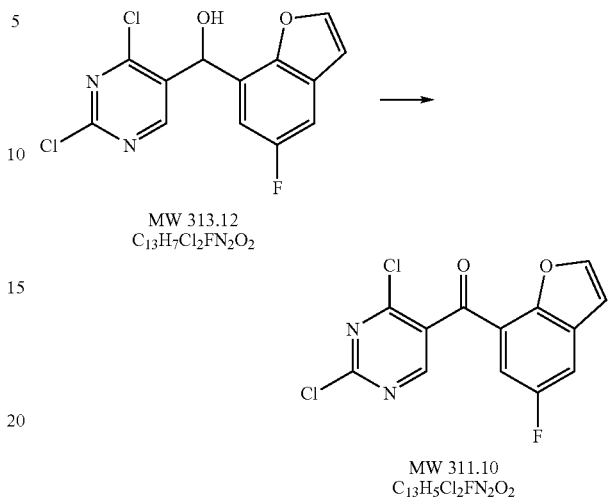

At 20° C., a solution of (2,4-dichloro-pyrimidin-5-yl)-(5-fluoro-benzofuran-7-yl)-methanol (0.9 g, 0.29 mmol, Step D) in ethylacetate (110 mL) was treated with a slurry of manganese oxide (9.0 g, Aldrich) in ethyl acetate (110 mL). After stirring for 3.5 hours, the reaction was filtered through celite and solvent removed in vacuo to give 0.82 g of (2,4-dichloro-pyrimidin-5-yl)-(5-fluoro-benzofuran-7-yl)-methanone as a foam and taken to the next step.

F) (4-Amino-2-chloro-pyrimidin-5-yl)-(5-fluoro-benzofuran-7-yl)-methanone

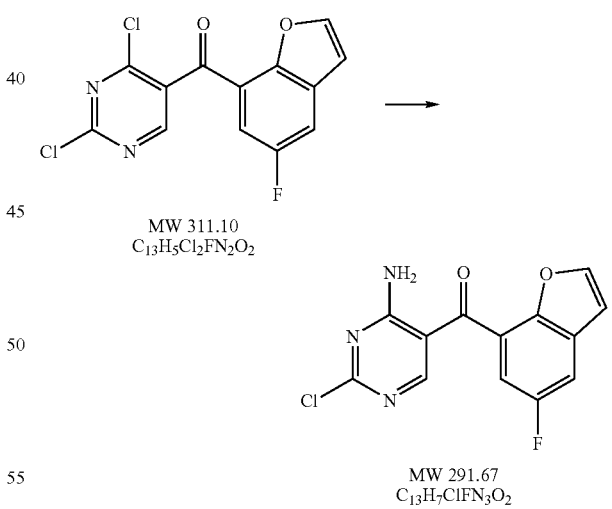

At 20° C., a stirred suspension of (2,4-dichloro-pyrimidin-5-yl)-(5-fluoro-benzofuran-7-yl)-methanone (0.80 g, 2.6 mmol, Step E) in toluene (70 mL) was treated with a slow stream of ammonia gas (Matheson) for 1 hour. The suspension was cooled, filtered and the filter cake washed with water. The filter cake was dissolved in acetonitrile, filtered through celite and the solvent removed to give a solid. This was crystallized from acetonitrile to give 0.4 g of (4-amino-2-chloro-pyrimidin-5-yl)-(5-fluoro-benzofuran-7-yl)- methanone (52%) as a white solid. HRMS, observed: 291.0208; Calcd for (M+H)+: 291.0211

G) [4-Amino-2-(1-methanesulfonyl-piperidin-4-ylamino)-pyrimidin-5-yl]-(2,3-difluoro-6-hydroxy-phenyl)-methanone

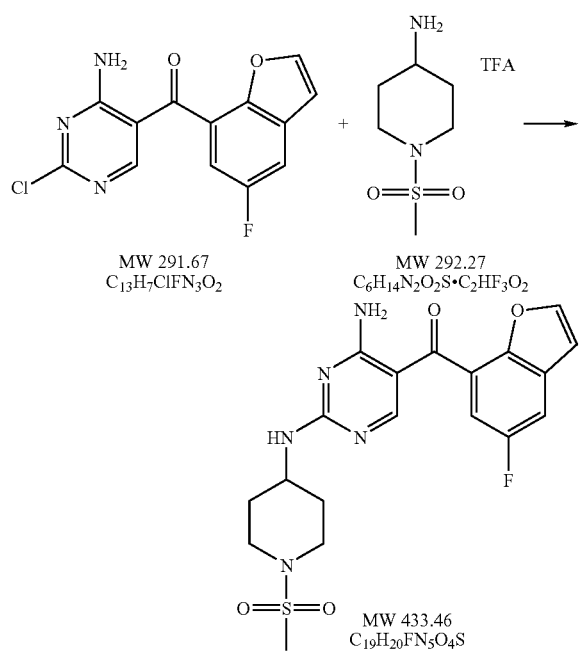

Methanesulfonyl-piperidin-4-ylamine trifluoroacetic acid salt (0.68 g, 2.3 mmol, Example 162), (4-amino-2-chloro-pyrimidin-5-yl)-(5-fluoro-benzofuran-7-yl)-methanone (0.5 g, 1.7 mmol, Step F), and diisopropylethylamine (1 mL, Aldrich) were combined with ethanol (20 mL) and refluxed for 12 hours. The reaction was cooled and diluted with ice water (~60 mL). After 2 hours, the suspension was filtered and dried at 50° C. and high vacuum to give 0.35 g (57%) of [4-amino-2-(1-methanesulfonyl-piperidin-4-ylamino)-pyrimidin-5-yl]-(2,3-difluoro-6-hydroxy-phenyl)-methanone as a white solid. HRMS, observed: 434.1297; Calcd for (M+H)+: 434.1293. CDK4 $IC_{50}$=0.030 µM; CDK1 $IC_{50}$=0.058 µM; CDK2 $IC_{50}$=0.002 µM; HCT 116 $IC_{90}$=3.300 µM.

Example 281

4-amino-2-methylsulfanyl-pyrimidin-5-yl)-phenyl-methanone

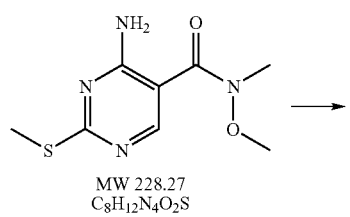

-continued

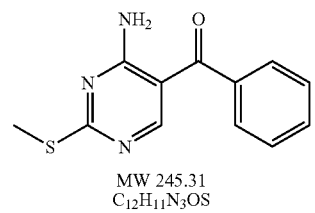

A solution of 4-amino-2-methylsulfanyl-pyrimidine-5-carboxylic acid methoxy-methyl-amide (456 mg, 3 mmol, Example 168) in tetrahydrofuran (3 mL) chilled to 0° C. and added phenylmagnesium chloride (4 mL, 2M in tetrahydrofuran, Aldrich). The mixture was stirred cold for 0.5 hours and at room temperature for 2 hours and then quenched with aqueous ammonium chloride. The product was extracted with ethyl acetate, washed with aqueous sodium bicarbonate, brine, and dried (MgSO4). Removal of solvent and chromatography on silica gel (3:1 hexane/ethyl acetate) gave, after crystallization from dichloromethane/hexane, 310 mg of 4-amino-2-methylsulfanyl-pyrimidin-5-yl)-phenyl-methanone, MP 137–138° C. MS(ES) MH+ 246

Example 282

(4-Amino-2-methanesulfinyl-pyrimidin-5-yl)-phenyl-methanone

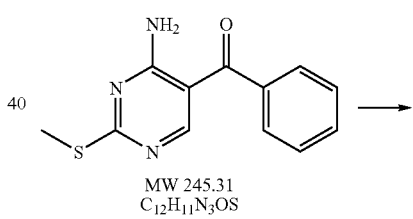

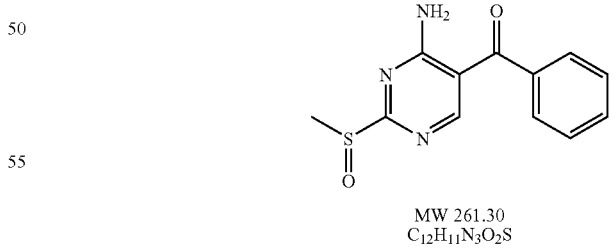

The title compound was prepared in a similar manner as described in Example 163 using material prepared in Example 281 and the crude product used without purification.

Example 283

[4-Amino-2-(1-methanesulfonyl-piperidin-4-ylamino)-pyrimidin-5-yl]-phenyl-methanone

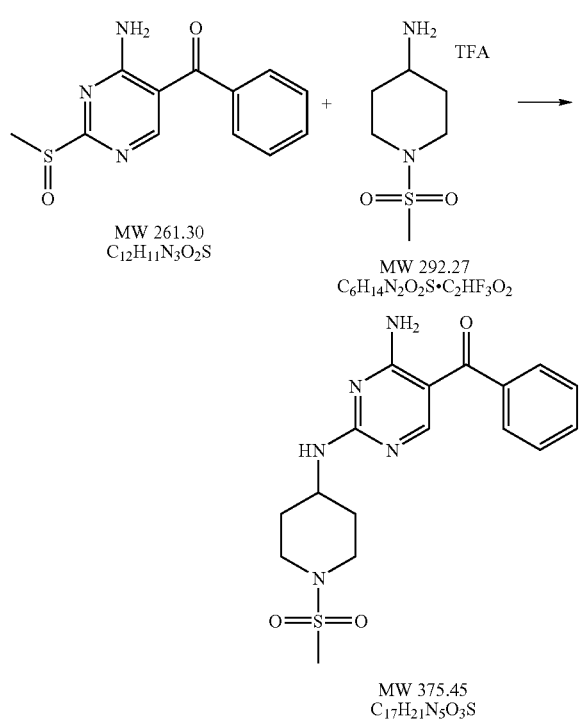

Treatment of the material prepared in Example 282 with material prepared in Example 162 in ethanol containing triethylamine at reflux for one hour, gave, after chilling and filtering, [4-amino-2-(1-methanesulfonyl-piperidin-4-ylamino)-pyrimidin-5-yl]-phenyl-methanone, as a colorless solid, MP 249–250° C. MS(ES) MH+ 376

Example 284

4-[4-Amino-5-(2,3-difluoro-6-methoxy-benzoyl)-pyrimidin-2-ylamino]-piperidine-1-carbaldehyde

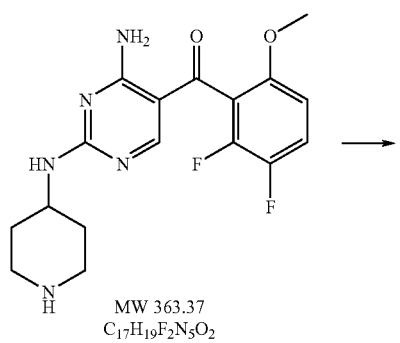

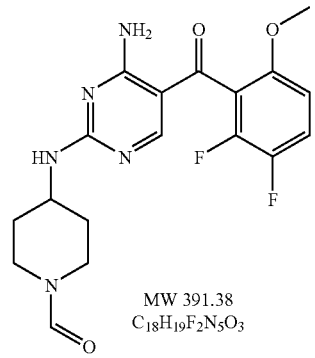

Treatment of [4-amino-2-(piperidin-4-ylamino)-pyrimidin-5-yl]-(2,3-difluoro-6-methoxy-phenyl)-methanone (Example 107) in tetrahydrofuran and diisopropylethyl amine with 98% formic acid gave the title compound after extraction and chromatography on silica gel using methanol/triethylamine/dichloromethane (2:2:96) and crystallization from dichloromethane/hexane, MP 263° C. (dec). MS(ES) MH+ 392

Example 285

4-[4-Amino-5-(2,3-difluoro-6-methoxy-benzoyl)-pyrimidin-2-ylamino]-piperidine-1-sulfonic acid amide

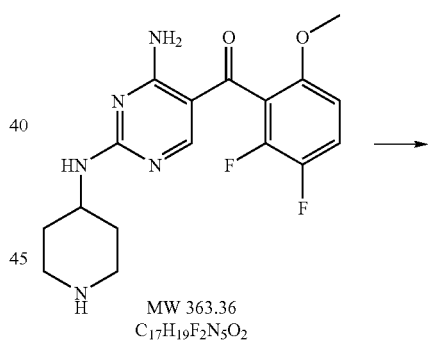

[4-Amino-2-(piperidin-4-ylamino)-pyrimidin-5-yl]-(2,3-difluoro-6-methoxy-phenyl)-methanone (308 mg, 0.848 mmol, Example 107) in dioxane (3 mL) and sulfamide (814

245 mg, 8.48 mmol, Aldrich) refluxed overnight. The mixture was diluted with water and sodium bicarbonate and extracted with dichloromethane. The organic solution was washed with water, dried (MgSO4), filtered and evaporated. Chromatography on silica gel (methanol/triethylamine/ethyl acetate 5:2:95) gave, after crystallization from ethanol/ethyl ether, 255 mg of colorless solid, MP 217–218° C. MS(ES) MH+ 443

Example 286

4-[4-Amino-5-(2,3-difluoro-6-methoxy-benzoyl)-pyrimidin-2-ylamino]-piperidine-1-sulfonic acid acetyl-amide

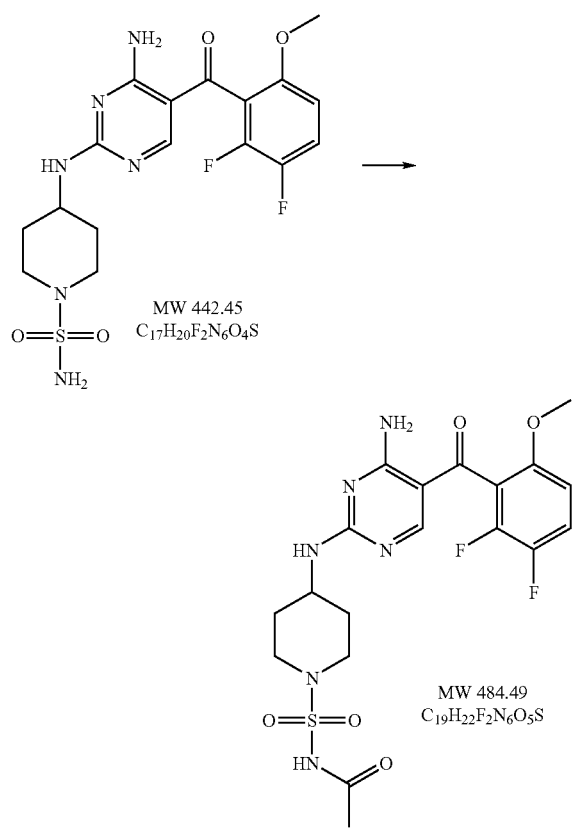

4-[4-Amino-5-(2,3-difluoro-6-methoxy-benzoyl)-pyrimidin-2-ylamino]-piperidine-1-sulfonic acid amide (50 mg, Example 285) in dichloromethane (10 mL), N-methyl morpholine (0.1 mL, Aldrich) and dimethylaminopyridine (1 mg, Aldrich) was chilled in ice and added acetic anhydride (5 drops). The mixture was stirred cold for two hours and quenched with methanol. The mixture was evaporated to dryness and chromatographed on silica gel (dichloromethane, then ethyl acetate). Fractions corresponding to product were combined and crystallized from dichloromethane/ethyl ether to give 45 mg of colorless material, MP 153° C. (dec). MS(ES) MH+ 485

246

Example 287 rac-(2,4-Dichloro-pyrimidin-5-yl)-(2,3-difluoro-6-methoxy-phenyl)-methanol

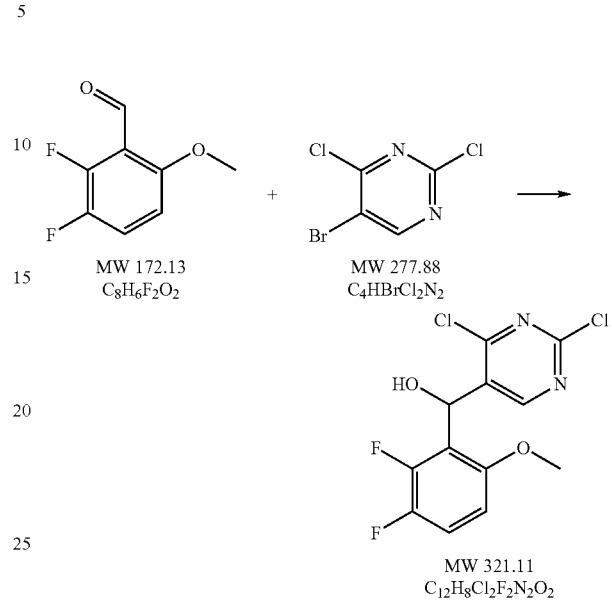

A solution of 5-bromo-2,4-dichloropyrimidine (18.8 g, 82.5 mmol, Aldrich) in tetrahydrofuran (50 mL) was chilled to −30° C. and isopropylmagnesium chloride (41.25 mL, 82.5 mmol, 2M in tetrahydrofuran, Aldrich) was added. The mixture was stirred at −30° C. for 20 minutes and a solution of 2,3-difluoro-6-methoxybenzaldehyde (12.91 g, 75 mmol, Apollo) in tetrahydrofuran (40 mL) was added slowly at this temperature. The mixture was then stirred at 0° C. for one hour and quenched with aqueous ammonium chloride. Extraction with ethyl acetate and crystallization from ethyl ether/hexanes gave 20.5 g of rac-(2,4-dichloro-pyrimidin-5-yl)-(2,3-difluoro-6-methoxy-phenyl)-methanol as a light yellow solid, MP 99–101° C. MS(ES) MH+ 322

Example 288

(2,4-Dichloro-pyrimidin-5-yl)-(2,3-difluoro-6-methoxy-phenyl)-methanone

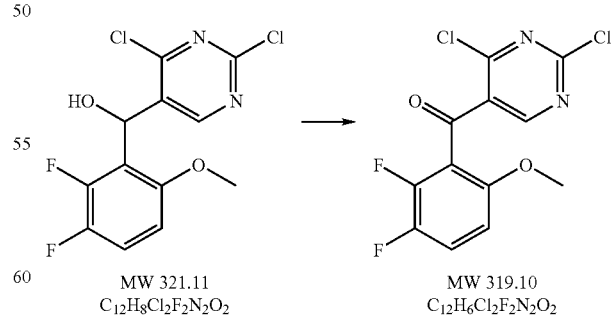

A mixture of rac-(2,4-dichloro-pyrimidin-5-yl)-(2,3-difluoro-6-methoxy-phenyl)-methanol (20.5 g, 63.8 mmol, Example 287) in dichloromethane (180 mL) was chilled with stirring to 0° C. and added water (20 mL), sodium bicarbonate powder (2.42 g, 28.73 mmol, Aldrich), tetrabutylammonium bromide (0.617 g, 1.915 mmol, Aldrich), and 2,2,6,6-tetramethyl-1-piperidinyloxy, free radical (0.1 g, 0.638 mmol, TEMPO, Aldrich). Sodium hypochlorite solution (6.15%, Aldrich) was added portionwise until all starting material was oxidized (TLC ethyl acetate/hexanes 3:1). The cold reaction mixture was then washed with water (2×), dried (MgSO$_4$) and concentrated adding hexanes. Filtration of the cold mixture gave 17.4 g of (2,4-dichloro-pyrimidin-5-yl)-(2,3-difluoro-6-methoxy-phenyl)-methanone, MP 137–139° C.

Example 289

(4-Amino-2-chloro-pyrimidin-5-yl)-(2,3-difluoro-6-methoxy-phenyl)-methanone

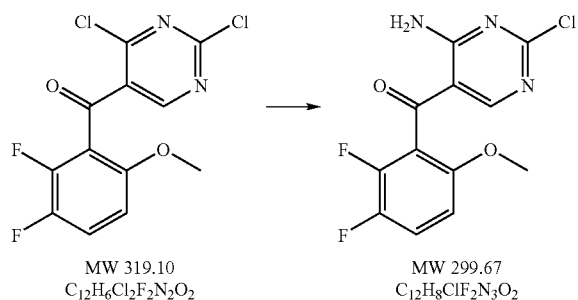

MW 319.10
C$_{12}$H$_6$Cl$_2$F$_2$N$_2$O$_2$

MW 299.67
C$_{12}$H$_8$ClF$_2$N$_3$O$_2$

A solution of (2,4-dichloro-pyrimidin-5-yl)-(2,3-difluoro-6-methoxy-phenyl)-methanone (13.7 g, Example 288) in toluene (200 mL) was stirred at room temperature and ammonia gas was bubbled in for 30 minutes. Water (200 mL) was then added and the mixture was stirred for 15 minutes. Hexane (200 mL) was added and the solids filtered and washed with water and hexane. The solids were dissolved in hot acetonitrile (~700 mL), filtered hot, concentrated to about 300 mL and chilled. Filtration gave 10.6 g of (4-amino-2-chloro-pyrimidin-5-yl)-(2,3-difluoro-6-methoxy-phenyl)-methanone, MP 238–239° C. (dec). MS(ES) MH+ 300

Example 290

Trans-[4-Amino-2-[4-(2-hydroxy-ethylamino)-cyclohexylamino]-pyrimidin-5-yl}-(2,3-difluoro-6-methoxy-phenyl)-methanone

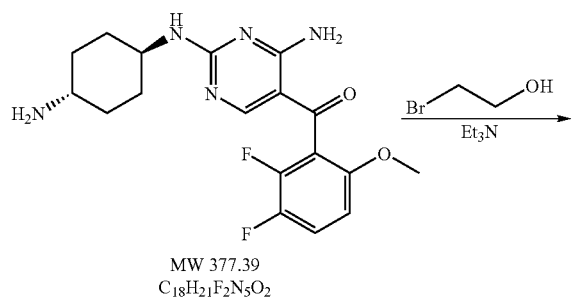

MW 377.39
C$_{18}$H$_{21}$F$_2$N$_5$O$_2$

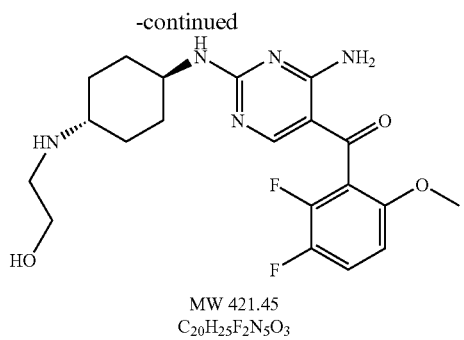

MW 421.45
C$_{20}$H$_{25}$F$_2$N$_5$O$_3$

To a stirred solution of trans-[4-amino-2-(4-amino-cyclohexylamino)-pyrimidin-5-yl]-(2,3-difluoro-6-methoxy-phenyl)-methanone (100 mg, 0.27 mmol, Example 120) and triethylamine (200 uL) in tetrahydrofuran (3 mL), 2-bromoethanol (20 uL, 0.28 mmol, Aldrich) was added and the mixture was stirred at reflux for 5 hours. The reaction was quenched with water and the mixture was extracted with ethyl acetate (3×10 mL) and the extracts were dried with sodium sulfate. Removal of solvent gave a yellow solid which was purified by reverse phase HPLC to give a pale yellow solid. 86 mg, 75%. MS (ES) MH+=422. CDK4 IC$_{50}$=0.020 μM; CDK1 IC$_{50}$=0.018 μM; CDK2 IC$_{50}$=0.005 μM; HCT 116 IC$_{90}$=0.179 μM.

Example 291

Trans-(4-Amino-2-[4-[bis-(2-hydroxy-ethyl)-amino]-cyclohexylamino]-pyrimidin-5-yl)-(2,3-difluoro-6-methoxy-phenyl)-methanone

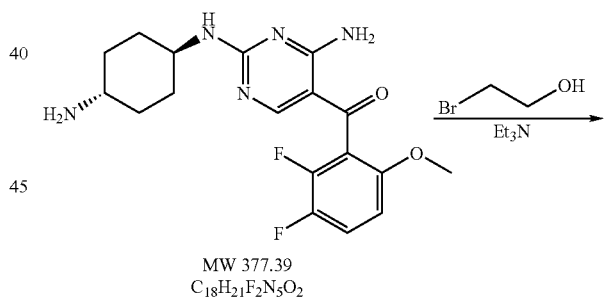

MW 377.39
C$_{18}$H$_{21}$F$_2$N$_5$O$_2$

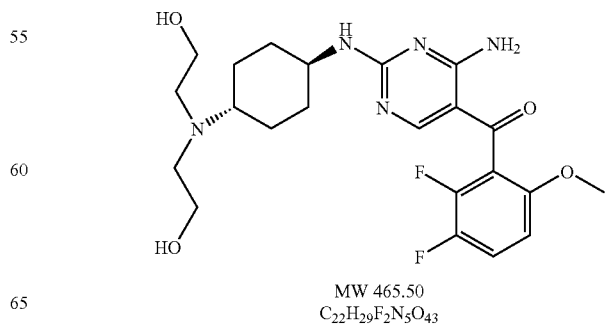

MW 465.50
C$_{22}$H$_{29}$F$_2$N$_5$O$_43$

To a stirred solution of trans-[4-amino-2-[4-(2-hydroxy-ethylamino)-cyclohexylamino]-pyrimidin-5-yl]-(2,3-difluoro-6-methoxy-phenyl)-methanone (106 mg, 0.25 mmol, Example 120) in 1,4-dioxane (3 mL), 2-bromoethanol (80 uL, 1.12 mmol, Aldrich) and sodium bicarbonate (50 mg, 0.60 mmol) were added and the mixture was heated at 113° C. for 24 hours. The reaction was quenched with water and the mixture was extracted with ethyl acetate (3×10 mL) and the extracts were dried with sodium sulfate. The solvent was removed and the residue was chromatographed (8% 9N ammonia in methanol/dichloromethane) to give a pale yellow solid. 97 mg, 84%. MS (ES) MH+=466.

Example 292

Trans-N-[4-[4-Amino-5-(2,3-difluoro-6-methoxy-benzoyl)-pyrimidin-2-ylamino]-cyclohexyl]-succinamic acid

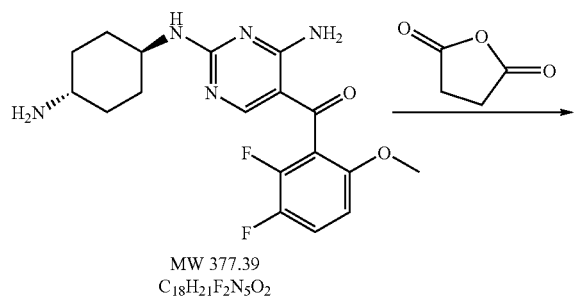

MW 377.39
C$_{18}$H$_{21}$F$_2$N$_5$O$_2$

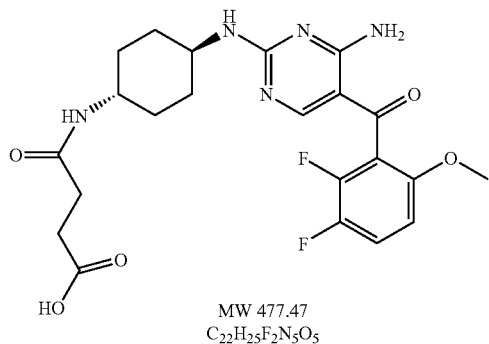

MW 477.47
C$_{22}$H$_{25}$F$_2$N$_5$O$_5$

To a stirred solution of trans-[4-amino-2-(4-amino-cyclohexylamino)-pyrimidin-5-yl]-(2,3-difluoro-6-methoxy-phenyl)-methanone (100 mg, 0.27 mmol, Example 120) and triethylamine (125 mg, 0.33 mmol) in tetrahydrofuran (5 mL), succinic anhydride (35 mg, 0.35 mmol, Aldrich,) was added and the mixture was refluxed for 2 hours. The mixture was cooled and the solid was filtered and dried to yield a white powder. 130 mg, 100%. MS (ES) MH+=478.

Example 293

Trans-3-Chloro-propane-1-sulfonic acid [4-[4-amino-5-(2,3-difluoro-6-methoxy-benzoyl)-pyrimidin-2-ylamino]-cyclohexyl]-amide

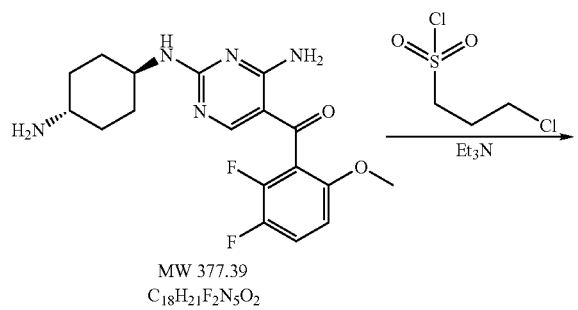

MW 377.39
C$_{18}$H$_{21}$F$_2$N$_5$O$_2$

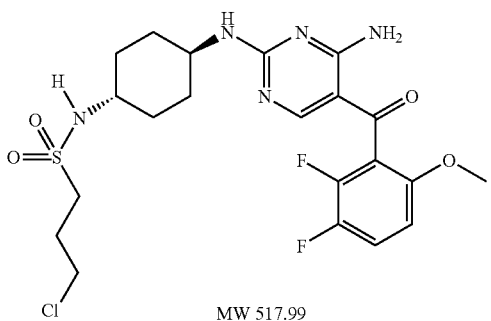

MW 517.99
C$_{21}$H$_{26}$ClF$_2$N$_5$O$_4$S

To a stirred solution of trans-[4-amino-2-(4-amino-cyclohexylamino)-pyrimidin-5-yl]-(2,3-difluoro-6-methoxy-phenyl)-methanone (565 mg, 1.5 mmol, Example 120) and triethylamine (167 mg, 0.25 mL, 1.69 mmol) in tetrahydrofuran (20 mL) at 0° C., 3-chloropropane sulfonyl chloride (0.20 mL, 1.65 mmol, Aldrich) was added. The mixture was stirred for 10 minutes and the reaction was quenched with water. The mixture was extracted with ethyl acetate and the extracts were combined and dried with sodium sulfate. The solvent was removed and the residue was chromatographed (4% methanol/dichloromethane) to give 600 mg of yellow solid. Yield, 77%. MS (ES) MH+=518.

Example 294

Trans-3-Morpholin-4-yl-propane-1-sulfonic acid [4-[4-amino-5-(2,3-difluoro-6-methoxy-benzoyl)-pyrimidin-2-ylamino]-cyclohexyl]-amide

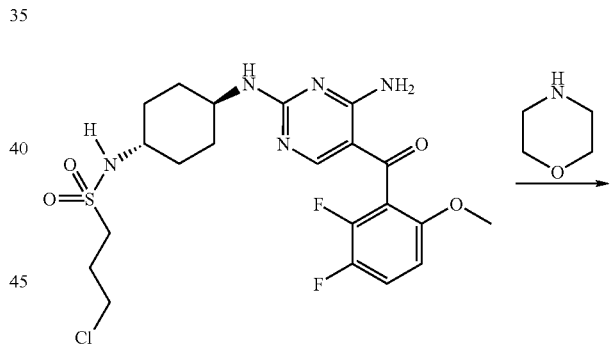

MW 517.99
C$_{21}$H$_{26}$ClF$_2$N$_5$O$_4$S

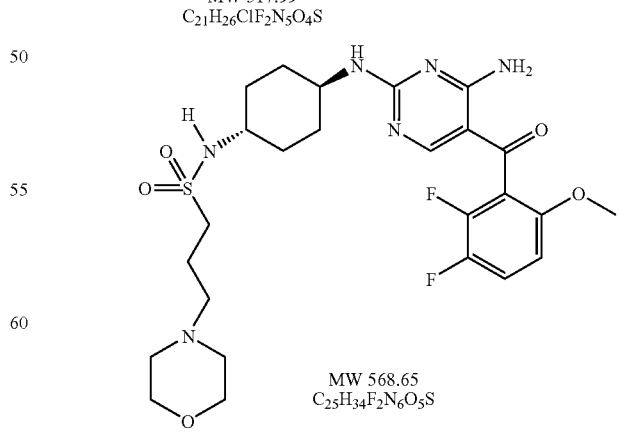

MW 568.65
C$_{25}$H$_{34}$F$_2$N$_6$O$_5$S

To a stirred solution of 3-chloro-propane-1-sulfonic acid [4-[4-amino-5-(2,3-difluoro-6-methoxy-benzoyl)-pyrimidin-2-ylamino]-cyclohexyl]-amide (104 mg, 0.20 mmol, Example 293) in tetrahydrofuran (5 mL), morpholine (100 mg, 1.15 mmol, Aldrich) was added and the mixture was heated at reflux for 24 hours. The reaction was quenched with water and the mixture was extracted with ethyl acetate (3×5 mL). The extracts were combined and dried with sodium sulfate and concentrated. The residue was chromatographed (8% 9N ammonia in methanol/dichloromethane) to give a pale yellow solid. 57 mg, 50%. MS (ES) MH$^+$=569. CDK4 IC$_{50}$=0.015 µM; CDK1 IC$_{50}$=0.008 µM; CDK2 IC$_{50}$=0.005 µM; HCT 116 IC$_{90}$=0.374 µM.

Example 295

Trans-3-(4-Methyl-piperazin-1-yl)-propane-1-sulfonic acid [4-[4-amino-5-(2,3-difluoro-6-methoxy-benzoyl)-pyrimidin-2-ylamino]-cyclohexyl]-amide

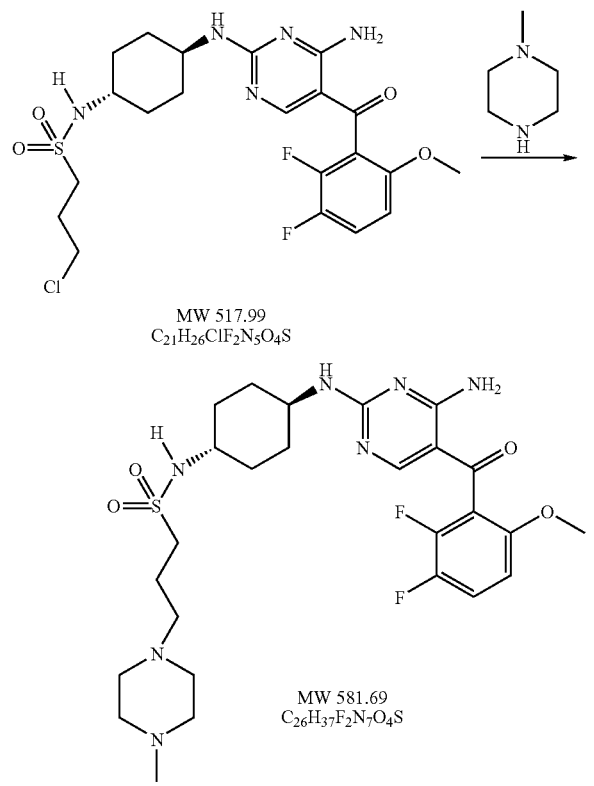

To a stirred solution of 3-chloro-propane-1-sulfonic acid [4-[4-amino-5-(2,3-difluoro-6-methoxy-benzoyl)-pyrimidin-2-ylamino]-cyclohexyl]-amide (104 mg, 0.20 mmol, Example 293) in tetrahydrofuran (5 mL), N-methylpiperizine (100 mg, 1 mmol, Aldrich,) was added and the mixture was heated at reflux for 24 hours. The reaction was quenched with water and the mixture was extracted with ethyl acetate (3×5 mL). The extracts were combined and dried with sodium sulfate and concentrated. The residue was chromatographed (8% 9N ammonia in methanol/dichloromethane) to give a pale yellow solid. 85 mg, 73%. MS (ES) MH$^+$=582.

Example 296

Trans-3-Pyrrolidin-1-yl-propane-1-sulfonic acid [4-[4-amino-5-(2,3-difluoro-6-methoxy-benzoyl)-pyrimidin-2-ylamino]-cyclohexyl]-amide

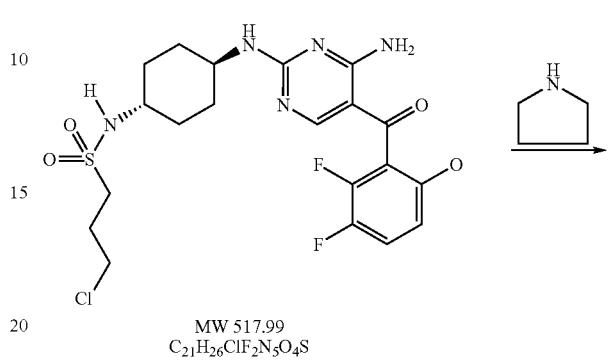

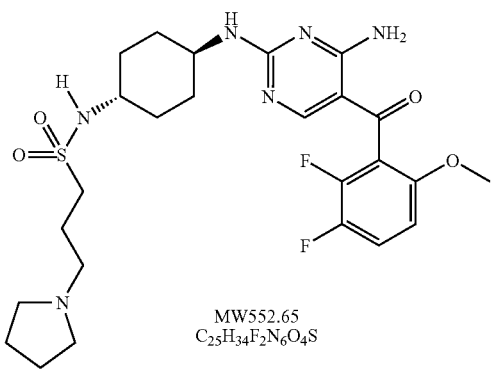

This compound was made with Example 293 and pyrolidine (Aldrich) by a similar procedure to the synthesis of Example 295. MS (ES) MH$^+$=553.

Example 297

Trans-3-Hydroxy-propane-1-sulfonic acid [4-[4-amino-5-(2,3-difluoro-6-methoxy-benzoyl)-pyrimidin-2-ylamino]-cyclohexyl]-amide

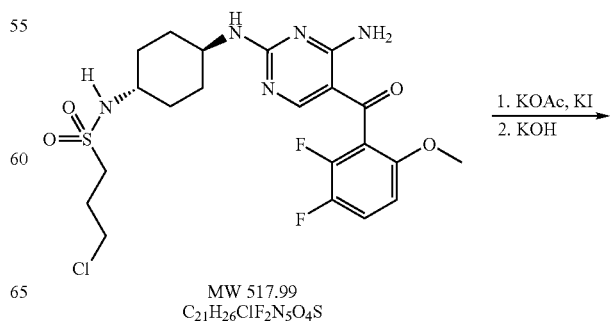

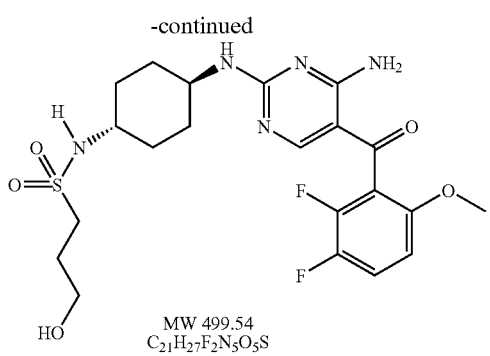

The chloride (80 mg, 0.18 mmol, Example 293) was dissolved in ethanol (1 mL). To it was added potassium acetate (86.5 mg, 0.88 mmol) and potassium iodide (8 mg, 0.05 mmol). The mixture was heated in a pressure tube in a microwave for 30 minutes. The mixture was filtered and the solid was washed with ethanol (4 mL). The filtrate (about 5 mL) was treated with 5% potassium hydroxide (2 mL) and the solution was stirred at room temperature for 30 minutes. The solution was neutralized with trifluoroacetic acid and concentrated. The residue was purified by reversed phase HPLC to give a pale yellow solid. 25 mg, 28%. MS (ES) MH$^+$=500.

Example 298

Trans-[4-Amino-2-[4-(1,1-dioxo-1$\lambda^6$-isothiazolidin-2-yl)-cyclohexylamino]-pyrimidin-5-yl]-(2,3-difluoro-6-methoxy-phenyl)-methanone

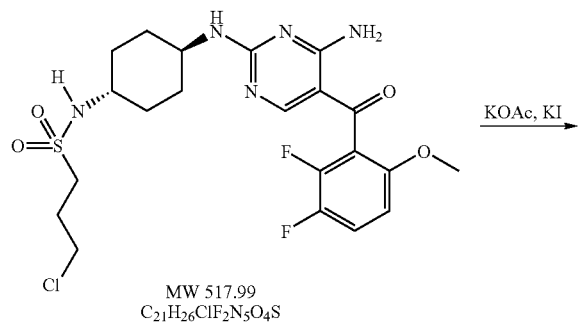

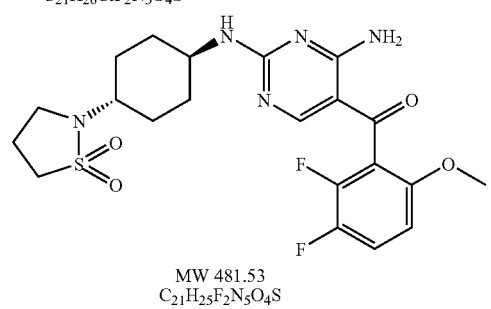

The chloride (530 mg, 1.02 mmol, Example 293) was dissolved in tetrahydrofuran (8 mL). To it was added potassium t-butoxide (395 mg, 3.53 mmol, Aldrich) and potassium iodide (10 mg). The mixture was heated at reflux for 3 hours and the reaction was quenched with 0.5N hydrochloric acid (1 mL). The mixture was extracted with ethyl acetate (3×10 mL) and the extracts were combined and dried with sodium sulfate. Removal of solvent gave the crude which was chromatographed (5% methanol/dichloromethane) to give a pale yellow solid. 412 mg, 85%. MS (ES) MH$^+$=482. CDK4 IC$_{50}$=0.005 μM; CDK1 IC$_{50}$=0.028 μM; CDK2 IC$_{50}$=0.008 μM; HCT 116 IC$_{90}$=0.320 μM.

Example 299

Trans-[4-Amino-2-[4-(4-methyl-piperazin-1-yl)-cyclohexylamino]-pyrimidin-5-yl]-(2,3-difluoro-6-methoxy-phenyl)-methanone

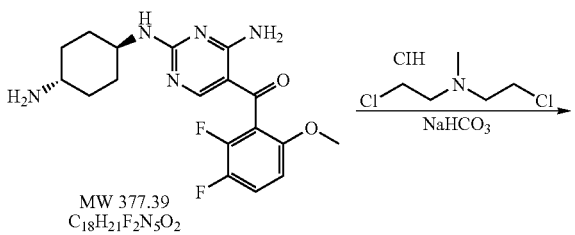

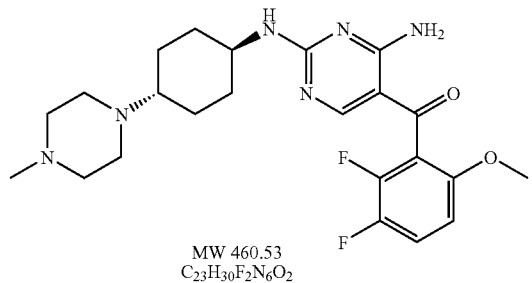

To a stirred solution of trans-[4-amino-2-(4-amino-cyclohexylamino)-pyrimidin-5-yl]-(2,3-difluoro-6-methoxy-phenyl)-methanone (105 mg, 0.28 mmol, Example 120) and sodium bicarbonate (84 mg, 1 mmol) in 1,4-dioxane (3 mL), bis-2-chloroethyl-methylamine hydrochloride (58 mg, 0.30 mmol, Aldrich) was added and the mixture was stirred at reflux overnight. An additional 20 mg of bis-2-chloroethyl-methylamine hydrochloride (Aldrich) was added and the reaction was refluxed for another 12 hours. The reaction was quenched with water and the mixture was extracted with ethyl acetate (3×10 mL) and the extracts were dried with sodium sulfate. Removal of solvent gave a yellow solid which was chromatographed (8% 9N ammonia in methanol/dichloromethane) to give a pale yellow solid. 16 mg, 12%. MS (ES) MH$^+$=461.

Example 300

Trans-[4-Amino-2-(4-pyrrolidin-1-yl-cyclohexylamino)-pyrimidin-5-yl]-(2,3-difluoro-6-methoxyphenyl)-methanone

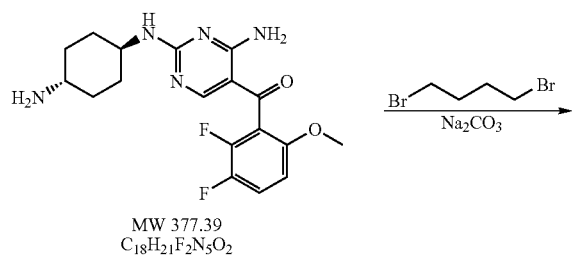

MW 377.39
C₁₈H₂₁F₂N₅O₂

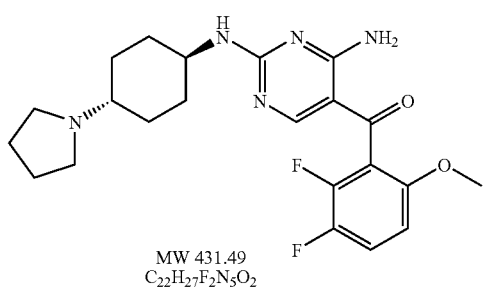

MW 431.49
C₂₂H₂₇F₂N₅O₂

To a stirred solution of trans-[4-amino-2-(4-amino-cyclohexylamino)-pyrimidin-5-yl]-(2,3-difluoro-6-methoxy-phenyl)-methanone (64 mg, 0.16 mmol, Example 120) and sodium carbonate (0.49 mmol, 52 mg) in ethanol (3 mL), 1,4-dibromobutane (22 uL, 0.16 mmol, Aldrich) was added and the mixture was stirred at reflux for 3 days. The solvent was removed under reduced pressure and the residue was purified by reversed phase HPLC to give a white solid. 30 mg, 43%. MS (ES) MH⁺=432.

Example 301

Trans-[4-Amino-2-(4-dimethylamino-cyclohexylamino)-pyrimidin-5-yl]-(2,3-difluoro-6-methoxyphenyl)-methanone

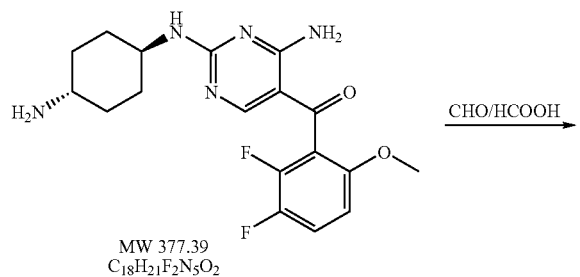

MW 377.39
C₁₈H₂₁F₂N₅O₂

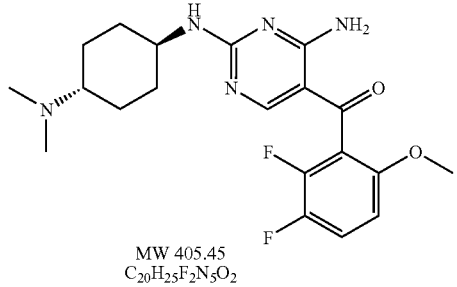

MW 405.45
C₂₀H₂₅F₂N₅O₂

To a stirred solution of trans-[4-amino-2-(4-amino-cyclohexylamino)-pyrimidin-5-yl]-(2,3-difluoro-6-methoxy-phenyl)-methanone (60 mg, 0.16 mmol, Example 120) in ethylene glycol dimethyl ether, formaldehyde (37% in water, 36 uL, 0.477 mmol, Aldrich) and formic acid (30 uL, 0.785 mmol, Aldrich) were added and the mixture was stirred at reflux for 2 hours. The solvent was removed under reduced pressure and the residue was purified by reversed phase HPLC to give a white solid. 27 mg, 67%. MS (ES) MH⁺=406.

Example 302

N-Methanesulfonyl-1,2,3,6-tetrahydro-pyridine

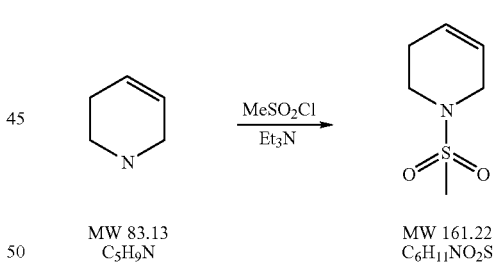

MW 83.13
C₅H₉N

MW 161.22
C₆H₁₁NO₂S

To a stirred solution of 1,2,3,6-tetrahydropyridine (1.5 g, 18.04 mmol, Aldrich) and triethylamine (36.12 mmol, 5.05 mL) in methylene chloride (60 mL) at 0° C., methane sulfonyl chloride (1.82 mL, 23.45 mmol, Aldrich) was added and the mixture was stirred for 2.5 hours. The reaction was quenched with water and the mixture was extracted with methylene chloride. The extracts were dried with MgSO₄ and the solvent was removed under reduced pressure to give the desired product as an off-white solid. 2.20 g, 76%. MS (ES) MH⁺=162.

Example 303 rac-3-Methanesulfonyl-7-oxa-3-aza-bicyclo[4.1.0]heptane

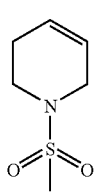 MCPBA → 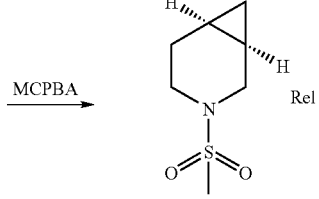

MW 161.22   MW 177.22
C$_6$H$_{11}$NO$_2$S   C$_6$H$_{11}$NO$_3$S

To a stirred solution of N-methanesulfony-1,2,3,4-tetrahydropyridine (2.18 g, 13.52 mmol, Example 302) in methylene chloride (30 mL) at 0° C., meta-chloroperoxybenzoic acid (3.94 g, 77%, 17.5 mmol, Aldrich) in 20 mL of methylene chloride was added and the mixture was stirred for 30 minutes. An additional 600 mg of meta-chloroperoxybenzoic acid was added and the mixture was stirred for 6 hours. The reaction was quenched with 30% sodium thiosulfate solution and the mixture was extracted with methylene chloride. The extracts were combined, washed with 5% sodium carbonate and dried with MgSO$_4$. The solvent was removed to give the desired product as a white solid. 2.40 g, 100%. The compound was used directly for the next step.

Example 304 rac-4-Azido-1-methanesulfonyl-piperidin-3-ol

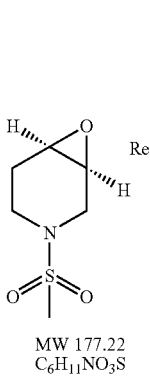 NaN$_3$/DMF → 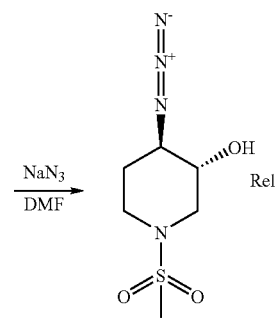

MW 177.22   MW 220.2515
C$_6$H$_{11}$NO$_3$S   C$_6$H$_{12}$N$_4$O$_3$S

To a stirred solution of rac-3-methanesulfonyl-7-oxa-3-aza-bicyclo[4.1.0]heptane (0.92 g, 5.19 mmol, Example 303) in dimethylformamide (20 mL), sodium azide (550 mg, 8.46 mmol) was added and the mixture was stirred at 80° C. for 6 hours. The mixture was cooled and poured into water and extracted with ethyl acetate (3×10 mL). The extracts were combined, washed with water, brine and dried with MgSO$_4$. The solvent was removed to give the desired product as colorless oil. 304 mg, 30.4%. The compound was used directly for the next step.

Example 305 rac-4-Amino-1-methanesulfonyl-piperidin-3-ol

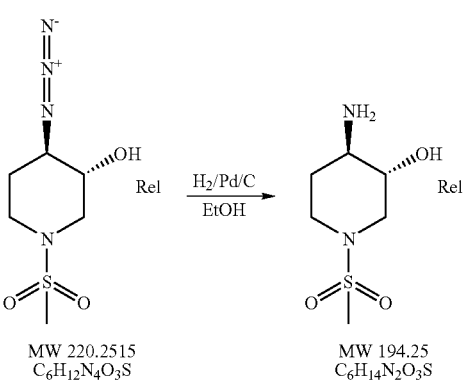

MW 220.2515   MW 194.25
C$_6$H$_{12}$N$_4$O$_3$S   C$_6$H$_{14}$N$_2$O$_3$S

The azide (300 mg, 1.36 mmol, Example 304) was dissolved in ethanol and hydrogenated at 45 psi under the catalyst of 10% palladium on carbon (30 mg) for 1 hour. The mixture was filtered and the filtrate was concentrated to give a white solid. 245 mg, 93%. The compound was used directly for the next step.

Example 306 rac-[4-Amino-2-(3-hydroxy-1-methanesulfonyl-piperidin-4-ylamino)-pyrimidin-5-yl]-(2,3-difluoro-6-methoxy-phenyl)-methanone

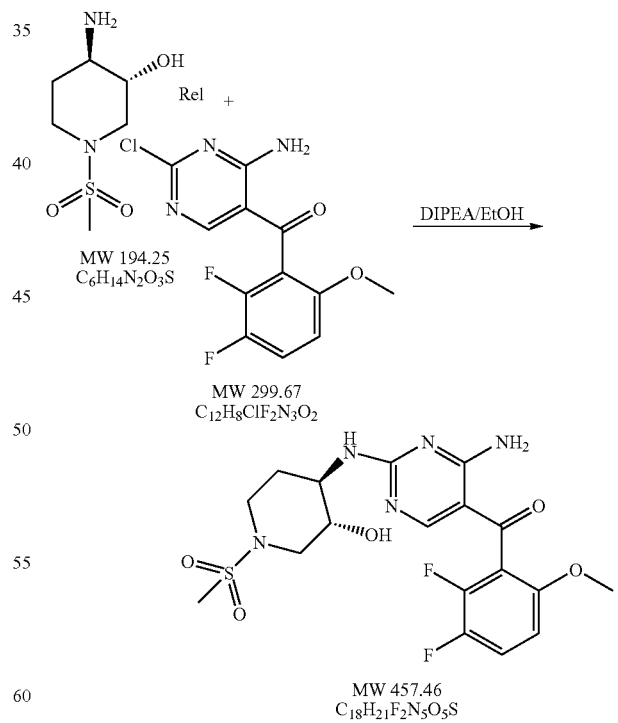

The amine (44 mg, 0.22 mmol, Example 305) and chloropyrimidine (55 mg, 0.18 mmol, Example 289) were dissolved in ethanol (5 mL). To the stirred mixture at reflux, diisopropylethylamine (64 uL, Aldrich) was added and the mixture was refluxed for 20 hours. The solvent was removed and the residue was purified by HPLC (10–60%, acetonitrile/water) to give a white solid, 25 mg, 30%. MS (ES) MH+=458.

Example 307 rac-4-Bromo-1-methanesulfonyl-piperidin-3-ol

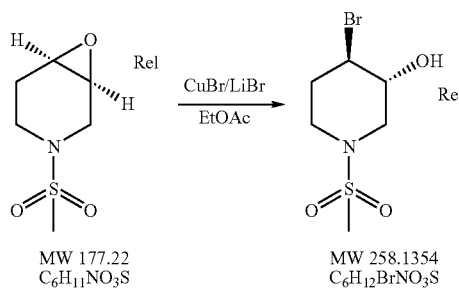

To a stirred solution of the epoxide (177 mg, 1 mmol, Example 303) in tetrahydrofuran (8 mL), lithium bromide (543 mg, 6.25 mmol, Aldrich) and copper(II)bromide (725 mg, 3.25 mmol, Aldrich) were added and the mixture was stirred at room temperature overnight. The mixture was poured into 0.1N hydrochloric acid (33 mL) and extracted with ethyl acetate (3×10 mL). The extracts were combined, washed with water, brine and dried with MgSO$_4$. The solvent was removed to give the desired product as colorless oil after passing through an aluminum column (eluted with 5% methanol/dichloromethane). 237 mg, 92%. H$^1$NMR (300 MHz, CDCl$_3$), ppm: 2.00–2.20 (m), 1H; 2.38–2.52 (m), 1H; 2.70 (br), 1H (OH); 2.99 (s), 3H; 3.0–3.20 (m), 2H; 3.50–3.51 (m), 1H; 3.80–3.97 (m), 2H; 4.0–4.10 (m), 1H. The compound was used directly for the next step.

Example 308 rac-4-Azido-1-methanesulfonyl-piperidin-3-ol

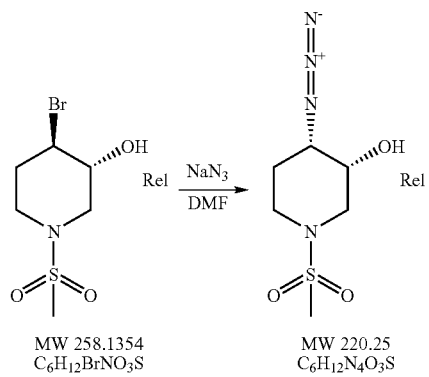

To a stirred solution of the bromide (70 mg, 0.27 mmol, Example 307) in dimethylformamide (3 mL), sodium azide (80 mg, 1.23 mmol) was added and the mixture was stirred at 84° C. overnight. The solvent was removed and the residue was chromatographed (50% ethyl acetate/hexane) to give the desired product as a colorless oil. 51 mg, 86%. H$^1$NMR (300 MHz, CDCl$_3$), ppm: 1.60–1.70 (m), 1H; 2.05–2.20(m), 1H; 2.80–3.05 (m), 2H; 2.83 (s), 3H; 3.10 (br), 1H (OH); 3.40–3.51 (m), 1H; 3.51–3.62 (m), 1H. 3.65–3.80 (m), 2H.

Example 309 rac-4-Amino-1-methanesulfonyl-piperidin-3-ol

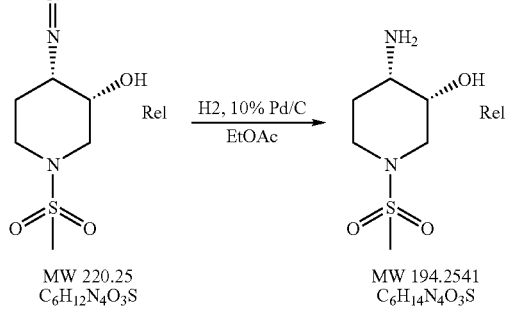

This cis-amino alcohol was made by a similar procedure to the synthesis of Example 305 using material from Example 308 and the compound was used directly for the next step.

Example 310 rac-[4-Amino-2-(3-hydroxy-1-methanesulfonyl-piperidin-4-ylamino)-pyrimidin-5-yl]-(2,3-difluoro-6-methoxy-phenyl)-methanone

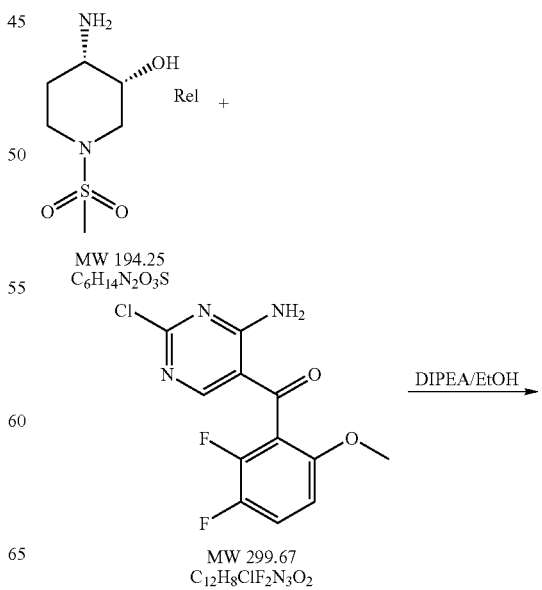

-continued

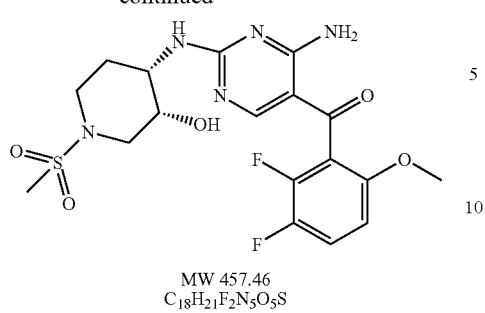

MW 457.46
$C_{18}H_{21}F_2N_5O_5S$

The compound was made with Example 309 and Example 289 by a similar procedure to the synthesis of Example 306. MS (ES) MH$^+$=458.

Example 311 rac-4-Azido-1-methanesulfonyl-3-methoxy-piperidine

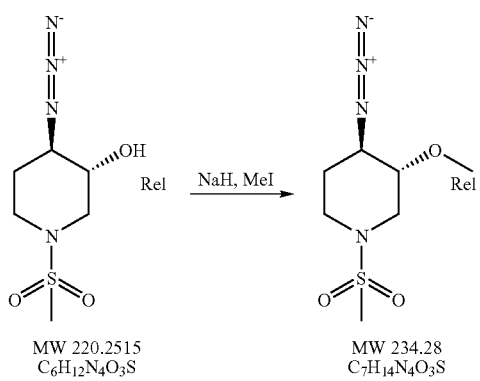

MW 220.2515
$C_6H_{12}N_4O_3S$

MW 234.28
$C_7H_{14}N_4O_3S$

To the stirred solution of the azide (500 mg, 2.27 mmol, Example 304) in tetrahydrofuran (8 mL) at 0° C., sodium hydride (60% in oil dispersion, 180 mg, 4.54 mmol, Aldrich) was added slowly and the mixture was stirred for 30 minutes. Methyl iodide (184 uL, 2.95 mmol, Aldrich) was then added and the mixture was stirred at room temperature overnight. The reaction was quenched with saturated ammonium chloride solution and the mixture was extracted with ethyl acetate. The extract was washed with brine and dried with sodium sulfate. The solvent was removed and the residue was purified by chromatography (15% ethyl acetate/hexanes first and then 35%) to give a yellow oil. 280 mg, 53%.

Example 312 rac-1-Methanesulfonyl-3-methoxy-piperidin-4-ylamine

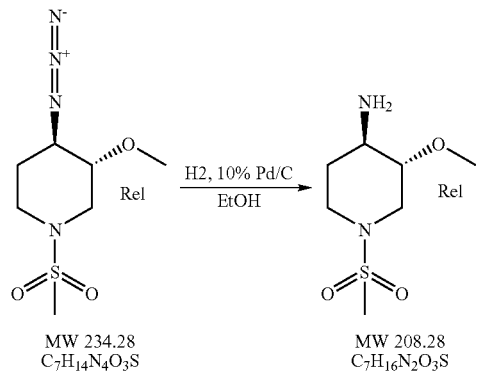

MW 234.28
$C_7H_{14}N_4O_3S$

MW 208.28
$C_7H_{16}N_2O_3S$

The azide (270 mg, 1.15 mmol, Example 311) in ethanol was hydrogenated at 40 psi under the catalysis of palladium on carbon for 1 hour. The mixture was filtered and the filtrate was concentrated to give an off-white solid. 230 mg, 96%. It was used directly for the next step.

Example 313 rac-[4-Amino-2-(1-methanesulfonyl-3-methoxy-piperidin-4-ylamino)-pyrimidin-5-yl]-(2,3-difluoro-6-methoxy-phenyl)-methanone

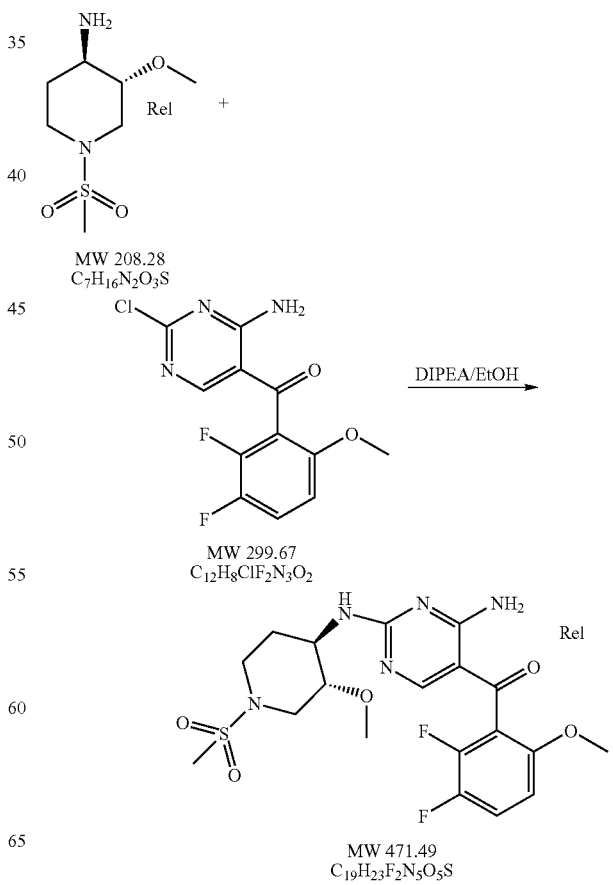

The compound was made with Example 312 and Example 289 by a similar procedure to the synthesis of Example 306. MS (ES) MH+=472.

Example 314 rac-4-[4-Amino-5-(2,3-difluoro-6-methoxy-benzoyl)-pyrimidin-2-ylamino]-1-methanesulfonyl-piperidin-3-one

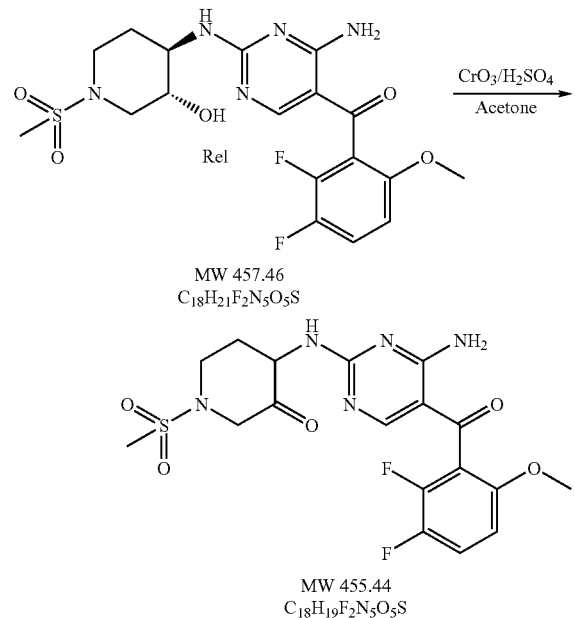

To a stirred solution of alcohol (65 mg, 0.14 mmol, Example 306) in acetone (4 mL), Jones reagent (made by adding 0.5 mL of concentrated sulfuric acid to a solution of chromium(VI) oxide, 0.67 g, Aldrich, in 2 mL of water) was slowly added until the orange color persisted for 20 minutes. The mixture was stirred for 1 hour and 2 mL of isopropanol was added. The mixture was again stirred for 30 minutes followed by slow addition of saturated sodium bicarbonate solution until pH=7. The mixture was extracted with ethyl acetate/tetrahydrofuran (2:1, 3×10 mL) and the extracts were combined and dried with sodium sulfate. The solvent was removed and the residue was chromatographed on HPLC (20–70%) to give a white solid, 4.3 mg, 7%. MS (ES) MH+=456.

Example 315

Hydroxy-azetidine-1-carboxylic acid tert-butyl ester

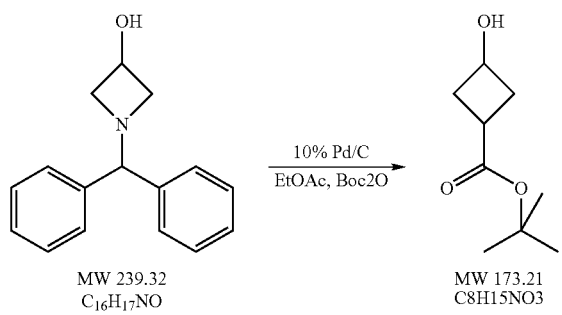

1-(Diphenylmethyl)-3-hydroxyazetidine (300 mg, 1.26 mmol, Oakwood,) was dissolved in ethyl acetate (10 mL). To it 10% palladium on carbon (100 mg) and di-tert-butyl dicarbonate (329 mg, 1.51 mmol, Aldrich) were added and the mixture was hydrogenated at 50 psi overnight. Filtration and removal of solvent gave the desired product. 218 mg, 100%. MS (ES) MH+=174.

Example 316

3-Methanesulfonyloxy-azetidine-1-carboxylic acid tert-butyl ester

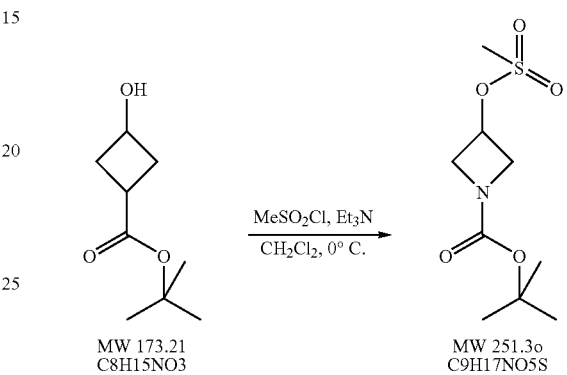

The alcohol (1.0 g, 5.77 mmol, Example 315) was dissolved in methylene chloride (20 mL). To it triethylamine (1.60 mL, 11.54 mmol) and methane sulfonyl chloride (536 uL, 5.77 mmol, Aldrich) were added and the mixture was stirred at 0° C. for 3 hours. The solvent was removed and the residue was partitioned between ethyl acetate and water. The organic layer was separated and dried with sodium sulfate and concentrated to give a white solid. 1.51 g, 100%. The compound was used directly for the next step.

Example 317

3-Azido-azetidine-1-carboxylic acid tert-butyl ester

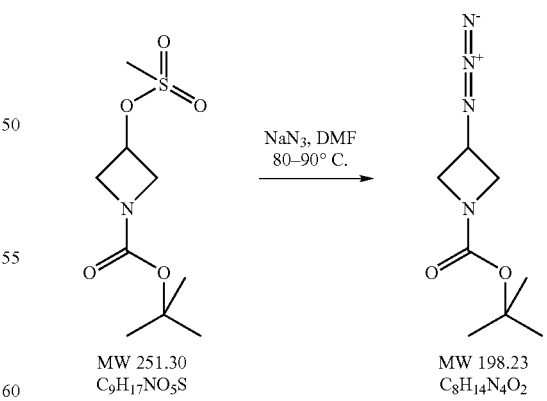

To a stirred solution of methane sulfonate (930 mg, 3.70 mmol, Example 316) in dimethylformamide (20 mL), sodium azide (962 mg, 14.8 mmol, Aldrich) was added and the mixture was stirred at 90° C. overnight. The mixture was poured into water and extracted with ethyl acetate (5×10 mL) and the extracts were combined, washed with water, brine and dried with sodium sulfate. The solvent was removed to give a clear oil. 710 mg, 97%. The compound was directly used for the next step.

Example 318

3-Amino-azetidine-1-carboxylic acid tert-butyl ester

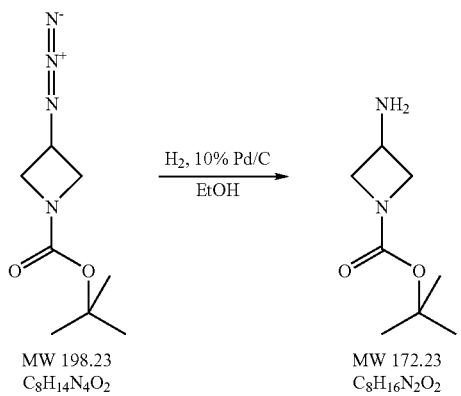

MW 198.23
C$_8$H$_{14}$N$_4$O$_2$

MW 172.23
C$_8$H$_{16}$N$_2$O$_2$

To a stirred solution of the azide (1.15 g, 5.80 mmol, Example 317) in ethanol (20 mL), 10% palladium on carbon (93 mg) was added and the mixture was hydrogenated for 1 hour at 48 psi. The mixture was filtered through a pad of celite and the solvent was removed to a colorless oil. 940 mg, 94%. The compound was directly used for the next step.

Example 319

3-[4-Amino-5-(2,3-difluoro-6-methoxy-benzoyl)-pyrimidin-2-ylamino]-azetidine-1-carboxylic acid tert-butyl ester

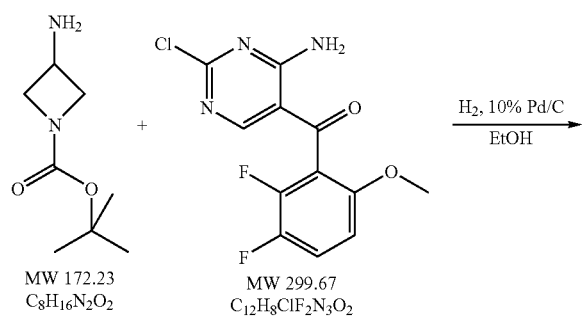

MW 172.23
C$_8$H$_{16}$N$_2$O$_2$

MW 299.67
C$_{12}$H$_8$ClF$_2$N$_3$O$_2$

-continued

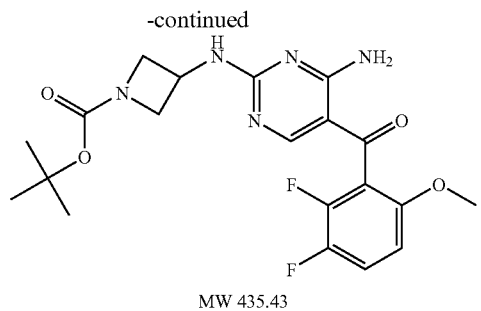

MW 435.43
C$_{20}$H$_{23}$F$_2$N$_5$O$_4$

To a stirred suspension of chloropyrimidine (700 mg, 2.34 mmol, Example 289) in methylene chloride (30 mL), amine (525 mg, 5.64 mmol, Example 318) in ethanol (30 mL) was added and the mixture heated at 80° C. for 4.5 hours. The solvent was removed and the residue was dissolved in ethyl acetate and the mixture was washed successively with 0.5N hydrochloric acid and water. The organic layer was dried with sodium sulfate and concentrated to give a white solid. 1.0 g, 98%. MS (ES) MH$^+$=436.

Example 320

[4-Amino-2-(azetidin-3-ylamino)-pyrimidin-5-yl]-(2,3-difluoro-6-methoxy-phenyl)-methanone

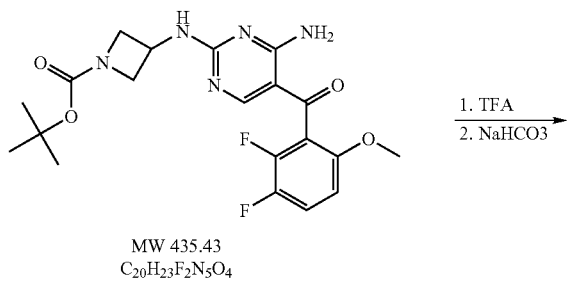

MW 435.43
C$_{20}$H$_{23}$F$_2$N$_5$O$_4$

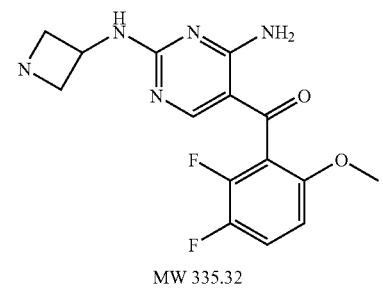

MW 335.32
C$_{15}$H$_{15}$F$_2$N$_5$O$_2$

To a stirred suspension of the protected amine (940 mg, 2.16 mmol, Example 319) in methylene chloride (30 mL), trifluoroacetic acid (20 mL) was added at 0° C. and the mixture stirred for 2 hours. The solvent was removed and the residue was partitioned between ethyl acetate and 5% sodium carbonate solution. The aqueous layer was extracted with ethyl acetate/tetrahydrofuran (1:1, 3×10 ml). The extracts were combined and the solution was dried with sodium sulfate. Removal of solvent gave a yellow solid. 711 mg, 98%. MS (ES) MH$^+$=336.

Example 321

[4-Amino-2-(1-methanesulfonyl-azetidin-3-ylamino)-pyrimidin-5-yl]-(2,3-difluoro-6-methoxy-phenyl)-methanone

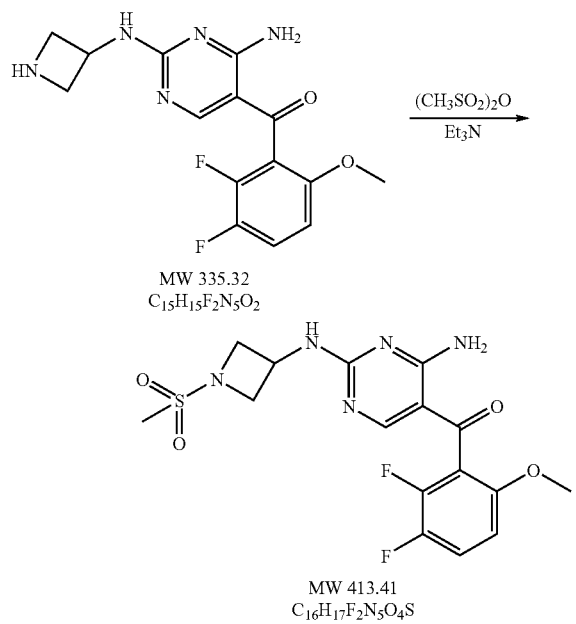

To a stirred solution of amine (80 mg, 0.239 mmol, Example 320) in tetrahydrofuran (30 mL), triethylamine (67 uL, 0.48 mmol) and methane sulfonic anhydride (50 mg, 0.29 mmol) were added successively and the mixture was stirred for 2 hours. Ice water was added and the mixture was extracted with ethyl acetate (3×10 mL). The extracts were combined and dried with sodium sulfate and the solvent was removed to give a yellow solid, which was purified on HPLC (10–80%, acetonitrile/water. 61 mg; 62%. MS (ES) MH$^+$=414.

Example 322

[4-Amino-2-(1-ethanesulfonyl-azetidin-3-ylamino)-pyrimidin-5-yl]-(2,3-difluoro-6-methoxy-phenyl)-methanone

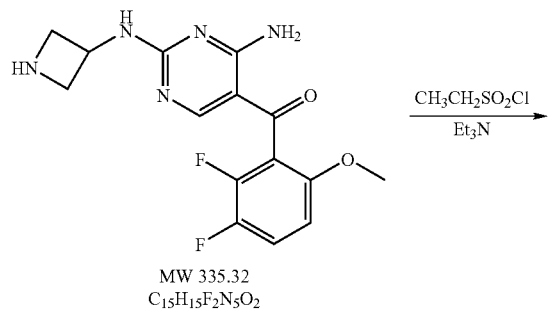

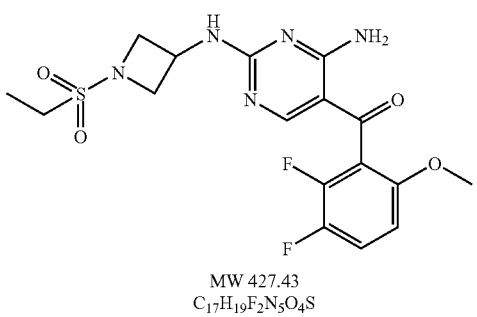

This compound was made with Example 320 and ethyl sulfonyl chloride (Aldrich) by a similar procedure to the synthesis of Example 321. MS (ES) MH$^+$=428.

Example 323

[4-Amino-2-[1-(propane-2-sulfonyl)-azetidin-3-ylamino]-pyrimidin-5-yl]-(2,3-difluoro-6-methoxy-phenyl)-methanone

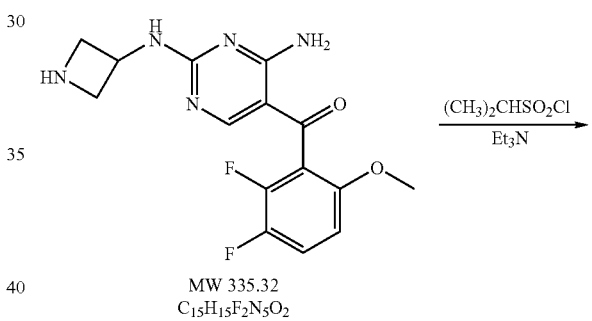

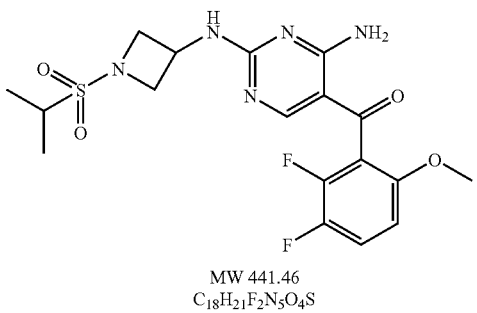

This compound was made with Example 320 and isopropyl sulfonyl chloride (Aldrich) by a similar procedure to the synthesis of Example 321. MS (ES) MH$^+$=442.

Example 324

(4-Amino-2-ethylsulfanyl-pyrimidin-5-yl)-(2-methoxy-5-methyl-phenyl)-methanone

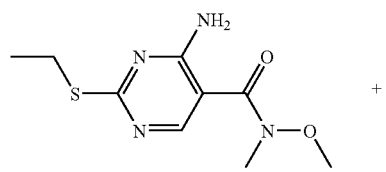

MW 242.30
C₉H₁₄N₄O₂S

+

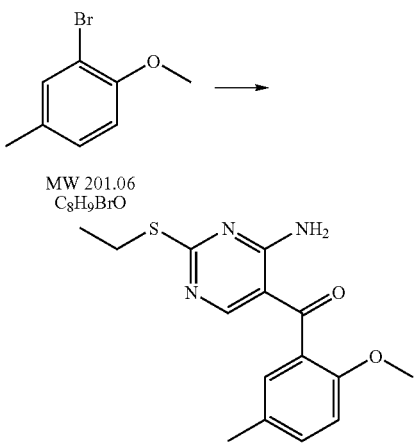

MW 201.06
C₈H₉BrO

MW 303.39
C₁₅H₁₇N₃O₂S

The same procedure as described in Example 47 was used, starting from 4-amino-2-ethylsulfanyl-pyrimidine-5-carboxylic acid methoxy-methyl-amide, Example 1, and 2-bromo-4-methylanisole (Aldrich), to give (4-amino-2-ethylsulfanyl-pyrimidin-5-yl)-(2-methoxy-5-methyl-phenyl)-methanone as a white solid. MS (M+H)⁺, 304.

Example 325

(4-Amino-2-ethanesulfinyl-pyrimidin-5-yl)-(2-methoxy-5-methyl-phenyl)-methanone

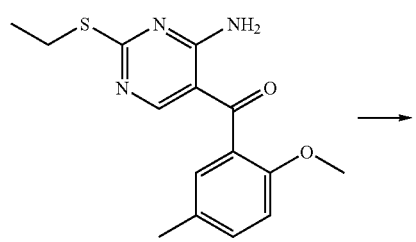

MW 303.39
C₁₅H₁₇N₃O₂S

-continued

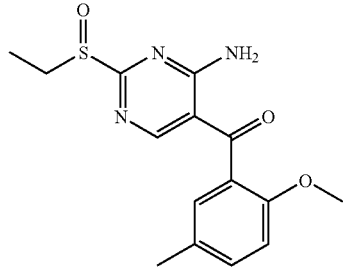

MW 319.39
C₁₅H₁₇N₃O₃S

A solution of (4-amino-2-ethylsulfanyl-pyrimidin-5-yl)-(2-methoxy-5-methyl-phenyl)-methanone, 571 mg, 1.885 mmol, Example 324) in chloroform (16 mL) was cooled to −15° C. and treated with 3-chloroperoxybenzoic acid (503.7 mg, ~2.25 mmol, ~70% purity from Aldrich) and the reaction was stirred at the same temperature for 1 hour. The reaction mixture was diluted with methylene chloride (20 mL) and washed with 10% aqueous sodium thiosulfate (2×5 mL), 10% aqueous sodium carbonate (2×5 mL), brine, dried and concentrated to give (4-amino-2-ethanesulfinyl-pyrimidin-5-yl)-(2-methoxy-5-methyl-phenyl)-methanone as a white solid. MS (M+H)⁺: 320.

Example 326

1-[4-[4-Amino-5-(2-methoxy-5-methyl-benzoyl)-pyrimidin-2-ylamino]-piperidin-1-yl]-ethanone

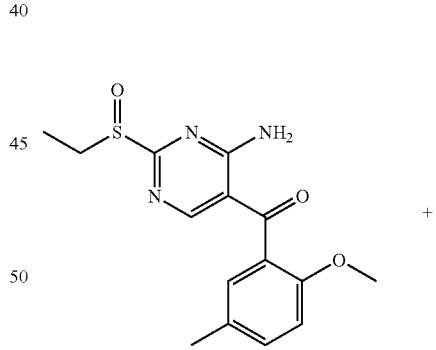

MW 319.39
C₁₅H₁₇N₃O₃S

+

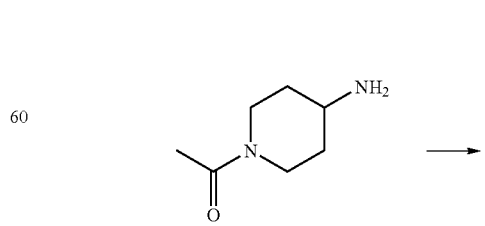

MW 142.20
C₇H₁₄N₂O

-continued

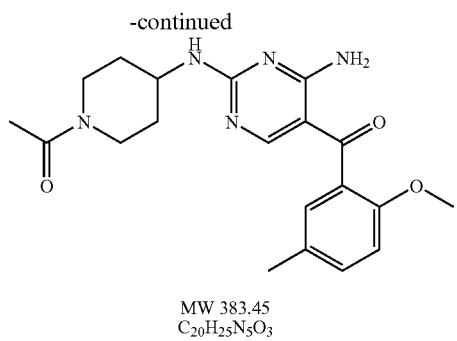

MW 383.45
$C_{20}H_{25}N_5O_3$

-continued

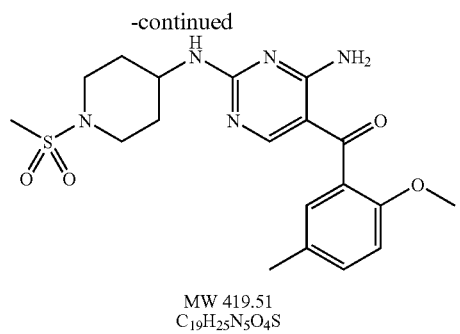

MW 419.51
$C_{19}H_{25}N_5O_4S$

A suspension of (4-amino-2-ethanesulfinyl-pyrimidin-5-yl)-(2-methoxy-5-methyl-phenyl)-methanone (22.3 mg, 0.0698 mmol, Example 325) and 1-(4-amino-piperidin-1-yl)-ethanone (14.9 mg, 0.105 mmol, prepared as described in U.S. Pat. No. 5,817,828) in isopropyl alcohol (2.5 mL) was heated at 120° C. in a sealed tube under microwave conditions for 0.3 to 1 hour. The resulting reaction mixture was evaporated in vacuo and crude product was purified on silica gel with 95:5 of dichloromethane/methanol to give 1-[4-[4-amino-5-(2-methoxy-5-methyl-benzoyl)-pyrimidin-2-ylamino]-piperidin-1-yl]-ethanone as a white solid (23.1 mg). MS (M+H)$^+$, 384.

The same procedure as described in Example 326 was used, starting with (4-amino-2-ethanesulfinyl-pyrimidin-5-yl)-(2-methoxy-5-methyl-phenyl)-methanone (Example 325) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(2-methoxy-5-methyl-phenyl)-methanone. MS (M+H)$^+$, 420

Example 328

(4-Amino-2-ethylsulfanyl-pyrimidin-5-yl)-(2,5-dimethoxy-phenyl)-methanone

Example 327

[4-Amino-2-(1-methanesulfonyl-piperidin-4-ylamino)-pyrimidin-5-yl]-(2-methoxy-5-methyl-phenyl)-methanone

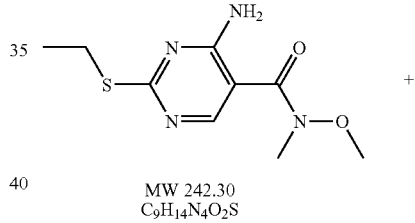

MW 242.30
$C_9H_{14}N_4O_2S$

+

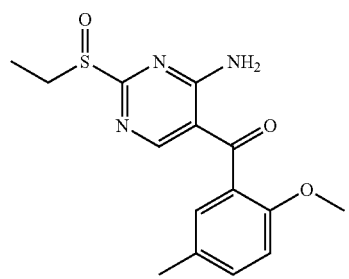

MW 319.39
$C_{15}H_{17}N_3O_3S$

+

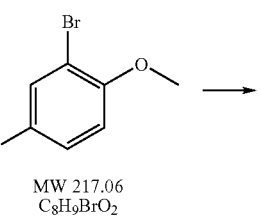

MW 217.06
$C_8H_9BrO_2$

→

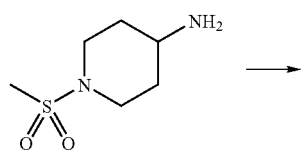

MW 178.25
$C_6H_{14}N_2O_2S$

→

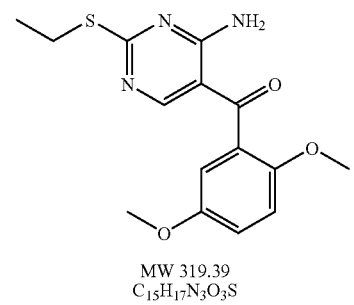

MW 319.39
$C_{15}H_{17}N_3O_3S$

The same procedure as described in Example 47 was used, starting from 4-amino-2-ethylsulfanyl-pyrimidine-5-carboxylic acid methoxy-methyl-amide, (Example 1), and 2-bromo-4-methoxyanisole (Aldrich), to give (4-amino-2-ethylsulfanyl-pyrimidin-5-yl)-(2,5-dimethoxy-phenyl)-methanone as a white solid. MS (M+H)+, 320.

Example 329

(4-Amino-2-ethanesulfinyl-pyrimidin-5-yl)-(2,5-Dimethoxyphenyl)-methanone

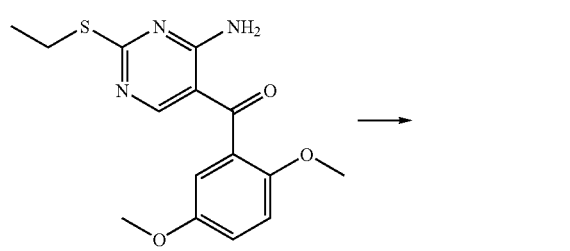

MW 319.39
C15H17N3O3S

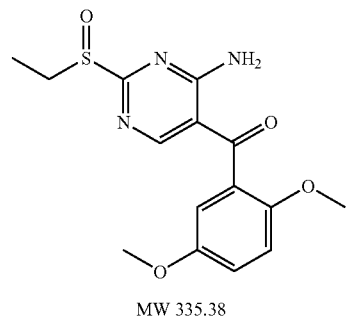

MW 335.38
C15H17N3O4S

The same procedure as described in Example 325 was used, starting from (4-amino-2-ethylsulfanyl-pyrimidin-5-yl)-(2,5-dimethoxy-phenyl)-methanone (Example 328) to give (4-amino-2-ethanesulfinyl-pyrimidin-5-yl)-(2,5-dimethoxyphenyl)-methanone as a white solid. MS (M+H)+: 336

Example 330

1-[4-[4-Amino-5-(2,5-dimethoxy-benzoyl)-pyrimidin-2-ylamino]-piperidin-1-yl]-ethanone

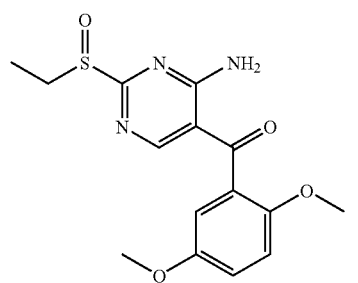

MW 335.38
C15H17N3O4S

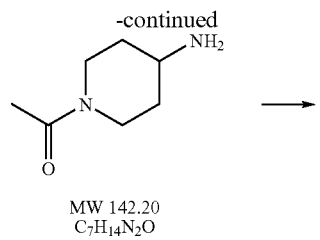

MW 142.20
C7H14N2O

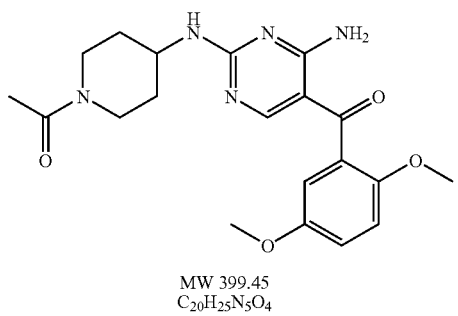

MW 399.45
C20H25N5O4

The same procedure as described in Example 326 was used, starting with (4-amino-2-ethanesulfinyl-pyrimidin-5-yl)-(2,5-dimethoxyphenyl)-methanone (Example 329) and 1-(4-amino-piperidin-1-yl)-ethanone to give 1-[4-[4-amino-5-(2,5-dimethoxy-benzoyl)-pyrimidin-2-ylamino]-piperidin-1-yl]-ethanone as a white solid. MS (M+H)+, 400.

Example 331

[4-Amino-2-(1-methanesulfonyl-piperidin-4-ylamino)-pyrimidin-5-yl]-(2,5-dimethoxy-phenyl)-methanone

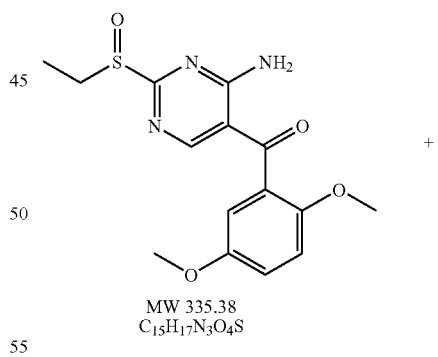

MW 335.38
C15H17N3O4S

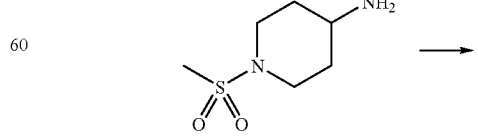

MW 178.25
C6H14N2O2S

-continued

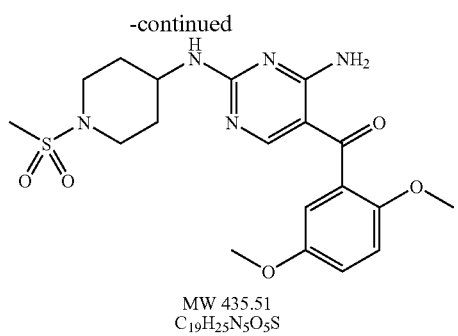

MW 435.51
C₁₉H₂₅N₅O₅S

The same procedure as described in Example 326 was used, starting with 1-[4-[4-amino-5-(2,5-dimethoxy-benzoyl)-pyrimidin-2-ylamino]-piperidin-1-yl]-ethanone (Example 330) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(2,5-dimethoxy-phenyl)-methanone. MS (M+H)⁺, 436

Example 332

(4-Amino-2-ethylsulfanyl-pyrimidin-5-yl)-(2,6-dimethoxy-phenyl)-methanone

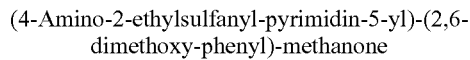

MW 242.30
C₉H₁₄N₄O₂S

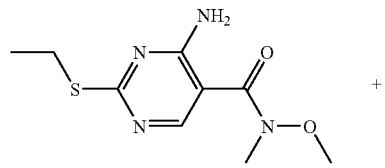

MW 217.06
C₈H₉BrO₂

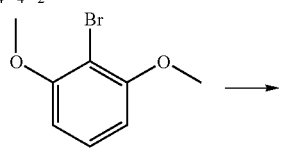

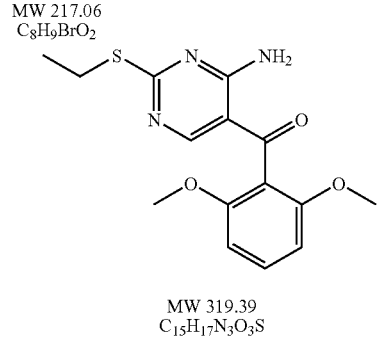

MW 319.39
C₁₅H₁₇N₃O₃S

The same procedure as described in Example 47 was used, starting from 4-amino-2-ethylsulfanyl-pyrimidine-5-carboxylic acid methoxy-methyl-amide (Example 1) and 2-bromo-3-methoxyanisole (Aldrich), to give (4-amino-2-ethylsulfanyl-pyrimidin-5-yl)-(2,6-dimethoxy-phenyl)-methanone as a white solid. MS (M+H)⁺, 320.

Example 333

(4-Amino-2-ethanesulfinyl-pyrimidin-5-yl)-(2,5-Dimethoxyphenyl)-methanon

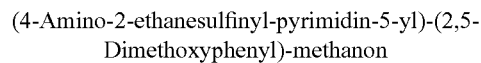

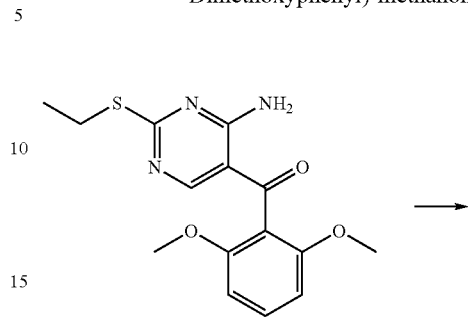

MW 319.39
C₁₅H₁₇N₃O₃S

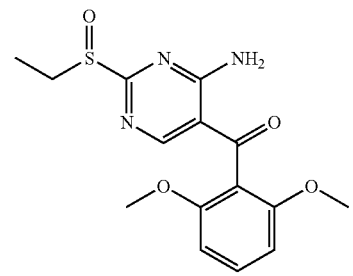

MW 335.38
C₁₅H₁₇N₃O₄S

The same procedure as described in Example 325 was used, starting from (4-amino-2-ethylsulfanyl-pyrimidin-5-yl)-(2,6-dimethoxy-phenyl)-methanone Example 328 to give (4-amino-2-ethanesulfinyl-pyrimidin-5-yl)-(2,6-dimethoxyphenyl)-methanone as a white solid. MS (M+H)⁺: 336

Example 334

1-[4-[4-Amino-5-(2,6-dimethoxy-benzoyl)-pyrimidin-2-ylamino]-piperidin-1-yl]-ethanone

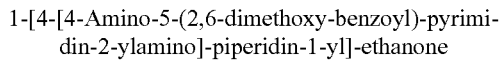

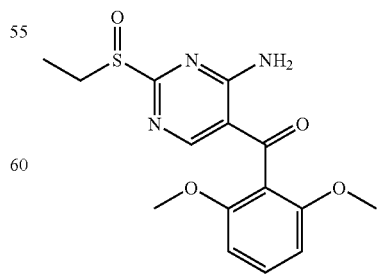

MW 335.38
C₁₅H₁₇N₃O₄S

-continued

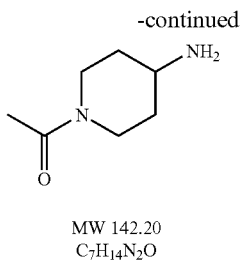

MW 142.20
C₇H₁₄N₂O

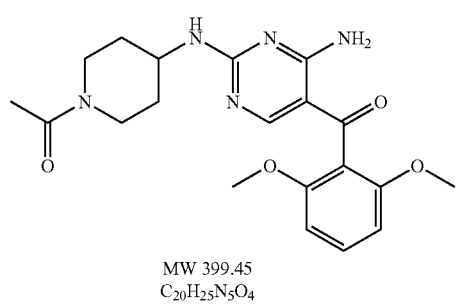

MW 399.45
C₂₀H₂₅N₅O₄

The same procedure as described in Example 326 was used, starting with (4-amino-2-ethanesulfinyl-pyrimidin-5-yl)-(2,6-dimethoxyphenyl)-methanone (Example 333) and 1-(4-amino-piperidin-1-yl)-ethanone to give 1-[4-[4-amino-5-(2,6-dimethoxy-benzoyl)-pyrimidin-2-ylamino]-piperidin-1-yl]-ethanone as a white solid. MS (M+H)⁺, 400.

Example 335

[4-Amino-2-(1-methanesulfonyl-piperidin-4-ylamino)-pyrimidin-5-yl]-(2,6-dimethoxy-phenyl)-methanone

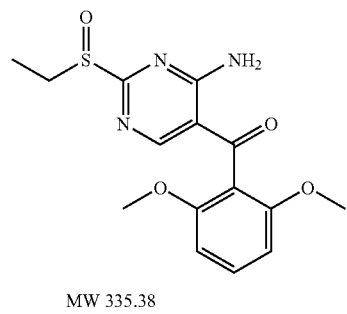

MW 335.38
C₁₅H₁₇N₃O₄S

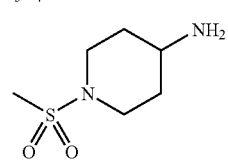

MW 178.25
C₆H₁₄N₂O₂S

-continued

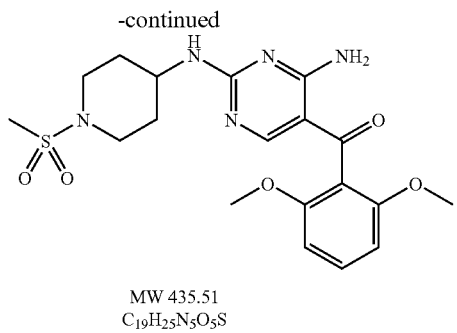

MW 435.51
C₁₉H₂₅N₅O₅S

The same procedure as described in Example 326 was used, starting with 1-[4-[4-amino-5-(2,6-dimethoxy-benzoyl)-pyrimidin-2-ylamino]-piperidin-1-yl}-ethanone (Example 333) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(2,6-dimethoxy-phenyl)-methanone. MS (M+H)⁺, 436

Example 336

[4-[4-Amino-5-(2-methoxy-5-methyl-benzyl)-pyrimidin-2-ylamino]-cyclohexyl]-carbamic acid tert-butyl ester

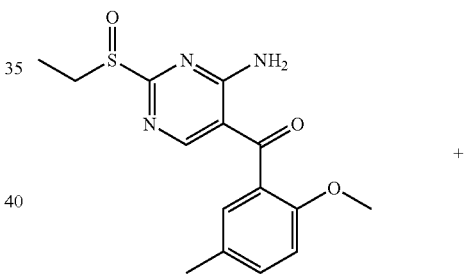

MW 319.39
C₁₅H₁₇N₃O₃S

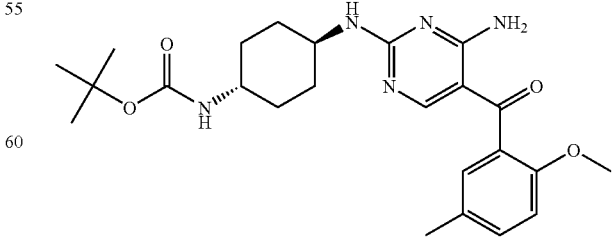

MW 214.31
C₁₁H₂₂N₂O₂

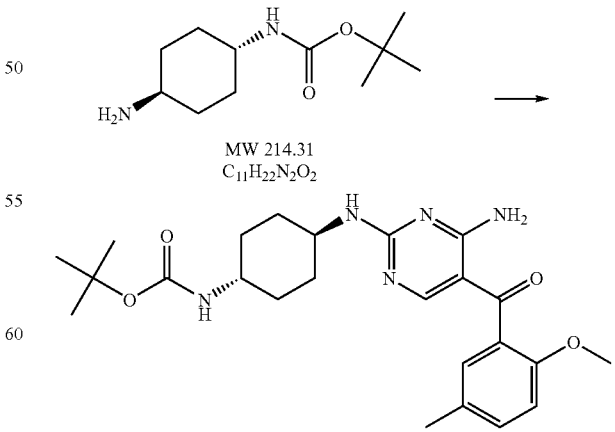

MW 455.56
C₂₄H₃₃N₅O₄

The same procedure as described in Example 326 was used, starting with (4-amino-2-ethanesulfinyl-pyrimidin-5-yl)-(2,5-dimethoxyphenyl)-methanone (Example 325) and (trans-4-amino-cyclohexyl)-carbamic acid tert-butyl ester (Astatech) to give [4-[4-amino-5-(2-methoxy-5-methyl-benzoyl)-pyrimidin-2-ylamino]-cyclohexyl]-carbamic acid tert-butyl ester as a white solid. MS (M+H)+, 456

Example 337

[4-Amino-2-(4-amino-cyclohexylamino)-pyrimidin-5-yl]-(2-methoxy-5-methyl-phenyl)-methanone

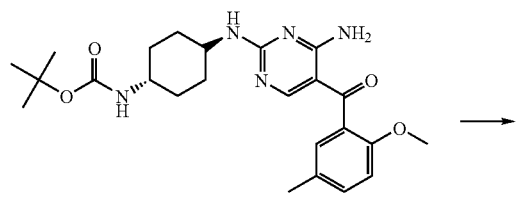

MW 455.56
C24H33N5O4

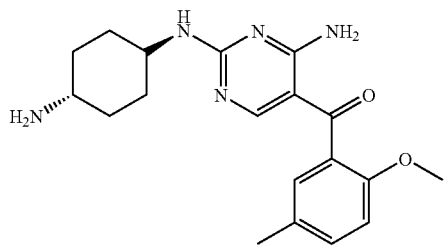

MW 355.44
C19H25N5O2

The same procedure was used as described in Example 59, using material from Example 336, to give [4-amino-2-(4-amino-cyclohexylamino)-pyrimidin-5-yl]-(2-methoxy-5-methyl-phenyl)-methanone as the free base. MS (M+H)+, 356.

Example 338

N-[4-[4-Amino-5-(2-methoxy-5-methyl-benzoyl)-pyrimidin-2-ylamino]-cyclohexyl]-acetamide

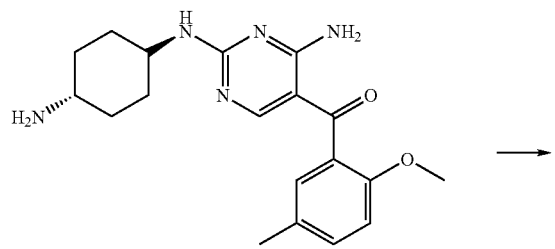

MW 355.44
C19H25N5O2

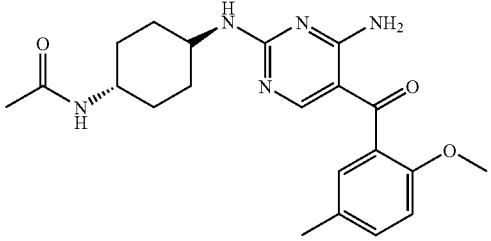

MW397.48
C19H27N5O3

The similar procedure as described in Example 60 was used, starting from [4-amino-2-(4-amino-cyclohexylamino)-pyrimidin-5-yl]-(2-methoxy-5-methyl-phenyl)-methanone (Example 337) and acetyl chloride (Aldrich) to give N-[4-[4-amino-5-(2-methoxy-5-methyl-benzoyl)-pyrimidin-2-ylamino]-cyclohexyl]-acetamide. MS (M+H)+, 398.

Example 339

N-[4-[4-Amino-5-(2-methoxy-5-methyl-benzoyl)-pyrimidin-2-ylamino]-cyclohexyl]-methanesulfonamide

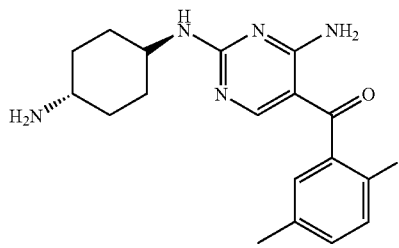

MW 355.44
C19H25N5O2

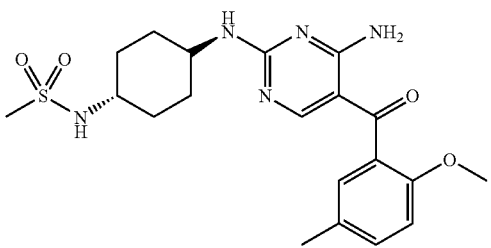

MW 433.53
C20H27N5O4S

A similar procedure as described in Example 60 was used, starting from [4-amino-2-(4-amino-cyclohexylamino)-pyrimidin-5-yl]-(2-methoxy-5-methyl-phenyl)-methanone (Example 337) and methanesulfonyl chloride (Aldrich) to give N-[4-[4-amino-5-(2-methoxy-5-methyl-benzoyl)-pyrimidin-2-ylamino]-cyclohexyl]-methanesulfonamide. MS (M+H)+, 398.

Example 340

(4-Amino-2-ethylsulfanyl-pyrimidin-5-yl)-(5-fluoro-2-methoxy-4-methyl-phenyl)-methanone and (4-Amino-2-ethylsulfanyl-pyrimidin-5-yl)-(3-fluoro-6-methoxy-2-methyl-phenyl)-methanone

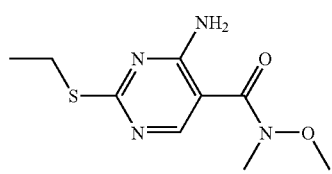

MW 242.30
$C_9H_{14}N_4O_2S$

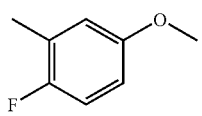

MW 140.16
$C_8H_9FO$

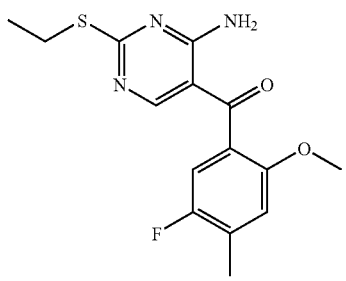

MW 321.38
$C_{15}H_{16}FN_3O_2S$

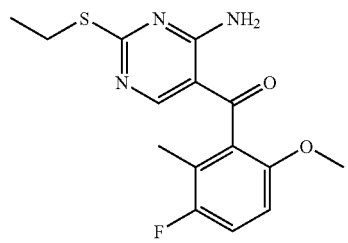

MW 321.38
$C_{15}H_{16}FN_3O_2S$

The same procedure as described in Example 170 was used, starting from 4-amino-2-ethylsulfanyl-pyrimidine-5-carboxylic acid methoxy-methyl-amide (Example 1) and 4-fluoro-3-methylanisole (Aldrich), to give (4-amino-2-ethylsulfanyl-pyrimidin-5-yl)-(5-fluoro-2-methoxy-4-methyl-phenyl)-methanone as a white solid, MS (M+H)+, 322 and (4-amino-2-ethylsulfanyl-pyrimidin-5-yl)-(3-fluoro-6-methoxy-2-methyl-phenyl)-methanone as a white solid, MS (M+H)+, 322

Example 341
(4-Amino-2-ethanesulfinyl-pyrimidin-5-yl)-(5-fluoro-2-methoxy-4-methyl-phenyl)-methanone

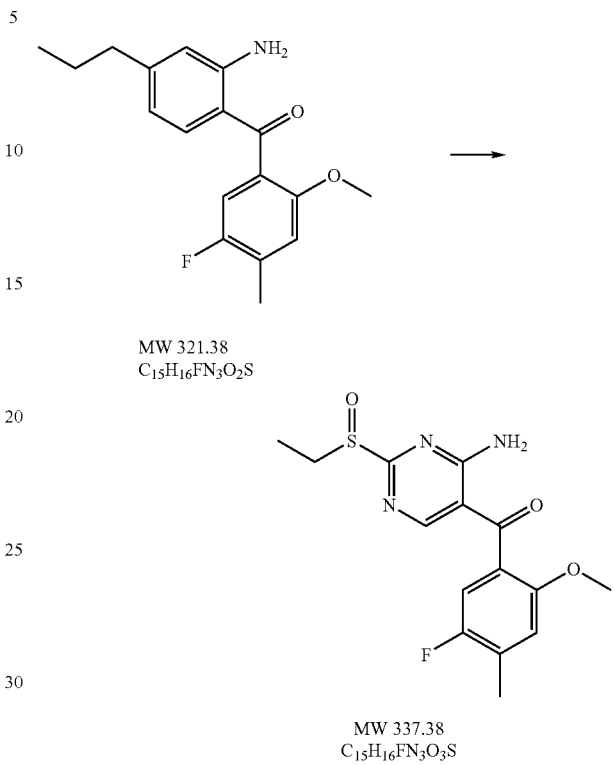

MW 321.38
$C_{15}H_{16}FN_3O_2S$

MW 337.38
$C_{15}H_{16}FN_3O_3S$

The procedure as described in Example 325 was used, starting from (4-amino-2-ethylsulfanyl-pyrimidin-5-yl)-(5-fluoro-2-methoxy-4-methyl-phenyl)-methanone (Example 340) to give (4-amino-2-ethanesulfinyl-pyrimidin-5-yl)-(5-fluoro-2-methoxy-4-methyl-phenyl)-methanone as a white solid. MS (M+H)+: 338

Example 342
1-[4-[4-Amino-5-(5-fluoro-2-methoxy-4-methyl-benzoyl)-pyrimidin-2-ylamino]-piperidin-1-yl]-ethanone

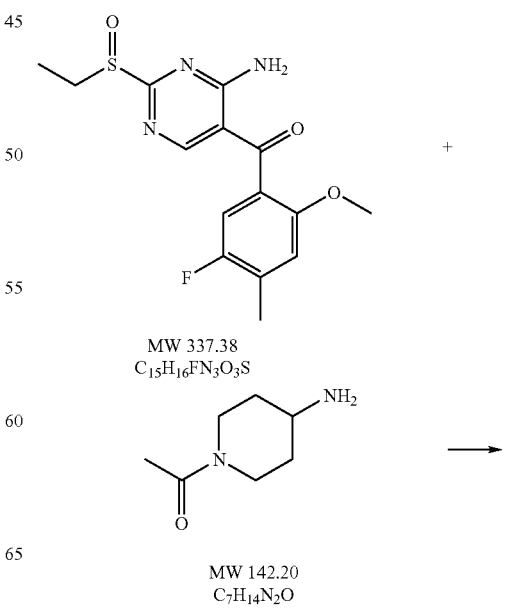

MW 337.38
$C_{15}H_{16}FN_3O_3S$

MW 142.20
$C_7H_{14}N_2O$

283

-continued

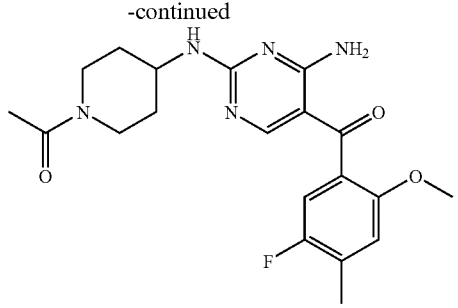

MW 401.44
$C_{20}H_{24}FN_5O_3$

The same procedure as described in Example 326 was used, starting with (4-amino-2-ethanesulfinyl-pyrimidin-5-yl)-(5-fluoro-2-methoxy-4-methyl-phenyl)-methanone (Example 341) and 1-(4-amino-piperidin-1-yl)-ethanone to give 1-[4-[4-amino-5-(5-fluoro-2-methoxy-4-methyl-benzoyl)-pyrimidin-2-ylamino]-piperidin-1-yl]-ethanone as a white solid. MS (M+H)$^+$, 402.

Example 343

[4-Amino-2-(1-methanesulfonyl-piperidin-4-ylamino)-pyrimidin-5-yl]-(5-fluoro-2-methoxy-4-methyl-phenyl)-methanone

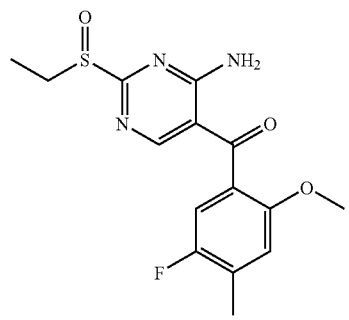

MW 337.38
$C_{15}H_{16}FN_3O_3S$

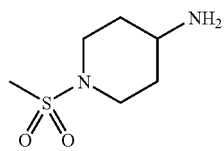

MW 178.25
$C_6H_{14}N_2O_2S$

284

-continued

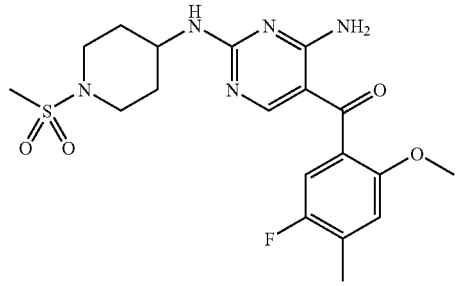

MW 437.50
$C_{19}H_{24}FN_5O_4S$

The same procedure as described in Example 326 was used, starting with 1-[4-[4-amino-5-(5-fluoro-2-methoxy-4-methyl-benzoyl)-pyrimidin-2-ylamino]-piperidin-1-yl]-ethanone (Example 341) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(5-fluoro-2-methoxy-4-methyl-phenyl)-methanone. MS (M+H)$^+$, 436

Example 344

[4-[4-Amino-5-(5-fluoro-2-methoxy-4-methyl-benzoyl)-pyrimidin-2-ylamino]-cyclohexyl]-carbamic acid tert-butyl ester

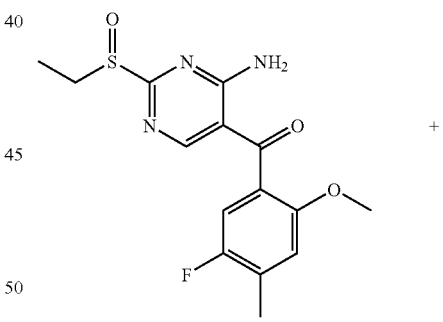

MW 337.38
$C_{15}H_{16}FN_3O_3S$

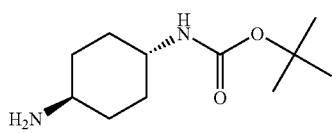

MW 214.31
$C_{11}H_{22}N_2O_2$

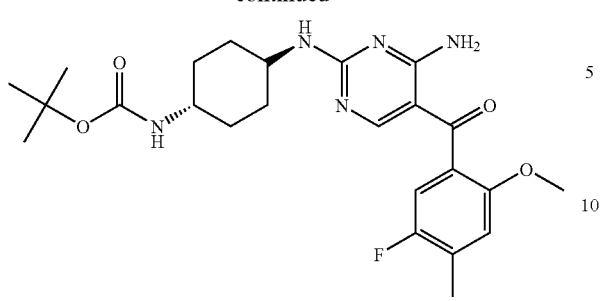

MW 473.55
C₂₄H₃₂FN₅O₄

The same procedure as described in Example 326 was used, starting with (4-amino-2-ethanesulfinyl-pyrimidin-5-yl)-(5-fluoro-2-methoxy-4-methyl-phenyl)-methanone (Example 341) and (trans-4-amino-cyclohexyl)-carbamic acid tert-butyl ester (Astatech) to give [4-[4-amino-5-(5-fluoro-2-methoxy-4-methyl-benzoyl)-pyrimidin-2-ylamino]-cyclohexyl]-carbamic acid tert-butyl ester as a white solid. MS (M+H)⁺, 474

Example 345

[4-Amino-2-(4-amino-cyclohexylamino)-pyrimidin-5-yl]-(5-fluoro-2-methoxy-4-methyl-phenyl)-methanone

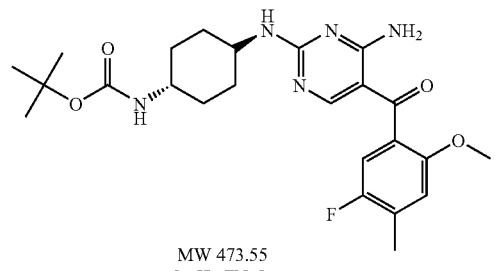

MW 473.55
C₂₄H₃₂FN₅O₄

MW 373.43
C₁₉H₂₄FN₅O₂

The same procedure was used as described in Example 59, using material from Example 344, to give [4-amino-2-(4-amino-cyclohexylamino)-pyrimidin-5-yl]-(5-fluoro-2-methoxy-4-methyl-phenyl)-methanone as the free base. MS (M+H)⁺, 374.

Example 346

N-[4-[4-Amino-5-(5-fluoro-2-methoxy-4-methyl-benzoyl)-pyrimidin-2-ylamino]-cyclohexyl]-acetamide

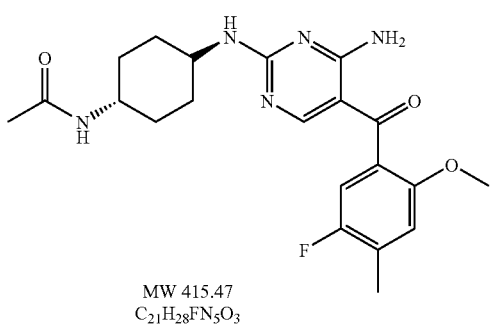

MW 373.43
C₁₉H₂₄FN₅O₂

MW 415.47
C₂₁H₂₈FN₅O₃

The similar procedure as described in Example 60 was used, starting from [4-amino-2-(4-amino-cyclohexylamino)-pyrimidin-5-yl]-(5-fluoro-2-methoxy-4-methyl-phenyl)-methanone (Example 345) and acetyl chloride (Aldrich) to give N-[4-[4-amino-5-(5-fluoro-2-methoxy-4-methyl-benzoyl)-pyrimidin-2-ylamino]-cyclohexyl]-acetamide. MS (M+H)⁺, 416.

Example 347

N-[4-[4-Amino-5-(5-fluoro-2-methoxy-4-methyl-benzoyl)-pyrimidin-2-ylamino]-cyclohexyl]-methanesulfonamide

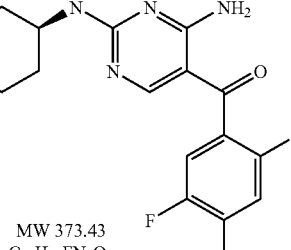

MW 373.43
C₁₉H₂₄FN₅O₂

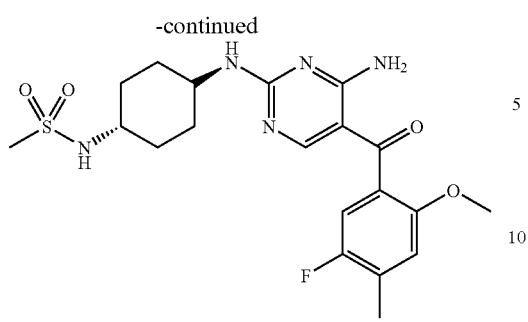

MW 451.51
C$_{20}$H$_{26}$FN$_5$O$_4$S

The similar procedure as described in Example 60 was used, starting from [4-amino-2-(4-amino-cyclohexylamino)-pyrimidin-5-yl]-(5-fluoro-2-methoxy-4-methyl-phenyl)-methanone (Example 345) and methanesulfonyl chloride (Aldrich) to give N-[4-[4-amino-5-(5-fluoro-2-methoxy-4-methyl-benzoyl)-pyrimidin-2-ylamino]-cyclohexyl]-methanesulfonamide. MS (M+H)$^+$, 452.

Example 348

[4-Amino-2-(1-methanesulfonyl-piperidin-4-ylamino)-pyrimidin-5-yl]-(3-fluoro-2,6-dimethoxy-phenyl)-methanone

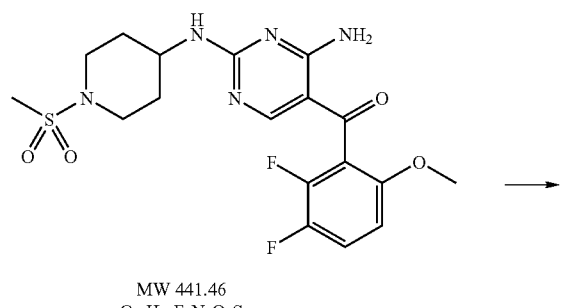

MW 441.46
C$_{18}$H$_{21}$F$_2$N$_5$O$_4$S

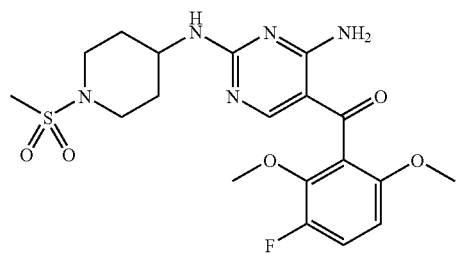

MW 453.50
C$_{19}$H$_{24}$FN$_5$O$_5$S

A solution of [4-amino-2-(1-methanesulfonyl-piperidin-4-ylamino)-pyrimidin-5-yl]-(2,3-difluoro-6-methoxy-phenyl)-methanone (49.7 mmol, 0.112 mmol, Example 105) in methanol (4 mL) was treated with sodium methoxide (25 wt % in methanol, 0.29 mL, Aldrich) and heated at 130° C. in microwave for 3 hours. The reaction was concentrated and the crude product was purified on silica gel (95:5 methylene chloride/methanol) to give [4-amino-2-(1-methanesulfonyl-piperidin-4-ylamino)-pyrimidin-5-yl]-(3-fluoro-2,6-dimethoxy-phenyl)-methanone as a white solid. MS (M+H)$^+$, 454.

Example 349

[4-Amino-2-(1-methanesulfonyl-piperidin-4-ylamino)-pyrimidin-5-yl]-(2-ethoxy-3-fluoro-6-methoxy-phenyl)-methanone

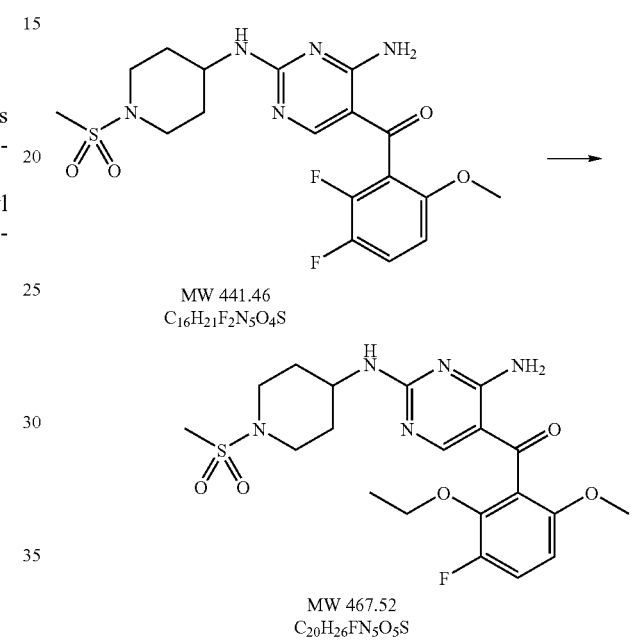

MW 441.46
C$_{16}$H$_{21}$F$_2$N$_5$O$_4$S

MW 467.52
C$_{20}$H$_{26}$FN$_5$O$_5$S

In a similar procedure as described in Example 348, sodium ethoxide in ethanol was used to give [4-amino-2-(1-methanesulfonyl-piperidin-4-ylamino)-pyrimidin-5-yl]-(2-ethoxy-3-fluoro-6-methoxy-phenyl)-methanone as a slightly yellow solid. MS (M+H)$^+$, 468.

Example 350

(4-Amino-2-ethanesulfinyl-pyrimidin-5-yl)-(3-fluoro-6-methoxy-2-methyl-phenyl)-methanone

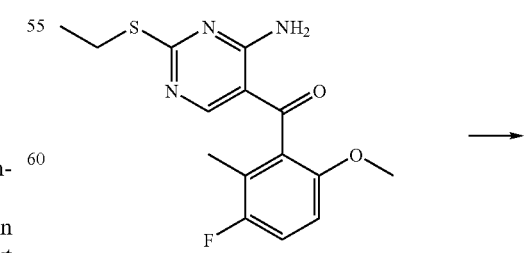

MW 321.38
C$_{15}$H$_{16}$FN$_3$O$_2$S

-continued

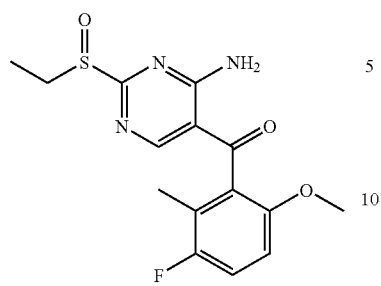

MW 337.38
C₁₅H₁₆FN₃O₃S

The procedure as described in Example 325 was used, starting from (4-amino-2-ethylsulfanyl-pyrimidin-5-yl)-(3-fluoro-6-methoxy-2-methyl-phenyl)-methanone (Example 340) to give (4-amino-2-ethanesulfinyl-pyrimidin-5-yl)-(3-fluoro-6-methoxy-2-methyl-phenyl)-methanone. MS (M+H)⁺: 338

Example 351

1-[4-[4-Amino-5-(3-fluoro-6-methoxy-2-methyl-benzoyl)-pyrimidin-2-ylamino]-piperidin-1-yl]-ethanone

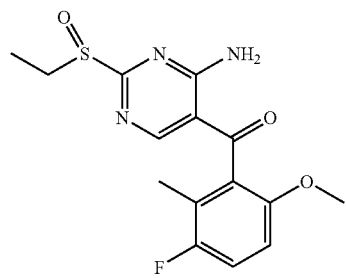

MW 337.38
C₁₅H₁₆FN₃O₃S

+

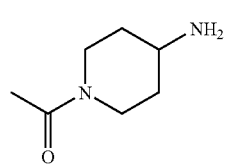

MW 142.20
C₇H₁₄N₂O

→

-continued

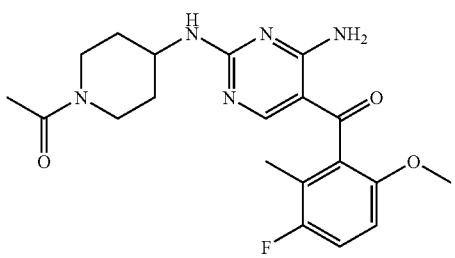

MW 401.44
C₂₀H₂₄FN₅O₃

The same procedure as described in Example 326 was used, starting with (4-amino-2-ethanesulfinyl-pyrimidin-5-yl)-(3-fluoro-6-methoxy-2-methyl-phenyl)-methanone (Example 350) and 1-(4-amino-piperidin-1-yl)-ethanone to give 1-[4-[4-amino-5-(3-fluoro-6-methoxy-2-methyl-benzoyl)-pyrimidin-2-ylamino]-piperidin-1-yl]-ethanone as a white solid. MS (M+H)⁺, 402.

Example 352

[4-Amino-2-(1-methanesulfonyl-piperidin-4-ylamino)-pyrimidin-5-yl]-(3-fluoro-6-methoxy-2-methyl-phenyl)-methanone

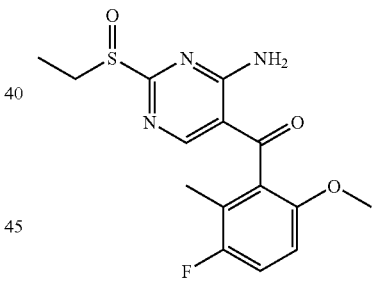

MW 337.38
C₁₅H₁₆FN₃O₃S

+

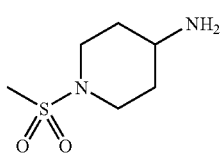

MW 178.25
C₆H₁₄N₂O₂S

→

-continued

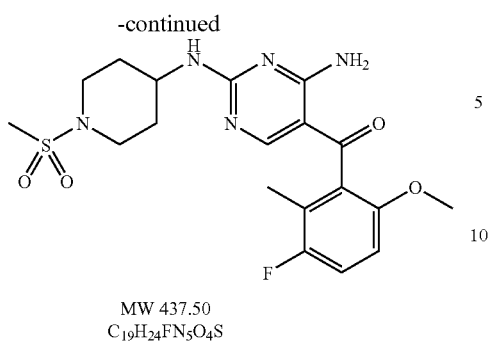

MW 437.50
$C_{19}H_{24}FN_5O_4S$

The same procedure as described in Example 326 was used, starting with (4-amino-2-ethanesulfinyl-pyrimidin-5-yl)-(3-fluoro-6-methoxy-2-methyl-phenyl)-methanone (Example 350) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(3-fluoro-6-methoxy-2-methyl-phenyl)-methanone. MS (M+H)$^+$, 438

Example 353

(4-Amino-2-ethylsulfanyl-pyrimidin-5-yl)-p-tolyl-methanone

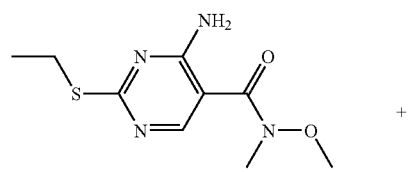

MW 242.30
$C_9H_{14}O_2S$

+

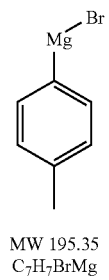

MW 195.35
$C_7H_7BrMg$

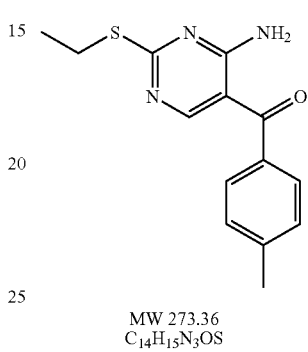 

MW 273.36
$C_{14}H_{15}N_3OS$

To a solution of 4-amino-2-ethylsulfanyl-pyrimidine-5-carboxylic acid methoxy-methyl-amide (500 mg, 2.06 mmol, Example 1) in dry tetrahydrofuran (6 mL) at −30~−40° C., was added 4-tolylmagnesium bromide (10.5 mL, Aldrich). The reaction was stirred at the same temperature for 2 hours before quenching with aqueous ammonium chloride. Work-up and purification as in Example 47 gave (4-amino-2-ethylsulfanyl-pyrimidin-5-yl)-p-tolyl-methanone as a white solid. MS (M+H)$^+$, 274.

Example 354

(4-Amino-2-ethanesulfinyl-pyrimidin-5-yl)-p-tolyl-methanone

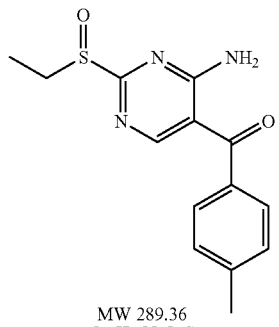

MW 273.36
$C_{14}H_{15}N_3OS$

→

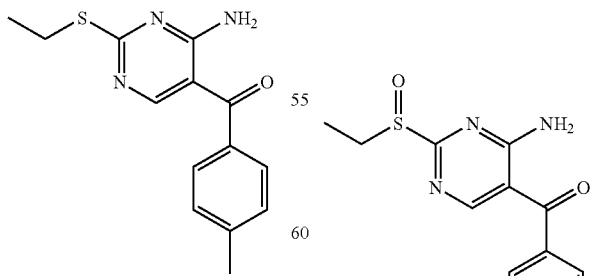

MW 289.36
$C_{14}H_{15}N_3O_2S$

The same procedure as described in Example 325 was used, starting from (4-amino-2-ethylsulfanyl-pyrimidin-5-yl)-p-tolyl-methanone (Example 353) to give (4-amino-2-ethanesulfinyl-pyrimidin-5-yl)-p-tolyl-methanone as a white solid. MS (M+H)$^+$: 290

Example 355

1-[4-[4-Amino-5-(4-methyl-benzoyl)-pyrimidin-2-ylamino]-piperidin-1-yl]-ethanone

+

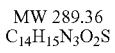

MW 289.36
$C_{14}H_{15}N_3O_2S$

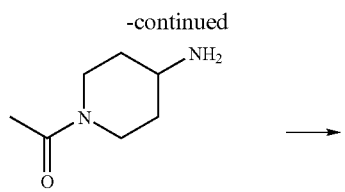

MW 142.20
C₇H₁₄N₂O

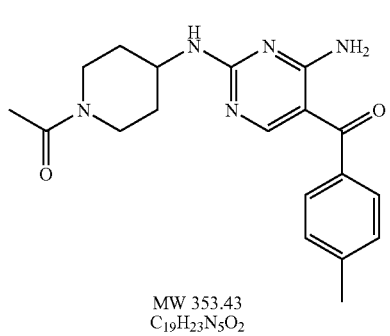

MW 353.43
C₁₉H₂₃N₅O₂

The same procedure as described in Example 326 was used, starting with (4-amino-2-ethanesulfinyl-pyrimidin-5-yl)-p-tolyl-methanone (Example 354) and 1-(4-amino-piperidin-1-yl)-ethanone to give 1-[4-[4-amino-5-(4-methyl-benzoyl)-pyrimidin-2-ylamino]-piperidin-1-yl]-ethanone as a white solid. MS (M+H)⁺, 354.

Example 356

[4-Amino-2-(1-methanesulfonyl-piperidin-4-ylamino)-pyrimidin-5-yl]-p-tolyl-methanone

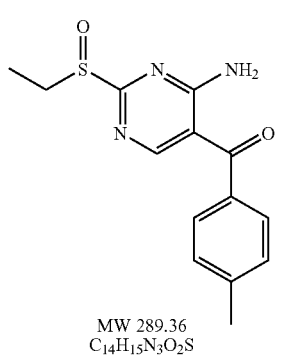

MW 289.36
C₁₄H₁₅N₃O₂S

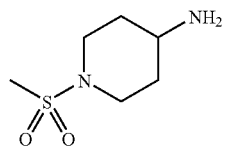

MW 178.25
C₆H₁₄N₂O₂S

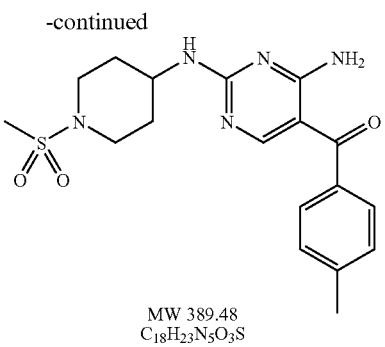

MW 389.48
C₁₈H₂₃N₅O₃S

The same procedure as described in Example 326 was used, starting with (4-amino-2-ethanesulfinyl-pyrimidin-5-yl)-p-tolyl-methanone (Example 354) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-p-tolyl-methanone. MS (M+H)⁺, 390

Example 357

(4-Amino-2-ethylsulfanyl-pyrimidin-5-yl)-4-methoxy-phenyl-methanone

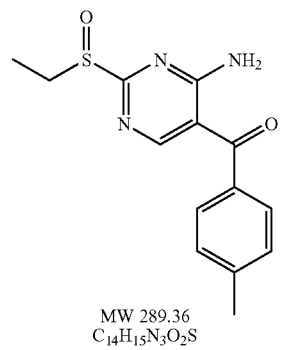

MW 289.36
C₁₄H₁₅N₃O₂S

The same procedure as described in Example 353 was used, starting from 4-amino-2-ethylsulfanyl-pyrimidine-5-carboxylic acid methoxy-methyl-amide (Example 1) and 4-methoxyphenylmagnesium bromide (Aldrich) to give (4-amino-2-ethylsulfanyl-pyrimidin-5-yl)-4-methoxy-phenyl-methanone. MS (M+H)+, 290.

Example 358

(4-Amino-2-ethanesulfinyl-pyrimidin-5-yl)-(4-methoxy-phenyl)-methanon

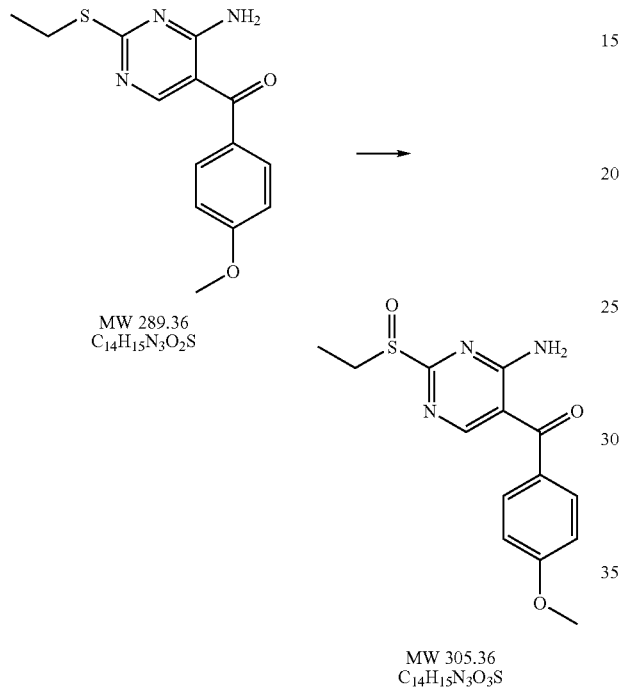

The same procedure as described in Example 325 was used, starting from (4-amino-2-ethylsulfanyl-pyrimidin-5-yl)4-methoxy-phenyl-methanone (Example 357) to give (4-amino-2-ethanesulfinyl-pyrimidin-5-yl)-(4-methoxy-phenyl)-methanone as a white solid. MS (M+H)+: 306

Example 359

1-[4-[4-Amino-5-(4-methoxy)-benzoyl)-pyrimidin-2-ylamino]-piperidin-1-yl]-ethanone

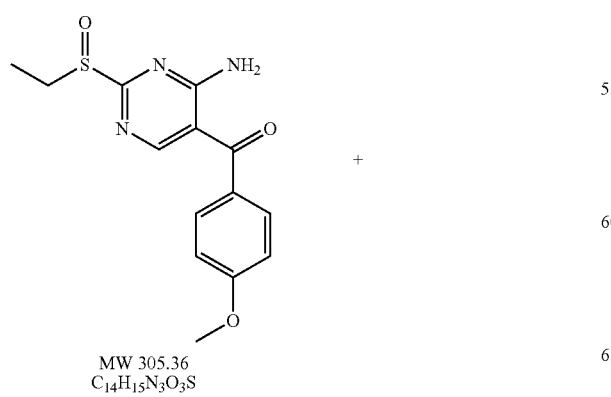

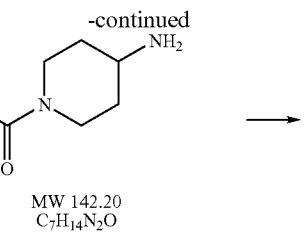

-continued

MW 142.20
C7H14N2O

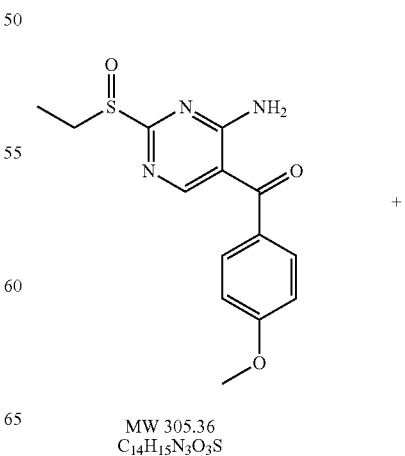

MW 369.43
C19H23N5O3

The same procedure as described in Example 326 was used, starting with (4-amino-2-ethanesulfinyl-pyrimidin-5-yl)-(4-methoxy-phenyl)-methanone (Example 358) and 1-(4-amino-piperidin-1-yl)-ethanone to give 1-[4-[4-amino-5-(4-methoxy]-benzoyl)-pyrimidin-2-ylamino]-piperidin-1-yl]-ethanone as a white solid. MS (M+H)+, 370.

Example 360

[4-Amino-2-(1-methanesulfonyl-piperidin-4-ylamino)-pyrimidin-5-yl]-(4-methoxy-phenyl)-methanone -continued

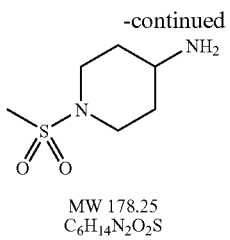 

MW 178.25
C_6H_14N_2O_2S

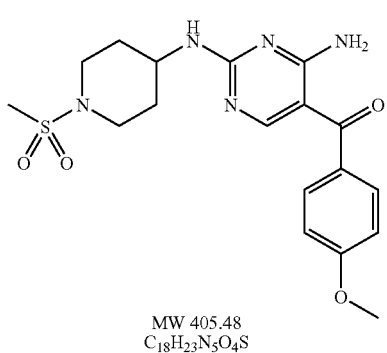

MW 405.48
C_18H_23N_5O_4S

The same procedure as described in Example 326 was used, starting with (4-amino-2-ethanesulfinyl-pyrimidin-5-yl)-(4-methoxy-phenyl)-methanone (Example 358) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(4-methoxy-phenyl)-methanone. MS (M+H)$^+$, 406

Example 361

(4-Amino-2-ethylsulfanyl-pyrimidin-5-yl)-(4-chloro-phenyl)-methanon

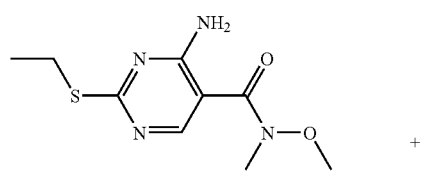

MW 242.30
C_9H_14N_4O_2S

+

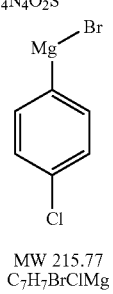

MW 215.77
C_7H_7BrClMg

-continued

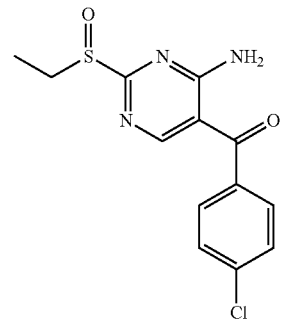

MW 293.78
C_13H_12ClN_3OS

The same procedure as described in Example 353 was used, starting from 4-amino-2-ethylsulfanyl-pyrimidine-5-carboxylic acid methoxy-methyl-amide (Example 1) and 4-chlorophenyl magnesium bromide (Aldrich) to give (4-amino-2-ethylsulfanyl-pyrimidin-5-yl)-(4-chloro-phenyl)-methanone. MS (M+H)$^+$, 294.

Example 362

(4-Amino-2-ethanesulfinyl-pyrimidin-5-yl)-(4-chloro-phenyl)-methanone

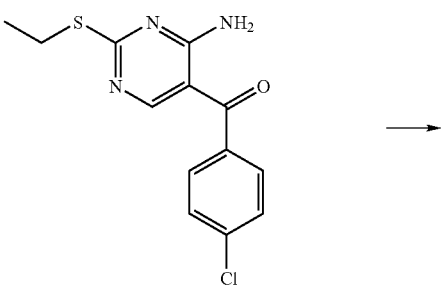

MW 293.78
C_13H_12ClN_3OS

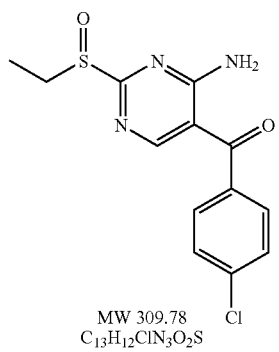

MW 309.78
C_13H_12ClN_3O_2S

The same procedure as described in Example 325 was used, starting from (4-amino-2-ethylsulfanyl-pyrimidin-5-yl)-(4-chloro-phenyl)-methanone (Example 361) to give (4-amino-2-ethanesulfinyl-pyrimidin-5-yl)-(4-chloro-phenyl)-methanone as a white solid. MS (M+H)+: 310

Example 363

1-[4-[4Amino-5-(4-chloro-benzoyl)-pyrimidin-2-yl]-ethanone

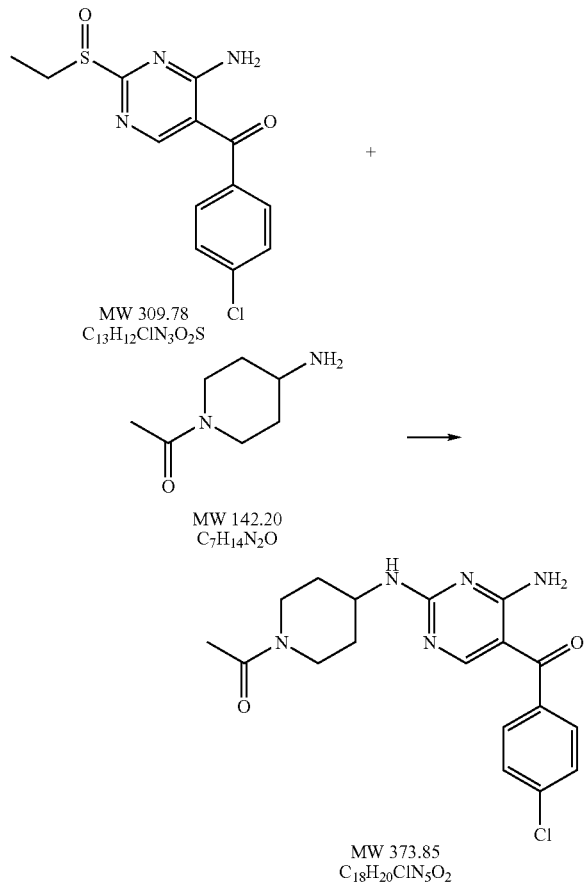

The same procedure as described in Example 326 was used, starting with (4-amino-2-ethanesulfinyl-pyrimidin-5-yl)-(4-chloro-phenyl)-methanone (Example 362) and 1-(4-amino-piperidin-1-yl)-ethanone to give 1-[4-[4-amino-5-(4-chloro-benzoyl)-pyrimidin-2-ylamino]-piperidin-1-yl]-ethanone as a white solid. MS (M+H)+, 374.

Example 364

[4-amino-2-(1-methanesulfonyl-piperidin-4-ylamine)-pyrimidin-5-yl]-(4-chloro-phenyl)-methanone

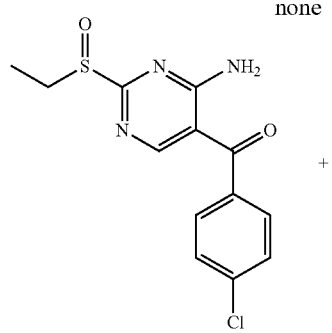

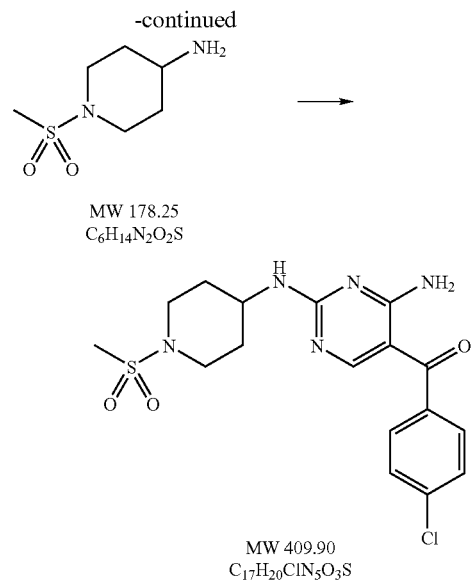

The same procedure as described in Example 326 was used, starting with (4-amino-2-ethanesulfinyl-pyrimidin-5-yl)-(4-chloro-phenyl)-methanone (Example 362) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(4-chloro-phenyl)-methanone. MS (M+H)+, 410

Example 365

(4-Amino-2-ethylsulfanyl-pyrimidin-5-yl)-(4-fluoro-phenyl)-methanone

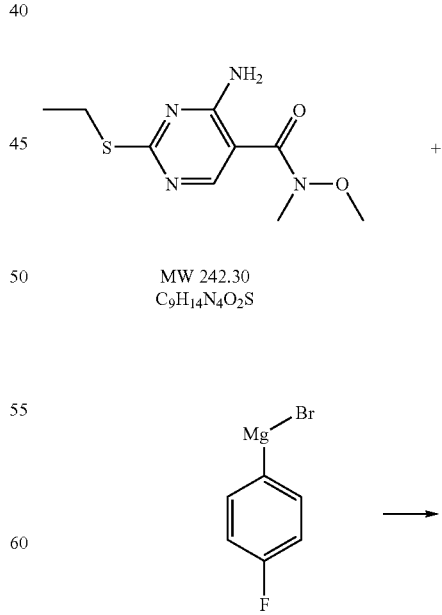

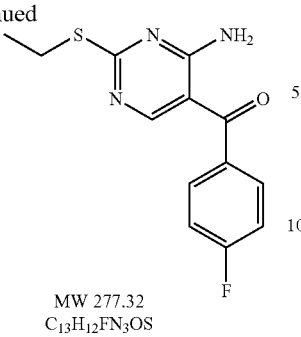

MW 277.32
C₁₃H₁₂FN₃OS

The same procedure as described in Example 353 was used, starting from 4-amino-2-ethylsulfanyl-pyrimidine-5-carboxylic acid methoxy-methyl-amide (Example 1) and 4-fluorophenyl magnesium bromide (Aldrich) to give (4-amino-2-ethylsulfanyl-pyrimidin-5-yl)-(4-fluoro-phenyl)-methanone. MS (M+H)⁺, 278.

Example 366

(4-Amino-2-ethanesulfinyl-pyrimidin-5-yl)-(4-fluoro-phenyl)-methanone

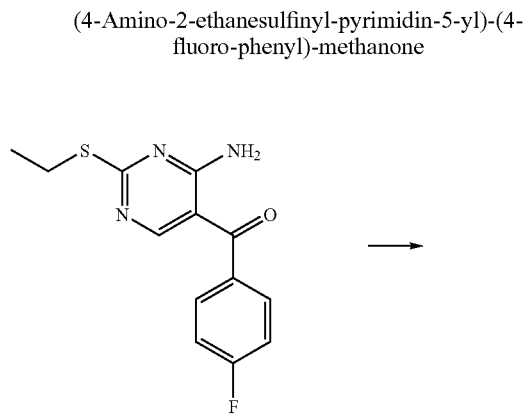

MW 277.32
C₁₃H₁₂FN₃OS

MW 293.32
C₁₃H₁₂FN₃O₂S

The same procedure as described in Example 325 was used, starting from (4-amino-2-ethylsulfanyl-pyrimidin-5-yl)-(4-fluoro-phenyl)-methanone (Example 365) to give (4-amino-2-ethanesulfinyl-pyrimidin-5-yl)-(4-fluoro-phenyl)-methanone as a white solid. MS (M+H)⁺: 294

Example 367

1-[4-[4-Amino-5-(4-fluoro-benzoyl)-pyrimidin-2-ylamino]-piperidin-1-yl]-ethanone

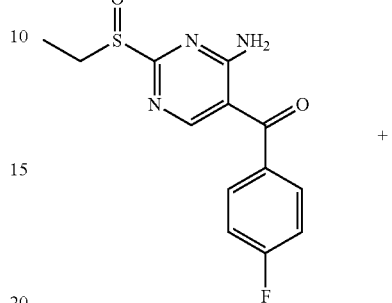

MW 293.32
C₁₃H₁₂FN₃O₂S

MW 142.20
C₇H₁₄N₂O

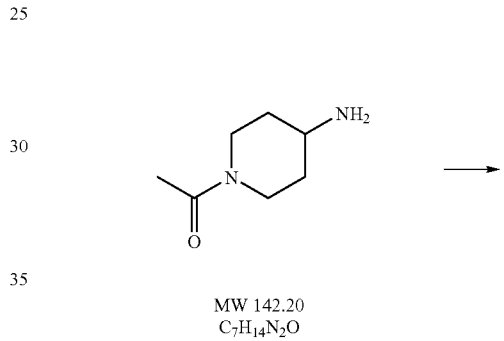

MW 357.39
C₁₈H₂₀FN₅O₂

The same procedure as described in Example 326 was used, starting with (4-amino-2-ethanesulfinyl-pyrimidin-5-yl)-(4-fluoro-phenyl)-methanone (Example 366) and 1-(4-amino-piperidin-1-yl)-ethanone to give 1-[4-[4-amino-5-(4-fluoro-benzoyl)-pyrimidin-2-ylamino]-piperidin-1-yl]-ethanone as a white solid. MS (M+H)⁺, 358.

Example 368

[4-Amino-2-(1-methanesulfonyl-piperidin-4-ylamino)-pyrimidin-5-yl]-(4-fluoro-phenyl)-methanone

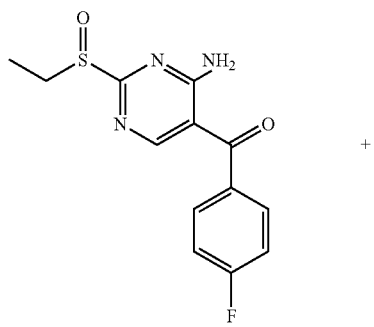

MW 293.32
$C_{13}H_{12}FN_3O_2S$

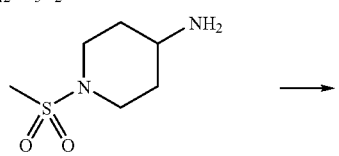

MW 178.25
$C_6H_{14}N_2O_2S$

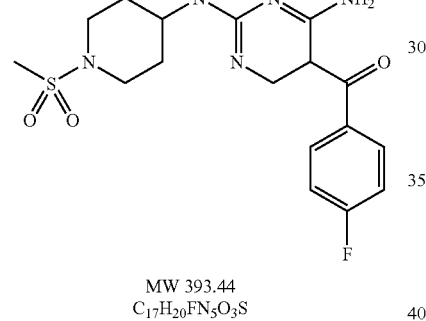

MW 393.44
$C_{17}H_{20}FN_5O_3S$

The same procedure as described in Example 326 was used, starting with (4-amino-2-ethanesulfinyl-pyrimidin-5-yl)-(4-fluoro-phenyl)-methanone (Example 366) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(4-fluoro-phenyl)-methanone. MS (M+H)+, 394

Example 369

[4-Amino-2-(1-methanesulfonyl-piperidin-4-ylamino)-pyrimidin-5-yl]-(5-fluoro-2,4-dimethoxy-phenyl)-methanone

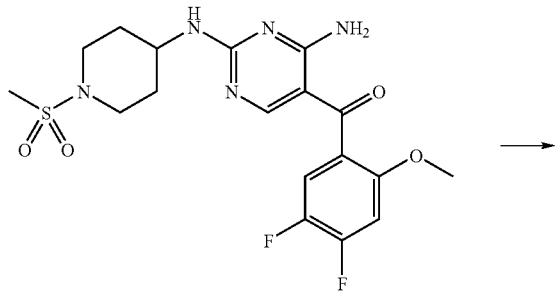

MW 441.46
$C_{18}H_{21}F_2N_5O_4S$

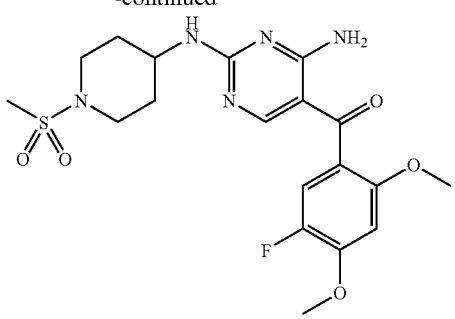

MW 453.50
$C_{19}H_{24}FN_5O_5S$

The same procedure as described in Example 348 was used to give [4-amino-2-(1-methanesulfonyl-piperidin-4-ylamino)-pyrimidin-5-yl]-(5-fluoro-2,4-dimethoxy-phenyl)-methanone as a white solid. MS (M+H)+, 454.

Example 370

[4-Amino-2-(1-methanesulfonyl-piperidin-4-ylamino)-pyrimidin-5-yl]-(4-ethoxy-5-fluoro-2-methoxy-phenyl)-methanone

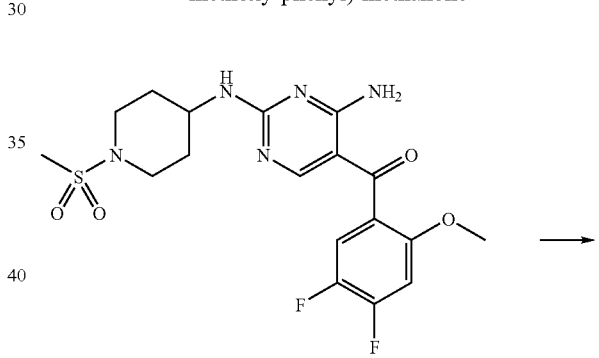

MW 441.46
$C_{18}H_{21}F_2N_5O_4S$

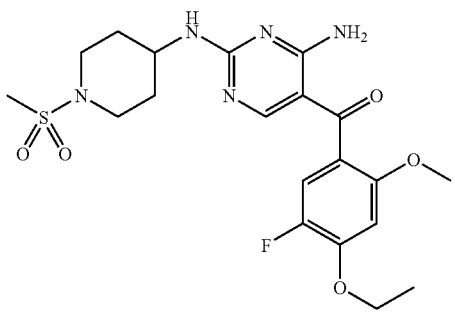

MW 467.52
$C_{20}H_{26}FN_5O_5S$

The same procedure as described in Example 349 was used to give [4-amino-2-(1-methanesulfonyl-piperidin-4-ylamino)-pyrimidin-5-yl]-(5-fluoro-2,4-dimethoxy-phenyl)-methanone as a white solid. MS (M+H)+, 468.

Example 371

(4-Amino-2-ethylsulfanyl-pyrimidin-5-yl)-(3-fluoro-4-methoxy-phenyl)-methanone

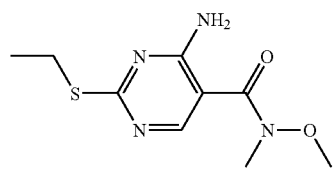

MW 242.30
C₉H₁₄N₄O₂S

+

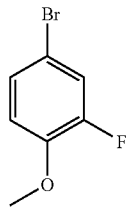

MW 205.03
C₇H₆BrFO

→

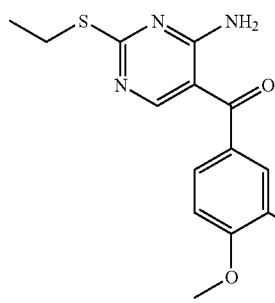

MW 307.35
C₁₄H₁₄FN₃O₂S

The same procedure as described in Example 47 was used, starting from 4-amino-2-ethylsulfanyl-pyrimidine-5-carboxylic acid methoxy-methyl-amide (Example 1) and 4-bromo-2-fluoroanisole (Aldrich), to give (4-amino-2-ethylsulfanyl-pyrimidin-5-yl)-(3-fluoro-4-methoxy-phenyl)-methanone as a white solid. MS (M+H)⁺, 308.

Example 372

(4-Amino-2-ethanesulfonyl-pyrimidin-5-yl)-(5-fluoro-4-methoxy-phenyl)-methanone

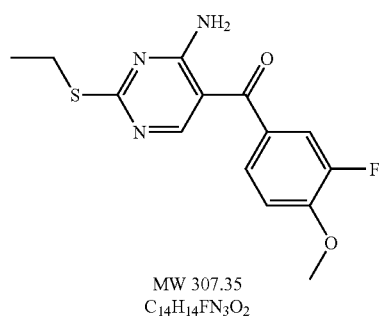

MW 307.35
C₁₄H₁₄FN₃O₂

→

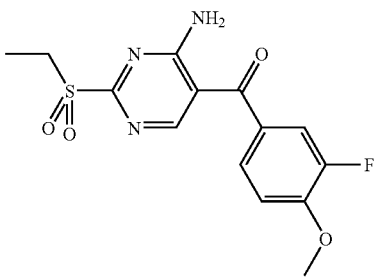

MW 339.35
C₁₄H₁₄FN₃O₄S

The same procedure as described in Example 3 was used, starting with (4-amino-2-ethylsulfanyl-pyrimidin-5-yl)-(5-fluoro-2-methoxy-phenyl)-methanone (Example 371) to give (4-amino-2-ethanesulfonyl-pyrimidin-5-yl)-(5-fluoro-4-methoxy-phenyl)-methanone as a white solid. MS (M+H)⁺: 340.

Example 373

[4-Amino-2-(1-methanesulfonyl-piperidin-4-ylamino)-pyrimidin-5-yl]-(3-fluoro-4-methoxy-phenyl)-methanone

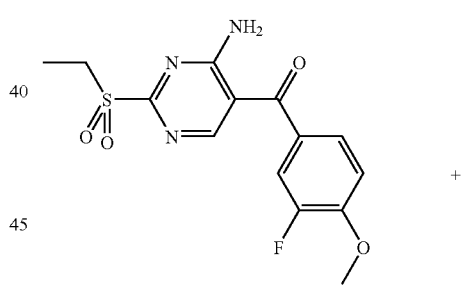

MW 339.35
C₁₄H₁₄FN₃O₄S

+

MW 178.25
C₆H₁₄N₂O₂S

→

-continued

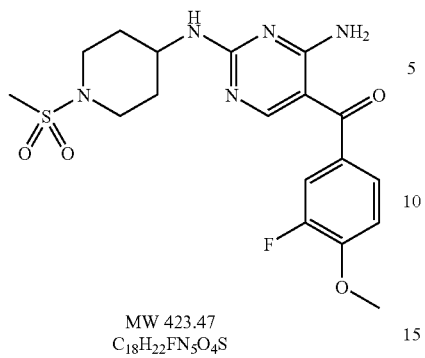

MW 423.47
$C_{18}H_{22}FN_5O_4S$

The same procedure as described in Example 90 was used starting with material from Example 372 and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(3-fluoro-4-methoxy-phenyl)-methanone as a white solid. MS (M+H)+: 424.

Example 374

4-[4-Amino-5-(5-fluoro-2-methoxy-4-methyl-benzoyl)-pyrimidin-2-ylamino]-piperidine-1-carboxylic acid tert-butyl ester

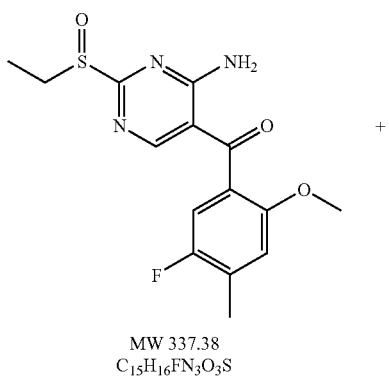

MW 337.38
$C_{15}H_{16}FN_3O_3S$

+

-continued

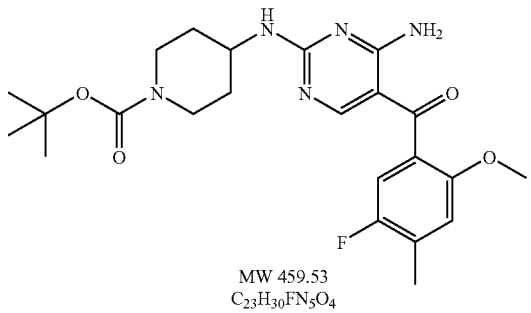

MW 459.53
$C_{23}H_{30}FN_5O_4$

The same procedure as described in Example 326 was used, starting with (4-amino-2-ethanesulfinyl-pyrimidin-5-yl)-(5-fluoro-2-methoxy-4-methyl-phenyl)-methanone (Example 341) and 4-amino-1-Boc-piperidine (Astatech) to give 4-[4-amino-5-(5-fluoro-2-methoxy-4-methyl-benzoyl)-pyrimidin-2-ylamino]-piperidine-1-carboxylic acid tert-butyl ester as a white solid. MS (M+H)+, 460.

Example 375

Chloro-4-fluoro-2-iodoanisole

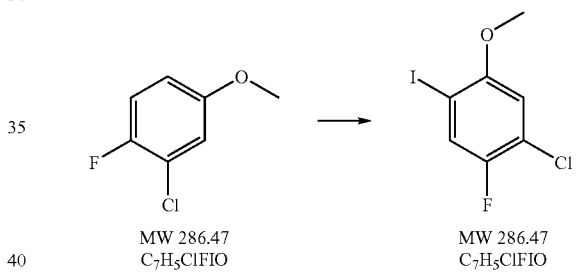

MW 286.47          MW 286.47
$C_7H_5ClFIO$       $C_7H_5ClFIO$

To a solution of 3-chloro-4-fluoroanisole (4.69 g, Lancaster) in chloroform (250 mL) was added silver trifluoroacetate (23.2 g, Aldrich) followed by iodine (15.8 g, Aldrich) in several portions. The reaction mixture was stirred for 2 hours and filtered through Celite. The filtrate was washed with water, brine, dried and concentrated. The crude product was purified by crystallization from ether/petroleum ether to give 5-chloro-4-fluoro-2-iodoanisole (5.0 g). MS (M+H)+, 285.

Example 376

(4-Amino-2-ethylsulfanyl-pyrimidin-5-yl)-(4-chloro-5-fluoro-2-methoxy-phenyl)-methanone

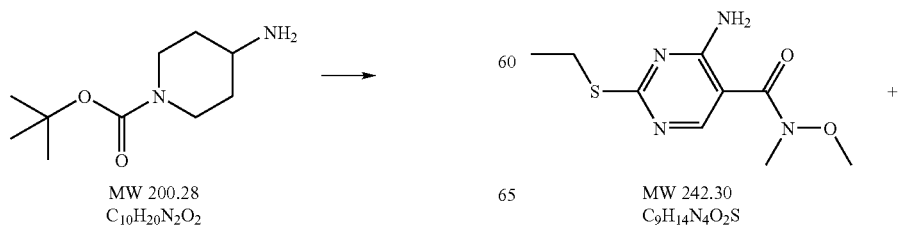

MW 200.28          MW 242.30
$C_{10}H_{20}N_2O_2$   $C_9H_{14}N_4O_2S$

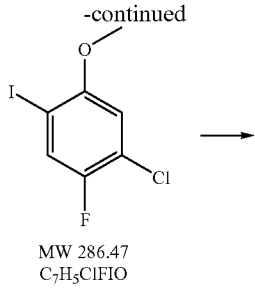

MW 286.47
C₇H₅ClFIO

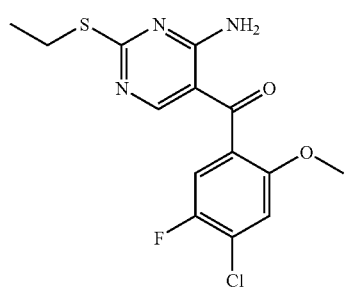

MW 341.79
C₁₄H₁₃ClFN₃O₂S

To a solution of 5-chloro-4-fluoro-2-iodoanisole (1.0 g, Example 375) was added isopropylmagnesium chloride (1.92 mL, 2M in tetrahydrofuran, Aldrich) and the reaction was stirred at −40 to −35° C. for 40 minutes before 4-amino-2-ethylsulfanyl-pyrimidine-5-carboxylic acid methoxy-methyl-amide (170 mg, Example 1) in tetrahydrofuran (4 mL) was added. The resulting reaction was quenched with aqueous ammonium chloride. Work-up and purification as in Example 47 gave (4-amino-2-ethylsulfanyl-pyrimidin-5-yl)-(4-chloro-5-fluoro-2-methoxy-phenyl)-methanone. MS (M+H)⁺, 342.

Example 377

(4-Amino-2-ethanesulfinyl-pyrimidin-5-yl)-(4-chloro-5-fluoro-2-methoxy-phenyl)-methanone

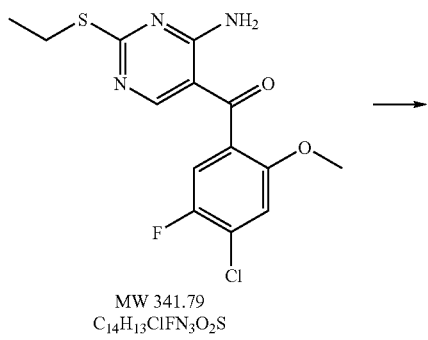

MW 341.79
C₁₄H₁₃ClFN₃O₂S

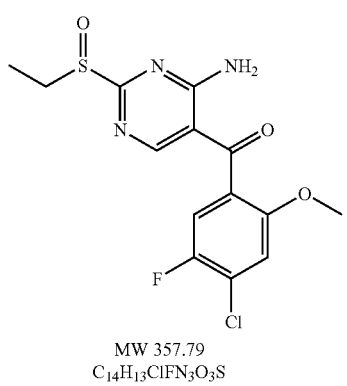

MW 357.79
C₁₄H₁₃ClFN₃O₃S

The same procedure as described in Example 325 was used, starting from (4-amino-2-ethylsulfanyl-pyrimidin-5-yl)-(4-chloro-5-fluoro-2-methoxy-phenyl)-methanone (Example 376) to give (4-amino-2-ethanesulfinyl-pyrimidin-5-yl)-(4-chloro-5-fluoro-2-methoxy-phenyl)-methanone as a white solid. MS (M+H)⁺: 358

Example 378

[4-Amino-2-(1-methanesulfonyl-piperidin-4-ylamino)-pyrimidin-5-yl]-(4-chloro-5-fluoro-2-methoxy-phenyl)-methanone

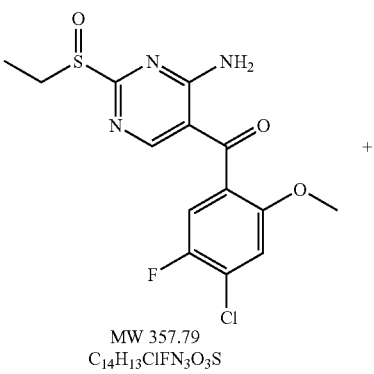

MW 357.79
C₁₄H₁₃ClFN₃O₃S

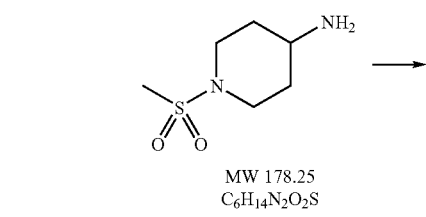

MW 178.25
C₆H₁₄N₂O₂S

-continued

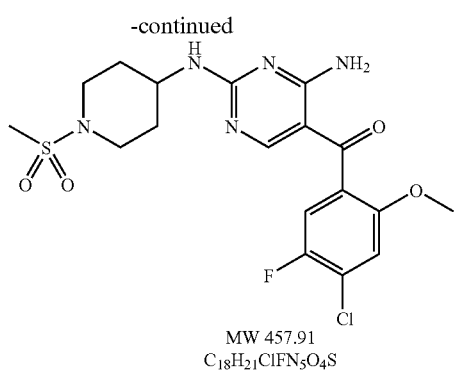

MW 457.91
C₁₈H₂₁ClFN₅O₄S

The same procedure as described in Example 326 was used, starting with (4-amino-2-ethanesulfinyl-pyrimidin-5-yl)-(4-chloro-5-fluoro-2-methoxy-phenyl)-methanone (Example 377) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(4-chloro-5-fluoro-2-methoxy-phenyl)-methanone as a white solid. MS (M+H)⁺, 458.

Example 379

(4-Amino-2-ethylsulfanyl-pyrimidin-5-yl)-(3,5-difluoro-2-methoxy-phenyl)-methanone

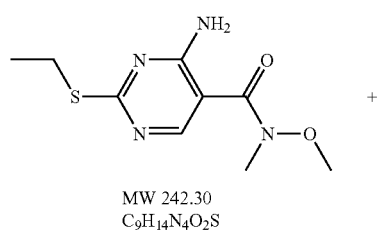

MW 242.30
C₉H₁₄N₄O₂S

+

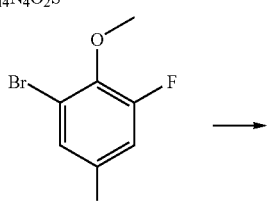

MW 223.02
C₇H₅BrF₂O

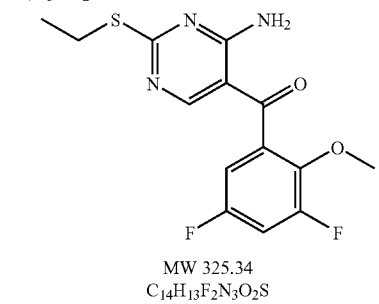

MW 325.34
C₁₄H₁₃F₂N₃O₂S

The same procedure as described in Example 376 was used, starting with 4-amino-2-ethylsulfanyl-pyrimidine-5-carboxylic acid methoxy-methyl-amide (Example 1) and 2-bromo-4,6-difluoroanisole (Metrix) to give (4-amino-2-ethylsulfanyl-pyrimidin-5-yl)-(3,5-difluoro-2-methoxy-phenyl)-methanone. MS (M+H)⁺, 326.

Example 380

(4-Amino-2-ethanesulfinyl-pyrimidin-5-yl)-(3,5-difluoro-2-methoxy-phenyl)-methanone

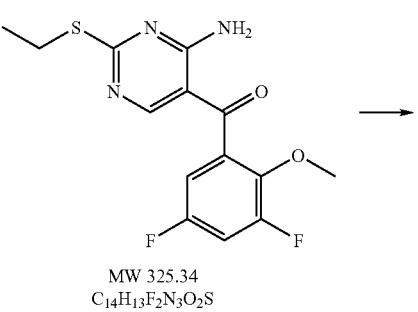

MW 325.34
C₁₄H₁₃F₂N₃O₂S

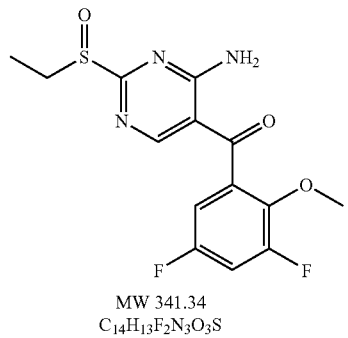

MW 341.34
C₁₄H₁₃F₂N₃O₃S

The same procedure as described in Example 325 was used, starting from (4-amino-2-ethylsulfanyl-pyrimidin-5-yl)-(3,5-difluoro-2-methoxy-phenyl)-methanone (Example 379) to give (4-amino-2-ethanesulfinyl-pyrimidin-5-yl)-(3,5-difluoro-2-methoxy-phenyl)-methanone. MS (M+H)⁺: 342

Example 381

[4-Amino-2-(1-methanesulfonyl-piperidin-4-ylamino)-pyrimidin-5-yl]-(3,5-difluoro-2-methoxy-phenyl)-methanone

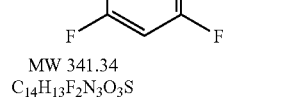

+

MW 341.34
C₁₄H₁₃F₂N₃O₃S

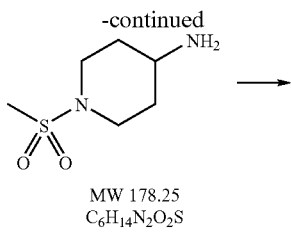

MW 178.25
C₆H₁₄N₂O₂S

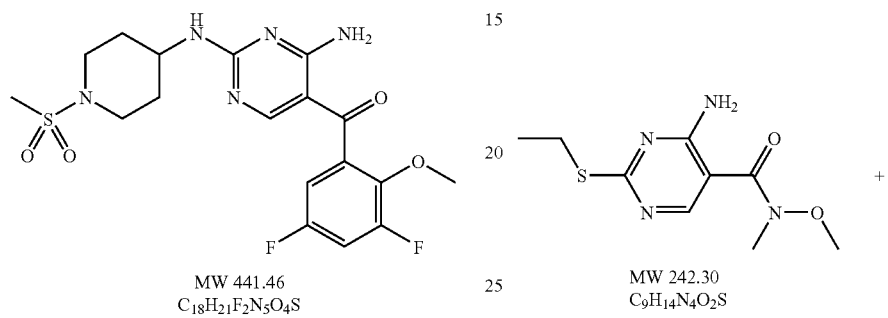

MW 441.46
C₁₈H₂₁F₂N₅O₄S

The same procedure as described in Example 326 was used, starting with (4-amino-2-ethanesulfinyl-pyrimidin-5-yl)-(3,5-difluoro-2-methoxy-phenyl)-methanone (Example 380) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(3,5-difluoro-2-methoxy-phenyl)-methanone as a white solid. MS (M+H)⁺, 442.

Example 382

1-Fluoro-2-iodo-4-methoxy-5-methylbenzene and

1-Fluoro-3-iodo-4-methoxy-5-methylbenzene

The same procedure as described in Example 375 was used, starting from 4-fluoro-2-methylanisole (Aldrich), to give 1-fluoro-2-iodo-4-methoxy-5-methyl-benzene, MS (M+H)⁺, 267 and 1-fluoro-3-iodo-4-methoxy-5-methyl-benzene, MS (M+H)⁺, 267.

Example 383

(4-Amino-2-ethylsulfanyl-pyrimidin-5-yl)-(2-fluoro-5-methoxy-4-methyl-phenyl)-methanone

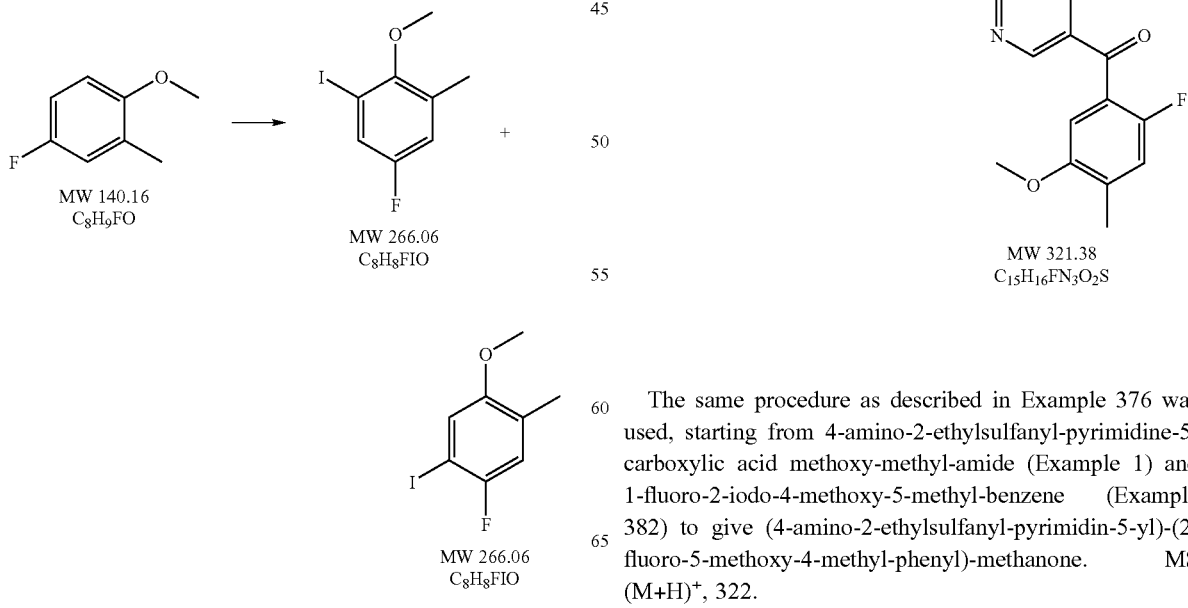

The same procedure as described in Example 376 was used, starting from 4-amino-2-ethylsulfanyl-pyrimidine-5-carboxylic acid methoxy-methyl-amide (Example 1) and 1-fluoro-2-iodo-4-methoxy-5-methyl-benzene (Example 382) to give (4-amino-2-ethylsulfanyl-pyrimidin-5-yl)-(2-fluoro-5-methoxy-4-methyl-phenyl)-methanone. MS (M+H)⁺, 322.

Example 384

(4-Amino-2-ethanesulfinyl-pyrimidin-5-yl)-(2-fluoro-5-methoxy-4-methyl-phenyl)-methanone

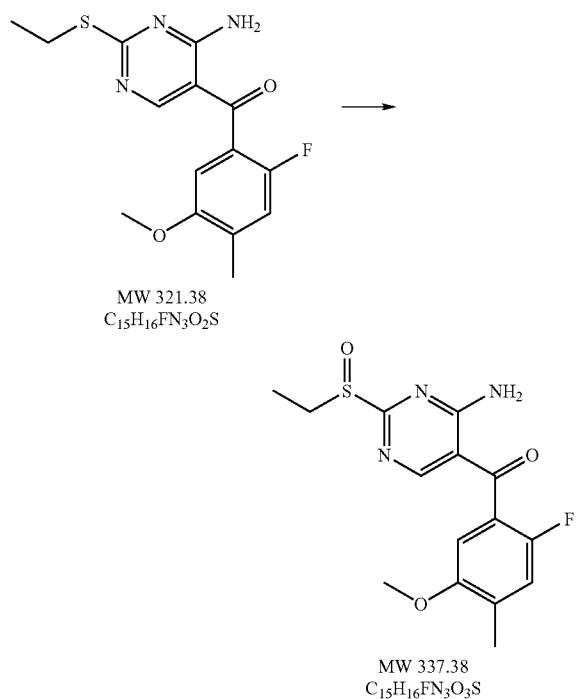

MW 321.38
C15H16FN3O2S

MW 337.38
C15H16FN3O3S

The same procedure as described in Example 325 was used, starting from (4-amino-2-ethylsulfanyl-pyrimidin-5-yl)-(2-fluoro-5-methoxy-4-methyl-phenyl)-methanone (Example 383) to give (4-amino-2-ethanesulfinyl-pyrimidin-5-yl)-(2-fluoro-5-methoxy-4-methyl-phenyl)-methanone as a white solid. MS (M+H)+: 338

Example 385

[4-Amino-2-(1-methanesulfonyl-piperidin-4-ylamino)-pyrimidin-5-yl]-(2-fluoro-5-methoxy-4-methyl-phenyl)-methanone

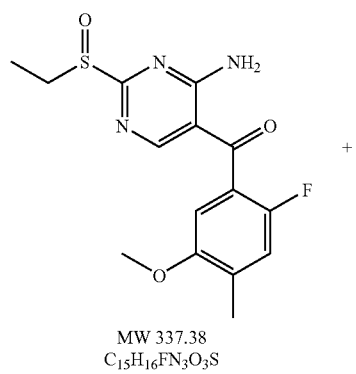

MW 337.38
C15H16FN3O3S

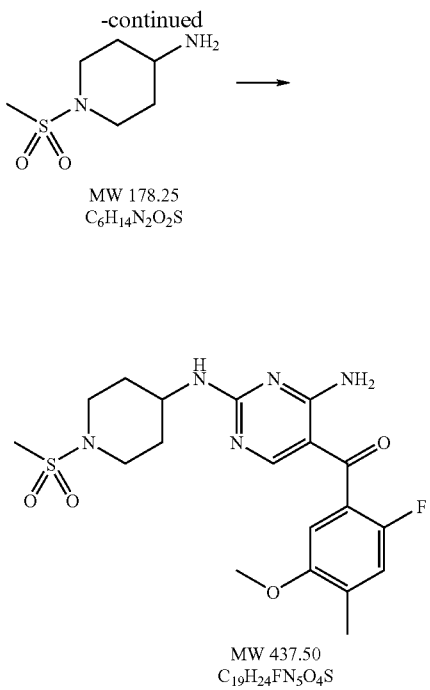

MW 178.25
C6H14N2O2S

MW 437.50
C19H24FN5O4S

The same procedure as described in Example 326 was used, starting with (4-amino-2-ethanesulfinyl-pyrimidin-5-yl)-(2-fluoro-5-methoxy-4-methyl-phenyl)-methanone (Example 384) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(2-fluoro-5-methoxy-4-methyl-phenyl)-methanone as a white solid. MS (M+H)+, 438.

Example 386

(4-Amino-2-ethylsulfanyl-pyrimidin-5-yl)-(5-fluoro-2-methoxy-3-methyl-phenyl)-methanone

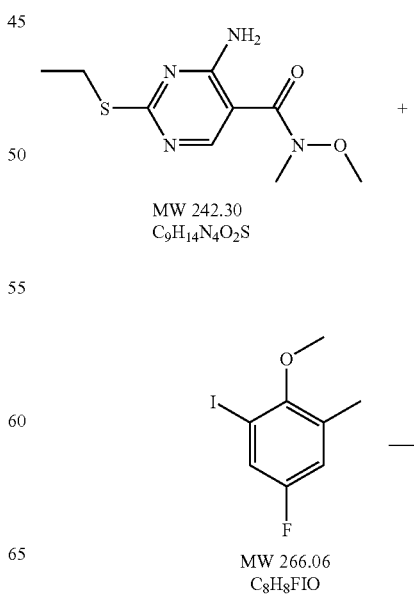

MW 242.30
C9H14N4O2S

MW 266.06
C8H8FIO

-continued

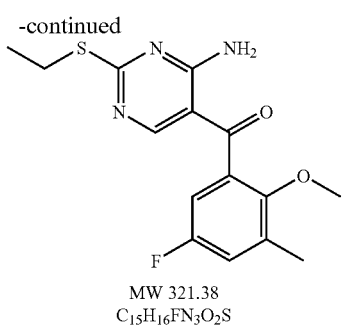

MW 321.38
$C_{15}H_{16}FN_3O_2S$

The same procedure as described in Example 376 was used, starting from 4-amino-2-ethylsulfanyl-pyrimidine-5-carboxylic acid methoxy-methyl-amide (Example 1) and 1-fluoro-3-iodo-4-methoxy-5-methyl-benzene (Example 382) to give (4-amino-2-ethylsulfanyl-pyrimidin-5-yl)-(5-fluoro-2-methoxy-3-methyl-phenyl)-methanone. MS (M+H)+, 322.

Example 387

(4-Amino-2-ethanesulfinyl-pyrimidin-5-yl)-(5-fluoro-2-methoxy-3-methyl-phenyl)-methanone

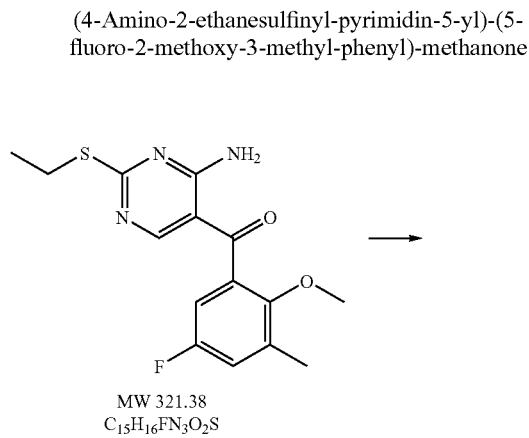

The same procedure as described in Example 325 was used, starting from (4-amino-2-ethylsulfanyl-pyrimidin-5-yl)-(5-fluoro-2-methoxy-3-methyl-phenyl)-methanone (Example 386) to give (4-amino-2-ethanesulfinyl-pyrimidin-5-yl)-(5-fluoro-2-methoxy-3-methyl-phenyl)-methanone as a white solid. MS (M+H)+: 338

Example 388

[4-Amino-2-(1-methanesulfonyl-piperidin-4-ylamino)-pyrimidin-5-yl]-(5-fluoro-2-methoxy-3-methyl-phenyl)-methanone

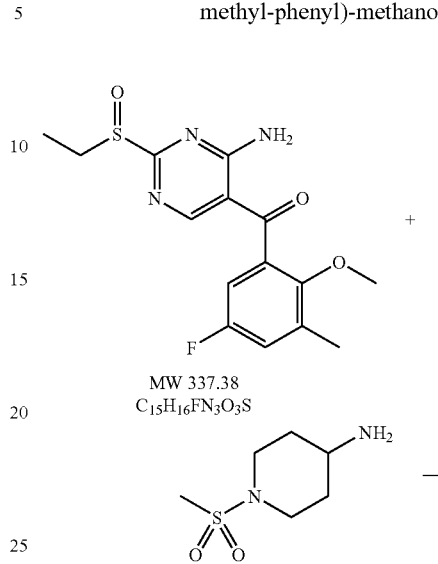

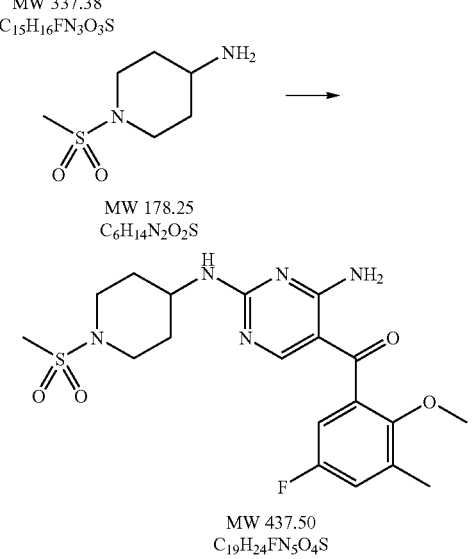

The same procedure as described in Example 326 was used, starting with (4-amino-2-ethanesulfinyl-pyrimidin-5-yl)-(5-fluoro-2-methoxy-3-methyl-phenyl)-methanone (Example 387) and 1-methanesulfonyl-piperidin-4-ylamine; compound with trifluoroacetic acid (Example 162) to give [4-amino-2-(1-methanesulfonyl-piperidin-4-ylamino)-pyrimidin-5-yl]-(5-fluoro-2-methoxy-3-methyl-phenyl)-methanone as a white solid. MS (M+H)+, 438.

Example 389

4-[4-Amino-5-(2,3-difluoro-6-methoxy-benzoyl)-pyrimidin-2-ylamino]-benzenesulfonamide

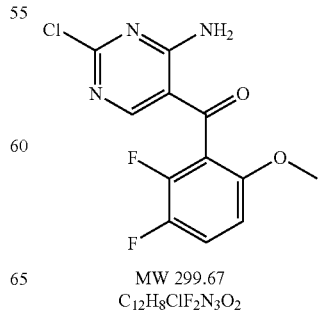

MW 299.67
$C_{12}H_8ClF_2N_3O_2$

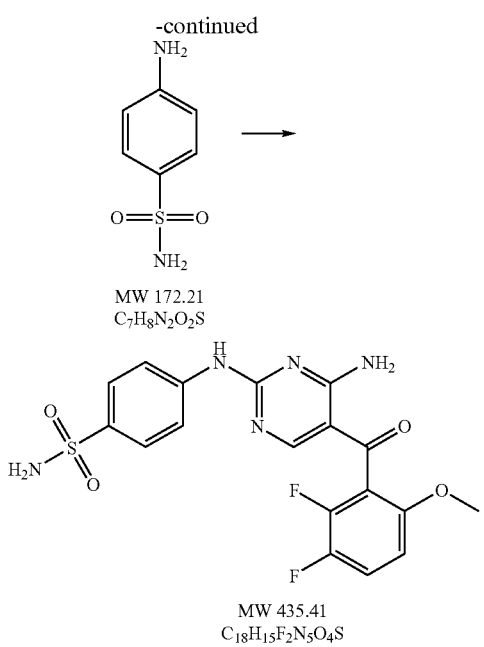

A solution of (4-amino-2-chloro-pyrimidin-5-yl)-(2,3-difluoro-6-methoxy-phenyl)-methanone (120 mg, 0.40 mmol, Example 289) and 4-amino-benzenesulfonamide (260 mg, 1.51 mmol, Aldrich) in isopropyl alcohol (30 mL) was stirred for 2 hours at 150° C. in a sealed pressure bottle. The reaction was cooled and poured into water (~60 mL) and the resulting precipitate was filtered and air dried. This residue was purified by silica gel chromatography (2% triethylamine/ethyl acetate) to give 4-[4-amino-5-(2,3-difluoro-6-methoxy-benzoyl)-pyrimidin-2-ylamino]-benzenesulfonamide as a white solid. MS: M+H; 436

The pharmacological properties of the compounds of this invention may be confirmed by a number of pharmacological assays. The exemplified pharmacological assays which follow have been carried out with the compounds according to the invention and their salts. The compounds of the invention exhibited cdk4/cyclin D activity with $IC_{50}$ values and Ki values of less than 1.0 μM. Additionally, the antiproliferative potency of some compounds of the invention was tested in the human colon tumor cell line HCT116 with $IC_{90}$ values reported from an MTT assay of less than 30 μM, preferably less than 5 μM.

Example 390

Kinase Assays

A: $IC_{50}$ Measurement

To determine inhibition of Cdk4, Cdk2 and Cdk1 activity, kinase assays were conducted using FlashPlate™ assays (NEN™-Life Science Products). FlashPlate assays were performed using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805–816). A 6×-Histidine tagged truncated form of retinoblastoma (Rb) protein (amino acid 386–928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss Eur. J. Biochem. Vol. 246 (1997) pp. 581–601 and the references cited therein).

The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well FlashPlates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 μl reaction mix (25 mM HEPES, 20 mM $MgCl_2$, 0.002% Tween 20, 2 mM DTT, 1 μM ATP, 4 nM $^{33}$P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CyclinD/Cdk4, etc., was added, and "total" refers to the average counts per minute when no compound was added. The $IC_{50}$ value is the concentration of test compound that reduces by 50% the protein-kinase induced incorporation of the radiolabel under the test conditions described.

B: $K_i$ Measurement

Alternatively, inhibition activity may be measured using Ki. Using the protein constructs described above in Example 390 A above, CDK1, CDK2, and CDK4 HTRF assays were set up. These were done in 96-well format and read in 384-well plate format. The assays were run at 3× their respective Kms for ATP.

In the CDK4 assay, test compounds were diluted to 3× their final concentrations in 25 mM Hepes, pH 7.0, 6.25 mM $MgCl_2$, 1.5 mM DTT, 135 μM ATP. The DMSO concentration was no greater than 4.76%. Twenty microliters were added to the wells of a 96-well plate. The kinase reaction was initiated by the addition of 40 μl /well of a solution containing 0.185 μM Rb and 2.25 μg/ml CDK4 in 25 mM Hepes, pH 7.0, 6.25 mM $MgCl_2$, 0.003% Tween-20, 0.3 mg/ml BSA, 1.5 mM DTT. Blank wells without CDK4 were included. The plates were incubated at 37° C. for 30 minutes with shaking. The kinase reaction was terminated by the addition of 15 μl/well of 1.6 uM anti-phospho-Rb (Ser 780) antibody (Cell Signaling Inc.) in 25 mM Hepes, pH 7.0, 24 mM EDTA, 0.2 mg/ml BSA. After 30 minutes at 37° C., 15 μl/well of 3 nM Lance-Eu-W1024 labeled anti-rabbit IgG and 60 nM Allophycocyanin conjugated anti-His6 (PerkinElmer Life Sciences) in 25 mM Hepes, pH 7.0, 0.5 mg/ml BSA were added. Following a one hour incubation at 37 deg C., 35 μl of each well, in duplicate, were transferred to 384-well black plates. The plates were read using either ViewLux or Victor V readers (PerkinElmer Life Sciences) using an excitation wavelength of 340 nm and dual emission wavelengths of 615 nm and 665 nm. IC50 values (the concentration of test compounds reducing the assay control fluorescence read-out by 50%) were first calculated from net readings at 665 nm, normalized for europium readings at 615 nm. For ATP competitive inhibitors, the Ki values were calculated according to the following equation:

$Ki=IC50/(1+S/Km)$ where S refers to the substrate concentration and Km refers to the Michaelis-Menten constant.

The CDK1 and CDK2 assays were similarly run except for small differences in reagent and protein concentrations:

The compound and enzyme buffers for both assays contained 10 mM $MgCl_2$. For CDK1 and CDK2, the respective reagent ATP concentrations were 162 uM and 90 uM. CDK1 at a reagent concentration of 0.15 ng/ul and CDK2 at a reagent concentration of 0.06 ng/ul were used. Reagent concentrations of detection reagents were adjusted between 3–12 nM Eu-Ab and 60–90 nM APC-antiHis 6 to give signal to background ratios of at least 10 to 1.

Example 391

Cell Based Assays (Tetrazolium Dye Proliferation Assay)("MTT Assay")

Proliferation was evaluated by the tetrazolium dye assay according to the procedure of Denizot and Lang (Denizot, F. and Lang, R. J *Immunol Methods* 1986, 89, 271–277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were) returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5–3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate ($S_{AVE}$) by the average of the controls ($C_{AVE}$) from 1.00. The final number is then multiplied by 100(% INH=(1.00−$S_{AVE}$/$C_{AVE}$)×100). The concentration at which 90% inhibition of cell proliferation is obtained (the $IC_{90}$) is determined from the linear regression of a plot of the logarithm of the concentration versus percent inhibition.

Example 392

| Tablet Formulation | | | | | | |
|---|---|---|---|---|---|---|
| Item | Ingredients | | | Mg/Tablet | | |
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 393

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 394

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 395

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While invention has been illustrated by reference to specific and preferred embodiments, those skilled in the art will understand that variations and modifications may be mad through routine experimentation and practice of the invention. Thus, the invention is intended not to be limited by the foregoing description, but to be defined by the appended claims and their equivalents.

What is claimed is:
1. A compound of the formula

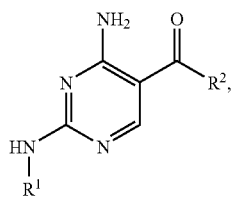

I wherein
$R^1$ is selected from the group
heterocycle and lower alkyl-heterocycle, wherein the heterocycle moiety in both instances optionally may be substituted by up to four substituents independently selected from
H,
lower alkyl,
lower alkyl substituted by oxo, $OR^{12}$, $CO_2R^{12}$, $NR^5R^6$, $S(O)_nR^{15}$ or $C(O)NR^5R^6$,
$CO_2R^7$,
$COR^{12}$,
$COR^{11}$,
$C(O)NR^{13}R^{14}$,
$S(O)_nR^{15}$,
oxo,
$OR^{12}$, or
$NR^5R^6$;
aryl;
aryl substituted by
H,
—$S(O)_n$—$R^{15}$,
$NR^5R^6$,
carbonyl,
carbonyl substituted by lower alkyl, $OR^{12}$ or $NR^5R^6$,
lower alkyl,
lower alkyl substituted by $OR^{10}$ or $NR^5R^6$,
$OR^8$, or
Halogen;
cycloalkyl;
cycloalkyl substituted by $OR^7$, $NR^5R^6$ or $S(O)_nR^{15}$;
lower alkyl; and
lower alkyl substituted by
$NR^5R^6$,
$NR^{11}SO_2R^{15}$,
$CO_2R^{10}$,
$S(O)_nR^{15}$,
heterocycle,
heterocycle substituted by
lower alkyl,
$CO_2R^{12}$ or
$SO_2R^{15}$, heteroaryl,
heteroaryl substituted by
lower alkyl,
$CO_2R^{12}$, or
$SO_2R^{15}$,
aryl, or
aryl substituted by
lower alkyl,
halogen,
$NR^5R^6$,
$COR^{12}$, or
$CO_2R^{12}$;
$R^2$ is selected from the group
aryl, heteroaryl, cycloalkyl and heterocycle, wherein each may be substituted by up to four substituents independently selected from the group
lower alkyl,
lower alkyl substituted by halogen or $OR^{10}$,
halogen,
$OR^{12}$,
$NO_2$,
CN,
$NR^5R^6$,
$S(O)_n$—$R^9$, and
$SO_2$—$NR^{16}R^{17}$;
$R^5$ and $R^6$ are each independently selected from the group
H;
lower alkyl;
lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo;
cycloalkyl;
cycloalkyl substituted by $CO_2R^{12}$, $OR^{12}$, $NR^{13}R^{14}$, $C(O)NR^{13}R^{14}$ or $SO_2R^{15}$;
aryl;
aryl substituted by $NR^{13}R^{14}$, $OR^{12}$, $CO_2R^{12}$, $C(O)NR^{13}R^{14}$, $SO_2R^{15}$, halogen, lower alkyl, or lower alkyl substituted by halogen, $OR^{12}$, oxo, $CO_2R^{12}$, $C(O)NR^{13}R^{14}$ or $NR^{13}R^{14}$;
$SO_2R^{15}$;
$CO_2R^{12}$;
$COR^{12}$; and

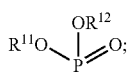

or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^{13}R^{14}$, lower alkyl and lower alkyl substituted by $OR^{12}$;
$R^7$ is selected from the group
H;
lower alkyl;
lower alkyl substituted by $OR^{12}$, $CO_2R^{12}$, $NR^5R^6$, or $C(O)NR^5R^6$;
halogen;
oxo;
aryl;
aryl substituted by up to three substituents independently selected from lower alkyl, halogen and $NR^5R^6$;
cycloalkyl;
cycloalkyl substituted by OH, oxo, or $NH_2$;
$SO_2R^{15}$; and
$COR^{12}$;
$R^8$ is selected from the group
H;
lower alkyl;
lower alkyl substituted by $NR^5R^6$;
heterocycle; and
heterocycle substituted by lower alkyl, $CO_2R^{12}$ or $SO_2R^{15}$;
$R^9$ is selected from the group
H; and
lower alkyl;
$R^{10}$ is selected from the group
lower alkyl;
aryl; and
aryl substituted by halogen or $NR^5R^6$;
$R^{11}$ is selected from the group
H;
lower alkyl; and
lower alkyl substituted by oxo or halogen;
$R^{12}$ is selected from the group
H;
lower alkyl; and
lower alkyl substituted by $NR^5R^6$ or $OR^{11}$;
$R^{13}$ and $R^{14}$ are each independently selected from the group
H;
lower alkyl;
lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo;
cycloalkyl;
cycloalkyl substituted by $CO_2R^{12}$, $OR^{12}$, $NR^5R^6$, $C(O)NR^5R^6$ or $SO_2R^{15}$;
aryl;
aryl substituted by $NR^5R^6$, $OR^{12}$, $CO_2R^{12}$, $CONR^5R^6$, $SO_2R^{15}$, halogen, lower alkyl, and lower alkyl substituted by halogen, $OR^{12}$, oxo, $CO_2R^{12}$, $C(O)NR^5R^6$ or $NR^5R^6$;
$SO_2R^{15}$;
$CO_2R^{12}$;
$COR^{12}$; and

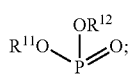

or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group

Aryl;

aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$;

heteroaryl;

heteroaryl substituted by the group halogen, $CO_2R^{12}$, $SO_2R^{10}$, $COR^{12}$, lower alkyl and lower alkyl alkyl substituted by halogen, $OR^{12}$, oxo, $CO_2R^{12}$, $NR^5R^6$ or $NR^5R^6$;

$NR^5R^6$;

lower alkyl;

lower alkyl substituted by halogen, $OR^{12}$, oxo, $CO_2R^{12}$, $C(O)NR^5R^6$ or $NR^5R^6$;

heterocycle, and heterocycle substituted by the group $CO_2R^{12}$, $COR^{12}$, $SO_2R^{12}$, $COR^{12}$, lower alkyl, $C(O)NR^5R^6$ or $NR^5R^6$;

$R^{16}$ and $R^{17}$ are each independently selected from the group

H; and lower alkyl;

or, alternatively, the group —$NR^{16}R^{17}$ can form a ring having a total of from 3 to 7 ring atoms, said ring atoms comprising in addition to the nitrogen to which $R^{16}$ and $R^{17}$ are bonded, carbon ring atoms, said carbon ring atoms optionally being replaced by one or more additional N or O ring atoms, and said ring atoms optionally being substituted by lower alkyl, OH, oxo and $NH_2$; and n is 0, 1 or 2;

or the pharmaceutically acceptable salts thereof.

2. The compound of claim 1 wherein $R^2$ is phenyl.

3. The compound of claim 2 wherein $R^2$ is phenyl substituted by halogen or $OR^{12}$, and $R^{12}$ is lower alkyl.

4. The compound of claim 3 wherein the halogen is F and the $R^{12}$ is methyl.

5. The compound of claim 1 wherein $R^1$ is selected from (a)

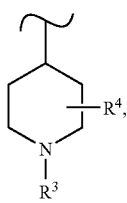

(b)

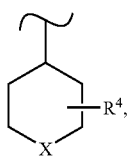

(c)

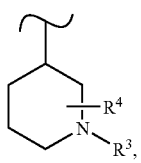

(d)

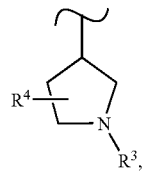

(e)

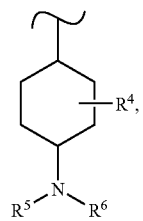

(f)

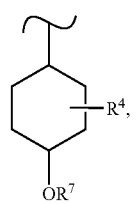

(g)

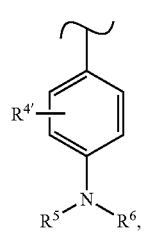

(h)

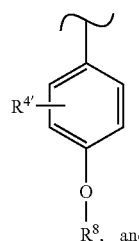

and (i)

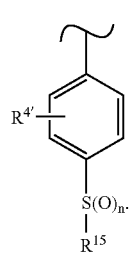

wherein $R^3$ is selected from the group

H, lower alkyl, lower alkyl substituted by oxo, $OR^{12}$, $CO_2R^{12}$, $NR^5R^6$, $SO_2R^{15}$ or $C(O)NR^5R^6$, $CO_2R^7$, $COR^{12}$, $C(O)NR^5R^6$, and $SO_2R^{15}$;

$R^4$ is selected from the group
 H,
 $OR^{11}$,
 lower alkyl,
 $NR^5R^6$,
 $NO_2$,
 oxo
 CN, and
 halogen;
$R^{4'}$ is selected from the group
 H,
 $OR^{11}$,
 lower alkyl,
 $NR^5R^6$,
 $NO_2$,
 CN, and
 halogen;
$R^5$ and $R^6$ are each independently selected from the group
 H,
 lower alkyl,
 lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
 cycloalkyl,
 cycloalkyl substituted by $CO_2R^{12}$, $OR^{12}$, $NR^{13}R^{14}$, $C(O)NR^{13}R^{14}$ or $SO_2R^{15}$,
 aryl,
 aryl substituted by $NR^{13}R^{14}$, $OR^{12}$, $CO_2R^{12}$, $C(O)NR^{13}R^{14}$, $SO_2R^{15}$, halogen, lower alkyl, and lower alkyl substituted by halogen, $OR^{12}$, oxo, $CO_2R^{12}$, $C(O)NR^{13}R^{14}$ and $NR^{13}R^{14}$;
 $SO_2R^{15}$,
 $CO_2R^{12}$,
 $COR^{12}$, and

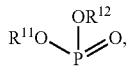

or alternatively, the group —$NR^5R^6$ can form a ring having a total of from 3 to 7 atoms, said ring atoms comprising in addition to the nitrogen to which $R^5$ and $R^6$ are bonded, carbon ring atoms, said carbon ring atoms optionally being replaced by one or more additional N or O atoms, and said ring atoms optionally being substituted by OH, oxo, $N^{13}R^{14}$, lower alkyl and lower alkyl substituted by $OR^{12}$;
$R^7$ is selected from the group
 H,
 lower alkyl,
 lower alkyl substituted by $OR^{12}$, $CO_2R^{12}$, $NR^5R^6$, or $CONR^5R^6$,
 halogen,
 oxo,
 aryl,
 aryl substituted by up to three substituents independently selected from lower alkyl, halogen, and $NR^5R^6$,
 cycloalkyl,
 cycloalkyl substituted by OH, oxo, or $NH_2$,
 $SO_2R^{15}$, and
 $COR^{12}$;

$R^8$ is selected from the group
 H,
 lower alkyl,
 lower alkyl substituted by $NR^5R^6$,
 heterocycle, and
 heterocycle substituted by lower alkyl, $CO_2R^{12}$ or $SO_2R^{15}$;
$R^{10}$ is selected from the group
 lower alkyl,
 aryl, and
 aryl substituted by halogen or $NR^5R^6$;
$R^{11}$ is selected from the group
 H,
 lower alkyl, and
 lower alkyl substituted by oxo and halogen;
$R^{12}$ is selected from the group
 H
 lower alkyl, and
 lower alkyl substituted by halogen, oxo, $NR^5R^6$ or $OR^{11}$;
$R^{13}$ and $R^{14}$ are independently selected from
 H,
 lower alkyl,
 lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
 cycloalkyl,
 cycloalkyl substituted by $CO_2R^{12}$, $OR^{12}$, $NR^5R^6$, $C(O)NR^5R^6$ or $SO_2R^{15}$,
 aryl,
 aryl substituted by $NR^5R^6$, $OR^{12}$, $CO_2R^{12}$, $C(O)NR^5R^6$, $SO_2R^{15}$, halogen, lower alkyl, and lower alkyl substituted by halogen, $OR^{12}$, oxo, $CO_2R^{12}$, $C(O)NR^5R^6$ and $NR^5R^6$;
 $SO_2R^{15}$,
 $CO_2R^{12}$,
 $COR^{12}$, and

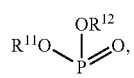

or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;
$R^{15}$ is selected from the group
 aryl,
 aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
 heteroaryl,
 heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
 $NR^5R^6$,
 lower alkyl,
 lower alkyl substituted by the group halogen, $OR^{12}$, oxo, $CO_2R^{12}$, $C(O)NR^5R^6$ or $NR^5R^6$, heterocycle, and
heterocycle substituted by the group $CO_2R^{12}$, $COR^{12}$, $SO_2R^{12}$, lower alkyl $C(O)NR^5R^6$ or $NR^5R^6$;
X is selected from the group
S,
SO,
$SO_2$, and
O; and
n is 0, 1 or 2;
or the pharmaceutically acceptable salts thereof.

6. The compound of claim 5 having the formula

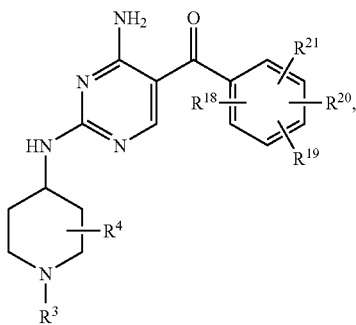

I(a)

wherein $R^{18}$, $R^{19}$, $R^{20}$ and $R^{21}$ are each independently selected from lower alkyl, halogen and $OR^{12}$.

7. The compound of claim 6 selected from the group
4-[4-Amino-5-(2-methoxy-benzoyl)-pyrimidin-2-ylamino]-piperidine-1-carboxylic acid ethyl ester,
4-[4-Amino-5-(2,6-difluoro-benzoyl)-pyrimidin-2-ylamino]-piperidine-1-carboxylic acid ethyl ester,
4-[4-Amino-5-(5-fluoro-2-methoxy-benzoyl)-pyrimidin-2-ylamino]-piperidine-1-carboxylic acid ethyl ester,
1-[4-[4-Amino-5-(2-methoxy-benzoyl)-pyrimidin-2-ylamino]-piperidin-1-yl]-ethanone,
1-[4-[4-Amino-5-(2-methoxy-benzoyl)-pyrimidin-2-ylamino]-piperidin-1-yl]-propan-1-one,
1-[4-[4-Amino-5-(2-methoxy-benzoyl)-pyrimidin-2-ylamino]-piperidin-1-yl]-butan-1-one,
1-[4-[4-Amino-5-(2-methoxy-benzoyl)-pyrimidin-2-ylamino]-piperidin-1-yl]-3-methyl-butan-1-one,
1-[4-[4-Amino-5-(2-methoxy-benzoyl)-pyrimidin-2-ylamino]-piperidin-1-yl]-3-diethylamino-propan-1-one,
4-[4-Amino-5-(2-methyl-benzoyl)-pyrimidin-2-ylamino]-piperidine-1-carboxylic acid ethyl ester, and
4-[4-Amino-5-(2-methoxy-benzoyl)-pyrimidin-2-ylamino]-piperidine-1-carboxylic acid methyl ester,
or a pharmaceutically acceptable salt of any of the foregoing compounds.

8. The compound of claim 6 selected from the group
4-[4-Amino-5-(2-methoxy-benzoyl)-pyrimidin-2-ylamino]-piperidine-1-carboxylic acid propyl ester,
4-[4-Amino-5-(2-methoxy-benzoyl)-pyrimidin-2-ylamino]-piperidine-1-carboxylic acid iso-butyl ester,
4-[4-Amino-5-(2-methoxy-benzoyl)-pyrimidin-2-ylamino]-piperidine-1-carboxylic acid methylamide,
4-[4-Amino-5-(2-methoxy-benzoyl)-pyrimidin-2-ylamino]-piperidine-1-carboxylic acid ethylamide,
4-[4-Amino-5-(2-methoxy-benzoyl)-pyrimidin-2-ylamino]-piperidine-1-carboxylic acid propylamide,
[4-Amino-2-(1-methanesulfonyl-piperidin-4-ylamino)-pyrimidin-5-yl]-(2-methoxy-phenyl)-methanone,
[4-Amino-2-(1-ethanesulfonyl-piperidin-4-ylamino)-pyrimidin-5-yl]-(2-methoxy-phenyl)-methanone,
[4-Amino-2-[1-(propane-1-sulfonyl)-piperidin-4-ylamino]-pyrimidin-5-yl]-(2-methoxy-phenyl)-methanone,
1-[4-[4-Amino-5-(5-fluoro-2-methoxy-benzoyl)-pyrimidin-2-ylamino]-piperidin-1-yl]-ethanone, and
4-[4-Amino-5-(5-fluoro-2-methoxy-benzoyl)-pyrimidin-2-ylamino]-piperidine-1-carboxylic acid methyl ester,
or a pharmaceutically acceptable salt of any of the foregoing compounds.

9. The compound of claim 6 selected from the group
4-[4-Amino-5-(5-fluoro-2-methoxy-benzoyl)-pyrimidin-2-ylamino]-piperidine-1-carboxylic acid propyl,
1-[4-[4-Amino-5-(5-fluoro-2-methoxy-benzoyl)-pyrimidin-2-ylamino]-piperidin-1-yl]-propan-1-one,
1-[4-[4-Amino-5-(5-fluoro-2-methoxy-benzoyl)-pyrimidin-2-ylamino]-piperidin-1-yl]-butan-1-one,
4-[4-Amino-5-(2-methoxy-benzoyl)-pyrimidin-2-ylamino]-piperidine-1-carboxylic acid dimethylamide,
[4-Amino-2-(1-methanesulfonyl-piperidin-4-ylamino)-pyrimidin-5-yl]-(5-fluoro-2-methoxy-phenyl)-methanone,
[4-Amino-2-(1-ethanesulfonyl-piperidin-4-ylamino)-pyrimidin-5-yl]-(5-fluoro-2-methoxy-phenyl)-methanone,
[4-Amino-2-[1-(propane-1-sulfonyl)-piperidin-4-ylamino]-pyrimidin-5-yl]-(5-fluoro-2-methoxy-phenyl)-methanone,
[4-Amino-2-(1-methanesulfonyl-piperidin-4-ylamino)-pyrimidin-5-yl]-(2-fluoro-phenyl)-methanone,
[4-Amino-2-(1-ethanesulfonyl-piperidin-4-ylamino)-pyrimidin-5-yl]-(2-fluoro-phenyl)-methanone, and
4-[4-Amino-5-(2-fluoro-benzoyl)-pyrimidin-2-ylamino]-piperidine-1-carboxylic acid ethyl ester,
or a pharmaceutically acceptable salt of any of the foregoing compounds.

10. The compound of claim 6 selected from the group
[4-Amino-2-(1-trifluoromethanesulfonyl-piperidin-4-ylamino)-pyrimidin-5-yl]-(5-fluoro-2-methoxy-phenyl)-methanone,
4-[4-Amino-5-(5-fluoro-2-methoxy-benzoyl)-pyrimidin-2-ylamino]-piperidine-1-sulfonic acid dimethylamide,
1-[4-[4-Amino-5-(5-fluoro-2-methoxy-benzoyl)-pyrimidin-2-ylamino]-piperidin-1-yl]-2-dimethylamino-ethanone,
1-[4-[4-Amino-5-(5-fluoro-2-methoxy-benzoyl)-pyrimidin-2-ylamino]-piperidin-1-yl]-2-diethylamino-ethanone,
1-[4-[4-Amino-5-(5-fluoro-2-methoxy-benzoyl)-pyrimidin-2-ylamino]-piperidin-1-yl]-2-morpholin-4-yl-ethanone,
1-[4-[4-Amino-5-(5-fluoro-2-methoxy-benzoyl)-pyrimidin-2-ylamino]-piperidin-1-yl]-3-dimethylamino-propan-1-one,
1-[4-[4-Amino-5-(5-fluoro-2-methoxy-benzoyl)-pyrimidin-2-ylamino]-piperidin-1-yl]-3-diethylamino-propan-1-one,
1-[4-[4-Amino-5-(5-fluoro-2-methoxy-benzoyl)-pyrimidin-2-ylamino]-piperidin-1-yl]-3-piperidin-1-yl-propan-1-one,
1-[4-[4-Amino-5-(5-fluoro-2-methoxy-benzoyl)-pyrimidin-2-ylamino]-piperidin-1-yl]-3-morpholin-4-yl-propan-1-one, and
[4-Amino-2-[1-(3,5-dimethyl-isoxazole-4-sulfonyl)-piperidin-4-ylamino)-pyrimidin-5-yl]-(5-fluoro-2-methoxy-phenyl)-methanone, or a pharmaceutically acceptable salt of any of the foregoing compounds.

11. The compound of claim 6 selected from the group
[4-[4-Amino-5-(5-fluoro-2-methoxy-benzoyl)-pyrimidin-2-ylamino]-piperidin-1-yl]-acetic acid methyl ester,
1-[4-[4-Amino-5-(2,6-difluoro-3-methoxy-benzoyl)-pyrimidin-2-ylamino]-piperidin-1-yl]-ethanone,
[4-Amino-2-(1-methanesulfonyl-piperidin-4-ylamino)-pyrimidin-5-yl]-(2,6-difluoro-3-methoxy-phenyl)-methanone,
4-[4-Amino-5-(2,6-difluoro-3-methoxy-benzoyl)-pyrimidin-2-ylamino]-piperidine-1-carboxylic acid methyl ester,
1-[4-[4-Amino-5-(2-ethoxy-benzoyl)-pyrimidin-2-ylamino]-piperidin-1-yl]-ethanone,
[4-Amino-2-[1-(thiophene-3-sulfonyl)-piperidin-4-ylamino]-pyrimidin-5-yl]-(5-fluoro-2-methoxy-phenyl)-methanone,
[4-Amino-2-[1-(benzo[b]thiophene-3-sulfonyl)-piperidin-4-ylamino]-pyrimidin-5-yl]-(5-fluoro-2-methoxy-phenyl)-methanone,
[4-Amino-2-[1-(1,3,5-trimethyl-1H-pyrazole-4-sulfonyl)-piperidin-4-ylamino]-pyrimidin-5-yl]-(5-fluoro-2-methoxy-phenyl)-methanone,
3-[4-[4-Amino-5-(5-fluoro-2-methoxy-benzoyl)-pyrimidin-2-ylamino]-piperidine-1-sulfonyl]-thiophene-2-carboxylic acid methyl ester, and
[4-Amino-2-[1-(2,5-dimethyl-thiophene-3-sulfonyl)-piperidin-4-ylamino]-pyrimidin-5-yl]-(5-fluoro-2-methoxy-phenyl)-methanone,
or a pharmaceutically acceptable salt of any of the foregoing compounds.

12. The compound of claim 6 selected from the group
4-[4-Amino-5-(5-fluoro-2-methoxy-benzoyl)-pyrimidin-2-ylamino]-piperidine-1-carboxylic acid cyclohexylamide,
1-[4-[4-Amino-5-(2,3-difluoro-6-methoxy-benzoyl)-pyrimidin-2-ylamino]-piperidin-1-yl]-ethanone,
[4-Amino-2-(1-methanesulfonyl-piperidin-4-ylamino)-pyrimidin-5-yl]-(2,3-difluoro-6-methoxy-phenyl)-methanone,
[4-Amino-2-(piperidin-4-ylamino)-pyrimidin-5-yl]-(2-methoxy-phenyl)-methanone,
[4-Amino-2-(piperidin-4-ylamino)-pyrimidin-5-yl]-(5-fluoro-2-methoxy-phenyl)-methanone, and
[4-Amino-2-(piperidin-4-ylamino)-pyrimidin-5-yl]-(2,3-difluoro-6-methoxy-phenyl)-methanone,
or a pharmaceutically acceptable salt of any of the foregoing compounds.

13. The compound of claim 6 selected from the group
1-[4-[4-Amino-5-(2,3,4-trifluoro-6-methoxy-benzoyl)-pyrimidin-2-ylamino]-piperidin-1-yl]-ethanone,
[4-Amino-2-(1-methanesulfonyl-piperidin-4-ylamino)-pyrimidin-5-yl]-(3,4,5-trifluoro-2-methoxy-phenyl)-methanone,
[4-Amino-2-(1-methanesulfonyl-piperidin-4-ylamino)-pyrimidin-5-yl]-(2,3,4-trifluoro-6-methoxy-phenyl)-methanone,
[4-Amino-2-[1-(2-methanesulfonyl-ethyl)-piperidin-4-ylamino]-pyrimidin-5-yl]-(5-fluoro-2-methoxy-phenyl)-methanone,
1-[4-[4-Amino-5-(5-fluoro-2-methyl-benzoyl)-pyrimidin-2-ylamino]-piperidin-1-yl]-ethanone,
[4-Amino-2-(1-methanesulfonyl-piperidin-4-ylamino)-pyrimidin-5-yl]-(5-fluoro-2-methyl-phenyl)-methanone,
[4-Amino-2-(1-methanesulfonyl-piperidin-4-ylamino)-pyrimidin-5-yl]-(5-fluoro-2-trifluoromethyl-phenyl)-methanone,
[4-Amino-2-(1-methanesulfonyl-piperidin-4-ylamino)-pyrimidin-5-yl]-(5-fluoro-2-isopropoxy-phenyl)-methanone,
[4-Amino-2-(1-methanesulfonyl-piperidin-4-ylamino)-pyrimidin-5-yl]-(2-ethoxy-5-fluoro-phenyl)-methanone, and
[4-Amino-2-(1-methanesulfonyl-piperidin-4-ylamino)-pyrimidin-5-yl]-(2-ethyl-5-fluoro-phenyl)-methanone,
or a pharmaceutically acceptable salt of any of the foregoing compounds.

14. The compound of claim 6 selected from the group
[4-Amino-2-(1-methanesulfonyl-piperidin-4-ylamino)-pyrimidin-5-yl]-(2-methoxy-4-trifluoromethyl-phenyl)-methanone,
4-[4-Amino-5-(2-fluoro-6-methoxy-benzoyl)-pyrimidin-2-ylamino]-piperidine-1-carboxylic acid tert-butyl ester,
[4-Amino-2-(piperidin-4-ylamino)-pyrimidin-5-yl]-(2-fluoro-6-methoxy-phenyl)-methanone,
[4-Amino-2-(1-methanesulfonyl-piperidin-4-ylamino)-pyrimidin-5-yl]-(2-fluoro-6-methoxy-phenyl)-methanone,
1-[4-[4-Amino-5-(2-fluoro-6-methoxy-benzoyl)-pyrimidin-2-ylamino]-piperidin-1-yl]-2,2,2-trifluoro-ethanone,
[4-Amino-2-[1-(3-chloro-propane-1-sulfonyl)-piperidin-4-ylamino]-pyrimidin-5-yl]-(2,3-difluoro-6-methoxy-phenyl)-methanone,
(4-Amino-2-[1-[3-(2-hydroxy-1-methyl-ethylamino)-propane-1-sulfonyl]-piperidin-4-ylamino]-pyrimidin-5-yl)-(2,3-difluoro-6-methoxy-phenyl)-methanone,
(4-Amino-2-[1-[3-(4-methyl-piperazin-1-yl)-propane-1-sulfonyl]-piperidin-4-ylamino]-pyrimidin-5-yl)-(2,3-difluoro-6-methoxy-phenyl)-methanone,
(4-Amino-2-[1-[3-((R)-1-hydroxymethyl-propylamino)-propane-1-sulfonyl]-piperidin-4-ylamino]-pyrimidin-5-yl)-(2,3-difluoro-6-methoxy-phenyl)-methanone, and
[4-Amino-2-[1-(3-hydroxy-propane-1-sulfonyl)-piperidin-4-ylamino]-pyrimidin-5-yl]-(2,3-difluoro-6-methoxy-phenyl)-methanone,
or a pharmaceutically acceptable salt of any of the foregoing compounds.

15. The compound of claim 6 selected from the group
[4-Amino-2-[1-(3-pyrrolidin-1-yl-propane-1-sulfonyl)-piperidin-4-ylamino]-pyrimidin-5-yl]-(2,3-difluoro-6-methoxy-phenyl)-methanone,
[4-Amino-2-[1-(3-morpholin-4-yl-propane-1-sulfonyl)-piperidin-4-ylamino]-pyrimidin-5-yl]-(2,3-difluoro-6-methoxy-phenyl)-methanone,
[4-Amino-2-(1-[3-[4-(2-hydroxy-ethyl)-piperazin-1-yl]-propane-1-sulfonyl]-piperidin-4-ylamino)-pyrimidin-5-yl]-(2,3-difluoro-6-methoxy-phenyl)-methanone,
[4-Amino-2-(1-[3-[(2-methoxy-ethyl)-methyl-amino]-propane-1-sulfonyl]-piperidin-4-ylamino)-pyrimidin-5-yl]-(2,3-difluoro-6-methoxy-phenyl)-methanone,
4-Amino-2-[1-[3-(2-hydroxy-1,1-dimethyl-ethylamino)-propane-1-sulfonyl]-piperidin-4-ylamino]-pyrimidin-5-yl)-(2,3-difluoro-6-methoxy-phenyl)-methanone,
4-Amino-2-[1-[3-(2-hydroxy-propylamino)-propane-1-sulfonyl]-piperidin-4-ylamino]-pyrimidin-5-yl)-(2,3-difluoro-6-methoxy-phenyl)-methanone, 4-Amino-2-[1-[3-((S)-2-hydroxy-1-methyl-ethylamino)-propane-1-sulfonyl]-piperidin-4-ylamino]-pyrimidin-5-yl)-(2,3-difluoro-6-methoxy-phenyl)-methanone, 4-Amino-2-[1-[3-((R)-1-hydroxymethyl-2-methyl-propylamino)-propane-1-sulfonyl]-piperidin-4-ylamino]-pyrimidin-5-yl)-(2,3-difluoro-6-methoxy-phenyl)-methanone, (4-Amino-2-[1-[3-((R)-2-hydroxy-1-methyl-ethylamino)-propane-1-sulfonyl]-piperidin-4-ylamino]-pyrimidin-5-yl)-(2,3-difluoro-6-methoxy-phenyl)-methanone, and (4-Amino-2-[1-[3-((S)-1-hydroxymethyl-propylamino)-propane-1-sulfonyl]-piperidin-4-ylamino]-pyrimidin-5-yl)-(2,3-difluoro-6-methoxy-phenyl)-methanone, or a pharmaceutically acceptable salt of any of the foregoing compounds.

16. The compound of claim 6 selected from the group

[4-Amino-2-(1-[3-[3-hydroxy-1-(2-hydroxy-ethyl)-propylamino]-propane-1-sulfonyl]-piperidin-4-ylamino)-pyrimidin-5-yl]-(2,3-difluoro-6-methoxy-phenyl)-methanone,

[4-Amino-2-[1-(3-chloro-propane-1-sulfonyl)-piperidin-4-ylamino]-pyrimidin-5-yl]-(5-fluoro-2-methoxy-phenyl)-methanone,

[4-Amino-2-(1-[3-[(2-methoxy-ethyl)-methyl-amino]-propane-1-sulfonyl]-piperidin-4-ylamino)-pyrimidin-5-yl]-(5-fluoro-2-methoxy-phenyl)-methanone,

[4-Amino-2-(1-[3-[4-(2-hydroxy-ethyl)-piperazin-1-yl]-propane-1-sulfonyl]-piperidin-4-ylamino)-pyrimidin-5-yl]-(5-fluoro-2-methoxy-phenyl)-methanone, 4-Amino-2-[1-[3-((S)-2-hydroxy-1-methyl-ethylamino)-propane-1-sulfonyl]-piperidin-4-ylamino]-pyrimidin-5-yl)-(5-fluoro-2-methoxy-phenyl)-methanone, (4-Amino-2-[1-[3-((R)-1-hydroxymethyl-propylamino)-propane-1-sulfonyl]-piperidin-4-ylamino]-pyrimidin-5-yl)-(5-fluoro-2-methoxy-phenyl)-methanone, (4-Amino-2-[1-[3-(2-hydroxy-propylamino)-propane-1-sulfonyl]-piperidin-4-ylamino]-pyrimidin-5-yl)-(5-fluoro-2-methoxy-phenyl)-methanone, (4-Amino-2-[1-[3-((R)-1-hydroxymethyl-2-methyl-propylamino)-propane-1-sulfonyl]-piperidin-4-ylamino]-pyrimidin-5-yl)-(5-fluoro-2-methoxy-phenyl)-methanone, (4-Amino-2-[1-[3-(2-methoxy-1-methyl-ethylamino)-propane-1-sulfonyl]-piperidin-4-ylamino]-pyrimidin-5-yl)-(5-fluoro-2-methoxy-phenyl)-methanone, and 4-Amino-2-[1-[3-(2-hydroxy-1,1-dimethyl-ethylamino)-propane-1-sulfonyl]-piperidin-4-ylamino]-pyrimidin-5-yl)-(5-fluoro-2-methoxy-phenyl)-methanone, or a pharmaceutically acceptable salt of any of the foregoing compounds.

17. The compound of claim 6 selected from the group (4-Amino-2-[1-[3-((R)-2-hydroxy-1-methyl-ethylamino)-propane-1-sulfonyl]-piperidin-4-ylamino]-pyrimidin-5-yl)-(5-fluoro-2-methoxy-phenyl)-methanone, (4-Amino-2-[1-[3-((S)-1-hydroxymethyl-propylamino)-propane-1-sulfonyl]-piperidin-4-ylamino]-pyrimidin-5-yl)-(5-fluoro-2-methoxy-phenyl)-methanone,

[4-Amino-2-[1-(4-hydroxy-butane-1-sulfonyl)-piperidin-4-ylamino]-pyrimidin-5-yl]-(5-fluoro-2-methoxy-phenyl)-methanone,

[4-Amino-2-[1-(4-chloro-butane-1-sulfonyl)-piperidin-4-ylamino]-pyrimidin-5-yl]-(5-fluoro-2-methoxy-phenyl)-methanone, (4-Amino-2-[1-[4-(4-methyl-piperazin-1-yl)-butane-1-sulfonyl]-piperidin-4-ylamino]-pyrimidin-5-yl)-(5-fluoro-2-methoxy-phenyl)-methanone,

[4-Amino-2-[1-(4-pyrrolidin-1-yl-butane-1-sulfonyl)-piperidin-4-ylamino]-pyrimidin-5-yl]-(5-fluoro-2-methoxy-phenyl)-methanone, (4-Amino-2-[1-[4-(2-hydroxy-propylamino)-butane-1-sulfonyl]-piperidin-4-ylamino]-pyrimidin-5-yl)-(5-fluoro-2-methoxy-phenyl)-methanone,

[4-Amino-2-(1-methanesulfonyl-piperidin-4-ylamino)-pyrimidin-5-yl]-(2,3-difluoro-5,6-dimethoxy-phenyl)-methanone,

[4-Amino-2-(1-methanesulfonyl-piperidin-4-ylamino)-pyrimidin-5-yl]-(2,3-difluoro-6-hydroxy-5-methoxy-phenyl)-methanone, and

[4-Amino-2-(1-methanesulfonyl-piperidin-4-ylamino)-pyrimidin-5-yl]-(2,3-difluoro-5,6-dihydroxy-phenyl)-methanone, or a pharmaceutically acceptable salt of any of the foregoing compounds.

18. The compound of claim 6 selected from the group

[4-Amino-2-(1-methanesulfonyl-piperidin-4-ylamino)-pyrimidin-5-yl]-(2,3-difluoro-5-hydroxy-6-methoxy-phenyl)-methanone,

[4-Amino-2-[1-(3-chloro-propane-1-sulfonyl)-piperidin-4-ylamino]-pyrimidin-5-yl]-(5-fluoro-2-methoxy-phenyl)-methanone,

[4-Amino-2-[1-(3-pyrrolidin-1-yl-propane-1-sulfonyl)-piperidin-4-ylamino]-pyrimidin-5-yl]-(5-fluoro-2-methoxy-phenyl)-methanone, Acetic acid 3-[4-[4-amino-5-(5-fluoro-2-methoxy-benzoyl)-pyrimidin-2-ylamino]-piperidine-1-sulfonyl]-propyl ester,

[4-Amino-2-[1-(3-hydroxy-propane-1-sulfonyl)-piperidin-4-ylamino]-pyrimidin-5-yl]-(5-fluoro-2-methoxy-phenyl)-methanone,

[4-Amino-2-[1-(3-morpholin-4-yl-propane-1-sulfonyl)-piperidin-4-ylamino]-pyrimidin-5-yl]-(5-fluoro-2-methoxy-phenyl)-methanone, N-(3-[4-[4-Amino-5-(5-fluoro-2-methoxy-benzoyl)-pyrimidin-2-ylamino]-piperidine-1-sulfonyl]-propyl)-methanesulfonamide, (4-Amino-2-[1-[3-(4-methyl-piperazin-1-yl)-propane-1-sulfonyl]-piperidin-4-ylamino]-pyrimidin-5-yl)-(5-fluoro-2-methoxy-phenyl)-methanone,

[4-Amino-2-(1-methanesulfonyl-piperidin-4-ylamino)-pyrimidin-5-yl]-(2,3-difluoro-6-hydroxy-phenyl)-methanone, and

[4-Amino-2-(1-methanesulfonyl-piperidin-4-ylamino)-pyrimidin-5-yl]-phenyl-methanone, or a pharmaceutically acceptable salt of any of the foregoing compounds.

19. The compound of claim 6 selected from the group

4-[4-Amino-5-(2,3-difluoro-6-methoxy-benzoyl)-pyrimidin-2-ylamino]-piperidine-1-carbaldehyde, 4-[4-Amino-5-(2,3-difluoro-6-methoxy-benzoyl)-pyrimidin-2-ylamino]-piperidine-1-sulfonic acid amide, 4-[4-Amino-5-(2,3-difluoro-6-methoxy-benzoyl)-pyrimidin-2-ylamino]-piperidine-1-sulfonic acid acetylamide, rac-[4-Amino-2-(3-hydroxy-1-methanesulfonyl-piperidin-4-ylamino)-pyrimidin-5-yl]-(2,3-difluoro-6-methoxy-phenyl)-methanone,
rac-[4-Amino-2-(3-hydroxy-1-methanesulfonyl-piperidin-4-ylamino)-pyrimidin-5-yl]-(2,3-difluoro-6-methoxy-phenyl)-methanone,
rac-[4-Amino-2-(1-methanesulfonyl-3-methoxy-piperidin-4-ylamino)-pyrimidin-5-yl]-(2,3-difluoro-6-methoxy-phenyl)-methanone,
rac-4-[4-Amino-5-(2,3-difluoro-6-methoxy-benzoyl)-pyrimidin-2-ylamino]-1-methanesulfonyl-piperidin-3-one,
1-[4-[4-Amino-5-(2-methoxy-5-methyl-benzoyl)-pyrimidin-2-ylamino]-piperidin-1-yl]-ethanone,
[4-Amino-2-(1-methanesulfonyl-piperidin-4-ylamino)-pyrimidin-5-yl]-(2-methoxy-5-methyl-phenyl)-methanone,
(4-Amino-2-ethylsulfanyl-pyrimidin-5-yl)-(2,5-dimethoxy-phenyl)-methanone,
1-[4-[4-Amino-5-(2,5-dimethoxy-benzoyl)-pyrimidin-2-ylamino]-piperidin-1-yl]-ethanone, and
[4-Amino-2-(1-methanesulfonyl-piperidin-4-ylamino)-pyrimidin-5-yl]-(2,5-dimethoxy-phenyl)-methanone,
or a pharmaceutically acceptable salt of any of the foregoing compounds.

20. The compound of claim 6 selected from the group
1-[4-[4-Amino-5-(2,6-dimethoxy-benzoyl)-pyrimidin-2-ylamino]-piperidin-1-yl]-ethanone,
[4-Amino-2-(1-methanesulfonyl-piperidin-4-ylamino)-pyrimidin-5-yl]-(2,6-dimethoxy-phenyl)-methanone,
1-[4-[4-Amino-5-(5-fluoro-2-methoxy-4-methyl-benzoyl)-pyrimidin-2-ylamino]-piperidin-1-yl]-ethanone,
[4-Amino-2-(1-methanesulfonyl-piperidin-4-ylamino)-pyrimidin-5-yl]-(5-fluoro-2-methoxy-4-methyl-phenyl)-methanone,
[4-Amino-2-(1-methanesulfonyl-piperidin-4-ylamino)-pyrimidin-5-yl]-(3-fluoro-2,6-dimethoxy-phenyl)-methanone,
[4-Amino-2-(1-methanesulfonyl-piperidin-4-ylamino)-pyrimidin-5-yl]-(2-ethoxy-3-fluoro-6-methoxy-phenyl)-methanone,
1-[4-[4-Amino-5-(3-fluoro-6-methoxy-2-methyl-benzoyl)-pyrimidin-2-ylamino]-piperidin-1-yl]-ethanone,
[4-Amino-2-(1-methanesulfonyl-piperidin-4-ylamino)-pyrimidin-5-yl]-(3-fluoro-6-methoxy-2-methyl-phenyl)-methanone,
1-[4-[4-Amino-5-(4-methyl-benzoyl)-pyrimidin-2-ylamino]-piperidin-1-yl]-ethanone, and
[4-Amino-2-(1-methanesulfonyl-piperidin-4-ylamino)-pyrimidin-5-yl]-p-tolyl-methanone,
or a pharmaceutically acceptable salt of any of the foregoing compounds.

21. The compound of claim 6 selected from the group
1-[4-[4-Amino-5-(4-methoxy-benzoyl)-pyrimidin-2-ylamino]-piperidin-1-yl]-ethanone,
[4-Amino-2-(1-methanesulfonyl-piperidin-4-ylamino)-pyrimidin-5-yl]-(4-methoxy-phenyl)-methanone,
1-[4-[4-Amino-5-(4-chloro-benzoyl)-pyrimidin-2-ylamino]-piperidin-1-yl]-ethanone,
[4-amino-2-(1-methanesulfonyl-piperidin-4-ylamino)-pyrimidin-5-yl]-(4-chloro-phenyl)-methanone,
1-[4-[4-Amino-5-(4-fluoro-benzoyl)-pyrimidin-2-ylamino]-piperidin-1-yl]-ethanone,
[4-Amino-2-(1-methanesulfonyl-piperidin-4-ylamino)-pyrimidin-5-yl]-(4-fluoro-phenyl)-methanone,
[4-Amino-2-(1-methanesulfonyl-piperidin-4-ylamino)-pyrimidin-5-yl]-(5-fluoro-2,4-dimethoxy-phenyl)-methanone,
[4-Amino-2-(1-methanesulfonyl-piperidin-4-ylamino)-pyrimidin-5-yl]-(4-ethoxy-5-fluoro-2-methoxy-phenyl)-methanone,
[4-Amino-2-(1-methanesulfonyl-piperidin-4-ylamino)-pyrimidin-5-yl]-(3-fluoro-4-methoxy-phenyl)-methanone, and
4-[4-Amino-5-(5-fluoro-2-methoxy-4-methyl-benzoyl)-pyrimidin-2-ylamino]-piperidine-1-carboxylic acid tert-butyl ester,
or a pharmaceutically acceptable salt of any of the foregoing compounds.

22. The compound of claim 6 selected from the group
[4-Amino-2-(1-methanesulfonyl-piperidin-4-ylamino)-pyrimidin-5-yl]-(4-chloro-5-fluoro-2-methoxy-phenyl)-methanone,
[4-Amino-2-(1-methanesulfonyl-piperidin-4-ylamino)-pyrimidin-5-yl]-(3,5-difluoro-2-methoxy-phenyl)-methanone,
[4-Amino-2-(1-methanesulfonyl-piperidin-4-ylamino)-pyrimidin-5-yl]-(2-fluoro-5-methoxy-4-methyl-phenyl)-methanone, and
[4-Amino-2-(1-methanesulfonyl-piperidin-4-ylamino)-pyrimidin-5-yl]-(5-fluoro-2-methoxy-3-methyl-phenyl)-methanone,
Trans-[4-Amino-2-[4-(2-hydroxy-ethylamino)-cyclohexylamino]-pyrimidin-5-yl]-(2,3-difluoro-6-methoxy-phenyl)-methanone,
Trans-(4-Amino-2-[4-[bis-(2-hydroxy-ethyl)-amino]-cyclohexylamino]-pyrimidin-5-yl)-(2,3-difluoro-6-methoxy-phenyl)-methanone,
Trans-N-[4-[4-Amino-5-(2,3-difluoro-6-methoxy-benzoyl)-pyrimidin-2-ylamino]-cyclohexyl]-succinamic acid,
Trans-3-Chloro-propane-1-sulfonic acid [4-[4-amino-5-(2,3-difluoro-6-methoxy-benzoyl)-pyrimidin-2-ylamino]-cyclohexyl]-amide,
Trans-3-Morpholin-4-yl-propane-1-sulfonic acid [4-[4-amino-5-(2,3-difluoro-6-methoxy-benzoyl)-pyrimidin-2-ylamino]-cyclohexyl]-amide,
Trans-3-(4-Methyl-piperazin-1-yl)-propane-1-sulfonic acid [4-[4-amino-5-(2,3-difluoro-6-methoxy-benzoyl)-pyrimidin-2-ylamino]-cyclohexyl]-amide,
Trans-3-Pyrrolidin-1-yl-propane-1-sulfonic acid [4-[4-amino-5-(2,3-difluoro-6-methoxy-benzoyl)-pyrimidin-2-ylamino]-cyclohexyl]-amide,
Trans-3-Hydroxy-propane-1-sulfonic acid [4-[4-amino-5-(2,3-difluoro-6-methoxy-benzoyl)-pyrimidin-2-ylamino]-cyclohexyl]-amide,
Trans-[4-Amino-2-[4-(1,1-dioxo-1$\lambda^6$-isothiazolidin-2-yl)-cyclohexylamino]-pyrimidin-5-yl]-(2,3-difluoro-6-methoxy-phenyl)-methanone, and
Trans-[4-Amino-2-[4-(4-methyl-piperazin-1-yl)-cyclohexylamino]-pyrimidin-5-yl]-(2,3-difluoro-6-methoxy-phenyl)-methanone,
or a pharmaceutically acceptable salt of any of the foregoing compounds.

23. The compound of claim 6 wherein $R^3$ is selected from the group $CO_2R^7$, $COR^{12}$ and $SO_2R^{15}$.

24. The compound of claim 5 having the formula

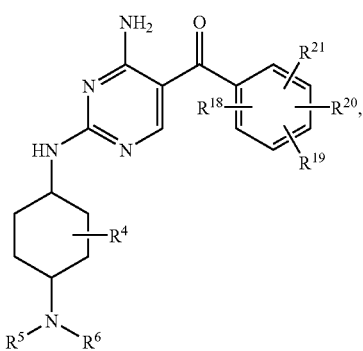

I(e)

wherein $R^{18}$, $R^{19}$, $R^{20}$ and $R^{21}$ are each independently selected from lower alkyl, halogen and $OR^{12}$.

25. The compound of claim 24 selected from the group
Trans-[4-[4-amino-5-(5-fluoro-2-methoxy-benzoyl)-pyrimidin-2-ylamino]-cyclohexyl]-carbamic acid tert-butyl ester,
Trans-[4-amino-2-(4-amino-cyclohexylamino)-pyrimidin-5-yl]-(5-fluoro-2-methoxy-phenyl)-methanone,
Trans-N-[4-[4-amino-5-(5-fluoro-2-methoxy-benzoyl)-pyrimidin-2-ylamino]-cyclohexyl]-acetamide,
N-[4-[4-Amino-5-(5-fluoro-2-methoxy-benzoyl)-pyrimidin-2-ylamino]-cyclohexyl]-methanesulfonamide,
Ethanesulfonic acid [4-[4-amino-5-(5-fluoro-2-methoxy-benzoyl)-pyrimidin-2-ylamino]-cyclohexyl]-amide,
[4-[4-Amino-5-(5-fluoro-2-methoxy-benzoyl)-pyrimidin-2-ylamino]-cyclohexyl]-carbamic acid ethyl ester,
[4-[4-Amino-5-(5-fluoro-2-methoxy-benzoyl)-pyrimidin-2-ylamino]-cyclohexyl]-carbamic acid isopropyl ester,
[4-[4-amino-5-(5-fluoro-2-methoxy-benzoyl)-pyrimidin-2-ylamino]-cyclohexyl]-carbamic acid 2-methoxy-ethyl ester,
Trans-N-[4-[4-Amino-5-(2,3-difluoro-6-methoxy-benzoyl)-pyrimidin-2-ylamino]-cyclohexyl]-acetamide, and
Trans-N-[4-[4-amino-5-(2,3-difluoro-6-methoxy-benzoyl)-pyrimidin-2-ylamino]-cyclohexyl]-methanesulfonamide.
or a pharmaceutically acceptable salt of any of the foregoing compounds.

26. The compound of claim 24 selected from the group
Trans-[4-Amino-2-[4-(2-hydroxy-ethylamino)-cyclohexylamino]-pyrimidin-5-yl]-(2,3-difluoro-6-methoxy-phenyl)-methanone,
Trans-(4-Amino-2-[4-[bis-(2-hydroxy-ethyl)-amino]-cyclohexylamino]-pyrimidin-5-yl)-(2,3-difluoro-6-methoxy-phenyl)-methanone,
Trans-N-[4-[4-Amino-5-(2,3-difluoro-6-methoxy-benzoyl)-pyrimidin-2-ylamino]-cyclohexyl]-succinamic acid,
Trans-3-Chloro-propane-1-sulfonic acid [4-[4-amino-5-(2,3-difluoro-6-methoxy-benzoyl)-pyrimidin-2-ylamino]-cyclohexyl]-amide,
Trans-Morpholin-4-yl-propane-1-sulfonic acid [4-[4-amino-5-(2,3-difluoro-6-methoxy-benzoyl)-pyrimidin-2-ylamino]-cyclohexyl]-amide,
Trans-3-(4-Methyl-piperazin-1-yl)-propane-1-sulfonic acid [4-[4-amino-5-(2,3-difluoro-6-methoxy-benzoyl)-pyrimidin-2-ylamino]-cyclohexyl]-amide,
Trans-3-Pyrrolidin-1-yl-propane-1-sulfonic acid [4-[4-amino-5-(2,3-difluoro-6-methoxy-benzoyl)-pyrimidin-2-ylamino]-cyclohexyl]-amide,
Trans-3-Hydroxy-propane-1-sulfonic acid [4-[4-amino-5-(2,3-difluoro-6-methoxy-benzoyl)-pyrimidin-2-ylamino]-cyclohexyl]-amide,
Trans-[4-Amino-2-[4-(1,1-dioxo-1$\lambda^6$-isothiazolidin-2-yl)-cyclohexylamino]-pyrimidin-5-yl]-(2,3-difluoro-6-methoxy-phenyl)-methanone, and
Trans-[4-Amino-2-[4-(4-methyl-piperazin-1-yl)-cyclohexylamino]-pyrimidin-5-yl]-(2,3-difluoro-6-methoxy-phenyl)-methanone,
or a pharmaceutically acceptable salt of any of the foregoing compounds.

27. The compound of claim 24 selected from the group
Trans-[4-Amino-2-(4-pyrrolidin-1-yl-cyclohexylamino)-pyrimidin-5-yl]-(2,3-difluoro-6-methoxy-phenyl)-methanone,
Trans-[4-Amino-2-(4-dimethylamino-cyclohexylamino)-pyrimidin-5-yl]-(2,3-difluoro-6-methoxy-phenyl)-methanone,
[4-[4-Amino-5-(2-methoxy-5-methyl-benzoyl)-pyrimidin-2-ylamino]-cyclohexyl]-carbamic acid tert-butyl ester,
[4-Amino-2-(4-amino-cyclohexylamino)-pyrimidin-5-yl]-(2-methoxy-5-methyl-phenyl)-methanone,
N-[4-[4-Amino-5-(2-methoxy-5-methyl-benzoyl)-pyrimidin-2-ylamino]-cyclohexyl]-acetamide,
N-[4-[4-Amino-5-(2-methoxy-5-methyl-benzoyl)-pyrimidin-2-ylamino]-cyclohexyl]-methanesulfonamide,
[4-[4-Amino-5-(5-fluoro-2-methoxy-4-methyl-benzoyl)-pyrimidin-2-ylamino]-cyclohexyl]-carbamic acid tert-butyl ester,
[4-Amino-2-(4-amino-cyclohexylamino)-pyrimidin-5-yl]-(5-fluoro-2-methoxy-4-methyl-phenyl)-methanone,
N-[4-[4-Amino-5-(5-fluoro-2-methoxy-4-methyl-benzoyl)-pyrimidin-2-ylamino]-cyclohexyl]-acetamide, and
N-[4-[4-Amino-5-(5-fluoro-2-methoxy-4-methyl-benzoyl)-pyrimidin-2-ylamino]-cyclohexyl]-methanesulfonamide,
or a pharmaceutically acceptable salt of any of the foregoing compounds.

28. The compound of claim 24 wherein $R^5$ and $R^6$ are independently selected from H, $COR^{12}$ and $SO_2R^{15}$.

29. The compound of claim 5 having the formula

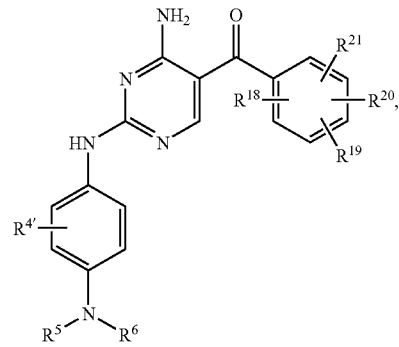

I(g)

wherein $R^{18}$, $R^{19}$, $R^{20}$ and $R^{21}$ are each independently selected from lower alkyl, halogen and $OR^{12}$.

30. The compound of claim 29 selected from the group
[4-Amino-2-[4-(4-methyl-piperazin-1-yl)-phenylamino]-pyrimidin-5-yl]-(3-fluoro-phenyl)-methanone,
[4-Amino-2-[4-(4-methyl-piperazin-1-yl)-phenylamino]-pyrimidin-5-yl]-(2-methoxyphenyl)-methanone,
[4-Amino-2-[4-(4-methyl-piperazin-1-yl)-phenylamino]-pyrimidin-5-yl]-(2,6-difluoro-phenyl)-methanone,
[4-Amino-2-[4-(4-isopropyl-piperazin-1-yl)-phenylamino]-pyrimidin-5-yl]-(2-methoxy-phenyl)-methanone,
[4-Amino-2-[4-(4-isopropyl-piperazin-1-yl)-phenylamino]-pyrimidin-5-yl]-(2,6-difluoro-phenyl)-methanone,
[4-Amino-2-[4-(4-methyl-piperazin-1-yl)-phenylamino]-pyrimidin-5-yl]-(5-fluoro-2-methoxy-phenyl)-methanone,
[4-Amino-2-[4-(4-isopropyl-piperazin-1-yl)-phenylamino]-pyrimidin-5-yl]-(5-fluoro-2-methoxy-phenyl)-methanone,
[4-Amino-2-[4-(4-methyl-piperazin-1-yl)-phenylamino]-pyrimidin-5-yl]-o-tolyl-methanone,
[4-Amino-2-[4-(4-isopropyl-piperazin-1-yl)-phenylamino]-pyrimidin-5-yl]-o-tolyl-methanone, and
4-[4-Amino-5-(5-fluoro-2-methoxy-benzoyl)-pyrimidin-2-ylamino]-piperidine-1-carboxylic acid (4-dimethylamino-phenyl)-amide,
or a pharmaceutically acceptable salt of any of the foregoing compounds.

31. The compound of claim 29 wherein $R^{4'}$ is selected from the group H, $OR^{11}$ and lower alkyl, and the group $NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms, and said ring atoms optionally being substituted by OH, oxo, $NH_2$, lower alkyl and lower alkyl substituted by $OR^{12}$.

32. A compound selected from the group
[4-Amino-2-(1-methanesulfonyl-piperidin-4-ylamino)-pyrimidin-5-yl]-(5-fluoro-2-methoxy-phenyl)-methanone,
Trans-N-[4-[4-amino-5-(2,3-difluoro-6-methoxy-benzoyl)-pyrimidin-2-ylamino]-cyclohexyl]-methanesulfonamide,
Trans-N-[4-[4-Amino-5-(5-fluoro-2-methoxy-benzoyl-pyrimidin-2-ylamino]-cyclohexyl]-methanesulfonamide,
[4-Amino-2-(1-methanesulfonyl-piperidin-4-ylamino)-pyrimidin-5-yl]-(2-methoxy-phenyl)-methanone,
1-[4-[4-Amino-5-(5-fluoro-2-methoxy-benzoyl)-pyrimidin-2-ylamino]-piperidin-1-yl]-ethanone,
1-[4-[4-Amino-5-(2,3-difluoro-6-methoxy-benzoyl)-pyrimidin-2-ylamino]-piperidin-1-yl]-ethanone and
Trans-N-[4-[4-Amino-5-(2,3-difluoro-6-methoxy-benzoyl)-pyrimidin-2-ylamino]-cyclohexyl]-acetamide,
or a pharmaceutically acceptable salt of any of the foregoing compounds.

33. A compound of formula 1-[4-[4-Amino-5-(5-fluoro-2-methoxy-benzoyl)-pyrimidin-2-ylamino]-piperidin-1-yl]-ethanone or a pharmaceutically acceptable salt thereof.

34. A compound of formula [4-Amino-2-(1-methanesulfonyl-piperidin-4-ylamino)-pyrimidin-5-yl]-(5-fluoro-2-methoxy-phenyl)-methanone or a pharmaceutically acceptable salt thereof.

35. A compound of formula [4-Amino-2-(1-methanesulfonyl-piperidin-4-ylamino)-pyrimidin-5-yl]-(2,3-difluoro-6-methoxy-phenyl)-methanone or a pharmaceutically acceptable salt thereof.

36. A compound of formula Trans-N-[4-[4-amino-5-(2,3-difluoro-6-methoxy-benzoyl)-pyrimidin-2-ylamino]-cyclohexyl]-methanesulfonamide or a pharmaceutically acceptable salt thereof.

37. A compound of formula
4-[4-Amino-5-(2,3-difluoro-6-methoxy-benzoyl)-pyrimidin-2-ylamino]-piperidine-1-sulfonic acid amide or a pharmaceutically acceptable salt thereof.

38. A compound selected from the group
[4-Amino-2-(4-amino-cyclohexylamino)-pyrimidin-5-yl]-(2,3-difluoro-6-methoxy-phenyl)-methanone,
[4-Amino-2-(1-methanesulfonyl-piperidin-4-ylamino)-pyrimidin-5-yl]-(2,3,4-trifluoro-6-methoxy-phenyl)-methanone,
[4-Amino-2-(1-methanesulfonyl-piperidin-4-ylamino)-pyrimidin-5-yl]-(2-fluoro-6-methoxy-phenyl)-methanone,
{4-Amino-2-[1-(3-pyrrolidin-1-yl-propane-1-sulfonyl)-piperidin-4-ylamino]-pyrimidin-5-yl}-(5-fluoro-2-methoxy-phenyl)-methanone,
(4-Amino-2-{1-[3-(4-methyl-piperazin-1-yl)-propane-1-sulfonyl]-piperidin-4-ylamino}-pyrimidin-5-yl)-(5-fluoro-2-methoxy-phenyl)-methanone,
[4-Amino-2-(1-methanesulfonyl-piperidin-4-ylamino)-pyrimidin-5-yl]-(5-fluoro-2-methoxy-4-methyl-phenyl)-methanone,
[4-Amino-2-[1-(3-chloro-propane-1-sulfonyl)-piperidin-4-ylamino]-pyrimidin-5-yl]-(2,3-difluoro-6-methoxy-phenyl)-methanone,
{4-Amino-2-[1-(3-pyrrolidin-1-yl-propane-1-sulfonyl)-piperidin-4-ylamino]-pyrimidin-5-yl}-(2,3-difluoro-6-methoxy-phenyl)-methanone,
{4-Amino-2-[1-(3-morpholin-4-yl-propane-1-sulfonyl)-piperidin-4-ylamino]-pyrimidin-5-yl}-(2,3-difluoro-6-methoxy-phenyl)-methanone,
[4-Amino-2-(1-{3-[4-(2-hydroxy-ethyl)-piperazin-1-yl]-propane-1-sulfonyl}-piperidin-4-ylamino)-pyrimidin-5-yl]-(2,3-difluoro-6-methoxy-phenyl)-methanone, and
[4-Amino-2-(1-{3-[(2-methoxy-ethyl)-methyl-amino]-propane-1-sulfonyl}-piperidin-4-ylamino)-pyrimidin-5-yl]-(2,3-difluoro-6-methoxy-phenyl)-methanone,
or a pharmaceutically acceptable salt of any of the foregoing compounds.

39. A compound selected from the group
1-[4-[4-Amino-5-(3-methoxy-pyridine-2-carbonyl)-pyrimidin-2-ylamino]-piperidin-1-yl]-ethanone,
[4-Amino-2-(1-methanesulfonyl-piperidin-4-ylamino)-pyrimidin-5-yl]-(3-methoxy-pyridin-2-yl)-methanone,
1-[4-[4-Amino-5-(3-methyl-thiophene-2-carbonyl)-pyrimidin-2-ylamino]-piperidin-1-yl]-ethanone,
[4-Amino-2-(1-methanesulfonyl-piperidin-4-ylamino)-pyrimidin-5-yl]-(3-methyl-thiophen-2-yl)-methanone,
[4-Amino-2-(1-methanesulfonyl-piperidin-4-ylamino)-pyrimidin-5-yl]-thiophen-2-yl-methanone,
[4-Amino-2-(1-methanesulfonyl-piperidin-4-ylamino)-pyrimidin-5-yl]-(2,3-difluoro-6-hydroxy-phenyl)-methanone,
[4-Amino-2-(azetidin-3-ylamino)-pyrimidin-5-yl]-(2,3-difluoro-6-methoxy-phenyl)-methanone,
[4-Amino-2-(1-methanesulfonyl-azetidin-3-ylamino)-pyrimidin-5-yl]-(2,3-difluoro-6-methoxy-phenyl)-methanone,

[4-Amino-2-(1-ethanesulfonyl-azetidin-3-ylamino)-pyrimidin-5-yl]-(2,3-difluoro-6-methoxy-phenyl)-methanone, and
[4-Amino-2-[1-(propane-2-sulfonyl)-azetidin-3-ylamino]-pyrimidin-5-yl]-(2,3-difluoro-6-methoxy-phenyl)-methanone,
or a pharmaceutically acceptable salt of any of the foregoing compounds.

40. A compound selected from the group
4-[4-Amino-5-(2-methoxy-benzoyl)-pyrimidin-2-ylamino]-piperidine-1-carboxylic acid tert-butyl ester,
4-[4-Amino-5-(5-fluoro-2-methoxy-benzoyl)-pyrimidin-2-ylamino]-piperidine-1-carboxylic acid tert-butyl ester, and
4-[4-Amino-5-(2,3-difluoro-6-methoxy-benzoyl)-pyrimidin-2-ylamino]-piperidine-1-carboxylic acid tert-butyl ester.

41. The compound
[4-Amino-2-(1-methanesulfonyl-piperidin-4-ylamino)-pyrimidin-5-yl]-[3-(tert-butyl-dimethyl-silanyloxy)-5,6-difluoro-2-methoxy-phenyl]-methanone.

42. A pharmaceutical composition comprising as an active ingredient an effective amount of a compound of claim 1 and a pharmaceutically acceptable carrier or excipient.

43. The pharmaceutical composition of claim 42 which is suitable for parenteral administration.

44. A method for treating a solid breast or colon tumor comprising administering to a subject in need of such treatment a therapeutically effective amount of at least one compound according to claim 1.

* * * * *